US008940884B2

(12) United States Patent
Apt et al.

(10) Patent No.: US 8,940,884 B2
(45) Date of Patent: Jan. 27, 2015

(54) POLYUNSATURATED FATTY ACID SYNTHASE NUCLEIC ACID MOLECULES AND POLYPEPTIDES, COMPOSITIONS, AND METHODS OF MAKING AND USES THEREOF

(75) Inventors: Kirk E. Apt, Ellicott City, MD (US);
Leslie Richter, Broomfield, CO (US);
David Simpson, Boulder, CO (US);
Ross Zirkle, Mt. Airy, MD (US)

(73) Assignee: DSM IP Assets B.V., Heerlen (NL)

(*) Notice: Subject to any disclaimer, the term of this patent is extended or adjusted under 35 U.S.C. 154(b) by 259 days.

(21) Appl. No.: 12/727,851

(22) Filed: Mar. 19, 2010

(65) Prior Publication Data

US 2010/0266564 A1 Oct. 21, 2010

Related U.S. Application Data

(60) Provisional application No. 61/161,742, filed on Mar. 19, 2009, provisional application No. 61/296,460, filed on Jan. 19, 2010.

(51) Int. Cl.
*C12N 15/52* (2006.01)
*C12P 7/64* (2006.01)
*C12N 9/04* (2006.01)
*C12N 15/82* (2006.01)
*C12N 15/63* (2006.01)
*C12N 5/10* (2006.01)
*A61K 38/43* (2006.01)
*A61K 38/00* (2006.01)

(52) U.S. Cl.
CPC .............. *C12P 7/6427* (2013.01); *C12N 9/0006* (2013.01); *C12N 15/8247* (2013.01); *C12P 7/6472* (2013.01); *A61K 38/00* (2013.01)
USPC ..................... 536/23.6; 514/44 R; 435/320.1; 435/6.1; 435/325; 435/419; 435/257.2

(58) Field of Classification Search
USPC .............. 536/23.2; 514/44 R; 435/320.1, 6.1, 435/325, 419, 257.2
See application file for complete search history.

(56) References Cited

U.S. PATENT DOCUMENTS

| | | | |
|---|---|---|---|
| 5,130,242 A | 7/1992 | Barclay | |
| 5,246,841 A | 9/1993 | Yazawa et al. | |
| 5,639,790 A | 6/1997 | Voelker et al. | |
| 5,672,491 A | 9/1997 | Khosla et al. | |
| 5,683,898 A | 11/1997 | Yazawa et al. | |
| 5,798,259 A | 8/1998 | Yazawa et al. | |
| 5,908,622 A | 6/1999 | Barclay | |
| 6,033,883 A | 3/2000 | Barr et al. | |
| 6,140,486 A | 10/2000 | Facciotti et al. | |
| 6,503,706 B1 | 1/2003 | Abken et al. | |
| 6,566,583 B1 | 5/2003 | Facciotti et al. | |
| 7,001,772 B2 | 2/2006 | Roessler et al. | |
| 7,125,672 B2 | 10/2006 | Picataggio et al. | |
| 7,211,418 B2 | 5/2007 | Metz et al | |
| 7,214,853 B2 | 5/2007 | Facciotti et al. | |
| 7,217,856 B2 | 5/2007 | Weaver et al. | |
| 7,247,461 B2 | 7/2007 | Metz et al. | |
| 7,256,022 B2 | 8/2007 | Metz et al. | |
| 7,256,023 B2 * | 8/2007 | Metz et al. | 435/134 |
| 7,259,295 B2 | 8/2007 | Metz et al. | |
| 7,271,315 B2 | 9/2007 | Metz et al. | |
| 7,368,552 B2 | 5/2008 | Mukerji et al. | |
| 7,560,539 B2 | 7/2009 | Weaver et al. | |
| 7,563,603 B2 | 7/2009 | Metz et al. | |
| 7,563,604 B2 | 7/2009 | Metz et al. | |
| 7,563,605 B2 | 7/2009 | Metz et al. | |
| 7,601,522 B2 | 10/2009 | Weaver et al. | |
| 7,605,245 B2 | 10/2009 | Metz et al. | |
| 7,608,702 B2 | 10/2009 | Metz et al. | |
| 7,608,703 B2 | 10/2009 | Metz et al. | |
| 7,608,753 B2 | 10/2009 | Metz et al. | |
| 7,611,874 B2 | 11/2009 | Metz et al. | |
| 7,611,875 B2 | 11/2009 | Metz et al. | |
| 7,611,876 B2 | 11/2009 | Metz et al. | |
| 7,626,009 B2 | 12/2009 | Weaver et al. | |
| 7,629,450 B2 | 12/2009 | Weaver et al. | |
| 7,638,315 B2 | 12/2009 | Metz et al. | |
| 7,642,074 B2 | 1/2010 | Metz et al. | |
| 7,645,597 B2 | 1/2010 | Metz et al. | |
| 7,645,598 B2 | 1/2010 | Metz et al. | |
| 7,662,597 B2 | 2/2010 | Metz et al. | |
| 7,718,431 B2 | 5/2010 | Weaver et al. | |
| 7,759,548 B2 | 7/2010 | Metz et al. | |

(Continued)

FOREIGN PATENT DOCUMENTS

CA 2 520 795 A1 10/2004
EP 0 594 868 A1 5/1994

(Continued)

OTHER PUBLICATIONS

Witkowski et al.; Conversion of b-ketoacyl synthase to a malonyl decarboxylase by replacement of the active site cysteine with glutamine; Biochemistry 38:11643-11650, 1999.*

(Continued)

*Primary Examiner* — Jim Ketter
*Assistant Examiner* — Antonio Galisteo Gonzalez
(74) *Attorney, Agent, or Firm* — Xi Chen; Shannon McGarrah

(57) ABSTRACT

The present invention is directed to isolated nucleic acid molecules and polypeptides of thraustochytrid polyunsaturated fatty acid (PUFA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

7 Claims, 38 Drawing Sheets

(56) References Cited

U.S. PATENT DOCUMENTS

| | | | |
|---|---|---|---|
| 7,799,564 | B2 | 9/2010 | Weaver et al. |
| 7,803,620 | B2 | 9/2010 | Weaver et al. |
| 7,807,442 | B2 | 10/2010 | Metz et al. |
| 7,816,504 | B2 | 10/2010 | Metz et al. |
| 7,816,505 | B2 | 10/2010 | Metz et al. |
| 7,838,649 | B2 | 11/2010 | Metz et al. |
| 7,842,796 | B2 | 11/2010 | Metz et al. |
| 7,847,077 | B2 | 12/2010 | Metz et al. |
| 7,879,608 | B2 | 2/2011 | Weaver et al. |
| 7,897,391 | B2 | 3/2011 | Weaver et al. |
| 7,897,392 | B2 | 3/2011 | Weaver et al. |
| 7,897,393 | B2 | 3/2011 | Weaver et al. |
| 7,897,844 | B2 | 3/2011 | Metz et al. |
| 7,902,427 | B2 | 3/2011 | Weaver et al. |
| 7,906,706 | B2 | 3/2011 | Weaver et al. |
| 7,919,320 | B2 | 4/2011 | Metz et al. |
| 7,939,305 | B2 | 5/2011 | Luy et al. |
| 7,939,716 | B2 | 5/2011 | Weaver et al. |
| 7,960,524 | B2 | 6/2011 | Metz et al. |
| 7,973,149 | B2 | 7/2011 | Metz et al. |
| 8,003,772 | B2 | 8/2011 | Weaver et al. |
| 2002/0138874 | A1 | 9/2002 | Mukerji et al. |
| 2002/0156254 | A1 | 10/2002 | Qiu et al. |
| 2002/0194641 | A1 | 12/2002 | Metz et al. |
| 2004/0005672 | A1 | 1/2004 | Santi et al. |
| 2004/0010817 | A1 | 1/2004 | Shockey et al. |
| 2004/0139498 | A1 | 7/2004 | Jaworski et al. |
| 2004/0172682 | A1 | 9/2004 | Kinney et al. |
| 2005/0014231 | A1 | 1/2005 | Mukerji et al. |
| 2005/0089865 | A1 | 4/2005 | Napier et al. |
| 2005/0164192 | A1 | 7/2005 | Graham et al. |
| 2007/0244192 | A1 | 10/2007 | Metz |
| 2007/0245431 | A1 | 10/2007 | Metz et al. |
| 2007/0259355 | A1 | 11/2007 | Luy et al. |
| 2008/0038378 | A1 | 2/2008 | Metz et al. |
| 2008/0038379 | A1 | 2/2008 | Metz et al. |
| 2009/0098622 | A1 | 4/2009 | Facciotti et al. |
| 2010/0313309 | A1 | 12/2010 | Metz et al. |
| 2011/0167508 | A1 | 7/2011 | Metz et al. |
| 2011/0250342 | A1 | 10/2011 | Metz et al. |
| 2012/0021470 | A1 | 1/2012 | Weaver et al. |

FOREIGN PATENT DOCUMENTS

| | | | |
|---|---|---|---|
| EP | 0 823 475 | A1 | 2/1998 |
| WO | WO 93/23545 | A1 | 11/1993 |
| WO | WO 96/21735 | A1 | 7/1996 |
| WO | WO 98/46764 | A1 | 10/1998 |
| WO | WO 98/55625 | A1 | 12/1998 |
| WO | WO 00/42195 | A2 | 7/2000 |
| WO | WO 02/083870 | A2 | 10/2002 |
| WO | WO 2004/071467 | A2 | 8/2004 |
| WO | WO 2004/087879 | A2 | 10/2004 |
| WO | WO 2005/097982 | A2 | 10/2005 |
| WO | WO 2006/008099 | A2 | 1/2006 |
| WO | WO 2006/034228 | A2 | 3/2006 |
| WO | WO 2006/044646 | A2 | 4/2006 |
| WO | WO 2006/135866 | A2 | 12/2006 |

OTHER PUBLICATIONS

Seffernick et al.; Melanine deaminase and atrazine chlorohydrolase: 98 percent identical but functionally different; J. Bacteriol. 183(8):2405-2410, 2001.*

Branden et al.; Introduction to Protein Structure, Garland Publishing Inc., New York, p. 247, (1991).*

Abbadi, A., et al., "Transgenic oilseeds as sustainable source of nutritionally relevant C20 and C22 polyunsaturated fatty acids?," *Eur. J. Lipid Sci. Technol.* 103:106-113, Wiley-VCH Verlag GmbH & Co. KGaA, Germany (Feb. 2001).

Allen, E.A. and Bartlett, D.H., "Structure and regulation of the omega-3 polyunsaturated fatty acid synthase genes from the deep-sea bacterium *Photobacterium profundum* strain SS9," *Microbiology* 148:1903-1913, Society for General Microbiology, United Kingdom (Jun. 2002).

Allen, E.E., et al., "Monounsaturated but not polyunsaturated fatty acids are required for growth of the deep-sea bacterium *Photobacterium profundum* SS9 at high pressure and low temperature," *Appl. Environ. Microbiol.* 65:1710-1720, American Society for Microbiology, United States (Apr. 1999).

Bateman, A., et al., "The Pfam Protein Families Database," *Nucleic Acids Research* 30:276-280, Oxford University Press, United Kingdom (Jan. 2002).

Bedford, D., et al., "A functional chimeric modular polyketide synthase generated via domain replacement," *Chem. Biol.* 3:827-831, Current Biology Ltd., United Kingdom (1996).

Bentley, R. and Bennett, J.W., "Constructing Polyketides: From Collie to Combinatorial Biosynthesis," *Annu. Rev. Microbiol.* 53:411-446, Annual Reviews Inc., United States (Oct. 1999).

Bisang, C., et al., "A chain initiation factor common to both modular and aromatic polyketide synthases," *Nature* 401:502-505, Macmillan Magazines Ltd., United Kingdom (Sep. 1999).

Bork, P., "Go hunting in sequence databases but watch out for the traps," *Trends in Genetics* 12:425-427, Elsevier Science Ltd., The Netherlands (1996).

Brenner, S.E., "Errors in genome annotation," *Trends in Genetics* 15:132-133, Elsevier Science Ltd., The Netherlands (Apr. 1999).

Broun, P., et al., "Catalytic Plasticity of Fatty Acid Modification Enzymes Underlying Chemical Diversity of Plan Lipids," *Science* 282:1315-1317, American Association for the Advancement of Science, United States (Nov. 1998).

Cane, D.E., et al., "Harnessing the Biosynthetic Code: Combinations, Permutations, and Mutations," *Science* 282:63-68, American Association for the Advancement of Science, United States (Oct. 1998).

Chuck, J.-A., et al., "Molecular recognition of diketide substrates by a β-ketoacyl-acyl carrier protein synthase domain within a bimodular polyketide synthase," *Chem. Biol.* 4:757-766, Current Biology Ltd., United Kingdom (1997).

Creelman, R.A. and Mullet, J.E., "Biosynthesis and action of jasmonates in plants," *Annu. Rev. Plant Physiol. Plant Mol. Biol.* 48:355-381, Annual Reviews Inc., United States (1997).

Delong, E.F. and Yayanos, A.A., "Biochemical Function and Ecological Significance of Novel Bacterial Lipids in Deep-Sea Procaryotes," *Appl. Environ. Microbiol.* 51:730-737, American Society for Microbiiolgy, United States (1986).

Doerks, T., et al., "Protein annotation: detective work for functin prediction," *Trends in Genetics* 14:248-250, Elsevier Science Ltd., The Netherlands (Jun. 1998).

Facciotti, D., et al., "Cloning and Characterization of Polyunsaturated Fatty Acids (PUFA) Genes from Marine Bacteria," (abstract) In: International Symposium on Progress and Prospect of Marine Biotechnology, p. 14, China Ocean Press, China (Oct. 1998).

Fan, K.W., et al., "Eicosapentaenoic and docosahexaenoic acids production by and okara-utilizing potential of thraustochytrids," *J. Ind. Microbiol. Biotechnol.* 27:199-202, Nature Publishing Group, United Kingdom (Oct. 2001).

GenBank Accession No. AF409100, "*Photobacterium profundum* strain SS9 methyl-accepting chemotaxis protein gene, partial cds," Jun. 14, 2002, 5 pages.

GenBank Accession No. U09865, "*Alcaligenes eutrophus* pyruvate dehydrogenase (pdhA), dihydrolipoamide acetyltransferase (pdhB), dihydrolipoamide dehydrogenase (pdhL), and ORF3 genes, complete cds," Sep. 23, 1994, 4 pages.

GeneSeq Assession No. AAA71567, "S. aggregatum PKS cluster ORF6 homolog DNA," Dec. 11, 2000, 4 pages.

Grimsley, N.H., et al., "Fatty Acid Composition of Mutants of the Moss *Physcomitrella patens*," *Phytochemistry* 20:1519-1524, Pergamon Press Ltd., United Kingdom (1981).

Harlow, E. and Lane, D. *Antibodies: A Laboratory Manual*, p. 76, Cold Spring Harbor Laboratory Press, United States (1988).

Heath, R.J. and Rock, C.O., "Roles of the FabA and FabZ β-Hydroxyacyl-Acyl Carrier Protein Dehydratases in *Escherichia coli* Fatty Acid Biosynthesis," *J. Biol. Chem.* 271:27795-17801, The American Society for Biochemistry and Molecular Biiology, Inc., United States (1996).

(56) References Cited

OTHER PUBLICATIONS

Hopwood, D.A. and Sherman, D.H., "Molecular genetics of polyketides and its comparison to fatty acid biosynthesis," *Annu. Rev. Genet.* 24:37-66, Annual Reviews Inc., United States (1990).

Hutchinson, C.R., "Polyketide Synthase Gene Manipulation: A Structure-Function Approach in Engineering Novel Antibiotics," *Annu. Rev. Microbiol.* 49:201-238, Annual Reviews Inc., United States (1995).

Jez, J.M., et al., "Structural control of polyketide formation in plant-specific polyketide synthases," *Chem. Biol.* 7:919-930, Elsevier Science Ltd., The Netherlands (2000).

Jøstensen, J.-P. and Landfald, B., "High prevalence of polyunsaturated-fatty-acid producing bacteria in arctic invertebrates," *FEMS Microbiology Letters* 151:95-101, Elsevier Science B.V., The Netherlands (1997).

Katz, L. and Don Adio, S., "Polyketide Synthesis: Prospects for Hybrid Antibiotics," *Annu. Rev. Microbiol.* 47:875-912, Annual Reviews Inc., United States (1993).

Kaulmann, U. and Hertweck, C., "Biosynthesis of Polyunsaturated Fatty Acids by Polyketide Synthases," *Angew. Chem. Int. Ed.* 41:1866-1869, Wiley-VCH Verlag GmbH, Germany (Jun. 2002).

Kealey, J.T., et al. "Production of a polyketide natural product in nonpolyketide-producing prokaryotic and eukaryotic hosts," *Proc. Nat. Acad. Sci.* 95:505-509, National Academy of Sciences, United States (Jan. 1998).

Keating, T. A. and Walsh, C.T., "Initiation, elongation, and termination strategies in polyketide and polypeptide antibiotic biosynthesis," *Curr. Opin. Chem. Biol.* 3:598-606, Elsevier Science Ltd., The Netherlands (Oct. 1999).

Khosla, C. et al., "Tolerance and Specificity of Polyketide Synthases," *Annu. Rev. Biochem.* 68:219-253, Annual Reviews Inc., United States (Jul. 1999).

Kyle, D. et al., "Long-chain Omega-3 Polyunsaturated Fatty Acids: Prospects for Introduction into Horticultural Food Plants," *HortScience* 25:1523-1526, American Society for Horticultural Science, United States (1990).

Leadlay, P.F., "Combinatorial approaches to polyketide biosynthesis," *Curr. Opin. Chem. Biol.* 1:162-168, Current Biology Ltd., United Kingdom (1997).

Magnuson, K. et al., "Regulation of fatty acid biosynthesis in *Escherichia coli*," *Microbiol. Rev.* 57:522-542, American Society for Microbiology, United States (1993).

Metz, J.G. et al., "Production of Polyunsaturated Fatty Acids by Polyketide Synthases in Both Prokaryotes and Eukaryotes," *Science* 293:290-293, American Association for the Advancement of Science, United States (2001).

Nakahara, T., "Physiological Activity of Docosahexaenoic Acid and Its Production by Microbial Culture," *Yukagaku* 44:821-827, Nihon Yushi Kagaku Kyōkai, Japan (1995).

Nakahara, T., et al., "Production of Docosahexaenoic and Docosapentaenoic Acids by *Schizochytrium* sp. Isolated from Yap Islands," *JAOCS* 73:1421-1426, AOCS Press, United States (1996).

Napier, J.A., "Plumbing the depths of PUFA biosynthesis: a novel polyketide synthase-like pathway from marine organisms," *Trends Plant Sci.* 7:51-54, Elsevier Science Ltd., The Netherlands (Feb. 2002).

Nasu, M. et al., "Efficient Transformation of *Marchantia polymorpha* That is Haploid and Has Very Small Genome DNA," *J. Ferment. Bioeng.* 84:519-523, Elsevier Science Publishers, The Netherlands (1997).

Nichols, D. et al., "Developments with antartic microorganisms: culture collections, bioactivity screening, taxonomy, PUFA production and cold-adapted enzymes," *Curr. Opin. Biotechnol.* 10:240-246, Elsevier Science Ltd., The Netherlands (Jun. 1999).

Nicholson, T.P., et al., "Design and utility of oligonucleotide gene probes for fungal polyketide synthases," *Chem. Biol.* 8:157-178, Elsevier Science Ltd., The Netherlands (Feb. 2001).

Nogi, Y., et al., "*Photobacterium profundum* sp. nov., a new, moderately barophilic bacterial species isolated from a deep-sea sediment," *Extremophiles* 2:1-7, Springer-Verlag, Germany (1998).

Oliynyk, M., et al., "A hybrid modular polyketide synthase obtained by domain swapping," *Chem. Biol.* 3:833-839, Current Biology Ltd., United Kingdom (1996).

Orikasa, Y., et al., "Characterization of the Eicosapentaenoic Acid Biosynthesis Gene Cluster From *Shewanella* SP. Strain SCRC-2738," *Cell. Mol. Biol.* 50:625-630, Noisy-le-Grand, France (Jul. 2004).

Parker-Barnes, J.M., et al., "Identification and characterization of an enzyme involved in the elongation of n-6 and n-3 polyunsaturated fatty acids," *Proc. Natl. Acad. Sci.* 97:8284-8289, The National Academy of Sciences, United States (2000).

Qiu, X., et al., "Identification of Δ4 Fatty Acid Desaturase from *Thraustochytrium* sp. Involved in the Biosyntheses of Docosahexaenoic Acid by Heterologous Expression in *Saccharomyces cerevisiae* and *Brassica juncea*," *J. Biol. Chem.* 276:31561-31566, The American Society for Biochemistry and Molecular Biology, Inc., United States (Aug. 2001).

Sánchez, C., et al., "Cloning and characterization of a phosphopantetheinyl transferase from *Streptomyces verticillus* ATCC15003, the producer of the hybride peptide-polyketide antitimour drug bleomycin," *Chem. Biol.* 8:725-738, Elsevier Science Ltd., The Netherlands (Jun. 2001).

Satomi, M., et al., "*Shewanella marinintestina* sp. nov., *Shewanella schlegeliana* sp. nov. and *Shewanella sairae* sp. nov., novel eicosapentaenoic-acid-producing marine bacteria isolated from sea-animal intestines," *Int. J. Syst. Evol. Microbiol.* 53:491-499, IUMS, United Kingdom (Mar. 2003; published online Aug. 2002).

Shanklin, J. and Cahoon, E.B., et al., "Desaturation and Related Modifications of Fatty Acids," *Annu. Rev. Plant Physiol. Plant Mol. Biol.* 49:611-641, Annual Reviews, Inc., United States (Jun. 1998).

Singh, A. and Ward, O.P., "Microbial Production of Docosahexaenoic Acid (DHA, C22:6)," *Adv. Appl. Microbiol.* 45:271-312, Academic Press, The Netherlands (1997).

Smith, T.F. and Zhang, X., "The challenges of genome sequence annotation or the devil is in the details," *Nat. Biotechnol.* 15:1222-1223, Nature Pub. Co., United Kingdom (1997).

Somerville, C.R., "Future prospects for genetic modification of the composition of edible oils from higher plants," *Am. J. Clin. Nutr.* 58(suppl):270s-275s, American Society for Clinical Nutrition, United States (1993).

Takeyama, H., et al. "Expression of eicosapentaenoic acid synthesis gene cluster from *Shewanella* sp. in a transgenic marine cyanobacterium, *Synechococcus* sp.," *Microbiology* 143:2725-2731, Society for General Microbiology, United Kingdom (1997).

UniProt Accession No. Q93CG6 PHOPR, "Omega-3 polyunsaturated fatty acid synthase PfaC," Dec. 1, 2001, 2 pages.

Van De Loo, F.J., et al., "An oleate 12-hydroxylase from *Ricinus communis* L. is a fatty acyl desaturase homolog," *Proc. Natl. Acad. Sci.* 92:6743-6747, The National Academy of Sciences, United States (1995).

Wallis, J.G., et al., "Polyunsaturated fatty acid synthesis: what will they think of next?," *Trends Biochem. Sci.* 27:467-473, Elsevier Science Ltd., The Netherlands (Sep. 2002; published online Aug. 2002).

Watanabe, K., et al., "Fatty Acid Synthesis of an Eicosapentaenoic Acid-Producing Bacterium: De Novo Synthesis, Chain Elongation, and Desaturation Systems," *J. Biochem.* 122:467-473, Japanese Biochemical Society, Japan (1997).

Weete, J.D., et al., "Lipids and Ultrastructure of *Thraustochytrium* sp. ATCC 26185," *Lipids* 32:839-845, AOCS Press, United States (1997).

Weismann, K.J., et al., "Origin of Starter Units for Erythromycin Biosynthesis," *Biochemistry* 37:11012-11017, American Chemical Society, United States (Aug. 1998; published online Jul. 1998).

Wiesmann, K.E.H., et al., "Polyketide snythesis in vitro on a modular polyketide synthase," *Chem. Biol.* 2:583-589, Current Biology Ltd., United Kingdom (Sep. 1995).

Weissmann, K.J., et al., "The Molecular Basis of Celmer's Rules: The Stereochemistry of the Condensation Step in Chain Extension on the Erythromycin Polyketide Synthase," *Biochemistry* 36:13849-13855, American Chemical Society, United States (1997).

(56) References Cited

OTHER PUBLICATIONS

Wolff, R. L., et al., "Arachidonic, Eicosapentaenoic, and Biosynthetically Related Fatty Acids in the Seed Lipids from a Primitive Gymnosperm, *Agathis robusta*," *Lipids* 34:1083-1097, AOCS Press, United States (Oct. 1999).

Yalpani, N., et al., "Production of 6-Methylsalicylic Acid by Expression of a Fungal Polyketide Synthase Activates Disease Resistance in Tobacco," *The Plant Cell* 13:1401-1409, American Society of Plant Physiologists, United States (Jun. 2001).

Yazawa, K., "Production of Eicosapentaenoic Acid from Marine Bacteria," *Lipids* 31(*suppl*):S-297-S-300, AOCS, United States (1996).

Yokochi, T., et al., "Optimization of docosahexaenoic acid production by *Schizochytrium limacinum* SR21," *Appl. Microbiol. Biotechnol.* 49:72-76, Springer-Verlag, Germany (1998).

International Preliminary Examination Report for International Patent Application No. PCT/US00/00956, mailed Apr. 19, 2001, 5 pages.

International Preliminary Examination Report for International Patent Application No. PCT/US02/12254, mailed Oct. 16, 2006, 7 pages.

International Preliminary Examination Report for International Patent Application No. PCT/US04/009323, mailed May 9, 2007, 8 pages.

International Preliminary Report on Patentability for International Patent Application No. PCT/US2007/064106, mailed Sep. 25, 2008, 9 pages.

International Preliminary Report on Patentability for International Patent Application No. PCT/US2007/064106, mailed Oct. 30, 2008, 9 pages.

International Search Report for International Patent Application No. PCT/US00/00956, mailed Jul. 6, 2000, 5 pages.

International Search Report for International Patent Application No. PCT/US02/12254, mailed Nov. 15, 2002, 7 pages.

International Search Report for International Patent Application No. PCT/US04/009323, mailed Apr. 4, 2007, 8 pages.

International Search Report for International Patent Application No. PCT/US05/36998, mailed Mar. 22, 2007, 8 pages.

International Search Report for International Patent Application No. PCT/US06/22893, mailed Feb. 29, 2008, 5 pages.

International Search Report for International Patent Application No. PCT/US07/64104, mailed Dec. 5, 2008, 6 pages.

International Search Report for International Patent Application No. PCT/US07/64105, mailed Nov. 23, 2007, 4 pages.

International Search Report for International Patent Application No. PCT/US08/63835, 6 pages.

International Search Report for International Patent Application No. PCT/US07/64106, mailed Sep. 16, 2008, 6 pages.

Sequence alignment for SEQ ID No. 1 with SEQ ID No. 16 from U.S. Patent No. 5,683,898, search result dated Aug. 5, 2009.

Sequence alignment for SEQ ID No. 5 with SEQ ID No. 17 from U.S. Patent No. 5,683,898, search result dated Aug. 5, 2009.

Sequence alignment of SEQ ID No. 11 with SEQ ID No. 16 from U.S. Patent No. 5,798,259, search result dated Aug. 10, 2009.

Sequence alignment of SEQ ID No. 7 with SEQ ID No. 1 from U.S. Patent No. 5,798.259, search result dated Aug. 10, 2009.

Supplementary European Search Report for European Patent Application No. EP 08 75 5645, dated Jan. 13, 2012, 11 pages.

Written Opinion for International Patent Application No. PCT/US00/00956, mailed Dec. 19, 2000, 5 pages.

Written Opinion for International Patent Application No. PCT/US04/09323, mailed Arp. 4, 2007, 9 pages.

Written Opinion for International Patent Application No. PCT/US05/36998, mailed Mar. 22, 2007, 5 pages.

Written Opinion for International Patent Application No. PCT/US06/22893, mailed Feb. 29, 2008, 7 pages.

Written Opinion for International Patent Application No. PCT/US07/64104, mailed Dec. 5, 2008, 7 pages.

Written Opinion for International Patent Application No. PCT/US07/64105, mailed Nov. 23, 2007, 7 pages.

Written Opinion for International Patent Application No. PCT/US07/64106, mailed Sep. 16, 2008, 6 pages.

Written Opinion for International Patent Application No. PCT/US08/63835, mailed Nov. 3, 2008, 6 pages.

U.S. Appl. No. 11/781,861, inventors Weaver, C.A. et al., filed Jul. 23, 2007 (Not Published).

U.S. Appl. No. 11/781,882, inventors Weaver, C.A. et al., filed Jul. 23, 2007 (Not Published).

International Preliminary Report on Patentability for International Patent Application No. PCT/US2010/028009, mailed Oct. 29, 2010, 7 pages.

International Search Report for International Patent Application No. PCT/US2010/028009, mailed Oct. 29, 2010, 4 pages.

Roche, HM., "Unsaturated Fatty Acids," *Proc. Nutr. Soc.* 58(2):397-401, Cambridge Univ. Press, England (1999).

Lewis, T.E., et al., "The Biotechnological Potential of Thraustochytrids," *Mar. Biotechnol.* 1:580-587, Springer-Verlag, New York, Inc., United States (1999).

Huang, J., et al. "Profile of Polyunsaturated Fatty Acids Produced by Thraustrochytrium sp. KK17-3," *JAOCS* 78:605-610, AOCS Press, United States (2001).

Huang, J., et al., "Grouping Newly Isolated Docosahexaenoic Acid-Producing Thraustochytrids Based on Their Polyunsaturated Fatty Acid Profiles and Comparative Analysis of 18S rRNA Genes," *Mar. Biotechnol.* 5:450-457, Springer-Verlag New York, Inc., United States (2003).

Bergé, J.P. and Barnathan, G., "Fatty Acids from Lipids of Marine Organisms: Molecular Biodiversity, Roles as Biomarkers, Biologically Active Compounds, and Economical Aspects," *Adv. Biochem. Eng. Biotechnol.* 96:49-125, Springer-Verlag, Germany (2005).

Abbadi, A., et al., "Biosynthesis of very-long-chain polyunsaturated fatty acids in transgenic oilseeds: constraints on their accumulation," *Plant Cell.* 16(10):2734-48, American Society of Plant Physiologists, United States (2004).

Napier, J.A. and Sayanova, O., "The production of very-long-chain PUFA biosynthesis in transgenic plants: towards a sustainable source of fish oils," *Proc. Nutr. Soc.* 64(3):387-93, Cambridge Univ. Press, England (2005).

Robert S.S., et al., "Metabolic engineering of Arabidopsis to produce nutritionally important DHA in seed oil," *Functional Plant Biology* 32: 473-479, CSIRO Publishing, Australia (2005).

Qi B., et al., "Production of very long chain polyunsaturated omega-3 and omega-6 fatty acids in plants," *Nature Biotechnology* 22:739-745, Nature Publishing Co., United States (2004).

Bumpus, et al., "Polyunsaturated Fatty-Acid-Like Trans-Enoyl Reductases utilized in Polyketide Biosynthesis," J. American Chemical Society 2008, vol. 130, No. 35: 11614-11616, American Chemical Society (2006).

Rock, et al., "Roles of the FabA and FabZ B-Hydroxyacyl-Acyl Carrier Protein Dehydratases in *Escherichia coli* Fatty Acid Biosynthesis," J. of Biological Chemistry 1996, vol. 271, No. 44: 27795-27801, American Society for Biochemistry and molecular Biology, Inc., United States (1996).

Smith, et al., "Structure of a dehydratase-isomerase from the bacterial pathway for biosynthesis of unsaturated fatty acids: two catalytic activities in one active site," Research Article 1996 4:253-264, Structure, Mar. 15, 1996—USSN 0969-2126.

\* cited by examiner

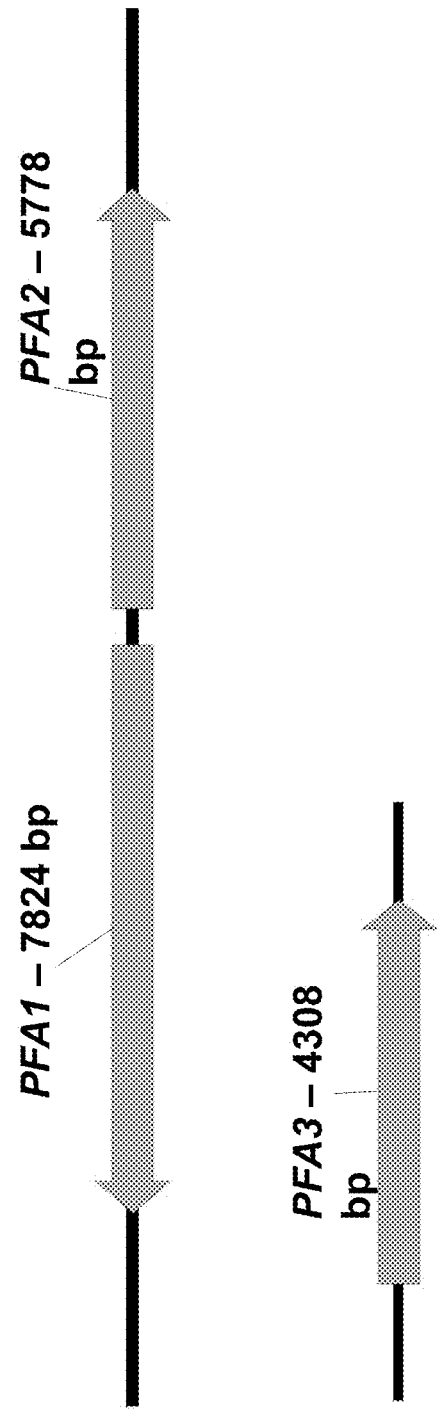
Figure 1. Schizochytrium sp. ATCC PTA-9695 Gene architecture

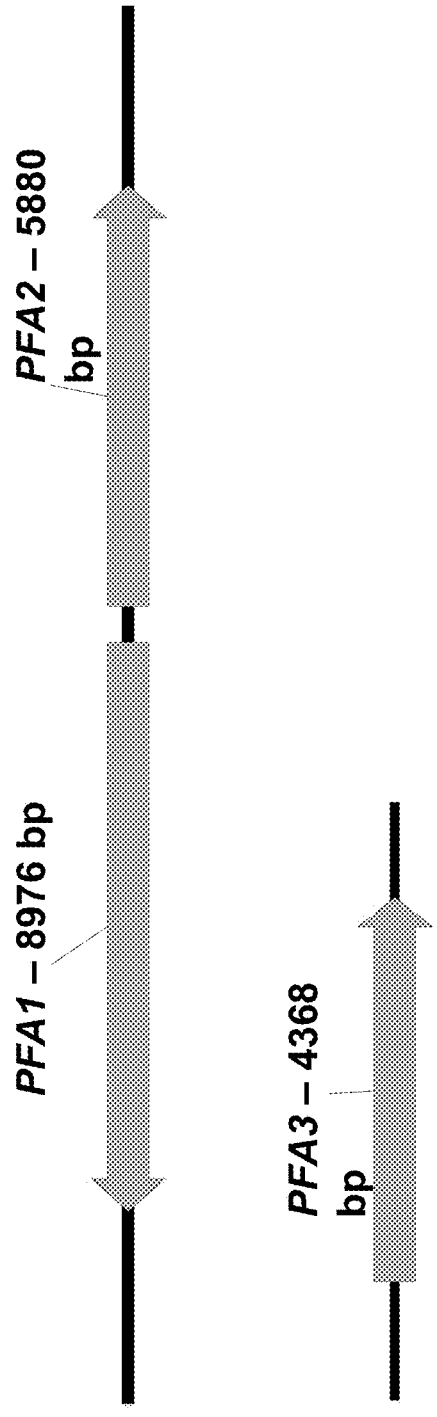
Figure 2. Thraustochytrium sp. ATCC PTA-10212 Gene architecture

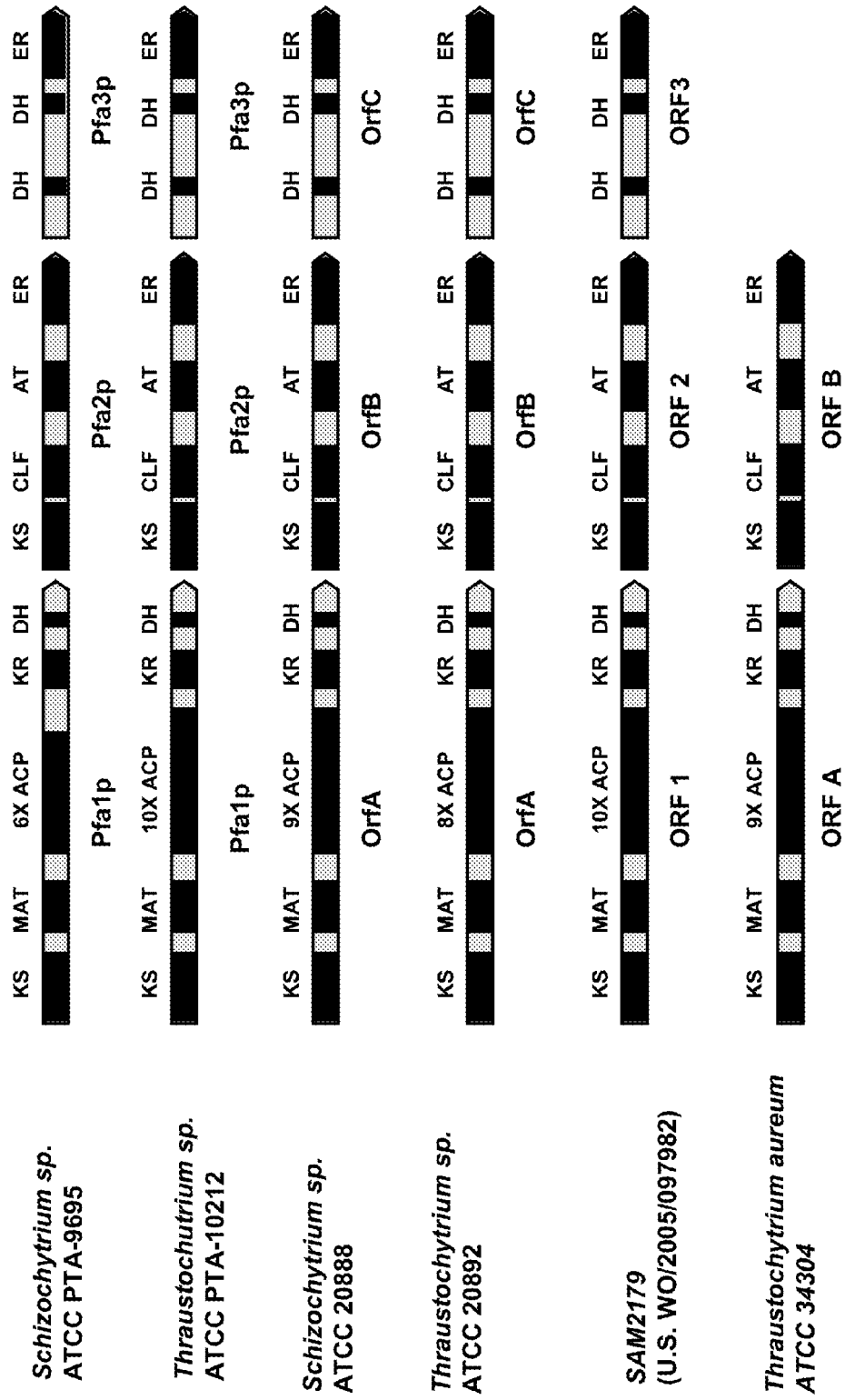
Figure 3. Domain architecture:

FIG. 4

```
                              1                                                  50
Sch. sp. 9695  Pfalp    (1)  --------------------------------------------------
    Thr. aureum ORF1    (1)  RKCIRPSLGHHWAIIGVLGRALRIVRPIRYEATNLRRLPRSGWLVALGLF
Sch. sp. 20888 OrfA     (1)  --------------------------------------------------
Thr. sp. 10212 Pfalp    (1)  --------------------------------------------------
Thr. sp. 20892 OrfA     (1)  --------------------------------------------------
                              51                                                100
Sch. sp. 9695  Pfalp    (1)  -------------------------------------------------M
    Thr. aureum ORF1   (51)  CDLSSCAGKLDLQTRDTAKDPCCKRKWSASRAPPRFRAEADKASNEMETK
Sch. sp. 20888 OrfA     (1)  ----------------------------------------MAARLQEQKGGEM
Thr. sp. 10212 Pfalp    (1)  ------------------------------------------------ME
Thr. sp. 20892 OrfA     (1)  ---------------------------------------------MKDME
                              101                                               150
Sch. sp. 9695  Pfalp    (2)  DTR AI G SA LPSG NV ESW IR G CL DLP DR D TAY  E
    Thr. aureum ORF1  (101)  DDR AI G SA LP G SV ESW IR G CLQDLP DR D TAY DPN
Sch. sp. 20888 OrfA    (14)  ETR AI G SA LP GTTV ESW TIPAG CL DLPED D TAY DPV
Thr. sp. 10212 Pfalp    (3)  DQR AI G SA LPSG NV ESW IR G NCL DLP DR D TAY  PT
Thr. sp. 20892 OrfA    (6)   DRR AI G SA HLP GTDV ESWQ IR G  CL DLP DR  TAY EN
                              151                                               200
Sch. sp. 9695  Pfalp   (52)  K  KDK YCKRGGF IP Y  D REFGLNM QMEDSDANQT  LLKVK AL
    Thr. aureum ORF1  (151)  K  KDK YCKRGGF IP Y  D REFGLNM QMEDSDANQT  LLKVK AL
Sch. sp. 20888 OrfA    (64)  K  KDK YCKRGGF IP Y  D REFGLNM QMEDSDANQT  LLKVK AL
Thr. sp. 10212 Pfalp   (53)  KGVKDK YCKRGGF IP Y  D REFGLNM LQMEDSDANQT  LLKVK AL
Thr. sp. 20892 OrfA    (56)  KA KDK YCKRGGF IPNY  DPREFGLNM QMEDSDANQT  LLKVKQAL
                              201                                               250
Sch. sp. 9695  Pfalp  (102)  TDAN PA  SGKKNIGCVLGIGGGQK SHEFYSRLNYVVV KVLRKM  P
    Thr. aureum ORF1  (201)   AG  P  KKKNIGCVLGIGGGQK SHEFYSRLNYVVV KVLRKMN P
Sch. sp. 20888 OrfA   (114)  QDAG   LG KKKNIGCVLGIGGGQK SHEFYSRLNYVVV RVLRKM  P
Thr. sp. 10212 Pfalp  (103)   DAN PA  N KKNIGCVLGIGGGQK SHEFYSRLNYVVV KVLRKM  P
Thr. sp. 20892 OrfA   (106)   DAS  P  KKNIGCVLGIGGGQK SHEFYSRLNYVVV RVLRKM  P
                              251                                               300
Sch. sp. 9695  Pfalp  (152)    VAAAV  KA SFPEWRLDSFPGFLGNVTAGRC N  PN  GKNCVVDA
    Thr. aureum ORF1  (251)   VV AAV  YKA FPEWRLDSFPGFLGNVTAGRC VRNM GKNCVVDA
Sch. sp. 20888 OrfA   (164)    VKVAV  KA FPEWRLDSFPGFLGNVTAGR  N PN  GMNCVVDA
Thr. sp. 10212 Pfalp  (153)    V TAV  KA FPEWRLDSFPGFLGNVTAGRC N PN  GMNCVVDA
Thr. sp. 20892 OrfA   (156)   A V EAV  KA FPEWRLDSFPGFLGNVTAGRC N PN  GMNCVVDA
                              301                                               350
Sch. sp. 9695  Pfalp  (202)  ACASSLIA KVA  ELL GDCDAM  GATCTDN  GMYMAFSKTPVFSTD
    Thr. aureum ORF1  (301)  ACASSLIA KVA  ELL GDCDTM  GATCTDN  GMYMAFSKTPVFSTD
Sch. sp. 20888 OrfA   (214)  ACASSLIA KVA  ELL GDCDMR TGATCTDN  GMYMAFSKTPVFSTD
Thr. sp. 10212 Pfalp  (203)  ACASSLIA KVA  ELL GDCDAM  GATCTDN  GMYMAFSKTPVFSTD
Thr. sp. 20892 OrfA   (206)  ACASSLIA KVA  ELLFGDCDTM  GATCTDN  GMYMAFSKTPVFSTD
                              351                                               400
Sch. sp. 9695  Pfalp  (252)   S  AYDAATK GMLIGEGSAM VLKRYADAVRDGD  HAV  GC SSSDG
    Thr. aureum ORF1  (351)  QS  AYDA TK GMLIGEGSAM VLKRYADAVRDGD  HAV  GC SSSDG
Sch. sp. 20888 OrfA   (264)   S  AYD  TK GMLIGEGSAM VLKRYADAVRDGD  HAV  GC SSSDG
Thr. sp. 10212 Pfalp  (253)  QSCLAYD  TK GMLIGEGSAMFVLKRYADAVRDGD  HAV  GC SSSDG
Thr. sp. 20892 OrfA   (256)   S  AYD  TK GMLIGEGSAMFVLKRYADAVRDGD  HAV  GC SSSDG
                              401                                               450
Sch. sp. 9695  Pfalp  (302)  KA GIY PT SGQEEA  RAY RAN  P T LVEGHGTGTPVGD IELT
    Thr. aureum ORF1  (401)  KA GIYAPT SGQEEA  RAY RA  VP T LVEGHGTGTPVGD IELT
Sch. sp. 20888 OrfA   (314)  KA GIY PT SGQEEA  RAYN AC VSP T LVEGHGTGTPVGD IELT
Thr. sp. 10212 Pfalp  (303)  KA GIY PT SGQEEA LRAYPRA VSP T LVEGHGTGTPVGD IELT
Thr. sp. 20892 OrfA   (306)  KA GIY PT SGQEEA  RAY RA VCP T GLVEGHGTGTPVGD IELT
                              451                                               500
Sch. sp. 9695  Pfalp  (352)  ALSN  S A  SANGGGAEEAEQ AVGSIKS IGHLK VAGLAG   K  A
    Thr. aureum ORF1  (451)  AL N  F  AANKGR------  ET AVGSIKS IGHLK VAGFAG KY  A
Sch. sp. 20888 OrfA   (364)  AL N  F  A EG-----NTEK AVGSIKS IGHLK VAGLAG    K  A
Thr. sp. 10212 Pfalp  (353)  AL N  F  A  PG-----H EE AVGSIKS IGHLK VAGCAG    K  A
Thr. sp. 20892 OrfA   (356)  AL N  F  A  SK------ EQ AVGSIKS IGHLK VAGFAG     KA
```

FIG. 4 (cont'd)

```
                                501                                              550
Sch. sp. 9695 Pfa1p      (402) LKHKTLP  INV KPFS VD     Q PLY N  NRFW  PV PRRAG
   Thr. aureum ORF1      (495) LKHKTLP  INVHDPFAL D      LY N NPFW A   PRRAG
Sch. sp. 20888 OrfA      (409) LKHKTLPG INV  PPNL N      LY N NRPW PP   RRAG
Thr. sp. 10212 Pfa1p     (398) LKHKTLP  INV  PPNLVD  VFS  LY N NRPWI K   PRRAG
Thr. sp. 20892 OrfA      (400) LKHKTLPG INV  PPL D  Q    LY NKTNRPW QNK PRRAG
                                551                                              600
Sch. sp. 9695 Pfa1p      (452) SSFGFGGANYHAVLEE EPE DSAYRYNN  VAL  GDV TLA TVR
   Thr. aureum ORF1      (545) SSFGFGGANYHAVLEEAEPE A YR NQ   L  AS A  LA
Sch. sp. 20888 OrfA      (459) SSFGFGGANYHAVLEEAEPE TTAYR NKR   L MAA P LQ
Thr. sp. 10212 Pfa1p     (448) SSFGFGGANYHAVLEE PEQT   NVSA   L AVNAN LQK  D
Thr. sp. 20892 OrfA      (450) SSFGFGGANYHAVLEE PE EK YR NT GH  KL  AP VE LKV ND
                                601                                              650
Sch. sp. 9695 Pfa1p      (502) K ALAT EQ  ARVVK A   YH FL EC    PQA  R  GL V DL
   Thr. aureum ORF1      (595)  ADA Q   SP-EASKHA  R IVAFH A     GYP G R G   GSA
Sch. sp. 20888 OrfA      (509)  KEFE   K NETVK TA  KCV FG Q  FP   TN R GI V DA
Thr. sp. 10212 Pfa1p     (498)  KL KE  R KCVNTK T    FS KFQ S     P Q  R CFA  SI
Thr. sp. 20892 OrfA      (500)  AE TI   AKTHK V K CGY FI E Q Q  CPPENPR   TLP
                                651                                              700
Sch. sp. 9695 Pfa1p      (552) S L    E   LAG  ATE T SVAT EAAFRVRG ATE NVAAL
   Thr. aureum ORF1      (644) A T    R  S  LKQSSATLE  T L   -- VTYRS A HTP  VAAL
Sch. sp. 20888 OrfA      (559) EDAC  T R IC QFAK V KEA R P   SVSFRAK IATN-  VAAL
Thr. sp. 10212 Pfa1p     (548) EDT    S  IVN FQK I TTS A P   - IFRST L NDNK VAAL
Thr. sp. 20892 OrfA      (550) T N I ALK ILAQLDAKPDAKKWDLPHKK FGATF SSSVK  VAAL
                                701                                              750
Sch. sp. 9695 Pfa1p      (602) GQG QY  MF  VAM WP FRE   A   RAQR RE -- PA   SSV
   Thr. aureum ORF1      (692) GQG QY  MF  VAM WP FRS  QEM AAQVTAA P---- P  SEV
Sch. sp. 20888 OrfA      (607) GQG QY  M   VAM WPQFRQ    AA SK A SD DFE  SQV
Thr. sp. 10212 Pfa1p     (597) GQG QY  MEN VAM WPQFRLC NDM KAQE  IN-D SV   SQV
Thr. sp. 20892 OrfA      (600) GQ TQ LNM  VAM WP FRD  V M EAQT  FEG--QVEF SKV
                                751                                              800
Sch. sp. 9695 Pfa1p      (650) R   DE F  HK E  QIR SQ A    G  T   F AAGL  S A GHS
   Thr. aureum ORF1      (738) R   A    A    INSQ AL A  AGA T   QAGL  H  GHS
Sch. sp. 20888 OrfA      (657) R  YERE   NP K    TA SQ    A G  T F EAG TP   AGHS
Thr. sp. 10212 Pfa1p     (646) R   RESPL  KF   K P SQT  A S  GL   DAG  FA   GHS
Thr. sp. 20892 OrfA      (648) RER  SES    GNEL   T E SQ    AA G F  F AAG KF M GHS
                                801                                              850
Sch. sp. 9695 Pfa1p      (700) LGEF AL AAGS  R A   DIVCARA  MS FTAQAS  SG      AK
   Thr. aureum ORF1      (788) LGEF AL AAGCAS     LVCSRA  MQ VPQG---------------
Sch. sp. 20888 OrfA      (707) LGEF AL AAGC     LVCRRA  IMGGKDAP-A PK C      N
Thr. sp. 10212 Pfa1p     (696) LGEF AL AAGL    F LVCNRAM MR APK--K AD        N
Thr. sp. 20892 OrfA      (698) LGEF AL AAGS SR    LVCKRAK MANASDG------      D
                                851                                              900
Sch. sp. 9695 Pfa1p      (750)  DQ S GG P    ANSNS  Q VIT  AE  A A D  RCSGN R  L
   Thr. aureum ORF1      (823) -----DG---A   NCNS   QVV I DKT  R   LAGLG- R
Sch. sp. 20888 OrfA      (756)  EN K Q- AN   NSNS Q VITG VE  Q    LQKE - FR  L
Thr. sp. 10212 Pfa1p     (744)  SS K S- P    NNNS   QVITGANS  Q    LKTQG-FR  L
Thr. sp. 20892 OrfA      (742)  RL TPQ-NS   NFKSA QVVI G VQ  KE   KLLISKG-FR  L
                                901                                              950
Sch. sp. 9695 Pfa1p      (800)   C AFHSP MRG  Q FA    QAP  APA ARFYSNVTG AAVTSPA
   Thr. aureum ORF1      (863)   C AFHSP MTA QA  PQ   DS  K  TPTNGARLYNNV KTCRSLG
Sch. sp. 20888 OrfA      (804)   S AFHSP CMEN SSA KDV  K SFRTPK  E--TKLFSNVSGETYPT
Thr. sp. 10212 Pfa1p     (792)   C AFHSP MEN  KQ QK   A KFNKP T S--SPKIF NVTGGVFT
Thr. sp. 20892 OrfA      (790) KCQ AFHSPLMGP  D EK  I ETCT  PPKNVK-FFCNV  KESP---N
                                951                                             1000
Sch. sp. 9695 Pfa1p      (850) V TNLG HMTSPV F QQ  AM AGAR F  FGP QVL  LFKET G A
   Thr. aureum ORF1      (913) L DC G HMTSPVLFQAD  L M AGAR F  FG  QVL  L GL  A K
Sch. sp. 20888 OrfA      (852) A EMLTQ HMTS VKF T Q   M QAGA F  EFG  QVL  L SET K D
Thr. sp. 10212 Pfa1p     (840) P TALS  HMTS V F T Q  M  AGAR F  FGP QVL L NE  FPGD
Thr. sp. 20892 OrfA      (836) P QT KS HMTS V FEE    M DAGAR F  FG  QVL  L AE FP--
```

FIG. 4 (cont'd)

```
                                1001                                            1050
Sch. sp. 9695  Pfa1p    (900)   GD....VN.DS...SDT.LRQAA.T...G.PLKDF...Q.P.....EP
    Thr. aureum ORF1    (963)   SDF....VNS.S...DSD..LKEAAAK..VLG.PLANE.PW...R..RE
Sch. sp. 20888 OrfA     (902)   P......VN..SGTDSD..LRDAA.Q..V.GNLQGE...AP...P.QA
Thr. sp. 10212 Pfa1p    (890)   T......VN.S...DSD..LRQAA.Q..V.G.ALTDF..W.K.P..KE
Thr. sp. 20892 OrfA     (884)   -.CTA..VN..S.GDSD..LRLAA.KF.V.GAALSTE.PW.YRKPQD.LI
                                1051                                            1100
Sch. sp. 9695  Pfa1p    (950)   V....T.L..SAATYVSAKT.RQR.A....GYT..GAT----------AV
    Thr. aureum ORF1    (1013)  CP.S.T.L.LSAATYVSNKT.AAR......EDNCDF.S.FASG--------P
Sch. sp. 20888 OrfA     (952)   I....T.L..SAATYVSDKTKKVR.AA....C...Y.KGAAPLIKAPEPV
Thr. sp. 10212 Pfa1p    (940)   FP...T.LT.SAATYVSKKT.QER.......T..C.Q-----------R
Thr. sp. 20892 OrfA     (933)   R.P..A.V..SAATYV.PKT.AEKK.A..DI.L..ITPR----------D
                                1101                                            1150
Sch. sp. 9695  Pfa1p    (990)   KEVDTANE...V.QA..L....AE.STA.QA..K.ELERT.QDLE.K
    Thr. aureum ORF1    (1055)  ASQEME...IAN..AE.EAA..LDT.KTQLARK.VQDPT.DRQRDMI..H
Sch. sp. 20888 OrfA     (1002)  .DEAAK.A...Q.E..A...DD..KRA.AE...K..A.EEAKT..A.
Thr. sp. 10212 Pfa1p    (979)   .ENTNTG.L.....Q..KENE.VRVQAL.TQ.C.D.QNT.AE.QK.QA.
Thr. sp. 20892 OrfA     (973)   SMVSIG.IAQE...TAK.PLETE.RRLNKELEHLKRE..A..AS.KS.
                                1151                                            1200
Sch. sp. 9695  Pfa1p    (1040)  ----------------------------------.QQQ.QE---------
    Thr. aureum ORF1    (1105)  R.TL.AMVKEFEALA.---------GSPQ..P..P.VDTAVEDVPF.DK.
Sch. sp. 20888 OrfA     (1052)  -.KP.VDT....E....KS..A.L.GYG..DA..S.QQQ.QQQTAP.PVK
Thr. sp. 10212 Pfa1p    (1029)  K.SN.ASD..A..N...LA..E.L.TGK..D..SFSKG.VASPATVRV.
Thr. sp. 20892 OrfA     (1023)  ----.KER..S...Q..QN..Q.Y.DLRV.P..VRSVAVDNTAPY.DQ.
                                1201                                            1250
Sch. sp. 9695  Pfa1p    (1047)  ------------------------------K-GEN--S--------
    Thr. aureum ORF1    (1146)  .T.PPQ----------VT.API.E.....A........V..E....A.
Sch. sp. 20888 OrfA     (1101)  .AAPAAP---VASAPAP..SNEL.E..T.V...............A.
Thr. sp. 10212 Pfa1p    (1079)  .A..VQAA---APVQVSA..DS.L...Q...................
Thr. sp. 20892 OrfA     (1069)  .T.ASERSASPLFEKRS..SS.R.AE..AA..S...D......SK.M.
                                1251                                            1300
Sch. sp. 9695  Pfa1p    (1052)  ----------------S..AAE.LR.HK.L.Q.MLQDC.EQAVPV.T
    Thr. aureum ORF1    (1187)  L..A.............A...Q.G.V......................
Sch. sp. 20888 OrfA     (1148)  ........................AM.NV..K.D..ALSR...G....N..E.
Thr. sp. 10212 Pfa1p    (1126)  ........................Q.NV..A...................
Thr. sp. 20892 OrfA     (1119)  ....................TL.SV.VS..V..L.R.......ML.
                                1301                                            1350
Sch. sp. 9695  Pfa1p    (1084)  .VPTPT...PT.S.V.GN-----------.K.TRG..DLQ...L.AET.
    Thr. aureum ORF1    (1237)  .QAT.....PM.Q.Q.SAPSPSPTASVLPK.V.LP...DP.KL..AEA.
Sch. sp. 20888 OrfA     (1198)  .SSAP..AAA.PAP.KA-----------....AP..SNE.LF.AKT.
Thr. sp. 10212 Pfa1p    (1176)  ..GQP..E.VQV.A.T.QVV-----------.VQ.S.P.DS..LL..AEQ.
Thr. sp. 20892 OrfA     (1169)  .PQGQTL.AE..IRQPPVSEPAVPTS----S...I.N.SS.R.L.EAEAA
                                1351                                            1400
Sch. sp. 9695  Pfa1p    (1123)  V.AU.A.KT.Y.A....M.L.AE..G..S.KR..E.I....V..LGV.E.
    Thr. aureum ORF1    (1287)  V..VLA.KTGY.V....E.DMLL.AE.G.DS.KR.EI.AV.Q..LGVE..D
Sch. sp. 20888 OrfA     (1237)  V..VLA.KT.GY........DM.L.AE..G.DS.KR.EI.VQ.M.NV.E..
Thr. sp. 10212 Pfa1p    (1215)  V..VLA.KT.GY.E..ELDM.LE.ELG.DS.KR.EII..VQ..LSVE..D
Thr. sp. 20892 OrfA     (1215)  V.GVLADKT.GY..S..EMDM.L.E..G.DS.KR.EI.L.VQTL.SVEVS.
                                1401                                            1450
Sch. sp. 9695  Pfa1p    (1173)  VDA.SRT.TVG.V..AMK.E..V----------------
    Thr. aureum ORF1    (1337)  VDALSRT.TVG.V..AMK.A...E.Q.TS..A.V.QPQASAPSPSATTASVL
Sch. sp. 20888 OrfA     (1287)  VDALSRT.TVG.V..NARK.E.....APA.A.A.PGPAAA.---------
Thr. sp. 10212 Pfa1p    (1265)  VDALSRT.TVG.V..AMK.E.....QPA..VQV.APTQVV.---------
Thr. sp. 20892 OrfA     (1265)  VDALSRT.TVG.V..AMKLE....PQGQTLT.EE.IRQPPV.EPAVPTS---
                                1451                                            1500
Sch. sp. 9695  Pfa1p    (1198)  ----------------------------------------
    Thr. aureum ORF1    (1387)  .KPV..PTSADP.K....A..........V...A...L.A....
Sch. sp. 20888 OrfA     (1327)  .AP..APA.SNEL.E..A.T..........S..............
Thr. sp. 10212 Pfa1p    (1305)  .VQ..P--.DS.L..Q........................L.....
Thr. sp. 20892 OrfA     (1312)  -S-..IAN.SS.R.AE.AA..S..AD..S.......SK.M..............
```

FIG. 4 (cont'd)

```
                              1501                                              1550
Sch. sp. 9695 Pfalp   (1198)  ----------------------------------------G####-P#V
     Thr. aureum ORF1 (1437)  #############A##Q##G##########################Q#TS#
Sch. sp. 20888 OrfA   (1377)  ##########L##V##M#N######D#L#PT############L#G###P##
Thr. sp. 10212 Pfalp  (1353)  ########L###Q#S####A##V########T##V########E#SG#QPA#
Thr. sp. 20892 OrfA   (1360)  ###############TL#S##VS#####################L##GPQ#QTL
                              1551                                              1600
Sch. sp. 9695 Pfalp   (1205)  P#APAASA#PT#AAST#PS#-----DLQ####AET#V##AVLA##KTGY#A
     Thr. aureum ORF1 (1487)  A##V#QPQI####TP####P#-----ADP#KL##AEA#V##VLA##KTGY#V
Sch. sp. 20888 OrfA   (1427)  A#A#PAPA#A##APA#P#P#-----##S##LE##AET#V##VLA##KTGY#
Thr. sp. 10212 Pfalp  (1403)  VQV#APTQI####VQ####P--------##S####APQ#V##VLA##KT#Y#
Thr. sp. 20892 OrfA   (1410)  T#P#IRQPP####EPA#PT#S#SSIAN#L##RL##EAEAAV#SVLAD#TGY#
                              1601                                              1650
Sch. sp. 9695 Pfalp   (1250)  ####EMDML##L##AELG##DS#KR#EI####VQ##LGVE###DVDALSPT#TVG#V
     Thr. aureum ORF1 (1532)  ####T#DML1##AELG#DS#KR##EI##AVQ###LGVE###DVDALSRT#TVG#V
Sch. sp. 20888 OrfA   (1472)  ####T#M#L##ELG#DS#KR#EI####VQMENVE###DVDALSRT#TVG#V
Thr. sp. 10212 Pfalp  (1446)  ####ELDM####L##ELG##DS#KP#EI####VQ##LSVE###DVDALSRT#TVG#V
Thr. sp. 20892 OrfA   (1460)  S##EMDM####L##ELG##DS#RR#EI####VQTLSVEVSDVDALSRT#TVG#V
                              1651                                              1700
Sch. sp. 9695 Pfalp   (1300)  ####AMK##E#V####G#AP----#P#VPS####S##PT#A#T#P##DLQ#
     Thr. aureum ORF1 (1582)  ####AMK#E####Q#TS#PASVAQPQ#S#####T##VL#K#V##PT#ADP#K
Sch. sp. 20888 OrfA   (1522)  ####AKK#AE#####P#PA-----#A#P##A##P#PAA##A###PAP#S#E#
Thr. sp. 10212 Pfalp  (1496)  ####AMK#E#S##QP-----------T##VQV#APTQIV##VQVS#P#D##
Thr. sp. 20892 OrfA   (1510)  ####AMKLE####PQ#-Q---TLT#E##IRQP#V#EP#VPT#S####I#N#S##R
                              1701                                              1750
Sch. sp. 9695 Pfalp   (1346)  L##AET#V##AVLA##KTGY#A####DM##L#AELG##DS#KR##EI##SVQ#
     Thr. aureum ORF1 (1632)  LA##AEA#VM#VLA##KTGY#V####EDML#L##AELG##DS#KR##EIL#AVQ##
Sch. sp. 20888 OrfA   (1568)  LE#AET#VM#VLA##KTGY####EDM##LE##ELG#DS#KR#EI##SVQM
Thr. sp. 10212 Pfalp  (1535)  LA##AEQ#V##VLA##KTGY####FLDN###L##ELG##DS#KR#EI##SVQ##
Thr. sp. 20892 OrfA   (1556)  L##EAEAAV#SVLAD#TGY##S##EMDM##L##ELG##DS#KR#EI###VQTL
                              1751                                              1800
Sch. sp. 9695 Pfalp   (1396)  LGVE##DVDALSRT##TVG#V##AMK#E#V#A#GGSAP#P#VP#APA##SA#
     Thr. aureum ORF1 (1682)  LGVE##DVDALSRT##TVG#V##AMK#E#####Q#T-----##A#M#QPQI#
Sch. sp. 20888 OrfA   (1618)  LNVE##DVDALSRT##T#TVG#V##AMK#AE##SS#-----##A#A#P#PA#
Thr. sp. 10212 Pfalp  (1585)  LSVE##DVDALSRT##T#TVG#V##AMK#E#SGQ-----P##V#VQV#APTQI
Thr. sp. 20892 OrfA   (1606)  LSVEVSDVDALSRT##TVG#V##AMKLE##PQGQTLT##EPIHQPPV#EP#
                              1801                                              1850
Sch. sp. 9695 Pfalp   (1446)  PT##A#T#PS##DLQ####AET#V##AVLA##KTGY#A#####DM##L#AELG
     Thr. aureum ORF1 (1727)  ####TPL##SP#ADPKL##AEA#V##VLA##KTGY#V#####DMLL##AELG
Sch. sp. 20888 OrfA   (1663)  A###P##AP#VSNE##LE#AET#V##VLA##KTGY##E####DM##L##ELG
Thr. sp. 10212 Pfalp  (1630)  ###VQ##P--#DS##LA#AEQ#V#EVLA##KTGY#E####ELDM##L##ELG
Thr. sp. 20892 OrfA   (1656)  #PT#S####IAN#SS#FL#EAEAAV#SVLAD#TGY##S##EMDM##L##ELG
                              1851                                              1900
Sch. sp. 9695 Pfalp   (1496)  #DS#KR#EI####VQR#LGVE###DVDALSRT#TVG#V##AMK#E#V####G
     Thr. aureum ORF1 (1777)  #DS#KR#EI##AVQ##LGVE###DVDALSRT#TVG#V##AMK#AE####Q#TS
Sch. sp. 20888 OrfA   (1713)  #DS#KR#EI####VQ#MLNVE###DVDALSRT#TVG#V##AMK#E#####P
Thr. sp. 10212 Pfalp  (1678)  #DS#KR#EI####VQ#LSVE###DVDALSRT#TVG#V##AMK#E#IS##QPA
Thr. sp. 20892 OrfA   (1706)  #DS#KR#EI####VQTLLSVEVSDVDALSRT#TVG#V##AMKME###PQ#Q
                              1901                                              1950
Sch. sp. 9695 Pfalp   (1546)  #AP#P#V#-----------------------------------------
     Thr. aureum ORF1 (1827)  #A##V#Q#-----------------------------------------
Sch. sp. 20888 OrfA   (1763)  #A#A#P-----APAAAAPAVSNELLEKAETVVMEVLAAKTGYETDMIES
Thr. sp. 10212 Pfalp  (1728)  ##VQV#A#TQIVAPVQVSAPVDSGLLAKAEQVVLEVLASKTGYETELIEL
Thr. sp. 20892 OrfA   (1756)  TLT#E#IR-----------------------------------------
                              1951                                              2000
Sch. sp. 9695 Pfalp   (1554)  -----------------------------------------
     Thr. aureum ORF1 (1835)  --------------------------------QASAP-----
Sch. sp. 20888 OrfA   (1808)  DMELETELGIDSIKRVEILSEVQAMLNVEAKDVDALSRTRTVGEVVDAMK
Thr. sp. 10212 Pfalp  (1778)  DMELETELGIDSIKRVEILSEVQAQLNVEAKDVDALSRTRTVGEVIDAMK
Thr. sp. 20892 OrfA   (1764)  -----------------------------------------
```

FIG. 4 (cont'd)

```
                          2001                                              2050
Sch. sp.  9695 Pfa1p (1554) --------------SxxAxSxxPTPxAxTxPxxDLQxxLxxAETxVxAVLAx
Thr. aureum ORF1     (1840) --------------xSxTxxAPVTxLxxPxxDPxKLxxAEAxxxVLAx
Sch. sp. 20888 OrfA  (1858) AEIAGSSAPAPAAxAPxPxxAAPxxxxAPxxSxExLExAETxVxxVLAx
Thr. sp. 10212 Pfa1p (1828) AEIAGGQP--AAPVQVxAPxPVVxVQVSTPxDxxxxAxQxVxxVxAC
Thr. sp. 20892 OrfA  (1764) --------------QPxVxEPxVPTxSxxIxNxSxxRLxEAEAAVxSVLAD
                          2051                                              2100
Sch. sp.  9695 Pfa1p (1592) KTGYxAxxxxDMxLxAELGxDSxKxxEIxxxVQxxLGVExxDVDALSRT
Thr. aureum ORF1     (1877) KTGYxVxxxxDMLLxAELGxDSxKRxEIxxxAVQxxLGVExxDVDALSRT
Sch. sp. 20888 OrfA  (1908) KTGYxxxxExMxxxExLGxDSxxxxEIxxxVQxxMLNVExxDVDALSRT
Thr. sp. 10212 Pfa1p (1876) KTGYxxxxELDMLxxELGxDSxKRxEIxxxVQRxLSVExxDVDALSRT
Thr. sp. 20892 OrfA  (1802) KTGYxxGxxEMxMxLxxELGxDSxKRxEIxxxVQALLSVEVSDVDALSRT
                          2101                                              2150
Sch. sp.  9695 Pfa1p (1642) xTVGxVxxAMKxExVxxGGSAPxAxVPSxFxAxA------APTxxTxP
Thr. aureum ORF1     (1927) xTVGxVxxAMKxExxQxTSAPAxVxQPQxxPxPSATASVLPKxVxxP
Sch. sp. 20888 OrfA  (1958) xTVGxVxxAMKxExSxQ-----xPxPAAxxP-----------xxxxAP
Thr. sp. 10212 Pfa1p (1926) xTVGxVxxAMKxExSxQ-----PTxPVQVxxxPxQ------VVxVKVST
Thr. sp. 20892 OrfA  (1852) xTVGxVxxAMKMExxxPQG----QTLTAExIREPPVSEPAVPTxSxxIx
                          2151                                              2200
Sch. sp.  9695 Pfa1p (1686) xDLQxxLxxAETxVxAVLAxKTGYxAxxxxDMxLxAELGxDSxKRxEIx
Thr. aureum ORF1     (1977) xDPxKLxxAEAxVxxxVLAxKTGYxVxxxxDMLLxAELGxDSxKRxEIx
Sch. sp. 20888 OrfA  (1992) xSNExxLExAETxVxxxLAxKTGYxxxxxxDMxLxEELGxDSxKRxEIx
Thr. sp. 10212 Pfa1p (1965) PxDSxxLxxAEQxVxxVLAxKTGIxxxxELDMxLxxELGxDSxKRxEIx
Thr. sp. 20892 OrfA  (1898) NxSSxRLxEAEAAVxSVLADKTGYxxSxxMDMxLxxxELGxDSxKRxEIx
                          2201                                              2250
Sch. sp.  9695 Pfa1p (1736) xxVQxxLGVExxDVDALSRTxTVGxVxxAMKxExVxxGGSxDxxPSxFx
Thr. aureum ORF1     (2027) xAVQxxLGVExxDVDALSRTxTVGxVxxAMKxExxxGPNDxQxxS----
Sch. sp. 20888 OrfA  (2042) xxVQxMLNVExxDVDALSRTxTVGxVxxAMKxExxxGxAPAPAxxAPxSx
Thr. sp. 10212 Pfa1p (2015) xxVQxxINVExxDVDALSRTxTVGxVxxAMKxExxxDQPAPxVVPVQxKx
Thr. sp. 20892 OrfA  (1948) xxVQxTLLSVEVSxDVDALSRTxTVGxVxxAMKLExExxSIETLNCTEVEH
                          2251                                              2300
Sch. sp.  9695 Pfa1p (1786) LLPT--------------------------------------------
Thr. aureum ORF1     (2073) -------------------------------------------------
Sch. sp. 20888 OrfA  (2092) GAAP--------------------------------------------
Thr. sp. 10212 Pfa1p (2065) GVANPALLAKAEQVVLEVLASKTGYETELIELDMELETELGIDSIKRVEI
Thr. sp. 20892 OrfA  (1998) TSYKS-------------------------------------------
                          2301                                              2350
Sch. sp.  9695 Pfa1p (1790) -------------------------------------------------
Thr. aureum ORF1     (2073) ----------------------------------G--------------
Sch. sp. 20888 OrfA  (2096) -------------------------------------------------
Thr. sp. 10212 Pfa1p (2115) LSEVQAELSVEAKDVDALSRTRTGEVIDAMKAEIAGSAVTVATLDDSTI
Thr. sp. 20892 OrfA  (2003) -------------------------------------------------
                          2351                                              2400
Sch. sp.  9695 Pfa1p (1790) ----------------xxxxxxxxxTPVxTTxPLxxxxxAEGGAxx
Thr. aureum ORF1     (2074) ---------------HxxxxxGCxxxCSxSxxxExAxCxxLAxxRPMxxx
Sch. sp. 20888 OrfA  (2096) ---------AVKIDSxxxxxxxxxMExKxDxRxxDxLxxRFENRx
Thr. sp. 10212 Pfa1p (2165) MEETDDEDEDFILYDHxxxxCxxxxSxxxSxKSxPxADKLxxxNIAxxR
Thr. sp. 20892 OrfA  (2003) ---------------xKxxGCxNxDTPxKxxQxSLxKxKSTVSHxxRx
                          2401                                              2450
Sch. sp.  9695 Pfa1p (1824) xxxVxxxALxxxxVSSxGDRxVxxQVQSSxACxPR-STTHxLxTxAxRx
Thr. aureum ORF1     (2109) xxVSxGxALPAxxLASRxGSCxVxxxTAxExDQxVR---STxHxDxEGWG
Sch. sp. 20888 OrfA  (2136) xxxxGxELLxxVxVxGACxVxxxExLQLAQxxGAAAIxHxLAKxLx
Thr. sp. 10212 Pfa1p (2215) xVxCxxKIxxEIAxAxxERxVAxxSxQxLVxx--FVCxSFTxGNTE
Thr. sp. 20892 OrfA  (2037) xVxxCxPIxExCxIxGGNIVxxxQxKPAGPx-------xExPxLx
                          2451                                              2500
Sch. sp.  9695 Pfa1p (1873) xxxQAxxTxxxQxGKxxGxxFxG-DDxVQAxxxxxxxAKxxxTxxLS
Thr. aureum ORF1     (2156) xDxVxxxExxRxxGVPxGVxVLERASETARDxLxxxxLAKxxSSKxxx
Sch. sp. 20888 OrfA  (2186) AExAExxxKEAxQRxAxxxxSxQAERFxPAEILxxxTLxCAKFAxAxLC
Thr. sp. 10212 Pfa1p (2263) xExxMxSxxSxGKxxGxxVxHFDSxxYGMxLxxxxIxAKxxExxLx
Thr. sp. 20892 OrfA  (2080) xFxxIQxxALxRxTxGVPIGxxCxQVSNVSTKAxLCxxLLxAKxxKDLx
```

FIG. 4 (cont'd)

```
                           2501                            2550
Sch. sp.   9695 Pfa1p (1922) EQ████████████████OLG███G--K---STTA█VD█SR███████████
    Thr. aureum ORF1  (2206) QQ███████ACF██V████K██G--█CAKGK█WA██AEI█████████████
Sch. sp.  20888 OrfA  (2236) TA████RPAF██V█R████LGF█-------SQ█T████KR█████████
Thr. sp. 10212 Pfa1p  (2313) DP█KN██████VR█NG█LG█DN---█SVHDQ█IV██CGI█████████████
Thr. sp. 20892 OrfA   (2130) AV█PDS█████VR█N█LGTFENI█DFSKFDL█K██DY██████████LG██
                           2551                            2600
Sch. sp.   9695 Pfa1p (1967) K████LEW█A---V█CR███████AD█DAAQAARC███GE██D███████A
    Thr. aureum ORF1  (2254) K████LEW█H--V█████D██EL█ANEETAAQA█FE█████T█████████K
Sch. sp.  20888 OrfA  (2279) K████LEWSESDV█████████████HPEDAAVA███████A██████IGA
Thr. sp. 10212 Pfa1p  (2361) K████LEW█N--V████D██E█SYSLAAEL█D█████AN█S█RE█████I
Thr. sp. 20892 OrfA   (2180) K████LEWEQ--V█CR███CD█MPLQAA█I█RNE██████P█REV█████DI
                           2601                            2650
Sch. sp.   9695 Pfa1p (2015) ██QRCT██TTKS█T████HQP█S██████LV█GGA█GITP█C███████QP█GG
    Thr. aureum ORF1  (2302) D█K████████RP█GLG███KQA█R█████LV█GGA█GITP█C████S█SG
Sch. sp.  20888 OrfA  (2329) NQQRCTIR█AK█E██ON█QRQ█AKD██████LV█GGA█GITP█C██RE█T█Q█AG
Thr. sp. 10212 Pfa1p  (2409) ██LP██TE█HK██V█G████HAP█KKKDA█LV█GGA█GITP█C██RE█A█KG
Thr. sp. 20892 OrfA   (2228) ██AR██TISTDD█LCGPSKAK██E███LV█GGA█GITPHC██RE█SRSPG
                           2651                            2700
Sch. sp.   9695 Pfa1p (2065) ████████GRSELPTT█P█W█VG█ESG█P████████F█K████AG█AK██
    Thr. aureum ORF1  (2352) ████████GRS-P██████P█W█CG█-EEAN█GT████H█████AG█PK██
Sch. sp.  20888 OrfA  (2379) █K████GRSKVS█S█P█W█CAG█TDE█A██████Q█████AG█GPK██
Thr. sp. 10212 Pfa1p  (2459) ████████GRS-A██████PLW█NGK-SG█D████████F█K█████AG█SK██
Thr. sp. 20892 OrfA   (2278) T███████GRS-E█████P█W█VG█H-YN█D████████KH█████AG-GVK██
                           2701                            2750
Sch. sp.   9695 Pfa1p (2115) ML███KI████V█G█REV█G████EIT█QG█T██YE█CDV██AK█V█F█V█F█
    Thr. aureum ORF1  (2400) ███████████LV█████G█REVLGSS█E█IR█QG████EY█████CD█V█CE██V█A█VDD█
Sch. sp.  20888 OrfA  (2429) ██VTKL████V█G█REV█████IE█LG██████YS█CDVN██ADVAKAVRDA
Thr. sp. 10212 Pfa1p  (2507) KV████L█DKV█GIREV█████NIE█HG██████Y█CDV█████V█AAVQ█
Thr. sp. 20892 OrfA   (2325) ██████████LNR█TG█REV██ES█R███IQEAG█NVEY████CDV█DEN█████VQ█
                           2751                            2800
Sch. sp.   9695 Pfa1p (2165) QQQG██R█████████FHASGV█RD█████████A█FSKV█DTKVGGI███████CV█
    Thr. aureum ORF1  (2450) ██RRV██-A████████HASGV█RD██S█ERLE█A██VV███KVDG█████Q█V█
Sch. sp.  20888 OrfA  (2479) █SQL█A██████████HASGV█RD███EK█LP████████V█KV█████EN███V█
Thr. sp. 10212 Pfa1p  (2557) █KEHLV█████████HASGV█RD█████FN█V█T█KVGI█N█████VN
Thr. sp. 20892 OrfA   (2375) █QKY█CE█████WHASGV█RD████T█████V█T█KV█GI█████████QVN
                           2801                            2850
Sch. sp.   9695 Pfa1p (2215) ██Q██H██████FSSLAG█HGN█GQ█YA█ANE█LNK██AHL██V█H█Q█CA█
    Thr. aureum ORF1  (2499) RPK████H██████FSSLAG█HGNTGQ█VYA█ANE█LNK██FHLETA█G█S█
Sch. sp.  20888 OrfA  (2529) R█N██H████████FSSLAG█HGN█GQ█YA█ANE█LNK██LEL█KD█S---██
Thr. sp. 10212 Pfa1p  (2607) █NF██H██████FSSLAG█HG██GQ█YA█ANE█LNK██FRLG█AYSQ█C█
Thr. sp. 20892 OrfA   (2425) █K█████HF██████FSSLAG█HGNKGQ██YA█ANE█LNK██HTL██F███K█NA█V
                           2851                            2900
Sch. sp.   9695 Pfa1p (2265) ██PG█W██G-GMV█████LN█A██IRKG██████P█Q█GAQ█V█N██████PG██
    Thr. aureum ORF1  (2549) █GFGPW██G-GMVND█L█AHFA██G█Q█TPL█GA█████G█-█PT█
Sch. sp.  20888 OrfA  (2576) ██F█PW██G-GMV███QL███QFMG████PR█GA██V█████G█PAF█
Thr. sp. 10212 Pfa1p  (2657) ██F█PW█G-GMV████L██G█Q█G█Q█TPR█GA██V█████NPS██
Thr. sp. 20892 OrfA   (2475) █DF█PWVGSGMV██ETLE█HFK████QTIPL█GARI█V█Q████E█PQ█S█
                           2901                            2950
Sch. sp.   9695 Pfa1p (2314) █GN█████P██V█S█TEH█████LQ██RQS-D███F█D█HV█████GR████VLPM█████A██
    Thr. aureum ORF1  (2598) █GN█████P██V██N█SVHK█TVR█GG█SA█R█F█S██HT█G██VLPM█████A█GL
Sch. sp.  20888 OrfA  (2625) █GK█RTFSKKVG█D██I██HRK██AK-S█████EDHV█████GR████VLPM█████A█GS
Thr. sp. 10212 Pfa1p  (2706) █GN█████P██S█L█K█A██V█Q█F█P█-L███F█K█RQ█HG█NVLPM█████A███
Thr. sp. 20892 OrfA   (2525) █GN█████FPATK█LQR██NV█TG████P█-EIE████ADHK██C████VLPMMAA████
                           2951                            3000
Sch. sp.   9695 Pfa1p (2363) █AHQ█QS██AG█████████████AQ█FKG██A██N██ADVP█R█ELSRRK████QEDA
    Thr. aureum ORF1  (2648) █AEA█R█████VG███V████████AQ█FQG█V█████ATCE█Q█RRE████STASP---
Sch. sp.  20888 OrfA  (2674) █AETCL█████PG█S███████████AQ█FKG█Y████GDVNCE█Y█T█TPS█APSG----
Thr. sp. 10212 Pfa1p  (2755) █AHLVKNF█AG█H█████████AQ█FSG█V█H███VQAQ█K█TEQ█LD████G---
Thr. sp. 20892 OrfA   (2574) █ASI█E█████PG████Q█████NAQ█FQG█T███NQETKFQ█T█TEEHNS████N---
```

FIG. 4 (cont'd)

```
                              3001                                              3050
Sch. sp. 9695 Pfalp    (2413) GKV  KV VL KSQVN-GKS PAY  T  LS-P P   V T  FD T----
    Thr. aureum ORF1   (2695) ---SEVVL ASLNVFAAGK  PAY  H  LGAS P TGG QL LKDLGVD
Sch. sp. 20888 OrfA    (2720) ---  NV  T KTFSS-GK PAY    LSNQ AP  NATMQPPSL---
Thr. sp. 10212 Pfalp   (2802) ---  KV  V TASNDNGK  PAY    LG-KTS   F L  FS Q---
Thr. sp. 20892 OrfA    (2621) ----  DVLTS GVMLESGK  PAY C  CLNTTQQQ KLSP ILN EVDP
                              3051                                              3100
Sch. sp. 9695 Pfalp    (2458) --PDP CTEHD YDC   FHCK      Q LSA PKQ T   C N    PE
    Thr. aureum ORF1   (2742) ADP  C VGKGA YDG   FHG   Y   E LRC PAELAV  V  SAAQ
Sch. sp. 20888 OrfA    (2763) --D  DPALQGS YDC   FHG  R   D LSC KSQLV  CSA  G DA
Thr. sp. 10212 Pfalp   (2845) --E  N RSADE YDC   FHG L  G TK LNV DTS TTQQTN D  AT
Thr. sp. 20892 OrfA    (2667) -------ACEVNP YDG   FHG LL F QQ LHS TKG V   A   KEA
                              3101                                              3150
Sch. sp. 9695 Pfalp    (2506) Q  Q VVNLSQQ  P QAD  F Q  L V ARM  Q A  L   C  FD
    Thr. aureum ORF1   (2792) D  Q VSRGVL  P   NDTVFQ  L V AEL  D A LPS      S  GQP
Sch. sp. 20888 OrfA    (2811) A  E ATDTDA  P  N   FQ  L VWVERTLGQA  LP S  Q   VQ
Thr. sp. 10212 Pfalp   (2893) E  - GQFADIEPVNP  ADA  F   L V KVRN  N A LP   C   DI
Thr. sp. 20892 OrfA    (2711) I  - GPFIKQTL   PI DD  IRQL L V CKNALG  A L P  R   S FGN
                              3151                                              3200
Sch. sp. 9695 Pfalp    (2556)   P-  AT       LAS SP-LV   C CTVA      G   F      V   K
    Thr. aureum ORF1   (2842) PSE  EV        LDS ASGPL P AKAQ F   RACGA  A    SV  L K
Sch. sp. 20888 OrfA    (2861) PQ-DKP  I    SNQ  G---GH QH HALQF N    G    IDVQ SV AT
Thr. sp. 10212 Pfalp   (2942)   P-  EK    QALGNT---SG  LKSV Y       L   SV
Thr. sp. 20892 OrfA    (2760)   E-  ST  A  FPVGPR-VPK P IKMQ L  Q   SGNT S  E SV  C
                              3201
Sch. sp. 9695 Pfalp    (2604) T  T  -
    Thr. aureum ORF1   (2892) A  S  -
Sch. sp. 20888 OrfA    (2907) S  A  -
Thr. sp. 10212 Pfalp   (2988) K     -
Thr. sp. 20892 OrfA    (2808) E  V  -
```

FIG. 5

```
                           1                                                  50
Sch. sp.  9695 Pfa2p   (1) --------------------------------------------MPCDN
Sch. sp. 20888 OrfB    (1) ------------------------------MAARNVSAAHEMHD K
Thr. sp. 10212 Pfa2p   (1) ------------------------------MVKLSVGDNICH  Q
   Thr. aureum ORF2    (1) QAIGHRAARWSCRSKSKARGHKAQKEMNQGGRNDEGVSVARADPCF T
Thr. sp. 20892 OrfB    (1) ------------------------------MQLPPAHSAD N
                           51                                                100
Sch. sp.  9695 Pfa2p   (7) AVVGMAVQYAGC  Q  FW     RKE   GPISAERLG P  LH  OK
Sch. sp. 20888 OrfB   (19) AVVGMAVQYAGC  T   FW VL  K E  VISDKRLG N RA H KA R
Thr. sp. 10212 Pfa2p  (17) AVVGMAVMYAGCQ QH  FWQ QGKN   SISQNRLG  R  H  K
   Thr. aureum ORF2   (51) AVVGMAVEYACC  Q  AFW     K   ACISDDRLG ARR H A
Thr. sp. 20892 OrfB   (15) AVVGMAVKYAGCD     FWK L  S    SISAARLG NK   H V  R
                           101                                               150
Sch. sp.  9695 Pfa2p  (57) SKY DTFCN  YG  AS   -EH LLADLA RA L  GIN--LDDASTT
Sch. sp. 20888 OrfB   (69) SKY DTFCN TYGT  ENEIDNE  LL NLA QA  TS---------V
Thr. sp. 10212 Pfa2p  (67) SKY DTFCN YG  EN QS-EH LL KLA DA  TKG---------S
   Thr. aureum ORF2  (101) SKY DTFCN RYG  PK  -EH LL GLAAAA Q  QDRRSDGGKFDP
Thr. sp. 20892 OrfB   (65) SKY DTFCN YG  QQGT -EH LL GLAQEA   AGRMEKQ-PSEA
                           151                                               200
Sch. sp.  9695 Pfa2p (104) AN RDFGIVSGCLSFPMDNLQG LLN YQV  EN  AQR   R-PWS
Sch. sp. 20888 OrfB  (109) K ST CGIVSGCLSFPMDNRLQG LLN YQN    ARV   S-HWS
Thr. sp. 10212 Pfa2p (107) I  NTGIVSGCLSFPMDNLQG LLN YQC      PNAL  VN-LWSK
   Thr. aureum ORF2  (150) AQ K CGIVSGCLSFPMDNLQG LLN YQAEA     KHC A QT-PWST
Thr. sp. 20892 OrfB  (113) F  ENTGISGCLSFPMDNLQG LLN YQS  EQ  PPSALV  VKL
                           201                                               250
Sch. sp.  9695 Pfa2p (153) RP  VS  E G P V SQPASFVAN LG    RY  DAACA A LYC  AS
Sch. sp. 20888 OrfB  (158) REQ NK E  D  I MDPASFVA LN GA    DAACA ALY  LA
Thr. sp. 10212 Pfa2p (156) RTNG---KDL A  FDPASFVA LD   YS DAACA ALY  LAQ
   Thr. aureum ORF2  (199) RT LH LP DP THRDPASFVAC LG    Y  DAACA ALY  LA
Thr. sp. 20892 OrfB  (163) RQ  TKAH  L RR IDPASFVA  LN    Y  DAACA ALY  LA
                           251                                               300
Sch. sp.  9695 Pfa2p (203) DHL SR    LCGA C P FFIL GFSTF AMP   PDDNP  S   RQ
Sch. sp. 20888 OrfB  (208) DHL  GA   LCGA CLP FFIL GFSTF ANP  TGQ--N S   P
Thr. sp. 10212 Pfa2p (203) DHL  S  DTM CGA  LP FFIL GFSTF HAMP S ----D SAF
   Thr. aureum ORF2  (249) DHL  E  D  LCGA C P FFIL GFSTF HAMP  EN---G S  F
Thr. sp. 20892 OrfB  (213) DHL    VE  LCGA  P FFIL GFSTF AMPX D---G S  F
                           301                                               350
Sch. sp.  9695 Pfa2p (253) G    LTPGEGG   MVLRRLEDA RDG RIYG LL TS  N G GLPL  H
Sch. sp. 20888 OrfB  (256) D    LTPGEGG   MVLKRIDDA RDG RIYG LL  N  N GTGLP KEL
Thr. sp. 10212 Pfa2p (249) T    LTPGEGG   MVLRRLNDA RDG RIYG LL  E  SN G GLPL PH
   Thr. aureum ORF2  (296) D    LTPGEGG   MVLKRIADA RDG RIYG LL  S  SN G GLP KE
Thr. sp. 20892 OrfB  (260) T  AG LTPGEGG  MVLKRKHA RDGN IYKVLLE N SN     P
                           351                                               400
Sch. sp.  9695 Pfa2p (303)  PGEK    T L TS    D -SE QY  CHATGTF  GV VE      FR
Sch. sp. 20888 OrfB  (306)  PSEKKC  M   TK  N H -HK QY  CHATSTP  GDRVE  A   PE
Thr. sp. 10212 Pfa2p (299)  PGEFDC  EKALQ  HRL -SG QY  CHATGTP  GDKVE   A  TK GE
   Thr. aureum ORF2  (346) QP EE    KA  EL  P -RD QY  CHATSTP  GDTVE  QA   A PE
Thr. sp. 20892 OrfB  (310)  P EE    R   R  R A  AADQS QY  CHATGTP  GDVVE   A ERV KK
                           401                                               450
Sch. sp.  9695 Pfa2p (352) NTDHPE       TKGNFGH LVAAGFAGMAK LL MQ GTIFPTP    RSN-
Sch. sp. 20888 OrfB  (355) ---K  RFG    TKGNFGH LVAAGFAGM K LL MK G  FPTFG   DETK
Thr. sp. 10212 Pfa2p (348) ---H  RFG    TKGNFGH LVAAGFAGM K LL MQ G  FPTFG   NPDN
   Thr. aureum ORF2  (395) ---AS  F     TKGNFGH LVAAGFAGM K LL MERG  FPTFG   SGT-
Thr. sp. 20892 OrfB  (360) ---N  R      TKGNFGH LVAAGFAGMA  LL  E K IFPTPG   ASN-
                           451                                               500
Sch. sp.  9695 Pfa2p (401) C DP  YD      NPY  QA  AGKPGDELKC SLSAFGFGGTNAHC  FRE
Sch. sp. 20888 OrfB  (402) MDPL  VSG    KF  NG E          --------A LSAFGFGGTNAH
Thr. sp. 10212 Pfa2p (395) I  HD V   TL  WFN N DL         --------ACLSAFGFGGTNAH
   Thr. aureum ORF2  (441) Q DP  V   A   WF   R G         --------A LSAFGFGGTNAH
Thr. sp. 20892 OrfB  (406) QASEHV  K   TWF  H A           --------A LSAFGFGGTNAH
```

FIG. 5 (cont'd)

```
                         501                                                550
Sch. sp.  9695 Pfa2p  (451)  RQIA TATASPVLP-------EV PGP   GM    LKG    EQA
Sch. sp. 20888 OrfB   (443)  DPSN  CTGHDSISALSARCGGE NM  TGM    AL    ERA
Thr. sp. 10212 Pfa2p  (436)  RSDLQ NKTLENE---S-KSHEIE SF   GM  F  LKG QE ERA
    Thr. aureum ORF2  (482)  IPSR  PPAVLCQPRLG-----SGPNR   CM   PG LKG S LEAA
Thr. sp. 20892 OrfB   (447)  FNAEGI YRPGKPP------VESN RPS VITGM C S LEG  ETA
                         551                                                600
Sch. sp.  9695 Pfa2p  (494)  YK TD AS LP RWRFLGADT FLT   DAVE GC  RV    RI
Sch. sp. 20888 OrfB   (493)  YT A  AIPLPE RWRFLGKDK  LDLC  KATPHGC  V   QRL
Thr. sp. 10212 Pfa2p  (483)  YN G  AC LPENE RFLGEDK  LQ C  QKLP GC K V T RI
    Thr. aureum ORF2  (527)  YE R  ARPLP  RWRFLGGDES LHE   ECSPHGC  V    RI
Thr. sp. 20892 OrfB   (491)  YE RD AR LP RWRFLGEDL  LR R KEKP GC   SV N  RI
                         601                                                650
Sch. sp.  9695 Pfa2p  (544)   P  ED LP QLLAV  D A QL   AT KVAV VGLGTDTELYR
Sch. sp. 20888 OrfB   (543)   P T ED LLP QLLAV  D A    G  NVAVFVGLGTD ELYR
Thr. sp. 10212 Pfa2p  (533)   LP  QED L PLQLLAV I D   NA G PN KVAV VGLGTD ELYR
    Thr. aureum ORF2  (577)   P  ED L P QLLAV  D A   G AK NVAV VGLGTD ELYR
Thr. sp. 20892 OrfB   (541)   P T ED L P QLLAV  D A     QHVAV VGLGTD ELYR
                         651                                                700
Sch. sp.  9695 Pfa2p  (594)  HRARVTIKE  DP---AAFSPEQ  F  MDY NDCGTSTSYTSYIGNLVAT
Sch. sp. 20888 OrfB   (593)  HRARV LKE  R-----P ASKK  D  GY NDCGTSTSYTSYIGNLVAT
Thr. sp. 10212 Pfa2p  (583)  HRARV LKE  QTA --K DIP  P  MY NDRGTSTSYTSYIGNLVAT
    Thr. aureum ORF2  (627)  HRARV LKE  QGLRSA GGA TS   MY NDSSTSYSYTSYIGNLVAT
Thr. sp. 20892 OrfB   (591)  HRARV LKEV HPS --KSDTA     MY NDAGTSTSYTSYIGNLVAT
                         701                                                750
Sch. sp.  9695 Pfa2p  (641)  R SS  WGFTGPSFT  TEGANSV RCL  L   L THQVD VV AGVDL
Sch. sp. 20888 OrfB   (638)  R SS  WGFTGPSFT  TEGNNSV RC   L  LS  VD VV AGVDL
Thr. sp. 10212 Pfa2p  (631)  R SSL WGFTGPSFT  TEGENSV RCL    FLAN  VD VV AGVDL
    Thr. aureum ORF2  (677)  R SS  WGFTGPSFT  TEGANSV RC QL    LR  VD VV AGVDL
Thr. sp. 20892 OrfB   (639)  R SS  WGFTGPSFT  TEGNNSV RC QL  D LQVNRVD VV AGVELN
                         751                                                800
Sch. sp.  9695 Pfa2p  (691)   AE       RSA S QDHPRANF   ADG F G GSGA V KRQA VGS
Sch. sp. 20888 OrfB   (688)   AL     RF  STSDTFRAS   ADG PVG G GAFV KRE  S TK
Thr. sp. 10212 Pfa2p  (681)   AE     RS  STQNEFFAN   NADG FAG G GAFV KR    TD
    Thr. aureum ORF2  (727)   AE AF     MQ   SQRPAAPF  F ADG F AG G GA FKR   VS
Thr. sp. 20892 OrfB   (689)   AE SF    NR Q    LSHFCAS RDADG F G G GA VFKRF   AP
                         801                                                850
Sch. sp.  9695 Pfa2p  (741)  -D   YA   AG TC AQ AE   SPL  L VHNDDN KRV    E  S
Sch. sp. 20888 OrfB   (738)  -D   YAC    KVP NV S C   E  DQ R KPG ---  E  A S
Thr. sp. 10212 Pfa2p  (731)  ST   YA    A   DEVGPT  Q   R S  AAK ---   AE  ASS
    Thr. aureum ORF2  (777)  -G   YA    V TT R    A AGS R DPAS---    E   SH
Thr. sp. 20892 OrfB   (739)  -Q   YA    A DKE T   AVK  Y DSSLS ---     S  
                         851                                                900
Sch. sp.  9695 Pfa2p  (790)   APHL NSPLSAE  QL  QVSKLLAHQVPG----SVA GS   A VGD C A
Sch. sp. 20888 OrfB   (784)   LKDPSV PKE    E  G  QT  RDDDKLPRNVATGS   ATVGDTC A
Thr. sp. 10212 Pfa2p  (778)   HSGRITCEDE NELG  FNEG---------IQRVA GS   A VGD C A
    Thr. aureum ORF2  (823)  FVRAP  T AQP    VE  C  RE  CTAGRGSRSVA GS  A VCDAG A
Thr. sp. 20892 OrfB   (785)  FAAFE  A EIQS  VE AQ K   SK  EPAK--GQGVA GST ATVGD C A
                         901                                                950
Sch. sp.  9695 Pfa2p  (836)   GAA L K ALC   NR YL ----A PQWERFV PVSEA  T PR  KWIKN
Sch. sp. 20888 OrfB   (834)   GAA L  AA L    NR YL SNGDE  APE P D  I  ACQT  RAWLKN
Thr. sp. 10212 Pfa2p  (819)   GAA L K ALC  NR YL -KLP  NK TKDVE SKSF  CEH  RAW KN
    Thr. aureum ORF2  (873)   GAA L K ALC  NRYLA-ATPG DA AAGVD  G E  CRE  PW KN
Thr. sp. 20892 OrfB   (833)   GAA L K ALC  NRYL -ALA  SG CEQ A C  N   CHE  PW KN
                         951                                               1000
Sch. sp.  9695 Pfa2p  (883)  P  SRLA   SAS      C      EY T  SSN   DA P    AR
Sch. sp. 20888 OrfB   (884)  P  RK  A    S R  S      AE H EREN    EE P    R
Thr. sp. 10212 Pfa2p  (868)  VD NK  AV    C N          VQ H  ESNL   KNEP  G Y
    Thr. aureum ORF2  (922)  A  VAR  A    D G  C   V   VP Q ETGN    QAE F   S
Thr. sp. 20892 OrfB   (882)  QN KR CAL    TDP H C  S      TG-C EEHN TCF VQ PQ   H
```

FIG. 5 (cont'd)

```
                        1001                                               1050
Sch. sp. 9695  Pfa2p  ( 933) ░V░░A░N░E░AL░RAHAE░G░░TDDDP░AAVAFTAHRLRFLRL░GE
Sch. sp. 20888 OrfB   ( 934) ░H░░░G░DKIRERF░░PT░A░PRESE░K░QARRIFLE---░░░░AQ
Thr. sp. 10212 Pfa2p  ( 918) ░V░░░░VQ░NKY░EKF░░ET░░░AQK░K░PTIDIDSN--░░░M░NL
    Thr. aureum ORF2  ( 972) PDHAA░░D░░A░E░AA░E░AD░L░░░AAA░DR---------░░░░VG
Thr. sp. 20892 OrfB   ( 931) FDGKT░░P░░E░Y░LE░░FGH░░P░----------EYFHK--░░O░LE
                        1051                                               1100
Sch. sp. 9695  Pfa2p  ( 983) TV░SHGATAT░C░░L░░░PE░LE░E░░LAA░G░░PSA░G░N░MSP░GSA
Sch. sp. 20888 OrfB   ( 982) D░░S░GSQ░P░A░░L░░░PS░L░K░E░LAA░G░░R░░M░░WSS░GSR
Thr. sp. 10212 Pfa2p  ( 966) PQDKN---░KFA░░L░░░PN░L░░L░░LAV░G░░░░░A░░WCSP░GGI
    Thr. aureum ORF2  (1012) C░░G░---GG░T░CL░A░PASLH░░L░ALAH░G░░░░░░░WASP░GSY
Thr. sp. 20892 OrfB   ( 969) N░KF░----░-░T░░L░CNPNQL░░K░░MLA░I░G░QRS░LTG░░WVSP░GSC
                        1101                                               1150
Sch. sp. 9695  Pfa2p  (1033) ░A░T░░TS░░AFMYGEGRSPYG░░L░░HR░WP░LHEP░░D░░AAL░EN
Sch. sp. 20888 OrfB   (1032) ░A░EP░░S░░AFMYGEGKSPYYG░TQ░░HR░WEE░LHEV░NE░░CNRLWA░
Thr. sp. 10212 Pfa2p  (1013) ░CNP░KS░N░AFMYGEGKGPYAG░░Y░░HR░VPMLHEL░NN░░ETELNDQ
    Thr. aureum ORF2  (1059) ░A░P░░░░A░AFMYGEGRSPYC░░░░HR░WP░LHEP░NA░VNL░WG░
Thr. sp. 20892 OrfB   (1015) ░A░NP░░SA░AFMYGEGKSPYC░░░LG░HR░WE░LHEN░NN░░VDL░WT░
                        1151                                               1200
Sch. sp. 9695  Pfa2p  (1083) GD░░░░P░░VDA░SQRA░QTAF░░D░░EMFRT░░░░░LT░Y░
Sch. sp. 20888 OrfB   (1082) ░DRW░░PR░░FKS░L░SQQQEF░R░M░EMFRLG░LTS░AFTN░A░░░N
Thr. sp. 10212 Pfa2p  (1063) GD░WY░P░░░VA░K░F░PGDF░K░░░EMPRLS░░░░░░GFT░░░T░░░
    Thr. aureum ORF2  (1109) GD░░░░P░A░A░░E░Q░CRNF░░░░EMFRTG░░░S░░LT░░A░S░░
Thr. sp. 20892 OrfB   (1065) GDGN░YPRTL░R░░HTKAIESFN░░░░EMFRAG░░░S░░QT░YVMN░░░
                        1201                                               1250
Sch. sp. 9695  Pfa2p  (1133) QP░A░FGLSLG░░SM░FA░░░NG░░Q░TQ░L░░░V░░Q░A░░░A
Sch. sp. 20888 OrfB   (1132) TP░A░FGLSLG░░SM░FAFS░░NGL░░░░O░TDL░E░DVWNKAS░A░░░A
Thr. sp. 10212 Pfa2p  (1113) KP░KA░FGLSLG░░SM░FAFS░░NT░░S░░T░KL░░░P░░KV░░QLA░░PAA
    Thr. aureum ORF2  (1159) GP░KA░FGLSLG░░SM░FA░SES░N░░░░░░T░RLS░A░░░VN░░EL░A░░EA
Thr. sp. 20892 OrfB   (1115) QF░KAGFGLSLG░░SM░FA░░░EN░░QSQ░░░TN░L░RG░░VW░NE░A░NE░A
                        1251                                               1300
Sch. sp. 9695  Pfa2p  (1183) ░░░WN░░AD░░░░FWQGY░░░░░░A░░░EK░I░P░░░VRL░░░ND░S░
Sch. sp. 20888 OrfB   (1182) ░REA░WG░PQSV░E░░░EFWOGY░░V░░░░░EA░I░P░S░░VRL░T░ND░
Thr. sp. 10212 Pfa2p  (1163) ░RD░WN░░ADKS░░░EFWQGYFVY░N░TL░ENTI░-░░░░░VRL░I░ND░
    Thr. aureum ORF2  (1209) ░P░░░WG░APG░░░░FWQGY░░V░░░░AQ░EQ░T░░░░Q░VRL░░░ND░
Thr. sp. 20892 OrfB   (1165) ░░░░░WK░░RG░░░░FWQGY░VH░░░░EH░I░LSEP░VRL░░░ND░R░
                        1301                                               1350
Sch. sp. 9695  Pfa2p  (1233) ░LI░GK░AECLR░░░E░░░░G░░PP░░VKQGM░GHC░░░A░░PG░░░I░H░
Sch. sp. 20888 OrfB   (1232) ░LI░GK░░░CK░A░░░░GN░P░░░░V░QQMCGHC░░G░░░K░░KE░AN
Thr. sp. 10212 Pfa2p  (1212) CLI░SKP░ECQK░░I░░HL░░░D░░░░KEAI░░LDQ░S░░H░░░
    Thr. aureum ORF2  (1259) VLI░GK░A░CE░░░░░SI░░PP░QV░QGM░GHCA░░L░░S░░R░EHN░
Thr. sp. 20892 OrfB   (1215) ░LI░GK░░A░QK░░░░NS░░P░░VKQGM░GHC░░RA░IK░░░░H░T
                        1351                                               1400
Sch. sp. 9695  Pfa2p  (1283) ░░░░DSPVKMYT░░VTNAELRG------------------G░NS░░T░░QK░
Sch. sp. 20888 OrfB   (1282) ░░F░VV░GLDLW░░INQ░RLV--------PRATGAKDEW░PS░FG░░A░Q░
Thr. sp. 10212 Pfa2p  (1262) ░L░░░KP░NVKLF░░SEN░----------------ELVSMKD░░SKL░░E░
    Thr. aureum ORF2  (1309) ░RF░SQ░ETGGCKMYSSVSNSRIGPVEESQMGPGTELVFSP░░E░░░░Q░
Thr. sp. 20892 OrfB   (1265) ░R░SNDYSDCQLF░AVT░G---------------ALDS░TME░KH░░░P░
                        1401                                               1450
Sch. sp. 9695  Pfa2p  (1317) Y░░░A░░FPG░I░░K░SRD-░░D░F░░░G░░░MFS░AVSD░LGKAATP░░░░
Sch. sp. 20888 OrfB   (1325) YE░░QAN░F░I░░T░░KQN-░D░F░L░G░░░HRSTAV░░TLG░QR-N░░░G
Thr. sp. 10212 Pfa2p  (1296) YQH░A░░P░I░NK░░KETCKTD░░░L░SH░YR░AV░░LG░---EL░░░
    Thr. aureum ORF2  (1359) Y░░░░A░PAIT░A░░QQ░-░D░F░░L░G░░DHSK░AV░░TLG░TR-R░░░░
Thr. sp. 20892 OrfB   (1300) Y░░░A░░P░I░NT░░SA░G-░D░F░░E░GCDASK░AVQN░LGQG-KF░░T
                        1451                                               1500
Sch. sp. 9695  Pfa2p  (1366) A░░D░PS░░AW░░T░░G░ALLT░H░░YFLHNP░LFADLYHPTFLTAID░░MQ
Sch. sp. 20888 OrfB   (1373) A░░D░QN░DAW░T░░░░A░LK░HLVE░░T░░P░░SK░░AEAQACY░░LC
Thr. sp. 10212 Pfa2p  (1343) A░░DRQN░░A░G░░░A░LI░HRV░F░░░KK░░░E░░KFDPQAKPNRF
    Thr. aureum ORF2  (1407) A░░DRK░░A░░░░░A░LA░HRV░F░░D░░S░░Y░A░░ERCRLAL░░QR
Thr. sp. 20892 OrfB   (1348) A░░KGH░AW░░░░░ATA░LA░HV░P░░S░LD░░░NFREMCCTMATT--
```

FIG. 5 (cont'd)

```
                            1501                                              1550
Sch. sp.  9695 Pfa2p (1416) E-P PKP    P    Y CPD  ISKQV AA  AK   THCM RLHPAKAV
Sch. sp. 20888 OrfB  (1423) KGEKPKK  F  RK  Q    NSK DP SS D ASF  PADPA  EAA S RI
Thr. sp. 10212 Pfa2p (1393) IRNIELNGF DK  NI VD QLSP DPKLAEI NNRNMPKDN YVP ERVK
   Thr. aureum ORF2  (1457) SGQ EQR  T  R  E   F DPADAT PE VA IL  TAAISPPK G PH
Thr. sp. 20892 OrfB  (1396) --- KVED F R  Q    EKEMIH EDTT  CL  PSEANIAA Q RS
                            1551                                              1600
Sch. sp.  9695 Pfa2p (1465)  VAA  AVVADSTPVVKAKQ SSS------------------------
Sch. sp. 20888 OrfB  (1473)  KPV PKFYARLNIDEQDETRDPILNK NAPSS SSSSSSSSSSSSPSPA
Thr. sp. 10212 Pfa2p (1443) TMIK EP NLQVSVGSKPVV ERISSD N FEKLSEITKSFDG-------
   Thr. aureum ORF2  (1507) DSQPE E RPVGEASVPRRA SSSKLART AID CDSDVRAALLDLDAPI
Thr. sp. 20892 OrfB  (1443)  RSA R GQSHDCASHSHEENKDSCP K KLD VSVAINFDN-------
                            1601                                              1650
Sch. sp.  9695 Pfa2p (1489) -----------------------------------------------
Sch. sp. 20888 OrfB  (1523) PSAPVQKKAAPAAETKAVASADALRSALLDLDSMLALSSASASGNLVETA
Thr. sp. 10212 Pfa2p (1486) --------------------------VN---------------------
   Thr. aureum ORF2  (1557) AVG--------------------G-------------------------
Thr. sp. 20892 OrfB  (1486) -------------------------------------------------
                            1651                                              1700
Sch. sp.  9695 Pfa2p (1489) -------------LL  GDD F  C DV   LYMGAMAEG  V  V AA
Sch. sp. 20888 OrfB  (1573) PSDASVIVPPCN AD GSR F  T G SA LY GAMA G  A S  V AA
Thr. sp. 10212 Pfa2p (1488) -------ACTEAM GDSG---F  T E   LY GAMA G A S  V AA
   Thr. aureum ORF2  (1561) --SSRAQVPPCP SA GSA FRAA G V ALYMGAMA G  A S  V AA
Thr. sp. 20892 OrfB  (1486) ---------DDRIQ GHA FREM NTR SLY GAMA G  A S  V AA
                            1701                                              1750
Sch. sp.  9695 Pfa2p (1526) E  LAS GA  RL  DQ  LQ  REI QRTS -A AVNL  PG D AAT---
Sch. sp. 20888 OrfB  (1623)  QG LAS GA  L  QVVP     I    AVNL   P  S  K
Thr. sp. 10212 Pfa2p (1529)   LAS GA  LA QV  KQ K  E GK   AVNL   P  PS  K
   Thr. aureum ORF2  (1609)   LAS GA  L  GEV  I  QA  PE G  AVNL   P  P  E
Thr. sp. 20892 OrfB  (1526)  EG LAS GA  LP ATYRKG  I  Q  S I AVNL  P  G  Q
                            1751                                              1800
Sch. sp.  9695 Pfa2p (1572) -V ALL T S  S  TGA AD V YRVTG R TSCG   SATH
Sch. sp. 20888 OrfB  (1673)    LE  TF AS -    Q V YR  GLT NA-  N R
Thr. sp. 10212 Pfa2p (1579)    YN  F EVS -    Q V Y   GLA AR-  K Q R
   Thr. aureum ORF2  (1659)    E    S  -    S V YRV GLE GPG- AR L
Thr. sp. 20892 OrfB  (1576)    LE N  AECS  T-   VP VHYR  GLV RQ   L K R
                            1801                                              1850
Sch. sp.  9695 Pfa2p (1621) K SR E AEH   P PAA   AL A KQ  P QAA AS VA  DD
Sch. sp. 20888 OrfB  (1721) K SR E AEH   P PEH  Q L A  E NQ QAE AR VR  DD  A E
Thr. sp. 10212 Pfa2p (1627) K SR E AE F  P PKN  AL ADG S  Q QAQ ALLV  DD T
   Thr. aureum ORF2  (1707) K SR A  AE H  PP AA  S L AQ L  E  QAS AEIV  VD
Thr. sp. 20892 OrfB  (1624) K SR E AE H  P PQI L  LV A EI  S QAR AA V   DD AV E
                            1851                                              1900
Sch. sp.  9695 Pfa2p (1671) A SGG TDNRP HV LP    AQP ----WR LVDTP R  GA GGI  CF R
Sch. sp. 20888 OrfB  (1771) A SGG TDNRP HV LP     PD  HR CG ANL  R  GA GGI  CPQ
Thr. sp. 10212 Pfa2p (1677) A SGG TDNRP HV LP     QR --RICK Q  KHL  R  GA GGI  CPK
   Thr. aureum ORF2  (1757) A SGG TDNRP HV LP    A PD  MR CK AAN  R  GA GGI  CPA
Thr. sp. 20892 OrfB  (1674) A SGG TDNRP HV LP    P T LA  YGCATAF  TR  GA GGI  CPS
                            1901                                              1950
Sch. sp.  9695 Pfa2p (1717) AA L FS GA    G  NQ    GTSDAVRL  LAT YSDVAMA
Sch. sp. 20888 OrfB  (1821) AA  TEN GA   PG  NQ  Q GT DNVRQL  A TYSDVCMA
Thr. sp. 10212 Pfa2p (1725) AAF  AF GA  A  G  NQ    GTCDYVRK LN ATYSDVAMA
   Thr. aureum ORF2  (1807) AAR  AF GA   TG  NQ T Q GT DSVRAA L ATYSDV AMA
Thr. sp. 20892 OrfB  (1724) AA   AF GA  TGS NQ  P  GT DTVRE  LN  YSD MAP
                            1951                                              2000
Sch. sp.  9695 Pfa2p (1766) --------- QVLK QTMFA PATMLAQLQA  GSF  PEPQ   G F
Sch. sp. 20888 OrfB  (1871)  E    QVLK   TMF  RA  EL   CK YDSF  PPA A    F
Thr. sp. 10212 Pfa2p (1775)  H E QVLK  TME RAK EL  LKK YKS EL PAD   EQ  F
   Thr. aureum ORF2  (1857)  Q   QVLK   TMF  RA  EL   TT QS   FRA A   S F
Thr. sp. 20892 OrfB  (1774)  Q   QVLK  TM  RA  L RKL VNES T PSK   Y ENI F
```

FIG. 5 (cont'd)

```
                           2001                                               2050
Sch. sp.  9695 Pfa2p (1809) KQ  A VWAAA EK GVDATAAS--------QE   LCVE Y  SQ  K
Sch. sp. 20888 OrfB  (1921) SR    VW       IN  H      Q        A  LC RN Y SL  K
Thr. sp. 10212 Pfa2p (1825)  K FL  VW       IN  HS    E A  LEA  E  LC RN Y S  SK
Thr. aureum  ORF2    (1907)  M    VWN       ET  N  A  A  E     M  LC RW Y SK SS
Thr. sp. 20892 OrfB  (1824)  Q    QVW     R  CE  N    A  M     K  LC RW Y SK SG
                           2051                                               2100
Sch. sp.  9695 Pfa2p (1851) ATE  T   RKADYQ  WC P    G    F    KLDAT GT  E  RV D NQH
Sch. sp. 20888 OrfB  (1971) A    A DRV DYQ  WC P  G  N  F  G- Y  P  ANE  PCV Q NKQ
Thr. sp. 10212 Pfa2p (1875) A    E  RVQDYQ  WC P  G  N  FA G PC  PE  L S PSV Q NKH
Thr. aureum  ORF2    (1957) AS   QV  RE  YQ  WC PT G N  F  G   LDAE CG R PCV R QE
Thr. sp. 20892 OrfB  (1874) A  A IKSRA DYQ  WC P  G     NEASG- S  WR T V PGVAE  MA
                           2101                              2140
Sch. sp.  9695 Pfa2p (1901)   LG SHYR  C  QQDDDV  YIIV----------------
Sch. sp. 20888 OrfB  (2020)   LRGAC LK   ILRNARLS GAAALVASIDDTYVPAEKL
Thr. sp. 10212 Pfa2p (1925)   LRGAC YQ  S LKYLNFNYEELDTLTYSASNFI-----
Thr. aureum  ORF2    (2007)   LCGAA EQ  ARFMLLAGR SADALAYTVAEAR------
Thr. sp. 20892 OrfB  (1923)   LDC ARELAAKR -------------------------
```

FIG. 6

```
                              1                                                  50
Sch. sp.  9695 Pfa3p    (1)   ---MT    KT  WE   K E LD      VF YNELLEFAEGD   QVFGP
Sch. sp. 20888 OrfC     (1)        K NK  CW M K E          EVFNY ELLEFAEGD   VFGF   A
Thr. sp. 20892 OrfC     (1)      P    GKV AWEM  RSE CDD   VF Y ELLEFAEGD  S VFSP  K
Thr. sp. 10212 Pfa3p    (1)   -M G QM   E  WE M K EQ     N VF Y ELLEFAEGD   VFSPK
                              51                                                100
Sch. sp.  9695 Pfa3p   (48)           RRVRLPAREYLLV  RVTLMDAEV   RVG RMVTEYD  PVNG
Sch. sp. 20888 OrfC    (51)        DK PRRVRLPAREYLLV RVTLMDAEV  N RVG RMVTEYD  PVNGE
Thr. sp. 20892 OrfC    (51)        DG  RRVRLPAKEYLLV  KVTLMDAEVGN RVG RMVTEYD  PVNGE
Thr. sp. 10212 Pfa3p   (50)        K SPRVRLPAREYLLV  RVTLMDAEVGN RVG RMVTEYD  PVNGE
                              101                                               150
Sch. sp.  9695 Pfa3p   (98)   S GGD   PWAVLVE  GQCDL  ISYMGIDFQ  G RVYRLLNT  LTF GVA
Sch. sp. 20888 OrfC   (101)   S GGDCPWAVLVE  GQCDL  ISYMGIDFQNQG RVYRLLNT  LTF GVA
Thr. sp. 20892 OrfC   (101)   S GGD  PWAVLVE  GQCDL  ISYMGIDFQ  G RVYRLLNT  LTF GVA
Thr. sp. 10212 Pfa3p  (100)   SQSGD  WAVLVE  GQCDL  ISYMGIDFQ   G RVYRLLNT  LTF GVA
                              151                                               200
Sch. sp.  9695 Pfa3p  (148)    EGETL YDIRVTG AKGAGG   SM F EYDC   D  LLIEMRDG AGE
Sch. sp. 20888 OrfC   (151)    ESETLEYDIRVTGXAK    GGI SM F EYDC   G LLIEMRDG AGE
Thr. sp. 20892 OrfC   (151)   KESETL YDIRVT  AR  P G SMF F EYDC C G LLIEMRDG SASE
Thr. sp. 10212 Pfa3p  (150)    EGETL YDIRVT AKG  HG  SM F FEYDC   G LLIEMRDG AGE
                              201                                               250
Sch. sp.  9695 Pfa3p  (198)    AK   AGKGV    T      K QIQ  D    AP    SHKT   DA    RL
Sch. sp. 20888 OrfC   (201)   TN ELDAGKGV  FT   R    IP  D   A     LHKTK
Thr. sp. 20892 OrfC   (201)   T     AGKGV  VT  QQNMRDK I     EP AL A  THPT     S
Thr. sp. 10212 Pfa3p  (200)   T  EL AGRGV   TV   HK KSI PK    P AL N AV KTMFS N  EK
                              251                                               300
Sch. sp.  9695 Pfa3p  (248)         RV --       DYK CARKMLMIDR TH   P GG  GLG
Sch. sp. 20888 OrfC   (251)   L   DW SV G KNG PE    YK CARKMLMIDR TS      GV  GLGQL
Thr. sp. 20892 OrfC   (251)   L        SNR   E     YK CARKMLMIDR T K    HGG   GLG L
Thr. sp. 10212 Pfa3p  (250)   LC    E VLG--    Q  DYK CARKMLMIDR TK Q NGG  GLG L
                              301                                               350
Sch. sp.  9695 Pfa3p  (296)   GEK    R HWY P CHFV  DEVMAGSLVSDGCSQ  LK YN  LG HT   A
Sch. sp. 20888 OrfC   (301)   GEK    P HWY P CHFV D  VMAGSLVSDGCSQ  LK YM  LG H   T  P
Thr. sp. 20892 OrfC   (301)   GEK    R HWY F CHFVND  VMAGSLVSDGCSQ  LK YM  LG H    H
Thr. sp. 10212 Pfa3p  (298)   GEK    P HWY F CHFV   VMAGSLVSDGCSQ  LK YM  LG HDV P
                              351                                               400
Sch. sp.  9695 Pfa3p  (346)   FQ   PV G  ANKVRCRGQ ISP  GKLVYVMEI   MG  AK     P AIADV
Sch. sp. 20888 OrfC   (351)   FQ  K PVNG  NKVRCRGQ ISP  GRLVYVMEI  NG  DN-  P AIADV
Thr. sp. 20892 OrfC   (351)   F   LPV    KNKVRCRGQ ISP  GKLVYVMEI  KM    Q   SP AIADV
Thr. sp. 10212 Pfa3p  (348)   FQF   PVGQ  NKVRCRGQ ISP  GRLVYVMEI   MG  N   QP AIADV
                              401                                               450
Sch. sp.  9695 Pfa3p  (396)    I DV   EEGQ  FAG       H YGQG  LRKKIVVDFKGIA S     KEQQK
Sch. sp. 20888 OrfC   (400)   N I DVD  EKGQD S-  P  DYG    LNKKIVVDFKGIAL      TN
Thr. sp. 20892 OrfC   (401)    I DV  EE GQ  F -  LN    YG K  LKKIVVDFKGIAL    KG  F   M
Thr. sp. 10212 Pfa3p  (398)    I DV   E GQ F - A   DYG  NL KKIVVDFKGIAL   EGTVK S
                              451                                               500
Sch. sp.  9695 Pfa3p  (446)   E  ---------------------------MT T  T TT      A
Sch. sp. 20888 OrfC   (449)   P  KVQPVFANGAATVGPEASKASSGASA    AAP  KPAF ADVLAP  P  A
Thr. sp. 20892 OrfC   (450)   S  ------------------------     LNE WQCVPK   Q MEHE
Thr. sp. 10212 Pfa3p  (447)   -----------------------------------I  D   --  T
                              501                                               550
Sch. sp.  9695 Pfa3p  (463)   F   G L   TA     WH M  EGNGGPGP P F  PC Y P    FSE F
Sch. sp. 20888 OrfC   (499)   LPE  IL  DA  P KE  WHPM    G-- P P P PS  KPRN A PE P
Thr. sp. 20892 OrfC   (474)   P     L ASL PA    WHPM     G-- PP P P PS Y P  D   FE FF
Thr. sp. 10212 Pfa3p  (459)   PPN  L     P   Q  WHPM G NG--APAP F PSDY PR   FK F F
                              551                                               600
Sch. sp.  9695 Pfa3p  (513)   NNP  DN     QMPL W NM E M GKVS  LGPEF   DASKTSRSP A
Sch. sp. 20888 OrfC   (547)   N FNDN    G  PL W NM E MAGKVSMCLGPEF   DS  TSRSP A
Thr. sp. 20892 OrfC   (522)   NP  DNNCKA E MPLNW NM E M GKVS  LGPEF   DKS  TSRSP A
Thr. sp. 10212 Pfa3p  (507)    NP  D      PL W NM E M GKVS  LGPEFK  DNSKTSRSP A
```

FIG. 6 (cont'd)

```
                              601                                               650
Sch. sp.  9695 Pfa3p  (563)  DLALVTR T V        YN  D  PGQGTM CEFDCP DAWF G  SRD
 Sch. sp. 20888 OrfC  (597)  DLALVTRA  V   K VN RN D DP  GTM GEFDCP DAWF K     D
 Thr. sp. 20892 OrfC  (572)  DLALVTR EV N    K  N DC P  GTM GEFDCPQDAWF D      
Thr. sp. 10212 Pfa3p  (557)  DLALVTR V V    FK HDN D PS GTM CEFDCP DAWF Q      
                              651                                               700
Sch. sp.  9695 Pfa3p  (613)  DHMPYSI  MEI  LQTSGVLTSVLKAPLTM KDDILFRNLD DAE  VGD M
 Sch. sp. 20888 OrfC  (647)   HMPYS   MEI  LQTSGVLTSVLKAPLTM KDDILFRNLDANA PV - 
 Thr. sp. 20892 OrfC  (622)   HMPYS   MEI  LQTSGVLTSVLKAPLTM KDDILFRNLDA AEHV -P
Thr. sp. 10212 Pfa3p  (607)   HMPYS   MEI  LQTSGVLTSVLKAPLTM KDDILFRNLDA AEHV - 
                              701                                               750
Sch. sp.  9695 Pfa3p  (663)  P   GKTI NPT  C GY MLG MG HR TE L VL A FYKGSTSFGWF 
 Sch. sp. 20888 OrfC  (696)   DYRGKTI N T  C GY MLG MG HR TE L YVDD  FYKGSTSFGWF 
 Thr. sp. 20892 OrfC  (671)   D RGKTI N T  C GY MLG M HR TF L VD   FYRGSTSFGWFT
Thr. sp. 10212 Pfa3p  (656)   DCRGKTI NFT  C GY MLG M  HR TF L VDD  FYRGSTSFGWFT
                              751                                               800
Sch. sp.  9695 Pfa3p  (713)  PEVF  QTGLDNG PRLPW          N  VDTLSAP S   S Q
 Sch. sp. 20888 OrfC  (746)  PEVFA Q GLDNG   PW   I  VPA  S   RPN SGRT IF N P
 Thr. sp. 20892 OrfC  (721)  PEVFAQQ GLDNG    PWCKT N--T VRRVEIA   K KEQLTEKLPD
Thr. sp. 10212 Pfa3p  (706)  PEVF  QVGLDNG   VQPN    S--   V       T GKDKLF KI 
                              801                                               850
Sch. sp.  9695 Pfa3p  (753)  G LQ   RRG  A  LD       GSG GV  QGYAHC  KAVNK DWFFSCH 
 Sch. sp. 20888 OrfC  (796)  G     RR DQG    LDA D  VSG- GK SLGYAHG SKTVN  DWFFSCH 
 Thr. sp. 20892 OrfC  (769)      LRR EQG  LDY N  D- GL  GYAH HKDVN  DW FSCH 
Thr. sp. 10212 Pfa3p  (754)  KD C   RRN  G      D    I N-  G N GYAHG KKV D DWFFSCH 
                              851                                               900
Sch. sp.  9695 Pfa3p  (803)  WFD VM GSLG  ESMFQL  A  C K          HPV      A  WK
 Sch. sp. 20888 OrfC  (845)  WFDSVMPGSLG  ESMFQL  AI AHED   ARHC PHLCAR R    WK
 Thr. sp. 20892 OrfC  (818)  WFD VMPGSLG  ESMFQL  A    N P  N  P      - G   NK
Thr. sp. 10212 Pfa3p  (803)  WFD VMPGSLG  ESMFQL  FA   D  S   V P     N-  G   WK
                              901                                               950
Sch. sp.  9695 Pfa3p  (852)  YRGQL   K D MD E HIK  A F S---  VD  ADG   A  GLRVY   
 Sch. sp. 20888 OrfC  (895)  YRGQL   KS  MD E HI    D HDG---VVD  ADG   RAD LRVY VS
 Thr. sp. 20892 OrfC  (867)  YRGQL   K  AMDCL HI   T SP NGG  VL   ADGAL DGLRVYE K
Thr. sp. 10212 Pfa3p  (852)  YRGQ NNKG  MD F HIKD VKN  G--TVD  ADG L  LRVY  
                              951                                              1000
Sch. sp.  9695 Pfa3p  (899)     RV  Q  A HVEEQEV KK      N----------S I DVDVAD QAL
 Sch. sp. 20888 OrfC  (942)     RV A   DSP AA S   V   A S ERTRSSPAV G P QT D K  L
 Thr. sp. 20892 OrfC  (917)  E RV    KPQ IPD QQQ P A ADPG----------P CA  PT  
Thr. sp. 10212 Pfa3p  (900)  D RV  VP TKA PK     RHVA P PGV-----P NT   E   ESL
                             1001                                              1050
Sch. sp.  9695 Pfa3p  (939)   QALLT   PLQ   AG----------------- E  ACA  DLG  GFM
 Sch. sp. 20888 OrfC  (992)   T L   A PL SQ P SGQ  KHT A      Q   Q  GDLG  FM
 Thr. sp. 20892 OrfC  (957)   DVLL   NPLY CV    NLVQFESKPAT SRIVS  K C   DLG   FM
Thr. sp. 10212 Pfa3p  (945)   K LLN   PL   PS HI-- QFG  NN       NDLG   FM
                             1051                                              1100
Sch. sp.  9695 Pfa3p  (972)  ETYGV APLY GAMAKGIASADLVIAMGQRK LGSFGAGGLP   VR 
 Sch. sp. 20888 OrfC (1042)  ETYGV APLY GAMAKGIASADLVIA Q RK LGSFGAGGLP HVR 
 Thr. sp. 20892 OrfC (1007)  ETY VSAPLY GAMAKGIASADLVIA  RK LGSFGAGGLP S VRE 
Thr. sp. 10212 Pfa3p (993)   ETY V APLY GAMAKGIASADLVIA  RK LGSFGAGGL   V  
                             1101                                              1150
Sch. sp.  9695 Pfa3p (1022)  EKIQ  LPAG FYAVNLIHSPFD NLEKQNVDLFLE GVRVVE SAF  LT
 Sch. sp. 20888 OrfC (1092)  EKIQ  LPQG FYAVNLIHSPFD NLEKGNVDLFLE GV VVE SAF TL 
 Thr. sp. 20892 OrfC (1057)  EKIQQHLPHG FYAVNLIHSPFD NLEKGNV LFLEMGV VVE SAF   
Thr. sp. 10212 Pfa3p (1043)  EKIQ  LPEG FYAVNLIHSPFD NLEKGNVDLFLE GVHVVE SAFTAL 
                             1151                                              1200
Sch. sp.  9695 Pfa3p (1072)   QVVRYRA GLS D RGGS  T H  IIGKVSRTELAEMF  RPAP A L K
 Sch. sp. 20888 OrfC (1142)   QVVRYRAAGLS N G-S N R  IIGKVSRTELAEMF  RPAPE   L 
 Thr. sp. 20892 OrfC (1107)  AQVVRYRA GLS   DG-S  H  IIGKVSRTELAEMF  RPAP NI LQK
Thr. sp. 10212 Pfa3p (1093)  TQVVRYPACGLS  K G-S L K  IIGKVSRTELAEMF RPAP N L K
```

FIG. 6 (cont'd)

```
                         1201                                              1250
Sch. sp.  9695 Pfa3p  (1122) LXASGEXTPEQAALAXXVPXADDXAVEADSGGHTDNRFIHVILPLIXSLR
Sch. sp. 20888 OrfC   (1191) LXASGEXTQEQAXLARRVPXADDXAVEADSGGHTDNRFIHVILPLIXXLR
Thr. sp. 20892 OrfC   (1156) LXASGEXTAEQAXLATQVPXADDXAVEADSGGHTDNRFIHVILPLIXXLR
Thr. sp. 10212 Pfa3p  (1142) LXASGEXTKEQASLAXXVPXADDXAVEADSGGHTDNRFIHVILPLIXXLR
                         1251                                              1300
Sch. sp.  9695 Pfa3p  (1172) NRXQXXXKXPXRHRVRVGAGGGXGCFXAAXXAXHMGAAFXXGXVNQX
Sch. sp. 20888 OrfC   (1241) NRXXXECXXPXXXRVRVGAGGGXGCFXAAAXALTMGAAFXXGXVNQX
Thr. sp. 20892 OrfC   (1206) NRXXXEXDXPXXXRVRVGAGGGXGCFXAAXXAXXMGAAFXXGXVNQX
Thr. sp. 10212 Pfa3p  (1192) NRXXXECXXPXAXRVRVGAGGGXGCFSAAXXAXMGAAFXXGXVNQX
                         1301                                              1350
Sch. sp.  9695 Pfa3p  (1222) XXGTCDXVRXXLSXAXYSDXXMAPAADMFXXGVXLQVLKKGTXFPSRAXK
Sch. sp. 20888 OrfC   (1291) XXGTCDXVRXXLSQAXYSDXCMAPAADMFXEGVKLQVLKKGTXFPSRANK
Thr. sp. 20892 OrfC   (1256) EXGTCDXVRLQLSXAXYSDXCMAPAADMFXXGVXLQVLKKGTXFPSRAXK
Thr. sp. 10212 Pfa3p  (1242) XXGTCDIVRXXLSEAXYSDXXMAPAADMFXXGVXLQVLKKGTXFPSRAXK
                         1351                                              1400
Sch. sp.  9695 Pfa3p  (1272) LXELFHXYXSFXXMFXDELARXEXRIFSXXLXEVWAXTXDFYITXXNPE
Sch. sp. 20888 OrfC   (1341) LXELFXXYXSFXXMFPAELEPXEXRIFKXXLQEVWXETKXFYIXGXKNPE
Thr. sp. 20892 OrfC   (1306) LXELFXXYXSFXXMFXEELXPXEXRIFSXXLXEVWQXTSXFYXHXXKNPE
Thr. sp. 10212 Pfa3p  (1292) LXELFXMYNSFXDMFKSELXPXEXRIXXXLXEVWXETKXFYXXXXNPE
                         1401                                              1450
Sch. sp.  9695 Pfa3p  (1322) XIRKAXNEDXXKLKMSLCFRWYLGLXSXWANXXGXAXRTMDYQXWCGPAIGX
Sch. sp. 20888 OrfC   (1391) -XXXAEHDXXKLKMSLCFRWYLGLXSRWAKMGAPXRXMDYQXWCGPAIGX
Thr. sp. 20892 OrfC   (1356) -XXXAASDGKXKMSLCFRWYLGLXSXWANSGAQXRXMDYQXWCGPAIGX
Thr. sp. 10212 Pfa3p  (1342) XIEHAXKKDXXKLKMSLCFRWYLGLXSXWANXXGXKXRSMDYQXWCGPAIGX
                         1451                                              1500
Sch. sp.  9695 Pfa3p  (1372) XNDFXADXYLDXXVXEXPDVXQINXQILSGAAXXRXLXXLA--XXX
Sch. sp. 20888 OrfC   (1440) XNDFXXXYLDPXVXNEXPVXQINXQILXGAXXLRRXNXXXNX--XXX
Thr. sp. 20892 OrfC   (1405) XNDFTXXYLDXTVXKXXPVAQINXQILQGAAXLKXXGVXXFXRMLLQA
Thr. sp. 10212 Pfa3p  (1392) XNDFXXXYLDPXVXXXPVXQINXQILXGAXXLXRXHX--XXX
                         1501              1517
Sch. sp.  9695 Pfa3p  (1420) XXXXFXYXPDHXL-
Sch. sp. 20888 OrfC   (1488) XXXAAXVXEXXXXL-
Thr. sp. 20892 OrfC   (1455) IXXPXXYVPXXPL-
Thr. sp. 10212 Pfa3p  (1440) VXXXFXYXPESTL-
```

MDTRIAIVGMSAILPSGENVRESWEAIRDGLDCLSDLPADRVDVTAYYNPEKTTKDKIYCKRGGFIPEYDFDAREFGLNMFQMEDSDANQTISLLKV
KEALTDANIPAFSSGKKNIGCVLGIGfGGQKASHEFYSRLNYVVDKVLRKMGLPEEDVAAAVDKYKASFPEWRLDSFPGFLGNVTAGRCCNTFNM
EGMNCVVDAACASSLIAVKVAIEELLYGDCDAMIAGATCTDNSIGMYMAFSKTPVFSTDPSVKAYDAATKGMLIGEGSAMLVLKRYADAVRDGD
TVHAVIKGCASSSDGKAAGIYTPTISGQEEALRRAYARANVDPATVTLVEGHGTGTPVGDKIELTALSNLFSKAFSANGGGAEEAEQVAVGSIKSQI
GHLKAVAGLAGLVKVVLALKHKTLPQTINVDKPPSLVDGTPIQQSPLYVNTMNRPWFTPVGVPRRAGVSSFGFGGANYHAVLEEFEPEHESAYRY
NNLPQVALLHAGDVATLAATVRAKLALATAEQEEARVVKNADYIAYHRFLDECKLRGAVPQAHARVGLLVRDLSSLIAVLEAAAAKLAGEESAT
EWTVSVATGEAAFRVRGVATEANVAALFSGQGAQYTHMFSDVAMNWPPFRESVAAMDRAQRERFGRPAKRVSSVLYPRKPYGDEPRQDHKEIS
QTRYSQPATLACSVGAFDIFKAAGLAPSFAAGHSLGEFAALYAAGSLDRDAVFDLVCARAKAMSDFTAQASSSGGAMAAVIGAKADQLSLGGAPD
VWLANSNSPSQTVTGTAEAVAAASDKLRCSGNFRVVPLACEAAFHSPHMRGAEQTFASALAQAPVSAPAAARFYSNVTGGAAVTSPADVKTNLG
KHMTSPVQFVQQVRAMHAAGARVFVEFGPKQVLSRLVKETLGEAGDVVTVAVNPDSAKDSDTQLRQAALTLAVAGVPLKDFDRWQLPDATRLE
PVKKKTLRLSAATYVSAKTLRQREAVLNDGYTVSGATAVVKEVDTANEERLVRQAQDLQRQLAEASTAAQAAQSKVAELERTIQDLERKVQQ
QQQEKGENSDSNAAAEVLRRHKELLQRMLQDCDEQAVPVATVVPTPTSSPTPTSSPVSGNSKSTRGSADLQALLAKAETVMAVLAAKTGYEAD
MVEADMDLEAELGIDSIKRVEILSEVQGQLGVEAKDVDALSRTRTVGEVVDAMKAEIVAASGGSAPAASAAPTPAASTAPSADLQALLSK
AETVVMAVLAAKTGYEADMVEADMDLEAELGIDSIKRVEILSEVQGQLGVEAKDVDALSRTRTVGEVVDAMKAEIVAASAGSAPAPAVPSAPAA
SAAPTPAASTAPSADLQALLSKAETVVMAVLAAKTGYEADMVEADMDLEAELGIDSIKRVEILSEVQGQLGVEAKDVDALSRTRTVGEVVDAMK
AEIVAASGGSAPAPAVPSAPAASAAPTPAATAPSADLQALLAKAETVVMAVLAAKTGYEADMVEADMDLEAELGIDSIKRVEILSEVQGQLGVE
AKDVDALSRTRTVGEVVDAMKAEIVAASGGSAPAPAVPSAPAASAAPTPAASTAPSADLQALLSKAETVVMAVLAAKTGYEADMVEADMDLEA
ELGIDSIKRVEILSEVQGQLGVEAKDVDALSRTRTVGEVVDAMKAEIVAASGGSAPAAPSAPALLPTLFGSECEDLSL
AKTGYEADMVEADMDLEAELGGARPVVVDDGSALTSSLVSSLGDRAVLLQVQSSSACSPRSTTHKLVTVADRSEAALQAALTSVEAQFGKVGGFVFQF
TFPVITTLPLPAELVLAEGGARPVVVDDGSALTSSLVSSLGDRAVLLQVQSSSACSPRSTTHKLVTVADRSEAALQAALTSVEAQFGKVGGFVFQF
GDDDVQAQLGWALLAAKHLKTSLSEQIEGGRTFFVAVARLDGQLGLSGKSTTATVDLSRAQQGSVFGLCKTLDLEWPAVFCRGIDLAADLDAAQ
AARCLLGELSDPDVAVRESGYSASGQRCTTTTKSLTTGKPHQPISSSDLFLVSGGARGITPLCVRELAQRVGGGTYVLIGRSELPTTEPAWAVGVESG
KPLEKAALAFLKAEFAAGRGAKPTPMLHKKLVGAVVGAREVRASLAEITAOGATAVYESCDVSSAAKVREMVERVQOOGGRRVSGVFHASGVL
RDKLVENKSLADFSAVYDTKVGGLINLLACVDLAQLRHLVLFSSLAGFHGNVGQSDYAMANEALNKLAAHLSAVHPQLCARSICFGPWDGGMVT
PALKANFIRMGIQIIPRQGGAQTVANMLVSSSPGQLLVGNWGVPPVVPSATEHTVLQTLRQSDNPFLDSHVIQGRRVLPMTLAVGYMAHQAQSIYA
GHQLWAVEDAQLFKGIAIDNGADVPVRVELSRRKEEQEDAGKVKVQVLLKSQVNGKSVPAYKATVVLSPAPRPSVITRDFDLTPDPACTEHDL
YDGKTLFHGKAFQGIEQVLSATPKQLTAKCRNLPLTPEQRGQFVVNLSQQDPFQADIAFQAMLVWARMLRQSAALPNNCERFDFYKPMAPGATY
YTSVKLASASPLVDSVCKCTVAMHDEQGEVYFSARASVVLNKTLTY (SEQ ID NO:2)

MPCDNIAVVGMAVQYAGCKNQDEFWDTLMRKEINSSPISAERLGTRYRDLHFHPQRSKYADTFCNDRYGCVDASVDNEHDLLADLARRALLDAG
INLDDASTTANLRDFGIVSGCLSFPMDNLQGELLNLYQVHVENRVGAQRFFRDSRPWSERPRAVSPEASDPRVYSDPASFVANQLGLGPVRYSLDAA
CASALYCLKLASDHLLSRSADVMLCGATCFPDPFFILSGFSTFQAMPLGGPDDNPLSVPLRQGSQGLTPGEGGAIMVLKRLEDAVRDGDRIYGTLLG
TSLSNAGCGLPLSPHLPSEKSCMEDLYTSVGIDPSEVQYVECHATGTPQGDVVEVEALRHCFRGNTDHPPRMGSTKGNFGHTLVAAGFAGMAKVL
LSMQHGTIPPTPGVDRSNCIDPLVVDEAIPWPYSSAQARAGKPGDELKCASLSAFGFGGTNAHCVFREHRQIAATATASPVLPEVTPGPIAIIGMDAT
FGTLKGLDAFEQAIYKGTDGASDLPSKRWRFLGADTDFLTAMGLDAVPRGCYVRDVDVDYKRLRSPMIPEDVLRPQQLLAVATMDRALQDAGM
ATGGKVAVLVGLGTDTELYRHRARVTLKERLDPAAFSPEQVQEMMDYINDCGTSTSYTSYIGNLVATRVSSQWGFTGPSFTVTEGANSVYRCLEL
GKFLLDTHQVDAVVAGVDLCATAENLYLKARRSAISRQDHPRANFEASADGYFAGEGSGALVLKRQADVGSDDKVYASVAGLTCAAQPAEAV
SPLLQVIHNDDNEKRVVEMVELAADSGRHAPHLANSPLSAESQLEQVSKLLAHQVPGSVAIGSVRANVGDVGYASGAASLIKTALCLHNRYLPAN
PQWERPVAPVSEALFTCPRSRAWLKNPGESRLAAVASASESGSCFGVLLTIDEYATHESSNRLSLDDAAPKLIAIRGDTVDDIMAKVNAELALLRAH
AETGSATDDDPAAAVAFTAHRLRFLRLVGETVASHGATATLCLALLTTPEKLEKELELAAKGVPRSAKAGRNWMSPSGSAFAPTPVTSDRVAFMY
GEGRSPYYGVGLDLHRLWPALHERINDKTAALWENGDSWLMPRAVDADSQRAVQTAFDADQIEMFRTGIFVSICLTDYARDVLGVQPKACFGLSL
GEISMLFALSRRNCGLSDQLTQRLRTSPVWSTQLAVEFQALRKLWNVPADAPVESFWQGYLVRASRAEIEKAIGPDNRFVRLLIVNDSSSALIAGKP
AECLRVLERLGGRLPPMPVKQGMIGHCPEVAPYTPGIAHIHEILEIPDSPVKMYTSVTNAELRGGSNSSITEFVQKLYTRIADFPGIVDKVSRDGHDVF
VEVGPNNMRSAAVSDILGKAATPHVSVALDRPSESAWTQTLKSLALLTAHRVPLHNPTLFADLYHPTFLTAIDSAMQEPPPKPNRFLRSVEVNGYFC
PDGISKQVAAASAKPSTHCMVRLHPAKAVVAAAGAVVADSTPVVKAKQTSSSLLVGDDAFLRCYDVDWPLYMGAMAEGISSVDLVVAAAEAR
MLASFGAARLPMDQVELQIREIQQRTSNAFAVNLMPGPDEAATVDALLRTGVSIVEASGYTGALSADLVRYRVTGLRRTSCGASVSATHRVVAKV
SRTEVAEHFLRPAPAAVLEALVAAKQITPEQAALASRVAMADDVAVEADSGGHTDNRPIHVLLPLVVAQRNRWRHLVDTPVRVGAGGIACPRA
ALLAFSLGAAFVVTGSVNQLAREAGTSDAVRLLLATATYSDVAMAPGGVQVLKKQTMFAARATMLAQLQAKFGSFDAVPEPQLRKLERSVFKQS
VADVWAAAREKFGVDATAASPQERMALCVRWYMSQSSRWATEATSARKADYQIWCGPAIGSFNDFVRGTKLDATAGTGEFPRVVDINQHILLGA
SHYRRVQQQQQDDDVEYHV (SEQ ID NO:4)

FIG. 11

(SEQ ID NO:5)

FIG. 12

MTSSKKTPVWEMSKEELLDGKTVVFDYNELLEFAEGDVGQVFGPEFDIIDKYRRRVRLPAREYLLVSRVTLMDAEVNNFRVGSRMVTEYDVPVNG
ELSEGGDVPWAVLVESGQCDLMLISYMGIDFQCKGDRVYRLLNTSLTFFGVAHEGETLVYDIRVTGFAKGAGGEISMFFFEYDCFVDGRLLIEMRD
GCAGFFTDAELAAGKGVLKTKAELAARAQIQKQDIAPFAPAPCSHKTSLDAREMRLLVDRQWARVFGSGMAGIDYKLCARKMLMIDRVTHLDPR
GGAHGLGLLIGEKVLERDHWYFPCHFVRDEVMAGSLVSDGCSQLLKVYMLWLGLHTTVGAFDFRPVSGHANKVRCRGQISPHKGKLVYVMEIKE
MGFDAKTGDPFAIADVDIIDVNFEEGQAFAGVEDLHSYGQQDLRKKIVDFKGIALSLQKRKEQQKESMTVTTTTTSRVIAPPSGCLKGDPTAPT
SVTWHPMAEGNGGPGPTPSFSPSAYPPRAVCFSPFPNNPLDNDHTPGQMPLTWFNMSEFMCGKVSNCLGPEFARFDASKTSRSPAFDLALVTRVTS
VADMEHGPFYNVDVNPGQGTMVGEFDCPADAWFFGASSRDDHMPYSILMEIALQTSGVLTSVLKAPLTMDKDDILFRNLDADAELVGDAMPDVR
GKTIRNFTKCTGYSMLGKMGIHRFTEELSVDGAVFYKGSTSFGWFVPEVFESQTGLDNGKPRLPWYRENNVAVDTLSAPASASSAQGQLQRRG
SQAQFLDTIHLAGSGAGVHGQGYAHGEKAVNKQDWFFSCHFWFDPVMPGSLGIESMFQLVEAWCVKQGLAARHGIAHPVFAHAPGATSWKYRG
QLTPKNDRMDSEVHIKSVAAFSSWDVVADGFLFVDGLRVYSADNLRVRIQTGAGHVEEQEVAAKATTKNSSIADVDVADIQALKQALLTLERPL
QLDAGSEVPACAVSDLGDRGFMETYGVVAPLYSGAMAKGIASADLVIAMGQRKMLGSFGAGGLPMHVRAGIEKIQAALPAGPYAVNLIHSPFD
ANLEKGNVDLFLEKGVRVVEASAFMELTPQVVRYRATGLSRDARGGSVRTAHKIIGKVSRTELAEMFIRPAPQAILDKLVASGEITPEQAALALEVP
MADDIAVEADSGGHTDNRPIHVILPLILSLRNRLQRELKYPARHRVRVGAGGIGCPQAALGAFHMGAAFVVTGTVNQLSRQAGTCDNVRRQLSR
ATYSDITMAPAADMFEQGVELQVLKKGTMFPSRAKKLFELFHKYDSFEAMPADELARVEKRIFSKSLAEVWAETKDFYTRLNNPEKIRKAENEDP
KLKMSLCFRWYLGLSSFWANNGHADRTMDYQIWCGPAIGAFNDFIADSYLDVAVSGEFPDVVQINLQILSGAAYLQRLLSVKLAPRIDVTEDDLF
TYRPDHAL (SEQ ID NO:6)

```
AATTGGATATGGAATTGGAAACCGAACTTGGTATTGATTCTATCAAGAGAGTAGAAATTCTTTCTGAAGTTCAAGCTCAATTGAGTTGTTGAAGCTAAAGATGAGATGCTCTTA
GTAGAACTCGTACTGTTGGTGAAGTCGATTGATTGATGCAATGAAAGCCGAAATTTCTGGTGGTCAGCAGCTGCTCGTTCAAGTTCAAGTTGCAGCTCCTACTCAAATAGTTGCTCTGTTC
AAGCATCTGCTCCTGTTGATTCTGTTGATTGTTGGCAAAAGCGGAACAAGTTGTATTGGAAGTGTTAGCATCCAAGACTGGTTATGAAACTGAGTTGATTGAATTAGATATGGAAT
TGGAAACCGAACTGGATTGGATTCTATCAAGAGAGTAGAAATTCTTCTGGTGGTCAACCAGCTGCTCCTGTTCAAGTTGCAGCTCCTACTCAAATAGTTGCTCTGTTCAAGTATCTGCTCCTGT
TGGTTCTGGTTGATTGTAGCAAAGGCGGAACAAGTTCTTTCTGGAAGTATTGGAAGTTCAAGCTCATGAAGACTGAGTTGATTGAATTAGATATGGAAATTGGAAACTGAACTTG
GTATTGATTCTATCAAGAGAGTTGCTGGTGGTCGTGTCCTGTTCAAGTTGCAGCTCCTGTTCAAGTTGCCAGTAGTTGCTCCTGTTCAAGTATCTACTCCTGTTGTTGGTGAAGTGATTG
ATGCAATGAAAGCCGAACAAGTTGTATTGGAAGTGTTAGCATCAAGAGTGTTGAAGCTCCTTAGTAGAACTGTTAGTATGGAAACTGAAGCTCGTTGGTGAAACTGAACTTGATTCATCA
AGAGAGTAGAAATTCTTTCTGAACCAAGCTCTCTGTTCAAGCTGCTCGTTCAGCTCGTGAAGTAAAGATGTTGAAGCTAAAGATATCTACTCCTGTTGATTCTGGTTGTTAGCAAAGGCGAAC
GAAATTTCTGGTGCTCAACCAAGCTATTGGAAGTATTGGCATCTAAGACTGGTTATGAAACTGAGTTGATTGAAACTGAACTGGATTCATCAAGAGAGTAGAAATT
CTTCTGAAGTTCAAGCTCAATTGAATGTGGAAGCTAAAGATGTGGAAGCTAAAGCGACATCCGTAGTAGAAGCTCCTAGATAGAACTCGTAGTTGGTGAAGTGATTATTGCAATGCAAAGCCGAAATTGCTGGTGA
TCAACCTGCTCCAGCTGTAGTTCAGTTGAATGGATTGTAGCGACAACCCTGCACTTTTGCCAAAGCGGAACAAGTTGAATCAAGAGAGTAGAAATTCGTCCGAAGTTGCCAACCGGTTGCATCCAAGACCGGTT
GAAACTGAGCTGATTGAATTGGATATGGAAACTGAACCCGTACTGTTCGGAAAGCTAGAACCGTATTCAATCAAGAGAGTTGCTGGCAGTGCGTTGCAACTTGGATGTCAACAAT
AAGCATGTACGACTGCTTGTGGTAGAACCAGATAGAAGATGAAGACTTATTTTATACGATCATGTATACGGAAGCGAATGTGAGATCTTAGTCTGAGTTTCATCCGTAAAGAGCATCCGCGGG
TATGGAGGAGCACAGATGATGAAGCTAAGAGCAATTGCTGAAAGGCCAATTGTTATTGTGGATTGTGGAACAAAGCTTACAACTGAACTTGCAAAAGCTATTGGAGAACCTGCCGTTGGTGCTA
CTGATAAACTTTGTTGTTGGATAACATTGCTGAAAGGCCAATTGTTATTGTGGATTGTGGAACCATTGTTAAATCATTTACTCTAGGAAATACAGGAAATGAAAGTGGAATGTTCAAGCATTGATCTTCGTAT
CATTCAGTGCACAGAGCTTGGTATCCGGTGATTCGTTGGTGTAAATCATTTCACTCTAGGAAATACAGGAAATACAGGAATGAAAGTGAGATCGAAAGAGTGTCAAGCATTGATCTTCGTAT
GGAAAAATTGCTGGCTTTGTTTTATCAACATTTCATGATAGCGACTATGGTATATGCAACTTGGTATGGACAACAATGCTCAGTCAGTCAAGGACAATGCAAGGAATCAAGGAAGATCGGTATTCCGTATGACAAGCCCGAT
GTGGCTATCTTTGGTTGTGCAAAACTTGGATTGAATGGCTAAATTGCTGGTGATTTCTCGTGGTATGTTCGTGAAGGTGCATTGAGCCTAAGGAATCATGCCGTATCGCCCAAC
TGATGAGATTCTTGTCGCAAATCTTTCCATTCGGGAATCTGGTTACACGATTAGCGCAGGAAAGATTCACAACTTCCACAAATGGTTACTGGAAAGCCCTCATGCTCCGAT
TAAGAAGAACAGGATGCTTCCTAGGTACAGCTTCCTAGTAGCGGGCTCTGATATTCCACTTTGTATTCGTAAAGCAGTGAAGGTGCACCTTACATTTTGATGGGTCGATC
AGCTTTGGCTGATGAACCCTGTGTGGCTAAATGGAACTTCGGCTAATGGCTAAAGTCCGGTATTAGGAGGTTAGAGCATCTAGTCGTATTACATAGTATGGAGGGACGTATATATTTGCTCTTGCGAT
CTCAAAAGTTCACAAATCTTGATTGATAAGTGCTCAGTGCAGTGCAAAAAGTAAGGCATCTAGTTCGTATTACTGTATTTGCTGCAGCATTTACTGGCAGATGAAACATGAATTTGTATGTAGCCAGTCAGTCAATTGTGGTTAGTTC
GAACAAAACTTGGATGATTTTCAACGCAGTATGGAAACTAACTGGACTGAACTTGCTGTCAGCAGTGAACATGAATTTGTTAGATTGGTGCAGCTATTCTCAATTGTGTTAAATCT
TTGGCTGGATATCATGGAAATGTGTTGCAATCTGATTATGCAAATGCTAACGAATCACTTAACAAGATTGGTTTTAGATTGGGTGCAGCTATTCTCAATTGTGTTAAATCT
ATTTGTTTGGATGGTGGAATGGTAACTCCAGCTTGCAACTTTGAAAAAACAATTCAATCAATGGGTGTCCAGATTATTCTCTGAAGGGCGCGGAGACTGTTGCAAG
AATAGTCTTATCTTCAACTCCTCTCAAGTTGTAGTTGGCAACTGGGGTGTTCCTCCAGTTGCCAACTTTGTCAACTATTGTTCAAACTTTTACCCTGAGTTAAATC
CATTTCTAAAGTCCATCAAATTCATGGATGTAAAATGTTTGCCTATGACTGTAAAATCTGGTTAACTGTATATCTGCTCACTGGTTCATCATTTGGTGGCAGATGCTCCTCATTGCGGGAGT
TGAAGATGCTCAAATTGCTCAGGGTGTTGTAATTGACCATGCCATACAAAGCAGTCAGTTGAATTTGAAACAAGTAGAACCTGCGTTATTTGAAAGATTTTCATTGCAAGAATCT
AATTCTCGCAGTGCTGATGAATGCCATGATATAAAATTTGTTCATGGTCCATTATTTGCTGTGAAAATTCCAGGTTTCTTGCATAACCCAATTCATGTATTCTACTACAACCTCAATGTA
CCAATATTGATTTGACTGCTACTCAAACAATTGTTGAAAGAGTTGGAATATCTATAAAACCATAGCACCTGGTGAAAAGTATTACACTCTTTGGTTAGAAATTTAA
GGAATAAGTGGCATCTTTATATGCACGAATGAACAAGGAGAAGTATTTCTATCTGAAGAGCTAGTGCTTGTGAATGACAAGATGAAGTTTTAG
TCTCAAGTCTGTATTTTATATGCACGAATGAACAAGGAGAAGTATTTCTATCTGAAGAGCTAGTGCTTGTGAATGACAAGATGAAGTTTTAG
```

(SEQ ID NO:68)

MEDQRIAIVGLSAILPSGENVRESWEAIRDGLNCLSDLPADRVDVTAYYNPTKGVKDKIYCKRGGFIPEYEFDSREFGLNMLQMEDSDANQTLTLLKVKEALDDANIPAFTNEKKNIG
CVLGIGGGQKASHEFYSRLNYVVVDKVLRKMGLPDEDVETAVEKFKANFPEWRLDSFPGFLGNVTAGRCTNTFNMEGMNCVVDAACASSLIAIKVAIDELLHGDCDAMIAGATCTD
NALGMYMAFSKTPVFSTDQSCLAYDEKTKGMLIGEGSAMFVLKRYADAVRDGDTVIIAVIRSCSSSSDGKASGIYTPTISGQEEAILRAYRRAGVSPNTITLVEGHGTGTPVGDKIELT
ALRNVFDKAYGPGHKEEVAVGSIKSQIGHLKAVAGCAGLVKLVMALKHKTLPQSINVENPPNLVDGTVISDTTLYINTMNRPWITKPGVPRRAGISSFGFGGANYHAVLEEFEPEQTK
PYRLNVSAQPMLLHAVNANSLQKLLCEDQLKLLKESREKCVNTKNTDYVAFSKFQDSFKLKGSVPSQHARVGFASKSIEDTISILSAIVNRFQKDITTTSWALPKEGAIFRSTALINDNKS
VAALFSGQGAQYTHMFNDVAMQWPQFRLCVNDMEKAQEEVINDKSVKRISQVMFPRKPYARESPLDNKEISKTEYSQTTTVASSVGLFEIFRDAGFAPAFVAGHSLGEFSALYAAGL
IDREDLFKLVCNRAMAMRDAPKKSADGAMAAVIGPNASSIKLSAPEVWVANNNSPSQTYITGANSGVQAETSKLKTQGFRVVHLACDGAFHSPHMENAEKQFQKALSAVKFNKPTG
SSPKIFSNVTGVFTDPKTALSRHMTSSVQFLTQIKNMYAAGARVFHEFGPGQVLSKLVNEIFPGDTSVLTVSVNPASAKDSDIQLRQAAVQMAVAGVALTDFDKWELKDPTRMKEFP
RKKTTLTLSAATYVSKKTLQERERIMNDGRTVSCVQRIENTNTGELEKLKKQLQDKENEVVRVQALATQASADLQNTKAELQKAQATKSSNAASDAVVAKHKAILLAMLEELETGK
AVDYSSFSKGQVASPATVRVVSAPVQAAAPVQVSASVDSGLLAKAEQVVLEVLASKTGYETELIELDMELETELGIDSIKRVEILSEVQAQLNVEAKDVDALSRTRTVGEVIDAMKAE
IAGGQPAAPVQVAAPTQVVAPVQASAPVDSGLLAKAEQVVLEVLASKTGYETELIELDMELETELGIDSIKRVEILSEVQAQLSVEAKDVDALSRTRTVGEVIDAMKAEIAGGQPAAP
VQVAAPTQVVAPVQVSAPVDSGLLAKAEQVVLEVLASKTGYETELIELDMELETELGIDSIKRVEILSEVQAQLSVEAKDVDALSRTRTVGEVIDAMKAEISGGQPTAPVQVAAPTQI
VAPVQASAPVDSGLLAKAEQVVLEVLASKTGYETELIELDMELETELGIDSIKRVEILSEVQAQLSVEAKDVDALSRTRTVGEVIDAMKAEISGGQPAAPVQVAAPTQIVAPVQASAPVDSGLLAKAEQVVLEVLASKT
GYETELIELDMELETELGIDSIKRVEILSEVQAQLNVEAKDVDALSRTRTVGEVIDAMKAEISGGQPTAPVQVAAPAPVVAPVQVAAPVKVSTPVDSGLLAKAEQVVLEVLACKTGYETELIELD
MELETELGIDSIKRVEILSEVQAQLNVEAKDVDALSRTRTVGEVIDAMKAEIAGDQPAPAVVPVQAKSGVANPALLAKAEQVVLEVLASKTGYETELIELDMELETELGIDSIKRVEILSEVQAELSVE
AKDVDALSRTRTVGEVIDAMKAEIAGSAVTVATLDDSTIMEETDDEDEDEFILYDHVYGSECEDLSLSFSSVKSIPRADKLLLDNIAERPIVIVDCGTKLTTELAKAIGERAVVATSAQS
LVSRGFVGKSFTLGNTEESEIEKMVSSIESSYGKIGGFVYQHFHDSDYGMQLGWALMAAKHLKESLNDPIKNGRITFFLAVARMNGKLGMDNASVHDQGIVESCGIAERGAIFGLCKT
LDLEWPNVFARGVDIAEGMSYSLAAELIVDEISCANLSIRESGYTISGERFTTEAHKLVTGKPHAPIKKKDAFLVSGGARGITPLCIREHAKAVKGGTYILMGRSALADEPLWANGKSGK
DLDKAGLAFLKEEFAAGRGSKPTPKVHKSLIDKV1GIREVRASIANIEAHGAKAIYLSCDVSSAEKVKAAVQKVEKEHLVRITGIVHASGVLRDKIVENKTLDDFNAVYGTKVTGLVN
LLSAVNMNFVRHLVMFSSLAGYHGNVGQSDYAMANESLNKIGFRLGAAYSQLCVKSICFGPWDGGMVTPALKKQFOQSMGVQHPREGGAETVARIVLSSNPSQVLVGNWGVPPVSP
LSKSATIVQTFTPELNPFLKSHQIHGKNVLPMTVAIGYLAHLVKNFYAGHHLWGVEDAQLFSGVVIDHAVQAQVKLTEQSLDDDGKVKVQAVLTASNDNGKMVPAYKAVIVLGKTS
RPAFILKDFSLQESNSRSADELYDGKTLFHGPLFRGHIKLLNVSDTSLTTQCTNIDLTATERGQFADIEPVNPFMADAAFQAMLVWVRNLRNSASLPNNCERVDIYKPIAPGEKYYTTLQ
ALGNTSGSVLKSVFYMHDEQGEVFLSGRASVVNDKMEF (SEQ ID NO:69)

TATCCGCATTTATGTCATTAACCCCTCAGGTTGTACGATACAGAGCCGCTGGTTGGCCAAAGCAAGAGATGGATCTGTGAAAATTCAAAATCGTATTATTGCCAAAATTCAA
GAACAGAGTTAGCGGAACTGTTCTTGAAACCAGCACCCAAAAATATTTGAGATGCATTGGTTGCGGATGGATCTATTAGTCAAGAACAAGCCCAACTTGCATTACTTGTGCCA
ATGGCTGATGATATTACTGTGGAAGCTGATTCTGGTGGCATACTGACAATCATGTTTGTTACCTTTGATAATTCAGCAAAGAAATAGAATTTGTAAACAATAC
CCAAAACATTTAAAAGTTCGAATCGGAGCAGCTGGTGGTTGATGCCCGAAGGCAGCATTTGCTGCGTTGAGATGGGTCTGCATACATTGCAACTGAACGGTAAATCA
ACTTTCAAAGGAAGCAGGTACTTGTGACTATGTAAAGTATTGAATAAAGCTACATATTGAATAAAACTATACGATTGTTCAAAAATACAAATCGATTGAGGAATTACCAGCAGATGTTCGATCATGGTGTTGAATT
ACAAGTTTGAAGAAAGGTACTATGTCTTCCTTCACGTGCTAAAAAGTCGTTGATGAGACCAAGAATTACTATATCGTTTACATTCTCCGAAAAAATTGAACGTGCTGAAAGAGATGCAAAA
AGCAAAAAGTTTTCAAAAGTCGTTTGATGAAGTATGGGATATGGGATTACAGAAATTACTGTTTACATTCTCCGAAAAATGGGCTAATACCGGTGAATCGGTGAAGAGTGCAGGATTATCAAATTGGTGTGGTCCAGCAATTGGG
CTTAAAATGTCGTTATGTTTCGTTGGTATTTGTCGAAAGTCTTCCAGATCCTGAGATTTTGGATCGTGAAGTGGTAGTTTCCAAGTGGTGTCCAAGTGTTCCAAGTGTTCCAGATTAATAAACATATTTTACGTGGTGCTTGTTTCTATCAAA
TCATATAATGATTTTGCGAAAGGATCACCATGTTTGGATCCTGAGATTTTGGATCGTGTTCCAAGTGGTAGTTTCCAAGTGTTCCAGATTAATAAACATATTTTACGTGGTGCTTGTTTCTATCAAA
GACTCTCTCAGTTGAAATATCTGAATTTAACTATGAGGAATTAGATACGTTAACATACTCTGCATCGAATTTATTTAA (SEQ ID NO:70)

AGGATGCCATTAAGCAGATCAAGGCTGAGCTTGGCAACGGTCCCTTTGCCGTCAACCTCATCCACTCGCCTTCGACCCCTGCTTGAGAAGGGCAACGTTGACCTTTCCTCA
AGTACAACGTTCGCTTTGTCGAGGTGAGCGTCGTTCATGAGCCTCACCCCCAGGTCGTTCGCTACCGCGTCGCTGCCGGCCTTGCCAAGGCCCGTGACGGCTCGGTCAAGATTCAG
AACCGCATCATCGCCAAGATTTCGCGCACGGAGCTGGCCGAGCTCTTCCTCAAGCCGAGAACATCCTCGTTGCCGACGGCTCGATTTCCCAGGAGCA
GGCTCAGCTGCGCGTCCTCGTCCGATGACATCACCGGTGAGGCCGACTCCGGTGGCCACACGACAACCGCTCCATTCATGTGCTCCTCCCCTCATCATCCAGCA
GCGCAACCGCCATTTGCAAGCAGTACCCGAGCTCAAGGTCCGCCGGTGCCATCGGCGCTGCCGGTGCCATCGGTTTGCCGCCCTTTGAGATGGGTGCGGCCT
ACATCGCCACGGGCACCGTTAACCAGCTCTCGAAGGAGGCCGGCACTGCGACTAGGTGCGCAAGGTGCTCAACAAGGCCACCTACTCCGACGTCACGATGGCTCCCGCTGCC
GACATGTTCGACGACGAGGTCAAGAAGCTGAGCAGCTCCAGGTTCTCAAGAAGGGCACCATGTTTCGTCGGCGCCAAGAAGCTCTTTAAGAAGTACAAGTCGATCGAGGAGCT
CCCTGCCGACGAGGTCAAGAAGCTGGAGCAGCAGAAGGTTTTAAGAAGATCGTTCGACGAGAGCTAAGAACTACTACATTAACCGCTCCACTCCCTGAGAAG
ATCGAGGCGCGCGGAGCGTGACGCCAAGCTGATGCCCATCGGCCCCCGACGACTTCGCGTACAACGACTTCGCGTACCTGAAGGGCTGCCCCTGACCCTGACCCGTGTCCAGGACTA
CCAGATCTGGTGCGGCCCCGCCATCGGCTCGTACAACGACTTCGCGTACCTGAAGGGCTACCTTAACTCGAAGTACCTTAACTCAACTACGAGGAGCTCGATACGCTCACCTACGCTCAGGCGCTAGCAACTTTATCTAA
TATTCTGCGGGCGGCCTTGCTTCTACCAGGCGTCTTTCGCAGCTCAAGTACCTTAACTCAACTACGAGGAGCTCGATACGCTCACCTACGCTCAGGCGCTAGCAACTTTATCTAA (SEQ ID NO: 121)

FIG. 18

MVKLSVGDNICHDQRVAVVGMAVMYAGCQNQHEFWQSLQGKNMNSKSISQNRLGSEYREEHFKPERSKYSDTFCNERYGCIDENVQSEHELLLKLAKDAIADTFKGSIDLNKTGIVS
GCLSFPMDNLQGDLLNLYQCHIEKKIGPNALKDVNLWSKRTTNGKDDKKAYFDPASFVAEQLDMGPLHYSLDAACASALYVLRLAQDHLLSGAADTMLCGASCLPEPFFILSGFSTF
HAMPLSGDVSAPLHKTSQGLTPGEGGAIMVLKRLNDAIRDGDRIYGTLLGAELSNAGCGLPLSPHMPSEFDCMEKALQRVHRLPSSIQYVECHATGTPQGDKVEIDAMTKCFGEHLPR
FGSTKGNFGHTLVAAGFAGMCKVLLSMQYGEIPPTPGLENPDNIMHDLVVTETIPWPNTNGDLKRACLSAFGFGGTNAHAVFEEYRSDLQANKTLENESKSHEIFSSFKJAIVGMESEF
GTLKGLQEFERAIYNGGHGACDLPENRWRFLGEDKEFLQACCGLQKLPRGCYIKEVETDFKRLRLPMIQEDILRPLQLLAVSIHDRALNASGVKPNGKVAVLVGLGTDLELYRHRARVA
LKERLQTAVKEDIPLLEKLMNYVNDRGTSTSTYSYIGNLVATRVSSLWGFTGPSFTITEGENSVYRCLDLGRWFLANGEVDAVVVAGVDLCGSAENLFVKSRRSKVSTQNEPFANFES
NADGYFAGDCCGALVLKRLSDCTDSTEKIYATYDSIAVGDEVGPTIKQALKNASIAAKDIELAELSASSGKIIIISGRITCEDELNELGEIFNEGIQRVAIGSVKANVGDVGYASGAASLI
KTALCLYNRYLPKLPNWNKPTKDVEWSKSFFVCEHSRAWLKNVDENRHAVVSGVCENGSCYGIVMSDVQGHHEESNLVSLDKNEPKVLGIYGDSVDDILVQLNKYLEKFLQETGT
AAAQKVKSPTIDIDSNVFAEMLNLPQDKNKKFAVALVTTPNKLQREIELAVKGIPRCVKAKRDWCSPSGSIFACNPLKSDNIAFMYGEGRSPYAGLGYDLHRIWPMLHELVNNRITTE
LWDQGDSWYLPRSSSVAEKEKVFGDFDKNQIEMFRLGIFVSMCFTDMATELLGLKPKAAFGLSLGEIISMLFAFSKKNTKLSKELTRRLKEAKVWASQLAVEFAAIRDLWNIPADKSID
EFWQGYFVYANRTLVENTIGENKFVRLLIVNDSQSCLIAGKPDECQKVIEKLHLKLPAVPVTQGMIGHCPEAIPYLDQISHIHEMLEIPKPENVKLFTTSENRELVSMKDSVSKLVAEIY
QHVADFPNIVNKVKETCKTDIFHELGSNNYRSGAVKTILGPEIVSVAIDRQNETAWGQLMKMVASLISHRVPGVELKKLYHPELLKFDPQAKPNRFIRNIELNGFFDRTNIIVDKQLSPA
DPKLAEIVNNRNMPKDNVYPIERVKTMIKAEPANLQVSVGSKPVVTERISSDDNLFEKLSEITKSFDGVNACTEAMLGDSGFLKTYEVDYPLYTGAMAKGIASADLVIAAGKSKILA
SFGAGGLALQVVEDAIKQIKAELGNGPFAVNLIHSPEDPSLEKGNVDLFLKYNVRFVEVSAFMSLTPQVVRYRAAGLAKARDGSVKIQNRIIAKISRTELAELFLKRAPKNILDALVAD
GSISQEQAQLALLVPMADDITVEADSGGHTDNRPIHVLPLIIQQRNRICKQYPKHLKVRIGAAGGIGCPKAAFAAFEMGAAYIATGTVNQLSKEAGTCDYVRKVLNKATYSDVTMAP
AADMFDHGVELQVLKKGTMFPSRAKKLYDLFKKYKSIEELPADEVKKLEQKVFKKSFDEVWDETKNYYINRLHSPEKIERAERDAKLKMSLCFRWYLSKSSRWANTGESGRVQDY
QIWCGPAIGSYNDFAKGSPCLDPEILGSFPSVVQINKHILRGACFYQRLSQLKYLNFNYEELDTLTYSASNFI (SEQ ID NO:71)

FIG. 19

ATGGTTGGTTACAAATGAAATGAAAAGAAACCAGTAGTGGGAGATGAGTAAGGAAGAACAAAGTTCTGAAAGAATGTTGACTATGATGAATTGTGCTGAAG
GTGATATTGGTAAAGTCTTTGGACCTAAGTTGTGATATATCGATAAGTAAGTATAGTGCGAGTGTAGAGTTACCTGCGAGAGAATATCTTCTAGTTACCAGAGTTACTTTGATGGATG
CTGAAGTTGGGAATTTCAGAGTTGGATCTAGAAATGTTACTGAATATGATGTTCAGTAACTTGTGAACTTTGAAGGTGTGATGTTCCATGGCTGTTCTTGTTGAATCTG
GACAATGTGATCTTATGTAATACGATATCGTGATTGTAAACTGGAATTGCAAAAGGTATGCACGGTAAAGGTATGCAGCGGTAGAAGAACTGCGTGAAATCTCCATGTTTTTTTGAATATGATTGTATGTAATGGACGATTATTAATCGA
TGAAACACTAGTATACAGATATTCGTGTAAACTGGATTGTCAAAAGGTATGCACGGTAAAGGTATGCAGCGGTAGAAGAACTGCGTGAAATCTCCATGTTTTTTTGAATATGATTGTATGTAATGGACGATTATTAATCGA
AATGAGAGATGGTTGTGCGGGATTTTTACTGATGAAGAACTTGCAGTAGTACACAAACAATGTTTCTGAAAATGATATGGAAAATGTGTGAGCGTCAATGGCATATGGCTTGGATTATTGGTTGGCGAAAAATTCTTGAA
TTAAACCTTTGCTCTAAATCCAGCAGTACAGTACACAAACAATGTTTCTGAAAATGATATGGAAAATGTGTGAGCGTCAATGGCATATGGCTTGGATTATTGGTTGGCGAAAAATTCTTGAA
CGTGATCATTGGTATTTCCACGGAAAATGTCTATGGCTGTCCCTGTTAGTGCAGGTTGCAGTACTAAAACTTATATGTTAGTGGTTTAC
ATGATGTGGTTCCAGATTTCACAATTCGTCCAGTTCCTGACAACCAAATAAGTTCGTTGCGTGACAACATAATTGTCCATCGTGGTCAATCATTTGATGTTGATATTGCTGATATGGCTAATTGGCTGATATTGATAGTT
ATGGACGTGGTAATTGTCAAAGAAAATGTGTGCTTGCATTTAAGGAATGCTTTGCACAAGTTACCGGTGATCCACTGGCACCATCAACCTGGTAAATGCGCAGGAGTAATGGGCACCAGCTCCTCATTAGTCCATCTG
TAATACAACACCTCCACACGTCGTTGCTTCAAATGTCCTCGTGGTGATCCACTGGCACCATCAACCTGGTAAATGCGCAGGAGTAATGGGCACCAGCTCCTCATTAGTCCATCTG
ATTATCCACCACGGCTGTTGCTTGGACCAGAATTTAAGAGATTGATAACTCTAAAACATCCAGAAGTTCCTCGTGAGATGTCCGAGTTATGTGTGG
GGAATTTAAACCTCATTTAAATATTGTCTTTATGATGTTTATGATGAAAATGTGCTCTCAAACTCTGTGTATTAACTTCAAAAACTATCAAATTGTTGTTCTCAACCCTGCAAGGATCAATCGAATGGAATTCATAGATTCAC
TATGCCGTATTCTATTGTTCTATGGAATGTGCTCTTCAAACTCTGTGTATTAACTTCAAAAACTATCAAATTGTTGTTCTCAACCCTGCAAGGATCAATCGAATGGAATTCATAGATTCAC
GCCACTGCTGAAATGGTTGAAGTGATGTTCTACAAGATCAAGTAGTTCTACAAAAGGATCAACATCTTTGGTTGTTCACCCTGCAAGGATCAATCGAATGGAATTCATAGATTCAC
ATTTGAATTATCGTTGGAACAAAAATCATCTAATGTAGTAACTTATGACGTTGCGTCCACTGGCAAGGATAACTTATTTCAAGATGGTCTCTGATAATGGTAAAAAGTACA
AAGAAATATACACAATGTGAGTTTCTAGATGTTCTAGATAGCATATATTATTCCAAATACTGAAAGTTACAACAAAAGGTTATGCTCATGAGAAAAGAAAGTTTATCCAAACGACTGGTTC
TTTTCCTGTCAATTCTCTGGGTTTGATCCCTGGAATGCCTGGTTCATTAGGATATGTTCAATGAAAGTATGCTTCAAATTGAAGCATTTTCAAAAATCAAGAATGCGCTTCAAACATGGTA
TGTGAATCGTCAACTTTGCTCATTCCAATGGAAAACTTCTTGAAATACAGAGTTCTTGAAATACGATAAGTCATATCAAAGATATTGTC
AAAAGTGCTAAATCGTCTGTGGATTTGATTGCTGATATTTTGGTTGATTGCATTCACTAAGTATACTCTGCGATCATTCTCGCGTAAAATTGTACCGGGAACCAAAGCT
GCAACTAAATCAGTAGCTGTCCCTGCTCCAACAATTGCAACACATTCGGTGACGTTAAACAATTCGGTGACGTTAAACAACCAAGCAGTTGGAATCATGCACATCAATGATTGCG
AAATCTTGAGAAACCATTGTATCTTGAAACATACAATGTTGTTTGCACAACAATGTCCACCACTGGTTCTCGTGCTCACCACTTGTTGCACACCTATAAACAATTCGTGACCATCCGTAAGTGAACTGGACCGGCCATACGGCTAAACCTGGCTCAAGTATCTGCAACTGGTCACTGCCATAGTCATCCAGAAGGTCCATACGGCTCAACCGACCTGGTCAAGTATCTGCAACTGGTCACTGCCATAGTCATG
TGAGCGTAGTTTATGGAAACATACAAGGCTTACCAATGGCTTACCAATGTTGTTGCCAACACTGGTTCTCGTGCTCACCACTTGTTGCACACCTATAAACAATTCGTGACCATCCGTAAGTGAACTGGACCGGCCATACGGCTAAACCTGGCTCAAGTATCTGCAACTGGTCACTGCCATAGTCATG
CGACTCAAATCTCGGCTAAAGACGATCTGTATTGATCAAAAATAGAATCATCGGTAAAGTTGTTGAAGTACGGCTACCTGACACTTCATTCACTGCTGAAATGTTTTCAGACCTGCACCACAAACTTGCT
TGGTTTATCTCGACTGGATGCTAAAGACGATCTGTATTGATCAAAAATAGAATCATCGGTAAAGTTGTTGAAGTACGGCTACCTGACACTTCATTCACTGCTGAAATGTTTTCAGACCTGCACCACAAACTTGCT
ATAGACCAATTCATGTTATCCTATCGTACCTTGATTATCAATCTGATTATCAATGGGACTGCATTCTTGATTACTGGAGCTGCATTCTTGATTACTGGAGCCAACCAAGATTGCATGGACCAAGCTTCAACAAGTCGAGCTTCAAAAAAACTGGGGACTGGATCTGGACATCGAATCTGATTATCAATGGGACTGCATTCTTGATTACTGGAGCCAACCAAGATTGCATGGACCAAGCTTCAACAAGTCGAGCTTCAAAAAAACTGGGGA
GTTGTCCAAGGTCAGTCGTGCAGTTGCTGCATTCTTGATTACTGGAGCTGCATTCTTGATTACTGGAGCCAACCAAGATTGCATGGACCAAGCTTCAACAAGTCGAGCTTCAAAAAAACTGGGGA
TATCTGAAGCTTCGTATTCGTATCAGATATTCCATGGCACCAGCCGCTAGCCGCTAGCAATGGCACCATTGATGACATGCAAAAAGCGAACTTCAAGACTTCAAGAGAGAAGCGAATTTCAAAAATCGTTAAAGGAACTAGAAGAAGCGAATTTCAAAAATCGTTGGGAAGAA
AATTGATGAAGATTTTTATACCAATCGTGAATTGAATAATCCTGAGAAGAATTGAAGAAGATCAAAGTTGAAGATGTCATTATGCTTTAGATGGTATTGGGGTTTAAGT
TCATTTGGGCAAACATGTTCATGTCAGTTCCATGTCCATGTTCAACAATTTGGTGTGGTCCAGCGATTGGTCATCACAAATTTGGTGTGGTCCAGCGATTGGTCATCACAAATTTGTAAAGGAACTTATTTGGATCCTGCA
GTAGCAGGTCATATCCATGTGTTCAAATTACACTGAATGCAAATTAACAATGCAAATTAACAATGCAAATTAACAATTCTCTTCAACGAGTCGAATCAAGCACGATCCACGAGTATTGGATATTGATGTC
GATGAAGATGTATTTACCTATCGTCCAGAATCAACCCTATAG (SEQ ID NO:72)

FIG. 20

ATGGTTGGCCTGCAGATGAAGAAGAAGCCTGTGTGGAGATGTGAAGGAGGAGCAGTCGTCCGGCAAGAACCTCGTCTTTGACTACGACGAGCTCCTCGAATTCGGAGG
GTGACATCGGCAAGGTGTTCGGCCCCAAGTTGACATCGACAAGTTTGACATCGACAAGCCGAGTACGAAGCCCGTGTGCCGCCATCCTCGTCACGCTCACGCTCATGAT
GCCGAGGTCGGCAACTTCGCGTCGCTCGCATGGTCGTACGAGTACGACGTCCGGTGAACGGCGAACGTCCCTGGGCGTCGCGTCCCTCGGCTCACGCTCACGGTCCACGA
GGGCCAGTGCGACTCTCATGTACGACATCCGCGTCACTCGTTTCGCCAAGGGCATGCACGGCGAGATTAGCATGTTCTTCTTCGAGTACGACGTCTACGTCTACGGTCTCCACGA
GGGCGAGACTGCGACGGTTGCGCTGCCGGCTTCTTCACGGACGAGGAGCTGCGCGGCAAGGGCGTCATCAAGACCGTCGTGAGCTGCTGAGCGCCAAGCGCAAGTCGATTGTGCCAAG
CGAGATCGACTACAAGCTGGTACTTCGCCCCAACCCCGCGTCCACAAGACGCATCAGCGACAAGATCCAGCACGAAGATCCAGCGAAGCGGTGCTACGGCCTCCGTTGGCGAGAAGATTC
GGGCATCGACTACAAGCATTGGTACTTCCCTGCCCACTTCGTCAAGGACCACTTCCCTGGGACCTGCGGCTGCCCCTCGTTTAGCGACGCGCGTCCCGTTTACGCTGCTTACATGCTTTCGGTCCG
TTGAGCGCGACCATTGGTCAATTCCCAGTCCGAGCCAGCCAGCCATCGCGCTGCTGCCTGCGGCGCCAGCCAATCATGTGACATTATGCGATCTCGAGACTCTGACATGTGAACTACGAGCTCGTTGACATGCCGACATC
GACTCGTACGGCGTRGCAACCTCTCCAAGAGATTGTCGTCGATTCCAGATGGAGGGCAGTGAAGARCTCCAACATCATCGATTCGTCCCCAA
GTCCAACGATTATCCAGCGCGCCCAACTGCCTCTCCGCGCGATCCTCGCCCCTGCACCTGGCACCGATGGCCGGTGTCAACGGCGCCCTCCTCTCAG
CCCGTCGATTACCCTCGTGCGTTTGCTTTAAGCCCTTCCCTGGACAACGATCATACGCCGGGCAAGATGCCTGACCTGGTTAACATGTCGGAGTT
TATGTCGGCAAGGTCAGCAACTGCTTGGCCTGAGTTTAAGCCTTCGACAACTCCAAGACGAGCGCTCCCGGCCTTCGACCTGCCTGGTTACGGCGTGGTCGGT
CAGCGATATGGAGTTCAAGCCCGACTACCCTCAACATCGCAACCCCGTCAACCCGTGAAGGCACGATGATTGGCGAGACTGATTCAACGATCGCGCCGCCTTCTTTCAGGCTCCGCA
ACGAGGCCACATGCCGTACACGCATCGTCATGGAGATCGCCTTCAGACAGCGGTGTCCACTTCAAGGCCGTTACTATGGACAAGGACGACATTCTTTC
GCAACCTGCACGCCACCGCGAGATGGTCCGTTCCGACGTCGATTGCCGCGGGTAAGACATCAAGAACTTCACCCAGTGCGCCAGTGCGCTACCAGCATGCTTGGCAAGATGGCATC
CACCCGCTTCACTTTGAGCTCTCGTCGATGAGCAGCCTTGGTTGTTCACGCCCCGGCAAGGACTCTCTCTGAAGATCCAGGTCGGCCTCGATAACGGC
AAGAAGGTCCAGCGTGCAGCGGTGATCTGGAGCAGAAGATCGTCGAAACGGTGACTACCAGCTACGGCGCCAAGGACAACGGGCTAGCGCACGGTGAGAAGTCAACGG
CTCAAGGTCAGCGTGCAACACCCAGTGCGAGTTTCTGGAACCGTCCACCGGCAACCGGCAAGACCTCAACCACAAGGCTACGCGCAGTCATCGAGGGCTTTCGATTGACCAGGTATCGCCG
TCAAACGACTGGTTCTCTCCTGCCACTTGCACCTGCACCTCCGACGAATCGTGAACGGCCGTGAAGCAGCAGCTCCAACACAGGCAAGGCAAGCGAAGCAGCGAGATTCACA
TCAAGGATATTGTCAAGAACGCCGACGTACTGTCGATCTCATCGCGACGGTTTCCTCCGTTTACGCGATGACCTCCGCGTCAAGATCGTCC
CCGGCACTAAGGCTGCTCCAAGAGCGTCGCGAAGCCCCTCTACTTGAGAAGCTCCAACCTCCCGATCGCCACCTCCGTTGGAGATCTGCTTGAGTCGTCCTTA
AGAAGGAGCTCCTCAACTGGAGAAGCTCGGTGAGGCTCGTTATGGAGACTTACACCTGACGTTCAAGCAGTTCGGCGACGTTAACACGGCCAGGTGCCAGCCATCGCCGTCATCCGTCACC
ATTAACGATCTCGGTGAGCCGTCGTTATGGAGACTTACAACGCTGTAGAGACTTACAACGTTCCCTGCTGATTAAGAACCGCATCAGCGACGTTGCCGAGCTTGCCGAGGCTGTTCTTCGCCTGC
AAGCCCGCAAGATCCTCGGCACTCGGACTAAGCCTGCCTCGGCGCCGGATGCCTCCCGATGCACTCGTGGCCGATGCGAGAAGATCCAGCGCCTCGGTGCCGAGGCCCGTACGCGGTCAACCT
CATCCACTCGCCTTCGACTCGAACCTTGAGAAGGGTAACGTGACCTCTTTCTGGAAGAGGCGTCACGTGGTCGGGCCTCGCCTTTACTGCCGCCCTCACTACCCAGGTCGT
TGCTACCGCGCTCGCGGCCTCTCGGTGCTCAAGCCTCGTCGCGGCCGTCGCTCGTCGCCATCCACGCCTCGGCCGCTGTGAACCCATATGCGCGGTAAGCCGGAAGAATCACGACCGGCAAGCTTGACGATTTCTCC
CCCCGAGAACCTCCTGATAAGCCCACCTCATCGGCACGGAGATCAACACCCCGCAGATCCAAGCGACCTCAAGGCAATGCTGAAGGTGCTGAGCCGACCTCG
GCGGCCACACCTCGACTCGATAACGTCCACATCCACGTCATCAAGGACGCTGATTATTAACCTCGCGCCGCCTATCAACCTCGCCTGTGATCTGGCGGCTCAAGATGGGCGCACTCGGCACGTCGGCG
CTGGTGGTGGCATCGGTTGCCCTGGACTCCGGCCCTCTGCCGCCTCCTCGACCATCACGATGGCTCCCGCGCTGACATCACGATGTTCCAGGCGTGAGCCGTCCAAGCGCAGGTGAGCCAGCGCCAAGGGTACGATGTT
TCCCCTCGCGCGCCAAGAAGTCTCTACGAGCTCTTTGCATGTACAACAGCTTGACATGCTGGAGTCCGAGCTCCAGCGGCTCTGAGAAGCGCATTTCCAGAAGAGCCTCG
CTGAGGTCTGGGAGGAGACTAAGGACTTTTGGCCAACCGACTAAGGAGATGAGCGCCTCAACATCAACGCCGTCACGCGAGAAGAAGATGAAGATGCCCGGCATTGGCGCCGGCTCAAGATGCTCCGGTCGTCGGCG
CTTGATCTCGGCGTTTCGACCCCGCTCGACCGTCGCGTCGTACCCGTGGGTCCAGATCAACATGCAGATCCGATCCTCCAGCGGCTCCTCCAGCGGCTCTACACAACGACTTCGTAAGG
GCAACTACCTCGACCCTGCTGCCGCCTCGCCTGGTCGTACCCGTGGGTCCAGATCAACATGCAGATCCTCCAGCGGCTCCTCCAGCGGCTCTACAACGACTCGTAAGG
CGGCCGCCTCGACATCGACGTTGATGAGGACGGTCGTCTTTACCTACCGCGCCCCGAGAGCACCCTCTAA (SEQ ID NO:122)

FIG. 21

MVGLQMKKKPVWEMSKEEQSSGKNVVFDYDELLEFAFGDIGKVFGPKFDIIDKYSRRVRLPAREYLLVTRVTLMDAEVGNFRVGSRMVTEYDVPVNGELSQGGDVPWAVLVESGQ
CDLMLISYMGIDFQCKGDRVYRLLNTTLTFYGVAHEGETLVYDIRVTGFAKGMHGEISMFFEYDCYVNGRLLIEMRDGCAGFFTDEELAAGKGVIKTVAELHKRKSIVPKSIKPFAL
NPAVHKTMFSENDMEKLCERQWENVLGSGLQGIDYKLCARKMLMIDRITKIQHNGGAYGLGLLVGEKILERDHWYFPCHFVKDQVMAGSLVSDGCSQLLKLYMLWLGLHDVVPD
FQFRPVPGQPNKVRCRGQJSPHRGKLVYVMEJREMGFNESTGQPYAIADVDIIDVNYELGQSFDMADIDSYGRGNLSKKIVVDFKGIALQMEGTVKSSNIIDSSPKSTIQPPNCLRGIDP
LAPSQVTWIIPMAGVNGAPAPSFSPSDYPPRAVCFKPFPGNPLLDNDIITPGKMPLTWFNMSEFMCGKVSNCLGPEFKRFDNSKTSRSPAFDLALVTRVVSVSDMEFKPIILNIDVNPSKG
TMIGEFDCPADAWFFQGSCNDGHMPYSIVMEIALQTSGVLTSVLKAPLTMDKDDILFRNLDATAEMVRSDVDCRGKTIKNFTQCTGYSMLGKMGHRFTFELSVDDVVFYKGSTSFG
WFTPEVFESQVGLDNGKKVQPWYLEQKSSNVVTYDVASTAGKDKLFSKIGSKDAQVQRRNTQCEFLDTMHIIPNTGKYNKGYAHGEKKVNPNDWFFSCHFWFDPVMPGSLGIESMF
QLIEAFSIDQGIASKIIGIVNPTFAIISNGKTSWKYRGQLNNKGKRMDSEHHIKDIVKNADGTVDLIADGFLLVDSLRVYSADDLRVKIVPGTKAAPKSVAAAPRIIVATPIPGVPSNTSSV
EISLSLKKELLNLEKPLYLETSSNHIVKQFGIDVNNGQASVIPPCTINDLGERSFMETYNVVAPLYTGAMAKGIASADLVIAAGKRKILGSFGAGGLPMHLVRASVEKIQAALPEGPYAV
NLJHSPFDSNLEKGNVDLFLEKGVHVVEASAFTALTTQVVRYRACGLSRAKDGSVLIKNRIIGKVSRTELAEMFFRPAPQNLLDKLIASGEITKEQASLALEVPMADDVAVEADSGGHT
DNRPIHVILPLIINLRNRIHHKECGFPAALRVRVGAGGIGCPSAAVAAFNMGAAFLITGSVNQVSKQSGTCDIVRKQLSEASYSDITMAPAADMFDQGVELQVLKKGTMFPSRAKKLYE
LFCMYNSFDDMPKSELQRLEKRIFQKSLAEVWEETKDFYINRLNNPEKIEHAEKKDPKLKMSLCFRWYLGLSSFWANNGIKERSMDYQIWCGPAIGSYNDFVKGTYLDPAVAGSYPC
VVQINMQILRGACFLQRVRAIKHDPRLDIDVDEDVFTYRPESTL (SEQ ID NO:73)

FIG. 22

*Schizochytrium* Codon Usage

| AA* | Codon | Fraction | AA* | Codon | Fraction | AA* | Codon | Fraction | AA* | Codon | Fraction |
|---|---|---|---|---|---|---|---|---|---|---|---|
| Ala | GCC | 0.64 | End | TAA | 0.34 | Leu | CTT | 0.16 | Ser | TCG | 0.33 |
| Ala | GCA | 0.03 | End | TGA | 0.33 | Leu | TTG | 0.02 | Ser | TCC | 0.31 |
| Ala | GCT | 0.18 | End | TAG | 0.33 | Leu | CTG | 0.12 | Ser | AGT | 0.03 |
| Ala | GCG | 0.16 | Gln | CAA | 0.08 | Leu | CTC | 0.69 | Ser | TCA | 0 |
| Arg | CGG | 0.01 | Gln | CAG | 0.92 | Leu | TTA | 0 | Ser | TCT | 0.09 |
| Arg | AGA | 0 | Glu | GAA | 0.09 | Leu | CTA | 0 | Thr | ACG | 0.3 |
| Arg | CGC | 0.8 | Glu | GAG | 0.91 | Lys | AAA | 0.04 | Thr | ACC | 0.54 |
| Arg | CGA | 0.01 | Gly | GGA | 0.1 | Lys | AAG | 0.96 | Thr | ACA | 0.02 |
| Arg | AGG | 0 | Gly | GGT | 0.2 | Met | ATG | 1 | Thr | ACT | 0.14 |
| Arg | CGT | 0.17 | Gly | GGG | 0 | Phe | TTT | 0.45 | Trp | TGG | 1 |
| Asn | AAC | 0.94 | Gly | GGC | 0.7 | Phe | TTC | 0.55 | Tyr | TAC | 0.94 |
| Asn | AAT | 0.06 | His | CAC | 0.83 | Pro | CCT | 0.21 | Tyr | TAT | 0.06 |
| Asp | GAT | 0.24 | His | CAT | 0.17 | Pro | CCG | 0.34 | Val | GTC | 0.62 |
| Asp | GAC | 0.76 | Ile | ATC | 0.7 | Pro | CCC | 0.43 | Val | GTA | 0 |
| Cys | TGC | 0.95 | Ile | ATA | 0 | Pro | CCA | 0.02 | Val | GTT | 0.14 |
| Cys | TGT | 0.05 | Ile | ATT | 0.3 | Ser | AGC | 0.24 | Val | GTG | 0.24 |

* AA=Amino Acid

POLYUNSATURATED FATTY ACID SYNTHASE NUCLEIC ACID MOLECULES AND POLYPEPTIDES, COMPOSITIONS, AND METHODS OF MAKING AND USES THEREOF

CROSS-REFERENCE TO RELATED APPLICATION

This application claims the benefit of the filing date of U.S. Appl. No. 61/161,742, filed Mar. 19, 2009, and U.S. Appl. No. 61/296,460, filed Jan. 19, 2010, which are hereby incorporated by reference in their entireties.

REFERENCE TO A SEQUENCE LISTING SUBMITTED ELECTRONICALLY

The content of the electronically submitted sequence listing ("sequence listing.txt", 507,769 bytes, created on Mar. 12, 2010) filed with the application is incorporated herein by reference in its entirety.

BACKGROUND OF THE INVENTION

1. Field of the Invention

The present invention is directed to isolated nucleic acid molecules and polypeptides of polyunsaturated fatty acid (PUFA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

2. Background of the Invention

Thraustochytrids are microorganisms of the order Thraustochytriales, including members of the genus *Thraustochytrium* and the genus *Schizochytrium*, and have been recognized as an alternative source of PUFAs. See, e.g., U.S. Pat. No. 5,130,242. It has recently been shown that polyketide synthase (PKS)-like systems in marine bacteria and thraustochytrids are capable of synthesizing polyunsaturated fatty acids (PUFAs) from acetyl-CoA and malonyl-CoA. These PKS synthase-like systems are also referred to herein as PUFA synthase systems. PUFA synthase systems in the marine bacteria *Shewanella* and *Vibrio marinus* are described in U.S. Pat. No. 6,140,486. A PUFA synthase system in a thraustochytrid of the genus *Schizochytrium* is described in U.S. Pat. No. 6,566,583. PUFA synthase systems in thraustochytrids of the genus *Schizochytrium* and the genus *Thraustochytrium* are also described in U.S. Pat. No. 7,247,461. U.S. Pat. No. 7,211,418 describes a PUFA synthase system in a thraustochytrid of the genus *Thraustochytrium* and the production of eicosapentaenoic acid (C20:5, omega-3) (EPA) and other PUFAs using the system. U.S. Pat. No. 7,217,856 describes PUFA synthase systems in *Shewanella olleyana* and *Shewanella japonica*. WO 2005/097982 describes a PUFA synthase system in strain SAM2179. U.S. Pat. Nos. 7,208,590 and 7,368,552 describe PUFA synthase genes and proteins from *Thraustochytrium aureum*.

PKS systems have been traditionally described in the literature as falling into one of three basic types, typically referred to as Type I (modular or iterative), Type II, and Type III. The Type I modular PKS system has also been referred to as a "modular" PKS system, and the Type I iterative PKS system has also been referred to as a "Type I" PKS system. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the fatty acid synthase (FAS) systems found in plants and bacteria. Type I iterative PKS systems are similar to the Type II system in that the enzymes are used in an iterative fashion to produce the end product. The Type I iterative system differs from the Type II system in that enzymatic activities, instead of being associated with separable proteins, occur as domains of larger proteins. This system is analogous to the Type I FAS systems found in animals and fungi.

In contrast to the Type II systems, each enzyme domain in the Type I modular PKS systems is used only once in the production of the end product. The domains are found in very large proteins and the product of each reaction is passed on to another domain in the PKS protein.

Type III systems have been more recently discovered and belong to the plant chalcone synthase family of condensing enzymes. Type III PKSs are distinct from Type I and Type II PKS systems and utilize free CoA substrates in iterative condensation reactions to usually produce a heterocyclic end product.

In the conventional or standard pathway for PUFA synthesis, medium chain-length saturated fatty acids (products of a fatty acid synthase (FAS) system) are modified by a series of elongation and desaturation reactions. The substrates for the elongation reaction are fatty acyl-CoA (the fatty acid chain to be elongated) and malonyl-CoA (the source of the two carbons added during each elongation reaction). The product of the elongase reaction is a fatty acyl-CoA that has two additional carbons in the linear chain. The desaturases create cis double bonds in the preexisting fatty acid chain by extraction of two hydrogens in an oxygen-dependant reaction. The substrates for the desaturases are either acyl-CoA (in some animals) or the fatty acid that is esterified to the glycerol backbone of a phospholipid (e.g., phosphatidylcholine).

Fatty acids are classified based on the length and saturation characteristics of the carbon chain. Fatty acids are termed short chain, medium chain, or long chain fatty acids based on the number of carbons present in the chain, are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

PUFAs are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 PUFA with a chain length of 22 carbons and 6 double bonds, often designated as "22:6 n-3." Other omega-3 PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates. Roche, H. M., *Proc. Nutr. Soc.* 58: 397-401 (1999). DHA, for example, accounts for approximately 15%-20% of lipids in the human cerebral cortex, and 30%-60% of lipids in the retina, is concentrated in the testes and sperm, and is an important component of breast milk. Bergé, J. P., and Barnathan, G. *Adv. Biochem. Eng. Biotechnol.* 96:49-125 (2005). DHA accounts for up to 97% of the omega-3 fatty acids in the brain and up to 93% of the omega-3 fatty acids in the retina. Moreover, DHA is essential for both fetal and infant development, as well as maintenance of cognitive functions in adults. Id. Because omega-3 fatty acids are not synthesized de novo in the human body, these fatty acids must be derived from nutritional sources.

Flaxseed oil and fish oils are considered good dietary sources of omega-3 fatty acids. Flaxseed oil contains no EPA, DHA, DPA, or ARA but rather contains linolenic acid (C18:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

Oils produced from thraustochytrids often have simpler polyunsaturated fatty acid profiles than corresponding fish or microalgal oils. Lewis, T. E., *Mar. Biotechnol.* 1: 580-587 (1999). Strains of thraustrochytrid species have been reported to produce omega-3 fatty acids as a high percentage of the total fatty acids produced by the organisms. U.S. Pat. No. 5,130,242; Huang, J. et al., *J. Am. Oil. Chem. Soc.* 78: 605-610 (2001); Huang, J. et al., *Mar. Biotechnol.* 5: 450-457 (2003). However, isolated thraustochytrids vary in the identity and amounts of PUFAs produced, such that some previously described strains can have undesirable PUFA profiles.

Efforts have been made to produce PUFAs in oil-seed crop plants by modification of the endogenously-produced fatty acids. Genetic modification of these plants with various individual genes for fatty acid elongases and desaturases has produced leaves or seeds containing measurable levels of PUFAs such as EPA, but also containing significant levels of mixed shorter-chain and less unsaturated PUFAs (Qi et al., *Nature Biotech.* 22:739 (2004); PCT Publ. No. WO 04/071467; Abbadi et al., *Plant Cell* 16:1 (2004)); Napier and Sayanova, *Proc. Nutrition Society* 64:387-393 (2005); Robert et al., *Functional Plant Biology* 32:473-479 (2005); and U.S. Appl. Publ. No. 2004/0172682).

As such, a continuing need exists for the isolation of nucleic acid molecules and polypeptides associated with desirable PUFA profiles and methods to produce desirable PUFA profiles through use of such nucleic acid molecules and polypeptides.

BRIEF SUMMARY OF THE INVENTION

The present invention is directed to an isolated nucleic acid molecule selected from the group consisting of: (a) a nucleic acid molecule comprising a polynucleotide sequence at least 80% identical to SEQ ID NO:1, wherein the polynucleotide sequence encodes a polypeptide comprising PUFA synthase activity selected from the group consisting of beta-ketoacyl-ACP synthase (KS) activity, malonyl-CoA:ACP acyltransferase (MAT) activity, acyl carrier protein (ACP) activity, ketoreductase (KR) activity, beta-hydroxyacyl-ACP dehydrase (DH) activity, and combinations thereof; (b) a nucleic acid molecule comprising a polynucleotide sequence at least 80% identical to SEQ ID NO:7, wherein the polynucleotide sequence encodes a polypeptide comprising KS activity; (c) a nucleic acid molecule comprising a polynucleotide sequence at least 80% identical to SEQ ID NO:9, wherein the polynucleotide sequence encodes a polypeptide comprising MAT activity; (d) a nucleic acid molecule comprising a polynucleotide sequence at least 80% identical to any one of SEQ ID NOs:13, 15, 17, 19, 21, or 23, wherein the polynucleotide sequence encodes a polypeptide comprising ACP activity; (e) a nucleic acid molecule comprising a polynucleotide sequence at least 80% identical to SEQ ID NO:11, wherein the polynucleotide sequence encodes a polypeptide comprising ACP activity; (f) a nucleic acid molecule comprising a polynucleotide sequence at least 80% identical to SEQ ID NO:25, wherein the polynucleotide sequence encodes a polypeptide comprising KR activity; and (g) a nucleic acid molecule comprising a polynucleotide sequence at least 80% identical to SEQ ID NO:27, wherein the polynucleotide sequence encodes a polypeptide comprising DH activity. In some embodiments, the polynucleotide sequences are at least 90% identical or at least 95% identical to SEQ ID NOs:1, 7, 9, 11, 13, 15, 17, 19, 21, 23, 25, and 27, respectively. In some embodiments, the nucleic acid molecules comprise the polynucleotide sequences of SEQ ID NOs:1, 7, 9, 11, 13, 15, 17, 19, 21, 23, 25, and 27, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:2, and wherein the polypeptide comprises a PUFA synthase activity selected from the group consisting of KS activity, MAT activity, ACP activity, KR activity, DH activity, and combinations thereof; (b) a nucleic acid molecule comprising a polynucleotide sequence encoding a polypeptide, wherein the polypeptide comprises an amino acid sequence at least 80% identical to SEQ ID NO:8, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:10, and wherein the polypeptide comprises MAT activity; (d) a nucleic acid molecule comprising a polynucleotide sequence encoding a polypeptide, wherein the polypeptide comprises an amino acid sequence at least 80% identical to any one of SEQ ID NOs:14, 16, 18, 20, 22, or 24, and wherein the polypeptide comprises ACP activity; (e) a nucleic acid molecule comprising a polynucleotide sequence encoding a polypeptide, wherein the polypeptide comprises an amino acid sequence at least 80% identical to SEQ ID NO:12, and wherein the polypeptide comprises ACP activity; (f) a nucleic acid molecule comprising a polynucleotide sequence encoding a polypeptide, wherein the polypeptide comprises an amino acid sequence at least 80% identical to SEQ ID NO:26, and wherein the polypeptide comprises KR activity; and (g) a nucleic acid molecule comprising a polynucleotide sequence encoding a polypeptide, wherein the polypeptide comprises an amino acid sequence at least 80% identical to SEQ ID NO:28, and wherein the polypeptide comprises DH activity. In some embodiments, the amino acid sequences are at least 90% identical or at least 95% identical to SEQ ID NOs:2, 8, 10, 12, 14, 16, 18, 20, 22, 24, 26, and 28, respectively. In some embodiments, the polypeptides comprise the amino acid sequences of SEQ ID NOs:2, 8, 10, 12, 14, 16, 18, 20, 22, 24, 26, and 28, respectively.

The present invention is directed to an isolated nucleic acid molecule selected from the group consisting of: (a) a nucleic acid molecule comprising a polynucleotide sequence at least 80% identical to SEQ ID NO:3, wherein the polynucleotide sequence encodes a polypeptide comprising PUFA synthase activity selected from the group consisting of KS activity, chain length factor (CLF) activity, acyltransferase (AT) activity, enoyl-ACP reductase (ER) activity, and combinations thereof; (b) a nucleic acid molecule comprising a polynucleotide sequence at least 80% identical to SEQ ID NO:29, wherein the polynucleotide sequence encodes a polypeptide comprising KS activity; (c) a nucleic acid molecule comprising a polynucleotide sequence at least 80% identical to SEQ ID NO:31, wherein the polynucleotide sequence encodes a polypeptide comprising CLF activity; (d) a nucleic acid molecule comprising a polynucleotide sequence at least 80% identical to SEQ ID NO:33, wherein the polynucleotide sequence encodes a polypeptide comprising AT activity; and (e) a nucleic acid molecule comprising a polynucleotide sequence at least 80% identical to SEQ ID NO:35, wherein the polynucleotide sequence encodes a polypeptide comprising ER activity. In some embodiments, the polynucleotide sequences are at least 90% identical or at least 95% identical to SEQ ID NOs:3, 29, 31, 33, and 35, respectively. In some embodiments, the nucleic acid molecules comprise the polynucleotide sequences of SEQ ID NOs:3, 29, 31, 33, and 35, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:4, and wherein the polypeptide comprises a PUFA synthase activity selected from the group consisting of KS activity, CLF activity, AT activity, ER activity, and combinations thereof; (b) a nucleic acid molecule comprising a polynucleotide sequence encoding a polypeptide, wherein the polypeptide comprises an amino acid sequence at least 80% identical to SEQ ID NO:30, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:32, and wherein the polypeptide comprises CLF activity; (d) a nucleic acid molecule comprising a polynucleotide sequence encoding a polypeptide, wherein the polypeptide comprises an amino acid sequence at least 80% identical to SEQ ID NO:34, and wherein the polypeptide comprises AT activity; and (e) a nucleic acid molecule comprising a polynucleotide sequence encoding a polypeptide, wherein the polypeptide comprises an amino acid sequence at least 80% identical to SEQ ID NO:36, and wherein the polypeptide comprises ER activity. In some embodiments, the amino acid sequences are at least 90% identical or at least 95% identical to SEQ ID NOs:4, 30, 32, 34, and 36, respectively. In some embodiments, the polypeptides comprise the amino acid sequence of SEQ ID NOs:4, 30, 32, 34, and 36, respectively.

The present invention is directed to an isolated nucleic acid molecule selected from the group consisting of: (a) an nucleic acid molecule comprising a polynucleotide sequence at least 80% identical to SEQ ID NO:5, wherein the polynucleotide sequence encodes a polypeptide comprising PUFA synthase activity selected from the group consisting of DH activity, ER activity, and combinations thereof; (b) a nucleic acid molecule comprising a polynucleotide sequence at least 80% identical to SEQ ID NO:37, wherein the polynucleotide sequence encodes a polypeptide comprising DH activity; (c) a nucleic acid molecule comprising a polynucleotide sequence at least 80% identical to SEQ ID NO:39, wherein the polynucleotide sequence encodes a polypeptide comprising DH activity; and (d) a nucleic acid molecule comprising a polynucleotide sequence at least 80% identical to SEQ ID NO:41, wherein the polynucleotide sequence encodes a polypeptide comprising ER activity. In some embodiments, the polynucleotide sequences are at least 90% identical or at least 95% identical to SEQ ID NOs:5, 37, 39, and 41, respectively. In some embodiments, the nucleic acid molecules comprise the polynucleotide sequences of SEQ ID NOs:5, 37, 39, and 41, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:6, wherein the polypeptide comprises PUFA synthase activity selected from the group consisting of DH activity, ER activity, and combinations thereof; (b) a nucleic acid molecule comprising a polynucleotide sequence encoding a polypeptide, wherein the polypeptide comprises an amino acid sequence at least 80% identical to SEQ ID NO:38, and wherein the polypeptide comprises DH activity; (c) a nucleic acid molecule comprising a polynucleotide sequence encoding a polypeptide, wherein the polypeptide comprises an amino acid sequence at least 80% identical to SEQ ID NO:40, and wherein the polypeptide comprises DH activity; and (d) a nucleic acid molecule comprising a polynucleotide sequence encoding a polypeptide, wherein the polypeptide comprises an amino acid sequence at least 80% identical to SEQ ID NO:42, and wherein the polypeptide comprises ER activity. In some embodiments, the amino acid sequences are at least 90% identical or at least 95% identical to SEQ ID NOs:6, 38, 40, and 42, respectively. In some embodiments, the polypeptides comprise the amino acid sequences of SEQ ID NOs:6, 38, 40, and 42, respectively.

The present invention is directed to an isolated nucleic acid molecule selected from the group consisting of: (a) a nucleic acid molecule comprising a polynucleotide sequence at least 80% identical to SEQ ID NO:68 or SEQ ID NO:120, wherein the polynucleotide sequence encodes a polypeptide comprising PUFA synthase activity selected from the group consisting of KS activity, MAT activity, ACP activity, KR activity, DH activity, and combinations thereof; (b) a nucleic acid molecule comprising a polynucleotide sequence at least 80% identical to SEQ ID NO:74, wherein the polynucleotide sequence encodes a polypeptide comprising KS activity; (c) a nucleic acid molecule comprising a polynucleotide sequence at least 80% identical to SEQ ID NO:76, wherein the polynucleotide sequence encodes a polypeptide comprising MAT activity; (d) a nucleic acid molecule comprising a polynucleotide sequence at least 80% identical to any one of SEQ ID NOs: 80, 82, 84, 86, 88, 90, 92, 94, 96, or 98, wherein the polynucleotide sequence encodes a polypeptide comprising ACP activity; (e) a nucleic acid molecule comprising a polynucleotide sequence at least 80% identical to SEQ ID NO:78, wherein the polynucleotide sequence encodes a polypeptide comprising ACP activity; (f) a nucleic acid molecule comprising a polynucleotide sequence at least 80% identical to SEQ ID NO:100, wherein the polynucleotide sequence encodes a polypeptide comprising KR activity; and (g) a nucleic acid molecule comprising a polynucleotide sequence at least 80% identical to SEQ ID NO:118, wherein the polynucleotide sequence encodes a polypeptide comprising DH activity. In some embodiments, the polynucleotide sequences are at least 90% identical or at least 95% identical to SEQ ID NOs:68, 74, 76, 78, 80, 82, 84, 86, 88, 90, 92, 94, 96, 98, 100, 118, and 120, respectively. In some embodiments, the nucleic acid molecules comprise the polynucleotide sequences of SEQ ID NOs:68, 74, 76, 78, 80, 82, 84, 86, 88, 90, 92, 94, 96, 98, 100, 118, and 120, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:69, and wherein the polypeptide comprises a PUFA synthase activity selected from the group consisting of KS activity, MAT activity, ACP activity, KR activity, DH activity, and combinations thereof; (b) a nucleic acid molecule comprising a polynucleotide sequence encoding a polypeptide, wherein the polypeptide comprises an amino acid sequence at least 80% identical to SEQ ID NO:75, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:77, and wherein the polypeptide comprises MAT activity; (d) a nucleic acid molecule comprising a polynucleotide sequence encoding a polypeptide, wherein the polypeptide comprises an amino acid sequence at least 80% identical to any one of SEQ ID NOs:81, 83, 85, 87, 89, 91, 93, 95, 97, or 99, and wherein the polypeptide comprises ACP activity; (e) a nucleic acid molecule comprising a polynucleotide sequence encoding a polypeptide, wherein the polypeptide comprises an amino acid sequence at least 80% identical to SEQ ID NO:79, and wherein the polypeptide comprises ACP activity; (f) a nucleic acid molecule comprising a polynucleotide sequence encoding a polypeptide, wherein the polypeptide comprises an amino acid sequence at least 80% identical to SEQ ID NO:101, and wherein the polypeptide comprises KR activity; and (g) a nucleic acid molecule comprising a polynucleotide sequence encoding a polypeptide, wherein the polypeptide comprises an amino acid sequence at least 80% identical to SEQ ID NO:119, and wherein the polypeptide comprises DH activity. In some embodiments, the amino acid sequences are at least 90% identical or at least 95% identical to SEQ ID NOs:69, 75, 77, 79, 81, 83, 85, 87, 89, 91, 93, 95, 97, 99, 101, and 119, respectively. In some embodiments, the polypeptides comprise the amino acid sequences of SEQ ID NOs:69, 75, 77, 79, 81, 83, 85, 87, 89, 91, 93, 95, 97, 99, 101, and 119, respectively.

The present invention is directed to an isolated nucleic acid molecule selected from the group consisting of: (a) a nucleic acid molecule comprising a polynucleotide sequence at least 80% identical to SEQ ID NO:70 or SEQ ID NO:121, wherein the polynucleotide sequence encodes a polypeptide comprising PUFA synthase activity selected from the group consisting of KS activity, chain length factor (CLF) activity, acyltransferase (AT) activity, enoyl-ACP reductase (ER) activity, and combinations thereof; (b) a nucleic acid molecule comprising a polynucleotide sequence at least 80% identical to SEQ ID NO:102, wherein the polynucleotide sequence encodes a polypeptide comprising KS activity; (c) a nucleic acid molecule comprising a polynucleotide sequence at least 80% identical to SEQ ID NO:104, wherein the polynucleotide sequence encodes a polypeptide comprising CLF activity; (d) a nucleic acid molecule comprising a polynucleotide sequence at least 80% identical to SEQ ID NO:106, wherein the polynucleotide sequence encodes a polypeptide comprising AT activity; and (e) a nucleic acid molecule comprising a polynucleotide sequence at least 80% identical to SEQ ID NO:108, wherein the polynucleotide sequence encodes a polypeptide comprising ER activity. In some embodiments, the polynucleotide sequences are at least 90% identical or at least 95% identical to SEQ ID NOs:70, 102, 104, 106, 108, and 121, respectively. In some embodiments, the nucleic acid molecules comprise the polynucleotide sequences of SEQ ID NOs:70, 102, 104, 106, 108, and 121, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:71, and wherein the polypeptide comprises a PUFA synthase activity selected from the group consisting of KS activity, CLF activity, AT activity, ER activity, and combinations thereof; (b) a nucleic acid molecule comprising a polynucleotide sequence encoding a polypeptide, wherein the polypeptide comprises an amino acid sequence at least 80% identical to SEQ ID NO:103, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:105, and wherein the polypeptide comprises CLF activity; (d) a nucleic acid molecule comprising a polynucleotide sequence encoding a polypeptide, wherein the polypeptide comprises an amino acid sequence at least 80% identical to SEQ ID NO:107, and wherein the polypeptide comprises AT activity; and (e) a nucleic acid molecule comprising a polynucleotide sequence encoding a polypeptide, wherein the polypeptide comprises an amino acid sequence at least 80% identical to SEQ ID NO:109, and wherein the polypeptide comprises ER activity. In some embodiments, the amino acid sequences are at least 90% identical or at least 95% identical to SEQ ID NOs:71, 103, 105, 107, and 109, respectively. In some embodiments, the polypeptides comprise the amino acid sequence of SEQ ID NOs:71, 103, 105, 107, and 109, respectively.

The present invention is directed to an isolated nucleic acid molecule selected from the group consisting of: (a) an nucleic acid molecule comprising a polynucleotide sequence at least 80% identical to SEQ ID NO:72 or SEQ ID NO:122, wherein the polynucleotide sequence encodes a polypeptide comprising PUFA synthase activity selected from the group consisting of DH activity, ER activity, and combinations thereof; (b) a nucleic acid molecule comprising a polynucleotide sequence at least 80% identical to SEQ ID NO:110, wherein the polynucleotide sequence encodes a polypeptide comprising DH activity; (c) a nucleic acid molecule comprising a polynucleotide sequence at least 80% identical to SEQ ID NO:112, wherein the polynucleotide sequence encodes a polypeptide comprising DH activity; and (d) a nucleic acid molecule comprising a polynucleotide sequence at least 80% identical to SEQ ID NO:114, wherein the polynucleotide sequence encodes a polypeptide comprising ER activity. In some embodiments, the polynucleotide sequences are at least 90% identical or at least 95% identical to SEQ ID NOs:72, 110, 112, 114, and 122, respectively. In some embodiments, the nucleic acid molecules comprise the polynucleotide sequences of SEQ ID NOs:72, 110, 112, 114, and 122, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:73, wherein the polypeptide comprises PUFA synthase activity selected from the group consisting of DH activity, ER activity, and combinations thereof; (b) a nucleic acid molecule comprising a polynucleotide sequence encoding a polypeptide, wherein the polypeptide comprises an amino acid sequence at least 80% identical to SEQ ID NO:111, and wherein the polypeptide comprises DH activity; (c) a nucleic acid molecule comprising a polynucleotide sequence encoding a polypeptide, wherein the polypeptide comprises an amino acid sequence at least 80% identical to SEQ ID NO:113, and wherein the polypeptide comprises DH activity; and (d) a nucleic acid molecule comprising a polynucleotide sequence encoding a polypeptide, wherein the polypeptide comprises an amino acid sequence at least 80% identical to SEQ ID NO:115, and wherein the polypeptide comprises ER activity. In some embodiments, the amino acid sequences are at least 90% identical or at least 95% identical to SEQ ID NOs:73, 111, 113, and 115, respectively. In some embodiments, the polypeptides comprise the amino acid sequences of SEQ ID NOs:73, 111, 113, and 115, respectively.

The present invention is directed to an isolated nucleic acid molecule comprising a polynucleotide sequence encoding a polypeptide comprising PUFA synthase activity selected from the group consisting of KS activity, MAT activity, ACP activity, KR activity, CLF activity, AT activity, ER activity, DH activity, and combinations thereof, wherein the polynucleotide hybridizes under stringent conditions to the complement of any of the polynucleotide sequences described above.

The present invention is directed to an isolated nucleic acid molecule comprising a polynucleotide sequence that is fully complementary to any of the polynucleotide sequences described above.

The present invention is directed to a recombinant nucleic acid molecule comprising any of the nucleic acid molecules described above or combinations thereof and a transcription control sequence. In some embodiments, the recombinant nucleic acid molecule is a recombinant vector.

The present invention is directed to a host cell that expresses any of the nucleic acid molecules described above, any of the recombinant nucleic acid molecules described above, and combinations thereof. In some embodiments, the host cell is selected from the group consisting of a plant cell, a microbial cell, and an animal cell. In some embodiments, the microbial cell is a bacterium. In some embodiments, the bacterium is *E. coli*. In some embodiments, the bacterium is a marine bacterium. In some embodiments, the microbial cell is a thraustochytrid. In some embodiments, the thraustochytrid is a *Schizochytrium*. In some embodiments, the thraustochytrid is a *Thraustochytrium*. In some embodiments, the thraustochytrid is an *Ulkenia*.

The present invention is directed to a method to produce at least one PUFA, comprising: expressing a PUFA synthase gene in a host cell under conditions effective to produce PUFA, wherein the PUFA synthase gene comprises any of the isolated nucleic acid molecules described above, any of the recombinant nucleic acid molecules described above, or combinations thereof, and wherein at least one PUFA is produced. In one aspect of this embodiment, the host cell is selected from the group consisting of a plant cell, an isolated animal cell, and a microbial cell. In another aspect of this embodiment, the at least one PUFA comprises docosahexaenoic acid (DHA) or eicosapentaenoic acid (EPA).

The present invention is directed to a method to produce lipids enriched for DHA, EPA, or a combination thereof, comprising: expressing a PUFA synthase gene in a host cell under conditions effective to produce lipids, wherein the PUFA synthase gene comprises any of the isolated nucleic acid molecules described above, any of the recombinant nucleic acid molecules described above, or combinations thereof in the host cell, and wherein lipids enriched with DHA, EPA, or a combination thereof are produced. The present invention is directed to a method for making a recombinant vector comprising inserting any one of the isolated nucleic acid molecules described above into a vector.

The present invention is directed to a method of making a recombinant host cell comprising introducing a recombinant vector as described above into a host cell. In some embodiments, the host cell is selected from the group consisting of a plant cell, an isolated animal cell, and a microbial cell.

The present invention is directed to an isolated polypeptide encoded by any of the polynucleotide sequences described above.

The present invention is directed to an isolated polypeptide selected from the group consisting of: (a) a polypeptide comprising an amino acid sequence at least 80% identical to SEQ ID NO:2, wherein the polypeptide comprises a PUFA synthase activity selected from the group consisting of KS activity, MAT activity, ACP activity, KR activity, DH activity, and combinations thereof; (b) a polypeptide comprising an amino acid sequence at least 80% identical to SEQ ID NO:8, wherein the polypeptide comprises KS activity; (c) a polypeptide comprising an amino acid sequence at least 80% identical to SEQ ID NO:10, wherein the polypeptide comprises MAT activity; (d) a polypeptide comprising an amino acid sequence at least 80% identical to any one of SEQ ID NOs:14, 16, 18, 20, 22, or 24, wherein the polypeptide comprises ACP activity; (e) a polypeptide comprising an amino acid sequence at least 80% identical to SEQ ID NO:12, wherein the polypeptide comprises ACP activity; (f) a polypeptide comprising an amino acid sequence at least 80% identical to SEQ ID NO:26, wherein the polypeptide comprises KR activity; and (g) a polypeptide comprising an amino acid sequence at least 80% identical to SEQ ID NO:28, wherein the polypeptide comprises DH activity. In some embodiments, the amino acid sequences are at least 90% identical or at least 95% identical to SEQ ID NOs:2, 8, 10, 12, 14, 16, 18, 20, 22, 24, 26, and 28, respectively. In some embodiments, the polypeptides comprise the amino acid sequences of SEQ ID NOs:2, 8, 10, 12, 14, 16, 18, 20, 22, 24, 26, and 28, respectively.

The present invention is directed to an isolated polypeptide selected from the group consisting of: (a) a polypeptide comprising an amino acid sequence at least 80% identical to SEQ ID NO:4, wherein the polypeptide comprises a PUFA synthase activity selected from the group consisting of KS activity, CLF activity, AT activity, ER activity, and combinations thereof; (b) a polypeptide comprising an amino acid sequence at least 80% identical to SEQ ID NO:30, wherein the polypeptide comprises KS activity; (c) a polypeptide comprising an amino acid sequence at least 80% identical to SEQ ID NO:32, wherein the polypeptide comprises CLF activity; (d) a polypeptide comprising an amino acid sequence at least 80% identical to SEQ ID NO:34, wherein the polypeptide comprises AT activity; and (e) a polypeptide comprising an amino acid sequence at least 80% identical to SEQ ID NO:36, wherein the polypeptide comprises ER activity. In some embodiments, the amino acid sequences are at least 90% identical or at least 95% identical to SEQ ID NOs:4, 30, 32, 34, and 36, respectively. In some embodiments, the polypeptides comprise the amino acid sequence of SEQ ID NOs:4, 30, 32, 34, and 36, respectively.

The present invention is directed to an isolated polypeptide selected from the group consisting of: (a) a polypeptide comprising an amino acid sequence at least 80% identical to SEQ ID NO:6, wherein the polypeptide comprises a PUFA synthase activity selected from the group consisting of DH activity, ER activity, and combinations thereof; (b) a polypeptide comprising an amino acid sequence at least 80% identical to SEQ ID NO:38, wherein the polypeptide comprises DH activity; (c) a polypeptide comprising an amino acid sequence at least 80% identical to SEQ ID NO:40, wherein the polypeptide comprises DH activity; and (d) a polypeptide comprising an amino acid sequence at least 80% identical to SEQ ID NO:42, wherein the polypeptide comprises ER activity. In some embodiments, the amino acid sequences are at least 90% identical or at least 95% identical to SEQ ID NOs:6, 38, 40, and 42, respectively. In some embodiments, the polypeptides comprise the amino acid sequences of SEQ ID NOs:6, 38, 40, and 42, respectively.

The present invention is directed to an isolated polypeptide selected from the group consisting of: (a) a polypeptide comprising an amino acid sequence at least 80% identical to SEQ ID NO:69, wherein the polypeptide comprises a PUFA synthase activity selected from the group consisting of KS activity, MAT activity, ACP activity, KR activity, DH activity, and combinations thereof; (b) a polypeptide comprising an amino acid sequence at least 80% identical to SEQ ID NO:75, wherein the polypeptide comprises KS activity; (c) a polypeptide comprising an amino acid sequence at least 80% identical to SEQ ID NO:77, wherein the polypeptide comprises MAT activity; (d) a polypeptide comprising an amino acid sequence at least 80% identical to any one of SEQ ID NOs:81, 83, 85, 87, 89, 91, 93, 95, 97, or 99, wherein the polypeptide comprises ACP activity; (e) a polypeptide comprising an amino acid sequence at least 80% identical to SEQ ID NO:79, wherein the polypeptide comprises ACP activity; (f) a polypeptide comprising an amino acid sequence at least 80% identical to SEQ ID NO:101, wherein the polypeptide comprises KR activity; and (g) a polypeptide comprising an amino acid sequence at least 80% identical to SEQ ID NO:119, wherein the polypeptide comprises DH activity. In some embodiments, the amino acid sequences are at least 90% identical or at least 95% identical to SEQ ID NOs:69, 75, 77, 79, 81, 83, 85, 87, 89, 91, 93, 95, 97, 99, 101, and 119, respectively. In some embodiments, the polypeptides comprise the amino acid sequences of SEQ ID NOs:69, 75, 77, 79, 81, 83, 85, 87, 89, 91, 93, 95, 97, 99, 101, and 119, respectively.

The present invention is directed to an isolated polypeptide selected from the group consisting of: (a) a polypeptide comprising an amino acid sequence at least 80% identical to SEQ ID NO:71, wherein the polypeptide comprises a PUFA synthase activity selected from the group consisting of KS activity, CLF activity, AT activity, ER activity, and combinations thereof; (b) a polypeptide comprising an amino acid sequence at least 80% identical to SEQ ID NO:103, wherein the polypeptide comprises KS activity; (c) a polypeptide comprising an amino acid sequence at least 80% identical to SEQ ID NO:105, wherein the polypeptide comprises CLF activity; (d) a polypeptide comprising an amino acid sequence at least 80% identical to SEQ ID NO:107, wherein the polypeptide comprises AT activity; and (e) a polypeptide comprising an amino acid sequence at least 80% identical to SEQ ID NO:109, wherein the polypeptide comprises ER activity. In some embodiments, the amino acid sequences are at least 90% identical or at least 95% identical to SEQ ID NOs:71, 103, 105, 107, and 109, respectively. In some embodiments, the polypeptides comprise the amino acid sequence of SEQ ID NOs:71, 103, 105, 107, and 109, respectively.

The present invention is directed to an isolated polypeptide selected from the group consisting of: (a) a polypeptide comprising an amino acid sequence at least 80% identical to SEQ ID NO:73, wherein the polypeptide comprises a PUFA synthase activity selected from the group consisting of DH activity, ER activity, and combinations thereof; (b) a polypeptide comprising an amino acid sequence at least 80% identical to SEQ ID NO:111, wherein the polypeptide comprises DH activity; (c) a polypeptide comprising an amino acid sequence at least 80% identical to SEQ ID NO:113, wherein the polypeptide comprises DH activity; and (d) a polypeptide comprising an amino acid sequence at least 80% identical to SEQ ID NO:115, wherein the polypeptide comprises ER activity. In some embodiments, the amino acid sequences are at least 90% identical or at least 95% identical to SEQ ID NOs:73, 111, 113, and 115, respectively. In some embodiments, the polypeptides comprise the amino acid sequences of SEQ ID NOs:73, 111, 113, and 115, respectively.

In some embodiments, any of the isolated polypeptides of the invention can be a fusion polypeptide.

The present invention is directed to a composition comprising any of the polypeptides described above and a biologically acceptable carrier.

The present invention is directed to a method of increasing production of DHA, EPA, or a combination thereof in an organism having PUFA synthase activity, comprising: expressing any of the isolated nucleic acid molecules described above, any of the recombinant nucleic acid molecules described above, or combinations thereof in the organism under conditions effective to produce DHA, EPA, or a combination thereof, wherein the PUFA synthase activity replaces an inactive or deleted activity, introduces a new activity, or enhances an existing activity in the organism, and wherein production of DHA, EPA, or a combination thereof in the organism is increased.

The present invention is directed to a method of isolating lipids from a host cell, comprising: (a) expressing a PUFA synthase gene in the host cell under conditions effective to produce lipids, wherein the PUFA synthase gene comprises any of the isolated nucleic acid molecules described above, any of the recombinant nucleic acid molecules described above, or combinations thereof in the host cell, and (b) isolating lipids from the host cell. In some embodiments, the host cell is selected from the group consisting of a plant cell, an isolated animal cell, and a microbial cell. In some embodiments, the lipids comprise DHA, EPA, or a combination thereof.

BRIEF DESCRIPTION OF THE
DRAWINGS/FIGURES

FIG. 1 shows the gene architecture of the *Schizochytrium* sp. ATCC PTA-9695 PUFA synthases of the invention.

FIG. 2 shows the gene architecture of the *Thraustochytrium* sp. ATCC PTA-10212 PUFA synthases of the invention.

FIG. 3 shows the domain architecture of the *Schizochytrium* sp. ATCC PTA-9695 and *Thraustochytrium* sp. ATCC PTA-10212 PUFA synthases of the invention and synthases from *Schizochytrium* sp. ATCC 20888, *Thraustochytrium* sp. ATCC 20892, *Thraustochytrium aureum*, and SAM2179.

FIG. 4 shows an alignment of a *Schizochytrium* sp. ATCC PTA-9695 Pfa1p amino acid sequence (SEQ ID NO:2) and a *Thraustochytrium* sp. ATCC PTA-10212 Pfa1p amino acid sequence (SEQ ID NO:69) of the invention with the OrfA sequences from *Schizochytrium* sp. ATCC 20888 (SEQ ID NO:54) and *Thraustochytrium* sp. ATCC 20892 (SEQ ID NO:56) and the ORF A sequence from *Thraustochytrium aureum* (SEQ ID NO:55).

FIG. 5 shows an alignment of a *Schizochytrium* sp. ATCC PTA-9695 Pfa2p amino acid sequence (SEQ ID NO:4) and a *Thraustochytrium* sp. ATCC PTA-10212 Pfa2p amino acid sequence (SEQ ID NO:71) of the invention with the OrfB sequences from *Schizochytrium* sp. ATCC 20888 (SEQ ID NO:57) and *Thraustochytrium* sp. ATCC 20892 (SEQ ID NO:58) and the ORF B sequence from *Thraustochytrium aureum* (SEQ ID NO:59).

FIG. 6 shows an alignment of a *Schizochytrium* sp. ATCC PTA-9695 Pfa3p amino acid sequence (SEQ ID NO:6) and a *Thraustochytrium* sp. ATCC PTA-10212 Pfa3p amino acid sequence (SEQ ID NO:73) of the invention with the OrfC sequences from *Schizochytrium* sp. ATCC 20888 (SEQ ID NO:61) and *Thraustochytrium* sp. ATCC 20892 (SEQ ID NO:60).

Figure 7:
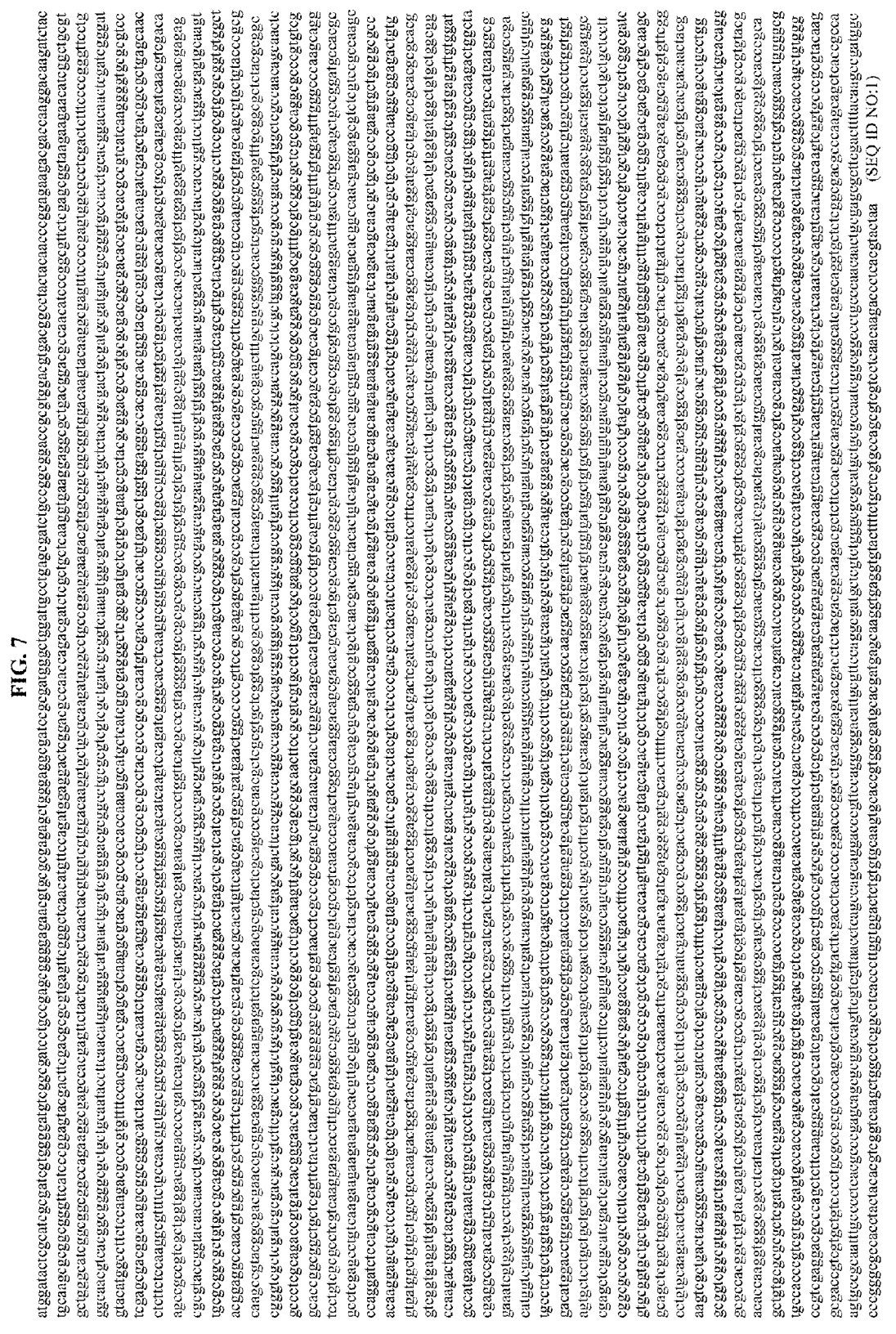

FIG. 7 shows the *Schizochytrium* sp. ATCC PTA-9695 PFA1 polynucleotide sequence (SEQ ID NO:1).

FIG. 8 shows the *Schizochytrium* sp. ATCC PTA-9695 Pfa1p amino acid sequence (SEQ ID NO:2).

Figure 9:
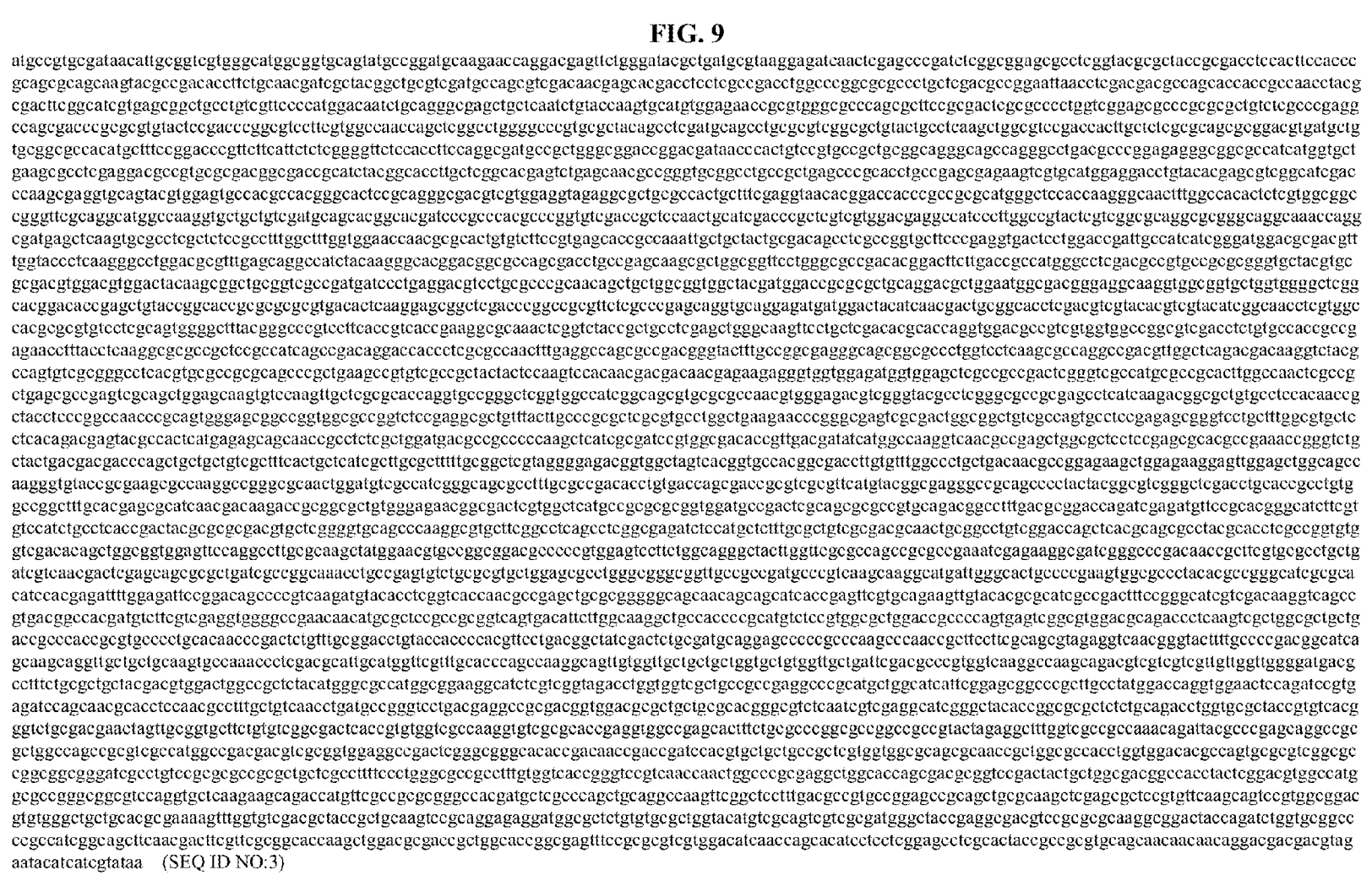

FIG. 9 shows the *Schizochytrium* sp. ATCC PTA-9695 PFA2 polynucleotide sequence (SEQ ID NO:3).

FIG. 10 shows the *Schizochytrium* sp. ATCC PTA-9695 Pfa2p amino acid sequence (SEQ ID NO:4).

Figure 11:
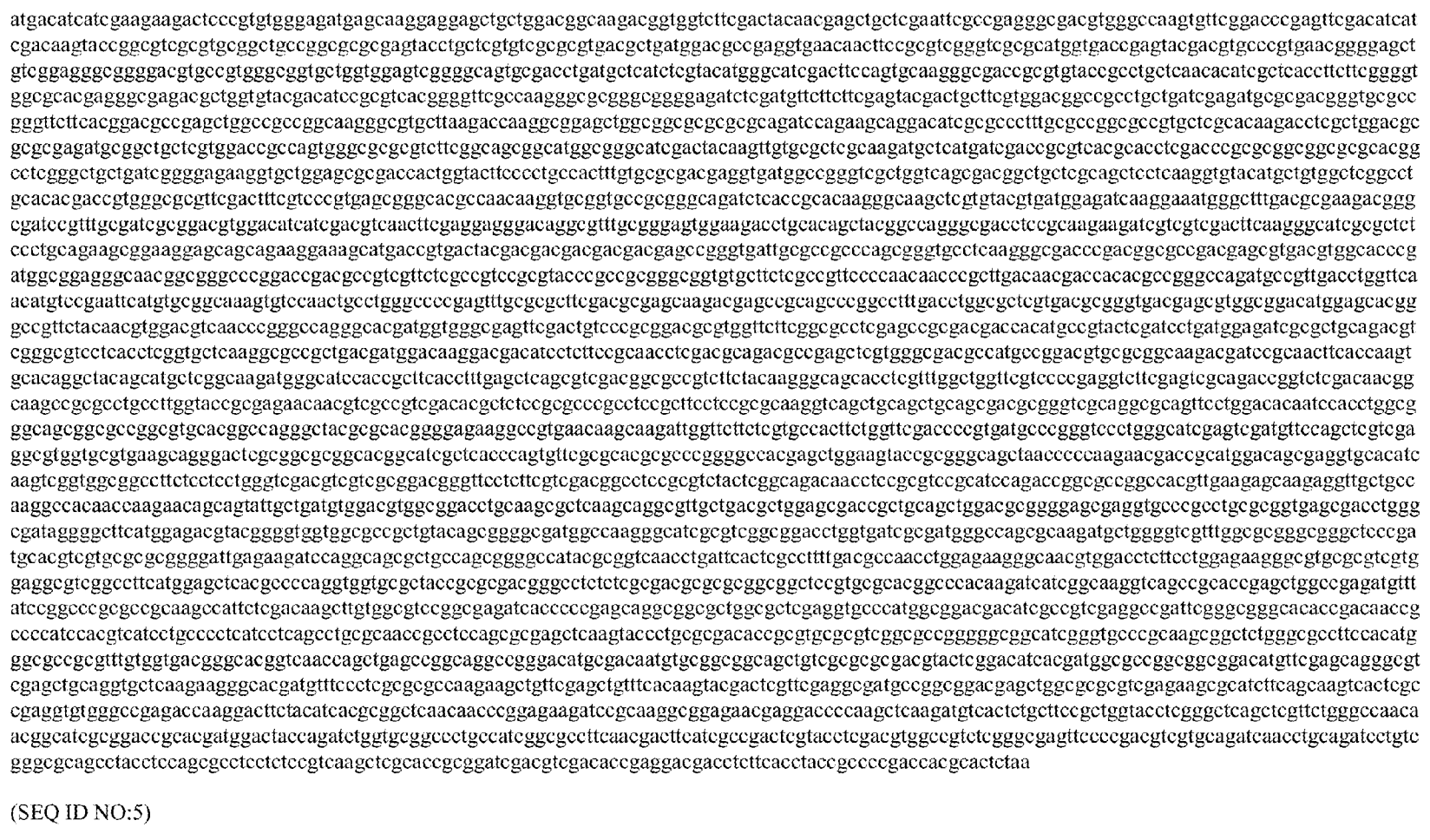

FIG. 11 shows the *Schizochytrium* sp. ATCC PTA-9695 PFA3 polynucleotide sequence (SEQ ID NO:5).

FIG. 12 shows the *Schizochytrium* sp. ATCC PTA-9695 Pfa3p amino acid sequence (SEQ ID NO:6).

FIG. 13 shows the *Thraustochytrium* sp. ATCC PTA-10212 PFA1 polynucleotide sequence (SEQ ID NO:68).

Figure 14:
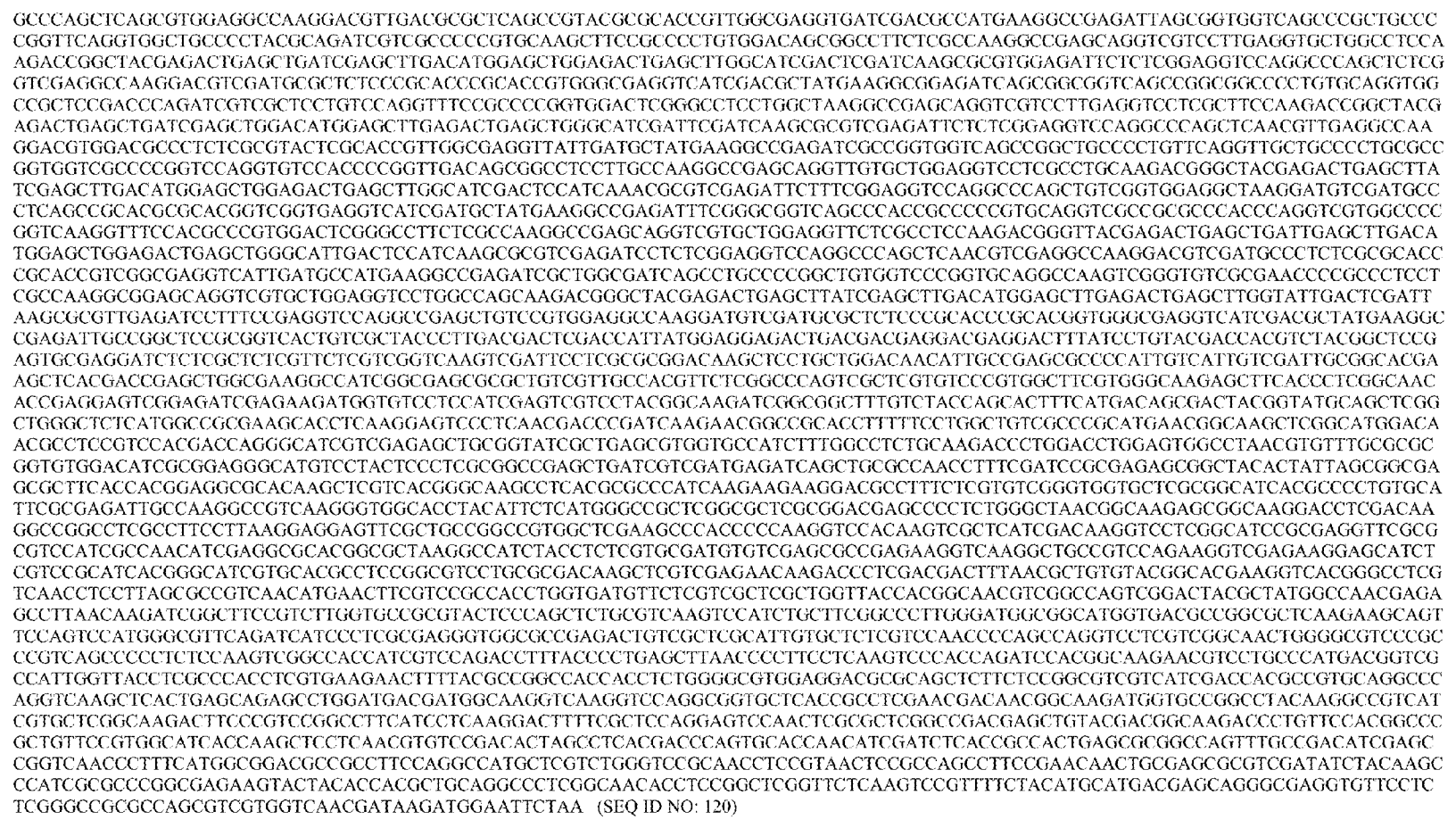

FIG. 14 shows a *Thraustochytrium* sp. ATCC PTA-10212 PFA1 polynucleotide sequence (SEQ ID NO:120) that has been codon-optimized for expression in *Schizochytrium*.

FIG. 15 shows the *Thraustochytrium* sp. ATCC PTA-10212 Pfa1p amino acid sequence (SEQ ID NO:69).

FIG. 16 shows the *Thraustochytrium* sp. ATCC PTA-10212 PFA2 polynucleotide sequence (SEQ ID NO:70).

FIG. 17 shows a *Thraustochytrium* sp. ATCC PTA-10212 PFA2 polynucleotide sequence (SEQ ID NO:121) that has been codon-optimized for expression in *Schizochytrium*.

FIG. 18 shows the *Thraustochytrium* sp. ATCC PTA-10212 Pfa2p amino acid sequence (SEQ ID NO:71).

FIG. 19 shows the *Thraustochytrium* sp. ATCC PTA-10212 PFA3 polynucleotide sequence (SEQ ID NO:72).

FIG. 20 shows a *Thraustochytrium* sp. ATCC PTA-10212 PFA3 polynucleotide sequence (SEQ ID NO:122) that has been codon-optimized for expression in *Schizochytrium*.

FIG. 21 shows the *Thraustochytrium* sp. ATCC PTA-10212 Pfa3p amino acid sequence (SEQ ID NO:73).

FIG. 22 shows a codon usage table for *Schizochytrium*.

DETAILED DESCRIPTION OF THE INVENTION

The present invention is directed to isolated nucleic acid molecules and polypeptides of polyunsaturated fatty acid (PUFA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

PUFA Synthases

As used herein, the term "PUFA synthase" refers to an enzyme that is involved in the production of polyunsaturated fatty acids. See, e.g., Metz et al., *Science* 293:290-293 (2001).

The present invention is directed in part to three PUFA synthase subunits termed Pfa1p (SEQ ID NO:2 or SEQ ID NO:69), Pfa2p (SEQ ID NO:4 or SEQ ID NO:71), and Pfa3p (SEQ ID NO:6 or SEQ ID NO:73), as well as the genes that encode the subunits termed PFA1 (SEQ ID NO:1, SEQ ID NO:68, or SEQ ID NO:120), PFA2 (SEQ ID NO:3, SEQ ID NO:70, or SEQ ID NO:121), and PFA3 (SEQ ID NO:5, SEQ ID NO:72, or SEQ ID NO:122). See, FIGS. 1-3 and 7-21. PUFA synthases in other thraustochytrids have also been designated as ORF 1, ORF 2, and ORF 3, respectively, or as OrfA, OrfB, and OrfC, respectively. See, e.g., *Schizochytrium* sp. (ATCC 20888) and *Thraustochytrium* sp. (ATCC 20892) in U.S. Pat. Nos. 7,247,461 and 7,256,022, referring to orfA, orfB, and orfC genes and corresponding OrfA, OrfB, and OrfC proteins, and *Thraustochytrium aureum* (ATCC 34304) in U.S. Pat. No. 7,368,552, referring to ORF A, ORF B, and ORF C genes and proteins. See also, strain SAM2179 in WO/2005/097982, referring to ORF 1, ORF 2, and ORF 3 genes and proteins.

Nucleic Acid Molecules

The present invention is directed to isolated nucleic acid molecules comprising polynucleotide sequences for PUFA synthase genes and domains derived from an isolated microorganism that is the subject of co-pending U.S. application Ser. No. 12/407,687, filed on Mar. 19, 2009, incorporated herein by reference in its entirety. The microorganism was deposited under the Budapest Treaty at the American Type Culture Collection, Patent Depository, 10801 University Boulevard, Manassas, Va. 20110-2209, on Jan. 7, 2009, and given ATCC Accession No. PTA-9695, and is also referred to as *Schizochytrium* sp. ATCC PTA-9695. When expressed, these genes produce unique fatty acid profiles, characterized in part by high levels of omega-3 fatty acids, in particular high levels of DHA.

The present invention is directed to isolated nucleic acid molecules comprising polynucleotide sequences for PUFA synthase genes and domains derived from an isolated microorganism that is the subject of co-pending U.S. Appl. No. 61/296,456, filed on Jan. 19, 2010, incorporated herein by reference in its entirety. The microorganism was deposited under the Budapest Treaty at the American Type Culture Collection, Patent Depository, 10801 University Boulevard, Manassas, Va. 20110-2209, on Jul. 14, 2009, and given ATCC Accession No. PTA-10212, and is also referred to as *Thraustochytrium* sp. ATCC PTA-10212. When expressed, these genes produce unique fatty acid profiles, characterized in part by high levels of omega-3 fatty acids, in particular high levels of DHA, EPA, or a combination thereof.

As used herein, a "polynucleotide" can comprise a conventional phosphodiester bond or a non-conventional bond (e.g., an amide bond, such as found in peptide nucleic acids (PNA)). A polynucleotide can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotides can be composed of triple-stranded regions comprising RNA or DNA or both RNA and DNA. Polynucleotides can contain ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters. Polynucleotides can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms. The term nucleic acid molecule refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

The terms "isolated" nucleic acid molecule refers to a nucleic acid molecule, DNA or RNA, which has been removed from its native environment. Further examples of isolated nucleic acid molecules include nucleic acid molecules comprising recombinant polynucleotides maintained in heterologous host cells or purified (partially or substantially) polynucleotides in solution. Isolated RNA molecules include in vivo or in vitro RNA transcripts of polynucleotides of the present invention. Isolated nucleic acid molecules according to the present invention further include such molecules produced synthetically. In addition, a nucleic acid molecule or polynucleotide can include a regulatory element such as a promoter, ribosome binding site, or a transcription terminator.

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

The present invention is directed to isolated nucleic acid molecules comprising polynucleotide sequences at least 80% identical to the polynucleotide sequences of Schizochytrium sp. ATCC PTA-9695 PFA1 (SEQ ID NO:1), Schizochytrium sp. ATCC PTA-9695 PFA2 (SEQ ID NO:3), Schizochytrium sp. ATCC PTA-9695 PFA3 (SEQ ID NO:5), Thraustochytrium sp. ATCC PTA-10212 PFA1 (SEQ ID NO:68 or SEQ ID NO:120), Thraustochytrium sp. ATCC PTA-10212 PFA2 (SEQ ID NO:70 or SEQ ID NO:121), Thraustochytrium sp. ATCC PTA-10212 PFA3 (SEQ ID NO:72 or SEQ ID NO:122), and combinations thereof, wherein the polynucleotides encode polypeptides comprising one or more PUFA synthase activities.

The PUFA synthase activities are associated with one or more domains in each synthase polypeptide, wherein the domains can be identified by their conserved structural or functional motifs based on their homology to known motifs and can also be identified based upon their specific biochemical activities. See, e.g., U.S. Pat. No. 7,217,856, incorporated by reference herein, in its entirety. Examples of PUFA synthase domains include: the beta-ketoacyl-ACP synthase (KS) domain, malonyl-CoA:ACP acyltransferase (MAT) domain, acyl carrier protein (ACP) domains, ketoreductase (KR) domain, and beta-hydroxyacyl-ACP dehydrase (DH) domain in Pfa1p; the KS domain, chain length factor (CLF) domain, acyltransferase (AT) domain, and enoyl-ACP reductase (ER) domain in Pfa2p; and the DH domains and the ER domain in Pfa3p.

A polypeptide or domain of a polypeptide having beta-ketoacyl-ACP synthase (KS) biological activity (function) has been previously shown to be capable of carrying out the initial step of the fatty acid elongation reaction cycle. The term "beta-ketoacyl-ACP synthase" has been used interchangeably with the terms "3-keto acyl-ACP synthase," "beta-ketoacyl-ACP synthase," and "keto-acyl ACP synthase." In other systems, it has been shown that the acyl group for elongation is linked to a cysteine residue at the active site of KS by a thioester bond, and the acyl-KS undergoes condensation with malonyl-ACP to form -ketoacyl-ACP, $CO_2$, and unbound ("free") KS. In such systems, KS has been shown to possess greater substrate specificity than other polypeptides of the reaction cycle. Polypeptides (or domains of polypeptides) can be readily identified as belonging to the KS family by homology to known KS sequences.

A polypeptide or a domain of a polypeptide having malonyl-CoA:ACP acyltransferase (MAT) activity has been previously shown to be capable of transferring the malonyl moiety from malonyl-CoA to ACP. The term "malonyl-CoA:ACP acyltransferase" has been used interchangeably with "malonyl acyltransferase." In addition to the active site motif (GxSxG), MATs have been shown to possess an extended motif (R and Q amino acids in key positions). Polypeptides (or domains of polypeptides) can be readily identified as belonging to the MAT family by their homology to known MAT sequences and by their extended motif structure.

A polypeptide or a domain of a polypeptide having acyl carrier protein (ACP) activity has been previously shown to be capable of functioning as a carrier for growing fatty acyl chains via a thioester linkage to a covalently bound co-factor. ACPs are typically about 80 to about 100 amino acids long and have been shown to be converted from inactive apo-forms to functional holo-forms by transfer of the phosphopantetheinyl moiety of CoA to a highly conserved serine residue of the ACP. It has also been shown that acyl groups are attached to ACPs by a thioester linkage at the free terminus of the phosphopantetheinyl moiety. The presence of variations of an active site motif (LGIDS*) has also been recognized as a signature of ACPs. The functionality of the active site serine (S*) has been demonstrated in a bacterial PUFA synthase (Jiang et al., J. Am. Chem. Soc. 130:6336-7 (2008)). Polypeptides (or domains of polypeptides) can be readily identified as belonging to the ACP family by labeling with radioactive pantetheine and by sequence homology to known ACPs.

A polypeptide or a domain of a polypeptide having dehydrase or dehydratase (DH) activity has been previously shown to be capable of catalyzing a dehydration reaction. Reference to DH activity typically refers to FabA-like beta-hydroxyacyl-ACP dehydrase biological activity. FabA-like beta-hydroxyacyl-ACP dehydrase biological activity removes HOH from a beta-ketoacyl-ACP and initially produces a trans double bond in the carbon chain. The term "FabA-like beta-hydroxyacyl-ACP dehydrase" has been used interchangeably with the terms "FabA-like beta-hydroxy acyl-ACP dehydrase," "beta-hydroxyacyl-ACP dehydrase," and "dehydrase." The DH domains of PUFA synthase systems have previously been demonstrated as showing homology to bacterial DH enzymes associated with FAS systems (rather than to the DH domains of other PKS systems). See, e.g., U.S. Pat.

No. 7,217,856, incorporated by reference herein in its entirety. A subset of bacterial DHs, the FabA-like DHs, possesses cis-trans isomerase activity (Heath et al., *J. Biol. Chem.*, 271, 27795 (1996)). Based on homology to the FabA-like DH proteins, one or all of the PUFA synthase system DH domains can be responsible for insertion of cis double bonds in the PUFA synthase products. A polypeptide or domain can also have non-FabA-like DH activity, or non-FabA-like beta-hydroxyacyl-ACP dehydrase (DH) activity. More specifically, a conserved active site motif of about 13 amino acids in length has been previously identified in PUFA synthase DH domains: LxxHxxxGxxxxP (the L position can also be an I in the motif). See, e.g., U.S. Pat. No. 7,217,856, and Donadio S, Katz L., *Gene* 111(1):51-60 (1992), each of which is incorporated by reference herein in its entirety. This conserved motif is found in a similar region of all known PUFA synthase sequences and could be responsible for a non-FabA like dehydration.

A polypeptide or a domain of a polypeptide having beta-ketoacyl-ACP reductase (KR) activity has been previously shown to be capable of catalyzing the pyridine-nucleotide-dependent reduction of 3-ketoacyl forms of ACP. The term "beta-ketoacyl-ACP reductase" has been used interchangeably with the terms "ketoreductase," "3-ketoacyl-ACP reductase," and "keto-acyl ACP reductase." It has been determined in other systems that KR function involves the first reductive step in the de novo fatty acid biosynthesis elongation cycle. Polypeptides (or domains of polypeptides) can be readily identified as belonging to the KR family by sequence homology to known PUFA synthase KRs.

A polypeptide or a domain of a polypeptide having chain length factor (CLF) activity has been previously defined as having one or more of the following activities or characteristics: (1) it can determine the number of elongation cycles and hence chain length of the end product, (2) it has homology to KS, but lacks the KS active site cysteine, (3) it can heterodimerize with KS, (4) it can provide the initial acyl group to be elongated, or (5) it can decarboxylate malonate (as malonyl-ACP), thus forming an acetate group that can be transferred to the KS active site and that can act as the 'priming' molecule that undergoes the initial elongation (condensation) reaction. A CLF domain is found in all currently identified PUFA synthase systems and in each case is found as part of a multidomain protein. Polypeptides (or domains of polypeptides) can be readily identified as belonging to the CLF family by sequence homology to known PUFA synthase CLFs.

A polypeptide or a domain of a polypeptide having acyl-transferase (AT) activity has been previously defined as having one or more of the following activities or characteristics: (1) it can transfer the fatty acyl group from the ACP domain(s) to water (i.e., a thioesterase), releasing the fatty acyl group as a free fatty acid, (2) it can transfer a fatty acyl group to an acceptor such as CoA, (3) it can transfer the acyl group among the various ACP domains, or (4) it can transfer the fatty acyl group to a lipophilic acceptor molecule (e.g. to lysophosphadic acid). Polypeptides (or domains of polypeptides) can be readily identified as belonging to the AT family by sequence homology to known PUFA synthase ATs.

A polypeptide or a domain of a polypeptide having enoyl-ACP reductase (ER) biological activity has been previously shown to be capable of reducing the trans-double bond (introduced by the DH activity) in the fatty acyl-ACP, resulting in saturation of the associated carbons. The ER domain in PUFA synthase systems has previously been shown to have homology to a family of ER enzymes (Heath et al., *Nature* 406: 145-146 (2000), incorporated by reference herein in its entirety), and an ER homolog has been shown to function as an enoyl-ACP reductase in vitro (Bumpus et al. *J. Am. Chem. Soc.*, 130: 11614-11616 (2008), incorporated by reference herein in its entirety). The term "enoyl-ACP reductase" has been used interchangeably with "enoyl reductase," "enoyl ACP-reductase," and "enoyl acyl-ACP reductase." Polypeptides (or domains of polypeptides) can be readily identified as belonging to the ER family by sequence homology to known PUFA synthase ERs.

In some embodiments, the present invention is directed to nucleic acid molecules comprising a polynucleotide sequence at least 80% identical to a polynucleotide sequence within PFA1 (SEQ ID NO:1, SEQ ID NO:68, or SEQ ID NO:120) that encodes one or more PUFA synthase domains. In some embodiments, the nucleic acid molecule comprises a polynucleotide sequence at least 80% identical to a polynucleotide sequence within PFA1 (SEQ ID NO:1, SEQ ID NO:68, or SEQ ID NO:120) that encodes one or more PUFA synthase domains such as a KS domain (SEQ ID NO:7 or SEQ ID NO:74), a MAT domain (SEQ ID NO:9 or SEQ ID NO:76), an ACP domain (such as any one of SEQ ID NOs:13, 15, 17, 19, 21, 23, 80, 82, 84, 86, 88, 90, 92, 94, 96, or 98), a combination of two or more ACP domains, such as two, three, four, five, six, seven, eight, nine, or ten ACP domains, including tandem domains (SEQ ID NO:11 or SEQ ID NO:78, and portions thereof), a KR domain (SEQ ID NO:25 or SEQ ID NO:100), a DH domain (SEQ ID NO:27 or SEQ ID NO:118), and combinations thereof. In some embodiments, the nucleic acid molecule comprises two or more polynucleotide sequences, wherein each of the at least two or more polynucleotide sequences is 80% identical to a polynucleotide sequence within PFA1 (SEQ ID NO:1, SEQ ID NO:68, or SEQ ID NO:120) that encodes one or more PUFA synthase domains. In some embodiments, the at least two or more polynucleotide sequences are 80% identical to the same polynucleotide sequence within SEQ ID NO:1, SEQ ID NO:68, or SEQ ID NO:120 that encodes one or more PUFA synthase domains. In some embodiments, the at least two or more polynucleotide sequences are 80% identical to different polynucleotide sequences within SEQ ID NO:1, SEQ ID NO:68, or SEQ ID NO:120 that each encode one or more PUFA synthase domains. In some embodiments, the at least two or more polynucleotide sequences are 80% identical to different polynucleotide sequences within SEQ ID NO:1, SEQ ID NO:68, or SEQ ID NO:120, wherein the at least two or more polynucleotide sequences are located in the same order or a different order in the nucleic acid molecule as compared to the order of the corresponding sequences within SEQ ID NO:1, SEQ ID NO:68, or SEQ ID NO:120. In some embodiments, each of the at least two or more polynucleotide sequences are 80% identical to a polynucleotide sequence within PFA1 (SEQ ID NO:1, SEQ ID NO:68, or SEQ ID NO:120) that encodes one or more PUFA synthase domains such as a KS domain (SEQ ID NO:7 or SEQ ID NO:74), a MAT domain (SEQ ID NO:9 or SEQ ID NO:76), an ACP domain (such as any one of SEQ ID NOs:13, 15, 17, 19, 21, 23, 80, 82, 84, 86, 88, 90, 92, 94, 96, or 98), a combination of two, three, four, five, six, seven, eight, nine, or ten ACP domains, including tandem domains (SEQ ID NO:11 or SEQ ID NO:78, and portions thereof), a KR domain (SEQ ID NO:25 or SEQ ID NO:100), a DH domain (SEQ ID NO:27 or SEQ ID NO:118), and combinations thereof. In some embodiments, the nucleic acid molecule comprises one or more polynucleotide sequences within PFA1 (SEQ ID NO:1, SEQ ID NO:68, or SEQ ID NO:120) that encodes one or more PUFA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA2 (SEQ ID NO:3, SEQ ID NO:70, or SEQ ID NO:121) that encodes one or more PUFA synthase domains. In some embodiments, the nucleic acid molecule comprises a polynucleotide sequence at least 80% identical to the polynucleotide sequence within PFA2 (SEQ ID NO:3, SEQ ID NO:70, or SEQ ID NO:121) that encodes one or more PUFA synthase domains such as a KS domain (SEQ ID NO:29 or SEQ ID NO:102), a CLF domain (SEQ ID NO:31 or SEQ ID NO:104), an AT domain (SEQ ID NO:33 or SEQ ID NO:106), an ER domain (SEQ ID NO:35 or SEQ ID NO:108), and combinations thereof. In some embodiments, the nucleic acid molecule comprises two or more polynucleotide sequences, wherein each of the at least two or more polynucleotide sequences is 80% identical to a polynucleotide sequence within PFA2 (SEQ ID NO:3, SEQ ID NO:70, or SEQ ID NO:121) that encodes one or more PUFA synthase domains. In some embodiments, the at least two or more polynucleotide sequences are 80% identical to the same polynucleotide sequence within SEQ ID NO:3, SEQ ID NO:70, or SEQ ID NO:121 that encodes one or more PUFA synthase domains. In some embodiments, the at least two or more polynucleotide sequences are 80% identical to different polynucleotide sequences within SEQ ID NO:3, SEQ ID NO:70, or SEQ ID NO:121 that each encode one or more PUFA synthase domains. In some embodiments, the at least two or more polynucleotide sequences are 80% identical to different polynucleotide sequences within SEQ ID NO:3, SEQ ID NO:70, or SEQ ID NO:121, wherein the at least two or more polynucleotide sequences are located in the same order or a different order in the nucleic acid molecule as compared to the order of the corresponding sequences within SEQ ID NO:3, SEQ ID NO:70, or SEQ ID NO:121. In some embodiments, each of the at least two or more polynucleotide sequences are 80% identical to a polynucleotide sequence within PFA2 (SEQ ID NO:3, SEQ ID NO:70, or SEQ ID NO:121) that encodes one or more PUFA synthase domains such as a KS domain (SEQ ID NO:29 or SEQ ID NO:102), a CLF domain (SEQ ID NO:31 or SEQ ID NO:104), an AT domain (SEQ ID NO:33 or SEQ ID NO:106), an ER domain (SEQ ID NO:35 or SEQ ID NO:108), and combinations thereof. In some embodiments, the nucleic acid molecule comprises one or more polynucleotide sequences within PFA2 (SEQ ID NO:3, SEQ ID NO:70, or SEQ ID NO:121) that encodes one or more PUFA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA3 (SEQ ID NO:5, SEQ ID NO:72, or SEQ ID NO:122) that encodes one or more PUFA synthase domains. In some embodiments, the nucleic acid molecule comprises a polynucleotide sequence at least 80% identical to a polynucleotide sequence within PFA3 (SEQ ID NO:5, SEQ ID NO:72, or SEQ ID NO:122) that encodes one or more PUFA synthase domains such as a DH domain (such as SEQ ID NO:37, SEQ ID NO:39, SEQ ID NO:110, or SEQ ID NO:112), an ER domain (SEQ ID NO:41 or SEQ ID NO:114), and combinations thereof. In some embodiments, the nucleic acid molecule comprises two or more polynucleotide sequences, wherein each of the at least two or more polynucleotide sequences is 80% identical to a polynucleotide sequence within PFA3 (SEQ ID NO:5, SEQ ID NO:72, or SEQ ID NO:122) that encodes one or more PUFA synthase domains. In some embodiments, the at least two or more polynucleotide sequences are 80% identical to the same polynucleotide sequence within SEQ ID NO:5, SEQ ID NO:72, or SEQ ID NO:122 that encodes one or more PUFA synthase domains. In some embodiments, the at least two or more polynucleotide sequences are 80% identical to different polynucleotide sequences within SEQ ID NO:5, SEQ ID NO:72, or SEQ ID NO:122 that each encode one or more PUFA synthase domains. In some embodiments, the at least two or more polynucleotide sequences are 80% identical to different polynucleotide sequences within SEQ ID NO:5, SEQ ID NO:72, or SEQ ID NO:122, wherein the at least two or more polynucleotide sequences are located in the same order or a different order in the nucleic acid molecule as compared to the order of the corresponding sequences within SEQ ID NO:5, SEQ ID NO:72, or SEQ ID NO:122. In some embodiments, each of the at least two or more polynucleotide sequences is 80% identical to a polynucleotide sequence within PFA3 (SEQ ID NO:5, SEQ ID NO:72, or SEQ ID NO:122) that encodes one or more PUFA synthase domains such as a DH domain (such as SEQ ID NO:37, SEQ ID NO:39, SEQ ID NO:110, or SEQ ID NO:112), an ER domain (SEQ ID NO:41 or SEQ ID NO:114), and combinations thereof. In some embodiments, the nucleic acid molecule comprises one or more polynucleotide sequences within PFA3 (SEQ ID NO:5, SEQ ID NO:72, or SEQ ID NO:122) that encodes one or more PUFA synthase domains, including one or more copies of any individual domain in combination with one or more copies of any other individual domain.

In some embodiments, the present invention is directed to a nucleic acid molecule comprising a polynucleotide sequence at least 80% identical to SEQ ID NO:1, SEQ ID NO:68, or SEQ ID NO:120, wherein the polynucleotide sequence encodes a polypeptide comprising PUFA synthase activity selected from the group consisting of KS activity, MAT activity, ACP activity, KR activity, DH activity, and combinations thereof.

In some embodiments, the present invention is directed to a nucleic acid molecule comprising a polynucleotide sequence at least 80% identical to SEQ ID NO:7 or SEQ ID NO:74, wherein the polynucleotide sequence encodes a polypeptide comprising KS activity.

In some embodiments, the present invention is directed to a nucleic acid molecule comprising a polynucleotide sequence at least 80% identical to SEQ ID NO:9 or SEQ ID NO:76, wherein the polynucleotide sequence encodes a polypeptide comprising MAT activity.

In some embodiments, the present invention is directed to a nucleic acid molecule comprising a polynucleotide sequence at least 80% identical to any one of SEQ ID NOs:13, 15, 17, 19, 21, 23, 80, 82, 84, 86, 88, 90, 92, 94, 96, or 98, wherein the polynucleotide sequence encodes a polypeptide comprising ACP activity.

In some embodiments, the present invention is directed to a nucleic acid molecule comprising a polynucleotide sequence at least 80% identical to SEQ ID NO:11 or SEQ ID NO:78, wherein the polynucleotide sequence encodes a polypeptide comprising ACP activity.

In some embodiments, the nucleic acid molecule comprises a polynucleotide sequence at least 80% identical to a polynucleotide sequence within SEQ ID NO:11 that encodes one, two, three, four, five, or six ACP domains, wherein the polynucleotide sequence encodes a polypeptide comprising ACP activity associated with one or more ACP domains. SEQ ID NOs:13, 15, 17, 19, 21, and 23 are representative polynucleotides sequence that each encode a single ACP domain within SEQ ID NO:11.

In some embodiments, the nucleic acid molecule comprises a polynucleotide sequence at least 80% identical to a polynucleotide sequence within SEQ ID NO:78 that encodes one, two, three, four, five, six, seven, eight, nine, or ten ACP domains, wherein the polynucleotide sequence encodes a polypeptide comprising ACP activity associated with one or more ACP domains. SEQ ID NOs:80, 82, 84, 86, 88, 90, 92, 94, 96, and 98 are representative polynucleotides sequence that each encode a single ACP domain within SEQ ID NO:78.

In some embodiments, the present invention is directed to a nucleic acid molecule comprising a polynucleotide sequence at least 80% identical to SEQ ID NO:25 or SEQ ID NO:100, wherein the polynucleotide sequence encodes a polypeptide comprising KR activity.

In some embodiments, the present invention is directed to a nucleic acid molecule comprising a polynucleotide sequence at least 80% identical to SEQ ID NO:27 or SEQ ID NO:118, wherein the polynucleotide sequence encodes a polypeptide comprising DH activity.

In some embodiments, the present invention is directed to a nucleic acid molecule comprising a polynucleotide sequence at least 80% identical to SEQ ID NO:3, SEQ ID NO:70, or SEQ ID NO:121, wherein the polynucleotide sequence encodes a polypeptide comprising PUFA synthase activity selected from the group consisting of KS activity, CLF activity, AT activity, ER activity, and combinations thereof.

In some embodiments, the present invention is directed to a nucleic acid molecule comprising a polynucleotide sequence at least 80% identical to SEQ ID NO:29 or SEQ ID NO:102, wherein the polynucleotide sequence encodes a polypeptide comprising KS activity.

In some embodiments, the present invention is directed to a nucleic acid molecule comprising a polynucleotide sequence at least 80% identical to SEQ ID NO:31 or SEQ ID NO:104, wherein the polynucleotide sequence encodes a polypeptide comprising CLF activity.

In some embodiments, the present invention is directed to a nucleic acid molecule comprising a polynucleotide sequence at least 80% identical to SEQ ID NO:33 or SEQ ID NO:106, wherein the polynucleotide sequence encodes a polypeptide comprising AT activity.

In some embodiments, the present invention is directed to a nucleic acid molecule comprising a polynucleotide sequence at least 80% identical to SEQ ID NO:35 or SEQ ID NO:108, wherein the polynucleotide sequence encodes a polypeptide comprising ER activity.

In some embodiments, the present invention is directed to a nucleic acid molecule comprising a polynucleotide sequence at least 80% identical to SEQ ID NO:5, SEQ ID NO:72, or SEQ ID NO:122, wherein the polynucleotide sequence encodes a polypeptide comprising PUFA synthase activity selected from the group consisting of DH activity, ER activity, and combinations thereof.

In some embodiments, the present invention is directed to a nucleic acid molecule comprising a polynucleotide sequence at least 80% identical to SEQ ID NO:37, wherein the polynucleotide sequence encodes a polypeptide comprising DH activity.

In some embodiments, the present invention is directed to a nucleic acid molecule comprising a polynucleotide sequence at least 80% identical to SEQ ID NO:39, wherein the polynucleotide sequence encodes a polypeptide comprising DH activity.

In some embodiments, the present invention is directed to a nucleic acid molecule comprising a polynucleotide sequence at least 80% identical to SEQ ID NO:110, wherein the polynucleotide sequence encodes a polypeptide comprising DH activity.

In some embodiments, the present invention is directed to a nucleic acid molecule comprising a polynucleotide sequence at least 80% identical to SEQ ID NO:112, wherein the polynucleotide sequence encodes a polypeptide comprising DH activity.

In some embodiments, the present invention is directed to a nucleic acid molecule comprising a polynucleotide sequence at least 80% identical to SEQ ID NO:41 or SEQ ID NO:114, wherein the polynucleotide sequence encodes a polypeptide comprising ER activity.

The present invention is directed to isolated nucleic acid molecules comprising polynucleotide sequences encoding polypeptides, wherein the polypeptides comprise amino acid sequences that are at least 80% identical to the amino acid sequences of Pfa1p (SEQ ID NO:2 or SEQ ID NO:69), Pfa2p (SEQ ID NO:4 or SEQ ID NO:71), or Pfa3p (SEQ ID NO:6 or SEQ ID NO:73), wherein the polynucleotides encode polypeptides comprising one or more PUFA synthase activities.

The present invention is directed to nucleic acid molecules comprising a polynucleotide sequence encoding a polypeptide, wherein the polypeptide comprises an amino acid sequence at least 80% identical to the amino acid sequences of one or more PUFA synthase domains of the PUFA synthases of the invention.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa1p (SEQ ID NO:2 or SEQ ID NO:69) comprising one or more PUFA synthase domains. In some embodiments, the polypeptide comprises an amino acid sequence at least 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two or more ACP domains, such as two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises two or more amino acid sequences, wherein each of the at least two or more amino acid sequences is 80% identical to an amino acid sequence within Pfa1p (SEQ ID NO:2 or SEQ ID NO:69) comprising one or more PUFA synthase domains. In some embodiments, the at least two or more amino acid sequences are 80% identical to the same amino acid sequence within Pfa1p (SEQ ID NO:2 or SEQ ID NO:69) comprising one or more PUFA synthase domains. In some embodiments, the at least two or more amino acid sequences are 80% identical to different amino acid sequences within Pfa1p (SEQ ID NO:2 or SEQ ID NO: 69) that each comprise one or more PUFA synthase domains. In some embodiments, the at least two or more amino acid sequences are 80% identical to different amino acid sequences within Pfa1p (SEQ ID NO:2 or SEQ ID NO:69), wherein the at least two or more amino acid sequences are located in the same order or a different order in the polypeptide as compared to the order of the corresponding domains within Pfa1p (SEQ ID NO:2 or SEQ ID NO:69). In some embodiments, the at least two or more amino acid sequences are 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO: 77), an ACP domain (such as any one of SEQ ID NOs:14, 16, 18, 20, 22, 24, 81, 83, 85, 87, 89, 91, 93, 95, 97, or 99), a combination of two, three, four, five, six, seven, eight, nine, or ten ACP domains, including tandem domains (SEQ ID NO:12 or SEQ ID NO: 79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises one or more amino acid sequences within Pfa1p (SEQ ID NO:2 or SEQ ID NO:69) comprising one or more PUFA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa2p (SEQ ID NO:4 or SEQ ID NO:71) comprising one or more PUFA synthase domains. In some embodiments, the polypeptide comprises an amino acid sequence at least 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises two or more amino acid sequences, wherein each of the at least two or more amino acid sequences is 80% identical to an amino acid sequence within Pfa2p (SEQ ID NO:4 or SEQ ID NO:71) comprising one or more PUFA synthase domains. In some embodiments, the at least two or more amino acid sequences are 80% identical to the same amino acid sequence within Pfa2p (SEQ ID NO:4 or SEQ ID NO:71). In some embodiments, the at least two or more amino acid sequences are 80% identical to different amino acid sequences within Pfa2p (SEQ ID NO:4 or SEQ ID NO:71) that each comprise one or more PUFA synthase domains. In some embodiments, the at least two or more amino acid sequences are 80% identical to different amino acid sequences within Pfa2p (SEQ ID NO:4 or SEQ ID NO:71), wherein the at least two or more amino acid sequences are located in the same order or a different order in the polypeptide as compared to the order of the corresponding domains within Pfa2p (SEQ ID NO:4 or SEQ ID NO:71). In some embodiments, the at least two or more amino acid sequences are 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises one or more amino acid sequences within Pfa2p (SEQ ID NO:4 or SEQ ID NO:71) comprising one or more PUFA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa3p (SEQ ID NO:6 or SEQ ID NO:73) comprising one or more PUFA synthase domains. In some embodiments, the polypeptide comprises an amino acid sequence at least 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises two or more amino acid sequences, wherein each of the at least two or more amino acid sequences is 80% identical to an amino acid sequence within Pfa3p (SEQ ID NO:6 or SEQ ID NO:73) comprising one or more PUFA synthase domains. In some embodiments, the at least two or more amino acid sequences are 80% identical to the same amino acid sequence within Pfa3p (SEQ ID NO:6 or SEQ ID NO:73) comprising one or more PUFA synthase domains. In some embodiments, the at least two or more amino acid sequences are 80% identical to different amino acid sequences within Pfa3p (SEQ ID NO:6 or SEQ ID NO:73) that each comprise one or more PUFA synthase domains. In some embodiments, the at least two or more amino acid sequences are 80% identical to different amino acid sequences within Pfa3p (SEQ ID NO:6 or SEQ ID NO:73), wherein the at least two or more amino acid sequences are located in the same order or a different order in the polypeptide as compared to the order of the corresponding domains within Pfa3p (SEQ ID NO:6 or SEQ ID NO:73). In some embodiments, the at least two or more amino acid sequences are 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises one or more amino acid sequences within Pfa3p (SEQ ID NO:6 or SEQ ID NO:73) comprising one or more PUFA synthase domains, including one or more copies of any individual domain in combination with one or more copies of any other individual domain.

In some embodiments, the present invention is directed to a nucleic acid molecule comprising a polynucleotide sequence encoding a polypeptide, wherein the polypeptide comprises an amino acid sequence at least 80% identical to SEQ ID NO:2 or SEQ ID NO:69, and wherein the polypeptide comprises a PUFA synthase activity selected from the group consisting of KS activity, MAT activity, ACP activity, KR activity, DH activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:8 or SEQ ID NO:75, and wherein the polypeptide comprises KS activity.

In some embodiments, the present invention is directed to a nucleic acid molecule comprising a polynucleotide sequence encoding a polypeptide, wherein the polypeptide comprises an amino acid sequence at least 80% identical to SEQ ID NO:10 or SEQ ID NO:77, and wherein the polypeptide comprises MAT activity.

In some embodiments, the present invention is directed to a nucleic acid molecule comprising a polynucleotide sequence encoding a polypeptide, wherein the polypeptide comprises an amino acid sequence at least 80% identical to any one of SEQ ID NOs:14, 16, 18, 20, 22, 24, 81, 83, 85, 87, 89, 91, 93, 95, 97, or 99, and wherein the polypeptide comprises ACP activity.

In some embodiments, the present invention is directed to a nucleic acid molecule comprising a polynucleotide sequence encoding a polypeptide, wherein the polypeptide comprises an amino acid sequence at least 80% identical to SEQ ID NO:12 or SEQ ID NO:79, and wherein the polypeptide comprises ACP activity.

In some embodiments, the present invention is directed to nucleic acid molecules comprising a polynucleotide sequence encoding a polypeptide, wherein the polypeptide comprises an amino acid sequence at least 80% identical to an amino acid sequence within SEQ ID NO:12, wherein the polypeptide comprises ACP activity. In some embodiments, the amino acid sequence is at least 80% identical to an amino acid sequence within SEQ ID NO:12 comprising one, two, three, four, five, or six ACP domains, wherein the polypeptide comprises ACP activity associated with one or more ACP domains. SEQ ID NOs:14, 16, 18, 20, 22 and 24 are representative amino acid sequences, each comprising a single ACP domain within SEQ ID NO: 12.

In some embodiments, the present invention is directed to nucleic acid molecules comprising a polynucleotide sequence encoding a polypeptide, wherein the polypeptide comprises an amino acid sequence at least 80% identical to an amino acid sequence within SEQ ID NO:79, wherein the polypeptide comprises ACP activity. In some embodiments, the amino acid sequence is at least 80% identical to an amino acid sequence within SEQ ID NO:79 comprising one, two, three, four, five, six, seven, eight, nine, or ten ACP domains, wherein the polypeptide comprises ACP activity associated with one or more ACP domains. SEQ ID NOs:81, 83, 85, 87, 89, 91, 93, 95, 97, and 99 are representative amino acid sequences, each comprising a single ACP domain within SEQ ID NO:79.

In some embodiments, the present invention is directed to a nucleic acid molecule comprising a polynucleotide sequence encoding a polypeptide, wherein the polypeptide comprises an amino acid sequence at least 80% identical to SEQ ID NO:26 or SEQ ID NO:101, and wherein the polypeptide comprises KR activity.

In some embodiments, the present invention is directed to a nucleic acid molecule comprising a polynucleotide sequence encoding a polypeptide, wherein the polypeptide comprises an amino acid sequence at least 80% identical to SEQ ID NO:28 or SEQ ID NO:119, and wherein the polypeptide comprises DH activity.

In some embodiments, the present invention is directed to nucleic acid molecules comprising a polynucleotide sequence encoding a polypeptide, wherein the polypeptide comprises an amino acid sequence at least 80% identical to SEQ ID NO:4 or SEQ ID NO:71, wherein the polypeptide comprises a PUFA synthase activity selected from the group consisting of KS activity, CLF activity, AT activity, ER activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:30 or SEQ ID NO:103, and wherein the polypeptide comprises KS activity.

In some embodiments, the present invention is directed to a nucleic acid molecule comprising a polynucleotide sequence encoding a polypeptide, wherein the polypeptide comprises an amino acid sequence at least 80% identical to SEQ ID NO:32 or SEQ ID NO:105, and wherein the polypeptide comprises CLF activity.

In some embodiments, the present invention is directed to a nucleic acid molecule comprising a polynucleotide sequence encoding a polypeptide, wherein the polypeptide comprises an amino acid sequence at least 80% identical to SEQ ID NO:34 or SEQ ID NO:107, and wherein the polypeptide comprises AT activity.

In some embodiments, the present invention is directed to a nucleic acid molecule comprising a polynucleotide sequence encoding a polypeptide, wherein the polypeptide comprises an amino acid sequence at least 80% identical to SEQ ID NO:36 or SEQ ID NO:109, and wherein the polypeptide comprises ER activity.

In some embodiments, the present invention is directed to a nucleic acid molecule comprising a polynucleotide sequence encoding a polypeptide, wherein the polypeptide comprises an amino acid sequence at least 80% identical to SEQ ID NO:6 or SEQ ID NO:73, wherein the polypeptide comprises a PUFA synthase activity selected from the group consisting of DH activity, ER activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:38, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:40, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:111, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:113, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:42 or SEQ ID NO:115, and wherein the polypeptide comprises ER activity.

In some embodiments, the nucleic acid molecules comprise polynucleotide sequences at least about 80%, 85%, or 90% identical to the polynucleotide sequences reported herein, or at least about 95%, 96%, 97%, 98%, 99%, or 100% identical to the polynucleotide sequences reported herein. The term "percent identity," as known in the art, is a relationship between two or more amino acid sequences or two or more polynucleotide sequences, as determined by comparing the sequences. In the art, "identity" also means the degree of sequence relatedness between amino acid or polynucleotide sequences, as the case may be, as determined by the match between strings of such sequences.

By a nucleic acid molecule having a polynucleotide sequence at least, for example, 95% "identical" to a reference polynucleotide sequence of the present invention, it is intended that the polynucleotide sequence of the nucleic acid molecule is identical to the reference sequence except that the polynucleotide sequence can include up to five nucleotide differences per each 100 nucleotides of the reference polynucleotide sequence. In other words, to obtain a nucleic acid molecule having a polynucleotide sequence at least 95% identical to a reference polynucleotide sequence, up to 5% of the nucleotides in the reference sequence can be deleted or substituted with another nucleotide, or a number of nucleotides up to 5% of the total nucleotides in the reference sequence can be inserted into the reference sequence.

As a practical matter, whether any particular polynucleotide sequence or amino acid sequence is at least 80%, 85%, 90%, 95%, 96%, 97%, 98% or 99% identical to a polynucleotide sequence or amino acid sequence of the present invention can be determined conventionally using known computer programs. A method for determining the best overall match between a query sequence (a sequence of the present invention) and a subject sequence can be determined using the alignment of sequences and calculation of identity scores. The alignments were done using the computer program AlignX, which is a component of the Vector NTI Suite 10.0 package from Invitrogen (www.invitrogen.com). The alignments were performed using a ClustalW alignment (Thompson, J. D., et al. *Nucl. Acids Res.* 22: 4673-4680 (1994)) for both amino acid and polynucleotide sequence alignments. The default scoring matrices Blosum62mt2 and swgapdnamt were used for amino acid and polynucleotide sequence alignments, respectively. For amino acid sequences, the default gap opening penalty is 10 and the gap extension penalty 0.1. For polynucleotide sequences, the default gap opening penalty is 15 and the gap extension penalty is 6.66.

The present invention is directed to an isolated nucleic acid molecule comprising a polynucleotide sequence encoding a polypeptide comprising PUFA synthase activity selected from the group consisting of KS activity, MAT activity, ACP activity, KR activity, CLF activity, AT activity, ER activity, DH activity, and combinations thereof, wherein the polynucleotide hybridizes under stringent conditions to the complement of any of the polynucleotide sequences described above.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified. See, e.g., Sambrook J. and Russell D. 2001. Molecular cloning: A laboratory manual, 3rd edition. Cold Spring Harbor Laboratory Press, Cold Spring Harbor, N.Y. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

The present invention is directed to an isolated nucleic acid molecule comprising a polynucleotide sequence that is fully complementary to any of the polynucleotide sequences described above. The term "complementary" is used to describe the relationship between nucleotide bases that are capable to hybridizing to one another. For example, with respect to DNA, adenosine is complementary to thymine and cytosine is complementary to guanine.

In certain embodiments, the polynucleotide or nucleic acid is DNA. In the case of DNA, a nucleic acid molecule comprising a polynucleotide sequence which encodes a polypeptide can normally include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a polynucleotide sequence encoding a polypeptide if the promoter was capable of effecting transcription of that polynucelotide sequence. The promoter can be a cell-specific promoter that directs substantial transcription of the DNA only in predetermined cells. In general, a coding region is located 3' to a promoter. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

Suitable regulatory regions include nucleic acid regions located upstream (5' non-coding sequences), within, or downstream (3' non-coding sequences) of a coding region, and which influence the transcription, RNA processing or stability, or translation of the associated coding region. Regulatory regions can include promoters, translation leader sequences, RNA processing sites, effector binding sites, and stem-loop structures. Other transcription control elements, besides a promoter, for example enhancers, operators, repressors, and transcription termination signals, can be operably associated with the polynucleotide to direct cell-specific transcription. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

In certain aspects of the invention, polynucleotide sequences having at least 20 bases, at least 30 bases, or at least 50 bases and that hybridize to a polynucleotide sequence of the present invention can be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences can be used in polymerase chain reaction (PCR) protocols to amplify longer nucleic acid fragments encoding homologous genes from DNA or RNA. The polymerase chain reaction can also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence can be based upon sequences derived from the cloning vector.

In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Therefore, the nucleic acid molecules of the present invention can be used to isolate genes encoding homologous proteins from the same or other species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683,202; ligase chain reaction (LCR) (Tabor, S. et al., *Proc. Acad. Sci. USA* 82: 1074 (1985)); or strand displacement amplification (SDA; Walker, et al., *Proc. Natl. Acad. Sci. U.S.A.* 89: 392 (1992)).

In some embodiments, the isolated nucleic acid molecules of the present invention are used to isolate homologous nucleic acid molecules from other organisms in order to identify PUFA synthases that produce similar or improved PUFA profiles. In some embodiments, the isolated nucleic acid molecules of the present invention are used to isolate homologous nucleic acid molecules from other organisms that are involved in producing high amounts of DHA.

The nucleic acid molecules of the present invention also comprise polynucleotide sequences encoding a PUFA synthase gene, a domain of a PUFA synthase gene, or a fragment of the PUFA synthase gene fused in frame to a marker sequence which allows for detection of the polypeptide of the present invention. Marker sequences include auxotrophic or dominant markers known to one of ordinary skill in the art such as ZEO (zeocin), NEO (G418), hygromycin, arsenite, HPH, NAT, and the like.

The present invention also encompasses variants of the PUFA synthase gene. Variants can contain alterations in the coding regions, non-coding regions, or both. Examples are polynucleotide sequence variants containing alterations which produce silent substitutions, additions, or deletions, but do not alter the properties or activities of the encoded polypeptide. In certain embodiments, polynucleotide sequence variants are produced by silent substitutions due to the degeneracy of the genetic code. In further embodiments, polynucleotide sequence variants can be produced for a variety of reasons, e.g., to optimize codon expression for a particular host (e.g., changing codons in the thraustochytrid mRNA to those preferred by other organisms such as *E. coli* or *Saccharomyces cerevisiae*).

Also provided in the present invention are allelic variants, orthologs, and/or species homologs. Procedures known in the art can be used to obtain full-length genes, allelic variants, splice variants, full-length coding portions, orthologs, and/or species homologs of the genes described herein using information from the sequences disclosed herein. For example, allelic variants and/or species homologs can be isolated and identified by making suitable probes or primers from the sequences provided herein and screening a suitable nucleic acid source for allelic variants and/or the desired homologue.

The present invention is directed to a recombinant nucleic acid molecule comprising any of the nucleic acid molecules described above or combinations thereof and a transcription control sequence. In some embodiments, the recombinant nucleic acid molecule is a recombinant vector.

The present invention is directed to a method for making a recombinant vector comprising inserting one or more isolated nucleic acid molecules as described herein into a vector.

The vectors of this invention can be, for example, a cloning vector or an expression vector. The vector can be, for example, in the form of a plasmid, a viral particle, a phage, etc.

The polynucleotide sequences of the invention can be included in any one of a variety of expression vectors for expressing a polypeptide. Such vectors include chromosomal, nonchromosomal, and synthetic DNA or RNA sequences, e.g., derivatives of SV40; bacterial plasmids; and yeast plasmids. However, any other appropriate vector known to one of ordinary skill in the art can be used.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The present invention also includes recombinant constructs comprising one or more of the polynucleotide sequences described above. The constructs comprise a vector, such as a plasmid or viral vector, into which one or more sequences of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available.

Polypeptides

The present invention is directed to isolated polypeptides comprising amino acid sequences for PUFA synthase proteins and domains derived from the isolated microorganisms deposited as ATCC Accession Nos. PTA-9695 and PTA-10212.

As used herein, the term "polypeptide" is intended to encompass a singular "polypeptide" as well as plural "polypeptides" and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids.

Polypeptides as described herein can include fragment, variant, or derivative molecules thereof without limitation. The terms "fragment," "variant," "derivative" and "analog" when referring to a polypeptide include any polypeptide which retains at least some biological activity. Polypeptide fragments can include proteolytic fragments, deletion fragments, and fragments which more easily reach the site of action when delivered to an animal. Polypeptide fragments further include any portion of the polypeptide which comprises an antigenic or immunogenic epitope of the native polypeptide, including linear as well as three-dimensional epitopes. Polypeptide fragments can comprise variant regions, including fragments as described above, and also polypeptides with altered amino acid sequences due to amino acid substitutions, deletions, or insertions. Variants can occur naturally, such as an allelic variant. By an "allelic variant" is intended alternate forms of a gene occupying a given locus on a chromosome of an organism. Non-naturally occurring variants can be produced using art-known mutagenesis techniques. Polypeptide fragments of the invention can comprise conservative or non-conservative amino acid substitutions, deletions, or additions. Variant polypeptides can also be referred to herein as "polypeptide analogs." Polypeptide fragments of the present invention can also include derivative molecules. As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

Polypeptides of the invention can be encoded by any of the nucleic acid molecules of the invention.

The present invention is directed to isolated polypeptides comprising amino acid sequences that are at least 80% identical to the amino acid sequences of Pfa1p (SEQ ID NO:2 or SEQ ID NO:69), Pfa2p (SEQ ID NO:4 or SEQ ID NO:71), Pfa3p (SEQ ID NO:6 or SEQ ID NO:73), and combinations thereof, wherein the polypeptides comprise one or more PUFA synthase activities.

The present invention is directed to polypeptides comprising amino acid sequences that are at least 80% identical to the amino acid sequences of one or more PUFA synthase domains of the PUFA synthases of the invention.

In some embodiments, the present invention is directed to polypeptides comprising amino acid sequences that are at least 80% identical to an amino acid sequence within Pfa1p (SEQ ID NO:2 or SEQ ID NO:69) comprising one or more PUFA synthase domains. In some embodiments, the polypeptide comprises an amino acid sequence at least 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two or more ACP domains such as two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises two or more amino acid sequences, wherein each of the at least two or more amino acid sequences is 80% identical to an amino acid sequence within Pfa1p (SEQ ID NO:2 or SEQ ID NO:69) comprising one or more PUFA synthase domains. In some embodiments, the at least two or more amino acid sequences are 80% identical to the same amino acid sequence within Pfa1p (SEQ ID NO:2 or SEQ ID NO:69) comprising one or more PUFA synthase domains. In some embodiments, the at least two or more amino acid sequences are 80% identical to different amino acid sequences within Pfa1p (SEQ ID NO:2 or SEQ ID NO:69) that each comprise one or more PUFA synthase domains. In some embodiments, the at least two or more amino acid sequences are 80% identical to different amino acid sequences within Pfa1p (SEQ ID NO:2 or SEQ ID NO:69), wherein the at least two or more amino acid sequences are located in the same order or a different order in the polypeptide as compared to the order of the corresponding domains within Pfa1p (SEQ ID NO:2 or SEQ ID NO:69). In some embodiments, the at least two or more amino acid sequences are 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises one or more amino acid sequences within Pfa1p (SEQ ID NO:2 or SEQ ID NO:69) comprising one or more PUFA synthase domains, including one or more copies of any individual domain in combination with one or more copies of any other individual domain.

In some embodiments, the present invention is directed to polypeptides comprising amino acid sequences that are at least 80% identical to an amino acid sequence within Pfa2p (SEQ ID NO:4 or SEQ ID NO:71) comprising one or more PUFA synthase domains. In some embodiments, the polypeptide comprises an amino acid sequence at least 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises two or more amino acid sequences, wherein each of the at least two or more amino acid sequences is 80% identical to an amino acid sequence within Pfa2p (SEQ ID NO:4 or SEQ ID NO:71) comprising one or more PUFA synthase domains. In some embodiments, the at least two or more amino acid sequences are 80% identical to the same amino acid sequence within Pfa2p (SEQ ID NO:4 or SEQ ID NO:71). In some embodiments, the at least two or more amino acid sequences are 80% identical to different amino acid sequences within Pfa2p (SEQ ID NO:4 or SEQ ID NO:71) that each comprise one or more PUFA synthase domains. In some embodiments, the at least two or more amino acid sequences are 80% identical to different amino acid sequences within Pfa2p (SEQ ID NO:4 or SEQ ID NO:71), wherein the at least two or more amino acid sequences are located in the same order or a different order in the polypeptide as compared to the order of the corresponding domains within Pfa2p (SEQ ID NO:4 or SEQ ID NO:71). In some embodiments, the at least two or more amino acid sequences are 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:24 or SEQ ID NO:107), an ER domain (SEQ ID NO:36 or SEQ ID NO:109), and combinations thereof. In some embodiments, the polypeptide comprises one or more amino acid sequences sequence within Pfa2p (SEQ ID NO:4 or SEQ ID NO:71) comprising one or more PUFA synthase domains, including one or more copies of any individual domain in combination with one or more copies of any other individual domain.

In some embodiments, the present invention is directed to polypeptides comprising amino acid sequences that are at least 80% identical to an amino acid sequence within Pfa3p (SEQ ID NO:6 or SEQ ID NO:73) comprising one or more PUFA synthase domains. In some embodiments, the polypeptide comprises an amino acid sequence at least 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises two or more amino acid sequences, wherein each of the at least two or more amino acid sequences is 80% identical to an amino acid sequence within Pfa3p (SEQ ID NO:6 or SEQ ID NO:73) comprising one or more PUFA synthase domains. In some embodiments, the at least two or more amino acid sequences are 80% identical to the same amino acid sequence within Pfa3p (SEQ ID NO:6 or SEQ ID NO:73) comprising one or more PUFA synthase domains. In some embodiments, the at least two or more amino acid sequences are 80% identical to different amino acid sequences within Pfa3p (SEQ ID NO:6 or SEQ ID NO:73) that each comprise one or more PUFA synthase domains. In some embodiments, the at least two or more amino acid sequences are 80% identical to different amino acid sequences within Pfa3p (SEQ ID NO:6 or SEQ ID NO:73), wherein the at least two or more amino acid sequences are located in the same order or a different order in the polypeptide as compared to the order of the corresponding domains within Pfa3p (SEQ ID NO:6 or SEQ ID NO:73). In some embodiments, the at least two or more amino acid sequences are 80% identical to an amino acid sequence within Pfa3p (SEQ ID NO:6 or SEQ ID NO:73) comprising one or more PUFA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises one or more amino acid sequences within Pfa3p (SEQ ID NO:6 or SEQ ID NO:73) comprising one or more PUFA synthase domains, including one or more copies of any individual domain in combination with one or more copies of any other individual domain.

In some embodiments, the present invention is directed to a polypeptide comprising an amino acid sequence at least 80% identical to SEQ ID NO:2 or SEQ ID NO:69, wherein the polypeptide comprises a PUFA synthase activity selected from the group consisting of KS activity, MAT activity, ACP activity, KR activity, DH activity, and combinations thereof.

In some embodiments, the present invention is directed to a polypeptide comprising an amino acid sequence at least 80% identical to SEQ ID NO:8 or SEQ ID NO:75, wherein the polypeptide comprises KS activity.

In some embodiments, the present invention is directed to a polypeptide comprising an amino acid sequence at least 80% identical to SEQ ID NO:10 or SEQ ID NO:77, wherein the polypeptide comprises MAT activity.

In some embodiments, the present invention is directed to a polypeptide comprising an amino acid sequence at least 80% identical to such as any one of SEQ ID NOs:14, 16, 18, 20, 22, 24, 81, 83, 85, 87, 89, 91, 93, 95, 97, or 99, wherein the polypeptide comprises ACP activity.

In some embodiments, the present invention is directed to a polypeptide comprising an amino acid sequence at least 80% identical to SEQ ID NO:12 or SEQ ID NO:79, wherein the polypeptide comprises ACP activity.

In some embodiments, the present invention is directed to a polypeptide comprising an amino acid sequence at least 80% identical to an amino acid sequence within SEQ ID NO:12, wherein the polypeptide comprises ACP activity. In some embodiments, the amino acid sequence is at least 80% identical to an amino acid sequence within SEQ ID NO:12 comprising one, two, three, four, five, or six ACP domains, wherein the polypeptide comprises ACP activity associated with one or more ACP domains. SEQ ID NOs:14, 16, 18, 20, 22, and 24 are representative amino acid sequences comprising a single ACP domain within SEQ ID NO: 12.

In some embodiments, the present invention is directed to a polypeptide comprising an amino acid sequence at least 80% identical to an amino acid sequence within SEQ ID NO:79, wherein the polypeptide comprises ACP activity. In some embodiments, the amino acid sequence is at least 80% identical to an amino acid sequence within SEQ ID NO:79 comprising one, two, three, four, five, six, seven, eight, nine, or ten ACP domains, wherein the polypeptide comprises ACP activity associated with one or more ACP domains. SEQ ID NOs:81, 83, 85, 87, 89, 91, 93, 95, 97, and 99 are representative amino acid sequences comprising a single ACP domain within SEQ ID NO:79.

In some embodiments, the present invention is directed to a polypeptide comprising an amino acid sequence at least 80% identical to SEQ ID NO:26 or SEQ ID NO:101, wherein the polypeptide comprises KR activity.

In some embodiments, the present invention is directed to a polypeptide comprising an amino acid sequence at least 80% identical to SEQ ID NO:28 or SEQ ID NO:119, wherein the polypeptide comprises DH activity.

In some embodiments, the present invention is directed to a polypeptide comprising an amino acid sequence at least 80% identical to SEQ ID NO:4 or SEQ ID NO:71, wherein the polypeptide comprises a PUFA synthase activity selected from the group consisting of KS activity, CLF activity, AT activity, ER activity, and combinations thereof.

In some embodiments, the present invention is directed to a polypeptide comprising an amino acid sequence at least 80% identical to SEQ ID NO:30 or SEQ ID NO:103, wherein the polypeptide comprises KS activity.

In some embodiments, the present invention is directed to a polypeptide comprising an amino acid sequence at least 80% identical to SEQ ID NO:32 or SEQ ID NO:105, wherein the polypeptide comprises CLF activity.

In some embodiments, the present invention is directed to a polypeptide comprising an amino acid sequence at least 80% identical to SEQ ID NO:34 or SEQ ID NO:107, wherein the polypeptide comprises AT activity.

In some embodiments, the present invention is directed to a polypeptide comprising an amino acid sequence at least 80% identical to SEQ ID NO:36 or SEQ ID NO:109, wherein the polypeptide comprises ER activity.

In some embodiments, the present invention is directed to a polypeptide comprising an amino acid sequence at least 80% identical to SEQ ID NO:6 or SEQ ID NO:73, wherein the polypeptide comprises a PUFA synthase activity selected from the group consisting of DH activity, ER activity, and combinations thereof.

In some embodiments, the present invention is directed to a polypeptide comprising an amino acid sequence at least 80% identical to SEQ ID NO:38, wherein the polypeptide comprises DH activity.

In some embodiments, the present invention is directed to a polypeptide comprising an amino acid sequence at least 80% identical to SEQ ID NO:40, wherein the polypeptide comprises DH activity.

In some embodiments, the present invention is directed to a polypeptide comprising an amino acid sequence at least 80% identical to SEQ ID NO:111, wherein the polypeptide comprises DH activity.

In some embodiments, the present invention is directed to a polypeptide comprising an amino acid sequence at least 80% identical to SEQ ID NO:113, wherein the polypeptide comprises DH activity.

In some embodiments, the present invention is directed to a polypeptide comprising an amino acid sequence at least 80% identical to SEQ ID NO:42 or SEQ ID NO:115, wherein the polypeptide comprises ER activity.

In some embodiments, the polypeptides comprise amino acid sequences at least about 80%, 85%, or 90% identical to the amino acid sequences reported herein, or at least about 95%, 96%, 97%, 98%, 99%, or 100% identical to the amino acid sequences reported herein.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide having an amino acid sequence that is at least 80%, 85%, 90%, 95%, 96%, 97%, 98% or 99% identical to, for instance, the amino acid sequence of the present invention can be determined conventionally using known computer programs. As discussed above, a method for determining the best overall match between a query sequence (a sequence of the present invention) and a subject sequence can be determined using the alignment of sequences and calculation of identity scores. The alignments were done using the computer program AlignX, which is a component of the Vector NTI Suite 10.0 package from Invitrogen (www.invitrogen.com). The alignments were performed using a ClustalW alignment (J. Thompson et al., *Nucleic Acids Res.* 22(22):4673-4680 (1994). The default scoring matrix Blosum62mt2 was used. The default gap opening penalty is 10 and the gap extension penalty 0.1.

In further aspects of the invention, nucleic acid molecules having polynucleotide sequences at least 80%, 85%, 90%, 95%, 96%, 97%, 98% or 99% identical to the polynucleotide sequences disclosed herein, encode a polypeptide having one or more PUFA synthase activities. Polypeptides having one or more PUFA synthase activities exhibit one or more activities similar to, but not necessarily identical to, one or more activities of a PUFA synthase of the present invention.

Of course, due to the degeneracy of the genetic code, one of ordinary skill in the art will immediately recognize that a large portion of the nucleic acid molecules having a polynucleotide sequence at least 80%, 85%, 90%, 95%, 96%, 97%, 98%, or 99% identical to the polynucleotide sequences described herein will encode polypeptides "having PUFA synthase functional activity." In fact, since degenerate variants of any of these polynucleotide sequences all encode the same polypeptide, in many instances, it can be predicted by the skilled artisan based on knowledge of conservative substitutions as well as conserved functional domains, which polypeptides will exhibit activity. In certain aspects of the invention, the polypeptides and polynucleotides of the present invention are provided in an isolated form, e.g., purified to homogeneity. Alternatively, the polypeptides and polynucleotides of the invention can be synthetically produced by conventional synthesizers.

As known in the art "similarity" between two polypeptides is determined by comparing the amino acid sequence and conserved amino acid substitutes thereto of the polypeptide to the sequence of a second polypeptide.

In some embodiments, a polypeptide of the invention is a fusion polypeptide.

As used herein, "fusion polypeptide" means a polypeptide comprising a first polypeptide linearly connected, via peptide bonds, to a second polypeptide. The first polypeptide and the second polypeptide can be identical or different, and they can be directly connected, or connected via a peptide linker. As used herein, the terms "linked," "fused," or "fusion" are used interchangeably. These terms refer to the joining together of two more elements or components by any means including chemical conjugation or recombinant means. An "in-frame fusion" refers to the joining of two or more open reading frames to form a continuous longer open reading frame, in a manner that maintains the correct reading frame of the original open reading frames. Thus, the resulting recombinant fusion protein is a single protein containing two or more segments that correspond to polypeptides encoded by the original open reading frames (which segments are not normally so joined in nature). Although the reading frame is thus made continuous throughout the fused segments, the segments can be physically or spatially separated by, for example, in-frame linker sequence. A "linker" sequence is a series of one or more amino acids separating two polypeptide coding regions in a fusion protein.

The invention is directed to a composition comprising one or more polypeptides of the invention and a biologically acceptable carrier.

In some embodiments, the composition includes a biologically acceptable "excipient," wherein the excipient is a component, or mixture of components, that is used in a composition of the present invention to give desirable characteristics to the composition, and also include carriers. "Biologically acceptable" means a compound, material, composition, salt, and/or dosage form which is, within the scope of sound medical judgment, suitable for contact with the tissues of living cells without excessive toxicity, irritation, inflammatory response, or other problematic complications over the desired duration of contact commensurate with a reasonable benefit/risk ratio. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, *Remington: The Science and Practice of Pharmacy*, 21$^{st}$ ed. (2005). Inclusion of an excipient in a particular classification herein (e.g., "solvent") is intended to illustrate rather than limit the role of the excipient. A particular excipient can fall within multiple classifications.

The present invention further relates to a fragment, variant, derivative, or analog of any of the polypeptide disclosed herein.

The polypeptide of the present invention can be a recombinant polypeptide, a natural polypeptide, or a synthetic polypeptide.

Host Cells

The present invention is directed to a host cell that expresses any of the nucleic acid molecules and recombinant nucleic acid molecules described above as well as combinations thereof.

The term "expression" as used herein refers to a process by which a gene produces a biochemical, for example, a RNA or polypeptide. The process includes any manifestation of the functional presence of the gene within the cell including, without limitation, gene knockdown as well as both transient expression and stable expression. It includes, without limitation, transcription of the gene into messenger RNA (mRNA), transfer RNA (tRNA), small hairpin RNA (shRNA), small interfering RNA (siRNA), or any other RNA product, and the translation of such mRNA into polypeptide(s). If the final desired product is biochemical, expression includes the creation of that biochemical and any precursors.

To produce one or more desired polyunsaturated fatty acids, a host cell can be genetically modified to introduce a PUFA synthase system of the present invention into the host cell.

When genetically modifying organisms to express a PUFA synthase system according to the present invention, some host organisms can endogenously express accessory proteins that are required in conjunction with a PUFA synthase system in order to produce PUFAs. However, it may be necessary to transform some organisms with nucleic acid molecules encoding one or more accessory protein(s) in order to enable or to enhance production of PUFAs by the organism, even if the organism endogenously produces a homologous accessory protein. Some heterologous accessory proteins can operate more effectively or efficiently with the transformed PUFA synthase proteins than the host cells' endogenous accessory protein(s).

Accessory proteins are defined herein as proteins that are not considered to be part of the core PUFA synthase system (i.e., not part of the PUFA synthase enzyme complex itself) but which may be necessary for PUFA production or efficient PUFA production using the core PUFA synthase enzyme complex of the present invention. For example, in order to produce PUFAs, a PUFA synthase system must work with an accessory protein that transfers a 4'-phosphopantetheinyl moiety from coenzyme A to the acyl carrier protein (ACP) domain(s). Therefore, a PUFA synthase system can be considered to include at least one 4'-phosphopantetheinyl transferase (PPTase) domain, or such a domain can be considered to be an accessory domain or protein to the PUFA synthase system. Structural and functional characteristics of PPTases have been described in detail, e.g., in U.S. Appl. Publ. Nos. 2002/0194641; 2004/0235127; and 2005/0100995.

A domain or protein having 4'-phosphopantetheinyl transferase (PPTase) biological activity (function) is characterized as the enzyme that transfers a 4'-phosphopantetheinyl moiety from Coenzyme A to the acyl carrier protein (ACP). This transfer to an invariant serine reside of the ACP activates the inactive apo-form to the holo-form. In both polyketide and fatty acid synthesis, the phosphopantetheine group forms thioesters with the growing acyl chains. The PPTases are a family of enzymes that have been well characterized in fatty acid synthesis, polyketide synthesis, and non-ribosomal peptide synthesis. The sequences of many PPTases are known, crystal structures have been determined (e.g., Reuter K., et al., *EMBO J.* 18(23):6823-31 (1999)), and mutational analysis has identified amino acid residues important for activity (Mofid M. R., et al., *Biochemistry* 43(14):4128-36 (2004)).

One heterologous PPTase which has been previously demonstrated to recognize *Schizochytrium* ACP domains as substrates is the Het I protein of *Nostoc* sp. PCC 7120 (formerly called *Anabaena* sp. PCC 7120). Het I is present in a cluster of genes in *Nostoc* known to be responsible for the synthesis of long chain hydroxy-fatty acids that are a component of a glyco-lipid layer present in heterocysts of that organism (Black and Wolk, *J. Bacteriol.* 176: 2282-2292 (1994); Campbell et al., *Arch. Microbiol.* 167: 251-258 (1997)). Het I is likely to activate the ACP domains of a protein, Hgl E, present in that cluster. Sequences and constructs containing Het I have been described in, e.g., U.S. Appl. Publ. No. 2007/0244192, incorporated by reference herein in its entirety.

Another heterologous PPTase which has been demonstrated previously to recognize the *Schizochytrium* ACP domains is Sfp, derived from *Bacillus subtilis*. Sfp has been well characterized and is widely used due to its ability to recognize a broad range of substrates. Based on published sequence information (Nakana, et al., *Molecular and General Genetics* 232: 313-321 (1992)), an expression vector was previously produced for Sfp by cloning the coding region, along with defined up- and downstream flanking DNA sequences, into a pACYC-184 cloning vector. This construct encodes a functional PPTase as demonstrated by its ability to be co-expressed with *Schizochytrium* Orfs in *E. coli* which, under appropriate conditions, resulted in the accumulation of DHA in those cells (see, U.S. Appl. Publ. No. 2004/0235127, incorporated by reference herein in its entirety).

Host cells can include microbial cells; animal cells; plant cells; and insect cells. Representative examples of appropriate hosts include bacterial cells; thermophilic or mesophilic bacteria; marine bacteria; thraustochytrids; fungal cells, such as yeast; plant cells; insect cells; and isolated animal cells. Host cells can be either untransfected cells or cells that are already transfected with at least one other recombinant nucleic acid molecule. Host cells can also include transgenic cells that have been engineered to express a PUFA synthase. The selection of an appropriate host is deemed to be within the scope of those skilled in the art from the teachings herein.

Host cells include any microorganism of the order Thraustochytriales, such as microorganisms from a genus including, but not limited to: *Thraustochytrium, Labyrinthuloides, Japonochytrium,* and *Schizochytrium.* Species within these genera include, but are not limited to: any *Schizochytrium* species, including *Schizochytrium aggregatum, Schizochytrium limacinum, Schizochytrium minutum;* any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum;* and any *Japonochytrium* species. Strains of Thraustochytriales include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (Goldstein et Belsky) (ATCC 28209); *Schizochytrium limacinum* (Honda et Yokochi) (IFO 32693); *Thraustochytrium* sp. (23B) (ATCC 20891); *Thraustochytrium striatum* (Schneider) (ATCC 24473); *Thraustochytrium aureum* (Goldstein) (ATCC 34304); *Thraustochytrium roseum* (Goldstein) (ATCC 28210); and *Japonochytrium* sp. (L1) (ATCC 28207). Other examples of suitable host microorganisms for genetic modification include, but are not limited to, yeast including *Saccharomyces cerevisiae, Saccharomyces carlsbergensis,* or other yeast such as *Candida, Kluyveromyces,* or other fungi, for example, filamentous fungi such as *Aspergillus, Neurospora, Penicillium,* etc. Bacterial cells also can be used as hosts. This includes *Escherichia coli,* which can be useful in fermentation processes. Alternatively, a host such as a *Lactobacillus* species or *Bacillus* species can be used as a host.

Plant host cells include, but are not limited to, any higher plants, including both dicotyledonous and monocotyledonous plants, and consumable plants, including crop plants and plants used for their oils. Such plants can include, for example: canola, soybeans, rapeseed, linseed, corn, safflowers, sunflowers, and tobacco. Other plants include those plants that are known to produce compounds used as pharmaceutical agents, flavoring agents, neutraceutical agents, functional food ingredients, cosmetically active agents, or plants that are genetically engineered to produce these compounds/agents. Thus, any plant species or plant cell can be selected. Examples of plants and plant cells, and plants grown or derived therefrom, include, but are not limited to, plants and plant cells obtainable from canola (*Brassica rapa* L.); canola cultivars NQC02CNX12 (ATCC PTA-6011), NQC02CNX21 (ATCC PTA-6644), and NQC02CNX25 (ATCC PTA-6012) as well as cultivars, breeding cultivars, and plant parts derived from canola cultivars NQC02CNX12, NQC02CNX21, and NQC02CNX25 (see, U.S. Pat. Nos. 7,355,100, 7,456,340, and 7,348,473, respectively); soybean (*Glycine max*); rapeseed (*Brassica* spp.); linseed/flax (*Linum usitatissimum*); maize (corn) (*Zea mays*); safflower (*Carthamus tinctorius*); sunflower (*Helianthus annuus*); tobacco (*Nicotiana tabacum*); *Arabidopsis thaliana,* Brazil nut (*Betholettia excelsa*); castor bean (*Riccinus communis*); coconut (*Cocus nucifera*); coriander (*Coriandrum sativum*); cotton (*Gossypium* spp.); groundnut (*Arachis hypogaea*); jojoba (*Simmondsia chinensis*); mustard (*Brassica* spp. and *Sinapis alba*); oil palm (*Elaeis guineeis*); olive (*Olea eurpaea*); rice (*Oryza sativa*); squash (*Cucurbita maxima*); barley (*Hordeum vulgare*); wheat (*Traeticum aestivum*); and duckweed (*Lemnaceae* sp.). Plant lines from these and other plants can be produced, selected, or optimized for a desirable trait such as or associated with, but not limited to, seed yield, lodging resistance, emergence, disease resistance or tolerance, maturity, late season plant intactness, plant height, shattering resistance, ease of plant transformation, oil content, or oil profile. Plant lines can be selected through plant breeding such as pedigree breeding, recurrent selection breeding, intercross and backcross breeding, as well as methods such as marker assisted breeding and tilling. See, e.g., U.S. Pat. No. 7,348,473.

Animal cells include any isolated animal cells.

The present invention is directed to a host cell that expresses one or more nucleic acid molecules or recombinant nucleic acid molecules, including vectors, of the invention.

The present invention is directed to a method for making a recombinant host cell comprising introducing a recombinant vector into a host cell.

Host cells can be genetically engineered (transduced or transformed or transfected) with the vectors of this invention that can be, for example, a cloning vector or an expression vector. The vector can be, for example, in the form of a plasmid, a viral particle, a phage, etc. The vector containing a polynucleotide sequence as described herein, as well as an appropriate promoter or control sequence, can be employed to transform an appropriate host to permit expression of the polypeptide encoded by the polynucleotide sequence. The genetic modification of host cells can also include the optimization of genes for preferred or optimal host codon usage.

The engineered host cells can be cultured in conventional nutrient media modified as appropriate for activating promoters, selecting transformants, or amplifying the genes of the present invention. The culture conditions, such as temperature, pH, and the like, are those previously used with the host cell selected for expression, and will be apparent to the ordinarily skilled artisan.

In some embodiments, the present invention is directed to genetically modifying a plant or part of a plant to express a PUFA synthase system described herein, which includes at least the core PUFA synthase enzyme complex. A "part of a plant" or "plant part" as defined herein includes any part of a plant, such as, but not limited to, seeds (immature or mature), oils, pollen, embryos, flowers, fruits, shoots, leaves, roots, stems, explants, etc. In some embodiments, the genetically modified plant or part of a plant produces one or more PUFAs, such as EPA, DHA, DPA (n-3 or n-6), ARA, GLA, SDA, other PUFAs, and combinations thereof. Plants are not known to endogenously contain a PUFA synthase system; therefore, the PUFA synthase systems of the present invention can be used to engineer plants with unique fatty acid production capabilities. In a further embodiment, the plant or part of a plant is further genetically modified to express at least one PUFA synthase accessory protein, (e.g., a PPTase). In some embodiments, the plant is an oil seed plant, wherein the oil seeds, and/or the oil in the oil seeds, contain PUFAs produced by the PUFA synthase system. In some embodiments, the genetically modified plants, parts of plants, oil seeds, and/or oils in the oil seeds contain a detectable amount of at least one PUFA that is the product of the PUFA synthase system. In further embodiments, such plants, parts of plants, oil seeds, and/or oils in the oil seeds can be substantially free of intermediate or side products that are not the primary PUFA products of the introduced PUFA synthase system and that are not naturally produced by the endogenous FAS system in the wild-type plants. While wild-type plants produce some short or medium chain PUFAs, such as 18 carbon PUFAs via the FAS system, new or additional PUFAs will be produced in the plant, parts of plants, oil seeds, and/or oils in the oil seeds as a result of genetic modification with a PUFA synthase system described herein.

Genetic modification of a plant can be accomplished using classical strain development and/or molecular genetic techniques. See, U.S. Appl. Publ. No. 2007/0244192. Methods for producing a transgenic plant, wherein a recombinant nucleic acid molecule encoding a desired amino acid sequence is incorporated into the genome of the plant, are known in the art. For example, viral vectors can be used to produce transgenic plants, such as by transformation of a monocotyledonous plant with a viral vector using the methods described in U.S. Pat. Nos. 5,569,597; 5,589,367; and 5,316,931. Methods for the genetic engineering or modification of plants by transformation are also well known in the art, including biological and physical transformation protocols. See, e.g., B. L. Miki et al., *Procedures for Introducing Foreign DNA into Plants*, in METHODS IN PLANT MOLECULAR BIOLOGY AND BIOTECHNOLOGY 67-88 (Glick, B. R. and Thompson, J. E. eds., CRC Press, Inc., Boca Raton, 1993). In addition, vectors and in vitro culture methods for plant cell or tissue transformation and regeneration of plants are available. See, e.g., M. Y. Gruber et al., *Vectors for Plant Transformation*, in METHODS IN PLANT MOLECULAR BIOLOGY AND BIOTECHNOLOGY 89-119 (Glick, B. R. and Thompson, J. E. eds., CRC Press, Inc., Boca Raton, 1993).

A widely utilized method for introducing an expression vector into plants is based on the natural transformation system of *Agrobacterium*. See, e.g., Horsch et al., *Science* 227: 1229 (1985) and U.S. Pat. No. 6,051,757. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, e.g., Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra; Miki et al., supra; Moloney et al., *Plant Cell Reports* 8:238 (1989); U.S. Pat. Nos. 5,177,010; 5,104,310; 5,149,645; 5,469,976; 5,464,763; 4,940,838; 4,693,976; 5,591,616; 5,231,019; 5,463,174; 4,762,785; 5,004,863; and 5,159,135; and European Patent Appl. Nos. 0131624, 120516, 159418, 176112, 116718, 290799, 320500, 604662, 627752, 0267159, and 0292435.

Other methods of plant transformation include microprojectile-mediated transformation, wherein DNA is carried on the surface of microprojectiles. The expression vector is introduced into plant tissues with a biolistic device that accelerates the microprojectiles to speeds sufficient to penetrate plant cell walls and membranes. See, e.g., Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992), and U.S. Pat. Nos. 5,015,580 and 5,322,783. Techniques for accelerating genetic material coated onto microparticles directed into cells is also described, e.g., in U.S. Pat. Nos. 4,945,050 and 5,141,141. Another method for physical delivery of DNA to plants is sonication of target cells. See, e.g., Zhang et al., *Bio/Technology* 9:996 (1991). Alternatively, liposome or spheroplast fusion have been used to introduce expression vectors into plants. See, e.g., Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, DNA injection, polyvinyl alcohol or poly-L-ornithine have also been reported. See, e.g., Hain et al., *Mol. Gen. Genet.* 199:161 (1985) and Draper et al., *Plant Cell Physiol.* 23:451 (1982). Electroporation of protoplasts and whole cells and tissues has also been described. See, e.g., Donn et al., in Abstracts of VIIth International Congress on Plant Cell and Tissue Culture IAPTC, A2-38, p. 53 (1990); D'Halluin et al., *Plant Cell* 4:1495-1505 (1992); Spencer et al., *Plant Mol. Biol.* 24:51-61 (1994); International Appl. Publ. Nos. WO 87/06614, WO 92/09696, and WO 93/21335; and U.S. Pat. Nos. 5,472,869 and 5,384,253. Other transformation technology includes whiskers technology, see, e.g., U.S. Pat. Nos. 5,302,523 and 5,464,765.

Chloroplasts or plastids can also be directly transformed. As such, recombinant plants can be produced in which only the chloroplast or plastid DNA has been modified with any of the nucleic acid molecules and recombinant nucleic acid molecules described above as well as combinations thereof. Promoters which function in chloroplasts and plastids are known in the art. See, e.g., Hanley-Bowden et al., *Trends in Biochemical Sciences* 12:67-70 (1987). Methods and compositions for obtaining cells containing chloroplasts into which heterologous DNA has been inserted have been described, e.g., in U.S. Pat. Nos. 5,693,507 and 5,451,513.

Any other methods which provide for efficient transformation can also be employed.

Vectors suitable for use in plant transformation are known in the art. See, e.g., U.S. Pat. Nos. 6,495,738; 7,271,315; 7,348,473; 7,355,100; 7,456,340; and references disclosed therein.

Expression vectors can include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which can be an antibiotic or an herbicide, or genes that encode an altered target which is insensitive to the inhibitor. Selectable markers suitable for use in plant transformation include, but are not limited to, the aminoglycoside phosphotransferase gene of transposon Tn5 (Aph II) which encodes resistance to the antibiotics kanamycin, neomycin, and G418, as well as those genes which encode for resistance or tolerance to glyphosate, hygromycin, methotrexate, phosphinothricin (bialophos), imidazolinones, sulfonylureas and triazolopyrimidine herbicides, such as chlorsulfuron, bromoxynil, dalapon, and the like. One commonly used selectable marker gene for plant transformation is the neomycin phosphotransferase II (nptII) gene under the control of plant regulatory signals which confers resistance to kanamycin. See, e.g., Fraley et al., *Proc. Natl. Acad. Sci. U.S.A.* 80: 4803 (1983). Another commonly used selectable marker gene is the hygromycin phosphotransferase gene which confers resistance to the antibiotic hygromycin. See, e.g., Vanden Elzen et al., *Plant Mol. Biol.* 5:299 (1985). Additional selectable marker genes of bacterial origin that confer resistance to antibiotics include gentamycin acetyl transferase, streptomycin phosphotransferase, aminoglycoside-3'-adenyl transferase, and the bleomycin resistance determinant. See, e.g., Hayford et al., *Plant Physiol.* 86:1216 (1988), Jones et al., *Mol. Gen. Genet.* 210: 86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate, or bromoxynil. See, e.g., Comai et al., *Nature* 317:741-744 (1985), Gordon-Kamm et al., *Plant Cell* 2:603-618 (1990) and Stalker et al., *Science* 242:419-423 (1988). Other selectable marker genes for plant transformation are not of bacterial origin. These genes include, for example, mouse dihydrofolate reductase, plant 5-enolpyruvylshikimate-3-phosphate synthase and plant acetolactate synthase. See, e.g., Eichholtz et al., *Somatic Cell Mol. Genet.* 13:67 (1987), Shah et al., *Science* 233:478 (1986), Charest et al., *Plant Cell Rep.* 8:643 (1990).

A reporter gene can be used with or without a selectable marker. Reporter genes are genes which are typically not present in the recipient organism or tissue and typically encode for proteins resulting in some phenotypic change or enzymatic property. See, e.g., K. Weising et al., *Ann. Rev. Genetics* 22: 421 (1988). Reporter genes include, but are not limited to beta-glucuronidase (GUS), beta-galactosidase, chloramphenicol acetyltransferase, green fluorescent protein, and luciferase genes. See, e.g., Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), and Chalfie et al., *Science* 263:802 (1994). An assay for detecting reporter gene expression can be performed at a suitable time after the gene has been introduced into recipient cells. One such assay entails the use of the gene encoding beta-glucuronidase (GUS) of the uida locus of *E. coli* as described by Jefferson et al., *Biochem. Soc. Trans.* 15: 17-19 (1987).

Promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter, as well as promoters of viral origin, such as the cauliflower mosaic virus (35S and 19S), 35T (which is a re-engineered 35S promoter, see International Appl. Publ. No. WO 97/13402) can be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Matrix attachment regions, scaffold attachment regions, introns, enhancers, and polyadenylation sequences can also be used to improve transcription efficiency or DNA integration. Such elements can be included to obtain optimal performance of the transformed DNA in the plant. Typical elements include, but are not limited to, Adh-intron 1, Adh-intron 6, the alfalfa mosaic virus coat protein leader sequence, the maize streak virus coat protein leader sequence, as well as others available to a skilled artisan. Constitutive promoter regulatory elements can also be used to direct continuous gene expression. Constitutive promoters include, but are not limited to, promoters from plant viruses such as the 35S promoter from CaMV (Odell et al., *Nature* 313:810-812 (1985)), and promoters from such genes as rice actin (McElroy et al., *Plant Cell* 2:163-171 (1990)), ubiquitin (Christensen et al., *Plant Mol. Biol.* 12:619-632 (1989) and Christensen et al., *Plant Mol. Biol.* 18:675-689 (1992)), pEMU (Last et al., *Theor. Appl. Genet.* 81:581-588 (1991)), MAS (Velten et al., *EMBO J.* 3:2723-2730 (1984)), maize H3 histone (Lepetit et al., *Mol. Gen. Genetics* 231:276-285 (1992) and Atanassova et al., *Plant Journal* 2(3): 291-300 (1992)), and the ALS promoter, XbaI/NcoI fragment 5' to the *Brassica napus* ALS3 structural gene (or a nucleotide sequence similar to the XbaI/NcoI fragment) (International Appl. Publ. No. WO 96/30530). Tissue-specific promoter regulatory elements can also be used for gene expression in specific cell or tissue types, such as leaves or seeds (e.g., zein, oleosin, napin, ACP, globulin, and the like). Tissue-specific or tissue-preferred promoters include, but are not limited to, a root-preferred promoter, such as from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as from cab or rubisco (Simpson et al., *EMBO J.* 4(11):2723-2729 (1985) and Timko et al., *Nature* 318:579-582 (1985)); an anther-specific promoter such as from LAT52 (Twell et al., *Mol. Gen. Genetics* 217:240-245 (1989)); a pollen-specific promoter such as from Zm13 (Guerrero et al., *Mol. Gen. Genetics* 244:161-168 (1993)); or a microspore-preferred promoter such as from apg (Twell et al., *Sex. Plant Reprod.* 6:217-224 (1993)). Promoter regulatory elements can also be active during a certain stage of a plants' development as well as plant tissues and organs, including, but not limited to, pollen-specific, embryo specific, corn silk specific, cotton fiber specific, root specific, and seed endosperm specific promoter regulatory elements. An inducible promoter regulatory element can be used, which is responsible for expression of genes in response to a specific signal, such as: physical stimulus (heat shock genes); light (RUBP carboxylase); hormone (Em); metabolites; chemicals; and stress. Inducible promoters include, but are not limited to, a promoter from the ACEI system which responds to copper (Mett et al., *PNAS* 90:4567-4571 (1993)); from the In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)), from the Tet repressor from Tn10 (Gatz et al., *Mol. Gen. Genetics* 227:229-237 (1991)); and from a steroid hormone gene, the transcriptional activity of which is induced by a glucocorticosteroid hormone (Schena et al., *Proc. Natl. Acad. Sci. U.S.A.* 88:0421 (1991).

Signal sequences can also be used to direct a polypeptide to either an intracellular organelle or subcellular compartment or for secretion to the apoplast. See, e.g., Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), and Steifel et al., *Plant Cell* 2:785-793 (1990). Such targeting sequences provide for the desired expressed protein to be transferred to the cell structure in which it most effectively functions or to areas of the cell in which cellular processes necessary for desired phenotypic functions are concentrated.

In some embodiments, signal sequences are used to direct proteins of the invention to a subcellular compartment, for example, to the plastid or chloroplast. Gene products, including heterologous gene products, can be targeted to the plastid or chloroplast by fusing the gene product to a signal sequence which is cleaved during chloroplast import yielding the mature protein. See, e.g., Comai et al., *J. Biol. Chem.* 263: 15104-15109 (1988) and van den Broeck et al., *Nature* 313: 358-363 (1985). DNA encoding for appropriate signal sequences can be isolated from cDNAs encoding the RUBISCO protein, the CAB protein, the EPSP synthase enzyme, the GS2 protein, or from any naturally occurring chloroplast targeted protein that contains a signal sequence (also termed a chloroplast transit peptide (CTP)) that directs the targeted protein to the chloroplast. Such chloroplast targeted proteins are well known in the art. The chloroplast targeted proteins are synthesized as larger precursor proteins that contain an amino-terminal CTP, which directs the precursor to the chloroplast import machinery. CTPs are generally cleaved by specific endoproteases located within the chloroplast organelle, thus releasing the targeted mature protein, including active proteins such as enzymes, from the precursor into the chloroplast milieu. Examples of sequences encoding peptides suitable for targeting a gene or gene product to the chloroplast or plastid of the plant cell include the petunia EPSPS CTP, the *Arabidopsis* EPSPS CTP2 and intron, and other sequences known in the art. Specific examples of CTPs include, but are not limited to, the *Arabidopsis thaliana* ribulose bisphosphate carboxylase small subunit ats1A transit peptide, an *Arabidopsis thaliana* EPSPS transit peptide, and a *Zea maize* ribulose bisphosphate carboxylase small subunit transit peptide. An optimized transit peptide is described, e.g., by Van den Broeck et al., *Nature* 313:358-363 (1985). Prokaryotic and eukaryotic signal sequences are disclosed, e.g., by Michaelis et al., *Ann. Rev. Microbiol.* 36: 425 (1982). Additional examples of transit peptides that can be used in the invention include chloroplast transit peptides described in Von Heijne et al., *Plant Mol. Biol. Rep.* 9:104-126(1991); Mazur et al., *Plant Physiol.* 85: 1110 (1987); Vorst et al., *Gene* 65: 59 (1988); Chen & Jagendorf, *J. Biol. Chem.* 268: 2363-2367 (1993); a transit peptide from the rbcS gene from *Nicotiana plumbaginifolia* (Poulsen et al. *Mol. Gen. Genet.* 205: 193-200 (1986)); and a transit peptide derived from *Brassica napus* acyl-ACP thioesterase (Loader et al., *Plant Mol. Biol.* 23: 769-778 (1993); Loader et al., *Plant Physiol.* 110:336-336 (1995).

Genetically modified plants of the invention can be further modified to delete or inactivate an endogenous fatty acid synthase, to reduce endogenous competition with the exogenous PUFA synthase system for malonyl CoA, to increase the level of malonyl CoA in the organism, and combinations thereof. See, e.g., U.S. Appl. Publ. No. 2007/0245431.

A genetically modified plant can be cultured in a fermentation medium or grown in a suitable medium such as soil. A suitable growth medium for higher plants includes any growth medium for plants, such as, but not limited to, soil, sand, any other particulate media that support root growth (e.g. vermiculite, perlite, etc.) or hydroponic culture as well as suitable light, water, and nutritional supplements which optimize the growth of the higher plant. PUFAs can be recovered from the genetically modified plants through purification processes which extract the compounds from the plant. PUFAs can be recovered by harvesting the plant as well as by harvesting the oil from the plant (e.g., from the oil seeds). The plant can also be consumed in its natural state or further processed into consumable products. In some embodiments, the present invention is directed to a genetically modified plant, wherein the plant produces at least one PUFA as a result of the genetic modification, and wherein the total fatty acid profile in the plant, or the part of the plant that accumulates PUFAs, comprises a detectable amount of the PUFA produced as a result of genetic modification of the plant. In some embodiments, the plant is an oil seed plant. In some embodiments, the oil seed plant produces PUFAs in its mature seeds or contains the PUFAs in the oil of its seeds.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

Methods Involving Heterologous Expression

The present invention is directed to a method to produce at least one PUFA comprising expressing a PUFA synthase system in a host cell under conditions effective to produce PUFA, wherein the PUFA synthase system comprises any of the isolated nucleic acid molecules and recombinant nucleic acid molecules described herein as well as combinations thereof, wherein at least on PUFA is produced. In some embodiments, the at least one PUFA includes DHA, EPA, or a combination thereof. In some embodiments, the host cell is a plant cell, an isolated animal cell, or a microbial cell. In some embodiments the host cell is a thraustochytrid.

The present invention is directed to a method to produce lipids enriched for DHA, EPA, or a combination thereof, comprising expressing a PUFA synthase gene in a host cell under conditions effective to produce lipids, wherein the PUFA synthase gene comprises any of the isolated nucleic acid molecules and recombinant nucleic acid molecules described herein as well as combinations thereof in the host cell, wherein lipids enriched with DHA, EPA, or a combination thereof are produced.

The invention is directed to a method of isolating lipids from a host cell, comprising expressing a PUFA synthase gene in the host cell under conditions effective to produce lipids, and isolating lipids from the host cell, wherein the PUFA synthase system in the host cell comprises any of the isolated nucleic acid molecules and recombinant nucleic acid molecules described herein as well as combinations thereof.

In some embodiments, one or more lipid fractions containing PUFAs are isolated from the host cells. In some embodiments, the one or more fractions isolated from the host cell includes the total fatty acid fraction, the sterol esters fraction, the triglyceride fraction, the free fatty acid fraction, the sterol fraction, the diglycerol fraction, the phospholipid fraction, or combination thereof. In some embodiments, PUFAs are isolated from the host cells, wherein the PUFAs are enriched for omega-3 fatty acids omega-6 fatty acids, or combinations thereof based on the composition of the PUFA synthase system introduced into a host cell. In some embodiments, the PUFAs are enriched for DHA, EPA, DPA n-6, ARA, or combinations thereof based on the composition of the PUFA synthase system introduced into a host cell. In some embodiments, the PUFAs are enriched for DHA, EPA, or a combination thereof. In some embodiments, the PUFA profile of PUFAs isolated from a host cell include high concentrations of DHA and lower concentrations of EPA, ARA, DPA n-6, or combinations thereof. In some embodiments, the PUFA profile of PUFAs isolated from a host cell include high concentrations of DHA and EPA, and lower concentrations of ARA, DPA n-6, or combinations thereof. In some embodiments, the PUFA profile of PUFAs isolated from a host cell include high concentrations of EPA and lower concentrations of DHA, ARA, DPA n-6, or combinations thereof.

The invention is directed to a method of replacing an inactive or deleted PUFA synthase activity, introducing a new PUFA synthase activity, or enhancing an existing PUFA synthase activity in an organism having PUFA synthase activity, comprising expressing any of the isolated nucleic acid molecules and recombinant nucleic acid molecules described herein as well as combinations thereof in the organism under conditions effective to express the PUFA synthase activity. In some embodiments, the nucleic acid molecule comprises one or more PFA1, PFA2, or PFA3 PUFA synthase polynucleotide sequences described herein that encode one or more PUFA synthase domains. In some embodiments, the PUFA profiles of the organisms are altered by the introduction of the one or more nucleic acid molecules of the invention. In some embodiments, the altered PUFA profiles include an increase in omega-3 fatty acids and a decrease in omega-6 fatty acids. In some embodiments, the altered PUFA profiles include an increase in omega-6 fatty acids and a decrease in omega-3 fatty acids. In some embodiments, both omega-3 and omega-6 fatty acids are increased. In some embodiments, the amount of DHA is increased while the amounts of one or more of EPA, ARA, DPA n-6, or combinations thereof are maintained or decrease. In some embodiments, the amounts of EPA and DHA are increased while the amounts of ARA, DPA n-6, or a combination thereof are maintained or decrease. In some embodiments, the amount of EPA is increased while the amounts of one or more of EPA, ARA, DPA n-6, or combinations thereof are maintained or decrease. In some embodiments, the nucleic acid molecule comprises the polynucleotide sequence of PFA3 or one or more domains therein. In some embodiments, the nucleic acid molecule comprises the polynucleotide sequence of PFA3 or one or more domains therein and the amount of omega-3 fatty acids in the organism is increased while the amount of omega-6 fatty acids is decreased. In some embodiments, the nucleic acid molecule comprises the polynucleotide sequence of PFA2 or one or more domains therein and the amount of DHA in the organism is increased while the amount of EPA is decreased.

The invention is directed to methods of increasing production of DHA, EPA, or a combination thereof in an organism having PUFA synthase activity, comprising expressing any of the isolated nucleic acid molecules and recombinant nucleic acid molecules described herein as well as combinations thereof in the organism under conditions effective to produce DHA, EPA, or a combination thereof, wherein the PUFA synthase activity replaces an inactive or deleted activity, introduces a new activity, or enhances an existing activity in the organism, and wherein production of DHA, EPA, or a combination thereof in the organism is increased.

Having generally described this invention, a further understanding can be obtained by reference to the examples provided herein. These examples are for purposes of illustration only and are not intended to be limiting.

EXAMPLE 1

Degenerate primers for the KS and DH PUFA synthase domains were designed in order to isolate the corresponding sequences from the isolated microorganism deposited under ATCC Accession No. PTA-9695, also known as *Schizochytrium* sp. ATCC PTA-9695.

Degenerate primers for the KS region of *Schizochytrium* sp. ATCC PTA-9695 PFA1 (i.e., the region containing the KS domain) were designed based on the published PFA1 (previously termed orfA or ORF 1) sequences for *Shewanella japonica*, *Schizochytrium* sp. ATCC 20888, *Thraustochytrium aureum* (ATCC 34304), and *Thraustochytrium* sp. 23B ATCC 20892:

prDS173 (forward):
GATCTACTGCAAGCGCGGNGGNTTYAT,    (SEQ ID NO: 62)
and prDS174 (reverse):
GGCGCAGGCGGCRTCNACNAC.    (SEQ ID NO: 63)

Degenerate primers for the DH region of *Schizochytrium* sp. ATCC PTA-9695 PFA3 (previously termed orfC or ORF 3) were designed based on the published sequences for *Moritella marina*; *Schizochytrium* sp. ATCC 20888; *Shewanella* sp. SCRC-2738; *Photobacter profundum*; and *Thraustochytrium* sp. 23B ATCC 20892:

JGM190 (forward):
CAYTGGTAYTTYCCNTGYCAYTT;    (SEQ ID NO: 64)
and

BLR242 (reverse):
CCNGGCATNACNGGRTC.    (SEQ ID NO: 65)

The PCR conditions with chromosomal DNA template were as follows: 0.2 µM dNTPs, 0.1 uM each primer, 8% DMSO, 200 ng chromosomal DNA, 2.5 U Herculase® II fusion polymerase (Stratagene), and 1× Herculase® buffer (Stratagene) in a 50 µL total volume. The PCR Protocol included the following steps: (1) 98° C. for 3 minutes; (2) 98° C. for 30 seconds; (3) 50° C. for 30 seconds; (4) 72° C. for 2 minutes; (5) repeat steps 2-4 for 40 cycles; (6) 72° C. for 5 minutes; and (7) hold at 6° C.

For both primer pairs, PCR yielded distinct DNA products with the expected sizes using chromosomal templates from *Schizochytrium* sp. ATCC Accession No. PTA-9695. The respective PCR products were cloned into the vector pJET1.2/blunt (Fermentas) according to the manufacturer's instructions, and the insert sequence was determined using supplied standard primers.

The DNA sequences obtained from the PCR products were compared with known sequences available from the NCBI GenBank in a standard BLASTx search (BLASTx parameters: Low complexity filter on; Matrix: BLOSUM62; Gap cost; Existence 11, Extenstion1. Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389-3402.).

At the amino acid level, the sequences with the highest level of homology to deduced amino acid sequence derived from the cloned DNA containing the KS fragment from *Schizochytrium* sp. ATCC PTA-9695 were: *Schizochytrium* sp. ATCC 20888 "polyunsaturated fatty acid synthase subunit A" (Identity=87%; positives=92%); *Shewanella oneidensis* MR-1 "multi-domain beta-ketoacyl synthase" (Identity=49%; positives=64%); and *Shewanella* sp. MR-4 "beta-ketoacyl synthase" (Identity=49%; positives=64%).

At the amino acid level, the sequences with the highest level of homology to the deduced amino acid sequence derived from the cloned DNA containing the DH fragment from *Schizochytrium* sp. ATCC PTA-9695 were: *Schizochytrium* sp. ATCC 20888 "polyunsaturated fatty synthase subunit C" (Identity=61%; positives=71%); *Shewanella pealeana* ATCC 700345 "Beta-hydroxyacyl-(acyl-carrier-protein) dehydratase FabA/FabZ" (Identity=35%; positives=50%); and *Shewanella sediminis* HAW-EB3 "omega-3 polyunsaturated fatty acid synthase PfaC" (Identity=34%; positives=50%).

EXAMPLE 2

PUFA synthase genes were identified from *Schizochytrium* sp. ATCC PTA-9695.

Genomic DNA was prepared from the microorganism by standard procedures. See, e.g., Sambrook J. and Russell D. 2001. Molecular cloning: A laboratory manual, 3rd edition. Cold Spring Harbor Laboratory Press, Cold Spring Harbor, N.Y. Briefly: (1) 500 µL of cells were pelleted from mid-log culture. The cells were Re-spun, and all traces of liquid were removed from the cell pellet with a small-bore tip; (2) pellets were resuspended with 200 µL lysis buffer (20 mM Tris pH 8.0, 125 µg/mL Proteinase K, 50 mM NaCl, 10 mM EDTA pH 8.0, 0.5% SDS); (3) cells were lysed at 50° C. for 1 hour; (4)

the lysis mixture was pipetted into phase-lock gel (PLG-Eppendorf) 2 mL tubes; (5) equal volume of P:C:I was added and allowed to mix for 1.5 hours; (6) the tubes were centrifuged at 12 k×g for 5 minutes; (7) the aqueous phase was removed from above the gel within the PLG tube and an equal volume of chloroform was added to the aqueous phase, and mixed for 30 minutes; (8) the tubes were centrifuged at 14 k for approximately 5 minutes; (9) the top layer (aqueous phase) was pipetted away from the chloroform, and placed in a new tube; (10) 0.1 volume of 3M NaOAC was added and mixed (inverted several times); (11) 2 volumes of 100% EtOH were added and mixed (inverted several times) with genomic DNA precipitant forming at this stage; (12) the tubes were spun at 4° C. in a microcentrifuge at 14 k for approximately 15 minutes; (13) the liquid was gently poured off with genomic DNA remaining at the bottom of the tube; (14) the pellet was washed with 0.5 mL 70% EtOH; (15) the tubes were spun at 4° C. in a microcentrifuge at 14 k for approximately 5 minutes; (16) the EtOH was gently poured off and the genomic DNA pellet was dried; and (17) a suitable volume of $H_2O$ and RNase was added directly to the genomic DNA pellet.

The isolated genomic DNA was used to generate recombinant libraries consisting of large fragments (approximately 40 kB) according to the manufacturer's instructions in the cosmid pWEB-TNC™ (Epicentre). The cosmid libraries were screened by standard colony hybridization procedures using $^{32}P$ radioactively labeled probes (Sambrook J. and Russell D. 2001. *Molecular cloning: A laboratory manual*, 3rd edition. Cold Spring Harbor Laboratory Press, Cold Spring Harbor, N.Y.). The probes contained DNA homologous to published PUFA synthase sequences from other organisms as described in Example 1. These probes were generated by a DNA restriction digest of the cloned fragments from respective clones from pJET1.2/blunt described above and labeled by standard methods. In all cases, strong hybridization of the individual probes to certain cosmids indicated clones containing DNA homologous to PUFA synthase genes.

Cosmid clone pDS115 demonstrated strong hybridization of probe to the KS region and was selected for DNA sequencing of the *Schizochytrium* sp. ATCC PTA-9695 PFA1 gene. Cosmid clone pDS115, containing the *Schizochytrium* sp. ATCC PTA-9695 PFA1 and PFA2 genes, was deposited under the Budapest Treaty, at the American Type Culture Collection, Patent Depository, 10801 University Boulevard, Manassas, Va. 20110-2209, on Jan. 27, 2009, and given ATCC Accession No. PTA-9737. Sequencing primers to the DNA sequence of the KS region determined in Example 1 were designed using standard methods. To determine the DNA sequence of *Schizochytrium* sp. ATCC PTA-9695 PFA1, successive rounds of DNA sequencing, involving subsequent sequencing primer design by standard methods, was carried out in order to "walk" the cosmid clone.

In previously published thraustochytrid PUFA synthase systems, the PUFA synthase genes PFA1 and PFA2 have been clustered together and arranged as to be divergently transcribed. This is also the case for PFA1 and PFA2 from *Schizochytrium* sp. ATCC PTA-9695. Through the "walking" of DNA sequence from cosmid clone pDS115, the conceptual start of PFA2 was found to be 493 nucleotides from the start of PFA1 and divergently transcribed. Each nucleotide base pair of the *Schizochytrium* sp. ATCC PTA-9695 PFA1 and PFA2 PUFA synthase genes were covered by at least two separate DNA sequencing reactions with high-quality with at least a minimum aggregated Phred score of 40 (confidence level of 99.99%).

Cosmid clone pBS4 demonstrated strong hybridization of probe to the DH region and was selected for DNA sequencing of the *Schizochytrium* sp. ATCC PTA-9695 PFA3 gene. Cosmid clone pBS4, containing the *Schizochytrium* sp. ATCC PTA-9695 PFA3 gene, was deposited under the Budapest Treaty, at the American Type Culture Collection, Patent Depository, 10801 University Boulevard, Manassas, Va. 20110-2209, on Jan. 27, 2009, and given ATCC Accession No. PTA-9736. Sequencing primers were designed using standard methods to the DH region DNA sequence determined in Example 1. To determine the DNA sequence of the *Schizochytrium* sp. ATCC PTA-9695 PFA3 gene, successive rounds of DNA sequencing, involving subsequent sequencing primer design by standard methods, was carried out in order to "walk" the cosmid clone. Each nucleotide base pair of the *Schizochytrium* sp. ATCC PTA-9695 PFA3 gene was covered by at least two separate DNA sequencing reactions of high-quality with at least a minimum aggregated Phred score of 40 (confidence level of 99.99%).

Table 1 shows identities for the *Schizochytrium* sp. ATCC PTA-9695 PFA1 (SEQ ID NO:1), PFA2 (SEQ ID NO:3), and PFA3 (SEQ ID NO:5) polynucleotide sequences as compared to previously published sequences. Identities were determined by the scoring matrix "swgapdnamt" within the "AlignX" program of the VectorNTI program, a standard for DNA alignment.

TABLE 1

PERCENT IDENTITY TO PFA1, PFA2, AND PFA3 POLYNUCLEOTIDE Sequences

| Source of Published PFA1, PFA2, and PFA3 Sequences | % Identity of published PFA1 (orfA) to PFA1 (SEQ ID NO: 1) | % Identity of published PFA2 (orfB) to PFA2 (SEQ ID NO: 3) | % Identity of published PFA3 (orfC) to PFA3 (SEQ ID NO: 5) |
|---|---|---|---|
| *Schizochytrium* sp. ATCC 20888 | 70 | 66 | 75 |
| *Thraustochytrium aureum* ATCC 34304 | 65 | 62 | not published |
| *Thraustochytrium* sp. 23B ATCC 20892 | 56 | 55 | 67 |

Table 2 shows identities for the *Schizochytrium* sp. ATCC PTA-9695 Pfa1p (SEQ ID NO:2), Pfa2p (SEQ ID NO:4), and Pfa3p (SEQ ID NO:6) amino acid sequences as compared to previously published PUFA synthase amino acid sequences. Identities were determined through use of the scoring matrix "blosum62mt2" within the "AlignX" program of the VectorNTI program, a standard for protein alignment.

TABLE 2

Percent Identity to Pfa1p, Pfa2p, and Pfa3p Amino Acid Sequences

| Source of Published Pfa1p, Pfa2p, and Pfa3p Sequences | % Identity of published Pfa1p (OrfA) to Pfa1p (SEQ ID NO: 2) | % Identity of published Pfa2p (OrfB) to Pfa2p (SEQ ID NO: 4) | % Identity of published Pfa3p (OrfC) to Pfa3p (SEQ ID NO: 6) |
|---|---|---|---|
| *Schizochytrium* sp. ATCC 20888 | 60 | 53 | 70 |
| *Thraustochytrium aureum* ATCC 34304 | 60 | 54 | not published |
| *Thraustochytrium* sp. 23B ATCC 20892 | 52 | 52 | 70 |

EXAMPLE 3

Domain analysis was performed to annotate the sequence coordinates for the PUFA synthase domains and active sites of *Schizochytrium* sp. ATCC PTA-9695 PFA1, PFA2, and PFA3, respectively. Domains were identified based on homology to known PUFA synthase, fatty acid synthase, and polyketide synthase domains.

Table 3 shows the domains and active sites associated with *Schizochytrium* sp. ATCC PTA-9695 PFA1.

TABLE 3

*Schizochytrium* sp. ATCC PTA-9695 PFA1 Domain Analysis

| Domain | DNA position | AA position | Sites | DNA position | AA position |
|---|---|---|---|---|---|
| KS | 7-1401 of SEQ ID NO: 1 (SEQ ID NO: 7) | 3-467 of SEQ ID NO: 2 (SEQ ID NO: 8) | Active - DXAC* (SEQ ID NO: 43) | 607-609 of SEQ ID NO: 1 | C203 of SEQ ID NO: 2 |
| | | | End - GFGG (SEQ ID NO: 44) | 1363-1374 of SEQ ID NO: 1 (SEQ ID NO: 45) | 455-458 of SEQ ID NO: 2 |
| MAT | 1798-2700 of SEQ ID NO: 1 (SEQ ID NO: 9) | 600-900 of SEQ ID NO: 2 (SEQ ID NO: 10) | Active GHS*LG (SEQ ID NO: 46) | 2095-2097 of SEQ ID NO: 1 | S699 of SEQ ID NO: 2 |
| ACP | 3298-5400 of SEQ ID NO: 1 (SEQ ID NO: 11) | 1100-1800 of SEQ ID NO: 2 (SEQ ID NO: 12) | ACP1 domain | 3325-3600 of SEQ ID NO: 1 (SEQ ID NO: 13) | 1109-1200 of SEQ ID NO: (SEQ ID NO: 14) |
| | | | ACP1 Active LGIDS* (SEQ ID NO: 47) | 3454-3456 of SEQ ID NO: 1 | S1152 of SEQ ID NO: 2 |
| | | | ACP2 domain | 3667-3942 of SEQ ID NO: 1 (SEQ ID NO: 15) | 1223-1314 of SEQ ID NO: 2 (SEQ ID NO: 16) |
| | | | ACP2 Active LGIDS* (SEQ ID NO: 47) | 3796-3798 of SEQ ID NO: 1 | S1266 of SEQ ID NO: 2 |
| | | | ACP3 domain | 4015-4290 of SEQ ID NO: 1 (SEQ ID NO: 17) | 1339-1430 of SEQ ID NO: 2 (SEQ ID NO: 18) |
| | | | ACP3 Active LGIDS* (SEQ ID NO: 47) | 4144-4146 of SEQ ID NO: 1 | S1382 of SEQ ID NO: 2 |
| | | | ACP4 domain | 4363-4638 of SEQ ID NO: 1 (SEQ ID NO: 19) | 1455-1546 of SEQ ID NO: 2 (SEQ ID NO: 20) |
| | | | ACP4 Active LGIDS* (SEQ ID NO: 47) | 4492-4494 of SEQ ID NO: 1 | S1498 of SEQ ID NO: 2 |
| | | | ACP5 domain | 4711-4986 of SEQ ID NO: 1 (SEQ ID NO: 21) | 1571-1662 of SEQ ID NO: 2 (SEQ ID NO: 22) |
| | | | ACP5 Active LGIDS* (SEQ ID NO: 47) | 4840-4842 of SEQ ID NO: 1 | S1614 of SEQ ID NO: 2 |
| | | | ACP6 domain | 5053-5328 of SEQ ID NO: 1 (SEQ ID NO: 23) | 1685-1776 of SEQ ID NO: 2 (SEQ ID NO: 24) |
| | | | ACP6 Active LGIDS* (SEQ ID NO: 47) | 5182-5184 of SEQ ID NO: 1 | S1728 of SEQ ID NO: 2 |
| KR | 5623-7800 of SEQ ID NO: 1 (SEQ ID NO: 25) | 1875-2600 of SEQ ID NO: 2 (SEQ ID NO: 26) | "core region" | 5998-6900 of SEQ ID NO: 1 (SEQ ID NO: 48) | 2000-2300 of SEQ ID NO: 2 (SEQ ID NO: 49) |
| DH Motif | 7027-7065 of SEQ ID NO: 1 (SEQ ID NO: 27) | 2343-2355 of SEQ ID NO: 2 (SEQ ID NO: 28) | LxxHxxxGxxxxP (SEQ ID NO:50) | 7027-7065 of SEQ ID NO: 1 (SEQ ID NO: 27) | 2343-2355 of SEQ ID NO: 2 (SEQ ID NO: 28) |

The first domain in *Schizochytrium* sp. ATCC PTA-9695 Pfa1 is a KS domain. The nucleotide sequence containing the sequence encoding the *Schizochytrium* sp. ATCC PTA-9695 Pfa1 KS domain is represented herein as SEQ ID NO:7, corresponding to positions 7-1401 of SEQ ID NO:1. The amino acid sequence containing the *Schizochytrium* sp. ATCC PTA-9695 Pfa1 KS domain is represented herein as SEQ ID NO:8, corresponding to positions 3-467 of SEQ ID NO:2. The KS domain contains an active site motif: DXAC* (SEQ ID NO:43), with an *acyl binding cite corresponding to C203 of SEQ ID NO:2. Also, a characteristic motif is present at the end of the KS domain: GFGG (SEQ ID NO:44), corresponding to positions 455-458 of SEQ ID NO:2 and positions 453-456 of SEQ ID NO:8.

The second domain in *Schizochytrium* sp. ATCC PTA-9695 Pfa1 is a MAT domain. The nucleotide sequence containing the sequence encoding the *Schizochytrium* sp. ATCC PTA-9695 Pfa1 MAT domain is represented herein as SEQ ID NO:9, corresponding to positions 1798-2700 of SEQ ID NO:1. The amino acid sequence containing the *Schizochytrium* sp. ATCC PTA-9695 Pfa1 MAT domain is represented herein as SEQ ID NO:10, corresponding to positions 600-900 of SEQ ID NO:2. The MAT domain contains an active site motif: GHS*XG (SEQ ID NO:46), with an *acyl binding cite corresponding to S699 of SEQ ID NO:2.

The third through eighth domains of *Schizochytrium* sp. ATCC PTA-9695 Pfa1 are six tandem ACP domains, also referred to herein as ACP1, ACP2, ACP3, ACP4, ACP5, and ACP6. The nucleotide sequence containing the first ACP domain, ACP1, is represented herein as SEQ ID NO:13 and is contained within the nucleotide sequence spanning from about position 3325 to about position 3600 of SEQ ID NO:1. The amino acid sequence containing ACP1, represented herein as SEQ ID NO:14, is contained within the amino acid sequence spanning from about position 1109 to about position 1200 of SEQ ID NO:2. The nucleotide sequence containing ACP2, represented herein as SEQ ID NO:15, is contained within the nucleotide sequence spanning from about position 3667 to about position 3942 of SEQ ID NO:1. The amino acid sequence containing ACP2, represented herein as SEQ ID NO:16, is contained within the amino acid sequence spanning from about position 1223 to about position 1314 of SEQ ID NO:2. The nucleotide sequence containing ACP3, represented herein as SEQ ID NO:17, is contained within the nucleotide sequence spanning from about position 4015 to about position 4290 of SEQ ID NO:1. The amino acid sequence containing ACP3, represented herein as SEQ ID NO:18, is contained within the amino acid sequence spanning from about position 1339 to about position 1430 of SEQ ID NO:2. The nucleotide sequence containing ACP4, represented herein as SEQ ID NO:19, is contained within the nucleotide sequence spanning from about position 4363 to about position 4638 of SEQ ID NO:1. The amino acid sequence containing ACP4, represented herein as SEQ ID NO:20, is contained within the amino acid sequence spanning from about position 1455 to about position 1546 of SEQ ID NO:2. The nucleotide sequence containing ACP5, represented herein as SEQ ID NO:21, is contained within the nucleotide sequence spanning from about position 4711 to about position 4986 of SEQ ID NO:1. The amino acid sequence containing ACP5, represented herein as SEQ ID NO:22, is contained within the amino acid sequence spanning from about position 1571 to about position 1662 of SEQ ID NO:2. The nucleotide sequence containing ACP6, represented herein as SEQ ID NO:23, is contained within the nucleotide sequence spanning from about position 5053 to about position 5328 of SEQ ID NO:1. The amino acid sequence containing ACP6, represented herein as SEQ ID NO:24, is contained within the amino acid sequence spanning from about position 1685 to about position 1776 of SEQ ID NO:2. All six ACP domains together span a region of *Schizochytrium* sp. ATCC PTA-9695 Pfa1 of from about position 3298 to about position 5400 of SEQ ID NO:1, corresponding to amino acid positions of about 1100 to about 1800 of SEQ ID NO:2. The nucleotide sequence for the entire ACP region containing all six domains is represented herein as SEQ ID NO:11; while the amino acid sequence for the entire ACP region containing all six domains is represented herein as SEQ ID NO:12. The repeat interval for the six ACP domains within SEQ ID NO:11 was found to be approximately every 342 nucleotides (the actual number of amino acids measured between adjacent active site serines ranges from 114 to 116 amino acids). Each of the six ACP domains contains a pantetheine binding motif LGIDS* (SEQ ID NO:47) wherein S* is the pantetheine binding site serine (S). The pantetheine binding site serine (S) is located near the center of each ACP domain sequence. The locations of the active site serine residues (i.e., the pantetheine binding site) for each of the six ACPD domains, with respect to the amino acid sequence of SEQ ID NO:2 are: ACP1=S1152, ACP2=S1266, ACP3=S1382, ACP4=S1498, ACP5=S1614, and ACP6=S1728.

The ninth domain in *Schizochytrium* sp. ATCC PTA-9695 Pfa1 is a KR domain. The nucleotide sequence containing the sequence encoding the *Schizochytrium* sp. ATCC PTA-9695 Pfa1 KR domain is represented herein as SEQ ID NO:25, corresponding to positions 5623-7800 of SEQ ID NO:1. The amino acid sequence containing the *Schizochytrium* sp. ATCC PTA-9695 Pfa1 KR domain is represented herein as SEQ ID NO:26, corresponding to positions 1875-2600 of SEQ ID NO:2. Within the KR domain is a core region (contained within the nucleotide sequence of SEQ ID NO:48, and the amino acid sequence of SEQ ID NO:49) with homology to short chain aldehyde-dehydrogenases (KR is a member of this family). This core region spans from about position 5998 to about 6900 of SEQ ID NO:1, which corresponds to amino acid positions 2000-2300 of SEQ ID NO:2.

The tenth domain in *Schizochytrium* sp. ATCC PTA-9695 Pfa1 is a DH domain. The nucleotide sequence containing the sequence encoding the *Schizochytrium* sp. ATCC PTA-9695 Pfa1 DH domain is represented herein as SEQ ID NO:27, corresponding to positions 7027-7065 of SEQ ID NO:1. The amino acid sequence containing the *Schizochytrium* sp. ATCC PTA-9695 Pfa1 DH domain is represented herein as SEQ ID NO:28, corresponding to positions 2343-2355 of SEQ ID NO:2. The DH domain contains a conserved active site motif (See, Donadio, S. and Katz., L., *Gene* 111(1): 51-60 (1992)): LxxHxxxGxxxxP (SEQ ID NO:50).

Table 4 shows the domains and active sites associated with *Schizochytrium* sp. ATCC PTA-9695 PFA2.

TABLE 4

*Schizochytrium* sp. ATCC PTA-9695 PFA2 Domain Analysis

| Domain | DNA positions | AA positions | Sites | DNA positions | AA positions |
|---|---|---|---|---|---|
| KS | 10-1350 of SEQ ID NO: 3 (SEQ ID NO: 29) | 4-450 of SEQ ID NO: 4 (SEQ ID NO: 30) | DXAC* (SEQ ID NO:43) | 571-573 of SEQ ID NO: 3 | C191 of SEQ ID NO: 4 |
|  |  |  | End - GFGG (SEQ ID NO: 44) | 1312-1323 of SEQ ID NO: 3 (SEQ ID NO: 51) | 438-441 of SEQ ID NO: 4 |
| CLF | 1408-2700 of SEQ ID NO: 3 (SEQ ID NO: 31) | 470-900 of SEQ ID NO: 4 (SEQ ID NO: 32) |  |  |  |
| AT | 2998-4200 of SEQ ID NO: 3 (SEQ ID NO: 33) | 1000-1400 of SEQ ID NO: 4 (SEQ ID NO: 34) | GxS*xG (SEQ ID NO: 52) | 3421-3423 of SEQ ID NO: 3 | S1141 of SEQ ID NO: 4 |

TABLE 4-continued

Schizochytrium sp. ATCC PTA-9695 PFA2 Domain Analysis

| Domain | DNA positions | AA positions | Sites | DNA positions | AA positions |
|---|---|---|---|---|---|
| ER | 4498-5700 of SEQ ID NO: 3 (SEQ ID NO: 35) | 1500-1900 of SEQ ID NO: 4 (SEQ ID NO: 36) | | | |

The first domain in *Schizochytrium* sp. ATCC PTA-9695 Pfa2 is a KS domain. The nucleotide sequence containing the sequence encoding the *Schizochytrium* sp. ATCC PTA-9695 Pfa2 KS domain is represented herein as SEQ ID NO:29, corresponding to positions 10-1350 of SEQ ID NO:3. The amino acid sequence containing the *Schizochytrium* sp. ATCC PTA-9695 Pfa2 KS domain is represented herein as SEQ ID NO:30, corresponding to positions 4-450 of SEQ ID NO:4. The KS domain contains an active site motif: DXAC* (SEQ ID NO:43), with an *acyl binding cite corresponding to C191 of SEQ ID NO:4. Also, a characteristic motif is present at the end of the KS domain: GFGG (SEQ ID NO:44), corresponding to positions 438-441 of SEQ ID NO:4 and positions 435-438 of SEQ ID NO:30.

The third domain in *Schizochytrium* sp. ATCC PTA-9695 Pfa2 is a CLF domain. The nucleotide sequence containing the sequence encoding the *Schizochytrium* sp. ATCC PTA-9695 Pfa2 CLF domain is represented herein as SEQ ID NO:31, corresponding to positions 1408-2700 of SEQ ID NO:3. The amino acid sequence containing the *Schizochytrium* sp. ATCC PTA-9695 Pfa2 CLF domain is represented herein as SEQ ID NO:32, corresponding to positions 470-900 of SEQ ID NO:4.

The third domain in *Schizochytrium* sp. ATCC PTA-9695 Pfa2 is an AT domain. The nucleotide sequence containing the sequence encoding the *Schizochytrium* sp. ATCC PTA-9695 Pfa2 AT domain is represented herein as SEQ ID NO:33, corresponding to positions 2998-4200 of SEQ ID NO:3. The amino acid sequence containing the *Schizochytrium* sp. ATCC PTA-9695 Pfa2 AT domain is represented herein as SEQ ID NO:34, corresponding to positions 1000-1400 of SEQ ID NO:4. The AT domain contains an active site motif of GxS*xG (SEQ ID NO:52) that is characteristic of acyltransferase (AT) proteins, with an active site serine residue corresponding to S1141 of SEQ ID NO:4.

The fourth domain of *Schizochytrium* sp. ATCC PTA-9695 Pfa2 is an ER domain. The nucleotide sequence containing the sequence encoding the *Schizochytrium* sp. ATCC PTA-9695 Pfa2 ER domain is represented herein as SEQ ID NO:35, corresponding to positions 4498-5700 of SEQ ID NO:3. The amino acid sequence containing the Pfa2 ER domain is represented herein as SEQ ID NO:36, corresponding to positions 1500-1900 of SEQ ID NO:4.

Table 5 shows the domains and active sites associated with *Schizochytrium* sp. ATCC PTA-9695 PFA3.

TABLE 5

Schizochytrium sp. ATCC PTA-9695 PFA3 Domain Analysis

| Domain | DNA positions | AA positions | Sites | DNA positions | AA positions |
|---|---|---|---|---|---|
| DH1 | 1-1350 of SEQ ID NO: 5 (SEQ ID NO: 37) | 1-450 of SEQ ID NO: 6 (SEQ ID NO: 38) | FxxH*F (SEQ ID NO: 53) | 931-933 of SEQ ID NO: 5 | H310 of SEQ ID NO: 6 |
| DH2 | 1501-2700 of SEQ ID NO: 5 (SEQ ID NO: 39) | 501-900 of SEQ ID NO: 6 (SEQ ID NO: 40) | FxxH*F (SEQ ID NO: 53) | 2401-2403 of SEQ ID NO: 5 | H801 of SEQ ID NO: 6 |
| ER | 2848-4200 of SEQ ID NO: 5 (SEQ ID NO: 41) | 950-1400 of SEQ ID NO: 6 (SEQ ID NO: 42) | | | |

The first and second domains of *Schizochytrium* sp. ATCC PTA-9695 Pfa3 are DH domains, referred to herein as DH1 and DH2, respectively. The nucleotide sequence containing the sequence encoding the *Schizochytrium* sp. ATCC PTA-9695 Pfa3 DH1 domain is represented herein as SEQ ID NO:37, corresponding to positions 1-1350 of SEQ ID NO:5. The amino acid sequence containing the *Schizochytrium* sp. ATCC PTA-9695 Pfa3 DH1 domain is represented herein as SEQ ID NO:38, corresponding to positions 1-450 of SEQ ID NO:6. The nucleotide sequence containing the sequence encoding the *Schizochytrium* sp. ATCC PTA-9695 Pfa3 DH2 domain is represented herein as SEQ ID NO:39, corresponding to positions 1501-2700 of SEQ ID NO:5. The amino acid sequence containing the *Schizochytrium* sp. ATCC PTA-9695 Pfa3 DH2 domain is represented herein as SEQ ID NO:40, corresponding to positions 501-900 of SEQ ID NO:6. The DH domains contain an active site motif: FxxH*F (SEQ ID NO:53). The nucleotide sequence containing the active site motif in DH1 corresponds to positions 931-933 of SEQ ID NO:5, while the nucleotide sequence containing the active site motif in DH2 corresponds to positions 2401-2403 of SEQ ID NO:5. The active site H* in the motif FxxH*F is based on data from Leesong et al., *Structure* 4:253-64 (1996) and Kimber et al. *J Biol Chem.* 279:52593-602 (2004), with the active site H* in DH1 corresponding to H310 of SEQ ID NO:6 and the active site H* in DH2 corresponding to H801 of SEQ ID NO:6.

The third domain of *Schizochytrium* sp. ATCC PTA-9695 Pfa3 is an ER domain. The nucleotide sequence containing the sequence encoding the *Schizochytrium* sp. ATCC PTA-9695 Pfa3 ER domain is represented herein as SEQ ID NO:41, corresponding to positions 2848-4200 of SEQ ID NO:5. The amino acid sequence containing the Schizochytrium sp. ATCC PTA-9695 Pfa3 ER domain is represented herein as SEQ ID NO:42, corresponding to positions 950-1400 of SEQ ID NO:6.

EXAMPLE 4

Degenerate primers for the KS, ER, and DH PUFA synthase domains were designed in order to isolate the corresponding sequences from the isolated microorganism deposited under ATCC Accession No. PTA-10212, also known as *Thraustochytrium* sp. ATCC PTA-10212.

Degenerate primers for the KS region of *Thraustochytrium* sp. ATCC PTA-10212 PFA1 (i.e., the region containing the KS domain) were designed based on the published PFA1 (previously termed orfA or ORF 1) sequences for *Schizochytrium* sp. ATCC 20888, *Thraustochytrium aureum* (ATCC 34304), and *Thraustochytrium* sp. 23B ATCC 20892:

```
                                       (SEQ ID NO: 123)
   prDS233 (forward):
   TGATATGGGAGGAATGAATTGTGTNGTNGAYGC (SEQ ID NO: 124)
   prDS235 (reverse):
   TTCCATAACAAAATGATAATTAGCTCCNCCRAANCC.
```

Degenerate primers for the ER region of *Thraustochytrium* sp. ATCC PTA-10212 PFA2 (i.e., the region containing the ER domain) were designed based on the published PFA2 (previously termed orfB or ORF 2) sequences for *Shewanella japonica*, *Schizochytrium* sp. ATCC 20888, *Thraustochytrium aureum* (ATCC 34304), and *Thraustochytrium* sp. 23B ATCC 20892:

```
   prDS183 (forward):
   GGCGGCCACACCGAYAAYMGNCC      (SEQ ID NO: 125)

prDS184 (reverse):
   CGGGGCCGCACCANAYYTGRTA.      (SEQ ID NO: 126)
```

Degenerate primers for the ER region of *Thraustochytrium* sp. ATCC PTA-10212 PFA3 (i.e., the region containing the ER domain) were designed based on the published PFA3 (previously termed orfC or ORF 3) sequences for *Shewanella japonica*, *Schizochytrium* sp. ATCC 20888, *Thraustochytrium aureum* (ATCC 34304), and *Thraustochytrium* sp. 23B ATCC 20892:

```
   prDS181 (forward):
   TCCTTCGGNGCNGSNGG            (SEQ ID NO: 127)

prDS184 (reverse):
   CGGGGCCGCACCANAYYTGRTA.      (SEQ ID NO: 126)
```

Degenerate primers JGM190 (forward, SEQ ID NO:64) and BLR242 (reverse, SEQ ID NO:65), as described above, were used to amplify the DH region of PFA3 from *Thraustochytrium* sp. ATCC PTA-10212.

The PCR conditions with chromosomal DNA template were as follows: 0.2 µM dNTPs, 0.1 uM each primer, 6% DMSO, 200 ng chromosomal DNA, 2.5 U Herculase® II fusion polymerase (Stratagene), and 1× Herculase® buffer (Stratagene) in a 50 µL total volume. The PCR Protocol included the following steps: (1) 98° C. for 3 minutes; (2) 98° C. for 30 seconds; (3) 54° C. for 45 seconds; (4) 72° C. for 1 minutes; (5) repeat steps 2-4 for 40 cycles; (6) 72° C. for 5 minutes; and (7) hold at 6° C.

For all primer pairs, PCR yielded distinct DNA products with the expected sizes using chromosomal templates from *Thraustochytrium* sp. ATCC PTA-10212. The respective PCR products were cloned into the vector pJET1.2/blunt (Fermentas) according to the manufacturer's instructions, and the insert sequence was determined using supplied standard primers.

The DNA sequences obtained from the PCR products were compared with known sequences available from the NCBI GenBank as described in Example 1.

At the amino acid level, the sequences with the highest level of homology to deduced amino acid sequence derived from the cloned DNA containing the KS fragment from PFA1 from *Thraustochytrium* sp. ATCC PTA-10212 were: *Schizochytrium* sp. ATCC 20888 "polyunsaturated fatty acid synthase subunit A" (Identity=80%; positives=90%); *Shewanella benthica* KT99 "omega-3 polyunsaturated fatty acid synthase PfaA" (Identity=51%; positives=67%); *Shewanella loihica* PV-4 "beta-ketoacyl synthase" (Identity=50%; positives=67%); *Shewanella woodyi* ATCC 51908 "polyketide-type polyunsaturated fatty acid synthase PfaA" (Identity=51%; positives=66%).

At the amino acid level, the sequences with the highest level of homology to deduced amino acid sequence derived from the cloned DNA containing the ER fragment from PFA2 from *Thraustochytrium* sp. ATCC PTA-10212 were: *Schizochytrium* sp. ATCC 20888 "polyunsaturated fatty acid synthase subunit B" (Identity=70%; positives=85%); *Schizochytrium* sp. ATCC 20888 "polyunsaturated fatty acid synthase subunit C" (Identity=66%; positives=83%); *Nodularia spumigena* CCY9414 "2-nitropropane dioxygenase" (Identity=57%; positives=74%); *Moritella* sp. PE36 "polyunsaturated fatty acid synthase PfaD" (Identity=57%; positives=71%).

At the amino acid level, the sequences with the highest level of homology to deduced amino acid sequence derived from the cloned DNA containing the ER fragment from PFA3 from *Thraustochytrium* sp. ATCC PTA-10212 were: *Schizochytrium* sp. ATCC 20888 "polyunsaturated fatty acid synthase subunit C" (Identity=80%; positives=90%); *Schizochytrium* sp. ATCC 20888 "polyunsaturated fatty acid synthase subunit B" (Identity=78%; positives=89%); *Moritella* sp. PE36 "polyunsaturated fatty acid synthase PfaD" (Identity=56%; positives=71%); *Shewanella amazonensis* SB2B "omega-3 polyunsaturated fatty acid synthase PfaD" (Identity=55%; positives=73%).

At the amino acid level, the sequences with the highest level of homology to deduced amino acid sequence derived from the cloned DNA containing the DH fragment from PFA3 from *Thraustochytrium* sp. ATCC PTA-10212 were: *Schizochytrium* sp. ATCC 20888 "polyunsaturated fatty acid synthase subunit C" (Identity=63%; positives=76%); *Shewanella pealeana* ATCC 700345 "Beta-hydroxyacyl-(acyl-carrier-protein) dehydratase FabA/FabZ" (Identity=35%; positives=53%); *Shewanella piezotolerans* WP3 "Multi-domain beta-ketoacyl synthase" (Identity=36%; positives=52%); *Shewanella benthica* KT99 "omega-3 polyunsaturated fatty acid synthase PfaC" (Identity=35%; positives=51%).

EXAMPLE 5

PUFA synthase genes were identified from *Thraustochytrium* sp. ATCC PTA-10212.

From a −80° C. cyrovial, 1 mL of cells were thawed at room temperature and added to 50 mL of liquid HSFM media (below) in a 250 mL non-baffled flask. The flask was incubated at 23° C. for 3 days. Cells were collected and utilized for standard Bacterial Artificial Chromosome (BAC) library construction (Lucigen Corporation, Middleton, Wis. USA).

TABLE 6

HSFM Media

| Ingredient | | concentration | ranges |
|---|---|---|---|
| Na$_2$SO$_4$ | g/L | 31.0 | 0-50, 15-45, or 25-35 |
| NaCl | g/L | 0.625 | 0-25, 0.1-10, or 0.5-5 |
| KCl | g/L | 1.0 | 0-5, 0.25-3, or 0.5-2 |
| MgSO$_4$•7H$_2$O | g/L | 5.0 | 0-10, 2-8, or 3-6 |
| (NH$_4$)$_2$SO$_4$ | g/L | 0.44 | 0-10, 0.25-5, or 0.05-3 |
| MSG*1H$_2$O | g/L | 6.0 | 0-10, 4-8, or 5-7 |
| CaCl$_2$ | g/L | 0.29 | 0.1-5, 0.15-3, or 0.2-1 |
| T 154 (yeast extract) | g/L | 6.0 | 0-20, 0.1-10, or 1-7 |
| KH$_2$PO$_4$ | g/L | 0.8 | 0.1-10, 0.5-5, or 0.6-1.8 |
| Post autoclave (Metals) | | | |
| Citric acid | mg/L | 3.5 | 0.1-5000, 10-3000, or 3-2500 |
| FeSO$_4$•7H$_2$O | mg/L | 10.30 | 0.1-100, 1-50, or 5-25 |
| MnCl$_2$•4H$_2$O | mg/L | 3.10 | 0.1-100, 1-50, or 2-25 |
| ZnSO$_4$•7H$_2$O | mg/L | 3.10 | 0.01-100, 1-50, or 2-25 |
| CoCl$_2$•6H$_2$O | mg/L | 0.04 | 0-1, 0.001-0.1, or 0.01-0.1 |
| Na$_2$MoO$_4$•2H$_2$O | mg/L | 0.04 | 0.001-1, 0.005-0.5, or 0.01-0.1 |
| CuSO$_4$•5H$_2$O | mg/L | 2.07 | 0.1-100, 0.5-50, or 1-25 |
| NiSO$_4$•6H$_2$O | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| Vitamin B12 | mg/L | 0.16 | 0.01-100, 0.05-5, or 0.1-1 |
| Ca$^1$/$_2$-pantothenate | mg/L | 2.06 | 0.1-100, 0.1-50, or 1-10 |
| Biotin | mg/L | 3.21 | 0.1-100, 0.1-50, or 1-10 |
| Post autoclave (Carbon) | | | |
| Glycerol | g/L | 30.0 | 5-150, 10-100, or 20-50 |
| Nitrogen Feed: | | | |
| MSG•1H$_2$O | g/L | 17 | 0-150, 10-100, or 15-50 |

Typical cultivation conditions would include the following:
pH about 6.5-about 9.5, about 6.5-about 8.0, or about 6.8-about 7.8;
temperature: about 15-about 30 degrees Celsius, about 18-about 28 degrees Celsius, or about 21 to about 23 degrees Celsius;
dissolved oxygen: about 0.1-about 100% saturation, about 5-about 50% saturation, or about 10-about 30% saturation; and/or
glycerol controlled @: about 5-about 50 g/L, about 10-about 40 g/L, or about 15-about 35 g/L.

The recombinant BAC libraries, consisting of large fragments (average of approximately 120 kB) were handled according to the manufacturer's instructions in the BAC vector pSMART® (Lucigen Corporation). The BAC libraries were screened by standard colony hybridization procedures using $^{32}$P radioactively labeled probes (Sambrook J. and Russell D. 2001. Molecular cloning: A laboratory manual, 3rd edition. Cold Spring Harbor Laboratory Press, Cold Spring Harbor, N.Y.). The probes contained DNA homologous to published PUFA synthase sequences from other organisms as described in Example 4. These probes were generated by a DNA restriction digest of the cloned fragments from respective clones from pJET1.2/blunt described above and labeled by standard methods. In all cases, strong hybridization of the individual probes to certain BACs indicated clones containing DNA homologous to PUFA synthase genes.

BAC clone pLR130 (also known as LuMaBAC 2M23) demonstrated strong hybridization of probe to both the KS region and ER region, indicating that it contained the PFA1 and PFA2 genes, and was selected for DNA sequencing of the *Thraustochytrium* sp. ATCC PTA-10212 PFA1 and PFA2 genes. The BAC was sequenced by standard procedures (Eurofins MWG Operon, Huntsville, Ala.). BAC clone pLR130, containing the PFA1 and PFA2 genes, was deposited under the Budapest Treaty, at the American Type Culture Collection, Patent Depository, 10801 University Boulevard, Manassas, Va. 20110-2209, on Dec. 1, 2009, and given ATCC Accession No. PTA-10511.

In previously published thraustochytrid PUFA synthase systems, the PUFA synthase genes PFA1 and PFA2 have been clustered together and arranged as to be divergently transcribed. This is also the case for PFA1 and PFA2 from *Thraustochytrium* sp. ATCC PTA-10212. The conceptual start of PFA2 was found to be 693 nucleotides from the start of PFA1 and divergently transcribed.

BAC clone pDS127 (also known as LuMaBAC 9K17) demonstrated strong hybridization of probe to both the DH region and ER region of PFA3 and was selected for DNA sequencing of the PFA3 gene. BAC clone pDS127, containing the PFA3 gene, was deposited under the Budapest Treaty, at the American Type Culture Collection, Patent Depository, 10801 University Boulevard, Manassas, Va. 20110-2209, on Dec. 1, 2009, and given ATCC Accession No. PTA-10510. Sequencing primers were designed using standard methods to the DH region and ER region and the DNA sequence determined in Example 4. To determine the DNA sequence of the *Thraustochytrium* sp. ATCC PTA-10212 PFA3 gene, successive rounds of DNA sequencing, involving subsequent sequencing primer design by standard methods, was carried out in order to "walk" the BAC clone. Each nucleotide base pair of the PFA3 gene was covered by at least two separate DNA sequencing reactions of high-quality with at least a minimum aggregated Phred score of 40 (confidence level of 99.99%).

Table 7 shows identities for the *Thraustochytrium* sp. ATCC PTA-10212 PFA1 (SEQ ID NO:68), PFA2 (SEQ ID NO:70), and PFA3 (SEQ ID NO:72) polynucleotide sequences as compared to previously published sequences and the sequences from *Schizochytrium* sp. PTA-9695. Identities were determined by the scoring matrix "swgapdnamt" within the "AlignX" program of the VectorNTI program, a standard for DNA alignment.

TABLE 7

Percent Identity to PFA1, PFA2, and PFA3 Polynucleotide Sequences

| Source of Comparison PFA1, PFA2, and PFA3 Sequences | % Identity of Comparison PFA1 (orfA) to PFA1 | % Identity of Comparison PFA2 (orfB) to PFA2 | % Identity of Comparison PFA3 (orfC) to PFA3 |
|---|---|---|---|
| *Schizochytrium* sp. ATCC 20888 | 55 | 54 | 59 |
| *Thraustochytrium aureum* ATCC 34304 | 55 | 53 | not published |
| *Thraustochytrium* sp. 23B ATCC 20892 | 55 | 57 | 62 |
| *Schizochytrium* sp. PTA-9695 | 55 | 52 | 59 |

Table 8 shows identities for the *Thraustochytrium* sp. ATCC PTA-10212 Pfa1p (SEQ ID NO:69), Pfa2p (SEQ ID NO:71), and Pfa3p (SEQ ID NO:73) amino acid sequences as compared to previously published PUFA synthase amino acid sequences and the sequences from *Schizochytrium* sp. PTA-9695. Identities were determined through use of the scoring matrix "blosum62mt2" within the "AlignX" program of the VectorNTI program, a standard for protein alignment.

TABLE 8

Percent Identity to Pfa1p, Pfa2p, and Pfa3p Amino Acid Sequences

| Source of Comparison Pfa1p, Pfa2p, and Pfa3p Sequences | % Identity of Comparison Pfa1p (OrfA) to Pfa1p | % Identity of Comparison Pfa2p (OrfB) to Pfa2p | % Identity of Comparison Pfa3p (OrfC) to Pfa3p |
|---|---|---|---|
| *Schizochytrium* sp. ATCC 20888 | 62 | 57 | 69 |
| *Thraustochytrium aureum* ATCC 34304 | 58 | 54 | not published |
| *Thraustochytrium* sp. 23B ATCC 20892 | 54 | 54 | 71 |
| *Schizochytrium* sp. PTA-9695 | 59 | 53 | 73 |

EXAMPLE 6

Domain analysis was performed to annotate the sequence coordinates for the PUFA synthase domains and active sites of *Thraustochytrium* sp. ATCC PTA-10212 PFA1, PFA2, and PFA3, respectively. Domains were identified based on homology to known PUFA synthase, fatty acid synthase, and polyketide synthase domains.

Table 9 shows the domains and active sites associated with *Thraustochytrium* sp. ATCC PTA-10212 PFA1.

TABLE 9

*Thraustochytrium* sp. ATCC PTA-10212 PFA1 Domain Analysis

| Domain | DNA position | AA position | Sites | DNA position | AA position |
|---|---|---|---|---|---|
| KS | 13-1362 of SEQ ID NO: 68 (SEQ ID NO: 74) | 5-545 of SEQ ID NO: 69 (SEQ ID NO: 75) | Active - DXAC* (SEQ ID NO: 43) | 601-612 of SEQ ID NO: 68 | C204 of SEQ ID NO: 69 |
| | | | End - GFGG (SEQ ID NO: 44) | 1351-1362 of SEQ ID NO: 68 (SEQ ID NO: 45) | 451-454 of SEQ ID NO: 69 |
| MAT | 1783-2703 of SEQ ID NO: 68 (SEQ ID NO: 76) | 595-901 of SEQ ID NO: 69 (SEQ ID NO: 77) | Active GHS*LG (SEQ ID NO: 46) | 2083-2085 of SEQ ID NO: 68 (SEQ ID NO: 116) | S695 of SEQ ID NO: 69 |
| ACP | 3208-6510 of SEQ ID NO: 68 (SEQ ID NO: 78) | 1070-2170 of SEQ ID NO: 69 (SEQ ID NO: 79) | ACP1 domain | 3280-3534 of SEQ ID NO: 68 (SEQ ID NO: 80) | 1094-1178 of SEQ ID NO: 69 (SEQ ID NO :81) |
| | | | ACP1 Active LGIDS* (SEQ ID NO: 47) | 3403-3405 of SEQ ID NO: 68 | S1135 of SEQ ID NO: 69 |
| | | | ACP2 domain | 3607-3861 of SEQ ID NO: 68 (SEQ ID NO: 82) | 1203-1287 of SEQ ID NO: 69 (SEQ ID NO: 83) |
| | | | ACP2 Active LGIDS* (SEQ ID NO: 47) | 3730-3732 of SEQ ID NO: 68 | S1244 of SEQ ID NO: 69 |
| | | | ACP3 domain | 3934-4185 of SEQ ID NO: 68 (SEQ ID NO: 84) | 1312-1396 of SEQ ID NO: 69 (SEQ ID NO: 85) |
| | | | ACP3 Active LGIDS* (SEQ ID NO: 47) | 4057-4059 of SEQ ID NO: 68 | S1353 of SEQ ID NO: 69 |
| | | | ACP4 domain | 4261-4515 of SEQ ID NO: 68 (SEQ ID NO: 86) | 1421-1505 of SEQ ID NO: 69 (SEQ ID NO: 87) |
| | | | ACP4 Active LGIDS* (SEQ ID NO: 47) | 4384-4386 of SEQ ID NO: 68 | S1462 of SEQ ID NO: 69 |
| | | | ACP5 domain | 4589-4842 of SEQ ID NO: 68 (SEQ ID NO: 88) | 1530-1614 of SEQ ID NO: 69 (SEQ ID NO: 89) |
| | | | ACP5 Active LGIDS* (SEQ ID NO: 47) | 4711-4713 of SEQ ID NO: 68 | S1571 of SEQ ID NO: 69 |
| | | | ACP6 domain | 4915-5169 of SEQ ID NO: 68 (SEQ ID NO: 90) | 1639-1723 of SEQ ID NO: 69 (SEQ ID NO: 91) |
| | | | ACP6 Active LGIDS* (SEQ ID NO: 47) | 5038-5040 of SEQ ID NO: 68 | S1680 of SEQ ID NO: 69 |
| | | | ACP7 domain | 5242-5496 of SEQ ID NO: 68 (SEQ ID NO: 92) | 1748-1832 of SEQ ID NO: 69 (SEQ ID NO: 93) |

TABLE 9-continued

Thraustochytrium sp. ATCC PTA-10212 PFA1 Domain Analysis

| Domain | DNA position | AA position | Sites | DNA position | AA position |
|---|---|---|---|---|---|
| | | | ACP7 Active LGIDS* (SEQ ID NO: 47) | 5365-5367 of SEQ ID NO: 68 | S1789 of SEQ ID NO: 69 |
| | | | ACP8 domain | 5569-5823 of SEQ ID NO: 68 (SEQ ID NO: 94) | 1857-1941 of SEQ ID NO: 69 (SEQ ID NO: 95) |
| | | | ACP8 Active LGIDS* (SEQ ID NO: 47) | 5692-5694 of SEQ ID NO: 68 | S1898 of SEQ ID NO: 69 |
| | | | ACP9 domain | 5896-6150 of SEQ ID NO: 68 (SEQ ID NO: 96) | 1966-2050 of SEQ ID NO: 69 (SEQ ID NO: 97) |
| | | | ACP9 Active LGIDS* (SEQ ID NO: 47) | 6019-6021 of SEQ ID NO: 68 | S2007 of SEQ ID NO: 69 |
| | | | ACP10 domain | 6199-6453 of SEQ ID NO: 68 (SEQ ID NO: 98) | 2067-2151 of SEQ ID NO: 69 (SEQ ID NO: 99) |
| | | | ACP10 Active LGIDS* (SEQ ID NO: 47) | 6322-6324 of SEQ ID NO: 68 | S2108 of SEQ ID NO: 69 |
| KR | 6808-8958 of SEQ ID NO: 68 (SEQ ID NO: 100) | 2270-2986 of SEQ ID NO: 69 (SEQ ID NO: 101) | "core region" | 7198-8100 of SEQ ID NO: 68 (SEQ ID NO: 116) | 2400-2600 of SEQ ID NO: 69 (SEQ ID NO: 117) |
| DH Motif | 8203-8241 of SEQ ID NO: 68 (SEQ ID NO: 118) | 2735-2747 of SEQ ID NO: 69 (SEQ ID NO: 119) | LxxHxxxGxxxxP (SEQ ID NO: 50) | 8203-8241 of SEQ ID NO: 68 (SEQ ID NO: 118) | 2735-2747 of SEQ ID NO: 69 (SEQ ID NO: 119) |

The first domain in *Thraustochytrium* sp. ATCC PTA-10212 Pfa1 is a KS domain. The nucleotide sequence containing the sequence encoding the *Thraustochytrium* sp. ATCC PTA-10212 Pfa1 KS domain is represented herein as SEQ ID NO:74, corresponding to positions 13-1362 of SEQ ID NO:68. The amino acid sequence containing the *Thraustochytrium* sp. ATCC PTA-10212 Pfa1 KS domain is represented herein as SEQ ID NO:75, corresponding to positions 5-454 of SEQ ID NO:69. The KS domain contains an active site motif: DXAC* (SEQ ID NO:43), with an *acyl binding cite corresponding to C204 of SEQ ID NO:69. Also, a characteristic motif is present at the end of the KS domain: GFGG (SEQ ID NO:44), corresponding to positions 451-454 of SEQ ID NO:69 and positions 447-450 of SEQ ID NO:75.

The second domain in *Thraustochytrium* sp. ATCC PTA-10212 Pfa1 is a MAT domain. The nucleotide sequence containing the sequence encoding the *Thraustochytrium* sp. ATCC PTA-10212 Pfa1 MAT domain is represented herein as SEQ ID NO:76, corresponding to positions 1783-2703 of SEQ ID NO:68. The amino acid sequence containing the *Thraustochytrium* sp. ATCC PTA-10212 Pfa1 MAT domain is represented herein as SEQ ID NO:77, corresponding to positions 595-901 of SEQ ID NO:69. The MAT domain contains an active site motif: GHS*XG (SEQ ID NO:46), with an *acyl binding cite corresponding to S695 of SEQ ID NO:69.

The third through twelfth domains of *Thraustochytrium* sp. ATCC PTA-10212 Pfa1p are ten tandem ACP domains, also referred to herein as ACP1, ACP2, ACP3, ACP4, ACP5, ACP6, ACP7, ACP8, ACP9, and ACP10. The nucleotide sequence containing the first ACP domain, ACP1, is represented herein as SEQ ID NO:80 and is contained within the nucleotide sequence spanning from about position 3280 to about position 3534 of SEQ ID NO:68. The amino acid sequence containing ACP1, represented herein as SEQ ID NO:81, is contained within the amino acid sequence spanning from about position 1094 to about position 1178 of SEQ ID NO:69. The nucleotide sequence containing ACP2, represented herein as SEQ ID NO:82, is contained within the nucleotide sequence spanning from about position 3607 to about position 3861 of SEQ ID NO:68. The amino acid sequence containing ACP2, represented herein as SEQ ID NO:83, is contained within the amino acid sequence spanning from about position 1203 to about position 1287 of SEQ ID NO:69. The nucleotide sequence containing ACP3, represented herein as SEQ ID NO:84, is contained within the nucleotide sequence spanning from about position 3934 to about position 4185 of SEQ ID NO:68. The amino acid sequence containing ACP3, represented herein as SEQ ID NO:85, is contained within the amino acid sequence spanning from about position 1312 to about position 1396 of SEQ ID NO:69. The nucleotide sequence containing ACP4, represented herein as SEQ ID NO:86, is contained within the nucleotide sequence spanning from about position 4261 to about position 4515 of SEQ ID NO:68. The amino acid sequence containing ACP4, represented herein as SEQ ID NO:87, is contained within the amino acid sequence spanning from about position 1421 to about position 1505 of SEQ ID NO:69. The nucleotide sequence containing ACP5, represented herein as SEQ ID NO:88, is contained within the nucleotide sequence spanning from about position 4589 to about position 4842 of SEQ ID NO:68. The amino acid sequence containing ACP5, represented herein as SEQ ID NO:89, is contained within the amino acid sequence spanning from about position 1530 to about position 1614 of SEQ ID NO:69. The nucleotide sequence containing ACP6, represented herein as SEQ ID NO:90, is contained within the nucleotide sequence spanning from about position 4915 to about position 5169 of SEQ ID NO:68. The amino acid sequence containing ACP6, represented herein as SEQ ID NO:91, is contained within the amino acid sequence spanning from about position 1639 to about position 1723 of SEQ ID NO:69. The nucleotide sequence containing ACP7, represented herein as SEQ ID NO:92, is contained within the nucleotide sequence spanning from about position 5242 to about position 5496 of SEQ ID NO:68. The amino acid sequence containing ACP7, represented herein as SEQ ID NO:93, is contained within the amino acid sequence spanning from about position 1748 to about position 1832 of SEQ ID NO:69. The nucleotide sequence containing ACP8, represented herein as SEQ ID NO:94, is contained within the nucleotide sequence spanning from about position 5569 to about position 5832 of SEQ ID NO:68. The amino acid sequence containing ACP8, represented herein as SEQ ID NO:95, is contained within the amino acid sequence spanning from about position 1857 to about position 1941 of SEQ ID NO:69. The nucleotide sequence containing ACP9, represented herein as SEQ ID NO:96, is contained within the nucleotide sequence spanning from about position 5896 to about position 6150 of SEQ ID NO:68. The amino acid sequence containing ACP9, represented herein as SEQ ID NO:97, is contained within the amino acid sequence spanning from about position 1966 to about position 2050 of SEQ ID NO:69. The nucleotide sequence containing ACP10, represented herein as SEQ ID NO:98, is contained within the nucleotide sequence spanning from about position 6199 to about position 6453 of SEQ ID NO:68. The amino acid sequence containing ACP10, represented herein as SEQ ID NO:99, is contained within the amino acid sequence spanning from about position 2067 to about position 2151 of SEQ ID NO:69. All ten ACP domains together span a region of *Thraustochytrium* sp. ATCC PTA-10212 Pfa1 of from about position 3208 to about position 6510 of SEQ ID NO:68, corresponding to amino acid positions of about 1070 to about 2170 of SEQ ID NO:69. The nucleotide sequence for the entire ACP region containing all 10 domains is represented herein as SEQ ID NO:78; while the amino acid sequence for the entire ACP region containing all six domains is represented herein as SEQ ID NO:79. The repeat interval for the 10 ACP domains within SEQ ID NO:78 was found to be approximately every 327 nucleotides (the actual number of amino acids measured between adjacent active site serines ranges from 101 to 109 amino acids). Each of the ten ACP domains contains a pantetheine binding motif LGIDS* (SEQ ID NO:47) wherein S* is the pantetheine binding site serine (S). The pantetheine binding site serine (S) is located near the center of each ACP domain sequence. The locations of the active site serine residues (i.e., the pantetheine binding site) for each of the six ACPD domains, with respect to the amino acid sequence of SEQ ID NO:69 are: ACP1=S1135, ACP2=S1244, ACP3=S1353, ACP4=S1462, ACP5=S1571, ACP6=S1680, APC7=S1789, ACP7=S1789, ACP8=S1898, ACP9=S=2007, and ACP10=S2108.

The thirteenth domain in *Thraustochytrium* sp. ATCC PTA-10212 Pfa1 is a KR domain. The nucleotide sequence containing the sequence encoding the Pfa1 KR domain is represented herein as SEQ ID NO:100, corresponding to positions 6808-8958 of SEQ ID NO:68. The amino acid sequence containing the Pfa1 KR domain is represented herein as SEQ ID NO:101, corresponding to positions 2270-2986 of SEQ ID NO:69. Within the KR domain is a core region (contained within the nucleotide sequence of SEQ ID NO:116, and the amino acid sequence of SEQ ID NO:117) with homology to short chain aldehyde-dehydrogenases (KR is a member of this family). This core region spans from about position 5998 to about position 6900 of SEQ ID NO:68, which corresponds to amino acid positions 2000-2300 of SEQ ID NO:69.

The fourteenth domain in *Thraustochytrium* sp. ATCC PTA-10212 Pfa1 is a DH domain. The nucleotide sequence containing the sequence encoding the Pfa1 DH domain is represented herein as SEQ ID NO:118, corresponding to positions 7027-7065 of SEQ ID NO:68. The amino acid sequence containing the Pfa1 DH domain is represented herein as SEQ ID NO:119, corresponding to positions 2343-2355 of SEQ ID NO:69. The DH domain contains a conserved active site motif (see, Donadio, S. and Katz., L., Gene 111(1): 51-60 (1992)): LxxHxxxGxxxxP (SEQ ID NO:50).

Table 10 shows the domains and active sites associated with *Thraustochytrium* sp. ATCC PTA-10212 PFA2.

TABLE 10

*Thraustochytrium sp.* ATCC PTA-10212 PFA2 Domain Analysis

| Domain | DNA positions | AA positions | Sites | DNA positions | AA positions |
|---|---|---|---|---|---|
| KS | 10-1320 of SEQ ID NO: 70 (SEQ ID NO: 102) | 4-440 of SEQ ID NO: 71 (SEQ ID NO: 103) | DXAC* (SEQ ID NO: 43) | 571-573 of SEQ ID NO: 70 | C191 of SEQ ID NO: 71 |
|  |  |  | End - GFGG (SEQ ID NO: 44) | 1267-1278 of SEQ ID NO: 70 | 423-426 of SEQ ID NO: 71 |
| CLF | 1378-2700 of SEQ ID NO: 70 (SEQ ID NO: 104) | 460-900 of SEQ ID NO: 71 (SEQ ID NO: 105) |  |  |  |
| AT | 2848-4200 of SEQ ID NO: 70 (SEQ ID NO: 106) | 950-1400 of SEQ ID NO: 71 (SEQ ID NO: 107) | GxS*xG (SEQ ID NO: 52) | 3361-3363 of SEQ ID NO: 70 | S1121 of SEQ ID NO: 71 |
| ER | 4498-5700 of SEQ ID NO: 70 (SEQ ID NO: 108) | 1500-1900 of SEQ ID NO: 71 (SEQ ID NO: 109) |  |  |  |

The first domain in *Thraustochytrium* sp. ATCC PTA-10212 Pfa2 is a KS domain. The nucleotide sequence containing the sequence encoding the *Thraustochytrium* sp.

ATCC PTA-10212 Pfa2 KS domain is represented herein as SEQ ID NO:102, corresponding to positions 10-1320 of SEQ ID NO:70. The amino acid sequence containing the *Thraustochytrium* sp. ATCC PTA-10212 Pfa2 KS domain is represented herein as SEQ ID NO:103, corresponding to positions 4-440 of SEQ ID NO:71. The KS domain contains an active site motif: DXAC* (SEQ ID NO:43), with an *acyl binding cite corresponding to C191 of SEQ ID NO:71. Also, a characteristic motif is present at the end of the KS domain: GFGG (SEQ ID NO:44), corresponding to positions 423-426 of SEQ ID NO:71 and positions 1267-1278 of SEQ ID NO:70.

The second domain in *Thraustochytrium* sp. ATCC PTA-10212 Pfa2 is a CLF domain. The nucleotide sequence containing the sequence encoding the *Thraustochytrium* sp. ATCC PTA-10212 Pfa2 CLF domain is represented herein as SEQ ID NO:104, corresponding to positions 1378-2700 of SEQ ID NO:70. The amino acid sequence containing the *Thraustochytrium* sp. ATCC PTA-10212 Pfa2 CLF domain is represented herein as SEQ ID NO:105, corresponding to positions 460-900 of SEQ ID NO:71.

The third domain in *Thraustochytrium* sp. ATCC PTA-10212 Pfa2 is an AT domain. The nucleotide sequence containing the sequence encoding the *Thraustochytrium* sp. ATCC PTA-10212 Pfa2 AT domain is represented herein as SEQ ID NO:106, corresponding to positions 2848-4200 of SEQ ID NO:70. The amino acid sequence containing the *Thraustochytrium* sp. ATCC PTA-10212 Pfa2 AT domain is represented herein as SEQ ID NO:107, corresponding to positions 950-1400 of SEQ ID NO:71. The AT domain contains an active site motif of GxS*xG (SEQ ID NO:50) that is characteristic of acyltransferse (AT) proteins, with an active site serine residue corresponding to S1121 of SEQ ID NO:71.

The fourth domain of *Thraustochytrium* sp. ATCC PTA-10212 Pfa2 is an ER domain. The nucleotide sequence containing the sequence encoding the *Thraustochytrium* sp. ATCC PTA-10212 Pfa2 ER domain is represented herein as SEQ ID NO:108, corresponding to positions 4498-5700 of SEQ ID NO:70. The amino acid sequence containing the *Thraustochytrium* sp. ATCC PTA-10212 Pfa2 ER domain is represented herein as SEQ ID NO:109, corresponding to positions 1500-1900 of SEQ ID NO:71.

Table 11 shows the domains and active sites associated with *Thraustochytrium* sp. ATCC PTA-10212 PFA3.

The first and second domains of *Thraustochytrium* sp. ATCC PTA-10212 Pfa3 are DH domains, referred to herein as DH1 and DH2, respectively. The nucleotide sequence containing the sequence encoding the *Thraustochytrium* sp. ATCC PTA-10212 Pfa3 DH1 domain is represented herein as SEQ ID NO:110, corresponding to positions 1-1350 of SEQ ID NO:72. The amino acid sequence containing the *Thraustochytrium* sp. ATCC PTA-10212 Pfa3 DH1 domain is represented herein as SEQ ID NO:111, corresponding to positions 1-450 of SEQ ID NO:73. The nucleotide sequence containing the sequence encoding the *Thraustochytrium* sp. ATCC PTA-10212 Pfa3 DH2 domain is represented herein as SEQ ID NO:112, corresponding to positions 1501-2700 of SEQ ID NO:72. The amino acid sequence containing the *Thraustochytrium* sp. ATCC PTA-10212 Pfa3 DH2 domain is represented herein as SEQ ID NO:113, corresponding to positions 501-900 of SEQ ID NO:73. The DH domains contain an active site motif: FxxH*F (SEQ ID NO:53). The nucleotide sequence containing the active site motif in DH1 corresponds to positions 934-936 of SEQ ID NO:72, while the nucleotide sequence containing the active site motif in DH2 corresponds to positions 2401-2403 of SEQ ID NO:72. The active site H* in the motif FxxH*F is based on data from Leesong et al., Structure 4:253-64 (1996) and Kimber et al. J Biol Chem. 279:52593-602 (2004), with the active site H* in DH1 corresponding to H312 of SEQ ID NO:73 and the active site H* in DH2 corresponding to H801 of SEQ ID NO:73.

The third domain of *Thraustochytrium* sp. ATCC PTA-10212 Pfa3 is an ER domain. The nucleotide sequence containing the sequence encoding the *Thraustochytrium* sp. ATCC PTA-10212 Pfa3 ER domain is represented herein as SEQ ID NO:114, corresponding to positions 2848-4200 of SEQ ID NO:72. The amino acid sequence containing the *Thraustochytrium* sp. ATCC PTA-10212 Pfa3 ER domain is represented herein as SEQ ID NO:115, corresponding to positions 950-1400 of SEQ ID NO:73.

EXAMPLE 7

The inactivation of native PUFA synthase genes in *Schizochytrium* sp. ATCC 20888, to generate PUFA auxotrophs, and the replacement of such inactivated genes with exogenously introduced homologous genes to restore PUFA synthesis has been previously demonstrated and described. See, e.g., U.S. Pat. No. 7,217,856, incorporated by reference herein in its entirety. The three PUFA synthase genes from *Schizochytrium* sp. ATCC 20888 have been previously

TABLE 11

*Thraustochytrium* sp. ATCC PTA-10212 PFA3 Domain Analysis

| Domain | DNA positions | AA positions | Sites | DNA positions | AA positions |
|---|---|---|---|---|---|
| DH1 | 1-1350 of SEQ ID NO: 72 (SEQ ID NO: 110) | 1-450 of SEQ ID NO: 73 (SEQ ID NO: 111) | FxxH*F (SEQ ID NO: 53) | 934-936 of SEQ ID NO: 72 | H312 of SEQ ID NO: 73 |
| DH2 | 1501-2700 of SEQ ID NO: 72 (SEQ ID NO: 112) | 501-900 of SEQ ID NO: 73 (SEQ ID NO: 113) | FxxH*F (SEQ ID NO: 53) | 2401-2403 of SEQ ID NO: 72 | H801 of SEQ ID NO: 73 |
| ER | 2848-4212 of SEQ ID NO: 72 (SEQ ID NO: 114) | 950-1404 of SEQ ID NO: 73 (SEQ ID NO: 115) | | | | termed orfA, orfB, and orfC, corresponding to the PFA1, PFA2, and PFA3 nomenclature used herein, respectively. Id.

The native orfA gene in *Schizochytrium* sp. ATCC 20888 was replaced by homologous recombination following transformation with a vector containing the Zeocin™ resistance marker surrounded by sequences from the orfA flanking region. A mutant strain was generated lacking a functional orfA gene. The mutant strain was auxotrophic and required PUFA supplementation for growth.

*Schizochytrium* sp. ATCC PTA-9695 PFA1 (SEQ ID NO:1) was cloned into expression vector pREZ37 to generate pREZ345. The expression vector contained approximately 2 kb of DNA from the flanking region of the native orfA gene locus from *Schizochytrium* sp. ATCC 20888. The *Schizochytrium* sp. ATCC 20888 mutant lacking functional orfA was transformed via electroporation with enzyme pretreatment (see below) with pREZ345 containing PFA1. Based on homologous regions flanking the Zeocin™ resistance marker in the mutant and flanking the PFA1 gene in pREZ345, double-crossover recombination occurred such that PFA1 was inserted into the native orfA locus. Recombination with *Schizochytrium* sp. ATCC PTA-9695 PFA1 (SEQ ID NO:1) restored PUFA production in the *Schizochytrium* sp. ATCC 20888 mutant lacking orfA. In brief, cells were grown in M2B liquid media (see following paragraph) at 30° C. with 200 rpm shaking for 3 days. Cells were harvested and the fatty acids were converted to methyl-esters using standard techniques. Fatty acid profiles were determined using gas chromatography with flame ionization detection (GC-FID) as fatty acid methyl esters (FAME). The native *Schizochytrium* sp. ATCC 20888 strain containing a functional orfA gene produced DHA and DPA n-6 in a ratio of 2.3:1. The recombinant strain containing *Schizochytrium* sp. ATCC PTA-9695 PFA1 (SEQ ID NO:1) in place of the inactivated orfA gene also produced DHA and DPA n-6 in a ratio of 2.4:1. The EPA content of the recombinant strain was 2.7% of fatty acid methyl-esters (FAME), the DPA n-3 content was 0.7%, the DPA n-6 content was 8.8%, and the DHA content was 21.2%.

M2B medium—

10 g/L glucose, 0.8 g/L $(NH_4)_2SO_4$, 5 g/L $Na_2SO_4$, 2 g/L $MgSO_4.7H_2O$, 0.5 g/L $KH_2PO_4$, 0.5 g/L KCl, 0.1 g/L $CaCl_2.2H_2O$, 0.1 M MES (pH 6.0) 0.1% PB26 metals, and 0.1% PB26 Vitamins (v/v). PB26 vitamins consisted of 50 mg/mL vitamin B12, 100 µg/mL thiamine, and 100 µg/mL Ca-pantothenate. PB26 metals were adjusted to pH 4.5 and consisted of 3 g/L $FeSO_4.7H_2O$, 1 g/L $MnCl_2.4H_2O$, 800 mg/mL $ZnSO_4.7H_2O$, 20 mg/mL $CoCl_2.6H_2O$, 10 mg/mL $Na_2MoO_4.2H_2O$, 600 mg/mL $CuSO_4.5H_2O$, and 800 mg/mL $NiSO_4.6H_2O$. PB26 stock solutions were filter-sterilized separately and added to the broth after autoclaving. Glucose, $KH_2PO_4$, and $CaCl_2.2H_2O$ were each autoclaved separately from the remainder of the broth ingredients before mixing to prevent salt precipitation and carbohydrate caramelizing. All medium ingredients were purchased from Sigma Chemical (St. Louis, Mo.).

Electroporation with Enzyme Pretreatment—

Cells were grown in 50 mL of M50-20 media (see U.S. Publ. No. 2008/0022422) on a shaker at 200 rpm for 2 days at 30° C. The cells were diluted at 1:100 into M2B media and grown overnight (16-24 h), attempting to reach mid-log phase growth (OD600 of 1.5-2.5). The cells were centrifuged in a 50 mL conical tube for 5 min at about 3000×g. The supernatant was removed and the cells were resuspended in 1 M mannitol, pH 5.5, in a suitable volume to reach a final concentration of 2 $OD_{600}$ units. 5 mL of cells were aliquoted into a 25 mL shaker flask and amended with 10 mM $CaCl_2$ (1.0 M stock, filter sterilized) and 0.25 mg/mL Protease XIV (10 mg/mL stock, filter sterilized; Sigma-Aldrich, St. Louis, Mo.). Flasks were incubated on a shaker at 30° C. and about 100 rpm for 4 h. Cells were monitored under the microscope to determine the degree of protoplasting, with single cells desired. The cells were centrifuged for 5 min at about 2500×g in round-bottom tubes (i.e., 14 mL Falcon™ tubes, BD Biosciences, San Jose, Calif.). The supernatant was removed and the cells were gently resuspended with 5 mL of ice cold 10% glycerol. The cells were re-centrifuged for 5 min at about 2500×g in round-bottom tubes. The supernatant was removed and the cells were gently resuspended with 500 µL of ice cold 10% glycerol, using wide-bore pipette tips. 90 µL of cells were aliquoted into a prechilled electro-cuvette (Gene Pulser® cuvette—0.1 cm gap or 0.2 cm gap, Bio-Rad, Hercules, Calif.). One µg to 5 µg of DNA (in less than or equal to a 10 µL volume) was added to the cuvette, mixed gently with a pipette tip, and placed on ice for 5 min. Cells were electroporated at 200 ohms (resistance), 25 µF (capacitance), and either 250V (for 0.1 cm gap) or 500V (0.2 cm gap). 0.5 mL of M50-20 media was added immediately to the cuvette. The cells were then transferred to 4.5 mL of M50-20 media in a 25 mL shaker flask and incubated for 2-3 h at 30° C. and about 100 rpm on a shaker. The cells were centrifuged for 5 min at about 2500×g in round bottom tubes. The supernatant was removed and the cell pellet was resuspended in 0.5 mL of M50-20 media. Cells were plated onto an appropriate number (2 to 5) of M2B plates with appropriate selection and incubated at 30° C.

The *Schizochytrium* sp. ATCC 20888 mutant lacking functional orfA is also transformed with pREZ345 containing PFA1, such that PFA1 is randomly integrated in the mutant and restores PUFA production.

EXAMPLE 8

*Thraustochytrium* sp. ATCC PTA-10212 PFA1 (SEQ ID NO:68) was re-synthesized (DNA2.0) and codon-optimized for expression in *Schizochytrium* (SEQ ID NO:120) and was cloned into an expression vector to generate pLR95. Codon-optimization occurred using the *Schizochytrium* codon usage table in FIG. 22. The expression vector contained approximately 2 kb of DNA from the flanking region of the native orfA gene locus from *Schizochytrium* sp. ATCC 20888.

The *Schizochytrium* sp. ATCC 20888 mutant lacking functional orfA from Example 7 was transformed via electroporation with enzyme pretreatment (See Example 7) with pLR95 containing codon-optimized *Thraustochytrium* sp. ATCC PTA-10212 PFA1 (SEQ ID NO:120). Based on homologous regions flanking the Zeocin™ resistance marker in the mutant and flanking the PFA1 gene in pLR95, double-crossover recombination occurred such that codon-optimized *Thraustochytrium* sp. ATCC PTA-10212 PFA1 was inserted into the native orfA locus. Recombination with codon-optimized *Thraustochytrium* sp. ATCC PTA-10212 PFA1 (SEQ ID NO:120) restored PUFA production in the *Schizochytrium* sp. ATCC 20888 mutant lacking orfA. Cells were grown and analyzed for FAMEs as described in Example 7. The native *Schizochytrium* sp. ATCC 20888 strain containing a functional orfA gene produced DHA and EPA in a ratio of 25:1. The recombinant strain containing codon-optimized *Thraustochytrium* sp. ATCC PTA-10212 PFA1 (SEQ ID NO:120) in place of the inactivated orfA gene produced DHA and EPA in a ratio of 5.4:1, further demonstrating that the PUFA profile of *Schizochytrium* can be altered by the nucleic acid molecules described herein. The EPA content of the recombinant strain was 4.4% of FAME, the DPA n-3 content was 2.3%, the DPA n-6 content was 4.9%, and the DHA content was 24.0%.

The *Schizochytrium* sp. ATCC 20888 mutant lacking functional orfA is also transformed with pLR95 containing PFA1, such that PFA1 is randomly integrated in the mutant and restores PUFA production.

EXAMPLE 9

The native orfB gene in *Schizochytrium* sp. ATCC 20888 was replaced by homologous recombination following transformation via electroporation with enzyme pretreatment (See Example 7) with a vector containing the Zeocin™ resistance marker surrounded by sequences from the orfB flanking region. A mutant strain was generated lacking a functional orfB gene. The mutant strain was auxotrophic and required PUFA supplementation for growth.

Schizochytrium sp. ATCC PTA-9695 PFA2 (SEQ ID NO:3) was cloned into expression vector pDS04 to generate pREZ331. The expression vector contained approximately 2 kb of DNA from the flanking region of the native orfB gene locus from Schizochytrium sp. ATCC 20888.

The Schizochytrium sp. ATCC 20888 mutant lacking functional orfB was transformed with pREZ331 containing PFA2. Based on random integration in the mutant, PUFA production was restored by Schizochytrium sp. ATCC PTA-9695 PFA2 (SEQ ID NO:3). Cells were grown and analyzed for FAMEs as described in Example 7. The native Schizochytrium sp. ATCC 20888 strain containing a functional orfB gene produced DHA and DPA n-6 in a ratio of 2.3:1. The recombinant strain containing Schizochytrium sp. ATCC PTA-9695 PFA2 (SEQ ID NO:3) as a replacement of the inactivated orfB gene produced DHA and DPA n-6 in a ratio of 3.5:1. The EPA content of the recombinant strain was 0.8% of FAME, the DPA n-3 content was 0.1%, the DPA n-6 content was 7.1%, and the DHA content was 25.1%.

The Schizochytrium sp. ATCC 20888 mutant lacking functional orfB is also transformed with pREZ331 containing PFA2, such that PFA2 is inserted into the native orfB locus and restores PUFA production.

EXAMPLE 10

Thraustochytrium sp. ATCC PTA-10212 PFA2 (SEQ ID NO:70) was re-synthesized (DNA2.0) and codon-optimized for expression in Schizochytrium (SEQ ID NO:121) and was cloned into an expression vector to generate pLR85. Codon-optimization occurred using the Schizochytrium codon usage table in FIG. 22. The expression vector contained approximately 2 kb of DNA from the flanking region of the native orfB gene locus from Schizochytrium sp. ATCC 20888.

Replacement of orf genes was also studied in a daughter strain of Schizochytrium sp. ATCC 20888 having improved DHA productivity. The native orfB gene in the daughter strain was replaced by homologous recombination following transformation via electroporation with enzyme pretreatment (See Example 7) with a vector containing the Zeocin™ resistance marker surrounded by sequences from the orfB flanking region. A mutant strain was generated lacking a functional orfB gene. The mutant strain was auxotrophic and required PUFA supplementation for growth. The mutant strain was transformed via electroporation with enzyme pretreatment (see Example 8) with pLR85 containing codon-optimized Thraustochytrium sp. ATCC PTA-10212 PFA2 (SEQ ID NO:121). Based on homologous regions flanking the Zeocin™ resistance marker in the mutant and flanking the PFA2 gene in pLR85, double-crossover recombination occurred such that codon-optimized Thraustochytrium sp. ATCC PTA-10212 PFA2 (SEQ ID NO:121) was inserted into the native orfB locus of the mutant strain. Recombination with codon-optimized Thraustochytrium sp. ATCC PTA-10212 PFA2 (SEQ ID NO:121) restored PUFA production in the daughter strain mutant lacking orfB. Cells were grown and analyzed for FAMEs as described in Example 7. The EPA content of the recombinant strain was 1.0% of FAME, the DPA n-3 content was 0.3%, the DPA n-6 content was 7.0%, and the DHA content was 31.0%.

In an experiment to be performed, the Schizochytrium sp. ATCC 20888 mutant lacking functional orfB from Example 9 is transformed via electroporation with enzyme pretreatment (see Example 8) with pLR85 containing codon-optimized Thraustochytrium sp. ATCC PTA-10212 PFA2 (SEQ ID NO:121). Based on homologous regions flanking the Zeocin™ resistance marker in the mutant and flanking the PFA2 gene in pLR85, double-crossover recombination occurs such that codon-optimized Thraustochytrium sp. ATCC PTA-10212 PFA2 (SEQ ID NO:121) is inserted into the native orfB locus. Recombination with codon-optimized Thraustochytrium sp. ATCC PTA-10212 PFA2 (SEQ ID NO:121) restores PUFA production in the Schizochytrium sp. ATCC 20888 mutant lacking orfB.

The Schizochytrium sp. ATCC 20888 and daughter strain mutants lacking functional orfB are also transformed with pLR85 containing PFA2, such that PFA2 is randomly integrated in the mutants and restores PUFA production in each of the mutants.

EXAMPLE 11

A plasmid containing a paromomycin resistance marker cassette functional in Schizochytrium was developed for Schizochytrium sp. ATCC 20888 by replacement of the bleomycin/Zeocin™ resistance gene (ble) coding region in pMON50000/pTUBZEO11-2 (U.S. Pat. No. 7,001,772 B2) with that of neomycin phosphotransferase II (npt), originally from bacterial transposon Tn5. In pMON50000, the ble resistance gene is driven by the Schizochytrium α-tubulin promoter and is followed by the SV40 transcription terminator. The ble region in pMON50000 encompasses a NcoI restriction site at the ATG start codon and a PmlI restriction site immediately following the TGA stop signal. PCR was used to amplify the npt coding region present in pCaMVnpt (Shimizu et al., Plant J. 26(4):375 (2001)) such that the product included a BspHI restriction site (underlined below, primer CAX055) at the start ATG (bold) and a PmlI restriction site (underlined below, primer CAX056) immediately following the stop signal (bold-reverse complement):

```
CAX055 (forward):
GTCATGATTGAACAAGATGGATTGCAC        (SEQ ID NO: 66)

CAX056 (reverse):
CCACGTGTCAGAAGAACTCGTCAAGAA.       (SEQ ID NO: 67)
```

PCR was carried out with the TaqMaster polymerase kit (5Prime), products were cloned into pCR4-TOPO (Invitrogen), and resulting plasmids were transformed into E. coli TOP10 (Invitrogen). DNA sequence analysis using vector primers identified multiple clones containing the desired 805 bp structure (i.e., the sequences match those of the source template plus the engineered restriction sites). The modified npt coding region was isolated by digestion with BspHI plus PmlI restriction enzymes, and the purified DNA fragment was ligated with a pMON50000 vector fragment generated by digestion with NcoI plus PmlI enzymes. Restriction enzymes BspHI and NcoI leave compatible overlapping ends, and PmlI leaves blunt ends. The resulting plasmid, pTS-NPT, contains the npt neomycin/paromomycin resistance gene in the identical context as that of the original ble gene in pMON50000.

Particle bombardment of Schizochytrium (U.S. Pat. No. 7,001,772 B2) was used to evaluate the function of the novel paromomycin resistance cassette in pTS-NPT. Selection for paromomycin (PAR) resistance was carried out on agar plates containing 50 µg/mL paromomycin sulfate (Sigma). Paromomycin-resistant *Schizochytrium* transformants were found at frequencies similar to those for Zeocin™-resistance from pMON50000. The "α-tubulin promoter/npt/SV40 terminator" cassette can be freed from pTS-NPT with various restriction enzymes for subsequent use in other development efforts.

EXAMPLE 12

The native orfC gene in *Schizochytrium* sp. ATCC 20888 was replaced by homologous recombination following transformation with a vector containing the paromomycin resistance marker surrounded by sequences from the orfC flanking region. A mutant strain was generated lacking a functional orfC gene. The mutant strain was auxotrophic and required PUFA supplementation for growth.

*Schizochytrium* sp. ATCC PTA-9695 PFA3 (SEQ ID NO:5) was cloned into expression vector pREZ22 to generate pREZ324. The expression vector contained approximately 2 kb of DNA from the flanking region of the native orfC gene locus from *Schizochytrium* sp. ATCC 20888.

The *Schizochytrium* sp. ATCC 20888 mutant lacking functional orfC was transformed with pREZ324 containing *Schizochytrium* sp. ATCC PTA-9695 PFA3. Based on homologous regions flanking the paromomycin resistance marker in the mutant and flanking the *Schizochytrium* sp. ATCC PTA-9695 PFA3 gene in pREZ324, double-crossover recombination occurred such that *Schizochytrium* sp. ATCC PTA-9695 PFA3 was inserted into the native orfC locus. Homologous recombination with *Schizochytrium* sp. ATCC PTA-9695 PFA3 (SEQ ID NO:5) restored PUFA production in the *Schizochytrium* sp. ATCC 20888 mutant lacking orfC. Cells were grown and analyzed for FAMEs as described in Example 7. The native *Schizochytrium* sp. ATCC 20888 strain containing a functional orfC gene produced DHA and DPA n-6 in a ratio of 2.3:1. The recombinant strain containing *Schizochytrium* sp. ATCC PTA-9695 PFA3 (SEQ ID NO:5) in place of the inactivated orfC gene produced DHA and DPA n-6 in a ratio of 14:9, further demonstrating that the PUFA profile of *Schizochytrium* can be altered by the nucleic acid molecules described herein. The EPA content of the recombinant strain was 1.2% of FAME, the DPA n-3 content was 0.2%, the DPA n-6 content was 2.9%, and the DHA content was 43.4%.

The *Schizochytrium* sp. ATCC 20888 mutant lacking functional orfC was also transformed with pREZ324 containing PFA3, such that PFA3 was randomly integrated in the mutant and restored PUFA production. The EPA content of the recombinant strain was 1.2% of FAME, the DPA n-3 content was 0.2%, the DPA n-6 content was 2.5%, and the DHA content was 39.1%.

The native orfC gene in the daughter strain discussed in Example 10 was replaced by homologous recombination following transformation with a vector containing the paromomycin resistance marker surrounded by sequences from the orfC flanking region. A mutant strain was generated lacking a functional orfC gene. The mutant strain was auxotrophic and required PUFA supplementation for growth. The mutant lacking functional orfC was transformed with pREZ324. Double-crossover recombination occurred such that *Schizochytrium* sp. ATCC PTA-9695 PFA3 was inserted into the native orfC locus of the mutant strain. Homologous recombination with *Schizochytrium* sp. ATCC PTA-9695 PFA3 (SEQ ID NO:5) restored PUFA production in the the daughter strain mutant lacking orfC. Cells were grown and analyzed for FAMEs as described in Example 7. The EPA content of the recombinant strain was 1.2% of FAME, the DPA n-3 content was 0.3%, the DPA n-6 content was 2.8%, and the DHA content was 43.1%.

The daughter strain mutant lacking functional orfB is also transformed with pREZ324 containing PFA3, such that PFA3 is randomly integrated in the mutant and restores PUFA production.

EXAMPLE 13

*Thraustochytrium* sp. ATCC PTA-10212 PFA3 (SEQ ID NO:72) was re-synthesized (DNA2.0) and codon-optimized for expression in *Schizochytrium* (SEQ ID NO:122) and was cloned into expression vector pREZ22 to generate pREZ337. Codon-optimization occurred using the *Schizochytrium* codon usage table in FIG. 22. The expression vector contained approximately 2 kb of DNA from the flanking region of the native orfC gene locus from *Schizochytrium* sp. ATCC 20888.

The daughter strain mutant lacking functional orfC from Example 12 was transformed via electroporation with enzyme pretreatment (see Example 8) with pREZ337 containing codon-optimized *Thraustochytrium* sp. ATCC PTA-10212 PFA3 (SEQ ID NO:122). Based on homologous regions flanking the Zeocin™ resistance marker in the mutant and flanking the PFA3 gene in pREZ337, double-crossover recombination occurred such that codon-optimized *Thraustochytrium* sp. ATCC PTA-10212 PFA3 (SEQ ID NO:122) was inserted into the native orfC locus. Recombination with codon-optimized *Thraustochytrium* sp. ATCC PTA-10212 PFA3 (SEQ ID NO:122) restored PUFA production in the daughter strain mutant lacking orfC. Cells were grown and analyzed for FAMEs as described in Example 7. The EPA content of the recombinant strain was 1.3% of FAME, the DPA n-3 content was 0.4%, the DPA n-6 content was 2.7%, and the DHA content was 50.2%.

In an experiment to be performed, the *Schizochytrium* sp. ATCC 20888 mutant lacking functional orfC from Example 12 is transformed via electroporation with enzyme pretreatment (see Example 8) with pREZ337 containing codon-optimized *Thraustochytrium* sp. ATCC PTA-10212 PFA3 (SEQ ID NO:122). Based on homologous regions flanking the Zeocin™ resistance marker in the mutant and flanking the PFA3 gene in pREZ337, double-crossover recombination occurs such that codon-optimized *Thraustochytrium* sp. ATCC PTA-10212 PFA3 (SEQ ID NO:122) is inserted into the native orfC locus. Recombination with codon-optimized *Thraustochytrium* sp. ATCC PTA-10212 PFA3 (SEQ ID NO:122) restores PUFA production in the *Schizochytrium* sp. ATCC 20888 mutant lacking orfC.

The *Schizochytrium* sp. ATCC 20888 and daughter strain mutants lacking functional orfC are also transformed with pREZ337 containing PFA3, such that PFA3 is randomly integrated in the mutants and restores PUFA production in each of the mutants.

EXAMPLE 14

Any two or all three of the orfA, orfB, and orfC genes in *Schizochytrium* sp. ATCC 20888 are replaced by homologous recombination following transformation with vectors containing either the Zeocin™ or paromomycin resistance marker surrounded by sequences from the appropriate orf flanking region. Mutant strains are generated lacking functional genes for any two or all three of orfA, orfB, and orfC. The mutant strains are auxotrophic and require PUFA supplementation for growth.

The *Schizochytrium* sp. ATCC 20888 mutants lacking functional orf genes are transformed with one or more expression vectors containing corresponding PFA genes (one or more of SED ID NOs: 1, 3, 5, 120, 121, or 122). Based on homologous regions flanking the Zeocin™ or paromomycin resistance markers in the mutants and flanking the PFA genes in the respective expression vectors, double-crossover recombination can occur such that PFA genes are inserted into the native orf loci. Random integration of these expression vectors can also occur with the selection of transformants based solely on the restoration of PUFA production. Homologous recombination with PFA genes restores PUFA production in the mutants, such that native PUFA profiles are restored or altered based on the combination of PFA genes inserted into the mutants.

In one performed experiment, the *Schizochytrium* sp. ATCC 20888 strain from Example 12 lacking a functional orfC gene and containing randomly integrated *Schizochytrium* sp. ATCC PTA-9695 PFA3 (SEQ ID NO:5) was used for replacement of the orfA and orfB genes. The native orfA and orfB genes in the strain were replaced by homologous recombination following transformation with a vector containing the Zeocin™ resistance marker surrounded by sequences from the orfA and orfB flanking regions. A strain was generated lacking functional orfA, orfB, and orfC, and containing randomly integrated *Schizochytrium* sp. ATCC PTA-9695 PFA3. The strain was transformed with pREZ345 containing codon-optimized *Schizochytrium* sp. ATCC PTA-9695 PFA1 (SEQ ID NO:1) and pREZ331 containing codon-optimized *Schizochytrium* sp. ATCC PTA-9695 PFA2 (SEQ ID NO:3) such that random integration of PFA1 and PFA2 occurred. The resulting recombinant strain lacked functional orfA, orfB, and orfC and contained random integrations of *Schizochytrium* sp. ATCC PTA-9695 PFA1, PFA2, and PFA3. Cells were grown and analyzed for FAMEs as described in Example 7. The EPA content of the recombinant strain was 6.6% of FAME, the DPA n-3 content was 0.8%, the DPA n-6 content was 1.6%, and the DHA content was 20.9%.

In another performed experiment, the daughter strain from Example 12 lacking a functional orfC gene and containing *Schizochytrium* sp. ATCC PTA-9695 PFA3 (SEQ ID NO:5) inserted into the native orfC locus was used for replacement of the orfA and orfB genes. The native orfA and orfB genes in the strain were replaced by homologous recombination following transformation with a vector containing the paromomycin resistance marker surrounded by sequences from the orfA and orfB flanking regions. A strain was generated lacking functional orfA, orfB, and orfC, and containing *Schizochytrium* sp. ATCC PTA-9695 PFA3 inserted into the native orfC locus. The strain was transformed with pREZ345 containing codon-optimized *Schizochytrium* sp. ATCC PTA-9695 PFA1 (SEQ ID NO:1) and pREZ331 containing codon-optimized *Schizochytrium* sp. ATCC PTA-9695 PFA2 (SEQ ID NO:3). Double-crossover recombinations occurred such that *Schizochytrium* sp. ATCC PTA-9695 PFA1 was inserted into the native orfA locus and *Schizochytrium* sp. ATCC PTA-9695 PFA2 was inserted into the native orfB locus of the strain. The resulting recombinant strain lacked functional orfA, orfB, and orfC and contained *Schizochytrium* sp. ATCC PTA-9695 PFA1, PFA2, and PFA3 inserted into the respective orfA, orfB, and orfC loci. Cells were grown and analyzed for FAMEs as described in Example 7. The EPA content of the recombinant strain was 7.3% of FAME, the DPA n-3 content was 0.4%, the DPA n-6 content was 1.5%, and the DHA content was 23.9%.

In another performed experiment, the daughter strain from Example 12 lacking a functional orfC gene and containing randomly integrated *Schizochytrium* sp. ATCC PTA-9695 PFA3 (SEQ ID NO:5) was used for replacement of the orfA and orfB genes. The native orfA and orfB genes in the strain were replaced by homologous recombination following transformation with a vector containing the Zeocin™ resistance marker surrounded by sequences from the orfA and orfB flanking regions. A strain was generated lacking functional orfA, orfB, and orfC, and containing randomly integrated *Schizochytrium* sp. ATCC PTA-9695 PFA3. The strain was transformed with pREZ345 containing codon-optimized *Schizochytrium* sp. ATCC PTA-9695 PFA1 (SEQ ID NO:1) and pREZ331 containing codon-optimized *Schizochytrium* sp. ATCC PTA-9695 PFA2 (SEQ ID NO:3) such that random integration of PFA1 and PFA2 occurred. The resulting recombinant strain lacked functional orfA, orfB, and orfC and contained random integrations of *Schizochytrium* sp. ATCC PTA-9695 PFA1, PFA2, and PFA3. Cells were grown and analyzed for FAMEs as described in Example 7. The EPA content of the recombinant strain was 6.2% of FAME, the DPA n-3 content was 1.3%, the DPA n-6 content was 0.9%, and the DHA content was 16.6%.

In another performed experiment, the daughter strain from Example 13 lacking a functional orfC gene and containing *Schizochytrium* sp. ATCC PTA-10212 PFA3 (SEQ ID NO:122) inserted into the native orfC locus was used for replacement of the orfA and orfB genes. The native orfA and orfB genes in the strain were replaced by homologous recombination following transformation with a vector containing the paromomycin resistance marker surrounded by sequences from the orfA and orfB flanking regions. A strain was generated lacking functional orfA, orfB, and orfC, and containing *Schizochytrium* sp. ATCC PTA-10212 PFA3 inserted into the native orfC locus. The strain was transformed with pLR95 containing codon-optimized *Schizochytrium* sp. ATCC PTA-10212 PFA1 (SEQ ID NO:120) and pLR85 containing codon-optimized *Schizochytrium* sp. ATCC PTA-10212 PFA2 (SEQ ID NO:121). Double-crossover recombinations occurred such that *Schizochytrium* sp. ATCC PTA-10212 PFA1 was inserted into the native orfA locus and *Schizochytrium* sp. ATCC PTA-10212 PFA2 was inserted into the native orfB locus of the strain. The resulting recombinant strain lacked functional orfA, orfB, and orfC and contained *Schizochytrium* sp. ATCC PTA-10212 PFA1, PFA2, and PFA3 inserted into the respective orfA, orfB, and orfC loci. Cells were grown and analyzed for FAMEs as described in Example 7. The EPA content of the recombinant strain was 5.2% of FAME, the DPA n-3 content was 0.6%, the DPA n-6 content was 2.1%, and the DHA content was 47.1%.

In another performed experiment, the daughter strain from Example 13 lacking a functional orfC gene and containing randomly integrated *Schizochytrium* sp. ATCC PTA-10212 PFA3 (SEQ ID NO:122) was used for replacement of the orfA and orfB genes. The native orfA and orfB genes in the strain were replaced by homologous recombination following transformation with a vector containing the Zeocin™ resistance marker surrounded by sequences from the orfA and orfB flanking regions. A strain was generated lacking functional orfA, orfB, and orfC, and containing randomly integrated *Schizochytrium* sp. ATCC PTA-10212 PFA3. The strain was transformed with pLR95 containing codon-optimized *Schizochytrium* sp. ATCC PTA-10212 PFA1 (SEQ ID NO:120) and pLR85 containing codon-optimized *Schizochytrium* sp. ATCC PTA-10212 PFA2 (SEQ ID NO:121) such that random integration of PFA1 and PFA2 occurred. The resulting recombinant strain lacked functional orfA, orfB, and orfC and contained random integrations of *Schizochytrium* sp. ATCC PTA-10212 PFA1, PFA2, and PFA3. Cells were grown and analyzed for FAMEs as described in Example 7. The EPA content of the recombinant strain was 1.8% of FAME, the DPA n-3 content was 1.8%, the DPA n-6 content was 2.3%, and the DHA content was 34.1%.

EXAMPLE 15

The orfA, orfB, and orfC genes from *Schizochytrium* sp. ATCC 20888 were cloned into a series of Duet vectors (Novagen). The Duet expression vectors are a set of compatible plasmids in which multiple target genes are cloned and co-expressed from the T7 inducible promoter in *E. coli*. Duet plasmid pREZ91 contained *Schizochytrium* sp. ATCC 20888 orfA in pETDuet-1; duet plasmid pREZ96 contained *Schizochytrium* sp. ATCC 20888 orfB in pCDFDuet-1; and duet plasmid pREZ101 contained *Schizochytrium* sp. ATCC 20888 orfC in pCOLADuet-1. Duet plasmids pREZ91, pREZ96, and pREZ101, along with plasmid pJK737, which contained the required accessory gene HetI (described in U.S. Pat. No. 7,217,856, incorporated by reference herein in its entirety), were transformed into *E. coli* strain BLR(DE3), which contains an inducible T7 RNA polymerase gene. Upon cell growth and addition of IPTG, according to manufacturer's instructions (Novagen), DHA and DPA n-6 were produced. Briefly, 1 mM IPTG was added for induction when cells reached an optical density of about 0.5 at 600 nm. Cells were the grown for 12 hours at 30° C. in Luria broth and harvested. The fatty acids were converted to methyl-esters using standard techniques. Fatty acid profiles were determined using gas chromatography with flame ionization detection (GC-FID) as fatty acid methyl esters (FAME).

The *Schizochytrium* sp. ATCC PTA-9695 PFA1 (SEQ ID NO:1) gene was cloned into the expression vector pETDuet-1, generating pREZ346. Duet plasmids pREZ346 (containing *Schizochytrium* sp. ATCC PTA-9695 PFA1), pREZ96 (containing orfB), and pREZ101 (containing orfC) were transformed into *E. coli* strain BLR(DE3) along with pJK737 (containing HetI). The *Schizochytrium* sp. ATCC PTA-9695 PFA1 gene was coexpressed with the *Schizochytrium* sp. ATCC 20888 orfB and orfC genes. The expression of *Schizochytrium* sp. ATCC PTA-9695 PFA1, in combination with *Schizochytrium* sp. ATCC 20888 orfB and orfC, supported DHA production in *E. coli* under induction conditions. The DHA content of the transformed *E. coli* was 2.8% of FAME, the DPA n-6 content was 1.1%, the DPA n-3 content was 0.6%, and the EPA content was 3.7%.

EXAMPLE 16

The codon-optimized *Thraustochytrium* sp. ATCC PTA-10212 PFA1 (SEQ ID NO:120) gene was cloned into the expression vector pETDuet-1, generating pLR100. Duet plasmids pLR100 (containing codon-optimized *Thraustochytrium* sp. ATCC PTA-10212 PFA1), pREZ96 (containing *Schizochytrium* sp. ATCC 20888 orfB), and pREZ101 (containing *Schizochytrium* sp. ATCC 20888 orfC) are transformed into *E. coli* strain BLR(DE3) along with pJK737 (containing HetI). See Example 15. The *Thraustochytrium* sp. ATCC PTA-10212 PFA1 gene is coexpressed with the *Schizochytrium* sp. ATCC 20888 orfB and orfC genes. The expression of *Thraustochytrium* sp. ATCC PTA-10212 PFA1, in combination with *Schizochytrium* sp. ATCC 20888 orfB and orfC, supports DHA and EPA production in *E. coli* under induction conditions.

EXAMPLE 17

The *Schizochytrium* sp. ATCC PTA-9695 PFA3 (SEQ ID NO:5) gene was cloned into the expression vector pCOLA-Duet-1, generating pREZ326. Duet plasmids pREZ326 (containing *Schizochytrium* sp. ATCC PTA-9695 PFA3), pREZ91 (containing *Schizochytrium* sp. ATCC 20888 orfA), and pREZ96 (containing *Schizochytrium* sp. ATCC 20888 orfB) were transformed into *E. coli* strain BLR(DE3) along with pJK737 (containing HetI). See Example 15. The expression of *Schizochytrium* sp. ATCC PTA-9695 PFA3, in combination with *Schizochytrium* sp. ATCC 20888 orfA and orfB, supported DHA production in *E. coli* under induction conditions. Cells were grown and analyzed for FAMEs as described in Example 15. The DHA content of the transformed *E. coli* was 0.3% of FAME.

EXAMPLE 18

The codon-optimized *Thraustochytrium* sp. ATCC PTA-10212 PFA3 (SEQ ID NO:122) gene was cloned into the expression vector pCOLADuet-1, generating pREZ348. Duet plasmids pREZ348 (containing codon-optimized *Thraustochytrium* sp. ATCC PTA-10212 PFA3), pREZ91 (containing *Schizochytrium* sp. ATCC 20888 orfA), and pREZ96 (containing *Schizochytrium* sp. ATCC 20888 orfB) were transformed into *E. coli* strain BLR(DE3) along with pJK737 (containing HetI). See Example 15. The expression of *Thraustochytrium* sp. ATCC PTA-10212 PFA3, in combination with *Schizochytrium* sp. ATCC 20888 orfA and orfB, supported DHA production in *E. coli* under induction conditions. Cells were grown and analyzed for FAMEs as described in Example 15. The DHA content of the transformed *E. coli* was 2.9% of FAME and the DPA n-6 content was 0.4%.

EXAMPLE 19

The *Schizochytrium* sp. ATCC PTA-9695 PFA2 (SEQ ID NO:3) gene was cloned into the expression vector pCDF-Duet-1, generating pREZ330. Duet plasmids pREZ330 (containing *Schizochytrium* sp. ATCC PTA-9695 PFA2), pREZ326 (containing *Schizochytrium* sp. ATCC PTA-9695 PFA3), and pREZ91 (containing *Schizochytrium* sp. ATCC 20888 orfA), were transformed into *E. coli* strain BLR(DE3) along with pJK737 (containing HetI). See Example 9. The expression of *Schizochytrium* sp. ATCC PTA-9695 PFA2 and PFA3, in combination with *Schizochytrium* sp. ATCC 20888 orfA, supported DHA production in *E. coli* under induction conditions. Cells were grown and analyzed for FAMEs as described in Example 15. The DHA content of the transformed *E. coli* was 0.8% of FAME and the DPA n-6 content was 0.2%.

EXAMPLE 20

The codon-optimized *Thraustochytrium* sp. ATCC PTA-10212 PFA2 (SEQ ID NO:121) gene was cloned into the expression vector pCDFDuet-1, generating pLR87. Duet plasmids pLR87 (containing codon-optimized *Thraustochytrium* sp. ATCC PTA-10212 PFA2), pREZ348 (containing codon-optimized *Thraustochytrium* sp. ATCC PTA-10212 PFA3), and pREZ91 (containing *Schizochytrium* sp. ATCC 20888 orfA), were transformed into *E. coli* strain BLR(DE3) along with pJK737 (containing HetI). See Example 15. The expression of codon-optimized *Thraustochytrium* sp. ATCC PTA-10212 PFA2 and PFA3, in combination with *Schizochytrium* sp. ATCC 20888 orfA, supported DHA and low levels of EPA production in *E. coli* under induction conditions. Cells were grown and analyzed for FAMEs as described in Example 15. The DHA content of the transformed *E. coli* was 4.4% of FAME, the DPA n-6 content was 1.1%, and the EPA content was 0.1%.

EXAMPLE 21

Duet plasmids pREZ346 (containing *Schizochytrium* sp. ATCC PTA-9695 PFA1), pREZ330 (containing *Schizochytrium* sp. ATCC PTA-9695 PFA2), and pREZ326 (containing *Schizochytrium* sp. ATCC PTA-9695 PFA3) were transformed into *E. coli* strain BLR(DE3) along with pJK737 (containing HetI). See Example 15. The expression of *Schizochytrium* sp. ATCC PTA-9695 PFA1, PFA2, and PFA3 supported DHA production in *E. coli* under induction conditions. Cells were grown and analyzed for FAMEs as described in Example 15. The DHA content of the transformed *E. coli* was 0.3% of FAME and the EPA content was 0.3%.

EXAMPLE 22

Duet plasmids pLR100 (containing codon-optimized *Thraustochytrium* sp. ATCC PTA-10212 PFA1), pLR87 (containing codon-optimized *Thraustochytrium* sp. ATCC PTA-10212 PFA2), and pREZ348 (containing codon-optimized *Thraustochytrium* sp. ATCC PTA-10212 PFA3) are transformed into *E. coli* strain BLR(DE3) along with pJK737 (containing HetI). See Example 15. The expression of codon-optimized *Thraustochytrium* sp. ATCC PTA-10212 PFA1, PFA2, and PFA3 supports DHA and EPA production in *E. coli* under induction conditions.

EXAMPLE 23

Duet plasmids pREZ330 (containing *Schizochytrium* sp. ATCC PTA-9695 PFA2), pREZ91 (containing *Schizochytrium* sp. ATCC 20888 orfA), and pREZ101 (containing *Schizochytrium* sp. ATCC 20888 orfC) were transformed into *E. coli* strain BLR(DE3) along with pJK737 (containing HetI). See Example 15. The expression of *Schizochytrium* sp. ATCC PTA-9695 PFA2, in combination with *Schizochytrium* sp. ATCC 20888 orfA and orfC, supported DHA production in *E. coli* under induction conditions. Cells were grown and analyzed for FAMEs as described in Example 15. The DHA content of the transformed *E. coli* was 0.6% of FAME and the DPA n-6 content was 0.3%.

EXAMPLE 24

Duet plasmids pLR87 (containing codon-optimized *Thraustochytrium* sp. ATCC PTA-10212 PFA2), pREZ91 (containing *Schizochytrium* sp. ATCC 20888 orfA), and pREZ101 (containing *Schizochytrium* sp. ATCC 20888 orfC) were transformed into *E. coli* strain BLR(DE3) along with pJK737 (containing HetI). See Example 15. The expression of codon-optimized *Thraustochytrium* sp. ATCC PTA-10212 PFA2, in combination with *Schizochytrium* sp. ATCC 20888 orfA and orfC, supported DHA and low levels of EPA production in *E. coli* under induction conditions. Cells were grown and analyzed for FAMEs as described in Example 15. The DHA content of the transformed *E. coli* was 1.7% of FAME, the DPA n-6 content was 0.9%, and the EPA content was 0.1%.

EXAMPLE 25

Duet plasmids pREZ346 (containing *Schizochytrium* sp. ATCC PTA-9695 PFA1), pREZ330 (containing *Schizochytrium* sp. ATCC PTA-9695 PFA2), and pREZ101 (containing *Schizochytrium* sp. ATCC 20888 orfC) were transformed into *E. coli* strain BLR(DE3) along with pJK737 (containing HetI). See Example 15. The expression of PFA1 and PFA2, in combination with *Schizochytrium* sp. ATCC 20888 orfC, supported DHA production in *E. coli* under induction conditions. Cells were grown and analyzed for FAMEs as described in Example 15. The DHA content of the transformed *E. coli* was 0.3% of FAME, the DPA n-6 content was 0.1%, and the EPA content was 0.5%.

EXAMPLE 26

Duet plasmids pLR100 (containing codon-optimized *Thraustochytrium* sp. ATCC PTA-10212 PFA1), pLR87 (containing codon-optimized *Thraustochytrium* sp. ATCC PTA-10212 PFA2), and pREZ101 (containing *Schizochytrium* sp. ATCC 20888 orfC) are transformed into *E. coli* strain BLR(DE3) along with pJK737 (containing HetI). See Example 15. The expression of codon-optimized *Thraustochytrium* sp. ATCC PTA-10212 PFA1 and PFA2, in combination with *Schizochytrium* sp. ATCC 20888 orfC, supports DHA and EPA production in *E. coli* under induction conditions.

EXAMPLE 27

Duet plasmids pREZ346 (containing *Schizochytrium* sp. ATCC PTA-9695 PFA1), pREZ96 (containing *Schizochytrium* sp. ATCC 20888 orfB), and pREZ326 (containing *Schizochytrium* sp. ATCC PTA-9695 PFA3) were transformed into *E. coli* strain BLR(DE3) along with pJK737 (containing HetI). See Example 15. The expression of *Schizochytrium* sp. ATCC PTA-9695 PFA1 and PFA3, in combination with *Schizochytrium* sp. ATCC 20888 orfB, supported DHA production in *E. coli* under induction conditions. Cells were grown and analyzed for FAMEs as described in Example 15. The DHA content of the transformed *E. coli* was 0.1% of FAME and the EPA content was 0.1%.

EXAMPLE 28

Duet plasmids pLR100 (containing codon-optimized *Thraustochytrium* sp. ATCC PTA-10212 PFA1), pREZ96 (containing *Schizochytrium* sp. ATCC 20888 orfB), and pREZ348 (containing codon-optimized *Thraustochytrium* sp. ATCC PTA-10212 PFA3) are transformed into *E. coli* strain BLR(DE3) along with pJK737 (containing HetI). See Example 15. The expression of codon-optimized *Thraustochytrium* sp. ATCC PTA-10212 PFA1 and PFA3, in combination with *Schizochytrium* sp. ATCC 20888 orfB, supports DHA and EPA production in *E. coli* under induction conditions.

EXAMPLE 29

Pfa1p, Pfa2p, and Pfa3p PUFA synthase activities in *Schizochytrium* sp. ATCC PTA-9695 and *Thraustochytrium* sp. ATCC PTA-10212 are individually knocked-out by standard procedures. See, e.g., U.S. Pat. No. 7,217,856, incorporated by reference herein in its entirety.

The Zeocin™, hygromycin, blasticidin, or other appropriate resistance marker is inserted into a restriction site of the PFA1 gene (SEQ ID NO:1 or SEQ ID NO:68) that is contained in a plasmid. Following insertion of the resistance marker, the plasmid is introduced into *Schizochytrium* sp. ATCC PTA-9695 or *Thraustochytrium* sp. ATCC PTA- 10212, respectively, by particle bombardment, electroporation, or other appropriate transformation method. Homologous recombination occurs, generating mutants in which the native PFA1 gene is either replaced or disrupted by the Zeocin™, hygromycin, blasticidin, or other appropriate resistance marker. Transformants are selected on plates containing Zeocin™, hygromycin, blasticidin, or other appropriate selection agent, supplemented with PUFAs. Colonies are further examined for the capacity to grow in the absence of PUFA supplementation. Genomic DNA is isolated from the colonies that are resistant to the selection agent and unable to grow in the absence of PUFA supplementation. PCR and Southern Blot analysis of the DNA is performed to demonstrate that the PFA1 gene is either deleted or disrupted.

PFA2 is knocked-out by similar procedures. Resultant knock-out mutants requiring PUFA supplementation are found to lack full-length PFA2.

PFA3 is knocked-out by similar procedures. Resultant knock-out mutants requiring PUFA supplementation are found to lack full-length PFA3.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A method of identifying a nucleic acid molecule comprising a polynucleotide sequence encoding a polypeptide comprising PUFA synthase activity of ER activity and DH activity, the method comprising: screening for a nucleic acid molecule from an organism that hybridizes to the complement of a polynucleotide sequence at least 95% identical to SEQ ID NO:5 or a polynucleotide sequence encoding a polypeptide which comprises an amino acid sequence at least 95% identical to SEQ ID NO:6, and determining the PUFA synthase activity of the nucleic acid molecule that hybridizes, wherein the nucleic acid molecule is capable of hybridizing under stringency conditions comprising post-hybridization washes selected from the group consisting of: (1) a series of washes starting with 6×SSC and 0.5% SDS at room temperature for 15 min., then repeated with 2×SSC and 0.5% SDS at 45° C. for 30 min., and then repeated twice with 0.2×SSC and 0.5% SDS at 50° C. for 30 min.; (2) a series of washes starting with 6×SSC and 0.5% SDS at room temperature for 15 min., then repeated with 2×SSC and 0.5% SDS at 45° C. for 30 min., and then repeated twice with 0.2×SSC and 0.5% SDS at 60° C. for 30 min.; and (3) a series of washes starting with 6×SSC and 0.5% SDS at room temperature for 15 min., then repeated with 2×SSC and 0.5% SDS at 45° C. for 30 min., and then repeated twice with 0.1×SSC and 0.1% SDS at 65° C.

2. A recombinant nucleic acid molecule comprising a polynucleotide sequence at least 95% identical to SEQ ID NO:5 or a polynucleotide sequence encoding a polypeptide which comprises an amino acid sequence at least 95% identical to SEQ ID NO:6, and a transcription control sequence, wherein said polynucleotide sequence is heterologous to said transcription control sequence.

3. A host cell that expresses a nucleic acid molecule comprising a polynucleotide sequence at least 95% identical to SEQ ID NO:5 or a polynucleotide sequence encoding a polypeptide which comprises an amino acid sequence at least 95% identical to SEQ ID NO:6, wherein said nucleic acid molecule is heterologous to the host cell, and wherein said host cell is not a human cell.

4. The host cell of claim 3, wherein the host cell is selected from the group consisting of a plant cell, a microbial cell, and an isolated animal cell.

5. The host cell of claim 4, wherein the microbial cell is a thraustochytrid, excluding *Schizochytrium* sp. ATCC PTA-9695.

6. The host cell of claim 5, wherein the thraustochytrid is a *Schizochytrium* or a *Thraustochytrium*, excluding *Schizochytrium* sp. ATCC PTA-9695.

7. The host cell of claim 4, wherein the plant cell is selected from the group consisting of: canola, soybean, rapeseed, linseed/flax, maize, safflower, sunflower, tobacco, *Arabidopsis thaliana*, Brazil nut, castor bean, coconut, coriander, cotton, groundnut, jojoba, mustard, oil palm, olive, rice, squash, barley, wheat, and duckweed.

* * * * *

SEQUENCE LISTING

<160> NUMBER OF SEQ ID NOS: 127

<210> SEQ ID NO 1
<211> LENGTH: 7824
<212> TYPE: DNA
<213> ORGANISM: Schizochytrium sp.

<400> SEQUENCE: 1

```
atggatactc gcatcgcgat cgtggggatg tcggcgatcc tgccgagcgg ggagaacgtg      60
cgcgagagct gggaggcgat ccgcgatggg ctggattgcc tgagcgatct gccggcggac     120
cgcgtggacg tgacggccta ctacaacccg gagaagacga ccaaggacaa gatctactgc     180
aagcgcggcg ggttcatccc ggagtacgac ttcgacgcgc gtgagttcgg gctcaacatg     240
ttccagatgg aggactcgga cgccaaccag acgatctcgc tgctcaaggt gaaggaggcg     300
ctgacggacg ccaacatccc ggcgttctcg agcggtaaga agaacatcgg ctgcgtgctg     360
ggcatcggcg gcggccagaa ggcgagccac gagttctact cgcggctcaa ctacgtggtc     420
gtggacaagg tgctgcgcaa gatgggcctg ccggaggaag acgtggcggc ggcggtggac     480
aagtacaagg cgagtttccc cgagtggcgc ctcgactctt tccccgggtt cctgggcaac     540
gtcacggcgg ggcgctgctg caataccttc aacatggagg gcatgaactg cgtcgtggac     600
gcggcctgcg cgtcgtcgct gatcgcggtc aaagtggcga tcgaggagct gctctacggc     660
gactgcgatg cgatgatcgc gggtgccacc tgcacggaca actcgatcgg gatgtacatg     720
gccttctcca agacgcccgt gttttccacg gacccgagcg tcaaggcgta cgacgccgcc     780
accaaaggca tgctcatcgg cgagggctcg gcgatgctcg tgctgaagcg ctacgcggac     840
gccgtgcgcg acggcgacac cgtgcacgcc gtcatcaagg ggtgcgcgtc ctcgagcgac     900
ggcaaggcgg cgggcatcta cacgccgaca atctcgggcc aggaggaggc cctgcgccgc     960
gcctacgccc gcgccaatgt cgacccggcc actgtgacgc tggtggaggg ccacggcacg    1020
ggtacgccgg tgggcgacaa gatcgagctg acggcgctga gcaacctctt ctccaaggcg    1080
ttttctgcca acggtggcgg cgcggaggaa gcagagcagg tggcggtggg cagcatcaag    1140
tcgcagatcg ggcacctcaa ggcggtggcc gggctggccg ggctggtcaa ggtggtgctg    1200
gcgctcaagc acaagacgct gccgcagacg atcaacgtcg acaagccgcc gtcgctggtg    1260
gacgggaccc cgatccagca gtcgccgctg tacgtcaaca cgatgaaccg ccctggttc     1320 acgcccgtag gggtgccgcg ccgcgccggc gtgtcgtcgt ttgggtttgg cggtgccaac    1380
taccacgccg tgctggagga gtttgagccc gagcacgaga gcgcgtaccg gtacaacaac    1440
ctgccgcagg tggcgctgct gcacgcgggg gacgtcgcga ccttggcggc gacggttcgc    1500
gccaagctgg cgctggccac cgccgagcag gaagaggcgc gtgtggtgaa gaacgcggac    1560
```

```
tacatcgcgt accaccggtt cctggacgag tgcaagttgc gcggcgctgt gccgcaggcg    1620
cacgcgcggg tgggactgct cgtacgggac ctgagctcgc tcatcgccgt gctcgaggcc    1680
gctgccgcca agctcgcggg cgaagagagc gcgacggagt ggacggtcag cgttgctacg    1740
ggcgaggcgg ccttccgcgt gcgcggtgtg gctacggagg ccaacgtggc ggcgctgttc    1800
tcgggccagg gcgcgcagta cacgcacatg ttcagcgacg tggcgatgaa ctggcccccg    1860
ttccgcgaga gcgtcgccgc catggaccgc gcccagcgcg agcgcttcgg gcggcctgcc    1920
aagcgcgtga gcagcgtgct gtacccgcgc aagccgtacg gcgacgaacc gcggcaggac    1980
cacaaggaga tctcgcaaac gcgctactcg cagcccgcaa cgctcgcgtg ctcggtcggc    2040
gcctttgaca tcttcaaagc ggcgggactg gcgccgagct ttgcggcggg ccactcgctg    2100
ggcgagtttg cggcgctcta cgcggccggg tcgctcgatc gcgacgccgt cttcgacctg    2160
gtctgcgcgc gcgccaaggc catgagcgac ttcacggccc aggccagcag cagcggtggc    2220
gccatggcgg ccgtgattgg cgccaaggcg gaccagctct cgctgggtgg cgcgcccgac    2280
gtgtggctcg ccaacagcaa ctcgccctcg cagaccgtga tcacgggaac cgccgaagca    2340
gtggctgcgg cctctgacaa gttgcgctgc agcggcaact tccgcgtcgt gcctctggcc    2400
tgcgaggcgg ccttccactc gccgcacatg cgcggcgcgg agcagacgtt tgcgtcggcg    2460
ctcgcgcagg cgcccgtgtc ggcaccggcg gctgctcggt tctactctaa cgtgacgggg    2520
ggcgccgcgg taacctcgcc cgcggacgtc aaaacgaacc tgggcaagca catgacgagc    2580
cctgtgcagt tcgtgcagca ggtgcgagcc atgcacgcgg cgggcgcgcg tgtgtttgtg    2640
gagtttgggc ccaagcaggt cctgtcgcgc ctcgtcaagg agacccttgg cgaggccggc    2700
gacgtggtca cggtcgccgt caacccagac tcggccaagg acagcgacac gcagctgcgc    2760
caggcggcgc tcacgttggc ggtcgccggc gtgccgctca aggactttga ccgctggcag    2820
ctgccggatg ccacgcgcct cgagcctgtc aagaagaaga agaccacgtt gcggctctcg    2880
gcagccacct acgtctccgc caagacgttg cgccagcgcg aggccgtgct caacgacggc    2940
tacactgtca gtggtgccac ggcggtagtc aaggaagtgg acacggccaa cgaggagcgt    3000
ctcgtccgcc aagcccagga tctccagcgc cagctcgcgg aggcctcgac ggcagcccag    3060
gcggcgcagt ccaaggtcgc ggagctcgag cgcacgatcc aggacttgga gcgcaaggtg    3120
cagcagcagc agcaagagaa gggtgagaac tcagacagca acgctgccgc cgaagtgctg    3180
cggcgccaca aggagctgct ccagcgcatg ctgcaggact gtgacgagca ggcagtgccc    3240
gtagccacgg tggttccgac acctacgtcc tccccgacgc ctacatcctc acccgtatcc    3300
ggcaacagca agagcactcg tggcagtgct gatctgcaag cgctgctggc caaggcggag    3360
actgtggtga tggctgtgct ggctgccaag actggctacg aggccgacat ggttgaggcg    3420
gacatggacc tggaggccga gctcggcatc gactcgatca agcgcgtgga gatcctttcc    3480
gaggtgcagg ccagctggg cgtcgaggcc aaggacgtgg atgcgctgag ccgcacgcgc    3540
acggtcggtg aggttgtgga cgccatgaag gcggagatcg tggctgcctc tggtggtagt    3600
gctcctgcgg ttccttcggc gcccgctgct tctgcagctc cgactcccgc tgcttcgact    3660
gcgccttctg ctgatctgca agcgctgctg tccaaggcgg agactgtggt gatggctgtg    3720
ctggcggcca agactggcta cgaggccgac atggtcgagg cggacatgga cctggaggcc    3780
gagctcggca tcgactcgat caagcgcgtg agatcctct cggaggtgca gggccagctg    3840
ggcgtcgagg ccaaggacgt ggatgcgctg agccgcacgc gcacggtcgg tgaggttgtg    3900
```

-continued

```
gatgccatga aggcggaaat cgtggctgcc tctgctggta gtgctcctgc tcctgctgtt    3960
ccttcggcgc ccgctgcttc tgcagctccg actcccgctg cttcgactgc gccttctgct    4020
gatctgcaag cgctgctgtc caaggcggag acggtggtga tggctgtgct ggcggccaag    4080
actggctacg aggccgacat ggtcgaggcg gacatggacc tggaggccga gctcggcatc    4140
gactcgatca agcgcgtgga gatcctctcg gaggtgcagg gccagctggg cgtcgaggcc    4200
aaggacgtgg atgcgctgag ccgcacgcgc acggtcggtg aggttgtgga tgccatgaag    4260
gcggaaatcg tggctgcctc tggtggtagt gctcctgctc ctgcggttcc ttcggcgccc    4320
gctgcttctg cagctccgac tcccgcggct gcgacagcgc cttctgctga tctgcaagcg    4380
ctgctggcca aggcggagac tgtggtgatg gctgtgctgg cggccaagac tggctacgag    4440
gccgacatgg tcgaggcgga catggacctg gaggccgagc tcggcatcga ctcgatcaag    4500
cgcgtggaga tcctttccga ggtgcagggc cagctgggcg tcgaggccaa ggacgtagat    4560
gcgctgagcc gcacgcgcac ggtcggtgag gttgtggatg ccatgaaggc ggagatcgtg    4620
gctgcctctg ctggtagtgc tcctgctcct gctgttcctt cggcgcccgc tgcttctgca    4680
gctccgactc ccgctgcttc gactgcgcct tctgctgatc tgcaagcgct gctgtccaag    4740
gcggagactg tggtgatggc tgtgctgcg gccaagactg gctacgaggc cgacatggtc    4800
gaggcggaca tggacctgga ggccgagctc ggcatcgact cgatcaagcg cgtggagatc    4860
ctctcggagg tgcagggcca gctgggcgtc gaggccaagg acgtggatgc gctgagccgc    4920
acgcgcacgg tcggtgaggt tgtggatgcc atgaaggcgg aaatcgtggc tgcctctggt    4980
ggtagtgctc tgctgctgc tgttccttcg gcgcccgctg cttctgcagc tccgactcct    5040
gcgactgcgc cttctgctga tctgcaagcg ctgctgtcca aggcggagac tgtggtgatg    5100
gctgtgctgg cggccaagac tggctacgag gccgacatgg tcgaggcgga catggacctg    5160
gaggccgagc tcggcatcga ctcgatcaag cgcgtggaga tcctttccga ggtgcagggc    5220
cagctgggcg tcgaggccaa ggacgtagat gcgctgagcc gcacgcgcac ggtcggtgaa    5280
gtggtggacg ccatgaaggc ggagatcgtg gctgcctctg tggtagtgc tcctgctgct    5340
ccttcggcgc ccgcgcttct tccaacgctg tttggttccg agtgcgagga cctgtctctg    5400
acctttcccg tgataacgac cctgccgctt cctgcagagc ttgtgctggc cgagggcggc    5460
gctcgccctg tagtcgtggt ggatgatgga tctgcactca cctcgtcgct ggtgtcctcg    5520
ctcggcgatc gtgcggtgct gctgcaggtg cagtcttcct ctgcctgctc gccgcgctcg    5580
accacgcaca agttggtgac cgtagcagac cgctctgaag cggcgctaca gcggcgctc    5640
acgtccgtcg aggcgcagtt cggcaaggtg ggtggctttg tgttccagtt cggcgacgac    5700
gacgtgcaag cgcagctcgg ctgggcgctg ctcgcggcca agcacctcaa aacttcgctg    5760
tcagaacaga tcgagggcgg tcgcaccttt ttcgtggccg tcgcgcggct cgacggccag    5820
ctggggctct ccggcaagtc gacgaccgct accgttgatc tctcccgcgc gcagcagggc    5880
agcgtgttcg gcctgtgcaa gacactcgac ctggagtggc ccgctgtctt ctgccgcgga    5940
atcgacctgg ccgccgacct cgacgccgca caggccgcgc ggtgcctgct gggcgagctg    6000
tcagaccccg acgtggccgt gcgcgagtct ggttactccg cctcgggcca cgctgcacg    6060
acaactacga agtcgctgac tacgggcaag ccgcaccagc cgatctcctc gtcggacctc    6120
tttctggtgt cgggcggcgc gcgcggcatc accccgctgt gcgtgcgcga gctggcgcag    6180
cgcgtgggcg gcgcacgta cgtgctcatc ggccgctcgg agctgcccac gacgagcct    6240
gcctgggcgg tcggcgtgga gtctggcaag ccgctggaga aggccgcgct ggcgttcctg    6300
```

-continued

```
aaggcggagt tgcagcggg ccgcggggcc aagccgacgc cgatgctgca caagaagctc    6360
gtgggcgccg tggtcggagc gcgcgaggtg cgagcctcgc tcgccgagat cactgcacag    6420
ggcgccacgg ctgtgtacga gtcgtgcgac gtgagctctg ccgccaaggt gcgtgagatg    6480
gtagagcgcg tgcagcagca gggcgggcgg cgcgtgtcgg gcgtgttcca cgcgtcgggc    6540
gtgctgcgcg acaagctcgt ggagaacaag tcgctggcgg acttcagcgc cgtgtacgac    6600
accaaggtgg cgccctcat caacctgctg gcctgcgtgg acctggcgca gctgcgtcac    6660
ctcgtgctct tcagctcgct cgcgggcttc cacggcaacg tcgggcagtc ggactacgca    6720
atggccaacg aggcgctcaa caagctggcg gcgcacctgt cggcggtgca cccgcagctg    6780
tgcgcgcgct cgatctgctt cggaccgtgg gacggcggca tggtgacccc cgcgctcaag    6840
gccaacttca tccgcatggg catccagatc atcccgcgcc aaggcggcgc gcagaccgtc    6900
gccaacatgc tcgtcagtag ctcccccggt cagctgctcg tgggcaactg ggcgtgcca    6960
cccgtcgtgc cgagtgccac cgagcacacc gtgctgcaga cgctccgcca gagcgacaac    7020
cccttcctcg actcgcacgt gatccagggc cgccgcgtgc tgcccatgac cctggccgtg    7080
ggctacatgg cgcaccaggc gcagagcatc tacgcgggcc accagctgtg ggccgtcgag    7140
gacgcccagc tcttcaaggg catcgccatc gacaatggcg ccgacgtgcc cgtgcgcgtg    7200
gagctgtcgc gccgcaagga ggagcaggag gacgccggca aggtcaaggt caaggtgcag    7260
gtgctgctca aatcgcaggt caacggcaag tcggtgcccg cgtacaaggc gaccgtcgtg    7320
ctgtcccctg cgccgcgccc cagcgtcatc acgcgtgact cgacctcac cccggacccg    7380
gcctgcacgg agcacgacct ctacgacggc aagacgctct tccacggcaa ggccttccag    7440
ggcatcgagc aggtgctctc ggcgacgccc aagcagctca ccgccaagtg ccgcaatttg    7500
cccctcacgc ccgagcagcg cggccagttc gtcgttaacc tcagccagca ggaccgttc    7560
caggcggaca ttgcgttcca ggcgatgctc gtctgggcgc gcatgctgcg ccaatcggcg    7620
gccctgccca caactgcga gcgcttcgac ttttacaagc cgatggcccc gggcgccacc    7680
tactacacgt cggtcaagct ggcctcggcc tcacccttgg tggactctgt gtgcaagtgc    7740
accgtggcga tgcacgatga gcaaggtgag gtgtacttt ctgctcgtgc cagcgtcgtc    7800
ctcaacaaga ccctcacgta ctaa                                         7824
```

<210> SEQ ID NO 2
<211> LENGTH: 2607
<212> TYPE: PRT
<213> ORGANISM: Schizochytrium sp.

<400> SEQUENCE: 2

```
Met Asp Thr Arg Ile Ala Ile Val Gly Met Ser Ala Ile Leu Pro Ser
1               5                   10                  15

Gly Glu Asn Val Arg Glu Ser Trp Glu Ala Ile Arg Asp Gly Leu Asp
                20                  25                  30

Cys Leu Ser Asp Leu Pro Ala Asp Arg Val Asp Val Thr Ala Tyr Tyr
            35                  40                  45

Asn Pro Glu Lys Thr Thr Lys Asp Lys Ile Tyr Cys Lys Arg Gly Gly
        50                  55                  60

Phe Ile Pro Glu Tyr Asp Phe Asp Ala Arg Glu Phe Gly Leu Asn Met
65                  70                  75                  80

Phe Gln Met Glu Asp Ser Asp Ala Asn Gln Thr Ile Ser Leu Leu Lys
                85                  90                  95
```

Val Lys Glu Ala Leu Thr Asp Ala Asn Ile Pro Ala Phe Ser Ser Gly
            100                 105                 110

Lys Lys Asn Ile Gly Cys Val Leu Gly Ile Gly Gly Gln Lys Ala
            115                 120                 125

Ser His Glu Phe Tyr Ser Arg Leu Asn Tyr Val Val Asp Lys Val
        130                 135                 140

Leu Arg Lys Met Gly Leu Pro Glu Glu Asp Val Ala Ala Val Asp
145                 150                 155                 160

Lys Tyr Lys Ala Ser Phe Pro Glu Trp Arg Leu Asp Ser Phe Pro Gly
                165                 170                 175

Phe Leu Gly Asn Val Thr Ala Gly Arg Cys Cys Asn Thr Phe Asn Met
                180                 185                 190

Glu Gly Met Asn Cys Val Val Asp Ala Ala Cys Ala Ser Ser Leu Ile
            195                 200                 205

Ala Val Lys Val Ala Ile Glu Glu Leu Leu Tyr Gly Asp Cys Asp Ala
        210                 215                 220

Met Ile Ala Gly Ala Thr Cys Thr Asp Asn Ser Ile Gly Met Tyr Met
225                 230                 235                 240

Ala Phe Ser Lys Thr Pro Val Phe Ser Thr Asp Pro Ser Val Lys Ala
                245                 250                 255

Tyr Asp Ala Ala Thr Lys Gly Met Leu Ile Gly Glu Gly Ser Ala Met
                260                 265                 270

Leu Val Leu Lys Arg Tyr Ala Asp Ala Val Arg Asp Gly Asp Thr Val
            275                 280                 285

His Ala Val Ile Lys Gly Cys Ala Ser Ser Asp Gly Lys Ala Ala
        290                 295                 300

Gly Ile Tyr Thr Pro Thr Ile Ser Gly Gln Glu Glu Ala Leu Arg Arg
305                 310                 315                 320

Ala Tyr Ala Arg Ala Asn Val Asp Pro Ala Thr Val Thr Leu Val Glu
                325                 330                 335

Gly His Gly Thr Gly Thr Pro Val Gly Asp Lys Ile Glu Leu Thr Ala
            340                 345                 350

Leu Ser Asn Leu Phe Ser Lys Ala Phe Ser Ala Asn Gly Gly Gly Ala
        355                 360                 365

Glu Glu Ala Glu Gln Val Ala Val Gly Ser Ile Lys Ser Gln Ile Gly
370                 375                 380

His Leu Lys Ala Val Ala Gly Leu Ala Gly Leu Val Lys Val Val Leu
385                 390                 395                 400

Ala Leu Lys His Lys Thr Leu Pro Gln Thr Ile Asn Val Asp Lys Pro
                405                 410                 415

Pro Ser Leu Val Asp Gly Thr Pro Ile Gln Gln Ser Pro Leu Tyr Val
                420                 425                 430

Asn Thr Met Asn Arg Pro Trp Phe Thr Pro Val Gly Val Pro Arg Arg
            435                 440                 445

Ala Gly Val Ser Ser Phe Gly Phe Gly Gly Ala Asn Tyr His Ala Val
        450                 455                 460

Leu Glu Glu Phe Glu Pro Glu His Glu Ser Ala Tyr Arg Tyr Asn Asn
465                 470                 475                 480

Leu Pro Gln Val Ala Leu Leu His Ala Gly Asp Val Ala Thr Leu Ala
                485                 490                 495

Ala Thr Val Arg Ala Lys Leu Ala Leu Ala Thr Ala Glu Gln Glu Glu
            500                 505                 510

Ala Arg Val Val Lys Asn Ala Asp Tyr Ile Ala Tyr His Arg Phe Leu

-continued

```
            515                 520                 525
Asp Glu Cys Lys Leu Arg Gly Ala Val Pro Gln Ala His Ala Arg Val
530                 535                 540
Gly Leu Leu Val Arg Asp Leu Ser Ser Leu Ile Ala Val Leu Glu Ala
545                 550                 555                 560
Ala Ala Ala Lys Leu Ala Gly Glu Glu Ser Ala Thr Glu Trp Thr Val
                565                 570                 575
Ser Val Ala Thr Gly Glu Ala Ala Phe Arg Val Arg Gly Val Ala Thr
                580                 585                 590
Glu Ala Asn Val Ala Ala Leu Phe Ser Gln Gly Ala Gln Tyr Thr
            595                 600                 605
His Met Phe Ser Asp Val Ala Met Asn Trp Pro Pro Phe Arg Glu Ser
        610                 615                 620
Val Ala Ala Met Asp Arg Ala Gln Arg Glu Arg Phe Gly Arg Pro Ala
625                 630                 635                 640
Lys Arg Val Ser Ser Val Leu Tyr Pro Arg Lys Pro Tyr Gly Asp Glu
                645                 650                 655
Pro Arg Gln Asp His Lys Glu Ile Ser Gln Thr Arg Tyr Ser Gln Pro
                660                 665                 670
Ala Thr Leu Ala Cys Ser Val Gly Ala Phe Asp Ile Phe Lys Ala Ala
            675                 680                 685
Gly Leu Ala Pro Ser Phe Ala Ala Gly His Ser Leu Gly Glu Phe Ala
        690                 695                 700
Ala Leu Tyr Ala Ala Gly Ser Leu Asp Arg Asp Ala Val Phe Asp Leu
705                 710                 715                 720
Val Cys Ala Arg Ala Lys Ala Met Ser Asp Phe Thr Ala Gln Ala Ser
                725                 730                 735
Ser Ser Gly Gly Ala Met Ala Ala Val Ile Gly Ala Lys Ala Asp Gln
                740                 745                 750
Leu Ser Leu Gly Gly Ala Pro Asp Val Trp Leu Ala Asn Ser Asn Ser
            755                 760                 765
Pro Ser Gln Thr Val Ile Thr Gly Thr Ala Glu Ala Val Ala Ala Ala
        770                 775                 780
Ser Asp Lys Leu Arg Cys Ser Gly Asn Phe Arg Val Val Pro Leu Ala
785                 790                 795                 800
Cys Glu Ala Ala Phe His Ser Pro His Met Arg Gly Ala Glu Gln Thr
                805                 810                 815
Phe Ala Ser Ala Leu Ala Gln Ala Pro Val Ser Ala Pro Ala Ala Ala
                820                 825                 830
Arg Phe Tyr Ser Asn Val Thr Gly Gly Ala Ala Val Thr Ser Pro Ala
            835                 840                 845
Asp Val Lys Thr Asn Leu Gly Lys His Met Thr Ser Pro Val Gln Phe
        850                 855                 860
Val Gln Gln Val Arg Ala Met His Ala Gly Ala Arg Val Phe Val
865                 870                 875                 880
Glu Phe Gly Pro Lys Gln Val Leu Ser Arg Leu Val Lys Glu Thr Leu
                885                 890                 895
Gly Glu Ala Gly Asp Val Thr Val Ala Val Asn Pro Asp Ser Ala
                900                 905                 910
Lys Asp Ser Asp Thr Gln Leu Arg Gln Ala Ala Leu Thr Leu Ala Val
            915                 920                 925
Ala Gly Val Pro Leu Lys Asp Phe Asp Arg Trp Gln Leu Pro Asp Ala
        930                 935                 940
```

```
Thr Arg Leu Glu Pro Val Lys Lys Lys Thr Leu Arg Leu Ser
945                 950                 955                 960

Ala Ala Thr Tyr Val Ser Ala Lys Thr Leu Arg Gln Arg Glu Ala Val
                965                 970                 975

Leu Asn Asp Gly Tyr Thr Val Ser Gly Ala Thr Ala Val Lys Glu
            980                 985                 990

Val Asp Thr Ala Asn Glu Glu Arg  Leu Val Arg Gln Ala  Gln Asp Leu
        995                 1000                 1005

Gln Arg  Gln Leu Ala Glu Ala  Ser Thr Ala Ala Gln  Ala Ala Gln
    1010                 1015                 1020

Ser Lys  Val Ala Glu Leu Glu  Arg Thr Ile Gln Asp  Leu Glu Arg
    1025                 1030                 1035

Lys Val  Gln Gln Gln Gln Gln  Glu Lys Gly Glu Asn  Ser Asp Ser
    1040                 1045                 1050

Asn Ala  Ala Ala Glu Val Leu  Arg Arg His Lys Glu  Leu Leu Gln
    1055                 1060                 1065

Arg Met  Leu Gln Asp Cys Asp  Glu Gln Ala Val Pro  Val Ala Thr
    1070                 1075                 1080

Val Val  Pro Thr Pro Thr Ser  Ser Pro Thr Pro Thr  Ser Ser Pro
    1085                 1090                 1095

Val Ser  Gly Asn Ser Lys Ser  Thr Arg Gly Ser Ala  Asp Leu Gln
    1100                 1105                 1110

Ala Leu  Leu Ala Lys Ala Glu  Thr Val Val Met Ala  Val Leu Ala
    1115                 1120                 1125

Ala Lys  Thr Gly Tyr Glu Ala  Asp Met Val Glu Ala  Asp Met Asp
    1130                 1135                 1140

Leu Glu  Ala Glu Leu Gly Ile  Asp Ser Ile Lys Arg  Val Glu Ile
    1145                 1150                 1155

Leu Ser  Glu Val Gln Gly Gln  Leu Gly Val Glu Ala  Lys Asp Val
    1160                 1165                 1170

Asp Ala  Leu Ser Arg Thr Arg  Thr Val Gly Glu Val  Val Asp Ala
    1175                 1180                 1185

Met Lys  Ala Glu Ile Val Ala  Ala Ser Gly Gly Ser  Ala Pro Ala
    1190                 1195                 1200

Val Pro  Ser Ala Pro Ala Ala  Ser Ala Ala Pro Thr  Pro Ala Ala
    1205                 1210                 1215

Ser Thr  Ala Pro Ser Ala Asp  Leu Gln Ala Leu Leu  Ser Lys Ala
    1220                 1225                 1230

Glu Thr  Val Val Met Ala Val  Leu Ala Ala Lys Thr  Gly Tyr Glu
    1235                 1240                 1245

Ala Asp  Met Val Glu Ala Asp  Met Asp Leu Glu Ala  Glu Leu Gly
    1250                 1255                 1260

Ile Asp  Ser Ile Lys Arg Val  Glu Ile Leu Ser Glu  Val Gln Gly
    1265                 1270                 1275

Gln Leu  Gly Val Glu Ala Lys  Asp Val Asp Ala Leu  Ser Arg Thr
    1280                 1285                 1290

Arg Thr  Val Gly Glu Val Val  Asp Ala Met Lys Ala  Glu Ile Val
    1295                 1300                 1305

Ala Ala  Ser Ala Gly Ser Ala  Pro Ala Pro Ala Val  Pro Ser Ala
    1310                 1315                 1320

Pro Ala  Ala Ser Ala Ala Pro  Thr Pro Ala Ala Ser  Thr Ala Pro
    1325                 1330                 1335
```

-continued

```
Ser Ala Asp Leu Gln Ala Leu Leu Ser Lys Ala Glu Thr Val Val
    1340                1345                1350

Met Ala Val Leu Ala Ala Lys Thr Gly Tyr Glu Ala Asp Met Val
    1355                1360                1365

Glu Ala Asp Met Asp Leu Glu Ala Glu Leu Gly Ile Asp Ser Ile
    1370                1375                1380

Lys Arg Val Glu Ile Leu Ser Glu Val Gln Gly Gln Leu Gly Val
    1385                1390                1395

Glu Ala Lys Asp Val Asp Ala Leu Ser Arg Thr Arg Thr Val Gly
    1400                1405                1410

Glu Val Val Asp Ala Met Lys Ala Glu Ile Val Ala Ala Ser Gly
    1415                1420                1425

Gly Ser Ala Pro Ala Pro Ala Val Pro Ser Ala Pro Ala Ala Ser
    1430                1435                1440

Ala Ala Pro Thr Pro Ala Ala Thr Ala Pro Ser Ala Asp Leu
    1445                1450                1455

Gln Ala Leu Leu Ala Lys Ala Glu Thr Val Val Met Ala Val Leu
    1460                1465                1470

Ala Ala Lys Thr Gly Tyr Glu Ala Asp Met Val Glu Ala Asp Met
    1475                1480                1485

Asp Leu Glu Ala Glu Leu Gly Ile Asp Ser Ile Lys Arg Val Glu
    1490                1495                1500

Ile Leu Ser Glu Val Gln Gly Gln Leu Gly Val Glu Ala Lys Asp
    1505                1510                1515

Val Asp Ala Leu Ser Arg Thr Arg Thr Val Gly Glu Val Val Asp
    1520                1525                1530

Ala Met Lys Ala Glu Ile Val Ala Ala Ser Ala Gly Ser Ala Pro
    1535                1540                1545

Ala Pro Ala Val Pro Ser Ala Pro Ala Ala Ser Ala Ala Pro Thr
    1550                1555                1560

Pro Ala Ala Ser Thr Ala Pro Ser Ala Asp Leu Gln Ala Leu Leu
    1565                1570                1575

Ser Lys Ala Glu Thr Val Val Met Ala Val Leu Ala Ala Lys Thr
    1580                1585                1590

Gly Tyr Glu Ala Asp Met Val Glu Ala Asp Met Asp Leu Glu Ala
    1595                1600                1605

Glu Leu Gly Ile Asp Ser Ile Lys Arg Val Glu Ile Leu Ser Glu
    1610                1615                1620

Val Gln Gly Gln Leu Gly Val Glu Ala Lys Asp Val Asp Ala Leu
    1625                1630                1635

Ser Arg Thr Arg Thr Val Gly Glu Val Val Asp Ala Met Lys Ala
    1640                1645                1650

Glu Ile Val Ala Ala Ser Gly Gly Ser Ala Pro Ala Ala Ala Val
    1655                1660                1665

Pro Ser Ala Pro Ala Ala Ser Ala Ala Pro Thr Pro Ala Thr Ala
    1670                1675                1680

Pro Ser Ala Asp Leu Gln Ala Leu Leu Ser Lys Ala Glu Thr Val
    1685                1690                1695

Val Met Ala Val Leu Ala Ala Lys Thr Gly Tyr Glu Ala Asp Met
    1700                1705                1710

Val Glu Ala Asp Met Asp Leu Glu Ala Glu Leu Gly Ile Asp Ser
    1715                1720                1725

Ile Lys Arg Val Glu Ile Leu Ser Glu Val Gln Gly Gln Leu Gly
```

-continued

```
            1730              1735              1740
Val Glu Ala Lys Asp Val Asp Ala Leu Ser Arg Thr Arg Thr Val
    1745              1750              1755
Gly Glu Val Val Asp Ala Met Lys Ala Glu Ile Val Ala Ala Ser
    1760              1765              1770
Gly Gly Ser Ala Pro Ala Ala Pro Ser Ala Pro Ala Leu Leu Pro
    1775              1780              1785
Thr Leu Phe Gly Ser Glu Cys Glu Asp Leu Ser Leu Thr Phe Pro
    1790              1795              1800
Val Ile Thr Thr Leu Pro Leu Pro Ala Glu Leu Val Leu Ala Glu
    1805              1810              1815
Gly Gly Ala Arg Pro Val Val Val Asp Asp Gly Ser Ala Leu
    1820              1825              1830
Thr Ser Ser Leu Val Ser Ser Leu Gly Asp Arg Ala Val Leu Leu
    1835              1840              1845
Gln Val Gln Ser Ser Ser Ala Cys Ser Pro Arg Ser Thr Thr His
    1850              1855              1860
Lys Leu Val Thr Val Ala Asp Arg Ser Glu Ala Ala Leu Gln Ala
    1865              1870              1875
Ala Leu Thr Ser Val Glu Ala Gln Phe Gly Lys Val Gly Gly Phe
    1880              1885              1890
Val Phe Gln Phe Gly Asp Asp Val Gln Ala Gln Leu Gly Trp
    1895              1900              1905
Ala Leu Leu Ala Ala Lys His Leu Lys Thr Ser Leu Ser Glu Gln
    1910              1915              1920
Ile Glu Gly Gly Arg Thr Phe Phe Val Ala Val Ala Arg Leu Asp
    1925              1930              1935
Gly Gln Leu Gly Leu Ser Gly Lys Ser Thr Thr Ala Thr Val Asp
    1940              1945              1950
Leu Ser Arg Ala Gln Gln Gly Ser Val Phe Gly Leu Cys Lys Thr
    1955              1960              1965
Leu Asp Leu Glu Trp Pro Ala Val Phe Cys Arg Gly Ile Asp Leu
    1970              1975              1980
Ala Ala Asp Leu Asp Ala Ala Gln Ala Ala Arg Cys Leu Leu Gly
    1985              1990              1995
Glu Leu Ser Asp Pro Asp Val Ala Val Arg Glu Ser Gly Tyr Ser
    2000              2005              2010
Ala Ser Gly Gln Arg Cys Thr Thr Thr Lys Ser Leu Thr Thr
    2015              2020              2025
Gly Lys Pro His Gln Pro Ile Ser Ser Ser Asp Leu Phe Leu Val
    2030              2035              2040
Ser Gly Gly Ala Arg Gly Ile Thr Pro Leu Cys Val Arg Glu Leu
    2045              2050              2055
Ala Gln Arg Val Gly Gly Gly Thr Tyr Val Leu Ile Gly Arg Ser
    2060              2065              2070
Glu Leu Pro Thr Thr Glu Pro Ala Trp Ala Val Gly Val Glu Ser
    2075              2080              2085
Gly Lys Pro Leu Glu Lys Ala Ala Leu Ala Phe Leu Lys Ala Glu
    2090              2095              2100
Phe Ala Ala Gly Arg Gly Ala Lys Pro Thr Pro Met Leu His Lys
    2105              2110              2115
Lys Leu Val Gly Ala Val Val Gly Ala Arg Glu Val Arg Ala Ser
    2120              2125              2130
```

```
Leu Ala Glu Ile Thr Ala Gln Gly Ala Thr Ala Val Tyr Glu Ser
    2135                2140                2145

Cys Asp Val Ser Ser Ala Ala Lys Val Arg Glu Met Val Glu Arg
    2150                2155                2160

Val Gln Gln Gln Gly Gly Arg Arg Val Ser Gly Val Phe His Ala
    2165                2170                2175

Ser Gly Val Leu Arg Asp Lys Leu Val Glu Asn Lys Ser Leu Ala
    2180                2185                2190

Asp Phe Ser Ala Val Tyr Asp Thr Lys Val Gly Leu Ile Asn
    2195                2200                2205

Leu Leu Ala Cys Val Asp Leu Ala Gln Leu Arg His Leu Val Leu
    2210                2215                2220

Phe Ser Ser Leu Ala Gly Phe His Gly Asn Val Gly Gln Ser Asp
    2225                2230                2235

Tyr Ala Met Ala Asn Glu Ala Leu Asn Lys Leu Ala Ala His Leu
    2240                2245                2250

Ser Ala Val His Pro Gln Leu Cys Ala Arg Ser Ile Cys Phe Gly
    2255                2260                2265

Pro Trp Asp Gly Gly Met Val Thr Pro Ala Leu Lys Ala Asn Phe
    2270                2275                2280

Ile Arg Met Gly Ile Gln Ile Ile Pro Arg Gln Gly Gly Ala Gln
    2285                2290                2295

Thr Val Ala Asn Met Leu Val Ser Ser Ser Pro Gly Gln Leu Leu
    2300                2305                2310

Val Gly Asn Trp Gly Val Pro Pro Val Pro Ser Ala Thr Glu
    2315                2320                2325

His Thr Val Leu Gln Thr Leu Arg Gln Ser Asp Asn Pro Phe Leu
    2330                2335                2340

Asp Ser His Val Ile Gln Gly Arg Arg Val Leu Pro Met Thr Leu
    2345                2350                2355

Ala Val Gly Tyr Met Ala His Gln Ala Gln Ser Ile Tyr Ala Gly
    2360                2365                2370

His Gln Leu Trp Ala Val Glu Asp Ala Gln Leu Phe Lys Gly Ile
    2375                2380                2385

Ala Ile Asp Asn Gly Ala Asp Val Pro Val Arg Val Glu Leu Ser
    2390                2395                2400

Arg Arg Lys Glu Glu Gln Glu Asp Ala Gly Lys Val Lys Val Lys
    2405                2410                2415

Val Gln Val Leu Leu Lys Ser Gln Val Asn Gly Lys Ser Val Pro
    2420                2425                2430

Ala Tyr Lys Ala Thr Val Val Leu Ser Pro Ala Pro Arg Pro Ser
    2435                2440                2445

Val Ile Thr Arg Asp Phe Asp Leu Thr Pro Asp Pro Ala Cys Thr
    2450                2455                2460

Glu His Asp Leu Tyr Asp Gly Lys Thr Leu Phe His Gly Lys Ala
    2465                2470                2475

Phe Gln Gly Ile Glu Gln Val Leu Ser Ala Thr Pro Lys Gln Leu
    2480                2485                2490

Thr Ala Lys Cys Arg Asn Leu Pro Leu Thr Pro Glu Gln Arg Gly
    2495                2500                2505

Gln Phe Val Val Asn Leu Ser Gln Gln Asp Pro Phe Gln Ala Asp
    2510                2515                2520
```

```
Ile Ala Phe Gln Ala Met Leu Val Trp Ala Arg Met Leu Arg Gln
2525                2530                    2535

Ser Ala Ala Leu Pro Asn Asn Cys Glu Arg Phe Asp Phe Tyr Lys
2540                2545                    2550

Pro Met Ala Pro Gly Ala Thr Tyr Tyr Thr Ser Val Lys Leu Ala
2555                2560                    2565

Ser Ala Ser Pro Leu Val Asp Ser Val Cys Lys Cys Thr Val Ala
2570                2575                    2580

Met His Asp Glu Gln Gly Glu Val Tyr Phe Ser Ala Arg Ala Ser
2585                2590                    2595

Val Val Leu Asn Lys Thr Leu Thr Tyr
2600                2605

<210> SEQ ID NO 3
<211> LENGTH: 5778
<212> TYPE: DNA
<213> ORGANISM: Schizochytrium sp.

<400> SEQUENCE: 3
```

| | | |
|---|---|---|
| atgccgtgcg ataacattgc ggtcgtgggc atggcggtgc agtatgccgg atgcaagaac | 60 |
| caggacgagt tctgggatac gctgatgcgt aaggagatca actcgagccc gatctcggcg | 120 |
| gagcgcctcg gtacgcgcta ccgcgacctc cacttccacc gcagcgcag caagtacgcc | 180 |
| gacaccttct gcaacgatcg ctacggctgc gtcgatgcca gcgtcgacaa cgagcacgac | 240 |
| ctcctcgccg acctggcccg gcgcgccctg ctcgacgccg aattaaacct cgacgacgcc | 300 |
| agcaccaccg ccaacctacg cgacttcggc atcgtgagcg gctgcctgtc gttccccatg | 360 |
| gacaatctgc agggcgagct gctcaatctg taccaagtgc atgtggagaa ccgcgtgggc | 420 |
| gcccagcgct ccgcgactc gcgccccctgg tcggagcgcc cgcgcgctgt ctcgcccgag | 480 |
| gccagcgacc cgcgcgtgta ctccgacccg cgtccttcg tggccaacca gctcggcctg | 540 |
| gggcccgtgc gctacagcct cgatgcagcc tgcgcgtcgg cgctgtactg cctcaagctg | 600 |
| gcgtccgacc acttgctctc gcgcagcgcg gacgtgatgc tgtgcggcgc cacatgcttt | 660 |
| ccggaccccgt tcttcattct ctcggggttc tccaccttcc aggcgatgcc gctgggcgga | 720 |
| ccggacgata acccactgtc cgtgccgctg cggcagggca gccagggcct gacgcccgga | 780 |
| gagggcggcg ccatcatggt gctgaagcgc ctcgaggacg ccgtgcgcga cggcgaccgc | 840 |
| atctacggca ccttgctcgg cacgagtctg agcaacgccg ggtgcggcct gccgctgagc | 900 |
| ccgcaccctgc cgagcgagaa gtcgtgcatg gaggacctgt acacgagcgt cggcatcgac | 960 |
| ccaagcgagg tgcagtacgt ggagtgccac gccacgggca ctccgcaggg cgacgtcgtg | 1020 |
| gaggtagagg cgctgcgcca ctgctttcga ggtaacacgg accacccgcc gcgcatgggc | 1080 |
| tccaccaagg gcaactttgg ccacactctc gtggcggccg ggttcgcagg catggccaag | 1140 |
| gtgctgctgt cgatgcagca cggcacgatc ccgcccacgc ccggtgtcga ccgctccaac | 1200 |
| tgcatcgacc cgctcgtcgt ggacgaggcc atcccttggc cgtactcgtc ggcgcaggcg | 1260 |
| cgggcaggca aaccaggcga tgagctcaag tgcgcctcgc tctccgcctt ggctttggt | 1320 |
| ggaaccaacg cgcactgtgt cttccgtgag caccgccaaa ttgctgctac tgcgacagcc | 1380 |
| tcgccggtgc ttcccgaggt gactcctgga ccgattgcca tcatcgggat ggacgcgacg | 1440 |
| tttggtaccc tcaagggcct ggacgcgtttt gagcaggcca tctacaaggg cacggacggc | 1500 |
| gccagcgacc tgccgagcaa cgctggcgg ttcctgggcg ccgacacgga cttcttgacc | 1560 |
| gccatgggcc tcgacgccgt gccgcgcggg tgctacgtgc gcgacgtgga cgtggactac | 1620 |

```
aagcggctgc ggtcgccgat gatccctgag gacgtcctgc gcccgcaaca gctgctggcg   1680
gtggctacga tggaccgcgc gctgcaggac gctggaatgg cgacgggagg caaggtggcg   1740
gtgctggtgg ggctcggcac ggacaccgag ctgtaccggc accgcgcgcg cgtgacactc   1800
aaggagcggc tcgacccggc cgcgttctcg cccgagcagg tgcaggagat gatggactac   1860
atcaacgact gcggcacctc gacgtcgtac acgtcgtaca tcggcaacct cgtggccacg   1920
cgcgtgtcct cgcagtgggg ctttacgggc ccgtccttca ccgtcaccga aggcgcaaac   1980
tcggtctacc gctgcctcga gctgggcaag ttcctgctcg acacgcacca ggtggacgcc   2040
gtcgtggtgg ccggcgtcga cctctgtgcc accgccgaga acctttacct caaggcgcgc   2100
cgctccgcca tcagccgaca ggaccaccct cgcgccaact ttgaggccag cgccgacggg   2160
tactttgccg gcgagggcag cggcgccctg gtcctcaagc gccaggccga cgttggctca   2220
gacgacaagg tctacgccag tgtcgcgggc ctcacgtgcg ccgcgcagcc cgctgaagcc   2280
gtgtcgccgc tactactcca gtccacaaac gacgacaacg agaagagggt ggtggagatg   2340
gtggagctcg ccgccgactc gggtcgccat gcgccgcact tggccaactc gccgctgagc   2400
gccgagtcgc agctggagca agtgtccaag ttgctcgcgc accaggtgcc gggctcggtg   2460
gccatcggca gcgtgcgcgc caacgtggga gacgtcgggt acgcctcggg cgccgcgagc   2520
ctcatcaaga cggcgctgtg cctccacaac cgctacctcc cggccaaccc gcagtgggag   2580
cggccggtgg cgccggtctc cgaggcgctg tttacttgcc cgcgctcgcg tgcctggctg   2640
aagaacccgg gcgagtcgcg actggcggct gtcgccagtg cctccgagag cgggtcctgc   2700
tttggcgtgc tcctcacaga cgagtacgcc actcatgaga gcagcaaccg cctctcgctg   2760
gatgacgccg cccccaagct catcgcgatc cgttgacga tatcatggcc   2820
aaggtcaacg ccgagctggc gctcctccga gcgcacgccg aaaccgggtc tgctactgac   2880
gacgacccag ctgctgctgt cgcttttcact gctcatcgct tgcgcttttt gcggctcgta   2940
ggggagacgg tggctagtca cggtgccacg gcgaccttgt gtttggccct gctgacaacg   3000
ccggagaagc tggagaagga gttggagctg gcagccaagg gtgtaccgcg aagcgccaag   3060
gccgggcgca actggatgtc gccatcgggc agcgcctttg cgccgacacc tgtgaccagc   3120
gaccgcgtcg cgttcatgta cggcgagggc cgcagcccct actacggcgt cgggctcgac   3180
ctgcaccgcc tgtggccggc tttgcacgag cgcatcaacg acaagaccgc ggcgctgtgg   3240
gagaacggcg actcgtggct catgccgcgc gcggtggatg ccgactcgca gcgcgccgtg   3300
cagacggcct ttgacgcgga ccagatcgag atgttccgca cgggcatctt cgtgtccatc   3360
tgcctcaccg actacgcgcg cgacgtgctc ggggtgcagc ccaaggcgtg cttcggcctc   3420
agcctcggcg agatctccat gctctttgcg ctgtcgcgac gcaactgcgg cctgtcggac   3480
cagctcacgc agcgcctacg cacctcgccg gtgtggtcga cacagctggc ggtggagttc   3540
caggccttgc gcaagctatg gaacgtgccg cgggacgccc ccgtggagtc cttctggcag   3600
ggctacttgg ttcgcgccag ccgcgccgaa atcgagaagg cgatcgggcc cgacaaccgc   3660
ttcgtgcgcc tgctgatcgt caacgactcg agcagcgcgc tgatcgccgg caaacctgcc   3720
gagtgtctgc gcgtgctgga gcgcctgggc gggcggttgc cgccgatgcc cgtcaagcaa   3780
ggcatgattg gcactgcccc gaagtggcg ccctacacgc cgggcatcgc gcacatccac   3840
gagattttgg agattccgga cagccccgtc aagatgtaca cctcggtcac caacgccgag   3900
ctgcgcgggg gcagcaacag cagcatcacc gagttcgtgc agaagttgta cacgcgcatc   3960
```

```
gccgactttc cgggcatcgt cgacaaggtc agccgtgacg gccacgatgt cttcgtcgag    4020
gtggggccga acaacatgcg ctccgccgcg gtcagtgaca ttcttggcaa ggctgccacc    4080
ccgcatgtct ccgtggcgct ggaccgcccc agtgagtcgg cgtggacgca gaccctcaag    4140
tcgctggcgc tgctgaccgc ccaccgcgtg cccctgcaca cccgactct gtttgcggac    4200
ctgtaccacc ccacgttcct gacggctatc gactctgcga tgcaggagcc cccgcccaag    4260
cccaaccgct tccttcgcag cgtagaggtc aacgggtact tttgccccga cggcatcagc    4320
aagcaggttg ctgctgcaag tgccaaaccc tcgacgcatt gcatggttcg tttgcaccca    4380
gccaaggcag ttgtggttgc tgctgctggt gctgtggttg ctgattcgac gcccgtggtc    4440
aaggccaagc agacgtcgtc gtcgttgttg gttggggatg acgcctttct gcgctgctac    4500
gacgtggact ggccgctcta catgggcgcc atggcggaag catctcgtc ggtagacctg    4560
gtggtcgctg ccgccgaggc ccgcatgctg gcatcattcg gagcggcccg cttgcctatg    4620
gaccaggtgg aactccagat ccgtgagatc cagcaacgca cctccaacgc ctttgctgtc    4680
aacctgatgc cgggtcctga cgaggccgcg acggtggacg cgctgctgcg cacgggcgtc    4740
tcaatcgtcg aggcatcggg ctacaccggc gcgctctctg cagacctggt gcgctaccgt    4800
gtcacgggtc tgcgacgaac tagttgcggt gcttctgtgt cggcgactca ccgtgtggtc    4860
gccaaggtgt cgcgcaccga ggtggccgag cactttctgc cccggcgcc ggccgccgta    4920
ctagaggctt tggtcgccgc caaacagatt acgcccgagc aggccgcgct ggccagccgc    4980
gtcgccatgg ccgacgacgt cgcggtggag gccgactcgg gcgggcacac cgacaaccga    5040
ccgatccacg tgctgctgcc gctcgtggtg gcgcagcgca accgctggcg ccacctggtg    5100
gacacgccag tgcgcgtcgg cgccggcggc gggatcgcct gtccgcgcgc cgcgctgctc    5160
gccttttccc tgggcgccgc ctttgtggtc accgggtccg tcaaccaact ggcccgcgag    5220
gctggcacca gcgacgcggt ccgactactg ctggcgacgg ccacctactc ggacgtggcc    5280
atggcgccgg cgcgcgtcca ggtgctcaag aagcagacca tgttcgccgc gcgggccacg    5340
atgctcgccc agctgcaggc caagttcggc tcctttgacg ccgtgccgga ccgcagctg    5400
cgcaagctcg agcgctccgt gttcaagcag tccgtggcgg acgtgtgggc tgctgcacgc    5460
gaaaagtttg gtgtcgacgc taccgctgca agtccgcagg agaggatggc gctctgtgtg    5520
cgctggtaca tgtcgcagtc gtcgcgatgg gctaccgagg cgacgtccgc gcgcaaggcg    5580
gactaccaga tctggtgcgg ccccgccatc ggcagcttca cgacttcgt tcgcggcacc    5640
aagctggacg cgaccgctgg caccggcgag tttccgcgcg tcgtggacat caaccagcac    5700
atcctcctcg gagcctcgca ctaccgccgc gtgcagcaac aacaacagga cgacgacgta    5760
gaatacatca tcgtataa                                                   5778
```

<210> SEQ ID NO 4
<211> LENGTH: 1925
<212> TYPE: PRT
<213> ORGANISM: Schizochytrium sp.

<400> SEQUENCE: 4

Met Pro Cys Asp Asn Ile Ala Val Val Gly Met Ala Val Gln Tyr Ala
1               5                   10                  15

Gly Cys Lys Asn Gln Asp Glu Phe Trp Asp Thr Leu Met Arg Lys Glu
                20                  25                  30

Ile Asn Ser Ser Pro Ile Ser Ala Glu Arg Leu Gly Thr Arg Tyr Arg
            35                  40                  45

-continued

```
Asp Leu His Phe His Pro Gln Arg Ser Lys Tyr Ala Asp Thr Phe Cys
 50                  55                  60

Asn Asp Arg Tyr Gly Cys Val Asp Ala Ser Val Asp Asn Glu His Asp
 65                  70                  75                  80

Leu Leu Ala Asp Leu Ala Arg Arg Ala Leu Leu Asp Ala Gly Ile Asn
                 85                  90                  95

Leu Asp Asp Ala Ser Thr Thr Ala Asn Leu Arg Asp Phe Gly Ile Val
             100                 105                 110

Ser Gly Cys Leu Ser Phe Pro Met Asp Asn Leu Gln Gly Glu Leu Leu
         115                 120                 125

Asn Leu Tyr Gln Val His Val Glu Asn Arg Val Gly Ala Gln Arg Phe
130                 135                 140

Arg Asp Ser Arg Pro Trp Ser Glu Arg Pro Arg Ala Val Ser Pro Glu
145                 150                 155                 160

Ala Ser Asp Pro Arg Val Tyr Ser Asp Pro Ala Ser Phe Val Ala Asn
                165                 170                 175

Gln Leu Gly Leu Gly Pro Val Arg Tyr Ser Leu Asp Ala Ala Cys Ala
            180                 185                 190

Ser Ala Leu Tyr Cys Leu Lys Leu Ala Ser Asp His Leu Leu Ser Arg
        195                 200                 205

Ser Ala Asp Val Met Leu Cys Gly Ala Thr Cys Phe Pro Asp Pro Phe
210                 215                 220

Phe Ile Leu Ser Gly Phe Ser Thr Phe Gln Ala Met Pro Leu Gly Gly
225                 230                 235                 240

Pro Asp Asp Asn Pro Leu Ser Val Pro Leu Arg Gln Gly Ser Gln Gly
                245                 250                 255

Leu Thr Pro Gly Glu Gly Gly Ala Ile Met Val Leu Lys Arg Leu Glu
            260                 265                 270

Asp Ala Val Arg Asp Gly Asp Arg Ile Tyr Gly Thr Leu Leu Gly Thr
        275                 280                 285

Ser Leu Ser Asn Ala Gly Cys Gly Leu Pro Leu Ser Pro His Leu Pro
290                 295                 300

Ser Glu Lys Ser Cys Met Glu Asp Leu Tyr Thr Ser Val Gly Ile Asp
305                 310                 315                 320

Pro Ser Glu Val Gln Tyr Val Glu Cys His Ala Thr Gly Thr Pro Gln
                325                 330                 335

Gly Asp Val Val Glu Val Glu Ala Leu Arg His Cys Phe Arg Gly Asn
            340                 345                 350

Thr Asp His Pro Pro Arg Met Gly Ser Thr Lys Gly Asn Phe Gly His
        355                 360                 365

Thr Leu Val Ala Ala Gly Phe Ala Gly Met Ala Lys Val Leu Leu Ser
370                 375                 380

Met Gln His Gly Thr Ile Pro Pro Thr Pro Gly Val Asp Arg Ser Asn
385                 390                 395                 400

Cys Ile Asp Pro Leu Val Val Asp Glu Ala Ile Pro Trp Pro Tyr Ser
                405                 410                 415

Ser Ala Gln Ala Arg Ala Gly Lys Pro Gly Asp Glu Leu Lys Cys Ala
            420                 425                 430

Ser Leu Ser Ala Phe Gly Phe Gly Gly Thr Asn Ala His Cys Val Phe
        435                 440                 445

Arg Glu His Arg Gln Ile Ala Ala Thr Ala Thr Ala Ser Pro Val Leu
450                 455                 460

Pro Glu Val Thr Pro Gly Pro Ile Ala Ile Ile Gly Met Asp Ala Thr
```

```
              465                 470                 475                 480
      Phe Gly Thr Leu Lys Gly Leu Asp Ala Phe Glu Gln Ala Ile Tyr Lys
                      485                 490                 495

Gly Thr Asp Gly Ala Ser Asp Leu Pro Ser Lys Arg Trp Arg Phe Leu
                      500                 505                 510

Gly Ala Asp Thr Asp Phe Leu Thr Ala Met Gly Leu Asp Ala Val Pro
                      515                 520                 525

Arg Gly Cys Tyr Val Arg Asp Val Asp Val Asp Tyr Lys Arg Leu Arg
                      530                 535                 540

Ser Pro Met Ile Pro Glu Asp Val Leu Arg Pro Gln Gln Leu Leu Ala
      545                 550                 555                 560

Val Ala Thr Met Asp Arg Ala Leu Gln Asp Ala Gly Met Ala Thr Gly
                              565                 570                 575

Gly Lys Val Ala Val Leu Val Gly Leu Gly Thr Asp Thr Glu Leu Tyr
                      580                 585                 590

Arg His Arg Ala Arg Val Thr Leu Lys Glu Arg Leu Asp Pro Ala Ala
                      595                 600                 605

Phe Ser Pro Glu Gln Val Gln Glu Met Met Asp Tyr Ile Asn Asp Cys
                      610                 615                 620

Gly Thr Ser Thr Ser Tyr Thr Ser Tyr Ile Gly Asn Leu Val Ala Thr
      625                 630                 635                 640

Arg Val Ser Ser Gln Trp Gly Phe Thr Gly Pro Ser Phe Thr Val Thr
                      645                 650                 655

Glu Gly Ala Asn Ser Val Tyr Arg Cys Leu Glu Leu Gly Lys Phe Leu
                      660                 665                 670

Leu Asp Thr His Gln Val Asp Ala Val Val Ala Gly Val Asp Leu
                      675                 680                 685

Cys Ala Thr Ala Glu Asn Leu Tyr Leu Lys Ala Arg Arg Ser Ala Ile
                      690                 695                 700

Ser Arg Gln Asp His Pro Arg Ala Asn Phe Glu Ala Ser Ala Asp Gly
      705                 710                 715                 720

Tyr Phe Ala Gly Glu Gly Ser Gly Ala Leu Val Leu Lys Arg Gln Ala
                      725                 730                 735

Asp Val Gly Ser Asp Asp Lys Val Tyr Ala Ser Val Ala Gly Leu Thr
                      740                 745                 750

Cys Ala Ala Gln Pro Ala Glu Ala Val Ser Pro Leu Leu Leu Gln Val
                      755                 760                 765

His Asn Asp Asp Asn Glu Lys Arg Val Val Glu Met Val Glu Leu Ala
                      770                 775                 780

Ala Asp Ser Gly Arg His Ala Pro His Leu Ala Asn Ser Pro Leu Ser
      785                 790                 795                 800

Ala Glu Ser Gln Leu Glu Gln Val Ser Lys Leu Leu Ala His Gln Val
                      805                 810                 815

Pro Gly Ser Val Ala Ile Gly Ser Val Arg Ala Asn Val Gly Asp Val
                      820                 825                 830

Gly Tyr Ala Ser Gly Ala Ala Ser Leu Ile Lys Thr Ala Leu Cys Leu
                      835                 840                 845

His Asn Arg Tyr Leu Pro Ala Asn Pro Gln Trp Glu Arg Pro Val Ala
                      850                 855                 860

Pro Val Ser Glu Ala Leu Phe Thr Cys Pro Arg Ser Arg Ala Trp Leu
      865                 870                 875                 880

Lys Asn Pro Gly Glu Ser Arg Leu Ala Ala Val Ala Ser Ala Ser Glu
                      885                 890                 895
```

```
Ser Gly Ser Cys Phe Gly Val Leu Leu Thr Asp Glu Tyr Ala Thr His
            900                 905                 910

Glu Ser Ser Asn Arg Leu Ser Leu Asp Asp Ala Ala Pro Lys Leu Ile
            915                 920                 925

Ala Ile Arg Gly Asp Thr Val Asp Ile Met Ala Lys Val Asn Ala
        930                 935                 940

Glu Leu Ala Leu Leu Arg Ala His Ala Glu Thr Gly Ser Ala Thr Asp
945                 950                 955                 960

Asp Asp Pro Ala Ala Val Ala Phe Thr Ala His Arg Leu Arg Phe
            965                 970                 975

Leu Arg Leu Val Gly Glu Thr Val Ala Ser His Gly Ala Thr Ala Thr
            980                 985                 990

Leu Cys Leu Ala Leu Leu Thr Thr Pro Glu Lys Leu Glu Lys Glu Leu
            995                 1000                1005

Glu Leu Ala Ala Lys Gly Val Pro Arg Ser Ala Lys Ala Gly Arg
        1010                1015                1020

Asn Trp Met Ser Pro Ser Gly Ser Ala Phe Ala Pro Thr Pro Val
        1025                1030                1035

Thr Ser Asp Arg Val Ala Phe Met Tyr Gly Glu Gly Arg Ser Pro
        1040                1045                1050

Tyr Tyr Gly Val Gly Leu Asp Leu His Arg Leu Trp Pro Ala Leu
        1055                1060                1065

His Glu Arg Ile Asn Asp Lys Thr Ala Ala Leu Trp Glu Asn Gly
        1070                1075                1080

Asp Ser Trp Leu Met Pro Arg Ala Val Asp Ala Asp Ser Gln Arg
        1085                1090                1095

Ala Val Gln Thr Ala Phe Asp Ala Asp Gln Ile Glu Met Phe Arg
        1100                1105                1110

Thr Gly Ile Phe Val Ser Ile Cys Leu Thr Asp Tyr Ala Arg Asp
        1115                1120                1125

Val Leu Gly Val Gln Pro Lys Ala Cys Phe Gly Leu Ser Leu Gly
        1130                1135                1140

Glu Ile Ser Met Leu Phe Ala Leu Ser Arg Arg Asn Cys Gly Leu
        1145                1150                1155

Ser Asp Gln Leu Thr Gln Arg Leu Arg Thr Ser Pro Val Trp Ser
        1160                1165                1170

Thr Gln Leu Ala Val Glu Phe Gln Ala Leu Arg Lys Leu Trp Asn
        1175                1180                1185

Val Pro Ala Asp Ala Pro Val Glu Ser Phe Trp Gln Gly Tyr Leu
        1190                1195                1200

Val Arg Ala Ser Arg Ala Glu Ile Glu Lys Ala Ile Gly Pro Asp
        1205                1210                1215

Asn Arg Phe Val Arg Leu Leu Ile Val Asn Asp Ser Ser Ser Ala
        1220                1225                1230

Leu Ile Ala Gly Lys Pro Ala Glu Cys Leu Arg Val Leu Glu Arg
        1235                1240                1245

Leu Gly Gly Arg Leu Pro Pro Met Pro Val Lys Gln Gly Met Ile
        1250                1255                1260

Gly His Cys Pro Glu Val Ala Pro Tyr Thr Pro Gly Ile Ala His
        1265                1270                1275

Ile His Glu Ile Leu Glu Ile Pro Asp Ser Pro Val Lys Met Tyr
        1280                1285                1290
```

-continued

Thr Ser Val Thr Asn Ala Glu Leu Arg Gly Gly Ser Asn Ser Ser
1295            1300                 1305

Ile Thr Glu Phe Val Gln Lys Leu Tyr Thr Arg Ile Ala Asp Phe
1310            1315                 1320

Pro Gly Ile Val Asp Lys Val Ser Arg Asp Gly His Asp Val Phe
1325            1330                 1335

Val Glu Val Gly Pro Asn Asn Met Arg Ser Ala Ala Val Ser Asp
1340            1345                 1350

Ile Leu Gly Lys Ala Ala Thr Pro His Val Ser Val Ala Leu Asp
1355            1360                 1365

Arg Pro Ser Glu Ser Ala Trp Thr Gln Thr Leu Lys Ser Leu Ala
1370            1375                 1380

Leu Leu Thr Ala His Arg Val Pro Leu His Asn Pro Thr Leu Phe
1385            1390                 1395

Ala Asp Leu Tyr His Pro Thr Phe Leu Thr Ala Ile Asp Ser Ala
1400            1405                 1410

Met Gln Glu Pro Pro Lys Pro Asn Arg Phe Leu Arg Ser Val
1415            1420                 1425

Glu Val Asn Gly Tyr Phe Cys Pro Asp Gly Ile Ser Lys Gln Val
1430            1435                 1440

Ala Ala Ala Ser Ala Lys Pro Ser Thr His Cys Met Val Arg Leu
1445            1450                 1455

His Pro Ala Lys Ala Val Val Val Ala Ala Ala Gly Ala Val Val
1460            1465                 1470

Ala Asp Ser Thr Pro Val Val Lys Ala Lys Gln Thr Ser Ser Ser
1475            1480                 1485

Leu Leu Val Gly Asp Asp Ala Phe Leu Arg Cys Tyr Asp Val Asp
1490            1495                 1500

Trp Pro Leu Tyr Met Gly Ala Met Ala Glu Gly Ile Ser Ser Val
1505            1510                 1515

Asp Leu Val Val Ala Ala Ala Glu Ala Arg Met Leu Ala Ser Phe
1520            1525                 1530

Gly Ala Ala Arg Leu Pro Met Asp Gln Val Glu Leu Gln Ile Arg
1535            1540                 1545

Glu Ile Gln Gln Arg Thr Ser Asn Ala Phe Ala Val Asn Leu Met
1550            1555                 1560

Pro Gly Pro Asp Glu Ala Ala Thr Val Asp Ala Leu Leu Arg Thr
1565            1570                 1575

Gly Val Ser Ile Val Glu Ala Ser Gly Tyr Thr Gly Ala Leu Ser
1580            1585                 1590

Ala Asp Leu Val Arg Tyr Arg Val Thr Gly Leu Arg Arg Thr Ser
1595            1600                 1605

Cys Gly Ala Ser Val Ser Ala Thr His Arg Val Ala Lys Val
1610            1615                 1620

Ser Arg Thr Glu Val Ala Glu His Phe Leu Arg Pro Ala Pro Ala
1625            1630                 1635

Ala Val Leu Glu Ala Leu Val Ala Ala Lys Gln Ile Thr Pro Glu
1640            1645                 1650

Gln Ala Ala Leu Ala Ser Arg Val Ala Met Ala Asp Asp Val Ala
1655            1660                 1665

Val Glu Ala Asp Ser Gly Gly His Thr Asp Asn Arg Pro Ile His
1670            1675                 1680

Val Leu Leu Pro Leu Val Val Ala Gln Arg Asn Arg Trp Arg His

```
                1685               1690                1695
Leu Val Asp Thr Pro Val Arg Val Gly Ala Gly Gly Ile Ala
        1700               1705                1710

Cys Pro Arg Ala Ala Leu Leu Ala Phe Ser Leu Gly Ala Ala Phe
    1715               1720               1725

Val Val Thr Gly Ser Val Asn Gln Leu Ala Arg Glu Ala Gly Thr
    1730               1735               1740

Ser Asp Ala Val Arg Leu Leu Leu Ala Thr Ala Thr Tyr Ser Asp
    1745               1750               1755

Val Ala Met Ala Pro Gly Gly Val Gln Val Leu Lys Lys Gln Thr
    1760               1765               1770

Met Phe Ala Ala Arg Ala Thr Met Leu Ala Gln Leu Gln Ala Lys
    1775               1780               1785

Phe Gly Ser Phe Asp Ala Val Pro Glu Pro Gln Leu Arg Lys Leu
    1790               1795               1800

Glu Arg Ser Val Phe Lys Gln Ser Val Ala Asp Val Trp Ala Ala
    1805               1810               1815

Ala Arg Glu Lys Phe Gly Val Asp Ala Thr Ala Ala Ser Pro Gln
    1820               1825               1830

Glu Arg Met Ala Leu Cys Val Arg Trp Tyr Met Ser Gln Ser Ser
    1835               1840               1845

Arg Trp Ala Thr Glu Ala Thr Ser Ala Arg Lys Ala Asp Tyr Gln
    1850               1855               1860

Ile Trp Cys Gly Pro Ala Ile Gly Ser Phe Asn Asp Phe Val Arg
    1865               1870               1875

Gly Thr Lys Leu Asp Ala Thr Ala Gly Thr Gly Glu Phe Pro Arg
    1880               1885               1890

Val Val Asp Ile Asn Gln His Ile Leu Leu Gly Ala Ser His Tyr
    1895               1900               1905

Arg Arg Val Gln Gln Gln Gln Gln Asp Asp Asp Val Glu Tyr Ile
    1910               1915               1920

Ile Val
    1925

<210> SEQ ID NO 5
<211> LENGTH: 4308
<212> TYPE: DNA
<213> ORGANISM: Schizochytrium sp.

<400> SEQUENCE: 5
atgacatcat cgaagaagac tcccgtgtgg gagatgagca aggaggagct gctggacggc     60
aagacggtgg tcttcgacta caacgagctg ctcgaattcg ccgagggcga cgtgggccaa    120
gtgttcggac ccgagttcga catcatcgac aagtaccggc gtcgcgtgcg gctgccggcg    180
cgcgagtacc tgctcgtgtc gcgcgtgacg ctgatggacg ccgaggtgaa caacttccgc    240
gtcgggtcgc gcatggtgac cgagtacgac gtgcccgtga acggggagct gtcggagggc    300
ggggacgtgc cgtgggcggt gctggtggag tcggggcagt gcgacctgat gctcatctcg    360
tacatgggca tcgacttcca gtgcaagggc gaccgcgtgt accgcctgct caacacatcg    420
ctcaccttct tcggggtggc gcacgagggc gagacgctgg tgtacgacat ccgcgtcacg    480
gggttcgcca agggcgcggg cggggagatc tcgatgttct tcttcgagta cgactgcttc    540
gtggacggcc gcctgctgat cgagatgcgc gacgggtgcg ccgggttctt cacggacgcc    600
gagctggccg ccggcaaggg cgtgcttaag accaaggcgg agctggcggc gcgcgcgcag    660
```

```
atccagaagc aggacatcgc gcccttttgcg ccggcgccgt gctcgcacaa gacctcgctg    720
gacgcgcgcg agatgcggct gctcgtggac cgccagtggg cgcgcgtctt cggcagcggc    780
atggcgggca tcgactacaa gttgtgcgct cgcaagatgc tcatgatcga ccgcgtcacg    840
cacctcgacc cgcgcggcgg cgcgcacggc ctcgggctgc tgatcgggga aaggtgctg    900 gagcgcgacc actggtactt cccctgccac tttgtgcgcg acgaggtgat ggccgggtcg    960
ctggtcagcg acggctgctc gcagctcctc aaggtgtaca tgctgtggct cggcctgcac   1020
acgaccgtgg gcgcgttcga ctttcgtccc gtgagcgggc acgccaacaa ggtgcggtgc   1080
cgcgggcaga tctcaccgca caagggcaag ctcgtgtacg tgatggagat caaggaaatg   1140
ggctttgacg cgaagacggg cgatccgttt gcgatcgcgg acgtggacat catcgacgtc   1200
aacttcgagg agggacaggc gttttgcggga gtggaagacc tgcacagcta cggccagggc   1260
gacctccgca agaagatcgt cgtcgacttc aagggcatcg cgctctccct gcagaagcgg   1320
aaggagcagc agaaggaaag catgaccgtg actacgacga cgacgacgac gagccgggtg   1380
attgcgccgc ccagcgggtg cctcaagggc gacccgacgg cgccgacgag cgtgacgtgg   1440
cacccgatgg cggagggcaa cggcgggccc ggaccgacgc cgtcgttctc gccgtccgcg   1500 taccccgccgc gggcggtgtg cttctcgccg ttccccaaca acccgcttga caacgaccac   1560
acgccgggcc agatgccgtt gacctggttc aacatgtccg aattcatgtg cggcaaagtg   1620
tccaactgcc tgggccccga gttttgcgcgc ttcgacgcga caagacgag ccgcagcccg   1680 gcctttgacc tggcgctcgt gacgcgggtg acgagcgtgg cggacatgga gcacgggccg   1740
ttctacaacg tggacgtcaa cccgggccag ggcacgatgg tgggcgagtt cgactgtccc   1800
gcggacgcgt ggttcttcgg cgcctcgagc cgcgacgacc acatgccgta ctcgatcctg   1860
atggagatcg cgctgcagac gtcgggcgtc ctcacctcgg tgctcaaggc gccgctgacg   1920
atggacaagg acgacatcct cttccgcaac ctcgacgcag acgccgagct cgtgggcgac   1980
gccatgccgg acgtgcgcgg caagacgatc cgcaacttca ccaagtgcac aggctacagc   2040
atgctcggca agatgggcat ccaccgcttc acctttgagc tcagcgtcga cggcgccgtc   2100
ttctacaagg gcagcacctc gtttggctgg ttcgtccccg aggtcttcga gtcgcagacc   2160
ggtctcgaca acggcaagcc gcgcctgcct tggtaccgcg agaacaacgt cgccgtcgac   2220
acgctctccg cgcccgcctc cgcttcctcc gcgcaaggtc agctgcagct gcagcgacgc   2280
gggtcgcagg cgcagttcct ggacacaatc cacctggcgg gcagcggcgc cggcgtgcac   2340
ggccagggct acgcgcacgg ggagaaggcc gtgaacaagc aagattggtt cttctcgtgc   2400
cacttctggt tcgaccccgt gatgcccggg tccctgggca tcgagtcgat gttccagctc   2460
gtcgaggcgt ggtgcgtgaa gcagggactc gcggcgcggc acggcatcgc tcacccagtg   2520
ttcgcgcacg cgcccgggc cacgagctgg aagtaccgcg ggcagctaac ccccaagaac   2580
gaccgcatgg acagcgaggt gcacatcaag tcggtggcgg ccttctcctc ctgggtcgac   2640
gtcgtcgcgg acgggttcct cttcgtcgac ggcctccgcg tctactcggc agacaacctc   2700
cgcgtccgca tccagaccgg cgccggccac gttgaagagc aagaggttgc tgccaaggcc   2760
acaaccaaga acagcagtat tgctgatgtg gactggcgc acctgcaagc gctcaagcag   2820
gcgttgctga cgctggagcg accgctgcag ctggacgcgg ggagcgaggt gcccgcctgc   2880
gcggtgagcg acctgggcga taggggcttc atggagacgt acggggtggt ggcgccgctg   2940
tacagcgggg cgatggccaa gggcatcgcg tcggcggacc tggtgatcgc gatgggccag   3000
```

```
cgcaagatgc tggggtcgtt tggcgcgggc gggctcccga tgcacgtcgt gcgcgcgggg    3060
attgagaaga tccaggcagc gctgccagcg gggccatacg cggtcaacct gattcactcg    3120
ccttttgacg ccaacctgga agggcaac gtggacctct tcctggagaa gggcgtgcgc      3180
gtcgtggagg cgtcggcctt catggagctc acgccccagg tggtgcgcta ccgcgcgacg    3240
ggcctctctc gcgacgcgcg cggcggctcc gtgcgcacgg cccacaagat catcggcaag    3300
gtcagccgca ccgagctggc cgagatgttt atccggcccg cgccgcaagc cattctcgac    3360
aagcttgtgg cgtccggcga gatcacccccc gagcaggcgg cgctggcgct cgaggtgccc   3420
atggcggacg acatcgccgt cgaggccgat tcgggcgggc acaccgacaa ccgccccatc    3480
cacgtcatcc tgcccctcat cctcagcctg cgcaaccgcc tccagcgcga gctcaagtac    3540
cctgcgcgac accgcgtgcg cgtcggcgcc ggggcggca  tcgggtgccc gcaagcgcgct  3600
ctgggcgcct tccacatggg cgccgcgttt gtggtgacgg gcacggtcaa ccagctgagc    3660
cggcaggccg ggacatgcga caatgtgcgg cggcagctgt cgcgcgcgac gtactcggac    3720
atcacgatgg cgccggcggc ggacatgttc gagcagggcg tcgagctgca ggtgctcaag    3780
aagggcacga tgtttccctc gcgcgccaag aagctgttcg agctgtttca caagtacgac    3840
tcgttcgagg cgatgccggc ggacgagctg gcgcgcgtcg agaagcgcat cttcagcaag    3900
tcactcgccg aggtgtgggc cgagaccaag gacttctaca tcacgcggct caacaacccg    3960
gagaagatcc gcaaggcgga gaacgaggac cccaagctca gatgtcact  ctgcttccgc    4020
tggtacctcg ggctcagctc gttctgggcc aacaacggca tcgcggaccg cacgatggac    4080
taccagatct ggtgcggccc tgccatcggc gccttcaacg acttcatcgc cgactcgtac    4140
ctcgacgtgg ccgtctcggg cgagttcccc gacgtcgtgc agatcaacct gcagatcctg    4200
tcgggcgcag cctacctcca cgcgctcctc tccgtcaagc tcgcaccgcg gatcgacgtc    4260
gacaccgagg acgacctctt cacctaccgc cccgaccacg cactctaa                 4308
```

<210> SEQ ID NO 6
<211> LENGTH: 1435
<212> TYPE: PRT
<213> ORGANISM: Schizochytrium sp.

<400> SEQUENCE: 6

Met Thr Ser Ser Lys Lys Thr Pro Val Trp Glu Met Ser Lys Glu Glu
1               5                   10                  15

Leu Leu Asp Gly Lys Thr Val Phe Asp Tyr Asn Glu Leu Leu Glu
            20                  25                  30

Phe Ala Glu Gly Asp Val Gly Val Phe Gly Pro Glu Phe Asp Ile
        35                  40                  45

Ile Asp Lys Tyr Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

```
Gly Val Ala His Glu Gly Glu Thr Leu Val Tyr Asp Ile Arg Val Thr
145                 150                 155                 160

Gly Phe Ala Lys Gly Ala Gly Glu Ile Ser Met Phe Phe Glu
            165                 170                 175

Tyr Asp Cys Phe Val Asp Gly Arg Leu Leu Ile Glu Met Arg Asp Gly
            180                 185                 190

Cys Ala Gly Phe Phe Thr Asp Ala Glu Leu Ala Ala Gly Lys Gly Val
            195                 200                 205

Leu Lys Thr Lys Ala Glu Leu Ala Ala Arg Ala Gln Ile Gln Lys Gln
    210                 215                 220

Asp Ile Ala Pro Phe Ala Pro Ala Pro Cys Ser His Lys Thr Ser Leu
225                 230                 235                 240

Asp Ala Arg Glu Met Arg Leu Leu Val Asp Arg Gln Trp Ala Arg Val
                245                 250                 255

Phe Gly Ser Gly Met Ala Gly Ile Asp Tyr Lys Leu Cys Ala Arg Lys
            260                 265                 270

Met Leu Met Ile Asp Arg Val Thr His Leu Asp Pro Arg Gly Gly Ala
    275                 280                 285

His Gly Leu Gly Leu Leu Ile Gly Glu Lys Val Leu Glu Arg Asp His
    290                 295                 300

Trp Tyr Phe Pro Cys His Phe Val Arg Asp Glu Val Met Ala Gly Ser
305                 310                 315                 320

Leu Val Ser Asp Gly Cys Ser Gln Leu Leu Lys Val Tyr Met Leu Trp
            325                 330                 335

Leu Gly Leu His Thr Thr Val Gly Ala Phe Asp Phe Arg Pro Val Ser
            340                 345                 350

Gly His Ala Asn Lys Val Arg Cys Arg Gly Gln Ile Ser Pro His Lys
            355                 360                 365

Gly Lys Leu Val Tyr Val Met Glu Ile Lys Glu Met Gly Phe Asp Ala
            370                 375                 380

Lys Thr Gly Asp Pro Phe Ala Ile Ala Asp Val Asp Ile Ile Asp Val
385                 390                 395                 400

Asn Phe Glu Glu Gly Gln Ala Phe Ala Gly Val Glu Asp Leu His Ser
                405                 410                 415

Tyr Gly Gln Gly Asp Leu Arg Lys Lys Ile Val Val Asp Phe Lys Gly
            420                 425                 430

Ile Ala Leu Ser Leu Gln Lys Arg Lys Glu Gln Gln Lys Glu Ser Met
            435                 440                 445

Thr Val Thr Thr Thr Thr Thr Thr Ser Arg Val Ile Ala Pro Pro
    450                 455                 460

Ser Gly Cys Leu Lys Gly Asp Pro Thr Ala Pro Thr Ser Val Thr Trp
465                 470                 475                 480

His Pro Met Ala Glu Gly Asn Gly Gly Pro Gly Pro Thr Pro Ser Phe
                485                 490                 495

Ser Pro Ser Ala Tyr Pro Pro Arg Ala Val Cys Phe Ser Pro Phe Pro
            500                 505                 510

Asn Asn Pro Leu Asp Asn Asp His Thr Pro Gly Gln Met Pro Leu Thr
            515                 520                 525

Trp Phe Asn Met Ser Glu Phe Met Cys Gly Lys Val Ser Asn Cys Leu
            530                 535                 540

Gly Pro Glu Phe Ala Arg Phe Asp Ala Ser Lys Thr Ser Arg Ser Pro
545                 550                 555                 560

Ala Phe Asp Leu Ala Leu Val Thr Arg Val Thr Ser Val Ala Asp Met
```

```
                    565                 570                 575
Glu His Gly Pro Phe Tyr Asn Val Asp Val Asn Pro Gly Gln Gly Thr
                580                 585                 590
Met Val Gly Glu Phe Asp Cys Pro Ala Asp Ala Trp Phe Gly Ala
                595                 600             605
Ser Ser Arg Asp Asp His Met Pro Tyr Ser Ile Leu Met Glu Ile Ala
                610                 615                 620
Leu Gln Thr Ser Gly Val Leu Thr Ser Val Leu Lys Ala Pro Leu Thr
625                 630                 635                 640
Met Asp Lys Asp Asp Ile Leu Phe Arg Asn Leu Asp Ala Asp Ala Glu
                    645                 650                 655
Leu Val Gly Asp Ala Met Pro Asp Val Arg Gly Lys Thr Ile Arg Asn
                660                 665                 670
Phe Thr Lys Cys Thr Gly Tyr Ser Met Leu Gly Lys Met Gly Ile His
                675                 680                 685
Arg Phe Thr Phe Glu Leu Ser Val Asp Gly Ala Val Phe Tyr Lys Gly
                690                 695                 700
Ser Thr Ser Phe Gly Trp Phe Val Pro Glu Val Phe Glu Ser Gln Thr
705                 710                 715                 720
Gly Leu Asp Asn Gly Lys Pro Arg Leu Pro Trp Tyr Arg Glu Asn Asn
                    725                 730                 735
Val Ala Val Asp Thr Leu Ser Pro Ala Ser Ala Ser Ser Ala Gln
                740                 745                 750
Gly Gln Leu Gln Leu Gln Arg Arg Gly Ser Gln Ala Gln Phe Leu Asp
                755                 760                 765
Thr Ile His Leu Ala Gly Ser Gly Ala Gly Val His Gly Gln Gly Tyr
                770                 775                 780
Ala His Gly Glu Lys Ala Val Asn Lys Gln Asp Trp Phe Phe Ser Cys
785                 790                 795                 800
His Phe Trp Phe Asp Pro Val Met Pro Gly Ser Leu Gly Ile Glu Ser
                    805                 810                 815
Met Phe Gln Leu Val Glu Ala Trp Cys Val Lys Gln Gly Leu Ala Ala
                820                 825                 830
Arg His Gly Ile Ala His Pro Val Phe Ala His Ala Pro Gly Ala Thr
                835                 840                 845
Ser Trp Lys Tyr Arg Gly Gln Leu Thr Pro Lys Asn Asp Arg Met Asp
                850                 855                 860
Ser Glu Val His Ile Lys Ser Val Ala Ala Phe Ser Ser Trp Val Asp
865                 870                 875                 880
Val Val Ala Asp Gly Phe Leu Phe Val Asp Gly Leu Arg Val Tyr Ser
                    885                 890                 895
Ala Asp Asn Leu Arg Val Arg Ile Gln Thr Gly Ala Gly His Val Glu
                900                 905                 910
Glu Gln Glu Val Ala Ala Lys Ala Thr Thr Lys Asn Ser Ser Ile Ala
                915                 920                 925
Asp Val Asp Val Ala Asp Leu Gln Ala Leu Lys Gln Ala Leu Leu Thr
                930                 935                 940
Leu Glu Arg Pro Leu Gln Leu Asp Ala Gly Ser Glu Val Pro Ala Cys
945                 950                 955                 960
Ala Val Ser Asp Leu Gly Asp Arg Gly Phe Met Glu Thr Tyr Gly Val
                    965                 970                 975
Val Ala Pro Leu Tyr Ser Gly Ala Met Ala Lys Gly Ile Ala Ser Ala
                980                 985                 990
```

```
Asp Leu Val Ile Ala Met Gly Gln Arg Lys Met Leu Gly Ser Phe Gly
        995                 1000                1005

Ala Gly Gly Leu Pro Met His Val Val Arg Ala Gly Ile Glu Lys
   1010                 1015                1020

Ile Gln Ala Ala Leu Pro Ala Gly Pro Tyr Ala Val Asn Leu Ile
   1025                 1030                1035

His Ser Pro Phe Asp Ala Asn Leu Glu Lys Gly Asn Val Asp Leu
   1040                 1045                1050

Phe Leu Glu Lys Gly Val Arg Val Glu Ala Ser Ala Phe Met
   1055                 1060                1065

Glu Leu Thr Pro Gln Val Val Arg Tyr Arg Ala Thr Gly Leu Ser
   1070                 1075                1080

Arg Asp Ala Arg Gly Gly Ser Val Arg Thr Ala His Lys Ile Ile
   1085                 1090                1095

Gly Lys Val Ser Arg Thr Glu Leu Ala Glu Met Phe Ile Arg Pro
   1100                 1105                1110

Ala Pro Gln Ala Ile Leu Asp Lys Leu Val Ala Ser Gly Glu Ile
   1115                 1120                1125

Thr Pro Glu Gln Ala Ala Leu Ala Leu Glu Val Pro Met Ala Asp
   1130                 1135                1140

Asp Ile Ala Val Glu Ala Asp Ser Gly Gly His Thr Asp Asn Arg
   1145                 1150                1155

Pro Ile His Val Ile Leu Pro Leu Ile Leu Ser Leu Arg Asn Arg
   1160                 1165                1170

Leu Gln Arg Glu Leu Lys Tyr Pro Ala Arg His Arg Val Arg Val
   1175                 1180                1185

Gly Ala Gly Gly Gly Ile Gly Cys Pro Gln Ala Ala Leu Gly Ala
   1190                 1195                1200

Phe His Met Gly Ala Ala Phe Val Val Thr Gly Thr Val Asn Gln
   1205                 1210                1215

Leu Ser Arg Gln Ala Gly Thr Cys Asp Asn Val Arg Arg Gln Leu
   1220                 1225                1230

Ser Arg Ala Thr Tyr Ser Asp Ile Thr Met Ala Pro Ala Ala Asp
   1235                 1240                1245

Met Phe Glu Gln Gly Val Glu Leu Gln Val Leu Lys Lys Gly Thr
   1250                 1255                1260

Met Phe Pro Ser Arg Ala Lys Lys Leu Phe Glu Leu Phe His Lys
   1265                 1270                1275

Tyr Asp Ser Phe Glu Ala Met Pro Ala Asp Glu Leu Ala Arg Val
   1280                 1285                1290

Glu Lys Arg Ile Phe Ser Lys Ser Leu Ala Glu Val Trp Ala Glu
   1295                 1300                1305

Thr Lys Asp Phe Tyr Ile Thr Arg Leu Asn Asn Pro Glu Lys Ile
   1310                 1315                1320

Arg Lys Ala Glu Asn Glu Asp Pro Lys Leu Lys Met Ser Leu Cys
   1325                 1330                1335

Phe Arg Trp Tyr Leu Gly Leu Ser Ser Phe Trp Ala Asn Asn Gly
   1340                 1345                1350

Ile Ala Asp Arg Thr Met Asp Tyr Gln Ile Trp Cys Gly Pro Ala
   1355                 1360                1365

Ile Gly Ala Phe Asn Asp Phe Ile Ala Asp Ser Tyr Leu Asp Val
   1370                 1375                1380
```

Ala Val Ser Gly Glu Phe Pro Asp Val Val Gln Ile Asn Leu Gln
1385             1390                 1395

Ile Leu Ser Gly Ala Ala Tyr Leu Gln Arg Leu Leu Ser Val Lys
1400             1405                 1410

Leu Ala Pro Arg Ile Asp Val Asp Thr Glu Asp Leu Phe Thr
1415             1420                 1425

Tyr Arg Pro Asp His Ala Leu
1430             1435

<210> SEQ ID NO 7
<211> LENGTH: 1395
<212> TYPE: DNA
<213> ORGANISM: Schizochytrium sp.

<400> SEQUENCE: 7

```
actcgcatcg cgatcgtggg gatgtcggcg atcctgccga gcggggagaa cgtgcgcgag      60
agctgggagg cgatccgcga tgggctggat tgcctgagcg atctgccggc ggaccgcgtg     120
gacgtgacgg cctactacaa cccggagaag acgaccaagg acaagatcta ctgcaagcgc     180
ggcgggttca tcccggagta cgacttcgac gcgcgtgagt tcgggctcaa catgttccag     240
atggaggact cggacgccaa ccagacgatc tcgctgctca aggtgaagga ggcgctgacg     300
gacgccaaca tcccggcgtt ctcgagcggt aagaagaaca tcggctgcgt gctgggcatc     360
ggcggcggcc agaaggcgag ccacgagttc tactcgcggc tcaactacgt ggtcgtggac     420
aaggtgctgc gcaagatggg cctgccggag gaagacgtgg cggcggcggt ggacaagtac     480
aaggcgagtt tccccgagtg cgcgcctcgac tctttccccg ggttcctggg caacgtcacg     540
gcggggcgct gctgcaatac cttcaacatg gagggcatga actgcgtcgt ggacgcggcc     600
tgcgcgtcgt cgctgatcgc ggtcaaagtg gcgatcgagg agctgctcta cggcgactgc     660
gatgcgatga tcgcgggtgc cacctgcacg gacaactcga tcgggatgta catggccttc     720
tccaagacgc ccgtgttttc cacggacccg agcgtcaagg cgtacgacgc cgccaccaaa     780
ggcatgctca tcggcgaggg ctcggcgatg ctcgtgctga gcgctacgc ggacgccgtg     840
cgcgacggcg acaccgtgca cgccgtcatc aaggggtgcg cgtcctcgag cgacggcaag     900
gcggcgggca tctacacgcc gacaatctcg ggccaggagg aggccctgcg ccgcgcctac     960
gcccgcgcca atgtcgaccc ggccactgtg acgctggtgg agggccacgg cacgggtacg    1020
ccggtgggcg acaagatcga gctgacggcg ctgagcaacc tcttctccaa ggcgttttct    1080
gccaacggtg cggcgcggga ggaagcagag caggtggcgg tgggcagcat caagtcgcag    1140
atcgggcacc tcaaggcggt ggccgggctg ccgggctgg tcaaggtggt gctggcgctc    1200
aagcacaaga cgctgccgca gacgatcaac gtcgacaagc cgccgtcgct ggtggacggg    1260
accccgatcc agcagtcgcc gctgtacgtc aacacgatga accgcccctg gttcacgccc    1320
gtaggggtgc cgcgccgcgc cggcgtgtcg tcgtttgggt ttggcggtgc caactaccac    1380
gccgtgctgg aggag                                                    1395
```

<210> SEQ ID NO 8
<211> LENGTH: 465
<212> TYPE: PRT
<213> ORGANISM: Schizochytrium sp.

<400> SEQUENCE: 8

Thr Arg Ile Ala Ile Val Gly Met Ser Ala Ile Leu Pro Ser Gly Glu
1               5                   10                  15

-continued

```
Asn Val Arg Glu Ser Trp Glu Ala Ile Arg Asp Gly Leu Asp Cys Leu
             20                  25                  30

Ser Asp Leu Pro Ala Asp Arg Val Asp Val Thr Ala Tyr Tyr Asn Pro
         35                  40                  45

Glu Lys Thr Thr Lys Asp Lys Ile Tyr Cys Lys Arg Gly Gly Phe Ile
     50                  55                  60

Pro Glu Tyr Asp Phe Asp Ala Arg Glu Phe Gly Leu Asn Met Phe Gln
65                  70                  75                  80

Met Glu Asp Ser Asp Ala Asn Gln Thr Ile Ser Leu Leu Lys Val Lys
                 85                  90                  95

Glu Ala Leu Thr Asp Ala Asn Ile Pro Ala Phe Ser Ser Gly Lys Lys
            100                 105                 110

Asn Ile Gly Cys Val Leu Gly Ile Gly Gly Gln Lys Ala Ser His
        115                 120                 125

Glu Phe Tyr Ser Arg Leu Asn Tyr Val Val Asp Lys Val Leu Arg
    130                 135                 140

Lys Met Gly Leu Pro Glu Glu Asp Val Ala Ala Val Asp Lys Tyr
145                 150                 155                 160

Lys Ala Ser Phe Pro Glu Trp Arg Leu Asp Ser Phe Pro Gly Phe Leu
                165                 170                 175

Gly Asn Val Thr Ala Gly Arg Cys Cys Asn Thr Phe Asn Met Glu Gly
            180                 185                 190

Met Asn Cys Val Val Asp Ala Ala Cys Ala Ser Ser Leu Ile Ala Val
        195                 200                 205

Lys Val Ala Ile Glu Glu Leu Leu Tyr Gly Asp Cys Asp Ala Met Ile
210                 215                 220

Ala Gly Ala Thr Cys Thr Asp Asn Ser Ile Gly Met Tyr Met Ala Phe
225                 230                 235                 240

Ser Lys Thr Pro Val Phe Ser Thr Asp Pro Ser Val Lys Ala Tyr Asp
                245                 250                 255

Ala Ala Thr Lys Gly Met Leu Ile Gly Glu Gly Ser Ala Met Leu Val
            260                 265                 270

Leu Lys Arg Tyr Ala Asp Ala Val Arg Asp Gly Asp Thr Val His Ala
        275                 280                 285

Val Ile Lys Gly Cys Ala Ser Ser Ser Asp Gly Lys Ala Ala Gly Ile
    290                 295                 300

Tyr Thr Pro Thr Ile Ser Gly Gln Glu Glu Ala Leu Arg Arg Ala Tyr
305                 310                 315                 320

Ala Arg Ala Asn Val Asp Pro Ala Thr Val Thr Leu Val Glu Gly His
                325                 330                 335

Gly Thr Gly Thr Pro Val Gly Asp Lys Ile Glu Leu Thr Ala Leu Ser
            340                 345                 350

Asn Leu Phe Ser Lys Ala Phe Ser Ala Asn Gly Gly Ala Glu Glu
        355                 360                 365

Ala Glu Gln Val Ala Val Gly Ser Ile Lys Ser Gln Ile Gly His Leu
    370                 375                 380

Lys Ala Val Ala Gly Leu Ala Gly Leu Val Lys Val Val Leu Ala Leu
385                 390                 395                 400

Lys His Lys Thr Leu Pro Gln Thr Ile Asn Val Asp Lys Pro Pro Ser
                405                 410                 415

Leu Val Asp Gly Thr Pro Ile Gln Gln Ser Pro Leu Tyr Val Asn Thr
            420                 425                 430

Met Asn Arg Pro Trp Phe Thr Pro Val Gly Val Pro Arg Arg Ala Gly
```

```
                435                 440                 445
Val Ser Ser Phe Gly Phe Gly Gly Ala Asn Tyr His Ala Val Leu Glu
    450                 455                 460

Glu
465

<210> SEQ ID NO 9
<211> LENGTH: 903
<212> TYPE: DNA
<213> ORGANISM: Schizochytrium sp.

<400> SEQUENCE: 9
ttctcgggcc agggcgcgca gtacacgcac atgttcagcg acgtggcgat gaactggccc      60
ccgttccgcg agagcgtcgc cgccatggac cgcgcccagc gcgagcgctt cgggcggcct     120
gccaagcgcg tgagcagcgt gctgtacccg cgcaagccgt acggcgacga accgcggcag     180
gaccacaagg agatctcgca aacgcgctac tcgcagcccg caacgctcgc gtgctcggtc     240
ggcgcctttg acatcttcaa agcggcggga ctggcgccga ctttgcggc gggccactcg      300 ctgggcgagt ttgcggcgct ctacgcggcc gggtcgctcg atcgcgacgc cgtcttcgac     360
ctggtctgcg cgcgcgccaa ggccatgagc gacttcacgg cccaggccag cagcagcggt     420
ggcgccatgg cggccgtgat tggcgccaag gcggaccagc tctcgctggg tggcgcgccc     480
gacgtgtggc tcgccaacag caactcgccc tcgcagaccg tgatcacggg aaccgccgaa     540
gcagtggctg cggcctctga caagttgcgc tgcagcggca acttccgcgt cgtgcctctg     600
gcctgcgagg cggccttcca ctcgccgcac atgcgcggcg cggagcagac gtttgcgtcg     660
gcgctcgcgc aggcgcccgt gtcggcaccg gcggctgctc ggttctactc taacgtgacg     720
gggggcgccc cggtaacctc gcccgcggac gtcaaaacga acctgggcaa gcacatgacg     780
agccctgtgc agttcgtgca gcaggtgcga gccatgcacg cggcgggcgc gcgtgtgttt     840
gtggagtttg ggcccaagca ggtcctgtcg cgcctcgtca aggagaccct tggcgaggcc     900
ggc                                                                   903

<210> SEQ ID NO 10
<211> LENGTH: 301
<212> TYPE: PRT
<213> ORGANISM: Schizochytrium sp.

<400> SEQUENCE: 10

Phe Ser Gly Gln Gly Ala Gln Tyr Thr His Met Phe Ser Asp Val Ala
1               5                   10                  15

Met Asn Trp Pro Pro Phe Arg Glu Ser Val Ala Ala Met Asp Arg Ala
            20                  25                  30

Gln Arg Glu Arg Phe Gly Arg Pro Ala Lys Arg Val Ser Ser Val Leu
        35                  40                  45

Tyr Pro Arg Lys Pro Tyr Gly Asp Glu Pro Arg Gln Asp His Lys Glu
    50                  55                  60

Ile Ser Gln Thr Arg Tyr Ser Gln Pro Ala Thr Leu Ala Cys Ser Val
65                  70                  75                  80

Gly Ala Phe Asp Ile Phe Lys Ala Ala Gly Leu Ala Pro Ser Phe Ala
                85                  90                  95

Ala Gly His Ser Leu Gly Glu Phe Ala Ala Leu Tyr Ala Ala Gly Ser
            100                 105                 110

Leu Asp Arg Asp Ala Val Phe Asp Leu Val Cys Ala Arg Ala Lys Ala
        115                 120                 125
```

```
Met Ser Asp Phe Thr Ala Gln Ala Ser Ser Gly Gly Ala Met Ala
130                 135                 140

Ala Val Ile Gly Ala Lys Ala Asp Gln Leu Ser Leu Gly Gly Ala Pro
145                 150                 155                 160

Asp Val Trp Leu Ala Asn Ser Asn Ser Pro Ser Gln Thr Val Ile Thr
            165                 170                 175

Gly Thr Ala Glu Ala Val Ala Ala Ala Ser Asp Lys Leu Arg Cys Ser
            180                 185                 190

Gly Asn Phe Arg Val Val Pro Leu Ala Cys Glu Ala Ala Phe His Ser
        195                 200                 205

Pro His Met Arg Gly Ala Glu Gln Thr Phe Ala Ser Ala Leu Ala Gln
210                 215                 220

Ala Pro Val Ser Ala Pro Ala Ala Arg Phe Tyr Ser Asn Val Thr
225                 230                 235                 240

Gly Gly Ala Ala Val Thr Ser Pro Ala Asp Val Lys Thr Asn Leu Gly
            245                 250                 255

Lys His Met Thr Ser Pro Val Gln Phe Val Gln Val Arg Ala Met
            260                 265                 270

His Ala Ala Gly Ala Arg Val Phe Val Glu Phe Gly Pro Lys Gln Val
        275                 280                 285

Leu Ser Arg Leu Val Lys Glu Thr Leu Gly Glu Ala Gly
290                 295                 300
```

<210> SEQ ID NO 11
<211> LENGTH: 2103
<212> TYPE: DNA
<213> ORGANISM: Schizochytrium sp.

<400> SEQUENCE: 11

```
tccggcaaca gcaagagcac tcgtggcagt gctgatctgc aagcgctgct ggccaaggcg      60
gagactgtgg tgatggctgt gctggctgcc aagactggct acgaggccga catggttgag     120
gcggacatgg acctggaggc cgagctcggc atcgactcga tcaagcgcgt ggagatcctt     180
tccgaggtgc agggccagct gggcgtcgag gccaaggacg tggatgcgct gagccgcacg     240
cgcacggtcg gtgaggttgt ggacgccatg aaggcggaga tcgtggctgc ctctggtggt     300
agtgctcctg cggttccttc ggcgcccgct gcttctgcag ctccgactcc cgctgcttcg     360
actgcgcctt ctgctgatct gcaagcgctg ctgtccaagg cggagactgt ggtgatggct     420
gtgctggcgg ccaagactgg ctacgaggcc gacatggtcg aggcggacat ggacctggag     480
gccgagctcg gcatcgactc gatcaagcgc gtggagatcc tctcggaggt gcagggccag     540
ctgggcgtcg aggccaagga cgtggatgcg ctgagccgca cgcgcacggt cggtgaggtt     600
gtggatgcca tgaaggcgga aatcgtggct gcctctgctg gtagtgctcc tgctcctgct     660
gttccttcgg cgcccgctgc ttctgcagct ccgactcccg ctgcttcgac tgcgccttct     720
gctgatctgc aagcgctgct gtccaaggcg gagacggtgg tgatggctgt gctggcggcc     780
aagactggct acgaggccga catggtcgag gcggacatgg acctggaggc cgagctcggc     840
atcgactcga tcaagcgcgt ggagatcctc tcggaggtgc agggccagct gggcgtcgag     900
gccaaggacg tggatgcgct gagccgcacg cgcacggtcg gtgaggttgt ggatgccatg     960
aaggcggaaa tcgtggctgc ctctggtggt agtgctcctg ctcctgcggt tccttcggcg    1020
cccgctgctt ctgcagctcc gactcccgcg ctgcgacag cgccttctgc tgatctgcaa    1080
gcgctgctgg ccaaggcgga gactgtggtg atggctgtgc tggcggccaa gactggctac    1140
```

```
gaggccgaca tggtcgaggc ggacatggac ctggaggccg agctcggcat cgactcgatc    1200
aagcgcgtgg agatcctttc cgaggtgcag ggccagctgg gcgtcgaggc caaggacgta    1260
gatgcgctga ccgcacgcg cacggtcggt gaggttgtgg atgccatgaa ggcggagatc     1320
gtggctgcct ctgctggtag tgctcctgct cctgctgttc cttcggcgcc cgctgcttct    1380
gcagctccga ctcccgctgc ttcgactgcg ccttctgctg atctgcaagc gctgctgtcc    1440
aaggcggaga ctgtggtgat ggctgtgctg gcggccaaga ctggctacga ggccgacatg    1500
gtcgaggcgg acatggacct ggaggccgag ctcggcatcg actcgatcaa gcgcgtggag    1560
atcctctcgg aggtgcaggg ccagctgggc gtcgaggcca aggacgtgga tgcgctgagc    1620
cgcacgcgca cggtcggtga ggttgtggat gccatgaagg cggaaatcgt ggctgcctct    1680
ggtggtagtg ctcctgctgc tgctgttcct tcggcgcccg ctgcttctgc agctccgact    1740
cctgcgactg cgccttctgc tgatctgcaa gcgctgctgt ccaaggcgga gactgtggtg    1800
atggctgtgc tggcggccaa gactggctac gaggccgaca tggtcgaggc ggacatggac    1860
ctggaggccg agctcggcat cgactcgatc aagcgcgtgg agatcctttc cgaggtgcag    1920
ggccagctgg gcgtcgaggc caaggacgta gatgcgctga ccgcacgcg cacggtcggt     1980 gaagtggtgg acgccatgaa ggcggagatc gtggctgcct ctggtggtag tgctcctgct    2040
gctccttcgg cgcccgcgct tcttccaacg ctgtttggtt ccgagtgcga ggacctgtct    2100
ctg                                                                 2103

<210> SEQ ID NO 12
<211> LENGTH: 701
<212> TYPE: PRT
<213> ORGANISM: Schizochytrium sp.

<400> SEQUENCE: 12

Ser Gly Asn Ser Lys Ser Thr Arg Gly Ser Ala Asp Leu Gln Ala Leu
1               5                   10                  15

Leu Ala Lys Ala Glu Thr Val Val Met Ala Val Leu Ala Ala Lys Thr
            20                  25                  30

Gly Tyr Glu Ala Asp Met Val Glu Ala Asp Met Asp Leu Glu Ala Glu
        35                  40                  45

Leu Gly Ile Asp Ser Ile Lys Arg Val Glu Ile Leu Ser Glu Val Gln
    50                  55                  60

Gly Gln Leu Gly Val Glu Ala Lys Asp Val Asp Ala Leu Ser Arg Thr
65                  70                  75                  80

Arg Thr Val Gly Glu Val Val Asp Ala Met Lys Ala Glu Ile Val Ala
                85                  90                  95

Ala Ser Gly Gly Ser Ala Pro Ala Val Pro Ser Ala Pro Ala Ala Ser
            100                 105                 110

Ala Ala Pro Thr Pro Ala Ala Ser Thr Ala Pro Ser Ala Asp Leu Gln
        115                 120                 125

Ala Leu Leu Ser Lys Ala Glu Thr Val Val Met Ala Val Leu Ala Ala
    130                 135                 140

Lys Thr Gly Tyr Glu Ala Asp Met Val Glu Ala Asp Met Asp Leu Glu
145                 150                 155                 160

Ala Glu Leu Gly Ile Asp Ser Ile Lys Arg Val Glu Ile Leu Ser Glu
                165                 170                 175

Val Gln Gly Gln Leu Gly Val Glu Ala Lys Asp Val Asp Ala Leu Ser
            180                 185                 190
```

```
Arg Thr Arg Thr Val Gly Glu Val Val Asp Ala Met Lys Ala Glu Ile
            195                 200                 205

Val Ala Ala Ser Ala Gly Ser Ala Pro Ala Pro Ala Val Pro Ser Ala
    210                 215                 220

Pro Ala Ala Ser Ala Ala Pro Thr Pro Ala Ala Ser Thr Ala Pro Ser
225                 230                 235                 240

Ala Asp Leu Gln Ala Leu Leu Ser Lys Ala Glu Thr Val Val Met Ala
                245                 250                 255

Val Leu Ala Ala Lys Thr Gly Tyr Glu Ala Asp Met Val Glu Ala Asp
            260                 265                 270

Met Asp Leu Glu Ala Glu Leu Gly Ile Asp Ser Ile Lys Arg Val Glu
    275                 280                 285

Ile Leu Ser Glu Val Gln Gly Gln Leu Gly Val Glu Ala Lys Asp Val
    290                 295                 300

Asp Ala Leu Ser Arg Thr Arg Thr Val Gly Glu Val Val Asp Ala Met
305                 310                 315                 320

Lys Ala Glu Ile Val Ala Ala Ser Gly Gly Ser Ala Pro Ala Pro Ala
                325                 330                 335

Val Pro Ser Ala Pro Ala Ala Ser Ala Ala Pro Thr Pro Ala Ala Ala
            340                 345                 350

Thr Ala Pro Ser Ala Asp Leu Gln Ala Leu Leu Ala Lys Ala Glu Thr
    355                 360                 365

Val Val Met Ala Val Leu Ala Ala Lys Thr Gly Tyr Glu Ala Asp Met
    370                 375                 380

Val Glu Ala Asp Met Asp Leu Glu Ala Glu Leu Gly Ile Asp Ser Ile
385                 390                 395                 400

Lys Arg Val Glu Ile Leu Ser Glu Val Gln Gly Gln Leu Gly Val Glu
                405                 410                 415

Ala Lys Asp Val Asp Ala Leu Ser Arg Thr Arg Thr Val Gly Glu Val
            420                 425                 430

Val Asp Ala Met Lys Ala Glu Ile Val Ala Ala Ser Ala Gly Ser Ala
    435                 440                 445

Pro Ala Pro Ala Val Pro Ser Ala Pro Ala Ala Ser Ala Ala Pro Thr
450                 455                 460

Pro Ala Ala Ser Thr Ala Pro Ser Ala Asp Leu Gln Ala Leu Leu Ser
465                 470                 475                 480

Lys Ala Glu Thr Val Val Met Ala Val Leu Ala Ala Lys Thr Gly Tyr
                485                 490                 495

Glu Ala Asp Met Val Glu Ala Asp Met Asp Leu Glu Ala Glu Leu Gly
            500                 505                 510

Ile Asp Ser Ile Lys Arg Val Glu Ile Leu Ser Glu Val Gln Gly Gln
    515                 520                 525

Leu Gly Val Glu Ala Lys Asp Val Asp Ala Leu Ser Arg Thr Arg Thr
    530                 535                 540

Val Gly Glu Val Val Asp Ala Met Lys Ala Glu Ile Val Ala Ala Ser
545                 550                 555                 560

Gly Gly Ser Ala Pro Ala Ala Val Pro Ser Ala Pro Ala Ala Ser
                565                 570                 575

Ala Ala Pro Thr Pro Ala Thr Ala Pro Ser Ala Asp Leu Gln Ala Leu
            580                 585                 590

Leu Ser Lys Ala Glu Thr Val Val Met Ala Val Leu Ala Ala Lys Thr
    595                 600                 605

Gly Tyr Glu Ala Asp Met Val Glu Ala Asp Met Asp Leu Glu Ala Glu
```

```
             610                615                620
Leu Gly Ile Asp Ser Ile Lys Arg Val Glu Ile Leu Ser Glu Val Gln
625                 630                635                640

Gly Gln Leu Gly Val Glu Ala Lys Asp Val Asp Ala Leu Ser Arg Thr
            645                 650                655

Arg Thr Val Gly Glu Val Val Asp Ala Met Lys Ala Glu Ile Val Ala
            660                 665                670

Ala Ser Gly Ser Ala Pro Ala Ala Pro Ser Ala Pro Ala Leu Leu
            675                 680                685

Pro Thr Leu Phe Gly Ser Glu Cys Glu Asp Leu Ser Leu
690                 695                700
```

<210> SEQ ID NO 13
<211> LENGTH: 276
<212> TYPE: DNA
<213> ORGANISM: Schizochytrium sp.

<400> SEQUENCE: 13

```
agtgctgatc tgcaagcgct gctggccaag gcggagactg tggtgatggc tgtgctggct      60
gccaagactg gctacgaggc cgacatggtt gaggcggaca tggacctgga ggccgagctc     120
ggcatcgact cgatcaagcg cgtggagatc ctttccgagg tgcagggcca gctgggcgtc     180
gaggccaagg acgtggatgc gctgagccgc acgcgcacgg tcggtgaggt tgtggacgcc     240
atgaaggcgg agatcgtggc tgcctctggt ggtagt                               276
```

<210> SEQ ID NO 14
<211> LENGTH: 92
<212> TYPE: PRT
<213> ORGANISM: Schizochytrium sp.

<400> SEQUENCE: 14

```
Ser Ala Asp Leu Gln Ala Leu Leu Ala Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
            35                  40                  45

Glu Ile Leu Ser Glu Val Gln Gly Gln Leu Gly Val Glu Ala Lys Asp
        50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Gly Gly Ser
            85                  90
```

<210> SEQ ID NO 15
<211> LENGTH: 276
<212> TYPE: DNA
<213> ORGANISM: Schizochytrium sp.

<400> SEQUENCE: 15

```
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctgct ggtagt                               276
```

<210> SEQ ID NO 16
<211> LENGTH: 92
<212> TYPE: PRT
<213> ORGANISM: Schizochytrium sp.

<400> SEQUENCE: 16

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Ala Gly Ser
                85                  90

<210> SEQ ID NO 17
<211> LENGTH: 276
<212> TYPE: DNA
<213> ORGANISM: Schizochytrium sp.

<400> SEQUENCE: 17
tctgctgatc tgcaagcgct gctgtccaag gcggagacgg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcgtgaggt tgtggatgcc     240 atgaaggcgg aaatcgtggc tgcctctggt ggtagt                              276

<210> SEQ ID NO 18
<211> LENGTH: 92
<212> TYPE: PRT
<213> ORGANISM: Schizochytrium sp.

<400> SEQUENCE: 18

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Gly Gly Ser
                85                  90

<210> SEQ ID NO 19
<211> LENGTH: 276
<212> TYPE: DNA
<213> ORGANISM: Schizochytrium sp.

<400> SEQUENCE: 19
tctgctgatc tgcaagcgct gctggccaag gcggagactg tggtgatggc tgtgctggcg      60

```
gccaagactg gctacgaggc cgacatggtc gaggcggaca tggacctgga ggccgagctc    120
ggcatcgact cgatcaagcg cgtggagatc ctttccgagg tgcagggcca gctgggcgtc    180
gaggccaagg acgtagatgc gctgagccgc acgcgcacgg tcggtgaggt tgtggatgcc    240
atgaaggcgg agatcgtggc tgcctctgct ggtagt                              276
```

<210> SEQ ID NO 20
<211> LENGTH: 92
<212> TYPE: PRT
<213> ORGANISM: Schizochytrium sp.

<400> SEQUENCE: 20

```
Ser Ala Asp Leu Gln Ala Leu Leu Ala Lys Ala Glu Thr Val Val Met
1               5                   10                  15

Ala Val Leu Ala Ala Lys Thr Gly Tyr Glu Ala Asp Met Val Glu Ala
                20                  25                  30

Asp Met Asp Leu Glu Ala Glu Leu Gly Ile Asp Ser Ile Lys Arg Val
            35                  40                  45

Glu Ile Leu Ser Glu Val Gln Gly Gln Leu Gly Val Glu Ala Lys Asp
        50                  55                  60

Val Asp Ala Leu Ser Arg Thr Arg Thr Val Gly Val Val Asp Ala
65                  70                  75                  80

Met Lys Ala Glu Ile Val Ala Ala Ser Ala Gly Ser
                85                  90
```

<210> SEQ ID NO 21
<211> LENGTH: 276
<212> TYPE: DNA
<213> ORGANISM: Schizochytrium sp.

<400> SEQUENCE: 21

```
tctgctgatc tgcaagcgct gctgtccaag gcggagactg tggtgatggc tgtgctggcg    60
gccaagactg gctacgaggc cgacatggtc gaggcggaca tggacctgga ggccgagctc    120
ggcatcgact cgatcaagcg cgtggagatc ctctcggagg tgcagggcca gctgggcgtc    180
gaggccaagg acgtggatgc gctgagccgc acgcgcacgg tcggtgaggt tgtggatgcc    240
atgaaggcgg aaatcgtggc tgcctctggt ggtagt                              276
```

<210> SEQ ID NO 22
<211> LENGTH: 92
<212> TYPE: PRT
<213> ORGANISM: Schizochytrium sp.

<400> SEQUENCE: 22

```
Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
                20                  25                  30

Asp Met Asp Leu Glu Ala Glu Leu Gly Ile Asp Ser Ile Lys Arg Val
            35                  40                  45

Glu Ile Leu Ser Glu Val Gln Gly Gln Leu Gly Val Glu Ala Lys Asp
        50                  55                  60

Val Asp Ala Leu Ser Arg Thr Arg Thr Val Gly Val Val Asp Ala
65                  70                  75                  80

Met Lys Ala Glu Ile Val Ala Ala Ser Gly Gly Ser
                85                  90
```

<210> SEQ ID NO 23
<211> LENGTH: 276
<212> TYPE: DNA
<213> ORGANISM: Schizochytrium sp.

<400> SEQUENCE: 23

```
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctttccgagg tgcagggcca gctgggcgtc     180
gaggccaagg acgtagatgc gctgagccgc acgcgcacgg tcggtgaagt ggtggacgcc     240
atgaaggcgg agatcgtggc tgcctctggt ggtagt                               276
```

<210> SEQ ID NO 24
<211> LENGTH: 92
<212> TYPE: PRT
<213> ORGANISM: Schizochytrium sp.

<400> SEQUENCE: 24

```
Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Gly Gly Ser
                85                  90
```

<210> SEQ ID NO 25
<211> LENGTH: 2178
<212> TYPE: DNA
<213> ORGANISM: Schizochytrium sp.

<400> SEQUENCE: 25

```
gcgctacagg cggcgctcac gtccgtcgag gcgcagttcg gcaaggtggg tggctttgtg      60
ttccagttcg gcgacgacga cgtgcaagcg cagctcggct gggcgctgct cgcggccaag     120
cacctcaaaa cttcgctgtc agaacagatc gagggcggtc gcacctttttt cgtgccgtc    180 gcgcggctcg acggccagct gggctctcc ggcaagtcga cgaccgctac cgttgatctc      240
tcccgcgcgc agcagggcag cgtgttcggc ctgtgcaaga cactcgacct ggagtggccc     300
gctgtcttct gccgcggaat cgacctggcc gccgacctcg acgccgcaca ggccgcgcgg     360
tgcctgctgg gcgagctgtc agaccccgac gtggccgtgc gcgagtctgg ttactccgcc     420
tcgggccagc gctgcacgac aactacgaag tcgctgacta cgggcaagcc gcaccagccg     480
atctcctcgt cggacctctt tctggtgtcg ggcggcgcgc gcggcatcac ccgctgtgc      540 gtgcgcgagc tggcgcagcg cgtgggcggc ggcacgtacg tgctcatcgg ccgctcggag     600
ctgcccacga cggagcctgc ctgggcggtc ggcgtggagt ctggcaagcc gctggagaag     660
gccgcgctgg cgttcctgaa ggcggagttt gcagcgggcc gcggggccaa gccgacgccg     720
atgctgcaca agaagctcgt gggcgccgtg gtcgagcgc gcgaggtgcg agcctcgctc      780
gccgagatca ctgcacaggg cgccacggct gtgtacgagt cgtgcgacgt gagctctgcc     840
```

```
gccaaggtgc gtgagatggt agagcgcgtg cagcagcagg gcgggcggcg cgtgtcgggc    900
gtgttccacg cgtcgggcgt gctgcgcgac aagctcgtgg agaacaagtc gctggcggac    960
ttcagcgccg tgtacgacac caaggtgggc ggcctcatca acctgctggc ctgcgtggac   1020
ctggcgcagc tgcgtcacct cgtgctcttc agctcgctcg cgggcttcca cggcaacgtc   1080
gggcagtcgg actacgcaat ggccaacgag gcgctcaaca agctggcggc gcacctgtcg   1140
gcggtgcacc cgcagctgtg cgcgcgctcg atctgcttcg accgtgggac ggcggcatg    1200
gtgacccccg cgctcaaggc caacttcatc cgcatgggca tccagatcat cccgcgccaa   1260
ggcggcgcgc agaccgtcgc caacatgctc gtcagtagct ccccggtca gctgctcgtg    1320
ggcaactggg gcgtgccacc cgtcgtgccg agtgccaccg agcacaccgt gctgcagacg   1380
ctccgccaga gcgacaaccc cttcctcgac tcgcacgtga tccagggccg ccgcgtgctg   1440
cccatgaccc tggccgtggg ctacatggcg caccaggcgc agagcatcta cgcgggccac   1500
cagctgtggg ccgtcgagga cgcccagctc ttcaagggca tcgccatcga caatggcgcc   1560
gacgtgcccg tgcgcgtgga gctgtcgcgc cgcaaggagg agcaggagga cgccggcaag   1620
gtcaaggtca aggtgcaggt gctgctcaaa tcgcaggtca acggcaagtc ggtgcccgcg   1680
tacaaggcga ccgtcgtgct gtcccctgcg ccgcgcccca gcgtcatcac gcgtgacttc   1740
gacctcaccc cggacccggc ctgcacggag cacgacctct acgacggcaa gacgctcttc   1800
cacggcaagg ccttccaggg catcgagcag gtgctctcgg cgacgcccaa gcagctcacc   1860
gccaagtgcc gcaatttgcc cctcacgccc gagcagcgcg gccagttcgt cgttaacctc   1920
agccagcagg acccgttcca ggcggacatt gcgttccagg cgatgctcgt ctgggcgcgc   1980
atgctgcgcc aatcggcggc cctgcccaac aactgcgagc gcttcgactt ttacaagccg   2040
atggccccgg gcgccaccta ctacacgtcg gtcaagctgg cctcggcctc acccttggtg   2100
gactctgtgt gcaagtgcac cgtggcgatg cacgatgagc aaggtgaggt gtacttttct   2160
gctcgtgcca gcgtcgtc                                                 2178
```

<210> SEQ ID NO 26
<211> LENGTH: 726
<212> TYPE: PRT
<213> ORGANISM: Schizochytrium sp.

<400> SEQUENCE: 26

```
Ala Leu Gln Ala Ala Leu Thr Ser Val Glu Ala Gln Phe Gly Lys Val
1               5                   10                  15

Gly Gly Phe Val Phe Gln Phe Gly Asp Asp Val Gln Ala Gln Leu
            20                  25                  30

Gly Trp Ala Leu Leu Ala Ala Lys His Leu Lys Thr Ser Leu Ser Glu
        35                  40                  45

Gln Ile Glu Gly Gly Arg Thr Phe Phe Val Ala Val Ala Arg Leu Asp
    50                  55                  60

Gly Gln Leu Gly Leu Ser Gly Lys Ser Thr Thr Ala Thr Val Asp Leu
65                  70                  75                  80

Ser Arg Ala Gln Gln Gly Ser Val Phe Gly Leu Cys Lys Thr Leu Asp
                85                  90                  95

Leu Glu Trp Pro Ala Val Phe Cys Arg Gly Ile Asp Leu Ala Ala Asp
            100                 105                 110

Leu Asp Ala Ala Gln Ala Ala Arg Cys Leu Leu Gly Glu Leu Ser Asp
        115                 120                 125
```

```
Pro Asp Val Ala Val Arg Glu Ser Gly Tyr Ser Ala Ser Gly Gln Arg
    130                 135                 140

Cys Thr Thr Thr Thr Lys Ser Leu Thr Thr Gly Lys Pro His Gln Pro
145                 150                 155                 160

Ile Ser Ser Ser Asp Leu Phe Leu Val Ser Gly Gly Ala Arg Gly Ile
                165                 170                 175

Thr Pro Leu Cys Val Arg Glu Leu Ala Gln Arg Val Gly Gly Gly Thr
            180                 185                 190

Tyr Val Leu Ile Gly Arg Ser Glu Leu Pro Thr Thr Glu Pro Ala Trp
        195                 200                 205

Ala Val Gly Val Glu Ser Gly Lys Pro Leu Glu Lys Ala Ala Leu Ala
    210                 215                 220

Phe Leu Lys Ala Glu Phe Ala Ala Gly Arg Gly Ala Lys Pro Thr Pro
225                 230                 235                 240

Met Leu His Lys Lys Leu Val Gly Ala Val Gly Ala Arg Glu Val
                245                 250                 255

Arg Ala Ser Leu Ala Glu Ile Thr Ala Gln Gly Ala Thr Ala Val Tyr
                260                 265                 270

Glu Ser Cys Asp Val Ser Ser Ala Ala Lys Val Arg Glu Met Val Glu
            275                 280                 285

Arg Val Gln Gln Gln Gly Gly Arg Val Ser Gly Val Phe His Ala
    290                 295                 300

Ser Gly Val Leu Arg Asp Lys Leu Val Glu Asn Lys Ser Leu Ala Asp
305                 310                 315                 320

Phe Ser Ala Val Tyr Asp Thr Lys Val Gly Gly Leu Ile Asn Leu Leu
                325                 330                 335

Ala Cys Val Asp Leu Ala Gln Leu Arg His Leu Val Leu Phe Ser Ser
            340                 345                 350

Leu Ala Gly Phe His Gly Asn Val Gly Gln Ser Asp Tyr Ala Met Ala
        355                 360                 365

Asn Glu Ala Leu Asn Lys Leu Ala Ala His Leu Ser Ala Val His Pro
370                 375                 380

Gln Leu Cys Ala Arg Ser Ile Cys Phe Gly Pro Trp Asp Gly Gly Met
385                 390                 395                 400

Val Thr Pro Ala Leu Lys Ala Asn Phe Ile Arg Met Gly Ile Gln Ile
                405                 410                 415

Ile Pro Arg Gln Gly Gly Ala Gln Thr Val Ala Asn Met Leu Val Ser
            420                 425                 430

Ser Ser Pro Gly Gln Leu Leu Val Gly Asn Trp Gly Val Pro Pro Val
        435                 440                 445

Val Pro Ser Ala Thr Glu His Thr Val Leu Gln Thr Leu Arg Gln Ser
    450                 455                 460

Asp Asn Pro Phe Leu Asp Ser His Val Ile Gln Gly Arg Arg Val Leu
465                 470                 475                 480

Pro Met Thr Leu Ala Val Gly Tyr Met Ala His Gln Ala Gln Ser Ile
                485                 490                 495

Tyr Ala Gly His Gln Leu Trp Ala Val Glu Asp Ala Gln Leu Phe Lys
            500                 505                 510

Gly Ile Ala Ile Asp Asn Gly Ala Asp Val Pro Val Arg Val Glu Leu
        515                 520                 525

Ser Arg Arg Lys Glu Glu Gln Glu Asp Ala Gly Lys Val Lys Val Lys
530                 535                 540

Val Gln Val Leu Leu Lys Ser Gln Val Asn Gly Lys Ser Val Pro Ala
```

```
                545                 550                 555                 560
            Tyr Lys Ala Thr Val Val Leu Ser Pro Ala Pro Arg Pro Ser Val Ile
                            565                 570                 575
            Thr Arg Asp Phe Asp Leu Thr Pro Asp Pro Ala Cys Thr Glu His Asp
                            580                 585                 590
            Leu Tyr Asp Gly Lys Thr Leu Phe His Gly Lys Ala Phe Gln Gly Ile
                            595                 600                 605
            Glu Gln Val Leu Ser Ala Thr Pro Lys Gln Leu Thr Ala Lys Cys Arg
                610                 615                 620
            Asn Leu Pro Leu Thr Pro Glu Gln Arg Gly Gln Phe Val Val Asn Leu
            625                 630                 635                 640
            Ser Gln Gln Asp Pro Phe Gln Ala Asp Ile Ala Phe Gln Ala Met Leu
                            645                 650                 655
            Val Trp Ala Arg Met Leu Arg Gln Ser Ala Ala Leu Pro Asn Asn Cys
                            660                 665                 670
            Glu Arg Phe Asp Phe Tyr Lys Pro Met Ala Pro Gly Ala Thr Tyr Tyr
                            675                 680                 685
            Thr Ser Val Lys Leu Ala Ser Ala Ser Pro Leu Val Asp Ser Val Cys
                            690                 695                 700
            Lys Cys Thr Val Ala Met His Asp Glu Gln Gly Glu Val Tyr Phe Ser
            705                 710                 715                 720
            Ala Arg Ala Ser Val Val
                            725

<210> SEQ ID NO 27
<211> LENGTH: 39
<212> TYPE: DNA
<213> ORGANISM: Schizochytrium sp.

<400> SEQUENCE: 27
ctcgactcgc acgtgatcca gggccgccgc gtgctgccc                              39

<210> SEQ ID NO 28
<211> LENGTH: 13
<212> TYPE: PRT
<213> ORGANISM: Schizochytrium sp.

<400> SEQUENCE: 28

Leu Asp Ser His Val Ile Gln Gly Arg Arg Val Leu Pro
1               5                   10

<210> SEQ ID NO 29
<211> LENGTH: 1341
<212> TYPE: DNA
<213> ORGANISM: Schizochytrium sp.

<400> SEQUENCE: 29
gataacattg cggtcgtggg catggcggtg cagtatgccg gatgcaagaa ccaggacgag      60
ttctgggata cgctgatgcg taaggagatc aactcgagcc cgatctcggc ggagcgcctc     120
ggtacgcgct accgcgacct ccacttccac ccgcagcgca gcaagtacgc cgacaccttc     180
tgcaacgatc gctacggctg cgtcgatgcc agcgtcgaca acgagcacga cctcctcgcc     240
gacctggccc ggcgcgccct gctcgacgcc ggaattaacc tcgacgacgc cagcaccacc     300
gccaacctac gcgacttcgg catcgtgagc ggctgcctgt cgttccccat ggacaatctg     360
cagggcgagc tgctcaatct gtaccaagtg catgtggaga accgcgtggg cgcccagcgc     420
ttccgcgact cgcgccccctg gtcggagcgc ccgcgcgctg tctcgcccga ggccagcgac     480
```

```
ccgcgcgtgt actccgaccc ggcgtccttc gtggccaacc agctcggcct ggggcccgtg    540
cgctacagcc tcgatgcagc ctgcgcgtcg gcgctgtact gcctcaagct ggcgtccgac    600
cacttgctct cgcgcagcgc ggacgtgatg ctgtgcggcg ccacatgctt tccggacccg    660
ttcttcattc tctcggggtt ctccaccttc caggcgatgc cgctgggcgg accgacgat    720 aacccactgt ccgtgccgct gcggcagggc agccagggcc tgacgcccgg agagggcggc    780
gccatcatgg tgctgaagcg cctcgaggac gccgtgcgcg acggcgaccg catctacggc    840
accttgctcg gcacgagtct gagcaacgcc gggtgcggcc tgccgctgag cccgcacctg    900
ccgagcgaga gtcgtgcat ggaggacctg tacacgagcg tcggcatcga cccaagcgag    960
gtgcagtacg tggagtgcca cgccacgggc actccgcagg gcgacgtcgt ggaggtagag   1020
gcgctgcgcc actgctttcg aggtaacacg gaccacccgc cgcgcatggg ctccaccaag   1080
ggcaactttg ccacactctc cgtggcggcc gggttcgcag gcatggccaa ggtgctgctg   1140
tcgatgcagc acggcacgat cccgcccacg cccggtgtcg accgctccaa ctgcatcgac   1200
ccgctcgtcg tggacgaggc catcccttgg ccgtactcgt cggcgcaggc gcgggcaggc   1260
aaaccaggcg atgagctcaa gtgcgcctcg ctctccgcct ttggctttgg tggaaccaac   1320
gcgcactgtg tcttccgtga g                                              1341
```

<210> SEQ ID NO 30
<211> LENGTH: 447
<212> TYPE: PRT
<213> ORGANISM: Schizochytrium sp.

<400> SEQUENCE: 30

```
Asp Asn Ile Ala Val Val Gly Met Ala Val Gln Tyr Ala Gly Cys Lys
1               5                   10                  15

Asn Gln Asp Glu Phe Trp Asp Thr Leu Met Arg Lys Glu Ile Asn Ser
            20                  25                  30

Ser Pro Ile Ser Ala Glu Arg Leu Gly Thr Arg Tyr Arg Asp Leu His
        35                  40                  45

Phe His Pro Gln Arg Ser Lys Tyr Ala Asp Thr Phe Cys Asn Asp Arg
    50                  55                  60

Tyr Gly Cys Val Asp Ala Ser Val Asp Asn Glu His Asp Leu Leu Ala
65                  70                  75                  80

Asp Leu Ala Arg Arg Ala Leu Leu Asp Ala Gly Ile Asn Leu Asp Asp
                85                  90                  95

Ala Ser Thr Thr Ala Asn Leu Arg Asp Phe Gly Ile Val Ser Gly Cys
            100                 105                 110

Leu Ser Phe Pro Met Asp Asn Leu Gln Gly Glu Leu Leu Asn Leu Tyr
        115                 120                 125

Gln Val His Val Glu Asn Arg Val Gly Ala Gln Arg Phe Arg Asp Ser
    130                 135                 140

Arg Pro Trp Ser Glu Arg Pro Arg Ala Val Ser Pro Glu Ala Ser Asp
145                 150                 155                 160

Pro Arg Val Tyr Ser Asp Pro Ala Ser Phe Val Ala Asn Gln Leu Gly
                165                 170                 175

Leu Gly Pro Val Arg Tyr Ser Leu Asp Ala Ala Cys Ala Ser Ala Leu
            180                 185                 190

Tyr Cys Leu Lys Leu Ala Ser Asp His Leu Leu Ser Arg Ser Ala Asp
        195                 200                 205

Val Met Leu Cys Gly Ala Thr Cys Phe Pro Asp Pro Phe Phe Ile Leu
```

Ser Gly Phe Ser Thr Phe Gln Ala Met Pro Leu Gly Gly Pro Asp Asp
225                 230                 235                 240

Asn Pro Leu Ser Val Pro Leu Arg Gln Gly Ser Gln Gly Leu Thr Pro
            245                 250                 255

Gly Glu Gly Gly Ala Ile Met Val Leu Lys Arg Leu Glu Asp Ala Val
        260                 265                 270

Arg Asp Gly Asp Arg Ile Tyr Gly Thr Leu Leu Gly Thr Ser Leu Ser
    275                 280                 285

Asn Ala Gly Cys Gly Leu Pro Leu Ser Pro His Leu Pro Ser Glu Lys
290                 295                 300

Ser Cys Met Glu Asp Leu Tyr Thr Ser Val Gly Ile Asp Pro Ser Glu
305                 310                 315                 320

Val Gln Tyr Val Glu Cys His Ala Thr Gly Thr Pro Gln Gly Asp Val
                325                 330                 335

Val Glu Val Glu Ala Leu Arg His Cys Phe Arg Gly Asn Thr Asp His
            340                 345                 350

Pro Pro Arg Met Gly Ser Thr Lys Gly Asn Phe Gly His Thr Leu Val
        355                 360                 365

Ala Ala Gly Phe Ala Gly Met Ala Lys Val Leu Leu Ser Met Gln His
370                 375                 380

Gly Thr Ile Pro Pro Thr Pro Gly Val Asp Arg Ser Asn Cys Ile Asp
385                 390                 395                 400

Pro Leu Val Val Asp Glu Ala Ile Pro Trp Pro Tyr Ser Ser Ala Gln
                405                 410                 415

Ala Arg Ala Gly Lys Pro Gly Asp Glu Leu Lys Cys Ala Ser Leu Ser
            420                 425                 430

Ala Phe Gly Phe Gly Gly Thr Asn Ala His Cys Val Phe Arg Glu
        435                 440                 445

<210> SEQ ID NO 31
<211> LENGTH: 1293
<212> TYPE: DNA
<213> ORGANISM: Schizochytrium sp.

<400> SEQUENCE: 31

```
ggaccgattg ccatcatcgg gatggacgcg acgtttggta ccctcaaggg cctggacgcg      60
tttgagcagg ccatctacaa gggcacggac ggcgccagcg acctgccgag caagcgctgg     120
cggttcctgg cgccgacac ggacttcttg accgccatgg gcctcgacgc cgtgccgcgc     180
gggtgctacg tgcgcgacgt ggacgtggac tacaagcggc tgcggtcgcc gatgatccct     240
gaggacgtcc tgcgcccgca acagctgctg cgcgtggcta cgatggaccg cgcgctgcag     300
gacgctggaa tggcgacggg aggcaaggtg gcggtgctgg tggggctcgg cacggacacc     360
gagctgtacc ggcaccgcgc gcgcgtgaca ctcaaggagc ggctcgaccc ggccgcgttc     420
tcgcccgagc aggtgcagga gatgatggac tacatcaacg actgcggcac ctcgacgtcg     480
tacacgtcgt acatcggcaa cctcgtggcc acgcgcgtgt cctcgcagtg gggctttacg     540
ggcccgtcct tcaccgtcac cgaaggcgca aactcggtct accgctgcct cgagctgggc     600
aagttcctgc tcgacacgca ccaggtggac gccgtcgtgg tggccggcgt cgacctctgt     660
gccaccgccg agaacccttta cctcaaggcg cgccgctccg ccatcagccg acaggaccac     720
cctcgcgcca actttgaggc cagcgccgac gggtactttg ccggcgaggg cagcggcgcc     780
ctggtcctca agcgccaggc cgacgttggc tcagacgaca aggtctacgc cagtgtcgcg     840
```

```
ggcctcacgt gcgccgcgca gcccgctgaa gccgtgtcgc cgctactact ccaagtccac   900
aacgacgaca acgagaagag ggtggtggag atggtggagc tcgccgccga ctcgggtcgc   960
catgcgccgc acttggccaa ctcgccgctg agcgccgagt cgcagctgga gcaagtgtcc  1020
aagttgctcg cgcaccaggt gccgggctcg gtggccatcg gcagcgtgcg cgccaacgtg  1080
ggagacgtcg ggtacgcctc gggcgccgcg agcctcatca agacggcgct gtgcctccac  1140
aaccgctacc tcccggccaa cccgcagtgg gagcggccgg tggcgccggt ctccgaggcg  1200
ctgtttactt gcccgcgctc gcgtgcctgg ctgaagaacc cgggcgagtc gcgactggcg  1260
gctgtcgcca gtgcctccga gagcgggtcc tgc                               1293
```

<210> SEQ ID NO 32
<211> LENGTH: 431
<212> TYPE: PRT
<213> ORGANISM: Schizochytrium sp.

<400> SEQUENCE: 32

```
Gly Pro Ile Ala Ile Gly Met Asp Ala Thr Phe Gly Thr Leu Lys
1               5                   10                  15

Gly Leu Asp Ala Phe Glu Gln Ala Ile Tyr Lys Gly Thr Asp Gly Ala
            20                  25                  30

Ser Asp Leu Pro Ser Lys Arg Trp Arg Phe Leu Gly Ala Asp Thr Asp
            35                  40                  45

Phe Leu Thr Ala Met Gly Leu Asp Ala Val Pro Arg Gly Cys Tyr Val
        50                  55                  60

Arg Asp Val Asp Val Asp Tyr Lys Arg Leu Arg Ser Pro Met Ile Pro
65                  70                  75                  80

Glu Asp Val Leu Arg Pro Gln Gln Leu Leu Ala Val Ala Thr Met Asp
                85                  90                  95

Arg Ala Leu Gln Asp Ala Gly Met Ala Thr Gly Gly Lys Val Ala Val
            100                 105                 110

Leu Val Gly Leu Gly Thr Asp Thr Glu Leu Tyr Arg His Arg Ala Arg
        115                 120                 125

Val Thr Leu Lys Glu Arg Leu Asp Pro Ala Ala Phe Ser Pro Glu Gln
    130                 135                 140

Val Gln Glu Met Met Asp Tyr Ile Asn Asp Cys Gly Thr Ser Thr Ser
145                 150                 155                 160

Tyr Thr Ser Tyr Ile Gly Asn Leu Val Ala Thr Arg Val Ser Ser Gln
                165                 170                 175

Trp Gly Phe Thr Gly Pro Ser Phe Thr Val Thr Glu Gly Ala Asn Ser
            180                 185                 190

Val Tyr Arg Cys Leu Glu Leu Gly Lys Phe Leu Leu Asp Thr His Gln
        195                 200                 205

Val Asp Ala Val Val Val Ala Gly Val Asp Leu Cys Ala Thr Ala Glu
    210                 215                 220

Asn Leu Tyr Leu Lys Ala Arg Arg Ser Ala Ile Ser Arg Gln Asp His
225                 230                 235                 240

Pro Arg Ala Asn Phe Glu Ala Ser Ala Asp Gly Tyr Phe Ala Gly Glu
                245                 250                 255

Gly Ser Gly Ala Leu Val Leu Lys Arg Gln Ala Asp Val Gly Ser Asp
            260                 265                 270

Asp Lys Val Tyr Ala Ser Val Ala Gly Leu Thr Cys Ala Ala Gln Pro
        275                 280                 285
```

```
Ala Glu Ala Val Ser Pro Leu Leu Gln Val His Asn Asp Asp Asn
    290                 295                 300

Glu Lys Arg Val Val Glu Met Val Glu Leu Ala Ala Asp Ser Gly Arg
305                 310                 315                 320

His Ala Pro His Leu Ala Asn Ser Pro Leu Ser Ala Glu Ser Gln Leu
                325                 330                 335

Glu Gln Val Ser Lys Leu Leu Ala His Gln Val Pro Gly Ser Val Ala
                340                 345                 350

Ile Gly Ser Val Arg Ala Asn Val Gly Asp Val Gly Tyr Ala Ser Gly
            355                 360                 365

Ala Ala Ser Leu Ile Lys Thr Ala Leu Cys Leu His Asn Arg Tyr Leu
    370                 375                 380

Pro Ala Asn Pro Gln Trp Glu Arg Pro Val Ala Pro Val Ser Glu Ala
385                 390                 395                 400

Leu Phe Thr Cys Pro Arg Ser Arg Ala Trp Leu Lys Asn Pro Gly Glu
                405                 410                 415

Ser Arg Leu Ala Ala Val Ala Ser Ala Ser Glu Ser Gly Ser Cys
            420                 425                 430

<210> SEQ ID NO 33
<211> LENGTH: 1203
<212> TYPE: DNA
<213> ORGANISM: Schizochytrium sp.

<400> SEQUENCE: 33
acgccggaga agctggagaa ggagttggag ctggcagcca agggtgtacc gcgaagcgcc      60
aaggccgggc gcaactggat gtcgccatcg ggcagcgcct ttgcgccgac acctgtgacc     120
agcgaccgcg tcgcgttcat gtacggcgag ggccgcagcc cctactacgg cgtcgggctc     180
gacctgcacc gcctgtggcc ggctttgcac gagcgcatca cgacaagac cgcggcgctg     240 tgggagaacg cgactcgtg gctcatgccg cgcgcggtgg atgccgactc gcagcgcgcc     300
gtgcagacgg cctttgacgc ggaccagatc gagatgttcc gcacgggcat cttcgtgtcc     360
atctgcctca ccgactacgc gcgcgacgtg ctcggggtgc agcccaaggc gtgcttcggc     420
ctcagcctcg gcgagatctc catgctcttt gcgctgtcgc gacgcaactg cggcctgtcg     480
gaccagctca cgcagcgcct acgcacctcg ccggtgtggt cgacacagct ggcggtggag     540
ttccaggcct gcgcaagct atggaacgtg ccggcggacg ccccgtgga gtccttctgg     600 cagggctact tggttcgcgc cagccgcgcc gaaatcgaga aggcgatcgg gcccgacaac     660
cgcttcgtgc gcctgctgat cgtcaacgac tcgagcagcg cgctgatcgc cggcaaacct     720
gccgagtgtc tgcgcgtgct ggagcgcctg gcggggcggt tgccgccgat gcccgtcaag     780
caaggcatga ttgggcactg ccccgaagtg gcgccctaca cgccgggcat cgcgcacatc     840
cacgagattt tggagattcc ggacagcccc gtcaagatgt acacctcggt caccaacgcc     900
gagctgcgcg ggggcagcaa cagcagcatc accgagttcg tgcagaagtt gtacacgcgc     960
atcgccgact tccgggcat cgtcgacaag gtcagccgtg acggccacga tgtcttcgtc    1020
gaggtggggc cgaacaacat gcgctccgcc gcggtcagtg acattcttgg caaggctgcc    1080
accccgcatg tctccgtggc gctgaccgc cccagtgagt cggcgtggac gcagaccctc    1140
aagtcgctgg cgctgctgac cgcccaccgc gtgcccctgc acaacccgac tctgtttgcg    1200
gac                                                                 1203

<210> SEQ ID NO 34
```

<211> LENGTH: 401
<212> TYPE: PRT
<213> ORGANISM: Schizochytrium sp.

<400> SEQUENCE: 34

```
Thr Pro Glu Lys Leu Glu Lys Glu Leu Ala Ala Lys Gly Val
1               5                   10                  15

Pro Arg Ser Ala Lys Ala Gly Arg Asn Trp Met Ser Pro Gly Ser
            20                  25                  30

Ala Phe Ala Pro Thr Pro Val Thr Ser Asp Arg Val Ala Phe Met Tyr
        35                  40                  45

Gly Glu Gly Arg Ser Pro Tyr Tyr Gly Val Gly Leu Asp Leu His Arg
50                  55                  60

Leu Trp Pro Ala Leu His Glu Arg Ile Asn Asp Lys Thr Ala Ala Leu
65                  70                  75                  80

Trp Glu Asn Gly Asp Ser Trp Leu Met Pro Arg Ala Val Asp Ala Asp
                85                  90                  95

Ser Gln Arg Ala Val Gln Thr Ala Phe Asp Ala Asp Gln Ile Glu Met
            100                 105                 110

Phe Arg Thr Gly Ile Phe Val Ser Ile Cys Leu Thr Asp Tyr Ala Arg
        115                 120                 125

Asp Val Leu Gly Val Gln Pro Lys Ala Cys Phe Gly Leu Ser Leu Gly
130                 135                 140

Glu Ile Ser Met Leu Phe Ala Leu Ser Arg Arg Asn Cys Gly Leu Ser
145                 150                 155                 160

Asp Gln Leu Thr Gln Arg Leu Arg Thr Ser Pro Val Trp Ser Thr Gln
                165                 170                 175

Leu Ala Val Glu Phe Gln Ala Leu Arg Lys Leu Trp Asn Val Pro Ala
            180                 185                 190

Asp Ala Pro Val Glu Ser Phe Trp Gln Gly Tyr Leu Val Arg Ala Ser
        195                 200                 205

Arg Ala Glu Ile Glu Lys Ala Ile Gly Pro Asp Asn Arg Phe Val Arg
210                 215                 220

Leu Leu Ile Val Asn Asp Ser Ser Ser Ala Leu Ile Ala Gly Lys Pro
225                 230                 235                 240

Ala Glu Cys Leu Arg Val Leu Glu Arg Leu Gly Gly Arg Leu Pro Pro
                245                 250                 255

Met Pro Val Lys Gln Gly Met Ile Gly His Cys Pro Glu Val Ala Pro
            260                 265                 270

Tyr Thr Pro Gly Ile Ala His Ile His Glu Ile Leu Glu Ile Pro Asp
        275                 280                 285

Ser Pro Val Lys Met Tyr Thr Ser Val Thr Asn Ala Glu Leu Arg Gly
290                 295                 300

Gly Ser Asn Ser Ser Ile Thr Glu Phe Val Gln Lys Leu Tyr Thr Arg
305                 310                 315                 320

Ile Ala Asp Phe Pro Gly Ile Val Asp Lys Val Ser Arg Asp Gly His
                325                 330                 335

Asp Val Phe Val Glu Val Gly Pro Asn Asn Met Arg Ser Ala Ala Val
            340                 345                 350

Ser Asp Ile Leu Gly Lys Ala Thr Pro His Val Ser Val Ala Leu
        355                 360                 365

Asp Arg Pro Ser Glu Ser Ala Trp Thr Gln Thr Leu Lys Ser Leu Ala
370                 375                 380

Leu Leu Thr Ala His Arg Val Pro Leu His Asn Pro Thr Leu Phe Ala
```

<210> SEQ ID NO 35
<211> LENGTH: 1273
<212> TYPE: DNA
<213> ORGANISM: Schizochytrium sp.

<400> SEQUENCE: 35

```
tacgacgtgg actggccgct ctacatgggc gccatggcgg aaggcatctc gtcggtagac    60
ctggtggtcg ctgccgccga ggcccgcatg ctggcatcat tcggagcggc ccgcttgcct   120
atggaccagg tggaactcca gatccgtgag atccagcaac gcacctccaa cgcctttgct   180
gtcaacctga tgccgggtcc tgacgaggcc gcgacggtgg acgcgctgct gcgcacgggc   240
gtctcaatcg tctgaggcatc gggctacacc ggcgcgctct ctgcagacct ggtgcgctac   300
cgtgtcacgg tctgcgacg aactagttgc ggtgcttctg tgtcggcgac tcaccgtgtg   360
gtcgccaagg tgtcgcgcac cgaggtggcc gagcactttc tgcgcccggc gccggccgcc   420
gtactagagg ctttggtcgc cgccaaacag attacgcccg agcaggccgc gctggccagc   480
cgcgtcgcca tggccgacga cgtcgcggtg gaggccgact cgggcgggca caccgacaac   540
cgaccgatcc acgtgctgct gccgctcgtg gtggcgcagc gcaaccgctg cgccacctg    600
gtggacacgc agtgcgcgt cggcgccggc ggcgggatcg cctgtccgcg cgccgcgctg   660
ctcgccttttt ccctgggcgc cgcctttgtg gtcaccgggt ccgtcaacca actggcccgc   720
gaggctggca ccagcgacgc ggtccgacta ctgctggcga cggccaccta ctcggacgtg   780
gccatggcgc cgggcggcgt ccaggtgctc aagaagcaga ccatgttcgc cgcgcgggcc   840
acgatgctcg cccagctgca ggccaagttc ggctcctttg acgccgtgcc ggagccgcag   900
ctgcgcaagc tcgagcgctc cgtgttcaag cagtccgtgg cggacgtgtg ggctgctgca   960
cgcgaaaagt ttggtgtcga cgctaccgct gcaagtccgc aggagaggat ggcgctctgt  1020
gtgcgctggt acatgtcgca gtcgtcgcga tgggctaccg aggcgacgtc cgcgcgcaag  1080
gcggactacc agatctggtg cggcccccgcc atcggcagct tcaacgactt cgttcgcggc  1140
accaagctgg acgcgaccgc tggcaccggc gagtttccgc gcgtcgtgga catcaaccag  1200
cacatcctcc tcgagccctc gcactaccgc cgcgtgcagc aacaacaaca ggacgacgac  1260
gtagaataca tca                                                    1273
```

<210> SEQ ID NO 36
<211> LENGTH: 401
<212> TYPE: PRT
<213> ORGANISM: Schizochytrium sp.

<400> SEQUENCE: 36

Tyr Asp Val Asp Trp Pro Leu Tyr Met Gly Ala Met Ala Glu Gly Ile
1               5                  10                  15

Ser Ser Val Asp Leu Val Val Ala Ala Glu Ala Arg Met Leu Ala
            20                  25                  30

Ser Phe Gly Ala Ala Arg Leu Pro Met Asp Gln Val Glu Leu Gln Ile
        35                  40                  45

Arg Glu Ile Gln Gln Arg Thr Ser Asn Ala Phe Ala Val Asn Leu Met
    50                  55                  60

Pro Gly Pro Asp Glu Ala Ala Thr Val Asp Ala Leu Leu Arg Thr Gly
65                  70                  75                  80

```
Val Ser Ile Val Glu Ala Ser Gly Tyr Thr Gly Ala Leu Ser Ala Asp
             85                  90                  95

Leu Val Arg Tyr Arg Val Thr Gly Leu Arg Arg Thr Ser Cys Gly Ala
        100                 105                 110

Ser Val Ser Ala Thr His Arg Val Val Ala Lys Val Ser Arg Thr Glu
        115                 120                 125

Val Ala Glu His Phe Leu Arg Pro Ala Pro Ala Ala Val Leu Glu Ala
        130                 135                 140

Leu Val Ala Ala Lys Gln Ile Thr Pro Glu Gln Ala Ala Leu Ala Ser
145                 150                 155                 160

Arg Val Ala Met Ala Asp Asp Val Ala Val Glu Ala Asp Ser Gly Gly
                165                 170                 175

His Thr Asp Asn Arg Pro Ile His Val Leu Leu Pro Leu Val Val Ala
                180                 185                 190

Gln Arg Asn Arg Trp Arg His Leu Val Asp Thr Pro Val Arg Val Gly
                195                 200                 205

Ala Gly Gly Gly Ile Ala Cys Pro Arg Ala Ala Leu Leu Ala Phe Ser
        210                 215                 220

Leu Gly Ala Ala Phe Val Val Thr Gly Ser Val Asn Gln Leu Ala Arg
225                 230                 235                 240

Glu Ala Gly Thr Ser Asp Ala Val Arg Leu Leu Leu Ala Thr Ala Thr
                245                 250                 255

Tyr Ser Asp Val Ala Met Ala Pro Gly Val Gln Val Leu Lys Lys
                260                 265                 270

Gln Thr Met Phe Ala Ala Arg Ala Thr Met Leu Ala Gln Leu Gln Ala
        275                 280                 285

Lys Phe Gly Ser Phe Asp Ala Val Pro Glu Pro Gln Leu Arg Lys Leu
        290                 295                 300

Glu Arg Ser Val Phe Lys Gln Ser Val Ala Asp Val Trp Ala Ala Ala
305                 310                 315                 320

Arg Glu Lys Phe Gly Val Asp Ala Thr Ala Ala Ser Pro Gln Glu Arg
                325                 330                 335

Met Ala Leu Cys Val Arg Trp Tyr Met Ser Gln Ser Ser Arg Trp Ala
                340                 345                 350

Thr Glu Ala Thr Ser Ala Arg Lys Ala Asp Tyr Gln Ile Trp Cys Gly
        355                 360                 365

Pro Ala Ile Gly Ser Phe Asn Asp Phe Val Arg Gly Thr Lys Leu Asp
        370                 375                 380

Ala Thr Ala Gly Thr Gly Glu Phe Pro Arg Val Val Asp Ile Asn Gln
385                 390                 395                 400

His

<210> SEQ ID NO 37
<211> LENGTH: 1350
<212> TYPE: DNA
<213> ORGANISM: Schizochytrium sp.

<400> SEQUENCE: 37
atgacatcat cgaagaagac tcccgtgtgg gagatgagca aggaggagct gctggacggc      60
aagacggtgg tcttcgacta caacgagctg ctcgaattcg ccgagggcga cgtgggccaa     120
gtgttcggac ccgagttcga catcatcgac aagtaccggc gtcgcgtgcg gctgccggcg     180
cgcgagtacc tgctcgtgtc gcgcgtgacg ctgatggacg ccgaggtgaa caacttccgc     240
gtcgggtcgc gcatggtgac cgagtacgac gtgcccgtga acggggagct gtcggagggc     300
```

```
ggggacgtgc cgtgggcggt gctggtggag tcggggcagt gcgacctgat gctcatctcg      360
tacatgggca tcgacttcca gtgcaagggc gaccgcgtgt accgcctgct caacacatcg      420
ctcaccttct tcggggtggc gcacgagggc gagacgctgg tgtacgacat ccgcgtcacg      480
gggttcgcca agggcgcggg cggggagatc tcgatgttct tcttcgagta cgactgcttc      540
gtggacggcc gcctgctgat cgagatgcgc gacgggtgcg ccgggttctt cacggacgcc      600
gagctggccg ccggcaaggg cgtgcttaag accaaggcgg agctggcggc gcgcgcgcag      660
atccagaagc aggacatcgc gcccttttgcg ccggcgccgt gctcgcacaa gacctcgctg      720
gacgcgcgcg agatgcggct gctcgtggac gccagtgggg cgcgcgtctt cggcagcggc      780
atggcgggca tcgactacaa gttgtgcgct cgcaagatgc tcatgatcga ccgcgtcacg      840
cacctcgacc cgcgcggcgg cgcgcacggc ctcgggctgc tgatcgggga aaggtgctg       900 gagcgcgacc actggtactt ccccctgccac tttgtgcgcg acgaggtgat ggccgggtcg      960
ctggtcagcg acggctgctc gcagctcctc aaggtgtaca tgctgtggct cggcctgcac     1020
acgaccgtgg gcgcgttcga ctttcgtccc gtgagcgggc acgccaacaa ggtgcggtgc     1080
cgcgggcaga tctcaccgca aagggcaag ctcgtgtacg tgatggagat caaggaaatg      1140
ggctttgacg cgaagacggg cgatccgttt gcgatcgcgg acgtggacat catcgacgtc     1200
aacttcgagg agggacaggc gtttgcggga gtggaagacc tgcacagcta cggccagggc     1260
gacctccgca agaagatcgt cgtcgacttc aagggcatcg cgctctccct gcagaagcgg     1320
aaggagcagc agaaggaaag catgaccgtg                                      1350
```

<210> SEQ ID NO 38
<211> LENGTH: 450
<212> TYPE: PRT
<213> ORGANISM: Schizochytrium sp.

<400> SEQUENCE: 38

```
Met Thr Ser Ser Lys Lys Thr Pro Val Trp Glu Met Ser Lys Glu Glu
1               5                   10                  15

Leu Leu Asp Gly Lys Thr Val Val Phe Asp Tyr Asn Glu Leu Leu Glu
            20                  25                  30

Phe Ala Glu Gly Asp Val Gly Gln Val Phe Gly Pro Glu Phe Asp Ile
        35                  40                  45

Ile Asp Lys Tyr Arg Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

Gly Val Ala His Glu Gly Glu Thr Leu Val Tyr Asp Ile Arg Val Thr
145                 150                 155                 160

Gly Phe Ala Lys Gly Ala Gly Gly Glu Ile Ser Met Phe Phe Phe Glu
                165                 170                 175

Tyr Asp Cys Phe Val Asp Gly Arg Leu Leu Ile Glu Met Arg Asp Gly
```

```
                180             185             190
Cys Ala Gly Phe Phe Thr Asp Ala Glu Leu Ala Ala Gly Lys Gly Val
        195                 200                 205
Leu Lys Thr Lys Ala Glu Leu Ala Ala Arg Ala Gln Ile Gln Lys Gln
        210                 215                 220
Asp Ile Ala Pro Phe Ala Pro Ala Pro Cys Ser His Lys Thr Ser Leu
225                 230                 235                 240
Asp Ala Arg Glu Met Arg Leu Leu Val Asp Arg Gln Trp Ala Arg Val
                245                 250                 255
Phe Gly Ser Gly Met Ala Gly Ile Asp Tyr Lys Leu Cys Ala Arg Lys
                260                 265                 270
Met Leu Met Ile Asp Arg Val Thr His Leu Asp Pro Arg Gly Gly Ala
                275                 280                 285
His Gly Leu Gly Leu Leu Ile Gly Glu Lys Val Leu Glu Arg Asp His
                290                 295                 300
Trp Tyr Phe Pro Cys His Phe Val Arg Asp Glu Val Met Ala Gly Ser
305                 310                 315                 320
Leu Val Ser Asp Gly Cys Ser Gln Leu Leu Lys Val Tyr Met Leu Trp
                325                 330                 335
Leu Gly Leu His Thr Thr Val Gly Ala Phe Asp Phe Arg Pro Val Ser
                340                 345                 350
Gly His Ala Asn Lys Val Arg Cys Arg Gly Gln Ile Ser Pro His Lys
                355                 360                 365
Gly Lys Leu Val Tyr Val Met Glu Ile Lys Glu Met Gly Phe Asp Ala
                370                 375                 380
Lys Thr Gly Asp Pro Phe Ala Ile Ala Asp Val Asp Ile Ile Asp Val
385                 390                 395                 400
Asn Phe Glu Glu Gly Gln Ala Phe Ala Gly Val Glu Asp Leu His Ser
                405                 410                 415
Tyr Gly Gln Gly Asp Leu Arg Lys Lys Ile Val Asp Phe Lys Gly
                420                 425                 430
Ile Ala Leu Ser Leu Gln Lys Arg Lys Glu Gln Gln Lys Glu Ser Met
            435                 440                 445
Thr Val
    450

<210> SEQ ID NO 39
<211> LENGTH: 1200
<212> TYPE: DNA
<213> ORGANISM: Schizochytrium sp.

<400> SEQUENCE: 39
tacccgccgc gggcggtgtg cttctcgccg ttccccaaca acccgcttga caacgaccac      60
acgccgggcc agatgccgtt gacctggttc aacatgtccg aattcatgtg cggcaaagtg     120
tccaactgcc tgggccccga gtttgcgcgc ttcgacgcga gcaagacgag ccgcagcccg     180
gcctttgacc tggcgctcgt gacgcgggtg acagcgtgg cggacatgga gcacgggccg     240
ttctacaacg tggacgtcaa cccggggcag ggcacgatgg tgggcgagtt cgactgtccc     300
gcggacgcgt ggttcttcgg cgcctcgagc gcgacgacc acatgccgta ctcgatcctg     360
atggagatcg cgctgcagac gtcgggcgtc ctcacctcgg tgctcaaggc gccgctgacg     420
atggacaagg acgacatcct cttccgcaac ctcgacgcag acgccgagct cgtgggcgac     480
gccatgccgg acgtgcgcgg caagacgatc cgcaacttca ccaagtgcac aggctacagc     540
```

```
atgctcggca agatgggcat ccaccgcttc acctttgagc tcagcgtcga cggcgccgtc    600
ttctacaagg gcagcacctc gtttggctgg ttcgtccccg aggtcttcga gtcgcagacc    660
ggtctcgaca acggcaagcc gcgcctgcct tggtaccgcg agaacaacgt cgccgtcgac    720
acgctctccg cgcccgcctc cgcttcctcc gcgcaaggtc agctgcagct gcagcgacgc    780
gggtcgcagg cgcagttcct ggacacaatc cacctggcgg cagcggcgc cggcgtgcac    840
ggccagggct acgcgcacgg ggagaaggcc gtgaacaagc aagattggtt cttctcgtgc    900
cacttctggt tcgaccccgt gatgcccggg tccctgggca tcgagtcgat gttccagctc    960
gtcgaggcgt ggtgcgtgaa gcagggactc gcggcgcggc acggcatcgc tcacccagtg   1020
ttcgcgcacg cgcccggggc cacgagctgg aagtaccgcg ggcagctaac ccccaagaac   1080
gaccgcatgg acagcgaggt gcacatcaag tcggtggcgg ccttctcctc ctgggtcgac   1140
gtcgtcgcgg acgggttcct cttcgtcgac ggcctccgcg tctactcggc agacaacctc   1200
```

<210> SEQ ID NO 40
<211> LENGTH: 400
<212> TYPE: PRT
<213> ORGANISM: Schizochytrium sp.

<400> SEQUENCE: 40

```
Tyr Pro Pro Arg Ala Val Cys Phe Ser Pro Phe Pro Asn Asn Pro Leu
1               5                   10                  15

Asp Asn Asp His Thr Pro Gly Gln Met Pro Leu Thr Trp Phe Asn Met
            20                  25                  30

Ser Glu Phe Met Cys Gly Lys Val Ser Asn Cys Leu Gly Pro Glu Phe
        35                  40                  45

Ala Arg Phe Asp Ala Ser Lys Thr Ser Arg Ser Pro Ala Phe Asp Leu
    50                  55                  60

Ala Leu Val Thr Arg Val Thr Ser Val Ala Asp Met Glu His Gly Pro
65                  70                  75                  80

Phe Tyr Asn Val Asp Val Asn Pro Gly Gln Gly Thr Met Val Gly Glu
                85                  90                  95

Phe Asp Cys Pro Ala Asp Ala Trp Phe Phe Gly Ala Ser Ser Arg Asp
            100                 105                 110

Asp His Met Pro Tyr Ser Ile Leu Met Glu Ile Ala Leu Gln Thr Ser
        115                 120                 125

Gly Val Leu Thr Ser Val Leu Lys Ala Pro Leu Thr Met Asp Lys Asp
    130                 135                 140

Asp Ile Leu Phe Arg Asn Leu Asp Ala Asp Ala Glu Leu Val Gly Asp
145                 150                 155                 160

Ala Met Pro Asp Val Arg Gly Lys Thr Ile Arg Asn Phe Thr Lys Cys
                165                 170                 175

Thr Gly Tyr Ser Met Leu Gly Lys Met Gly Ile His Arg Phe Thr Phe
            180                 185                 190

Glu Leu Ser Val Asp Gly Ala Val Phe Tyr Lys Gly Ser Thr Ser Phe
        195                 200                 205

Gly Trp Phe Val Pro Glu Val Phe Glu Ser Gln Thr Gly Leu Asp Asn
    210                 215                 220

Gly Lys Pro Arg Leu Pro Trp Tyr Arg Glu Asn Val Ala Val Asp
225                 230                 235                 240

Thr Leu Ser Ala Pro Ser Ala Ser Ser Ala Gln Gly Gln Leu Gln
                245                 250                 255

Leu Gln Arg Arg Gly Ser Gln Ala Gln Phe Leu Asp Thr Ile His Leu
```

```
                    260                 265                 270
Ala Gly Ser Gly Ala Gly Val His Gly Gln Gly Tyr Ala His Gly Glu
                275                 280                 285
Lys Ala Val Asn Lys Gln Asp Trp Phe Phe Ser Cys His Phe Trp Phe
            290                 295                 300
Asp Pro Val Met Pro Gly Ser Leu Gly Ile Glu Ser Met Phe Gln Leu
305                 310                 315                 320
Val Glu Ala Trp Cys Val Lys Gln Gly Leu Ala Arg His Gly Ile
                325                 330                 335
Ala His Pro Val Phe Ala His Ala Pro Gly Ala Thr Ser Trp Lys Tyr
                340                 345                 350
Arg Gly Gln Leu Thr Pro Lys Asn Asp Arg Met Asp Ser Glu Val His
                355                 360                 365
Ile Lys Ser Val Ala Ala Phe Ser Ser Trp Val Asp Val Ala Asp
            370                 375                 380
Gly Phe Leu Phe Val Asp Gly Leu Arg Val Tyr Ser Ala Asp Asn Leu
385                 390                 395                 400

<210> SEQ ID NO 41
<211> LENGTH: 1353
<212> TYPE: DNA
<213> ORGANISM: Schizochytrium sp.

<400> SEQUENCE: 41
```

| | | | | | |
|---|---|---|---|---|---|
| cagctggacg | cggggagcga | ggtgcccgcc | tgcgcggtga | gcgacctggg | cgataggggc | 60 |
| ttcatggaga | cgtacggggt | ggtggcgccg | ctgtacagcg | gggcgatggc | caagggcatc | 120 |
| gcgtcggcgg | acctggtgat | cgcgatgggc | cagcgcaaga | tgctggggtc | gtttggcgcg | 180 |
| ggcgggctcc | cgatgcacgt | cgtgcgcgcg | gggattgaga | agatccaggc | agcgctgcca | 240 |
| gcggggccat | acgcggtcaa | cctgattcac | tcgccttttg | acgccaacct | ggagaagggc | 300 |
| aacgtggacc | tcttcctgga | gaagggcgtg | cgcgtcgtgg | aggcgtcggc | cttcatggag | 360 |
| ctcacgcccc | aggtggtgcg | ctaccgcgcg | acgggcctct | ctcgcgacgc | gcgcggcggc | 420 |
| tccgtgcgca | cggcccacaa | gatcatcggc | aaggtcagcc | gcaccgagct | ggccgagatg | 480 |
| tttatccggc | ccgcgccgca | agccattctc | gacaagcttg | tggcgtccgg | cgagatcacc | 540 |
| cccgagcagg | cggcgctggc | gctcgaggtg | cccatggcgg | acgacatcgc | cgtcgaggcc | 600 |
| gattcgggcg | ggcacaccga | caaccgcccc | atccacgtca | tcctgcccct | catcctcagc | 660 |
| ctgcgcaacc | gcctccagcg | cgagctcaag | taccctgcgc | gacaccgcgt | gcgcgtcggc | 720 |
| gccgggggcg | gcatcgggtg | cccgcaagcg | gctctgggcg | ccttccacat | gggcgccgcg | 780 |
| tttgtggtga | cgggcacggt | caaccagctg | agccggcagg | ccgggacatg | cgacaatgtg | 840 |
| cggcggcagc | tgtcgcgcgc | gacgtactcg | gacatcacga | tggcgccggc | ggcggacatg | 900 |
| ttcgagcagg | gcgtcgagct | gcaggtgctc | aagaagggca | cgatgtttcc | ctcgcgcgcc | 960 |
| aagaagctgt | tcgagctgtt | tcacaagtac | gactcgttcg | aggcgatgcc | ggcggacgag | 1020 |
| ctggcgcgcg | tcgagaagcg | catcttcagc | aagtcactcg | ccgaggtgtg | ggccgagacc | 1080 |
| aaggacttct | acatcacgcg | gctcaacaac | ccggagaaga | tccgcaaggc | ggagaacgag | 1140 |
| gaccccaagc | tcaagatgtc | actctgcttc | cgctggtacc | tcgggctcag | ctcgttctgg | 1200 |
| gccaacaacg | gcatcgcgga | ccgcacgatg | gactaccaga | tctggtgcgg | ccctgccatc | 1260 |
| ggcgccttca | cgacttcat | cgccgactcg | tacctcgacg | tggccgtctc | gggcgagttc | 1320 |
| cccgacgtcg | tgcagatcaa | cctgcagatc | ctg | | | 1353 |

<210> SEQ ID NO 42
<211> LENGTH: 451
<212> TYPE: PRT
<213> ORGANISM: Schizochytrium sp.

<400> SEQUENCE: 42

```
Gln Leu Asp Ala Gly Ser Glu Val Pro Ala Cys Ala Val Ser Asp Leu
1               5                   10                  15

Gly Asp Arg Gly Phe Met Glu Thr Tyr Gly Val Val Ala Pro Leu Tyr
            20                  25                  30

Ser Gly Ala Met Ala Lys Gly Ile Ala Ser Ala Asp Leu Val Ile Ala
        35                  40                  45

Met Gly Gln Arg Lys Met Leu Gly Ser Phe Gly Ala Gly Leu Pro
    50                  55                  60

Met His Val Val Arg Ala Gly Ile Glu Lys Ile Gln Ala Ala Leu Pro
65                  70                  75                  80

Ala Gly Pro Tyr Ala Val Asn Leu Ile His Ser Pro Phe Asp Ala Asn
                85                  90                  95

Leu Glu Lys Gly Asn Val Asp Leu Phe Leu Glu Lys Gly Val Arg Val
            100                 105                 110

Val Glu Ala Ser Ala Phe Met Glu Leu Thr Pro Gln Val Val Arg Tyr
        115                 120                 125

Arg Ala Thr Gly Leu Ser Arg Asp Ala Arg Gly Gly Ser Val Arg Thr
    130                 135                 140

Ala His Lys Ile Ile Gly Lys Val Ser Arg Thr Glu Leu Ala Glu Met
145                 150                 155                 160

Phe Ile Arg Pro Ala Pro Gln Ala Ile Leu Asp Lys Leu Val Ala Ser
                165                 170                 175

Gly Glu Ile Thr Pro Glu Gln Ala Ala Leu Ala Leu Glu Val Pro Met
            180                 185                 190

Ala Asp Asp Ile Ala Val Glu Ala Asp Ser Gly Gly His Thr Asp Asn
        195                 200                 205

Arg Pro Ile His Val Ile Leu Pro Leu Ile Leu Ser Leu Arg Asn Arg
    210                 215                 220

Leu Gln Arg Glu Leu Lys Tyr Pro Ala Arg His Arg Val Arg Val Gly
225                 230                 235                 240

Ala Gly Gly Gly Ile Gly Cys Pro Gln Ala Ala Leu Gly Ala Phe His
                245                 250                 255

Met Gly Ala Ala Phe Val Val Thr Gly Thr Val Asn Gln Leu Ser Arg
            260                 265                 270

Gln Ala Gly Thr Cys Asp Asn Val Arg Arg Gln Leu Ser Arg Ala Thr
        275                 280                 285

Tyr Ser Asp Ile Thr Met Ala Pro Ala Ala Asp Met Phe Glu Gln Gly
    290                 295                 300

Val Glu Leu Gln Val Leu Lys Lys Gly Thr Met Phe Pro Ser Arg Ala
305                 310                 315                 320

Lys Lys Leu Phe Glu Leu Phe His Lys Tyr Asp Ser Phe Glu Ala Met
                325                 330                 335

Pro Ala Asp Glu Leu Ala Arg Val Glu Lys Arg Ile Phe Ser Lys Ser
            340                 345                 350

Leu Ala Glu Val Trp Ala Glu Thr Lys Asp Phe Tyr Ile Thr Arg Leu
        355                 360                 365

Asn Asn Pro Glu Lys Ile Arg Lys Ala Glu Asn Glu Asp Pro Lys Leu
```

```
                 370                 375                 380
Lys Met Ser Leu Cys Phe Arg Trp Tyr Leu Gly Leu Ser Ser Phe Trp
385                 390                 395                 400

Ala Asn Asn Gly Ile Ala Asp Arg Thr Met Asp Tyr Gln Ile Trp Cys
                405                 410                 415

Gly Pro Ala Ile Gly Ala Phe Asn Asp Phe Ile Ala Asp Ser Tyr Leu
            420                 425                 430

Asp Val Ala Val Ser Gly Glu Phe Pro Asp Val Val Gln Ile Asn Leu
        435                 440                 445

Gln Ile Leu
    450

<210> SEQ ID NO 43
<211> LENGTH: 4
<212> TYPE: PRT
<213> ORGANISM: Schizochytrium sp.
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Asp Xaa Ala Cys
1

<210> SEQ ID NO 44
<211> LENGTH: 4
<212> TYPE: PRT
<213> ORGANISM: Schizochytrium sp.

<400> SEQUENCE: 44

Gly Phe Gly Gly
1

<210> SEQ ID NO 45
<211> LENGTH: 12
<212> TYPE: DNA
<213> ORGANISM: Schizochytrium sp.

<400> SEQUENCE: 45
gggtttggcg gt                                                          12

<210> SEQ ID NO 46
<211> LENGTH: 5
<212> TYPE: PRT
<213> ORGANISM: Schizochytrium sp.

<400> SEQUENCE: 46

Gly Phe Ser Leu Gly
1               5

<210> SEQ ID NO 47
<211> LENGTH: 5
<212> TYPE: PRT
<213> ORGANISM: Schizochytrium sp.

<400> SEQUENCE: 47

Leu Gly Ile Asp Ser
1               5

<210> SEQ ID NO 48
<211> LENGTH: 903
<212> TYPE: DNA
```

<213> ORGANISM: Schizochytrium sp.

<400> SEQUENCE: 48

```
ctgtcagacc ccgacgtggc cgtgcgcgag tctggttact ccgcctcggg ccagcgctgc      60
acgacaacta cgaagtcgct gactacgggc aagccgcacc agccgatctc ctcgtcggac     120
ctctttctgg tgtcgggcgg cgcgcgcggc atcaccccgc tgtgcgtgcg cgagctggcg     180
cagcgcgtgg gcggcggcac gtacgtgctc atcggccgct cggagctgcc cacgacggag     240
cctgcctggg cggtcggcgt ggagtctggc aagccgctgg agaaggccgc gctggcgttc     300
ctgaaggcgg agtttgcagc gggccgcggg gccaagccga cgccgatgct gcacaagaag     360
ctcgtgggcg ccgtggtcgg agcgcgcgag gtgcgagcct cgctcgccga gatcactgca     420
cagggcgcca cggctgtgta cgagtcgtgc gacgtgagct ctgccgccaa ggtgcgtgag     480
atggtagagc gcgtgcagca gcagggcggg cggcgcgtgt cgggcgtgtt ccacgcgtcg     540
ggcgtgctgc gcgacaagct cgtggagaac aagtcgctgg cggacttcag cgccgtgtac     600
gacaccaagg tgggcggcct catcaacctg ctggcctgcg tggacctggc gcagctgcgt     660
cacctcgtgc tcttcagctc gctcgcgggc ttccacggca acgtcgggca gtcggactac     720
gcaatggcca acgaggcgct caacaagctg gcggcgcacc tgtcggcggt gcaccccgca     780
ctgtgcgcgc gctcgatctg cttcggaccg tgggacggcg gcatggtgac ccccgcgctc     840
aaggccaact tcatccgcat gggcatccag atcatcccgc gccaaggcgg cgcgcagacc     900
gtc                                                                   903
```

<210> SEQ ID NO 49
<211> LENGTH: 301
<212> TYPE: PRT
<213> ORGANISM: Schizochytrium sp.

<400> SEQUENCE: 49

```
Leu Ser Asp Pro Asp Val Ala Val Arg Glu Ser Gly Tyr Ser Ala Ser
  1               5                  10                  15

Gly Gln Arg Cys Thr Thr Thr Lys Ser Leu Thr Thr Gly Lys Pro
             20                  25                  30

His Gln Pro Ile Ser Ser Ser Asp Leu Phe Leu Val Ser Gly Gly Ala
         35                  40                  45

Arg Gly Ile Thr Pro Leu Cys Val Arg Glu Leu Ala Gln Arg Val Gly
     50                  55                  60

Gly Gly Thr Tyr Val Leu Ile Gly Arg Ser Glu Leu Pro Thr Thr Glu
 65                  70                  75                  80

Pro Ala Trp Ala Val Gly Val Glu Ser Gly Lys Pro Leu Glu Lys Ala
                 85                  90                  95

Ala Leu Ala Phe Leu Lys Ala Glu Phe Ala Ala Gly Arg Gly Ala Lys
            100                 105                 110

Pro Thr Pro Met Leu His Lys Lys Leu Val Gly Ala Val Gly Ala
        115                 120                 125

Arg Glu Val Arg Ala Ser Leu Ala Glu Ile Thr Ala Gln Gly Ala Thr
    130                 135                 140

Ala Val Tyr Glu Ser Cys Asp Val Ser Ser Ala Ala Lys Val Arg Glu
145                 150                 155                 160

Met Val Glu Arg Val Gln Gln Gln Gly Gly Arg Arg Val Ser Gly Val
                165                 170                 175

Phe His Ala Ser Gly Val Leu Arg Asp Lys Leu Val Glu Asn Lys Ser
            180                 185                 190
```

```
Leu Ala Asp Phe Ser Ala Val Tyr Asp Thr Lys Val Gly Gly Leu Ile
            195                 200                 205

Asn Leu Leu Ala Cys Val Asp Leu Ala Gln Leu Arg His Leu Val Leu
    210                 215                 220

Phe Ser Ser Leu Ala Gly Phe His Gly Asn Val Gly Gln Ser Asp Tyr
225                 230                 235                 240

Ala Met Ala Asn Glu Ala Leu Asn Lys Leu Ala His Leu Ser Ala
                245                 250                 255

Val His Pro Gln Leu Cys Ala Arg Ser Ile Cys Phe Gly Pro Trp Asp
                260                 265                 270

Gly Gly Met Val Thr Pro Ala Leu Lys Ala Asn Phe Ile Arg Met Gly
            275                 280                 285

Ile Gln Ile Ile Pro Arg Gln Gly Gly Ala Gln Thr Val
            290                 295                 300

<210> SEQ ID NO 50
<211> LENGTH: 13
<212> TYPE: PRT
<213> ORGANISM: Schizochytrium sp.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid

<400> SEQUENCE: 50

Leu Xaa Xaa His Xaa Xaa Xaa Gly Xaa Xaa Xaa Xaa Pro
1               5                   10

<210> SEQ ID NO 51
<211> LENGTH: 12
<212> TYPE: DNA
<213> ORGANISM: Schizochytrium sp.

<400> SEQUENCE: 51
ggctttggtg ga                                                             12

<210> SEQ ID NO 52
<211> LENGTH: 5
<212> TYPE: PRT
<213> ORGANISM: Schizochytrium sp.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 52

Gly Xaa Ser Xaa Gly
1               5

<210> SEQ ID NO 53
<211> LENGTH: 5
<212> TYPE: PRT
<213> ORGANISM: Schizochytrium sp.
```

```
<220> FEATURE:
<221> NAME/KEY: misc_feature
<222> LOCATION: (2)..(3)
<223> OTHER INFORMATION: Xaa can be any naturally occurring amino acid

<400> SEQUENCE: 53

Phe Xaa Xaa His Phe
1               5

<210> SEQ ID NO 54
<211> LENGTH: 2910
<212> TYPE: PRT
<213> ORGANISM: Schizochytrium sp.

<400> SEQUENCE: 54

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
                20                  25                  30

Arg Glu Ser Trp Glu Thr Ile Arg Ala Gly Ile Asp Cys Leu Ser Asp
            35                  40                  45

Leu Pro Glu Asp Arg Val Asp Val Thr Ala Tyr Phe Asp Pro Val Lys
        50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gln Lys Ser Ser His Glu Phe
130                 135                 140

Tyr Ser Arg Leu Asn Tyr Val Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
        195                 200                 205

Cys Val Val Asp Ala Ala Cys Ala Ser Ser Leu Ile Ala Val Lys Val
210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
        275                 280                 285

Arg Tyr Ala Asp Ala Val Arg Asp Gly Asp Glu Ile His Ala Val Ile
290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
```

```
                    325                 330                 335
Ala Cys Val Asp Pro Ala Thr Val Thr Leu Val Glu Gly His Gly Thr
                340                 345                 350
Gly Thr Pro Val Gly Asp Arg Ile Glu Leu Thr Ala Leu Arg Asn Leu
                355                 360                 365
Phe Asp Lys Ala Tyr Gly Glu Gly Asn Thr Glu Lys Val Ala Val Gly
                370                 375                 380
Ser Ile Lys Ser Ser Ile Gly His Leu Lys Ala Val Ala Gly Leu Ala
385                 390                 395                 400
Gly Met Ile Lys Val Ile Met Ala Leu Lys His Lys Thr Leu Pro Gly
                405                 410                 415
Thr Ile Asn Val Asp Asn Pro Pro Asn Leu Tyr Asp Asn Thr Pro Ile
                420                 425                 430
Asn Glu Ser Ser Leu Tyr Ile Asn Thr Met Asn Arg Pro Trp Phe Pro
                435                 440                 445
Pro Pro Gly Val Pro Arg Arg Ala Gly Ile Ser Ser Phe Gly Phe Gly
                450                 455                 460
Gly Ala Asn Tyr His Ala Val Leu Glu Glu Ala Glu Pro His Thr
465                 470                 475                 480
Thr Ala Tyr Arg Leu Asn Lys Arg Pro Gln Pro Val Leu Met Met Ala
                485                 490                 495
Ala Thr Pro Ala Ala Leu Gln Ser Leu Cys Glu Ala Gln Leu Lys Glu
                500                 505                 510
Phe Glu Ala Ala Ile Lys Glu Asn Glu Thr Val Lys Asn Thr Ala Tyr
                515                 520                 525
Ile Lys Cys Val Lys Phe Gly Glu Gln Phe Lys Phe Pro Gly Ser Ile
                530                 535                 540
Pro Ala Thr Asn Ala Arg Leu Gly Phe Leu Val Lys Asp Ala Glu Asp
545                 550                 555                 560
Ala Cys Ser Thr Leu Arg Ala Ile Cys Ala Gln Phe Ala Lys Asp Val
                565                 570                 575
Thr Lys Glu Ala Trp Arg Leu Pro Arg Glu Gly Val Ser Phe Arg Ala
                580                 585                 590
Lys Gly Ile Ala Thr Asn Gly Ala Val Ala Ala Leu Phe Ser Gly Gln
                595                 600                 605
Gly Ala Gln Tyr Thr His Met Phe Ser Glu Val Ala Met Asn Trp Pro
                610                 615                 620
Gln Phe Arg Gln Ser Ile Ala Ala Met Asp Ala Ala Gln Ser Lys Val
625                 630                 635                 640
Ala Gly Ser Asp Lys Asp Phe Glu Arg Val Ser Gln Val Leu Tyr Pro
                645                 650                 655
Arg Lys Pro Tyr Glu Arg Glu Pro Glu Gln Asn Pro Lys Lys Ile Ser
                660                 665                 670
Leu Thr Ala Tyr Ser Gln Pro Ser Thr Leu Ala Cys Ala Leu Gly Ala
                675                 680                 685
Phe Glu Ile Phe Lys Glu Ala Gly Phe Thr Pro Asp Phe Ala Ala Gly
                690                 695                 700
His Ser Leu Gly Glu Phe Ala Ala Leu Tyr Ala Ala Gly Cys Val Asp
705                 710                 715                 720
Arg Asp Glu Leu Phe Glu Leu Val Cys Arg Arg Ala Arg Ile Met Gly
                725                 730                 735
Gly Lys Asp Ala Pro Ala Thr Pro Lys Gly Cys Met Ala Ala Val Ile
                740                 745                 750
```

-continued

```
Gly Pro Asn Ala Glu Asn Ile Lys Val Gln Ala Ala Asn Val Trp Leu
        755                 760                 765
Gly Asn Ser Asn Ser Pro Ser Gln Thr Val Ile Thr Gly Ser Val Glu
    770                 775                 780
Gly Ile Gln Ala Glu Ser Ala Arg Leu Gln Lys Glu Gly Phe Arg Val
785                 790                 795                 800
Val Pro Leu Ala Cys Glu Ser Ala Phe His Ser Pro Gln Met Glu Asn
            805                 810                 815
Ala Ser Ser Ala Phe Lys Asp Val Ile Ser Lys Val Ser Phe Arg Thr
        820                 825                 830
Pro Lys Ala Glu Thr Lys Leu Phe Ser Asn Val Ser Gly Glu Thr Tyr
    835                 840                 845
Pro Thr Asp Ala Arg Glu Met Leu Thr Gln His Met Thr Ser Ser Val
850                 855                 860
Lys Phe Leu Thr Gln Val Arg Asn Met His Gln Ala Gly Ala Arg Ile
865                 870                 875                 880
Phe Val Glu Phe Gly Pro Lys Gln Val Leu Ser Lys Leu Val Ser Glu
            885                 890                 895
Thr Leu Lys Asp Asp Pro Ser Val Thr Val Ser Val Asn Pro Ala
        900                 905                 910
Ser Gly Thr Asp Ser Asp Ile Gln Leu Arg Asp Ala Ala Val Gln Leu
    915                 920                 925
Val Val Ala Gly Val Asn Leu Gln Gly Phe Asp Lys Trp Asp Ala Pro
930                 935                 940
Asp Ala Thr Arg Met Gln Ala Ile Lys Lys Lys Arg Thr Thr Leu Arg
945                 950                 955                 960
Leu Ser Ala Ala Thr Tyr Val Ser Asp Lys Thr Lys Val Arg Asp
            965                 970                 975
Ala Ala Met Asn Asp Gly Arg Cys Val Thr Tyr Leu Lys Gly Ala Ala
        980                 985                 990
Pro Leu Ile Lys Ala Pro Glu Pro  Val Val Asp Glu Ala  Ala Lys Arg
    995                 1000                1005
Glu Ala  Glu Arg Leu Gln Lys  Glu Leu Gln Asp Ala  Gln Arg Gln
    1010                1015                1020
Leu Asp  Asp Ala Lys Arg Ala  Ala Ala Glu Ala Asn  Ser Lys Leu
    1025                1030                1035
Ala Ala  Ala Lys Glu Glu Ala  Lys Thr Ala Ala Ala  Ser Ala Lys
    1040                1045                1050
Pro Ala  Val Asp Thr Ala Val  Val Glu Lys His Arg  Ala Ile Leu
    1055                1060                1065
Lys Ser  Met Leu Ala Glu Leu  Asp Gly Tyr Gly Ser  Val Asp Ala
    1070                1075                1080
Ser Ser  Leu Gln Gln Gln Gln  Gln Gln Gln Thr Ala  Pro Ala Pro
    1085                1090                1095
Val Lys  Ala Ala Ala Pro Ala  Ala Pro Val Ala Ser  Ala Pro Ala
    1100                1105                1110
Pro Ala  Val Ser Asn Glu Leu  Leu Glu Lys Ala Glu  Thr Val Val
    1115                1120                1125
Met Glu  Val Leu Ala Ala Lys  Thr Gly Tyr Glu Thr  Asp Met Ile
    1130                1135                1140
Glu Ala  Asp Met Glu Leu Glu  Thr Glu Leu Gly Ile  Asp Ser Ile
    1145                1150                1155
```

```
Lys Arg Val Glu Ile Leu Ser Glu Val Gln Ala Met Leu Asn Val
    1160                1165                1170

Glu Ala Lys Asp Val Asp Ala Leu Ser Arg Thr Arg Thr Val Gly
    1175                1180                1185

Glu Val Val Asn Ala Met Lys Ala Glu Ile Ala Gly Ser Ser Ala
    1190                1195                1200

Pro Ala Pro Ala Ala Ala Pro Ala Pro Ala Lys Ala Ala Pro
    1205                1210                1215

Ala Ala Ala Ala Pro Ala Val Ser Asn Glu Leu Leu Glu Lys Ala
    1220                1225                1230

Glu Thr Val Val Met Glu Val Leu Ala Ala Lys Thr Gly Tyr Glu
    1235                1240                1245

Thr Asp Met Ile Glu Ser Asp Met Glu Leu Glu Thr Glu Leu Gly
    1250                1255                1260

Ile Asp Ser Ile Lys Arg Val Glu Ile Leu Ser Glu Val Gln Ala
    1265                1270                1275

Met Leu Asn Val Glu Ala Lys Asp Val Asp Ala Leu Ser Arg Thr
    1280                1285                1290

Arg Thr Val Gly Glu Val Val Asn Ala Met Lys Ala Glu Ile Ala
    1295                1300                1305

Gly Gly Ser Ala Pro Ala Pro Ala Ala Ala Ala Pro Gly Pro Ala
    1310                1315                1320

Ala Ala Ala Pro Ala Pro Ala Ala Ala Pro Ala Val Ser Asn
    1325                1330                1335

Glu Leu Leu Glu Lys Ala Glu Thr Val Val Met Glu Val Leu Ala
    1340                1345                1350

Ala Lys Thr Gly Tyr Glu Thr Asp Met Ile Glu Ser Asp Met Glu
    1355                1360                1365

Leu Glu Thr Glu Leu Gly Ile Asp Ser Ile Lys Arg Val Glu Ile
    1370                1375                1380

Leu Ser Glu Val Gln Ala Met Leu Asn Val Glu Ala Lys Asp Val
    1385                1390                1395

Asp Ala Leu Ser Arg Thr Arg Thr Val Gly Glu Val Val Asp Ala
    1400                1405                1410

Met Lys Ala Glu Ile Ala Gly Gly Ser Ala Pro Ala Pro Ala Ala
    1415                1420                1425

Ala Ala Pro Ala Pro Ala Ala Ala Pro Ala Pro Ala Ala Pro
    1430                1435                1440

Ala Pro Ala Val Ser Ser Glu Leu Leu Glu Lys Ala Glu Thr Val
    1445                1450                1455

Val Met Glu Val Leu Ala Ala Lys Thr Gly Tyr Glu Thr Asp Met
    1460                1465                1470

Ile Glu Ser Asp Met Glu Leu Glu Thr Glu Leu Gly Ile Asp Ser
    1475                1480                1485

Ile Lys Arg Val Glu Ile Leu Ser Glu Val Gln Ala Met Leu Asn
    1490                1495                1500

Val Glu Ala Lys Asp Val Asp Ala Leu Ser Arg Thr Arg Thr Val
    1505                1510                1515

Gly Glu Val Val Asp Ala Met Lys Ala Glu Ile Ala Gly Gly Ser
    1520                1525                1530

Ala Pro Ala Pro Ala Ala Ala Pro Ala Pro Ala Ala Ala
    1535                1540                1545

Pro Ala Pro Ala Ala Pro Ala Pro Ala Ala Pro Ala Pro Ala Val
```

-continued

```
            1550                1555                1560

Ser Ser Glu Leu Leu Glu Lys Ala Glu Thr Val Val Met Glu Val
    1565                1570                1575

Leu Ala Ala Lys Thr Gly Tyr Glu Thr Asp Met Ile Glu Ser Asp
    1580                1585                1590

Met Glu Leu Glu Thr Glu Leu Gly Ile Asp Ser Ile Lys Arg Val
    1595                1600                1605

Glu Ile Leu Ser Glu Val Gln Ala Met Leu Asn Val Glu Ala Lys
    1610                1615                1620

Asp Val Asp Ala Leu Ser Arg Thr Arg Thr Val Gly Glu Val Val
    1625                1630                1635

Asp Ala Met Lys Ala Glu Ile Ala Gly Ser Ser Ala Ser Ala Pro
    1640                1645                1650

Ala Ala Ala Ala Pro Ala Pro Ala Ala Ala Ala Pro Ala Pro Ala
    1655                1660                1665

Ala Ala Ala Pro Ala Val Ser Asn Glu Leu Leu Glu Lys Ala Glu
    1670                1675                1680

Thr Val Val Met Glu Val Leu Ala Ala Lys Thr Gly Tyr Glu Thr
    1685                1690                1695

Asp Met Ile Glu Ser Asp Met Glu Leu Glu Thr Glu Leu Gly Ile
    1700                1705                1710

Asp Ser Ile Lys Arg Val Glu Ile Leu Ser Glu Val Gln Ala Met
    1715                1720                1725

Leu Asn Val Glu Ala Lys Asp Val Asp Ala Leu Ser Arg Thr Arg
    1730                1735                1740

Thr Val Gly Glu Val Val Asp Ala Met Lys Ala Glu Ile Ala Gly
    1745                1750                1755

Gly Ser Ala Pro Ala Pro Ala Ala Ala Pro Ala Pro Ala Ala
    1760                1765                1770

Ala Ala Pro Ala Val Ser Asn Glu Leu Leu Glu Lys Ala Glu Thr
    1775                1780                1785

Val Val Met Glu Val Leu Ala Ala Lys Thr Gly Tyr Glu Thr Asp
    1790                1795                1800

Met Ile Glu Ser Asp Met Glu Leu Glu Thr Glu Leu Gly Ile Asp
    1805                1810                1815

Ser Ile Lys Arg Val Glu Ile Leu Ser Glu Val Gln Ala Met Leu
    1820                1825                1830

Asn Val Glu Ala Lys Asp Val Asp Ala Leu Ser Arg Thr Arg Thr
    1835                1840                1845

Val Gly Glu Val Val Asp Ala Met Lys Ala Glu Ile Ala Gly Ser
    1850                1855                1860

Ser Ala Pro Ala Pro Ala Ala Ala Pro Ala Pro Ala Ala Ala
    1865                1870                1875

Ala Pro Ala Pro Ala Ala Ala Ala Pro Ala Val Ser Ser Glu Leu
    1880                1885                1890

Leu Glu Lys Ala Glu Thr Val Val Met Glu Val Leu Ala Ala Lys
    1895                1900                1905

Thr Gly Tyr Glu Thr Asp Met Ile Glu Ser Asp Met Glu Leu Glu
    1910                1915                1920

Thr Glu Leu Gly Ile Asp Ser Ile Lys Arg Val Glu Ile Leu Ser
    1925                1930                1935

Glu Val Gln Ala Met Leu Asn Val Glu Ala Lys Asp Val Asp Ala
    1940                1945                1950
```

-continued

```
Leu Ser Arg Thr Arg Thr Val Gly Glu Val Val Asp Ala Met Lys
    1955                1960                1965

Ala Glu Ile Ala Gly Gly Ser Ala Pro Ala Pro Ala Ala Ala
1970                1975                1980

Pro Ala Pro Ala Ala Ala Pro Ala Val Ser Asn Glu Leu Leu
1985                1990                1995

Glu Lys Ala Glu Thr Val Val Met Glu Val Leu Ala Ala Lys Thr
    2000                2005                2010

Gly Tyr Glu Thr Asp Met Ile Glu Ser Asp Met Glu Leu Glu Thr
    2015                2020                2025

Glu Leu Gly Ile Asp Ser Ile Lys Arg Val Glu Ile Leu Ser Glu
    2030                2035                2040

Val Gln Ala Met Leu Asn Val Glu Ala Lys Asp Val Asp Ala Leu
    2045                2050                2055

Ser Arg Thr Arg Thr Val Gly Glu Val Val Asp Ala Met Lys Ala
    2060                2065                2070

Glu Ile Ala Gly Gly Ser Ala Pro Ala Pro Ala Ala Ala Pro
    2075                2080                2085

Ala Ser Ala Gly Ala Ala Pro Ala Val Lys Ile Asp Ser Val His
    2090                2095                2100

Gly Ala Asp Cys Asp Asp Leu Ser Leu Met His Ala Lys Val Val
    2105                2110                2115

Asp Ile Arg Arg Pro Asp Glu Leu Ile Leu Glu Arg Pro Glu Asn
    2120                2125                2130

Arg Pro Val Leu Val Val Asp Asp Gly Ser Glu Leu Thr Leu Ala
    2135                2140                2145

Leu Val Arg Val Leu Gly Ala Cys Ala Val Val Leu Thr Phe Glu
    2150                2155                2160

Gly Leu Gln Leu Ala Gln Arg Ala Gly Ala Ala Ala Ile Arg His
    2165                2170                2175

Lys Ala Ile Lys Glu Ala Glu Gln Arg Phe Gly Ala Leu Gly Gly
    2180                2185                2190

Phe Ile Ser Gln Gln Ala Glu Arg Phe Glu Pro Ala Glu Ile Leu
    2195                2200                2205

Gly Phe Thr Leu Met Cys Ala Lys Phe Ala Lys Ala Ser Leu Cys
    2210                2215                2220

Thr Ala Val Ala Gly Val Leu Ala Lys Asp Leu Ser Ala Glu Ser
    2225                2230                2235

Ala Glu Gly Arg Pro Ala Phe Ile Gly Val Ala Arg Leu Asp Gly
    2240                2245                2250

Arg Leu Gly Phe Thr Ser Gln Gly Thr Ser Asp Ala Leu Lys Arg
    2255                2260                2265

Ala Gln Arg Gly Ala Ile Phe Gly Leu Cys Lys Thr Ile Gly Leu
    2270                2275                2280

Glu Trp Ser Glu Ser Asp Val Phe Ser Arg Gly Val Asp Ile Ala
    2285                2290                2295

Gln Gly Met His Pro Glu Asp Ala Ala Val Ala Ile Val Arg Glu
    2300                2305                2310

Met Ala Cys Ala Asp Ile Arg Ile Arg Glu Val Gly Ile Gly Ala
    2315                2320                2325

Asn Gln Gln Arg Cys Thr Ile Arg Ala Ala Lys Leu Glu Thr Gly
    2330                2335                2340
```

```
Asn Pro Gln Arg Gln Ile Ala Lys Asp Asp Val Leu Leu Val Ser
2345                2350                2355

Gly Gly Ala Arg Gly Ile Thr Pro Leu Cys Ile Arg Glu Ile Thr
2360                2365                2370

Arg Gln Ile Ala Gly Gly Lys Tyr Ile Leu Leu Gly Arg Ser Lys
2375                2380                2385

Val Ser Ala Ser Glu Pro Ala Trp Cys Ala Gly Ile Thr Asp Glu
2390                2395                2400

Lys Ala Val Gln Lys Ala Ala Thr Gln Glu Leu Lys Arg Ala Phe
2405                2410                2415

Ser Ala Gly Glu Gly Pro Lys Pro Thr Pro Arg Ala Val Thr Lys
2420                2425                2430

Leu Val Gly Ser Val Leu Gly Ala Arg Glu Val Arg Ser Ser Ile
2435                2440                2445

Ala Ala Ile Glu Ala Leu Gly Gly Lys Ala Ile Tyr Ser Ser Cys
2450                2455                2460

Asp Val Asn Ser Ala Ala Asp Val Ala Lys Ala Val Arg Asp Ala
2465                2470                2475

Glu Ser Gln Leu Gly Ala Arg Val Ser Gly Ile Val His Ala Ser
2480                2485                2490

Gly Val Leu Arg Asp Arg Leu Ile Glu Lys Lys Leu Pro Asp Glu
2495                2500                2505

Phe Asp Ala Val Phe Gly Thr Lys Val Thr Gly Leu Glu Asn Leu
2510                2515                2520

Leu Ala Ala Val Asp Arg Ala Asn Leu Lys His Met Val Leu Phe
2525                2530                2535

Ser Ser Leu Ala Gly Phe His Gly Asn Val Gly Gln Ser Asp Tyr
2540                2545                2550

Ala Met Ala Asn Glu Ala Leu Asn Lys Met Gly Leu Glu Leu Ala
2555                2560                2565

Lys Asp Val Ser Val Lys Ser Ile Cys Phe Gly Pro Trp Asp Gly
2570                2575                2580

Gly Met Val Thr Pro Gln Leu Lys Lys Gln Phe Gln Glu Met Gly
2585                2590                2595

Val Gln Ile Ile Pro Arg Glu Gly Gly Ala Asp Thr Val Ala Arg
2600                2605                2610

Ile Val Leu Gly Ser Ser Pro Ala Glu Ile Leu Val Gly Asn Trp
2615                2620                2625

Arg Thr Pro Ser Lys Lys Val Gly Ser Asp Thr Ile Thr Leu His
2630                2635                2640

Arg Lys Ile Ser Ala Lys Ser Asn Pro Phe Leu Glu Asp His Val
2645                2650                2655

Ile Gln Gly Arg Arg Val Leu Pro Met Thr Leu Ala Ile Gly Ser
2660                2665                2670

Leu Ala Glu Thr Cys Leu Gly Leu Phe Pro Gly Tyr Ser Leu Trp
2675                2680                2685

Ala Ile Asp Asp Ala Gln Leu Phe Lys Gly Val Thr Val Asp Gly
2690                2695                2700

Asp Val Asn Cys Glu Val Thr Leu Thr Pro Ser Thr Ala Pro Ser
2705                2710                2715

Gly Arg Val Asn Val Gln Ala Thr Leu Lys Thr Phe Ser Ser Gly
2720                2725                2730

Lys Leu Val Pro Ala Tyr Arg Ala Val Ile Val Leu Ser Asn Gln
```

```
                  2735              2740              2745

Gly Ala Pro Pro Ala Asn Ala  Thr Met Gln Pro Pro  Ser Leu Asp
        2750              2755              2760

Ala Asp Pro Ala Leu Gln Gly  Ser Val Tyr Asp Gly  Lys Thr Leu
    2765              2770              2775

Phe His Gly Pro Ala Phe Arg  Gly Ile Asp Asp Val  Leu Ser Cys
    2780              2785              2790

Thr Lys Ser Gln Leu Val Ala  Lys Cys Ser Ala Val  Pro Gly Ser
    2795              2800              2805

Asp Ala Ala Arg Gly Glu Phe  Ala Thr Asp Thr Asp  Ala His Asp
    2810              2815              2820

Pro Phe Val Asn Asp Leu Ala  Phe Gln Ala Met Leu  Val Trp Val
    2825              2830              2835

Arg Arg Thr Leu Gly Gln Ala  Ala Leu Pro Asn Ser  Ile Gln Arg
    2840              2845              2850

Ile Val Gln His Arg Pro Val  Pro Gln Asp Lys Pro  Phe Tyr Ile
    2855              2860              2865

Thr Leu Arg Ser Asn Gln Ser  Gly Gly His Ser Gln  His Lys His
    2870              2875              2880

Ala Leu Gln Phe His Asn Glu  Gln Gly Asp Leu Phe  Ile Asp Val
    2885              2890              2895

Gln Ala Ser Val Ile Ala Thr  Asp Ser Leu Ala Phe
    2900              2905              2910

<210> SEQ ID NO 55
<211> LENGTH: 2895
<212> TYPE: PRT
<213> ORGANISM: Thraustochytrium aureum

<400> SEQUENCE: 55

Arg Lys Cys Ile Arg Pro Ser  Leu Gly His His Trp  Ala Ile Ile Gly
1               5                   10                  15

Val Leu Gly Arg Ala Leu Arg  Ile Val Arg Pro Ile  Arg Tyr Glu Ala
            20                  25                  30

Thr Asn Leu Arg Arg Leu Pro  Arg Ser Gly Trp Leu  Val Ala Leu Gly
        35                  40                  45

Leu Phe Cys Asp Leu Ser Ser  Cys Ala Gly Lys Leu  Asp Leu Gln Thr
    50                  55                  60

Arg Asp Thr Ala Lys Asp Pro  Cys Cys Lys Arg Lys  Trp Ser Ala Ser
65                  70                  75                  80

Arg Ala Pro Pro Arg Pro Arg  Ala Glu Ala Asp Lys  Ala Ser Asn Glu
                85                  90                  95

Met Glu Thr Lys Asp Asp Arg  Val Ala Ile Val Gly  Met Ser Ala Ile
            100                 105                 110

Leu Pro Cys Gly Glu Ser Val  Arg Glu Ser Trp Glu  Ala Ile Arg Glu
        115                 120                 125

Gly Leu Asp Cys Leu Gln Asp  Leu Pro Ala Asp Arg  Val Asp Ile Thr
    130                 135                 140

Ala Tyr Tyr Asp Pro Asn Lys  Thr Thr Lys Asp Lys  Ile Tyr Cys Lys
145                 150                 155                 160

Arg Gly Gly Phe Ile Pro Glu  Tyr Asp Phe Asp Ala  Arg Glu Phe Gly
                165                 170                 175

Leu Asn Met Phe Gln Met Glu  Asp Ser Asp Ala Asn  Gln Thr Val Thr
            180                 185                 190
```

-continued

Leu Leu Lys Val Lys Glu Ala Leu Glu Asp Ala Gly Val Glu Pro Phe
        195                 200                 205

Thr Lys Lys Lys Asn Ile Gly Cys Val Leu Gly Ile Gly Gly
    210                 215                 220

Gln Lys Ala Ser His Glu Phe Tyr Ser Arg Leu Asn Tyr Val Val
225                 230                 235                 240

Glu Lys Val Leu Arg Lys Met Asn Leu Pro Asp Val Val Glu Ala
                245                 250                 255

Ala Val Glu Lys Tyr Lys Ala Asn Phe Pro Glu Trp Arg Leu Asp Ser
            260                 265                 270

Phe Pro Gly Phe Leu Gly Asn Val Thr Ala Gly Arg Cys Ser Asn Val
            275                 280                 285

Phe Asn Met Glu Gly Met Asn Cys Val Val Asp Ala Ala Cys Ala Ser
    290                 295                 300

Ser Leu Ile Ala Ile Lys Val Ala Ile Asp Glu Leu Leu His Gly Asp
305                 310                 315                 320

Cys Asp Thr Met Ile Ala Gly Ala Thr Cys Thr Asp Asn Ser Ile Gly
                325                 330                 335

Met Tyr Met Ala Phe Ser Lys Thr Pro Val Phe Ser Thr Asp Gln Ser
            340                 345                 350

Val Lys Ala Tyr Asp Ala Lys Thr Lys Gly Met Leu Ile Gly Glu Gly
    355                 360                 365

Ser Ala Met Val Val Leu Lys Arg Tyr Ala Asp Ala Val Arg Asp Gly
    370                 375                 380

Asp Glu Ile His Ala Val Ile Arg Ala Cys Ala Ser Ser Ser Asp Gly
385                 390                 395                 400

Lys Ala Ala Gly Ile Tyr Ala Pro Thr Val Ser Gly Gln Glu Ala
                405                 410                 415

Leu Arg Arg Ala Tyr Ala Arg Ala Gly Val Asp Pro Ser Thr Val Thr
            420                 425                 430

Leu Val Glu Gly His Gly Thr Gly Thr Pro Val Gly Asp Arg Ile Glu
            435                 440                 445

Leu Thr Ala Leu Arg Asn Val Phe Asp Ala Ala Asn Lys Gly Arg Lys
    450                 455                 460

Glu Thr Val Ala Val Gly Ser Ile Lys Ser Gln Ile Gly His Leu Lys
465                 470                 475                 480

Ala Val Ala Gly Phe Ala Gly Leu Val Lys Val Val Met Ala Leu Lys
                485                 490                 495

His Lys Thr Leu Pro Gln Thr Ile Asn Val His Asp Pro Pro Ala Leu
            500                 505                 510

His Asp Gly Ser Pro Ile Gln Asp Ser Ser Leu Tyr Ile Asn Thr Met
            515                 520                 525

Asn Arg Pro Trp Phe Thr Ala Pro Gly Val Pro Arg Arg Ala Gly Ile
    530                 535                 540

Ser Ser Phe Gly Phe Gly Gly Ala Asn Tyr His Ala Val Leu Glu Glu
545                 550                 555                 560

Ala Glu Pro Glu His Ala Lys Pro Tyr Arg Met Asn Gln Val Pro Gln
                565                 570                 575

Pro Val Leu Leu His Ala Ser Ala Ser Ala Leu Ala Ser Ile Cys
            580                 585                 590

Asp Ala Gln Ala Asp Ala Leu Gln Ala Ala Val Ser Pro Glu Ala Ser
            595                 600                 605

Lys His Ala Asp Tyr Arg Ala Ile Val Ala Phe His Glu Ala Phe Lys

-continued

```
            610                 615                 620
Leu Arg Ala Gly Val Pro Ala Gly His Ala Arg Ile Gly Phe Val Ser
625                 630                 635                 640

Gly Ser Ala Ala Ala Thr Leu Ala Val Leu Arg Ala Ala Ser Ala Lys
                645                 650                 655

Leu Lys Gln Ser Ser Ala Thr Leu Glu Trp Thr Leu Leu Arg Glu Gly
                660                 665                 670

Val Thr Tyr Arg Ser Ala Ala Met His Thr Pro Gly Ser Val Ala Ala
                675                 680                 685

Leu Phe Ala Gly Gln Gly Ala Gln Tyr Thr His Met Phe Ala Asp Val
            690                 695                 700

Ala Met Asn Trp Pro Pro Phe Arg Ser Ala Val Gln Glu Met Asp Ala
705                 710                 715                 720

Ala Gln Val Thr Ala Ala Pro Lys Arg Leu Ser Glu Val Leu Tyr
                725                 730                 735

Pro Arg Lys Pro Tyr Ala Ala Glu Pro Glu Gln Asp Asn Lys Ala Ile
                740                 745                 750

Ser Met Thr Ile Asn Ser Gln Pro Ala Leu Met Ala Cys Ala Ala Gly
                755                 760                 765

Ala Phe Glu Val Phe Arg Gln Ala Gly Leu Ala Pro Asp His Val Ala
770                 775                 780

Gly His Ser Leu Gly Glu Phe Ala Leu Leu Ala Ala Gly Cys Ala
785                 790                 795                 800

Ser Arg Glu Glu Leu Phe Arg Leu Val Cys Ser Arg Ala Lys Ala Met
                805                 810                 815

Gln Asp Val Pro Gln Gly Asp Gly Ala Trp Leu Ala Asn Cys Asn Ser
                820                 825                 830

Pro Ser Gln Val Val Ile Ser Gly Asp Lys Thr Ala Val Glu Arg Glu
                835                 840                 845

Ser Ser Arg Leu Ala Gly Leu Gly Phe Arg Ile Ile Pro Leu Ala Cys
                850                 855                 860

Glu Gly Ala Phe His Ser Pro His Met Thr Ala Ala Gln Ala Thr Phe
865                 870                 875                 880

Gln Ala Ala Leu Asp Ser Leu Lys Ile Ser Thr Pro Thr Asn Gly Ala
                885                 890                 895

Arg Leu Tyr Asn Asn Val Ser Gly Lys Thr Cys Arg Ser Leu Gly Glu
                900                 905                 910

Leu Arg Asp Cys Leu Gly Lys His Met Thr Ser Pro Val Leu Phe Gln
                915                 920                 925

Ala Gln Val Glu Asn Met Tyr Ala Ala Gly Ala Arg Ile Phe Val Glu
            930                 935                 940

Phe Gly Pro Lys Gln Val Leu Ser Lys Leu Val Gly Glu Ile Leu Ala
945                 950                 955                 960

Asp Lys Ser Asp Phe Val Thr Val Ala Val Asn Ser Ser Ser Ser Lys
                965                 970                 975

Asp Ser Asp Val Gln Leu Arg Glu Ala Ala Ala Lys Leu Ala Val Leu
            980                 985                 990

Gly Val Pro Leu Ala Asn Phe Asp Pro Trp Glu Leu Cys Asp Ala Arg
            995                 1000                1005

Arg Leu Arg Glu Cys Pro Ser Lys Thr Thr Leu Arg Leu Ser
    1010                1015                1020

Ala Ala Thr Tyr Val Ser Asn Lys Thr Leu Ala Ala Arg Glu Lys
    1025                1030                1035
```

-continued

```
Val Met Glu Asp Asn Cys Asp Phe Ser Ser Leu Phe Ala Ser Gly
1040                1045                1050

Pro Ala Ser Gln Glu Met Glu Arg Glu Ile Ala Asn Leu Arg Ala
1055                1060                1065

Glu Leu Glu Ala Ala Gln Arg Gln Leu Asp Thr Ala Lys Thr Gln
1070                1075                1080

Leu Ala Arg Lys Gln Val Gln Asp Pro Thr Ala Asp Arg Gln Arg
1085                1090                1095

Asp Met Ile Ala Lys His Arg Ser Thr Leu Ala Ala Met Val Lys
1100                1105                1110

Glu Phe Glu Ala Leu Ala Ser Gly Ser Pro Cys Ala Val Pro Phe
1115                1120                1125

Ala Pro Val Val Asp Thr Ala Val Glu Asp Val Pro Phe Ala Asp
1130                1135                1140

Lys Val Ser Thr Pro Pro Pro Gln Val Thr Ser Ala Pro Ile Ala
1145                1150                1155

Glu Leu Ala Arg Ala Glu Ala Val Val Met Glu Val Leu Ala Ala
1160                1165                1170

Lys Thr Gly Tyr Glu Val Asp Met Ile Glu Ala Asp Met Leu Leu
1175                1180                1185

Asp Ala Glu Leu Gly Ile Asp Ser Val Lys Arg Ile Glu Ile Leu
1190                1195                1200

Ala Ala Val Gln Ala Gln Leu Gly Val Glu Ala Lys Asp Val Asp
1205                1210                1215

Ala Leu Ser Arg Thr Arg Thr Val Gly Glu Val Val Asp Ala Met
1220                1225                1230

Lys Ala Glu Ile Gly Gly Gln Ala Thr Ser Ala Pro Ser Pro Met
1235                1240                1245

Ala Gln Pro Gln Ala Ser Ala Pro Ser Pro Ser Pro Thr Ala Ser
1250                1255                1260

Val Leu Pro Lys Pro Val Ala Leu Pro Ala Ser Val Asp Pro Ala
1265                1270                1275

Lys Leu Ala Arg Ala Glu Ala Val Val Met Glu Val Leu Ala Ala
1280                1285                1290

Lys Thr Gly Tyr Glu Val Asp Met Ile Glu Ala Asp Met Leu Leu
1295                1300                1305

Asp Ala Glu Leu Gly Ile Asp Ser Val Lys Arg Ile Glu Ile Leu
1310                1315                1320

Ala Ala Val Gln Ala Gln Leu Gly Val Glu Ala Lys Asp Val Asp
1325                1330                1335

Ala Leu Ser Arg Thr Arg Thr Val Gly Glu Val Val Asp Ala Met
1340                1345                1350

Lys Ala Glu Ile Gly Gly Gln Ala Thr Ser Ala Pro Ala Ser Val
1355                1360                1365

Ala Gln Pro Gln Ala Ser Ala Pro Ser Pro Ser Ala Thr Thr Ala
1370                1375                1380

Ser Val Leu Pro Lys Pro Val Ala Ala Pro Thr Ser Ala Asp Pro
1385                1390                1395

Ala Lys Leu Ala Arg Ala Glu Ala Val Val Met Glu Val Leu Ala
1400                1405                1410

Ala Lys Thr Gly Tyr Glu Val Asp Met Ile Glu Ala Asp Met Leu
1415                1420                1425
```

```
Leu Asp Ala Glu Leu Gly Ile Asp Ser Val Lys Arg Ile Glu Ile
1430              1435              1440

Leu Ala Ala Val Gln Ala Gln Leu Gly Val Glu Ala Lys Asp Val
1445              1450              1455

Asp Ala Leu Ser Arg Thr Arg Thr Val Gly Glu Val Val Glu Ala
1460              1465              1470

Met Lys Ala Glu Ile Gly Gly Gln Ala Thr Ser Ala Pro Ala Ser
1475              1480              1485

Val Ala Gln Pro Gln Ile Ser Val Ser Pro Thr Pro Leu Ala Ala
1490              1495              1500

Ser Pro Ser Ala Asp Pro Ala Lys Leu Ala Arg Ala Glu Ala Val
1505              1510              1515

Val Met Glu Val Leu Ala Ala Lys Thr Gly Tyr Glu Val Asp Met
1520              1525              1530

Ile Glu Ala Asp Met Leu Leu Asp Ala Glu Leu Gly Ile Asp Ser
1535              1540              1545

Val Lys Arg Ile Glu Ile Leu Ala Ala Val Gln Ala Gln Leu Gly
1550              1555              1560

Val Glu Ala Lys Asp Val Asp Ala Leu Ser Arg Thr Arg Thr Val
1565              1570              1575

Gly Glu Val Val Asp Ala Met Lys Ala Glu Ile Gly Gly Gln Ala
1580              1585              1590

Thr Ser Ala Pro Ala Ser Val Ala Gln Pro Gln Ala Ser Ala Pro
1595              1600              1605

Ser Pro Ser Ala Thr Ala Ser Val Leu Pro Lys Pro Val Ala Ala
1610              1615              1620

Pro Thr Ser Ala Asp Pro Ala Lys Leu Ala Arg Ala Glu Ala Val
1625              1630              1635

Val Met Glu Val Leu Ala Ala Lys Thr Gly Tyr Glu Val Asp Met
1640              1645              1650

Ile Glu Ala Asp Met Leu Leu Asp Ala Glu Leu Gly Ile Asp Ser
1655              1660              1665

Val Lys Arg Ile Glu Ile Leu Ala Ala Val Gln Ala Gln Leu Gly
1670              1675              1680

Val Glu Ala Lys Asp Val Asp Ala Leu Ser Arg Thr Arg Thr Val
1685              1690              1695

Gly Glu Val Val Glu Ala Met Lys Ala Glu Ile Gly Gly Gln Ala
1700              1705              1710

Thr Ser Ala Pro Ala Ser Met Ala Gln Pro Gln Ile Ser Val Ser
1715              1720              1725

Pro Thr Pro Leu Ala Ala Ser Pro Ser Ala Asp Pro Ala Lys Leu
1730              1735              1740

Ala Arg Ala Glu Ala Val Val Met Glu Val Leu Ala Ala Lys Thr
1745              1750              1755

Gly Tyr Glu Val Asp Met Ile Glu Ala Asp Met Leu Leu Asp Ala
1760              1765              1770

Glu Leu Gly Ile Asp Ser Val Lys Arg Ile Glu Ile Leu Ala Ala
1775              1780              1785

Val Gln Ala Gln Leu Gly Val Glu Ala Lys Asp Val Asp Ala Leu
1790              1795              1800

Ser Arg Thr Arg Thr Val Gly Glu Val Val Asp Ala Met Lys Ala
1805              1810              1815

Glu Ile Gly Gly Gln Ala Thr Ser Ala Pro Ala Ser Val Ala Gln
```

-continued

```
                1820                1825                1830

Pro Gln Ala Ser Ala Pro Ser Pro Ser Ala Thr Ala Ser Ala Pro
    1835                1840                1845

Val Thr Pro Leu Ala Ala Pro Ala Ser Val Asp Pro Ala Lys Leu
    1850                1855                1860

Ala Arg Ala Glu Ala Val Val Met Glu Val Leu Ala Ala Lys Thr
    1865                1870                1875

Gly Tyr Glu Val Asp Met Ile Glu Ala Asp Met Leu Leu Asp Ala
    1880                1885                1890

Glu Leu Gly Ile Asp Ser Val Lys Arg Ile Glu Ile Leu Ala Ala
    1895                1900                1905

Val Gln Ala Gln Leu Gly Val Glu Ala Lys Asp Val Asp Ala Leu
    1910                1915                1920

Ser Arg Thr Arg Thr Val Gly Glu Val Val Asp Ala Met Lys Ala
    1925                1930                1935

Glu Ile Gly Gly Gln Ala Thr Ser Ala Pro Ala Ser Val Ala Gln
    1940                1945                1950

Pro Gln Ala Ser Ala Pro Ser Pro Ser Ala Thr Ala Ser Val Leu
    1955                1960                1965

Pro Lys Pro Val Ala Ser Pro Ala Ser Val Asp Pro Ala Lys Leu
    1970                1975                1980

Ala Arg Ala Glu Ala Val Val Met Glu Val Leu Ala Ala Lys Thr
    1985                1990                1995

Gly Tyr Glu Val Asp Met Ile Asp Ala Asp Met Leu Leu Asp Ala
    2000                2005                2010

Glu Leu Gly Ile Asp Ser Val Lys Arg Ile Glu Ile Leu Ala Ala
    2015                2020                2025

Val Gln Ala Gln Leu Gly Val Glu Ala Lys Asp Val Asp Ala Leu
    2030                2035                2040

Ser Arg Thr Arg Thr Val Gly Glu Val Val Glu Ala Met Lys Ala
    2045                2050                2055

Glu Ile Gly Ala Ala Gly Pro Asn Asp Ala Gln Ala Ala Ser Gly
    2060                2065                2070

His Leu Phe Gly Thr Gly Cys Glu Asp Leu Ser Leu Cys Ser Ala
    2075                2080                2085

Ser Val Val Glu Ile Ala Arg Cys Ser Glu Leu Ala Leu Glu Arg
    2090                2095                2100

Pro Met Asp Arg Pro Ile Leu Ile Val Ser Asp Gly Ser Ala Leu
    2105                2110                2115

Pro Ala Ala Leu Ala Ser Arg Leu Gly Ser Cys Ala Val Ile Leu
    2120                2125                2130

Thr Thr Ala Gly Glu Thr Asp Gln Ser Val Arg Ser Thr Lys His
    2135                2140                2145

Val Asp Met Glu Gly Trp Gly Glu Ala Asp Leu Val Arg Ala Leu
    2150                2155                2160

Glu Ala Val Glu Ser Arg Phe Gly Val Pro Gly Gly Val Val Val
    2165                2170                2175

Leu Glu Arg Ala Ser Glu Thr Ala Arg Asp Gln Leu Gly Phe Ala
    2180                2185                2190

Leu Leu Leu Ala Lys His Ser Ser Lys Ala Leu Asn Gln Gln Ile
    2195                2200                2205

Pro Gly Gly Arg Ala Cys Phe Val Gly Val Ser Arg Ile Asp Gly
    2210                2215                2220
```

```
Lys Leu Gly Leu Ser Gly Ala Cys Ala Lys Lys Gly Trp Ala
    2225            2230                2235

Glu Ala Ala Glu Ile Ala Gln Gln Gly Ala Val Ala Gly Leu Cys
    2240            2245                2250

Lys Thr Leu Asp Leu Glu Trp Pro His Val Phe Ala Arg Ser Ile
    2255            2260                2265

Asp Ile Glu Leu Gly Ala Asn Glu Glu Thr Ala Ala Gln Ala Ile
    2270            2275                2280

Phe Glu Glu Leu Ser Cys Pro Asp Leu Thr Val Arg Glu Ala Gly
    2285            2290                2295

Tyr Thr Lys Asp Gly Lys Arg Trp Thr Thr Glu Ala Arg Pro Val
    2300            2305                2310

Gly Leu Gly Lys Pro Lys Gln Ala Leu Arg Ser Ser Asp Val Phe
    2315            2320                2325

Leu Val Ser Gly Gly Ala Arg Gly Ile Thr Pro Val Cys Val Arg
    2330            2335                2340

Glu Leu Ala Lys Ser Ile Ser Gly Gly Thr Phe Val Leu Leu Gly
    2345            2350                2355

Arg Ser Pro Leu Ala Asp Asp Pro Ala Trp Ala Cys Gly Val Glu
    2360            2365                2370

Glu Ala Asn Ile Gly Thr Ala Ala Met Ala His Leu Lys Ala Glu
    2375            2380                2385

Phe Ala Ala Gly Arg Gly Pro Lys Pro Thr Pro Lys Ala His Lys
    2390            2395                2400

Ala Leu Val Gly Ser Val Leu Gly Ala Arg Glu Val Leu Gly Ser
    2405            2410                2415

Leu Glu Ser Ile Arg Ala Gln Gly Ala Arg Ala Glu Tyr Val Ser
    2420            2425                2430

Cys Asp Val Ser Cys Ala Glu Arg Val Lys Ala Val Val Asp Asp
    2435            2440                2445

Leu Glu Arg Arg Val Gly Ala Val Thr Gly Val Val His Ala Ser
    2450            2455                2460

Gly Val Leu Arg Asp Lys Ser Val Glu Arg Leu Glu Leu Ala Asp
    2465            2470                2475

Phe Glu Val Val Tyr Gly Thr Lys Val Asp Gly Leu Leu Asn Leu
    2480            2485                2490

Leu Gln Ala Val Asp Arg Pro Lys Leu Arg His Leu Val Leu Phe
    2495            2500                2505

Ser Ser Leu Ala Gly Phe His Gly Asn Thr Gly Gln Ala Val Tyr
    2510            2515                2520

Ala Met Ala Asn Glu Ala Leu Asn Lys Met Ala Phe His Leu Glu
    2525            2530                2535

Thr Ala Met Pro Gly Leu Ser Val Lys Thr Ile Gly Phe Gly Pro
    2540            2545                2550

Trp Asp Gly Gly Met Val Asn Asp Ala Leu Lys Ala His Phe Ala
    2555            2560                2565

Ser Met Gly Val Gln Ile Ile Pro Leu Asp Gly Gly Ala Glu Thr
    2570            2575                2580

Val Ser Arg Ile Ile Gly Ala Cys Ser Pro Thr Gln Val Leu Val
    2585            2590                2595

Gly Asn Trp Gly Leu Pro Pro Val Val Pro Asn Ala Ser Val His
    2600            2605                2610
```

```
Lys Ile Thr Val Arg Leu Gly Gly Glu Ser Ala Asn Pro Phe Leu
    2615                2620                2625

Ser Ser His Thr Ile Gln Gly Arg Lys Val Leu Pro Met Thr Val
    2630                2635                2640

Ala Leu Gly Leu Leu Ala Glu Ala Ala Arg Gly Leu Tyr Val Gly
    2645                2650                2655

His Gln Val Val Gly Ile Glu Asp Ala Gln Val Phe Gln Gly Val
    2660                2665                2670

Val Leu Asp Lys Gly Ala Thr Cys Glu Val Gln Leu Arg Arg Glu
    2675                2680                2685

Ser Ser Thr Ala Ser Pro Ser Glu Val Val Leu Ser Ala Ser Leu
    2690                2695                2700

Asn Val Phe Ala Ala Gly Lys Val Val Pro Ala Tyr Arg Ala His
    2705                2710                2715

Val Val Leu Gly Ala Ser Gly Pro Arg Thr Gly Val Gln Leu
    2720                2725                2730

Glu Leu Lys Asp Leu Gly Val Asp Ala Asp Pro Ala Cys Ser Val
    2735                2740                2745

Gly Lys Gly Ala Leu Tyr Asp Gly Arg Thr Leu Phe His Gly Pro
    2750                2755                2760

Ala Phe Gln Tyr Met Asp Glu Val Leu Arg Cys Ser Pro Ala Glu
    2765                2770                2775

Leu Ala Val Arg Cys Arg Val Val Pro Ser Ala Ala Gln Asp Arg
    2780                2785                2790

Gly Gln Phe Val Ser Arg Gly Val Leu Tyr Asp Pro Phe Leu Asn
    2795                2800                2805

Asp Thr Val Phe Gln Ala Leu Leu Val Trp Ala Arg Leu Val Arg
    2810                2815                2820

Asp Ser Ala Ser Leu Pro Ser Asn Val Glu Arg Ile Ser Phe His
    2825                2830                2835

Gly Gln Pro Pro Ser Glu Gly Glu Val Phe Tyr Thr Thr Leu Lys
    2840                2845                2850

Leu Asp Ser Ala Ala Ser Gly Pro Leu Asp Pro Ile Ala Lys Ala
    2855                2860                2865

Gln Phe Phe Leu His Arg Ala Cys Gly Ala Val Phe Ala Ser Gly
    2870                2875                2880

Arg Ala Ser Val Val Leu Asn Lys Ala Leu Ser Phe
    2885                2890                2895

<210> SEQ ID NO 56
<211> LENGTH: 2811
<212> TYPE: PRT
<213> ORGANISM: Thraustochytrium sp.

<400> SEQUENCE: 56

Met Lys Asp Met Glu Asp Arg Arg Val Ala Ile Val Gly Met Ser Ala
1               5                   10                  15

His Leu Pro Cys Gly Thr Asp Val Lys Glu Ser Trp Gln Ala Ile Arg
                20                  25                  30

Asp Gly Ile Asp Cys Leu Ser Asp Leu Pro Ala Asp Arg Leu Asp Val
            35                  40                  45

Thr Ala Tyr Tyr Asn Pro Asn Lys Ala Thr Lys Asp Lys Ile Tyr Cys
        50                  55                  60

Lys Arg Gly Gly Phe Ile Pro Asn Tyr Asp Phe Asp Pro Arg Glu Phe
65                  70                  75                  80
```

-continued

```
Gly Leu Asn Met Phe Gln Met Glu Asp Ser Asp Ala Asn Gln Thr Leu
                 85                  90                  95

Thr Leu Leu Lys Val Lys Gln Ala Leu Glu Asp Ala Ser Ile Glu Pro
            100                 105                 110

Phe Thr Lys Glu Lys Lys Asn Ile Gly Cys Val Leu Gly Ile Gly Gly
        115                 120                 125

Gly Gln Lys Ala Ser His Glu Phe Tyr Ser Arg Leu Asn Tyr Val Val
    130                 135                 140

Val Glu Lys Val Leu Arg Lys Met Gly Leu Pro Asp Ala Asp Val Glu
145                 150                 155                 160

Glu Ala Val Glu Lys Tyr Lys Ala Asn Phe Pro Glu Trp Arg Leu Asp
                165                 170                 175

Ser Phe Pro Gly Phe Leu Gly Asn Val Thr Ala Gly Arg Cys Ser Asn
            180                 185                 190

Thr Phe Asn Met Glu Gly Met Asn Cys Val Val Asp Ala Ala Cys Ala
        195                 200                 205

Ser Ser Leu Ile Ala Ile Lys Val Ala Val Glu Glu Leu Leu Phe Gly
    210                 215                 220

Asp Cys Asp Thr Met Ile Ala Gly Ala Thr Cys Thr Asp Asn Ser Leu
225                 230                 235                 240

Gly Met Tyr Met Ala Phe Ser Lys Thr Pro Val Phe Ser Thr Asp Pro
                245                 250                 255

Ser Val Arg Ala Tyr Asp Glu Lys Thr Lys Gly Met Leu Ile Gly Glu
            260                 265                 270

Gly Ser Ala Met Phe Val Leu Lys Arg Tyr Ala Asp Ala Val Arg Asp
        275                 280                 285

Gly Asp Thr Ile His Ala Val Leu Arg Ser Cys Ser Ser Ser Ser Asp
    290                 295                 300

Gly Lys Ala Ala Gly Ile Tyr Thr Pro Thr Ile Ser Gly Gln Glu Glu
305                 310                 315                 320

Ala Leu Arg Arg Ala Tyr Ala Arg Ala Gly Val Cys Pro Ser Thr Ile
                325                 330                 335

Gly Leu Val Glu Gly His Gly Thr Gly Thr Pro Val Gly Asp Arg Ile
            340                 345                 350

Glu Leu Thr Ala Leu Arg Asn Leu Phe Asp Lys Ala Phe Gly Ser Lys
        355                 360                 365

Lys Glu Gln Ile Ala Val Gly Ser Ile Lys Ser Gln Ile Gly His Leu
    370                 375                 380

Lys Ser Val Ala Gly Phe Ala Gly Leu Val Lys Ala Val Leu Ala Leu
385                 390                 395                 400

Lys His Lys Thr Leu Pro Gly Ser Ile Asn Val Asp Gln Pro Pro Leu
                405                 410                 415

Leu Tyr Asp Gly Thr Gln Ile Gln Asp Ser Ser Leu Tyr Ile Asn Lys
            420                 425                 430

Thr Asn Arg Pro Trp Phe Thr Gln Asn Lys Leu Pro Arg Arg Ala Gly
        435                 440                 445

Val Ser Ser Phe Gly Phe Gly Gly Ala Asn Tyr His Ala Val Leu Glu
    450                 455                 460

Glu Phe Glu Pro Glu His Glu Lys Pro Tyr Arg Leu Asn Thr Val Gly
465                 470                 475                 480

His Pro Val Leu Leu Tyr Ala Pro Ser Val Glu Ala Leu Lys Val Leu
                485                 490                 495
```

-continued

```
Cys Asn Asp Gln Leu Ala Glu Leu Thr Ile Ala Leu Glu Glu Ala Lys
                500                 505                 510

Thr His Lys Asn Val Asp Lys Val Cys Gly Tyr Lys Phe Ile Asp Glu
    515                 520                 525

Phe Gln Leu Gln Gly Ser Cys Pro Pro Glu Asn Pro Arg Val Gly Phe
530                 535                 540

Leu Ala Thr Leu Pro Thr Ser Asn Ile Ile Val Ala Leu Lys Ala Ile
545                 550                 555                 560

Leu Ala Gln Leu Asp Ala Lys Pro Asp Ala Lys Lys Trp Asp Leu Pro
                565                 570                 575

His Lys Lys Ala Phe Gly Ala Thr Phe Ala Ser Ser Val Lys Gly
    580                 585                 590

Ser Val Ala Ala Leu Phe Ala Gly Gln Gly Thr Gln Tyr Leu Asn Met
    595                 600                 605

Phe Ser Asp Val Ala Met Asn Trp Pro Pro Phe Arg Asp Ser Ile Val
    610                 615                 620

Ala Met Glu Glu Ala Gln Thr Glu Val Phe Glu Gly Gln Val Glu Pro
625                 630                 635                 640

Ile Ser Lys Val Leu Phe Pro Arg Glu Arg Tyr Ala Ser Glu Ser Glu
                645                 650                 655

Gln Gly Asn Glu Leu Leu Cys Leu Thr Glu Tyr Ser Gln Pro Thr Thr
                660                 665                 670

Ile Ala Ala Val Gly Ala Phe Asp Ile Phe Lys Ala Ala Gly Phe
                675                 680                 685

Lys Pro Asp Met Val Gly Gly His Ser Leu Gly Glu Phe Ala Ala Leu
    690                 695                 700

Tyr Ala Ala Gly Ser Ile Ser Arg Asp Asp Leu Tyr Lys Leu Val Cys
705                 710                 715                 720

Lys Arg Ala Lys Ala Met Ala Asn Ala Ser Asp Gly Ala Met Ala Ala
                725                 730                 735

Val Ile Gly Pro Asp Ala Arg Leu Val Thr Pro Gln Asn Ser Asp Val
                740                 745                 750

Tyr Val Ala Asn Phe Asn Ser Ala Thr Gln Val Val Ile Ser Gly Thr
    755                 760                 765

Val Gln Gly Val Lys Glu Glu Ser Lys Leu Leu Ile Ser Lys Gly Phe
    770                 775                 780

Arg Val Leu Pro Leu Lys Cys Gln Gly Ala Phe His Ser Pro Leu Met
785                 790                 795                 800

Gly Pro Ser Glu Asp Ser Phe Lys Ser Leu Val Glu Thr Cys Thr Ile
                805                 810                 815

Ser Pro Pro Lys Asn Val Lys Phe Phe Cys Asn Val Ser Gly Lys Glu
                820                 825                 830

Ser Pro Asn Pro Lys Gln Thr Leu Lys Ser His Met Thr Ser Ser Val
    835                 840                 845

Gln Phe Glu Glu Gln Ile Arg Asn Met Tyr Asp Ala Gly Ala Arg Val
    850                 855                 860

Phe Leu Glu Phe Gly Pro Arg Gln Val Leu Ala Lys Leu Ile Ala Glu
865                 870                 875                 880

Met Phe Pro Ser Cys Thr Ala Ile Ser Val Asn Pro Ala Ser Ser Gly
                885                 890                 895

Asp Ser Asp Val Gln Leu Arg Leu Ala Ala Val Lys Phe Ala Val Ser
                900                 905                 910

Gly Ala Ala Leu Ser Thr Phe Asp Pro Trp Glu Tyr Arg Lys Pro Gln
```

-continued

```
            915                 920                 925
Asp Leu Leu Ile Arg Lys Pro Arg Lys Thr Ala Leu Val Leu Ser Ala
        930                 935                 940
Ala Thr Tyr Val Ser Pro Lys Thr Leu Ala Glu Arg Lys Lys Ala Met
945                 950                 955                 960
Glu Asp Ile Lys Leu Val Ser Ile Thr Pro Arg Asp Ser Met Val Ser
                965                 970                 975
Ile Gly Lys Ile Ala Gln Glu Val Arg Thr Ala Lys Gln Pro Leu Glu
                    980                 985                 990
Thr Glu Ile Arg Arg Leu Asn Lys Glu Leu Glu His Leu Lys Arg Glu
                    995                 1000                1005
Leu Ala Ala Ala Lys Ala Ser Val Lys Ser Ala Ser Lys Ser Ser
        1010                1015                1020
Lys Glu Arg Ser Val Leu Ser Lys His Arg Ala Leu Leu Gln Asn
        1025                1030                1035
Ile Leu Gln Asp Tyr Asp Asp Leu Arg Val Val Pro Phe Ala Val
        1040                1045                1050
Arg Ser Val Ala Val Asp Asn Thr Ala Pro Tyr Ala Asp Gln Val
        1055                1060                1065
Ser Thr Pro Ala Ser Glu Arg Ser Ala Ser Pro Leu Phe Glu Lys
        1070                1075                1080
Arg Ser Ser Val Ser Ser Ala Arg Leu Ala Glu Ala Glu Ala Ala
        1085                1090                1095
Val Leu Ser Val Leu Ala Asp Lys Thr Gly Tyr Asp Ser Ser Met
        1100                1105                1110
Ile Glu Met Asp Met Asp Leu Glu Ser Glu Leu Gly Val Asp Ser
        1115                1120                1125
Ile Lys Arg Val Glu Ile Met Ser Glu Val Gln Thr Leu Leu Ser
        1130                1135                1140
Val Glu Val Ser Asp Val Asp Ala Leu Ser Arg Thr Lys Thr Val
        1145                1150                1155
Gly Asp Val Ile Glu Ala Met Lys Leu Glu Leu Gly Gly Pro Gln
        1160                1165                1170
Gly Gln Thr Leu Thr Ala Glu Ser Ile Arg Gln Pro Pro Val Ser
        1175                1180                1185
Glu Pro Ala Val Pro Thr Ser Ser Ser Ser Ser Ile Ala Asn Val
        1190                1195                1200
Ser Ser Ala Arg Leu Ala Glu Ala Glu Ala Ala Val Leu Ser Val
        1205                1210                1215
Leu Ala Asp Lys Thr Gly Tyr Asp Ser Ser Met Ile Glu Met Asp
        1220                1225                1230
Met Asp Leu Glu Ser Glu Leu Gly Val Asp Ser Ile Lys Arg Val
        1235                1240                1245
Glu Ile Met Ser Glu Val Gln Thr Leu Leu Ser Val Glu Val Ser
        1250                1255                1260
Asp Val Asp Ala Leu Ser Arg Thr Lys Thr Val Gly Asp Val Ile
        1265                1270                1275
Glu Ala Met Lys Leu Glu Leu Gly Gly Pro Gln Gly Gln Thr Leu
        1280                1285                1290
Thr Ala Glu Ser Ile Arg Gln Pro Pro Val Ser Glu Pro Ala Val
        1295                1300                1305
Pro Thr Ser Ser Ser Ser Ser Ile Ala Asn Val Ser Ser Ala Arg
        1310                1315                1320
```

```
Leu Ala Glu Ala Glu Ala Ala Val Leu Ser Val Leu Ala Asp Lys
1325                1330                1335

Thr Gly Tyr Asp Ser Ser Met Ile Glu Met Asp Met Asp Leu Glu
1340                1345                1350

Ser Glu Leu Gly Val Asp Ser Ile Lys Arg Val Glu Ile Met Ser
1355                1360                1365

Glu Val Gln Thr Leu Leu Ser Val Glu Val Ser Asp Val Asp Ala
1370                1375                1380

Leu Ser Arg Thr Lys Thr Val Gly Asp Val Ile Glu Ala Met Lys
1385                1390                1395

Leu Glu Leu Gly Gly Pro Gly Gln Thr Leu Thr Ala Glu Ser
1400                1405                1410

Ile Arg Gln Pro Pro Val Ser Glu Pro Ala Val Pro Thr Ser Ser
1415                1420                1425

Ser Ser Ser Ile Ala Asn Val Leu Ser Ala Arg Leu Ala Glu Ala
1430                1435                1440

Glu Ala Ala Val Leu Ser Val Leu Ala Asp Lys Thr Gly Tyr Asp
1445                1450                1455

Ser Ser Met Ile Glu Met Asp Met Asp Leu Glu Ser Glu Leu Gly
1460                1465                1470

Val Asp Ser Ile Lys Arg Val Glu Ile Met Ser Glu Val Gln Thr
1475                1480                1485

Leu Leu Ser Val Glu Val Ser Asp Val Asp Ala Leu Ser Arg Thr
1490                1495                1500

Lys Thr Val Gly Asp Val Ile Glu Ala Met Lys Leu Glu Leu Gly
1505                1510                1515

Gly Pro Gln Gly Gln Thr Leu Thr Ala Glu Ser Ile Arg Gln Pro
1520                1525                1530

Pro Val Ser Glu Pro Ala Val Pro Thr Ser Ser Ser Ser Ile
1535                1540                1545

Ala Asn Val Ser Ser Ala Arg Leu Ala Glu Ala Glu Ala Ala Val
1550                1555                1560

Leu Ser Val Leu Ala Asp Lys Thr Gly Tyr Asp Ser Ser Met Ile
1565                1570                1575

Glu Met Asp Met Asp Leu Glu Ser Glu Leu Gly Val Asp Ser Ile
1580                1585                1590

Lys Arg Val Glu Ile Met Ser Glu Val Gln Thr Leu Leu Ser Val
1595                1600                1605

Glu Val Ser Asp Val Asp Ala Leu Ser Arg Thr Lys Thr Val Gly
1610                1615                1620

Asp Val Ile Glu Ala Met Lys Leu Glu Leu Gly Gly Pro Gln Gly
1625                1630                1635

Gln Thr Leu Thr Ser Glu Pro Ile His Gln Pro Pro Val Ser Glu
1640                1645                1650

Pro Ala Val Pro Thr Ser Ser Ser Ser Ile Ala Asn Val Ser
1655                1660                1665

Ser Ala Arg Leu Ala Glu Ala Glu Ala Ala Val Leu Ser Val Leu
1670                1675                1680

Ala Asp Lys Thr Gly Tyr Asp Ser Ser Met Ile Glu Met Asp Met
1685                1690                1695

Asp Leu Glu Ser Glu Leu Gly Val Asp Ser Ile Lys Arg Val Glu
1700                1705                1710
```

-continued

Ile Met Ser Glu Val Gln Thr Leu Leu Ser Val Glu Val Ser Asp
1715                1720                1725

Val Asp Ala Leu Ser Arg Thr Lys Thr Val Gly Asp Val Ile Glu
1730                1735                1740

Ala Met Lys Met Glu Leu Gly Gly Pro Gln Gly Gln Thr Leu Thr
1745                1750                1755

Ala Glu Ser Ile Arg Gln Pro Pro Val Ser Glu Pro Ala Val Pro
1760                1765                1770

Thr Ser Ser Ser Ser Ser Ile Ala Asn Val Ser Ser Ala Arg Leu
1775                1780                1785

Ala Glu Ala Glu Ala Ala Val Leu Ser Val Leu Ala Asp Lys Thr
1790                1795                1800

Gly Tyr Asp Ser Ser Met Ile Glu Met Asp Met Asp Leu Glu Ser
1805                1810                1815

Glu Leu Gly Val Asp Ser Ile Lys Arg Val Glu Ile Met Ser Glu
1820                1825                1830

Val Gln Ala Leu Leu Ser Val Glu Val Ser Asp Val Asp Ala Leu
1835                1840                1845

Ser Arg Thr Lys Thr Val Gly Asp Val Ile Glu Ala Met Lys Met
1850                1855                1860

Glu Leu Gly Gly Pro Gln Gly Gln Thr Leu Thr Ala Glu Ser Ile
1865                1870                1875

Arg Glu Pro Pro Val Ser Glu Pro Ala Val Pro Thr Ser Ser Ser
1880                1885                1890

Ser Ser Ile Ala Asn Val Ser Ser Ala Arg Leu Ala Glu Ala Glu
1895                1900                1905

Ala Ala Val Leu Ser Val Leu Ala Asp Lys Thr Gly Tyr Asp Ser
1910                1915                1920

Ser Met Ile Glu Met Asp Met Asp Leu Glu Ser Glu Leu Gly Val
1925                1930                1935

Asp Ser Ile Lys Arg Val Glu Ile Met Ser Glu Val Gln Thr Leu
1940                1945                1950

Leu Ser Val Glu Val Ser Asp Val Asp Ala Leu Ser Arg Thr Lys
1955                1960                1965

Thr Val Gly Asp Val Ile Glu Ala Met Lys Leu Glu Leu Gly Glu
1970                1975                1980

Ser Ser Ser Ile Glu Thr Leu Asn Cys Thr Glu Val Glu His Thr
1985                1990                1995

Ser Tyr Lys Ser Val Lys Ala Ser Gly Cys Glu Asn Val Asp Thr
2000                2005                2010

Arg Phe Ala Lys Val Val Gln Ile Ser Leu Pro Ser Lys Leu Lys
2015                2020                2025

Ser Thr Val Ser His Asp Arg Pro Val Ile Val Val Asp Asp Gly
2030                2035                2040

Thr Pro Leu Thr Thr Glu Leu Cys Lys Ile Leu Gly Gly Asn Ile
2045                2050                2055

Val Val Leu Ser Tyr Gln Gly Lys Pro Ala Gly Pro Arg Gly Val
2060                2065                2070

Glu Val Pro Asp Leu Ser Glu Glu Ala Leu Ile Gln Ala Leu Ala
2075                2080                2085

Leu Ile Arg Ser Thr Tyr Gly Val Pro Ile Gly Phe Ile Cys Gln
2090                2095                2100

Gln Val Ser Asn Val Ser Thr Lys Ala Gln Leu Cys Trp Ala Leu

```
                    2105                2110                2115
Leu Ala Ala Lys His Leu Lys Lys Asp Leu Asn Ala Val Leu Pro
            2120                2125                2130
Asp Ser Arg Ser Phe Phe Val Gly Val Val Arg Leu Asn Gly Lys
            2135                2140                2145
Leu Gly Thr Phe Glu Asn Ile Ser Asp Phe Ser Lys Phe Asp Leu
            2150                2155                2160
Thr Lys Ala Leu Asp Tyr Gly Gln Arg Gly Ser Leu Leu Gly Leu
            2165                2170                2175
Cys Lys Ser Leu Asp Leu Glu Trp Glu Gln Val Phe Cys Arg Gly
            2180                2185                2190
Ile Asp Leu Ala Cys Asp Leu Met Pro Leu Gln Ala Ala Arg Ile
            2195                2200                2205
Leu Arg Asn Glu Leu Gln Cys Pro Asn Met Arg Leu Arg Glu Val
            2210                2215                2220
Gly Tyr Asp Ile Ser Gly Ala Arg Tyr Thr Ile Ser Thr Asp Asp
            2225                2230                2235
Leu Leu Cys Gly Pro Ser Lys Ala Lys Val Glu Ala Ala Asp Leu
            2240                2245                2250
Phe Leu Val Thr Gly Gly Ala Arg Gly Ile Thr Pro His Cys Val
            2255                2260                2265
Arg Glu Ile Ala Ser Arg Ser Pro Gly Thr Thr Phe Val Leu Val
            2270                2275                2280
Gly Arg Ser Glu Met Ser Asp Glu Pro Asp Trp Ala Val Gly His
            2285                2290                2295
Tyr Asn Lys Asp Leu Asp Gln Ser Thr Met Lys His Leu Lys Ala
            2300                2305                2310
Thr His Ala Ala Gly Gly Val Lys Pro Thr Pro Lys Ala His Arg
            2315                2320                2325
Ala Leu Val Asn Arg Val Thr Gly Ser Arg Glu Val Arg Glu Ser
            2330                2335                2340
Leu Arg Ala Ile Gln Glu Ala Gly Ala Asn Val Glu Tyr Ile Ala
            2345                2350                2355
Cys Asp Val Ser Asp Glu Asn Lys Val Arg Gln Leu Val Gln Arg
            2360                2365                2370
Val Glu Gln Lys Tyr Gly Cys Glu Ile Thr Gly Ile Trp His Ala
            2375                2380                2385
Ser Gly Val Leu Arg Asp Lys Leu Val Glu Gln Lys Thr Thr Asp
            2390                2395                2400
Asp Phe Glu Ala Val Phe Gly Thr Lys Val Thr Gly Leu Val Asn
            2405                2410                2415
Ile Val Ser Gln Val Asn Met Ser Lys Leu Arg His Phe Ile Leu
            2420                2425                2430
Phe Ser Ser Leu Ala Gly Phe His Gly Asn Lys Gly Gln Thr Asp
            2435                2440                2445
Tyr Ala Ile Ala Asn Glu Ala Leu Asn Lys Ile Ala His Thr Leu
            2450                2455                2460
Ser Ala Phe Leu Pro Lys Leu Asn Ala Lys Val Leu Asp Phe Gly
            2465                2470                2475
Pro Trp Val Gly Ser Gly Met Val Thr Glu Thr Leu Glu Lys His
            2480                2485                2490
Phe Lys Ala Met Gly Val Gln Thr Ile Pro Leu Glu Pro Gly Ala
            2495                2500                2505
```

Arg Thr Val Ala Gln Ile Ile Leu Ala Ser Ser Pro Pro Gln Ser
2510                2515                2520

Leu Leu Gly Asn Trp Gly Phe Pro Ala Thr Lys Pro Leu Gln Arg
2525                2530                2535

Ser Asn Val Val Thr Gly Thr Leu Ser Pro Glu Glu Ile Glu Phe
2540                2545                2550

Ile Ala Asp His Lys Ile Gln Gly Arg Lys Val Leu Pro Met Met
2555                2560                2565

Ala Ala Ile Gly Phe Met Ala Ser Ile Ala Glu Gly Leu Tyr Pro
2570                2575                2580

Gly Tyr Asn Leu Gln Gly Val Glu Asn Ala Gln Leu Phe Gln Gly
2585                2590                2595

Leu Thr Ile Asn Gln Glu Thr Lys Phe Gln Ile Thr Leu Ile Glu
2600                2605                2610

Glu His Asn Ser Glu Glu Asn Leu Asp Val Leu Thr Ser Leu Gly
2615                2620                2625

Val Met Leu Glu Ser Gly Lys Val Leu Pro Ala Tyr Arg Cys Val
2630                2635                2640

Val Cys Leu Asn Thr Thr Gln Gln Gln Pro Lys Leu Ser Pro Lys
2645                2650                2655

Ile Leu Asn Leu Glu Val Asp Pro Ala Cys Glu Val Asn Pro Tyr
2660                2665                2670

Asp Gly Lys Ser Leu Phe His Gly Pro Leu Leu Gln Phe Val Gln
2675                2680                2685

Gln Val Leu His Ser Ser Thr Lys Gly Leu Val Ala Lys Cys Arg
2690                2695                2700

Ala Leu Pro Ile Lys Glu Ala Ile Arg Gly Pro Phe Ile Lys Gln
2705                2710                2715

Thr Leu His Asp Pro Ile Leu Asp Asp Val Ile Phe Gln Leu Met
2720                2725                2730

Leu Val Trp Cys Arg Asn Ala Leu Gly Ser Ala Ser Leu Pro Asn
2735                2740                2745

Arg Ile Glu Lys Met Ser Tyr Phe Gly Asn Val Ser Glu Gly Ser
2750                2755                2760

Thr Phe Phe Ala Ser Val Thr Pro Val Gly Pro Arg Val Pro Lys
2765                2770                2775

Asp Pro Val Ile Lys Met Gln Phe Leu Leu Gln Asp Glu Ser Gly
2780                2785                2790

Asn Thr Phe Ser Ser Gly Glu Gly Ser Val Val Leu Ser Asp Glu
2795                2800                2805

Leu Val Phe
2810

<210> SEQ ID NO 57
<211> LENGTH: 2059
<212> TYPE: PRT
<213> ORGANISM: Schizochytrium sp.

<400> SEQUENCE: 57

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys

```
                35                  40                  45
Val Ile Ser Asp Lys Arg Leu Gly Ser Asn Tyr Arg Ala Glu His Tyr
 50                  55                  60

Lys Ala Glu Arg Ser Lys Tyr Ala Asp Thr Phe Cys Asn Glu Thr Tyr
 65                  70                  75                  80

Gly Thr Leu Asp Glu Asn Glu Ile Asp Asn Glu His Glu Leu Leu Leu
                 85                  90                  95

Asn Leu Ala Lys Gln Ala Leu Ala Glu Thr Ser Val Lys Asp Ser Thr
                100                 105                 110

Arg Cys Gly Ile Val Ser Gly Cys Leu Ser Phe Pro Met Asp Asn Leu
                115                 120                 125

Gln Gly Glu Leu Leu Asn Val Tyr Gln Asn His Val Glu Lys Lys Leu
                130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
                180                 185                 190

Asp Ala Ala Cys Ala Thr Ala Leu Tyr Val Leu Arg Leu Ala Gln Asp
                195                 200                 205

His Leu Val Ser Gly Ala Ala Asp Val Met Leu Cys Gly Ala Thr Cys
                210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
                260                 265                 270

Arg Leu Asp Asp Ala Ile Arg Asp Gly Asp His Ile Tyr Gly Thr Leu
                275                 280                 285

Leu Gly Ala Asn Val Ser Asn Ser Gly Thr Gly Leu Pro Leu Lys Pro
                290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
                340                 345                 350

Glu Gly Lys Val Pro Arg Phe Gly Thr Thr Lys Gly Asn Phe Gly His
                355                 360                 365

Thr Leu Val Ala Ala Gly Phe Ala Gly Met Cys Lys Val Leu Leu Ser
                370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
                420                 425                 430

Gly Thr Asn Ala His Ala Val Phe Glu Glu His Asp Pro Ser Asn Ala
                435                 440                 445

Ala Cys Thr Gly His Asp Ser Ile Ser Ala Leu Ser Ala Arg Cys Gly
                450                 455                 460
```

```
Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
            485                 490                 495

Ala His Gly Ala Ile Pro Leu Pro Glu Lys Arg Trp Arg Phe Leu Gly
                500                 505                 510

Lys Asp Lys Asp Phe Leu Asp Leu Cys Gly Val Lys Ala Thr Pro His
        515                 520                 525

Gly Cys Tyr Ile Glu Asp Val Glu Val Asp Phe Gln Arg Leu Arg Thr
    530                 535                 540

Pro Met Thr Pro Glu Asp Met Leu Leu Pro Gln Gln Leu Leu Ala Val
545                 550                 555                 560

Thr Thr Ile Asp Arg Ala Ile Leu Asp Ser Gly Met Lys Lys Gly Gly
                565                 570                 575

Asn Val Ala Val Phe Val Gly Leu Gly Thr Asp Leu Glu Leu Tyr Arg
            580                 585                 590

His Arg Ala Arg Val Ala Leu Lys Glu Arg Val Arg Pro Glu Ala Ser
        595                 600                 605

Lys Lys Leu Asn Asp Met Met Gln Tyr Ile Asn Asp Cys Gly Thr Ser
610                 615                 620

Thr Ser Tyr Thr Ser Tyr Ile Gly Asn Leu Val Ala Thr Arg Val Ser
625                 630                 635                 640

Ser Gln Trp Gly Phe Thr Gly Pro Ser Phe Thr Ile Thr Glu Gly Asn
                645                 650                 655

Asn Ser Val Tyr Arg Cys Ala Glu Leu Gly Lys Tyr Leu Leu Glu Thr
            660                 665                 670

Gly Glu Val Asp Gly Val Val Ala Gly Val Asp Leu Cys Gly Ser
        675                 680                 685

Ala Glu Asn Leu Tyr Val Lys Ser Arg Arg Phe Lys Val Ser Thr Ser
    690                 695                 700

Asp Thr Pro Arg Ala Ser Phe Asp Ala Ala Ala Asp Gly Tyr Phe Val
705                 710                 715                 720

Gly Glu Gly Cys Gly Ala Phe Val Leu Lys Arg Glu Thr Ser Cys Thr
                725                 730                 735

Lys Asp Asp Arg Ile Tyr Ala Cys Met Asp Ala Ile Val Pro Gly Asn
            740                 745                 750

Val Pro Ser Ala Cys Leu Arg Glu Ala Leu Asp Gln Ala Arg Val Lys
        755                 760                 765

Pro Gly Asp Ile Glu Met Leu Glu Leu Ser Ala Asp Ser Ala Arg His
    770                 775                 780

Leu Lys Asp Pro Ser Val Leu Pro Lys Glu Leu Thr Ala Glu Glu
785                 790                 795                 800

Ile Gly Gly Leu Gln Thr Ile Leu Arg Asp Asp Lys Leu Pro Arg
                805                 810                 815

Asn Val Ala Thr Gly Ser Val Lys Ala Thr Val Gly Asp Thr Gly Tyr
            820                 825                 830

Ala Ser Gly Ala Ala Ser Leu Ile Lys Ala Ala Leu Cys Ile Tyr Asn
        835                 840                 845

Arg Tyr Leu Pro Ser Asn Gly Asp Asp Trp Asp Glu Pro Ala Pro Glu
    850                 855                 860

Ala Pro Trp Asp Ser Thr Leu Phe Ala Cys Gln Thr Ser Arg Ala Trp
865                 870                 875                 880
```

```
Leu Lys Asn Pro Gly Glu Arg Arg Tyr Ala Ala Val Ser Gly Val Ser
            885                 890                 895

Glu Thr Arg Ser Cys Tyr Ser Val Leu Leu Ser Glu Ala Glu Gly His
        900                 905                 910

Tyr Glu Arg Glu Asn Arg Ile Ser Leu Asp Glu Glu Ala Pro Lys Leu
        915                 920                 925

Ile Val Leu Arg Ala Asp Ser His Glu Glu Ile Leu Gly Arg Leu Asp
        930                 935                 940

Lys Ile Arg Glu Arg Phe Leu Gln Pro Thr Gly Ala Ala Pro Arg Glu
945                 950                 955                 960

Ser Glu Leu Lys Ala Gln Ala Arg Arg Ile Phe Leu Glu Leu Leu Gly
                965                 970                 975

Glu Thr Leu Ala Gln Asp Ala Ala Ser Ser Gly Ser Gln Lys Pro Leu
        980                 985                 990

Ala Leu Ser Leu Val Ser Thr Pro Ser Lys Leu Gln Arg Glu Val Glu
        995                 1000                1005

Leu Ala Ala Lys Gly Ile Pro Arg Cys Leu Lys Met Arg Arg Asp
    1010                1015                1020

Trp Ser Ser Pro Ala Gly Ser Arg Tyr Ala Pro Glu Pro Leu Ala
    1025                1030                1035

Ser Asp Arg Val Ala Phe Met Tyr Gly Glu Gly Arg Ser Pro Tyr
    1040                1045                1050

Tyr Gly Ile Thr Gln Asp Ile His Arg Ile Trp Pro Glu Leu His
    1055                1060                1065

Glu Val Ile Asn Glu Lys Thr Asn Arg Leu Trp Ala Glu Gly Asp
    1070                1075                1080

Arg Trp Val Met Pro Arg Ala Ser Phe Lys Ser Glu Leu Glu Ser
    1085                1090                1095

Gln Gln Gln Glu Phe Asp Arg Asn Met Ile Glu Met Phe Arg Leu
    1100                1105                1110

Gly Ile Leu Thr Ser Ile Ala Phe Thr Asn Leu Ala Arg Asp Val
    1115                1120                1125

Leu Asn Ile Thr Pro Lys Ala Ala Phe Gly Leu Ser Leu Gly Glu
    1130                1135                1140

Ile Ser Met Ile Phe Ala Phe Ser Lys Lys Asn Gly Leu Ile Ser
    1145                1150                1155

Asp Gln Leu Thr Lys Asp Leu Arg Glu Ser Asp Val Trp Asn Lys
    1160                1165                1170

Ala Leu Ala Val Glu Phe Asn Ala Leu Arg Glu Ala Trp Gly Ile
    1175                1180                1185

Pro Gln Ser Val Pro Lys Asp Glu Phe Trp Gln Gly Tyr Ile Val
    1190                1195                1200

Arg Gly Thr Lys Gln Asp Ile Glu Ala Ala Ile Ala Pro Asp Ser
    1205                1210                1215

Lys Tyr Val Arg Leu Thr Ile Ile Asn Asp Ala Asn Thr Ala Leu
    1220                1225                1230

Ile Ser Gly Lys Pro Asp Ala Cys Lys Ala Ala Ile Ala Arg Leu
    1235                1240                1245

Gly Gly Asn Ile Pro Ala Leu Pro Val Thr Gln Gly Met Cys Gly
    1250                1255                1260

His Cys Pro Glu Val Gly Pro Tyr Thr Lys Asp Ile Ala Lys Ile
    1265                1270                1275

His Ala Asn Leu Glu Phe Pro Val Val Asp Gly Leu Asp Leu Trp
```

```
                   1280                1285                1290

Thr  Thr  Ile  Asn  Gln  Lys  Arg  Leu  Val  Pro  Arg  Ala  Thr  Gly  Ala
          1295                1300                1305

Lys  Asp  Glu  Trp  Ala  Pro  Ser  Ser  Phe  Gly  Glu  Tyr  Ala  Gly  Gln
          1310                1315                1320

Leu  Tyr  Glu  Lys  Gln  Ala  Asn  Phe  Pro  Gln  Ile  Val  Glu  Thr  Ile
          1325                1330                1335

Tyr  Lys  Gln  Asn  Tyr  Asp  Val  Phe  Val  Glu  Val  Gly  Pro  Asn  Asn
          1340                1345                1350

His  Arg  Ser  Thr  Ala  Val  Arg  Thr  Thr  Leu  Gly  Pro  Gln  Arg  Asn
          1355                1360                1365

His  Leu  Ala  Gly  Ala  Ile  Asp  Lys  Gln  Asn  Glu  Asp  Ala  Trp  Thr
          1370                1375                1380

Thr  Ile  Val  Lys  Leu  Val  Ala  Ser  Leu  Lys  Ala  His  Leu  Val  Pro
          1385                1390                1395

Gly  Val  Thr  Ile  Ser  Pro  Leu  Tyr  His  Ser  Lys  Leu  Val  Ala  Glu
          1400                1405                1410

Ala  Gln  Ala  Cys  Tyr  Ala  Ala  Leu  Cys  Lys  Gly  Glu  Lys  Pro  Lys
          1415                1420                1425

Lys  Asn  Lys  Phe  Val  Arg  Lys  Ile  Gln  Leu  Asn  Gly  Arg  Phe  Asn
          1430                1435                1440

Ser  Lys  Ala  Asp  Pro  Ile  Ser  Ser  Ala  Asp  Leu  Ala  Ser  Phe  Pro
          1445                1450                1455

Pro  Ala  Asp  Pro  Ala  Ile  Glu  Ala  Ala  Ile  Ser  Ser  Arg  Ile  Met
          1460                1465                1470

Lys  Pro  Val  Ala  Pro  Lys  Phe  Tyr  Ala  Arg  Leu  Asn  Ile  Asp  Glu
          1475                1480                1485

Gln  Asp  Glu  Thr  Arg  Asp  Pro  Ile  Leu  Asn  Lys  Asp  Asn  Ala  Pro
          1490                1495                1500

Ser  Ser  Ser  Ser  Ser  Ser  Ser  Ser  Ser  Ser  Ser  Ser  Ser  Ser  Ser
          1505                1510                1515

Pro  Ser  Pro  Ala  Pro  Ser  Ala  Pro  Val  Gln  Lys  Lys  Ala  Ala  Pro
          1520                1525                1530

Ala  Ala  Glu  Thr  Lys  Ala  Val  Ala  Ser  Ala  Asp  Ala  Leu  Arg  Ser
          1535                1540                1545

Ala  Leu  Leu  Asp  Leu  Asp  Ser  Met  Leu  Ala  Leu  Ser  Ser  Ala  Ser
          1550                1555                1560

Ala  Ser  Gly  Asn  Leu  Val  Glu  Thr  Ala  Pro  Ser  Asp  Ala  Ser  Val
          1565                1570                1575

Ile  Val  Pro  Pro  Cys  Asn  Ile  Ala  Asp  Leu  Gly  Ser  Arg  Ala  Phe
          1580                1585                1590

Met  Lys  Thr  Tyr  Gly  Val  Ser  Ala  Pro  Leu  Tyr  Thr  Gly  Ala  Met
          1595                1600                1605

Ala  Lys  Gly  Ile  Ala  Ser  Ala  Asp  Leu  Val  Ile  Ala  Ala  Gly  Arg
          1610                1615                1620

Gln  Gly  Ile  Leu  Ala  Ser  Phe  Gly  Ala  Gly  Gly  Leu  Pro  Met  Gln
          1625                1630                1635

Val  Val  Arg  Glu  Ser  Ile  Glu  Lys  Ile  Gln  Ala  Ala  Leu  Pro  Asn
          1640                1645                1650

Gly  Pro  Tyr  Ala  Val  Asn  Leu  Ile  His  Ser  Pro  Phe  Asp  Ser  Asn
          1655                1660                1665

Leu  Glu  Lys  Gly  Asn  Val  Asp  Leu  Phe  Leu  Glu  Lys  Gly  Val  Thr
          1670                1675                1680
```

Phe Val Glu Ala Ser Ala Phe Met Thr Leu Thr Pro Gln Val Val
1685                1690                1695

Arg Tyr Arg Ala Ala Gly Leu Thr Arg Asn Ala Asp Gly Ser Val
1700                1705                1710

Asn Ile Arg Asn Arg Ile Ile Gly Lys Val Ser Arg Thr Glu Leu
1715                1720                1725

Ala Glu Met Phe Met Arg Pro Ala Pro Glu His Leu Leu Gln Lys
1730                1735                1740

Leu Ile Ala Ser Gly Glu Ile Asn Gln Glu Gln Ala Glu Leu Ala
1745                1750                1755

Arg Arg Val Pro Val Ala Asp Asp Ile Ala Val Glu Ala Asp Ser
1760                1765                1770

Gly Gly His Thr Asp Asn Arg Pro Ile His Val Ile Leu Pro Leu
1775                1780                1785

Ile Ile Asn Leu Arg Asp Arg Leu His Arg Glu Cys Gly Tyr Pro
1790                1795                1800

Ala Asn Leu Arg Val Arg Val Gly Ala Gly Gly Ile Gly Cys
1805                1810                1815

Pro Gln Ala Ala Leu Ala Thr Phe Asn Met Gly Ala Ser Phe Ile
1820                1825                1830

Val Thr Gly Thr Val Asn Gln Val Ala Lys Gln Ser Gly Thr Cys
1835                1840                1845

Asp Asn Val Arg Lys Gln Leu Ala Lys Ala Thr Tyr Ser Asp Val
1850                1855                1860

Cys Met Ala Pro Ala Ala Asp Met Phe Glu Glu Gly Val Lys Leu
1865                1870                1875

Gln Val Leu Lys Lys Gly Thr Met Phe Pro Ser Arg Ala Asn Lys
1880                1885                1890

Leu Tyr Glu Leu Phe Cys Lys Tyr Asp Ser Phe Glu Ser Met Pro
1895                1900                1905

Pro Ala Glu Leu Ala Arg Val Glu Lys Arg Ile Phe Ser Arg Ala
1910                1915                1920

Leu Glu Glu Val Trp Asp Glu Thr Lys Asn Phe Tyr Ile Asn Arg
1925                1930                1935

Leu His Asn Pro Glu Lys Ile Gln Arg Ala Glu Arg Asp Pro Lys
1940                1945                1950

Leu Lys Met Ser Leu Cys Phe Arg Trp Tyr Leu Ser Leu Ala Ser
1955                1960                1965

Arg Trp Ala Asn Thr Gly Ala Ser Asp Arg Val Met Asp Tyr Gln
1970                1975                1980

Val Trp Cys Gly Pro Ala Ile Gly Ser Phe Asn Asp Phe Ile Lys
1985                1990                1995

Gly Thr Tyr Leu Asp Pro Val Ala Asn Glu Tyr Pro Cys Val
2000                2005                2010

Val Gln Ile Asn Lys Gln Ile Leu Arg Gly Ala Cys Phe Leu Arg
2015                2020                2025

Arg Leu Glu Ile Leu Arg Asn Ala Arg Leu Ser Asp Gly Ala Ala
2030                2035                2040

Ala Leu Val Ala Ser Ile Asp Asp Thr Tyr Val Pro Ala Glu Lys
2045                2050                2055

Leu

```
<210> SEQ ID NO 58
<211> LENGTH: 1935
<212> TYPE: PRT
<213> ORGANISM: Thraustochytrium sp.

<400> SEQUENCE: 58

Met Gln Leu Pro Pro Ala His Ser Ala Asp Glu Asn Arg Ile Ala Val
1               5                   10                  15

Val Gly Met Ala Val Lys Tyr Ala Gly Cys Asp Asn Lys Glu Glu Phe
            20                  25                  30

Trp Lys Thr Leu Met Asn Gly Ser Ile Asn Thr Lys Ser Ile Ser Ala
        35                  40                  45

Ala Arg Leu Gly Ser Asn Lys Arg Asp Glu His Tyr Val Pro Glu Arg
    50                  55                  60

Ser Lys Tyr Ala Asp Thr Phe Cys Asn Glu Arg Tyr Gly Cys Ile Gln
65                  70                  75                  80

Gln Gly Thr Asp Asn Glu His Asp Leu Leu Gly Leu Ala Gln Glu
                85                  90                  95

Ala Leu Ala Asp Ala Ala Gly Arg Met Glu Lys Gln Pro Ser Glu Ala
            100                 105                 110

Phe Asp Leu Glu Asn Thr Gly Ile Val Ser Gly Cys Leu Ser Phe Pro
        115                 120                 125

Met Asp Asn Leu Gln Gly Glu Leu Leu Asn Leu Tyr Gln Ser His Val
130                 135                 140

Glu Lys Gln Leu Pro Pro Ser Ala Leu Val Glu Ala Val Lys Leu Trp
145                 150                 155                 160

Ser Glu Arg Gln Lys Ser Thr Lys Ala His Ala Gly Asp Lys Arg Arg
                165                 170                 175

Phe Ile Asp Pro Ala Ser Phe Val Ala Asp Lys Leu Asn Leu Gly Pro
            180                 185                 190

Leu His Tyr Ala Ile Asp Ala Ala Cys Ala Ser Ala Leu Tyr Val Leu
        195                 200                 205

Lys Leu Ala Gln Asp His Leu Val Ser Gly Ala Val Asp Met Met Leu
    210                 215                 220

Cys Gly Ala Thr Cys Phe Pro Glu Pro Phe Phe Ile Leu Ser Gly Phe
225                 230                 235                 240

Ser Thr Phe Gln Ala Met Pro Val Gly Ala Asp Gly Val Ser Leu Pro
                245                 250                 255

Leu His Lys Thr Ser Ala Gly Leu Thr Pro Gly Glu Gly Ser Ile
            260                 265                 270

Met Val Leu Lys Arg Leu Lys Asp Ala Ile Arg Asp Gly Asn His Ile
        275                 280                 285

Tyr Gly Val Leu Leu Glu Ala Asn Leu Ser Asn Ala Gly Cys Gly Leu
    290                 295                 300

Pro Leu Ser Pro His Leu Pro Ser Glu Glu Ser Cys Ile Arg Asp Thr
305                 310                 315                 320

Tyr Arg Arg Ala Gly Val Ala Ala Asp Gln Ser Ile Gln Tyr Ile Glu
                325                 330                 335

Cys His Ala Thr Gly Thr Pro Arg Gly Asp Val Val Glu Ile Glu Ala
            340                 345                 350

Val Glu Arg Val Phe Lys Lys Asn Val Pro Arg Leu Gly Ser Thr Lys
        355                 360                 365

Gly Asn Phe Gly His Ser Leu Val Ala Ala Gly Phe Ala Gly Met Ala
    370                 375                 380
```

```
Lys Leu Leu Leu Ala Met Glu His Gly Val Ile Pro Pro Thr Pro Gly
385                 390                 395                 400

Leu Asp Ala Ser Asn Gln Ala Ser Glu His Val Val Thr Lys Ala Ile
            405                 410                 415

Thr Trp Pro Glu Thr His Gly Ala Pro Lys Arg Ala Gly Leu Ser Ala
        420                 425                 430

Phe Gly Phe Gly Gly Thr Asn Ala His Ala Leu Phe Glu Glu Phe Asn
        435                 440                 445

Ala Glu Gly Ile Ser Tyr Arg Pro Gly Lys Pro Val Glu Ser Asn
    450                 455                 460

Thr Arg Pro Ser Val Val Ile Thr Gly Met Asp Cys Thr Phe Gly Ser
465                 470                 475                 480

Leu Glu Gly Ile Asp Ala Phe Glu Thr Ala Leu Tyr Glu Gly Arg Asp
            485                 490                 495

Ala Ala Arg Asp Leu Pro Ala Lys Arg Trp Arg Phe Leu Gly Glu Asp
        500                 505                 510

Leu Glu Phe Leu Arg Ala Ile Arg Leu Lys Lys Pro Arg Gly Cys
    515                 520                 525

Phe Val Glu Ser Val Asp Val Asn Phe Arg Arg Leu Lys Thr Pro Leu
        530                 535                 540

Thr Pro Glu Asp Met Leu Arg Pro Gln Gln Leu Leu Ala Val Ser Thr
545                 550                 555                 560

Met Asp Arg Ala Ile Ile Asp Ala Gly Leu Lys Lys Gly Gln His Val
            565                 570                 575

Ala Val Leu Val Gly Leu Gly Thr Asp Leu Glu Leu Tyr Arg His Arg
        580                 585                 590

Ala Arg Val Ala Leu Lys Glu Val Leu His Pro Ser Leu Lys Ser Asp
    595                 600                 605

Thr Ala Ile Leu Gln Lys Ile Met Gln Tyr Val Asn Asp Ala Gly Thr
        610                 615                 620

Ser Thr Ser Tyr Thr Ser Tyr Ile Gly Asn Leu Val Ala Thr Arg Ile
625                 630                 635                 640

Ser Ser Gln Trp Gly Phe Thr Gly Pro Ser Phe Thr Val Thr Glu Gly
            645                 650                 655

Asn Asn Ser Val Tyr Arg Cys Ala Gln Leu Ala Lys Asp Met Leu Gln
        660                 665                 670

Val Asn Arg Val Asp Ala Val Ile Ala Gly Val Asp Leu Asn Gly
    675                 680                 685

Ser Ala Glu Ser Phe Phe Val Arg Ala Asn Arg Gln Lys Ile Ser Lys
        690                 695                 700

Leu Ser His Pro Cys Ala Ser Phe Asp Arg Asp Ala Asp Gly Phe Phe
705                 710                 715                 720

Ala Gly Glu Gly Cys Gly Ala Leu Val Phe Lys Arg Leu Glu Asp Cys
            725                 730                 735

Ala Pro Gln Glu Lys Ile Tyr Ala Ser Ile Asp Ser Ile Ala Ile Asp
        740                 745                 750

Lys Glu Pro Thr Ser Ser Ala Val Lys Ala Val Tyr Gln Ser Asp Ser
    755                 760                 765

Ser Leu Ser Asp Ile Glu Leu Glu Ile Ser Gly Asp Ser Lys Arg
        770                 775                 780

Phe Ala Ala Phe Glu Gly Ala Val Glu Ile Gln Ser Ser Val Glu Ala
785                 790                 795                 800

Gln Leu Lys Gly Leu Ser Lys Val Leu Glu Pro Ala Lys Gly Gln Gly
```

```
                  805                 810                 815
Val Ala Val Gly Ser Thr Arg Ala Thr Val Gly Asp Ile Gly Tyr Ala
            820                 825                 830

Thr Gly Ala Ala Ser Leu Ile Lys Thr Ala Leu Cys Leu Tyr Asn Arg
            835                 840                 845

Tyr Leu Pro Ala Leu Ala Asn Trp Ser Gly Pro Cys Glu Gln Ser Ala
            850                 855                 860

Trp Gly Ser Asn Met Phe Val Cys His Glu Thr Arg Pro Trp Met Lys
865                 870                 875                 880

Asn Gln Asn Glu Lys Arg Cys Ala Leu Ile Ser Gly Thr Asp Pro Ser
            885                 890                 895

His Thr Cys Phe Ser Leu Val Leu Ser Asp Thr Gly Cys Tyr Glu Glu
            900                 905                 910

His Asn Arg Thr Cys Phe Asp Val Gln Ala Pro Gln Leu Val Leu Ile
            915                 920                 925

His Gly Phe Asp Gly Lys Thr Ile Val Arg Arg Leu Glu Gly Tyr Leu
            930                 935                 940

Leu Glu Leu Val Glu Gly His Ala Ser Pro Ser Glu Tyr Phe His Lys
945                 950                 955                 960

Leu Ile Gly Gln Ser Leu Leu Glu Asn Ser Lys Glu Ser Lys Leu Thr
            965                 970                 975

Leu Ser Leu Val Cys Asn Pro Asn Gln Leu Gln Lys Gly Leu Met Leu
            980                 985                 990

Ala Ile Lys Gly Val Gln Arg Ser Met Leu Thr Gly Lys Asp Trp Val
            995                1000                1005

Ser Pro Ser Gly Ser Cys Phe Ala Pro Asn Pro Leu Ser Ser Ala
        1010                1015                1020

Lys Val Ala Phe Met Tyr Gly Glu Gly Arg Ser Pro Tyr Cys Gly
        1025                1030                1035

Val Gly Leu Gly Leu His Arg Leu Trp Pro Gly Leu His Glu Asn
        1040                1045                1050

Val Asn Asn Lys Thr Val Asp Leu Trp Thr Glu Gly Asp Gly Trp
        1055                1060                1065

Leu Tyr Pro Arg Thr Leu Thr Arg Glu Glu His Thr Lys Ala Ile
        1070                1075                1080

Glu Ser Phe Asn Ala Asn Gln Ile Glu Met Phe Arg Ala Gly Ile
        1085                1090                1095

Phe Ile Ser Met Cys Gln Thr Asp Tyr Val Met Asn Val Leu Gly
        1100                1105                1110

Val Gln Pro Lys Ala Gly Phe Gly Leu Ser Leu Gly Glu Ile Ser
        1115                1120                1125

Met Leu Phe Ala Met Ser Lys Glu Asn Cys Arg Gln Ser Gln Glu
        1130                1135                1140

Met Thr Asn Arg Leu Arg Gly Ser Pro Val Trp Ser Asn Glu Leu
        1145                1150                1155

Ala Ile Asn Phe Asn Ala Ile Arg Lys Leu Trp Lys Ile Pro Arg
        1160                1165                1170

Gly Ala Pro Leu Glu Ser Phe Trp Gln Gly Tyr Leu Val His Gly
        1175                1180                1185

Thr Arg Glu Glu Val Glu His Ala Ile Gly Leu Ser Glu Pro Tyr
        1190                1195                1200

Val Arg Leu Leu Ile Val Asn Asp Ser Arg Ser Ala Leu Ile Ala
        1205                1210                1215
```

Gly Lys Pro Asp Ala Cys Gln Ala Val Ile Ser Arg Leu Asn Ser
1220                1225                1230

Lys Phe Pro Ser Leu Pro Val Lys Gln Gly Met Ile Gly His Cys
1235                1240                1245

Pro Glu Val Arg Ala Phe Ile Lys Asp Ile Gly Tyr Ile His Glu
1250                1255                1260

Thr Leu Arg Ile Ser Asn Asp Tyr Ser Asp Cys Gln Leu Phe Ser
1265                1270                1275

Ala Val Thr Lys Gly Ala Leu Asp Ser Ser Thr Met Glu Ile Lys
1280                1285                1290

His Phe Val Gly Glu Val Tyr Ser Arg Ile Ala Asp Phe Pro Gln
1295                1300                1305

Ile Val Asn Thr Val His Ser Ala Gly Tyr Asp Val Phe Leu Glu
1310                1315                1320

Leu Gly Cys Asp Ala Ser Arg Ser Ala Ala Val Gln Asn Ile Leu
1325                1330                1335

Gly Gly Gln Gly Lys Phe Leu Ser Thr Ala Ile Asp Lys Lys Gly
1340                1345                1350

His Ser Ala Trp Ser Gln Val Leu Arg Ala Thr Ala Ser Leu Ala
1355                1360                1365

Ala His Arg Val Pro Gly Ile Ser Ile Leu Asp Leu Phe His Pro
1370                1375                1380

Asn Phe Arg Glu Met Cys Cys Thr Met Ala Thr Thr Pro Lys Val
1385                1390                1395

Glu Asp Lys Phe Leu Arg Thr Ile Gln Ile Asn Gly Arg Phe Glu
1400                1405                1410

Lys Glu Met Ile His Leu Glu Asp Thr Thr Leu Ser Cys Leu Pro
1415                1420                1425

Ala Pro Ser Glu Ala Asn Ile Ala Ala Ile Gln Ser Arg Ser Ile
1430                1435                1440

Arg Ser Ala Ala Ala Arg Ser Gly Gln Ser His Asp Cys Ala Ser
1445                1450                1455

His Ser His Glu Glu Asn Lys Asp Ser Cys Pro Glu Lys Leu Lys
1460                1465                1470

Leu Asp Ser Val Ser Val Ala Ile Asn Phe Asp Asn Asp Asp Arg
1475                1480                1485

Ile Gln Leu Gly His Ala Gly Phe Arg Glu Met Tyr Asn Thr Arg
1490                1495                1500

Tyr Ser Leu Tyr Thr Gly Ala Met Ala Lys Gly Ile Ala Ser Ala
1505                1510                1515

Asp Leu Val Ile Ala Ala Gly Lys Glu Gly Ile Leu Ala Ser Tyr
1520                1525                1530

Gly Ala Gly Gly Leu Pro Leu Ala Thr Val Arg Lys Gly Ile Asp
1535                1540                1545

Lys Ile Gln Gln Ala Leu Pro Ser Gly Pro Tyr Ala Val Asn Leu
1550                1555                1560

Ile His Ser Pro Phe Asp Gly Asn Leu Glu Gln Gly Asn Val Asp
1565                1570                1575

Leu Phe Leu Glu Lys Asn Val Arg Val Ala Glu Cys Ser Ala Phe
1580                1585                1590

Thr Thr Leu Thr Val Pro Val Val His Tyr Arg Ala Ala Gly Leu
1595                1600                1605

```
Val Arg Arg Gln Asp Gly Ser Ile Leu Ile Lys Asn Arg Ile Ile
1610                1615                1620

Ala Lys Val Ser Arg Thr Glu Leu Ala Glu Met Phe Leu Arg Pro
    1625                1630                1635

Ala Pro Gln Ile Ile Leu Glu Lys Leu Val Ala Glu Ile Ile
1640                1645                1650

Ser Ser Asp Gln Ala Arg Met Ala Ala Lys Val Pro Met Ala Asp
    1655                1660                1665

Asp Ile Ala Val Glu Ala Asp Ser Gly Gly His Thr Asp Asn Arg
1670                1675                1680

Pro Met His Val Ile Leu Pro Leu Ile Ile Gln Leu Arg Asn Thr
    1685                1690                1695

Ile Leu Ala Glu Tyr Gly Cys Ala Thr Ala Phe Arg Thr Arg Ile
1700                1705                1710

Gly Ala Gly Gly Gly Ile Gly Cys Pro Ser Ala Ala Leu Ala Ala
    1715                1720                1725

Phe Asp Met Gly Ala Ser Phe Val Val Thr Gly Ser Ile Asn Gln
1730                1735                1740

Ile Cys Arg Glu Ala Gly Thr Cys Asp Thr Val Arg Glu Leu Leu
    1745                1750                1755

Ala Asn Ser Ser Tyr Ser Asp Val Thr Met Ala Pro Ala Ala Asp
1760                1765                1770

Met Phe Asp Gln Gly Val Lys Leu Gln Val Leu Lys Arg Gly Thr
    1775                1780                1785

Met Phe Pro Ser Arg Ala Asn Lys Leu Arg Lys Leu Phe Val Asn
1790                1795                1800

Tyr Glu Ser Leu Glu Thr Leu Pro Ser Lys Glu Leu Lys Tyr Leu
    1805                1810                1815

Glu Asn Ile Ile Phe Lys Gln Ala Val Asp Gln Val Trp Glu Glu
1820                1825                1830

Thr Lys Arg Phe Tyr Cys Glu Lys Leu Asn Asn Pro Asp Lys Ile
    1835                1840                1845

Ala Arg Ala Met Lys Asp Pro Lys Leu Lys Met Ser Leu Cys Phe
1850                1855                1860

Arg Trp Tyr Leu Ser Lys Ser Ser Gly Trp Ala Asn Ala Gly Ile
    1865                1870                1875

Lys Ser Arg Ala Leu Asp Tyr Gln Ile Trp Cys Gly Pro Ala Met
1880                1885                1890

Gly Ser Phe Asn Asn Phe Ala Ser Gly Thr Ser Leu Asp Trp Lys
    1895                1900                1905

Val Thr Gly Val Phe Pro Gly Val Ala Glu Val Asn Met Ala Ile
1910                1915                1920

Leu Asp Gly Ala Arg Glu Leu Ala Ala Lys Arg Asn
    1925                1930                1935

<210> SEQ ID NO 59
<211> LENGTH: 2037
<212> TYPE: PRT
<213> ORGANISM: Thraustochytrium aureum

<400> SEQUENCE: 59

Gln Ala Ile Gly His Arg Ala Ala Arg Trp Ser Cys Arg Ser Lys Ser
1               5                   10                  15

Lys Ala Arg Gly His Lys Ala Gln Lys Glu Met Asn Gln Gly Gly Arg
            20                  25                  30
```

-continued

```
Asn Asp Glu Gly Val Ser Val Ala Arg Ala Asp Pro Cys Pro Asp Thr
         35                  40                  45

Arg Ile Ala Val Val Gly Met Ala Val Glu Tyr Ala Gly Cys Arg Gly
 50                  55                  60

Lys Glu Ala Phe Trp Asp Thr Leu Met Asn Gly Lys Ile Asn Ser Ala
 65                  70                  75                  80

Cys Ile Ser Asp Asp Arg Leu Gly Ser Ala Arg Arg Glu Glu His Tyr
                 85                  90                  95

Ala Pro Glu Arg Ser Lys Tyr Ala Asp Thr Phe Cys Asn Glu Arg Tyr
                100                 105                 110

Gly Cys Ile Asp Pro Lys Val Asp Asn Glu His Asp Leu Leu Leu Gly
                115                 120                 125

Leu Ala Ala Ala Ala Leu Gln Asp Ala Gln Asp Arg Arg Ser Asp Gly
130                 135                 140

Gly Lys Phe Asp Pro Ala Gln Leu Lys Arg Cys Gly Ile Val Ser Gly
145                 150                 155                 160

Cys Leu Ser Phe Pro Met Asp Asn Leu Gln Gly Glu Leu Leu Asn Leu
                165                 170                 175

Tyr Gln Ala His Ala Glu Arg Arg Ile Gly Lys His Cys Phe Ala Asp
                180                 185                 190

Gln Thr Pro Trp Ser Thr Arg Thr Arg Ala Leu His Pro Leu Pro Gly
                195                 200                 205

Asp Pro Arg Thr His Arg Asp Pro Ala Ser Phe Val Ala Gly Gln Leu
                210                 215                 220

Gly Leu Gly Pro Leu His Tyr Ser Leu Asp Ala Ala Cys Ala Ser Ala
225                 230                 235                 240

Leu Tyr Val Leu Arg Leu Ala Gln Asp His Leu Leu Ser Gly Glu Ala
                245                 250                 255

Asp Leu Met Leu Cys Gly Ala Thr Cys Phe Pro Glu Pro Phe Phe Ile
                260                 265                 270

Leu Thr Gly Phe Ser Thr Phe His Ala Met Pro Val Gly Glu Asn Gly
                275                 280                 285

Val Ser Met Pro Phe His Arg Asp His Leu Leu Ser Gly Glu Ala Asp
                290                 295                 300

Leu Met Leu Cys Gly Ala Thr Cys Phe Pro Glu Pro Phe Phe Ile Leu
305                 310                 315                 320

Thr Gly Phe Ser Thr Phe His Ala Met Pro Val Gly Glu Asn Gly Val
                325                 330                 335

Ser Met Pro Phe His Arg Gln Pro Ser Glu Glu Ala Cys Leu Lys Ala
                340                 345                 350

Thr Tyr Glu Leu Val Gly Val Pro Pro Arg Asp Val Gln Tyr Val Glu
                355                 360                 365

Cys His Ala Thr Gly Thr Pro Gln Gly Asp Thr Val Glu Leu Gln Ala
                370                 375                 380

Val Lys Ala Cys Phe Glu Gly Ala Ser Pro Arg Ile Gly Ser Thr Lys
385                 390                 395                 400

Gly Asn Phe Gly His Thr Leu Val Ala Ala Gly Phe Ala Gly Met Cys
                405                 410                 415

Lys Val Leu Leu Ala Met Glu Arg Gly Val Ile Pro Pro Thr Pro Gly
                420                 425                 430

Val Asp Ser Gly Thr Gln Ile Asp Pro Leu Val Val Thr Ala Ala Leu
                435                 440                 445
```

-continued

```
Pro Trp Pro Asp Thr Arg Gly Gly Pro Lys Arg Ala Gly Leu Ser Ala
450                 455                 460

Phe Gly Phe Gly Gly Thr Asn Ala His Ala Val Phe Glu Glu His Ile
465                 470                 475                 480

Pro Ser Arg Ala Pro Pro Ala Val Leu Cys Gln Pro Arg Leu Gly Ser
                485                 490                 495

Gly Pro Asn Arg Lys Leu Ala Ile Val Gly Met Asp Ala Thr Phe Gly
                500                 505                 510

Ser Leu Lys Gly Leu Ser Ala Leu Glu Ala Ala Leu Tyr Glu Ala Arg
            515                 520                 525

His Ala Ala Arg Pro Leu Pro Ala Lys Arg Trp Arg Phe Leu Gly Gly
530                 535                 540

Asp Glu Ser Phe Leu His Glu Ile Gly Leu Glu Cys Ser Pro His Gly
545                 550                 555                 560

Cys Tyr Ile Glu Asp Val Asp Val Asp Phe Lys Arg Leu Arg Thr Pro
                565                 570                 575

Met Val Pro Glu Asp Leu Leu Arg Pro Gln Gln Leu Leu Ala Val Ser
                580                 585                 590

Thr Ile Asp Lys Ala Ile Leu Asp Ser Gly Leu Ala Lys Gly Gly Asn
            595                 600                 605

Val Ala Val Leu Val Gly Leu Gly Thr Asp Leu Glu Leu Tyr Arg His
            610                 615                 620

Arg Ala Arg Val Ala Leu Lys Glu Arg Leu Gln Gly Leu Val Arg Ser
625                 630                 635                 640

Ala Glu Gly Gly Ala Leu Thr Ser Arg Leu Met Asn Tyr Ile Asn Asp
                645                 650                 655

Ser Gly Thr Ser Thr Ser Tyr Thr Ser Tyr Ile Gly Asn Leu Val Ala
                660                 665                 670

Thr Arg Val Ser Ser Gln Trp Gly Phe Thr Gly Pro Ser Phe Thr Val
            675                 680                 685

Thr Glu Gly Ala Asn Ser Val His Arg Cys Ala Gln Leu Ala Lys Tyr
            690                 695                 700

Met Leu Asp Arg Gly Glu Val Asp Ala Val Val Ala Gly Val Asp
705                 710                 715                 720

Leu Cys Gly Ser Ala Glu Ala Phe Phe Val Arg Ser Arg Met Gln
                725                 730                 735

Ile Ser Lys Ser Gln Arg Pro Ala Ala Pro Phe Asp Arg Ala Ala Asp
                740                 745                 750

Gly Phe Phe Ala Gly Gly Cys Gly Ala Leu Val Phe Lys Arg Leu
            755                 760                 765

Thr Asp Cys Val Ser Gly Glu Arg Ile Tyr Ala Ser Leu Asp Ser Val
            770                 775                 780

Val Val Ala Thr Thr Pro Arg Ala Ala Leu Arg Ala Ala Gly Ser
785                 790                 795                 800

Ala Arg Val Asp Pro Ala Ser Ile Asp Met Val Glu Leu Ser Ala Asp
                805                 810                 815

Ser His Arg Phe Val Arg Ala Pro Gly Thr Val Ala Gln Pro Leu Thr
            820                 825                 830

Ala Glu Val Glu Val Gly Ala Arg Glu Val Ile Gly Thr Ala Gly
            835                 840                 845

Arg Gly Ser Arg Ser Val Ala Val Gly Ser Val Arg Ala Asn Val Gly
850                 855                 860

Asp Ala Gly Phe Ala Ser Gly Ala Ala Ala Leu Val Lys Thr Ala Leu
```

```
              865                 870                 875                 880
Cys Leu His Asn Arg Tyr Leu Ala Ala Thr Pro Gly Trp Asp Ala Pro
                        885                 890                 895
Ala Ala Gly Val Asp Phe Gly Ala Glu Leu Tyr Val Cys Arg Glu Ser
                900                 905                 910
Arg Ala Trp Val Lys Asn Ala Gly Val Ala Arg His Ala Ala Ile Ser
            915                 920                 925
Gly Val Asp Glu Gly Gly Ser Cys Tyr Gly Leu Val Leu Ser Asp Val
        930                 935                 940
Pro Gly Gln Tyr Glu Thr Gly Asn Arg Ile Ser Leu Gln Ala Glu Ser
945                 950                 955                 960
Pro Lys Leu Leu Leu Leu Ser Ala Pro Asp His Ala Ala Leu Leu Asp
                965                 970                 975
Lys Val Ala Ala Glu Leu Ala Ala Leu Glu Gln Ala Asp Gly Leu Ser
            980                 985                 990
Ala Ala Ala Ala Ala Val Asp Arg Leu Leu Gly Glu Ser Leu Val Gly
        995                 1000                1005
Cys Ala Ala Gly Ser Gly Gly Leu Thr Leu Cys Leu Val Ala Ser
        1010                1015                1020
Pro Ala Ser Leu His Lys Glu Leu Ala Leu Ala His Arg Gly Ile
        1025                1030                1035
Pro Arg Cys Ile Lys Ala Arg Arg Asp Trp Ala Ser Pro Ala Gly
        1040                1045                1050
Ser Tyr Phe Ala Pro Glu Pro Ile Ala Ser Asp Arg Val Ala Phe
        1055                1060                1065
Met Tyr Gly Glu Gly Arg Ser Pro Tyr Cys Gly Val Gly Arg Asp
        1070                1075                1080
Leu His Arg Ile Trp Pro Ala Leu His Glu Arg Val Asn Ala Lys
        1085                1090                1095
Thr Val Asn Leu Trp Gly Asp Gly Asp Ala Trp Leu Leu Pro Arg
        1100                1105                1110
Ala Thr Ser Ala Glu Glu Glu Gln Leu Cys Arg Asn Phe Asp
        1115                1120                1125
Ser Asn Gln Val Glu Met Phe Arg Thr Gly Val Tyr Ile Ser Met
        1130                1135                1140
Cys Leu Thr Asp Leu Ala Arg Ser Leu Ile Gly Leu Gly Pro Lys
        1145                1150                1155
Ala Ser Phe Gly Leu Ser Leu Gly Glu Val Ser Met Leu Phe Ala
        1160                1165                1170
Leu Ser Glu Ser Asn Cys Arg Leu Ser Glu Glu Met Thr Arg Arg
        1175                1180                1185
Leu Arg Ala Ser Pro Val Trp Asn Ser Glu Leu Ala Val Glu Phe
        1190                1195                1200
Asn Ala Leu Arg Lys Leu Trp Gly Val Ala Pro Gly Ala Pro Val
        1205                1210                1215
Asp Ser Phe Trp Gln Gly Tyr Val Val Arg Ala Thr Arg Ala Gln
        1220                1225                1230
Val Glu Gln Ala Ile Gly Glu Asp Asn Gln Phe Val Arg Leu Leu
        1235                1240                1245
Ile Val Asn Asp Ser Gln Ser Val Leu Ile Ala Gly Lys Pro Ala
        1250                1255                1260
Ala Cys Glu Ala Val Ile Ala Arg Ile Gly Ser Ile Leu Pro Pro
        1265                1270                1275
```

```
Leu Gln Val Ser Gln Gly Met Val Gly His Cys Ala Glu Val Leu
    1280            1285            1290

Pro Tyr Thr Ser Glu Ile Gly Arg Ile His Asn Met Leu Arg Phe
    1295            1300            1305

Pro Ser Gln Asp Glu Thr Gly Gly Cys Lys Met Tyr Ser Ser Val
    1310            1315            1320

Ser Asn Ser Arg Ile Gly Pro Val Glu Ser Gln Met Gly Pro
    1325            1330            1335

Gly Thr Glu Leu Val Phe Ser Pro Ser Met Glu Asp Phe Val Ala
    1340            1345            1350

Gln Leu Tyr Ser Arg Val Ala Asp Phe Pro Ala Ile Thr Glu Ala
    1355            1360            1365

Val Tyr Gln Gln Gly His Asp Val Phe Val Glu Val Gly Pro Asp
    1370            1375            1380

His Ser Arg Ser Ala Ala Val Arg Ser Thr Leu Gly Pro Thr Arg
    1385            1390            1395

Arg His Ile Ala Val Ala Met Asp Arg Lys Gly Glu Ser Ala Trp
    1400            1405            1410

Ser Gln Leu Leu Lys Met Leu Ala Thr Leu Ala Ser His Arg Val
    1415            1420            1425

Pro Gly Leu Asp Leu Ser Ser Met Tyr His Pro Ala Val Val Glu
    1430            1435            1440

Arg Cys Arg Leu Ala Leu Ala Ala Gln Arg Ser Gly Gln Pro Glu
    1445            1450            1455

Gln Arg Asn Lys Phe Leu Arg Thr Ile Glu Val Asn Gly Phe Tyr
    1460            1465            1470

Asp Pro Ala Asp Ala Thr Ile Pro Glu Ala Val Ala Thr Ile Leu
    1475            1480            1485

Pro Ala Thr Ala Ala Ile Ser Pro Pro Lys Leu Gly Ala Pro His
    1490            1495            1500

Asp Ser Gln Pro Glu Ala Glu Ala Arg Pro Val Gly Glu Ala Ser
    1505            1510            1515

Val Pro Arg Arg Ala Thr Ser Ser Ser Lys Leu Ala Arg Thr Leu
    1520            1525            1530

Ala Ile Asp Ala Cys Asp Ser Asp Val Arg Ala Ala Leu Leu Asp
    1535            1540            1545

Leu Asp Ala Pro Ile Ala Val Gly Gly Ser Ser Arg Ala Gln Val
    1550            1555            1560

Pro Pro Cys Pro Val Ser Ala Leu Gly Ser Ala Ala Phe Arg Ala
    1565            1570            1575

Ala His Gly Val Asp Tyr Ala Leu Tyr Met Gly Ala Met Ala Lys
    1580            1585            1590

Gly Val Ala Ser Ala Glu Met Val Ile Ala Ala Gly Lys Ala Arg
    1595            1600            1605

Met Leu Ala Ser Phe Gly Ala Gly Gly Leu Pro Leu Gly Glu Val
    1610            1615            1620

Glu Glu Ala Leu Asp Lys Ile Gln Ala Ala Leu Pro Glu Gly Pro
    1625            1630            1635

Phe Ala Val Asn Leu Ile His Ser Pro Phe Asp Pro Asn Leu Glu
    1640            1645            1650

Glu Gly Asn Val Glu Leu Phe Leu Arg Arg Gly Ile Arg Leu Val
    1655            1660            1665
```

```
Glu Ala Ser Ala Phe Met Ser Val Thr Pro Ser Leu Val Arg Tyr
1670            1675                1680

Arg Val Ala Gly Leu Glu Arg Gly Pro Gly Gly Thr Ala Arg Val
1685            1690                1695

Leu Asn Arg Val Ile Gly Lys Val Ser Arg Ala Glu Leu Ala Glu
1700            1705                1710

Met Phe Met Arg Pro Pro Ala Ala Ile Val Ser Lys Leu Leu
1715            1720                1725

Ala Gln Gly Leu Val Thr Glu Gln Ala Ser Leu Ala Glu Ile
1730            1735                1740

Val Pro Leu Val Asp Asp Val Ala Ile Glu Ala Asp Ser Gly Gly
1745            1750                1755

His Thr Asp Asn Arg Pro Ile His Val Val Leu Pro Val Val Leu
1760            1765                1770

Ala Leu Arg Asp Arg Val Met Arg Glu Cys Lys Tyr Pro Ala Ala
1775            1780                1785

Asn Arg Val Arg Val Gly Ala Gly Gly Ile Gly Cys Pro Ala
1790            1795                1800

Ala Ala Arg Ala Ala Phe Asp Met Gly Ala Ala Phe Val Leu Thr
1805            1810                1815

Gly Ser Ile Asn Gln Leu Thr Arg Gln Ala Gly Thr Ser Asp Ser
1820            1825                1830

Val Arg Ala Ala Leu Ala Arg Ala Thr Tyr Ser Asp Val Thr Met
1835            1840                1845

Ala Pro Ala Ala Asp Met Phe Asp Gln Gly Val Lys Leu Gln Val
1850            1855                1860

Leu Lys Arg Gly Thr Met Phe Pro Ala Arg Ala Asn Lys Leu Tyr
1865            1870                1875

Glu Leu Phe Thr Thr Tyr Gln Ser Leu Asp Ala Ile Pro Arg Ala
1880            1885                1890

Glu Leu Ala Arg Leu Glu Lys Arg Val Phe Arg Met Ser Ile Asp
1895            1900                1905

Glu Val Trp Asn Glu Thr Lys Gln Phe Tyr Glu Thr Arg Leu Asn
1910            1915                1920

Asn Pro Ala Lys Val Ala Arg Ala Glu Arg Asp Pro Lys Leu Lys
1925            1930                1935

Met Ser Leu Cys Phe Arg Trp Tyr Leu Ser Lys Ser Ser Lys Trp
1940            1945                1950

Ala Ser Thr Gly Gln Val Gly Arg Glu Leu Asp Tyr Gln Val Trp
1955            1960                1965

Cys Gly Pro Thr Ile Gly Ala Phe Asn Glu Phe Val Lys Gly Ser
1970            1975                1980

Ser Leu Asp Ala Glu Ala Cys Gly Gly Arg Phe Pro Cys Val Val
1985            1990                1995

Arg Val Asn Gln Glu Ile Leu Cys Gly Ala Ala Tyr Glu Gln Arg
2000            2005                2010

Leu Ala Arg Phe Met Leu Leu Ala Gly Arg Glu Ser Ala Asp Ala
2015            2020                2025

Leu Ala Tyr Thr Val Ala Glu Ala Arg
2030            2035
```

<210> SEQ ID NO 60
<211> LENGTH: 1470
<212> TYPE: PRT

```
<213> ORGANISM: Thraustochytrium sp.

<400> SEQUENCE: 60

Met Gly Pro Arg Val Ala Ser Gly Lys Val Pro Ala Trp Glu Met Ser
1               5                   10                  15

Lys Ser Glu Leu Cys Asp Asp Arg Thr Val Val Phe Asp Tyr Glu Glu
            20                  25                  30

Leu Leu Glu Phe Ala Glu Gly Asp Ile Ser Lys Val Phe Gly Pro Glu
        35                  40                  45

Phe Lys Val Val Asp Gly Phe Arg Arg Val Arg Leu Pro Ala Arg
    50                  55                  60

Glu Tyr Leu Leu Val Thr Arg Val Thr Leu Met Asp Ala Glu Val Gly
65                  70                  75                  80

Asn Phe Arg Val Gly Ala Arg Met Val Thr Glu Tyr Asp Val Pro Val
                85                  90                  95

Asn Gly Glu Leu Ser Glu Gly Asp Val Pro Trp Ala Val Leu Val
            100                 105                 110

Glu Ala Gly Gln Cys Asp Leu Leu Ile Ser Tyr Met Gly Ile Asp
            115                 120                 125

Phe Gln Cys Lys Gly Glu Arg Val Tyr Arg Leu Leu Asn Thr Thr Leu
    130                 135                 140

Thr Phe Phe Gly Val Ala Lys Glu Gly Glu Thr Leu Val Tyr Asp Ile
145                 150                 155                 160

Arg Val Thr Gly Phe Ala Lys Arg Pro Asp Gly Asp Ile Ser Met Phe
                165                 170                 175

Phe Phe Glu Tyr Asp Cys Tyr Cys Asn Gly Lys Leu Leu Ile Glu Met
            180                 185                 190

Arg Asp Gly Ser Ala Gly Phe Phe Thr Asp Glu Glu Leu Ala Ala Gly
            195                 200                 205

Lys Gly Val Val Thr Arg Ala Gln Gln Asn Met Arg Asp Lys Ile
    210                 215                 220

Val Arg Gln Ser Ile Glu Pro Phe Ala Leu Ala Ala Cys Thr His Lys
225                 230                 235                 240

Thr Thr Leu Asn Glu Ser Asp Met Gln Ser Leu Val Glu Arg Asn Trp
                245                 250                 255

Ala Asn Val Phe Gly Thr Ser Asn Lys Met Ala Glu Leu Asn Tyr Lys
            260                 265                 270

Ile Cys Ala Arg Lys Met Leu Met Ile Asp Arg Val Thr His Ile Asp
        275                 280                 285

His His Gly Gly Ala Tyr Gly Leu Gly Leu Leu Val Gly Glu Lys Ile
    290                 295                 300

Leu Asp Arg Asn His Trp Tyr Phe Pro Cys His Phe Val Asn Asp Gln
305                 310                 315                 320

Val Met Ala Gly Ser Leu Val Ser Asp Gly Cys Ser Gln Leu Leu Lys
                325                 330                 335

Leu Tyr Met Ile Trp Leu Gly Leu His Leu Lys Met Glu Glu Phe Asp
            340                 345                 350

Phe Leu Pro Val Ser Gly His Lys Asn Lys Val Arg Cys Arg Gly Gln
        355                 360                 365

Ile Ser Pro His Lys Gly Lys Leu Val Tyr Val Met Glu Ile Lys Lys
    370                 375                 380

Met Gly Tyr Asp Gln Ala Ser Gly Ser Pro Tyr Ala Ile Ala Asp Val
385                 390                 395                 400
```

```
Asp Ile Ile Asp Val Asn Glu Glu Leu Gly Gln Ser Phe Asp Ile Asn
            405                 410                 415
Asp Leu Ala Ser Tyr Gly Lys Gly Asp Leu Ser Lys Lys Ile Val Val
        420                 425                 430
Asp Phe Lys Gly Ile Ala Leu Gln Leu Lys Gly Arg Ala Phe Ser Arg
        435                 440                 445
Met Ser Ser Ser Ser Leu Asn Glu Gly Trp Gln Cys Val Pro Lys
450                 455                 460
Pro Ser Gln Arg Met Glu His Glu Gln Pro Ala His Cys Leu Ala
465                 470                 475                 480
Ser Asp Pro Glu Ala Pro Ser Thr Val Thr Trp His Pro Met Ser Lys
            485                 490                 495
Leu Pro Gly Asn Pro Thr Pro Phe Phe Ser Pro Ser Ser Tyr Pro Pro
            500                 505                 510
Arg Ala Ile Cys Phe Ile Pro Phe Pro Gly Asn Pro Leu Asp Asn Asn
            515                 520                 525
Cys Lys Ala Gly Glu Met Pro Leu Asn Trp Tyr Asn Met Ser Glu Phe
            530                 535                 540
Met Cys Gly Lys Val Ser Asn Cys Leu Gly Pro Glu Phe Ala Arg Phe
545                 550                 555                 560
Asp Lys Ser Asn Thr Ser Arg Ser Pro Ala Phe Asp Leu Ala Leu Val
                565                 570                 575
Thr Arg Val Val Glu Val Thr Asn Met Glu His Gly Lys Phe Leu Asn
            580                 585                 590
Val Asp Cys Asn Pro Ser Lys Gly Thr Met Val Gly Glu Phe Asp Cys
            595                 600                 605
Pro Gln Asp Ala Trp Phe Phe Asp Gly Ser Cys Asn Asp Gly His Met
610                 615                 620
Pro Tyr Ser Ile Ile Met Glu Ile Gly Leu Gln Thr Ser Gly Val Leu
625                 630                 635                 640
Thr Ser Val Leu Lys Ala Pro Leu Thr Met Asp Lys Asp Ile Leu
                645                 650                 655
Phe Arg Asn Leu Asp Ala Ser Ala Glu Met Val Arg Pro Asp Val Asp
            660                 665                 670
Val Arg Gly Lys Thr Ile Arg Asn Val Thr Lys Cys Thr Gly Tyr Ala
            675                 680                 685
Met Leu Gly Lys Met Gly Ile His Arg Phe Thr Phe Glu Leu Ser Val
            690                 695                 700
Asp Gly Val Val Phe Tyr Lys Gly Ser Thr Ser Phe Gly Trp Phe Thr
705                 710                 715                 720
Pro Glu Val Phe Ala Gln Gln Ala Gly Leu Asp Asn Gly Lys Lys Thr
                725                 730                 735
Glu Pro Trp Cys Lys Thr Asn Asn Thr Ser Val Arg Arg Val Glu Ile
            740                 745                 750
Ala Ser Ala Lys Gly Lys Glu Gln Leu Thr Lys Leu Pro Asp Ala
                755                 760                 765
Thr Asn Ala Gln Val Leu Arg Arg Ser Glu Gln Cys Glu Tyr Leu Asp
    770                 775                 780
Tyr Leu Asn Ile Ala Pro Asp Ser Gly Leu His Gly Lys Gly Tyr Ala
785                 790                 795                 800
His Gly His Lys Asp Val Asn Pro Gln Asp Trp Phe Phe Ser Cys His
                805                 810                 815
Phe Trp Phe Asp Pro Val Met Pro Gly Ser Leu Gly Ile Glu Ser Met
```

-continued

```
                820                 825                 830
Phe Gln Leu Ile Glu Ala Phe Ala Val Asp Gln Asn Ile Pro Gly Glu
                835                 840                 845
Tyr Asn Val Ser Asn Pro Thr Phe Ala His Ala Pro Gly Lys Thr Ala
                850                 855                 860
Trp Lys Tyr Arg Gly Gln Leu Thr Pro Lys Asn Arg Ala Met Asp Cys
865                 870                 875                 880
Glu Val His Ile Val Ser Ile Thr Ala Ser Pro Glu Asn Gly Gly Tyr
                            885                 890                 895
Val Asp Ile Val Ala Asp Gly Ala Leu Trp Val Asp Gly Leu Arg Val
                900                 905                 910
Tyr Glu Ala Lys Glu Leu Arg Val Arg Val Val Ser Ala Lys Pro Gln
                915                 920                 925
Ala Ile Pro Asp Val Gln Gln Pro Pro Ser Ala Lys Ala Asp Pro
                930                 935                 940
Gly Lys Thr Gly Val Ala Leu Ser Pro Thr Gln Leu Arg Asp Val Leu
945                 950                 955                 960
Leu Glu Val Asp Asn Pro Leu Tyr Leu Gly Val Glu Asn Ser Asn Leu
                965                 970                 975
Val Gln Phe Glu Ser Lys Pro Ala Thr Ser Ser Arg Ile Val Ser Ile
                980                 985                 990
Lys Pro Cys Ser Ile Ser Asp Leu  Gly Asp Lys Ser Phe  Met Glu Thr
                995                 1000                1005
Tyr Asn  Val Ser Ala Pro Leu  Tyr Thr Gly Ala Met  Ala Lys Gly
            1010                1015                1020
Ile Ala  Ser Ala Asp Leu Val  Ile Ala Ala Gly Lys  Arg Lys Ile
            1025                1030                1035
Leu Gly  Ser Phe Gly Ala Gly  Gly Leu Pro Ile Ser  Ile Val Arg
            1040                1045                1050
Glu Ala  Leu Glu Lys Ile Gln  Gln His Leu Pro His  Gly Pro Tyr
            1055                1060                1065
Ala Val  Asn Leu Ile His Ser  Pro Phe Asp Ser Asn  Leu Glu Lys
            1070                1075                1080
Gly Asn  Val Asp Leu Phe Leu  Glu Met Gly Val Thr  Val Val Glu
            1085                1090                1095
Cys Ser  Ala Phe Met Glu Leu  Thr Ala Gln Val Val  Arg Tyr Arg
            1100                1105                1110
Ala Ser  Gly Leu Ser Lys Ser  Ala Asp Gly Ser Ile  Arg Ile Ala
            1115                1120                1125
His Arg  Ile Ile Gly Lys Val  Ser Arg Thr Glu Leu  Ala Glu Met
            1130                1135                1140
Phe Ile  Arg Pro Ala Pro Gln  His Leu Leu Gln Lys  Leu Val Ala
            1145                1150                1155
Ser Gly  Glu Leu Thr Ala Glu  Gln Ala Glu Leu Ala  Thr Gln Val
            1160                1165                1170
Pro Val  Ala Asp Asp Ile Ala  Val Glu Ala Asp Ser  Gly Gly His
            1175                1180                1185
Thr Asp  Asn Arg Pro Ile His  Val Ile Leu Pro Leu  Ile Ile Asn
            1190                1195                1200
Leu Arg  Asn Arg Leu His Lys  Glu Leu Asp Tyr Pro  Ser His Leu
            1205                1210                1215
Arg Val  Arg Val Gly Ala Gly  Gly Gly Ile Gly Cys  Pro Gln Ala
            1220                1225                1230
```

```
Ala Leu Ala Ala Phe Gln Met Gly Ala Ala Phe Leu Ile Thr Gly
    1235                1240                1245

Thr Val Asn Gln Leu Ala Arg Glu Ser Gly Thr Cys Asp Asn Val
    1250                1255                1260

Arg Leu Gln Leu Ser Lys Ala Thr Tyr Ser Asp Val Cys Met Ala
    1265                1270                1275

Pro Ala Ala Asp Met Phe Asp Gln Gly Val Glu Leu Gln Val Leu
    1280                1285                1290

Lys Lys Gly Thr Leu Phe Pro Ser Arg Ala Lys Lys Leu Tyr Glu
    1295                1300                1305

Leu Phe Cys Lys Tyr Asp Ser Phe Glu Ala Met Pro Ala Glu Glu
    1310                1315                1320

Leu Gln Arg Val Glu Lys Arg Ile Phe Gln Lys Ser Leu Ala Glu
    1325                1330                1335

Val Trp Gln Glu Thr Ser Asp Phe Tyr Ile His Arg Ile Lys Asn
    1340                1345                1350

Pro Glu Lys Ile Asn Arg Ala Ala Ser Asp Gly Lys Leu Lys Met
    1355                1360                1365

Ser Leu Cys Phe Arg Trp Tyr Leu Gly Leu Ser Ser Phe Trp Ala
    1370                1375                1380

Asn Ser Gly Ala Gln Asp Arg Val Met Asp Tyr Gln Ile Trp Cys
    1385                1390                1395

Gly Pro Ala Ile Gly Ala Phe Asn Asp Phe Thr Lys Gly Thr Tyr
    1400                1405                1410

Leu Asp Val Thr Val Ala Lys Ser Tyr Pro Cys Val Ala Gln Ile
    1415                1420                1425

Asn Leu Gln Ile Leu Gln Gly Ala Ala Tyr Leu Lys Arg Leu Gly
    1430                1435                1440

Val Ile Arg Phe Asp Arg Met Leu Leu Gln Ala Val Asp Ile Asp
    1445                1450                1455

Asp Pro Val Phe Thr Tyr Val Pro Thr Gln Pro Leu
    1460                1465                1470

<210> SEQ ID NO 61
<211> LENGTH: 1503
<212> TYPE: PRT
<213> ORGANISM: Schizochytrium sp.

<400> SEQUENCE: 61

Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
                20                  25                  30

Leu Leu Glu Phe Ala Glu Gly Asp Ile Ala Lys Val Phe Gly Pro Glu
            35                  40                  45

Phe Ala Val Ile Asp Lys Tyr Pro Arg Arg Val Arg Leu Pro Ala Arg
        50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
```

```
            115                 120                 125
Phe Gln Asn Gln Gly Asp Arg Val Tyr Arg Leu Leu Asn Thr Thr Leu
    130                 135                 140
Thr Phe Tyr Gly Val Ala His Glu Gly Glu Thr Leu Glu Tyr Asp Ile
145                 150                 155                 160
Arg Val Thr Gly Phe Ala Lys Arg Leu Asp Gly Gly Ile Ser Met Phe
                165                 170                 175
Phe Phe Glu Tyr Asp Cys Tyr Val Asn Gly Arg Leu Leu Ile Glu Met
                180                 185                 190
Arg Asp Gly Cys Ala Gly Phe Phe Thr Asn Glu Glu Leu Asp Ala Gly
                195                 200                 205
Lys Gly Val Val Phe Thr Arg Gly Asp Leu Ala Ala Arg Ala Lys Ile
    210                 215                 220
Pro Lys Gln Asp Val Ser Pro Tyr Ala Val Ala Pro Cys Leu His Lys
225                 230                 235                 240
Thr Lys Leu Asn Glu Lys Glu Met Gln Thr Leu Val Asp Lys Asp Trp
                245                 250                 255
Ala Ser Val Phe Gly Ser Lys Asn Gly Met Pro Glu Ile Asn Tyr Lys
                260                 265                 270
Leu Cys Ala Arg Lys Met Leu Met Ile Asp Arg Val Thr Ser Ile Asp
                275                 280                 285
His Lys Gly Gly Val Tyr Gly Leu Gly Gln Leu Val Gly Glu Lys Ile
                290                 295                 300
Leu Glu Arg Asp His Trp Tyr Phe Pro Cys His Phe Val Lys Asp Gln
305                 310                 315                 320
Val Met Ala Gly Ser Leu Val Ser Asp Gly Cys Ser Gln Met Leu Lys
                325                 330                 335
Met Tyr Met Ile Trp Leu Gly Leu His Leu Thr Thr Gly Pro Phe Asp
                340                 345                 350
Phe Arg Pro Val Asn Gly His Pro Asn Lys Val Arg Cys Arg Gly Gln
                355                 360                 365
Ile Ser Pro His Lys Gly Lys Leu Val Tyr Val Met Glu Ile Lys Glu
                370                 375                 380
Met Gly Phe Asp Glu Asp Asn Asp Pro Tyr Ala Ile Ala Asp Val Asn
385                 390                 395                 400
Ile Ile Asp Val Asp Phe Glu Lys Gly Gln Asp Phe Ser Leu Asp Arg
                405                 410                 415
Ile Ser Asp Tyr Gly Lys Gly Asp Leu Asn Lys Lys Ile Val Val Asp
                420                 425                 430
Phe Lys Gly Ile Ala Leu Lys Met Gln Lys Arg Ser Thr Asn Lys Asn
    435                 440                 445
Pro Ser Lys Val Gln Pro Val Phe Ala Asn Gly Ala Ala Thr Val Gly
    450                 455                 460
Pro Glu Ala Ser Lys Ala Ser Ser Gly Ala Ser Ala Ser Ala Ser Ala
465                 470                 475                 480
Ala Pro Ala Lys Pro Ala Phe Ser Ala Asp Val Leu Ala Pro Lys Pro
                485                 490                 495
Val Ala Leu Pro Glu His Ile Leu Lys Gly Asp Ala Leu Ala Pro Lys
                500                 505                 510
Glu Met Ser Trp His Pro Met Ala Arg Ile Pro Gly Asn Pro Thr Pro
                515                 520                 525
Ser Phe Ala Pro Ser Ala Tyr Lys Pro Arg Asn Ile Ala Phe Thr Pro
                530                 535                 540
```

```
Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
            580                 585                 590

Ser Pro Ala Trp Asp Leu Ala Leu Val Thr Arg Ala Val Ser Val Ser
        595                 600                 605

Asp Leu Lys His Val Asn Tyr Arg Asn Ile Asp Leu Asp Pro Ser Lys
    610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
                645                 650                 655

Ile Ala Leu Gln Thr Ser Gly Val Leu Thr Ser Val Leu Lys Ala Pro
            660                 665                 670

Leu Thr Met Glu Lys Asp Asp Ile Leu Phe Arg Asn Leu Asp Ala Asn
        675                 680                 685

Ala Glu Phe Val Arg Ala Asp Leu Asp Tyr Arg Gly Lys Thr Ile Arg
    690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Asp Val Leu Phe Tyr Lys
                725                 730                 735

Gly Ser Thr Ser Phe Gly Trp Phe Pro Glu Val Phe Ala Ala Gln
            740                 745                 750

Ala Gly Leu Asp Asn Gly Arg Lys Ser Glu Pro Trp Phe Ile Glu Asn
        755                 760                 765

Lys Val Pro Ala Ser Gln Val Ser Ser Phe Asp Val Arg Pro Asn Gly
    770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
                805                 810                 815

Ser Gly Ser Gly Lys Lys Ser Leu Gly Tyr Ala His Gly Ser Lys Thr
            820                 825                 830

Val Asn Pro Asn Asp Trp Phe Phe Ser Cys His Phe Trp Phe Asp Ser
        835                 840                 845

Val Met Pro Gly Ser Leu Gly Val Glu Ser Met Phe Gln Leu Val Glu
    850                 855                 860

Ala Ile Ala Ala His Glu Asp Leu Ala Gly Lys Ala Arg His Cys Gln
865                 870                 875                 880

Pro His Leu Cys Ala Arg Pro Arg Ala Arg Ser Ser Trp Lys Tyr Arg
                885                 890                 895

Gly Gln Leu Thr Pro Lys Ser Lys Lys Met Asp Ser Glu Val His Ile
            900                 905                 910

Val Ser Val Asp Ala His Asp Gly Val Val Asp Leu Val Ala Asp Gly
        915                 920                 925

Phe Leu Trp Ala Asp Ser Leu Arg Val Tyr Ser Val Ser Asn Ile Arg
    930                 935                 940

Val Arg Ile Ala Ser Gly Glu Ala Pro Ala Ala Ser Ser Ala Ala
945                 950                 955                 960
```

```
Ser Val Gly Ser Ser Ala Ser Ser Val Glu Arg Thr Arg Ser Ser Pro
                965                 970                 975

Ala Val Ala Ser Gly Pro Ala Gln Thr Ile Asp Leu Lys Gln Leu Lys
        980                 985                 990

Thr Glu Leu Leu Glu Leu Asp Ala Pro Leu Tyr Leu Ser Gln Asp Pro
        995                 1000                1005

Thr Ser Gly Gln Leu Lys Lys His Thr Asp Val Ala Ser Gly Gln
    1010                1015                1020

Ala Thr Ile Val Gln Pro Cys Thr Leu Gly Asp Leu Gly Asp Arg
    1025                1030                1035

Ser Phe Met Glu Thr Tyr Gly Val Val Ala Pro Leu Tyr Thr Gly
    1040                1045                1050

Ala Met Ala Lys Gly Ile Ala Ser Ala Asp Leu Val Ile Ala Ala
    1055                1060                1065

Gly Lys Arg Lys Ile Leu Gly Ser Phe Gly Ala Gly Gly Leu Pro
    1070                1075                1080

Met His His Val Arg Ala Ala Leu Glu Lys Ile Gln Ala Ala Leu
    1085                1090                1095

Pro Gln Gly Pro Tyr Ala Val Asn Leu Ile His Ser Pro Phe Asp
    1100                1105                1110

Ser Asn Leu Glu Lys Gly Asn Val Asp Leu Phe Leu Glu Lys Gly
    1115                1120                1125

Val Thr Val Val Glu Ala Ser Ala Phe Met Thr Leu Thr Pro Gln
    1130                1135                1140

Val Val Arg Tyr Arg Ala Ala Gly Leu Ser Arg Asn Ala Asp Gly
    1145                1150                1155

Ser Val Asn Ile Arg Asn Arg Ile Ile Gly Lys Val Ser Arg Thr
    1160                1165                1170

Glu Leu Ala Glu Met Phe Ile Arg Pro Ala Pro Glu His Leu Leu
    1175                1180                1185

Glu Lys Leu Ile Ala Ser Gly Glu Ile Thr Gln Glu Gln Ala Glu
    1190                1195                1200

Leu Ala Arg Arg Val Pro Val Ala Asp Asp Ile Ala Val Glu Ala
    1205                1210                1215

Asp Ser Gly Gly His Thr Asp Asn Arg Pro Ile His Val Ile Leu
    1220                1225                1230

Pro Leu Ile Ile Asn Leu Arg Asn Arg Leu His Arg Glu Cys Gly
    1235                1240                1245

Tyr Pro Ala His Leu Arg Val Arg Val Gly Ala Gly Gly Gly Val
    1250                1255                1260

Gly Cys Pro Gln Ala Ala Ala Ala Ala Leu Thr Met Gly Ala Ala
    1265                1270                1275

Phe Ile Val Thr Gly Thr Val Asn Gln Val Ala Lys Gln Ser Gly
    1280                1285                1290

Thr Cys Asp Asn Val Arg Lys Gln Leu Ser Gln Ala Thr Tyr Ser
    1295                1300                1305

Asp Ile Cys Met Ala Pro Ala Ala Asp Met Phe Glu Glu Gly Val
    1310                1315                1320

Lys Leu Gln Val Leu Lys Lys Gly Thr Met Phe Pro Ser Arg Ala
    1325                1330                1335

Asn Lys Leu Tyr Glu Leu Phe Cys Lys Tyr Asp Ser Phe Asp Ser
    1340                1345                1350

Met Pro Pro Ala Glu Leu Glu Arg Ile Glu Lys Arg Ile Phe Lys
```

-continued

```
         1355                1360                1365

Arg Ala Leu Gln Glu Val Trp Glu Glu Thr Lys Asp Phe Tyr Ile
     1370                1375                1380

Asn Gly Leu Lys Asn Pro Glu Lys Ile Gln Arg Ala Glu His Asp
 1385                1390                1395

Pro Lys Leu Lys Met Ser Leu Cys Phe Arg Trp Tyr Leu Gly Leu
     1400                1405                1410

Ala Ser Arg Trp Ala Asn Met Gly Ala Pro Asp Arg Val Met Asp
 1415                1420                1425

Tyr Gln Val Trp Cys Gly Pro Ala Ile Gly Ala Phe Asn Asp Phe
     1430                1435                1440

Ile Lys Gly Thr Tyr Leu Asp Pro Ala Val Ser Asn Glu Tyr Pro
 1445                1450                1455

Cys Val Val Gln Ile Asn Leu Gln Ile Leu Arg Gly Ala Cys Tyr
     1460                1465                1470

Leu Arg Arg Leu Asn Ala Leu Arg Asn Asp Pro Arg Ile Asp Leu
 1475                1480                1485

Glu Thr Glu Asp Ala Ala Phe Val Tyr Glu Pro Thr Asn Ala Leu
     1490                1495                1500

<210> SEQ ID NO 62
<211> LENGTH: 27
<212> TYPE: DNA
<213> ORGANISM: Artificial Sequence
<220> FEATURE:
<223> OTHER INFORMATION: Synthetic Primer prDS173
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 62
gatctactgc aagcgcggng gnttyat                                          27

<210> SEQ ID NO 63
<211> LENGTH: 21
<212> TYPE: DNA
<213> ORGANISM: Artificial Sequence
<220> FEATURE:
<223> OTHER INFORMATION: Synthetic Primer prDS174
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 63
ggcgcaggcg gcrtcnacna c                                                21

<210> SEQ ID NO 64
<211> LENGTH: 23
<212> TYPE: DNA
<213> ORGANISM: Artificial Sequence
<220> FEATURE:
<223> OTHER INFORMATION: Synthetic Primer JGM190
<220> FEATURE:
<221> NAME/KEY: misc_feature
<222> LOCATION: (15)..(15)
```

<223> OTHER INFORMATION: n is a, c, g, or t

<400> SEQUENCE: 64
caytggtayt tyccntgyca ytt                                    23

<210> SEQ ID NO 65
<211> LENGTH: 17
<212> TYPE: DNA
<213> ORGANISM: Artificial Sequence
<220> FEATURE:
<223> OTHER INFORMATION: Synthetic Primer BLR242
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 65
ccnggcatna cnggrtc                                           17

<210> SEQ ID NO 66
<211> LENGTH: 27
<212> TYPE: DNA
<213> ORGANISM: Artificial Sequence
<220> FEATURE:
<223> OTHER INFORMATION: Synthetic Primer CAX055

<400> SEQUENCE: 66
gtcatgattg aacaagatgg attgcac                                27

<210> SEQ ID NO 67
<211> LENGTH: 27
<212> TYPE: DNA
<213> ORGANISM: Artificial Sequence
<220> FEATURE:
<223> OTHER INFORMATION: Synthetic Primer CAX056

<400> SEQUENCE: 67
ccacgtgtca gaagaactcg tcaagaa                                27

<210> SEQ ID NO 68
<211> LENGTH: 8976
<212> TYPE: DNA
<213> ORGANISM: Thraustochytrium sp.

<400> SEQUENCE: 68
atggaagatc aaagaattgc tattgttgga ttatctgcga ttttaccaag tggtgaaaat      60
gttagagaat cttgggaagc aatacgtgat ggtttgaatt gtttaagtga tttacctgcg    120
gatcgtgttg atgttactgc gtattataat ccaacaaaag gtgtaaagga taaaatttat    180
tgtaaacgtg gtgggtttat tcctgaatat gaatttgatt ctagagaatt tggacttaat    240
atgttcacaa tggaagattc tgatgctaat caaacgttaa cttttattaa ggttaaagaa    300
gcattagatg atgctaatat acctgcattt actaatgaga aaaaaaatat tggttgtgtt    360
cttggtattg gtggtggtca aaaagcatct catgaatttt attcaagact taattatgtt    420
gttgtggata agttttaag aaaaatggga ttacctgatg aggatgttga aactgctgtt    480
gaaaagttta agctaatttt tcctgaatgg agattagatt cctttcctgg ttttcttggt    540

```
aatgttactg ctggccgttg tactaataca ttcaatatgg aaggtatgaa ttgtgttgta    600
gatgctgctt gtgctagttc tttaattgct attaaagttg ctattgatga attattacat    660
ggtgattgtg atgcaatgat tgctggtgca acttgtactg ataacgctct tggtatgtat    720
atggcatttt caaaaacacc tgttttttca actgatcaaa gttgtcttgc atatgatgaa    780
aaaacaaaag gtatgcttat tggtgaaggt tcagctatgt ttgttttaaa acgttatgct    840
gacgcagtga gagatggtga tactgtacat gctgttatac gttcatgttc atcatcatct    900
gacggtaaag catctggtat ttatacacca actatttctg gtcaagaaga agctattctt    960
agagcatatc gtagagctgg tgtatcacca aatactatta ctttagttga aggacatggt   1020
actggtacac cagtgggtga taaaattgaa ttaacagctt tacgcaatgt atttgataaa   1080
gcatatggtc ctggtcataa ggaagaagtt gctgttggaa gtattaaaag tcaaattggt   1140
catttgaaag ctgttgctgg ttgtgctggt cttgtgaaat tggttatggc attgaaacat   1200
aaaacactac ctcaaagtat taatgttgaa aatccaccta atttagtgga tggtactgtc   1260
attagtgata ctactttata tattaataca atgaatcgtc catggattac taagcctggt   1320
gttccaagaa gagctggtat atctagtttc ggatttggtg gtgcaaatta tcatgctgtt   1380
ttagaagaat ttgagccgga acaaactaaa ccatatagat tgaatgtatc tgcacaacca   1440
atgcttcttc atgcggtaaa tgcaaattca ttacaaaagc tatgtgaaga tcaattaaaa   1500
cttttgaaag aatcaagaga aaaatgtgtc aacaccaaaa acactgatta tgttgcgttt   1560
tcaaaatttc aagattcttt taaattgaaa ggttctgttc catcacaaca tgctagagtt   1620
ggttttgcat caaaatctat tgaagatact atttctattt tatctgctat cgttaataga   1680
tttcaaaaag atattacaac aactagttgg gcttttaccaa agaaggtgc tattttttaga   1740
tctactgcat tgattaatga caataaaagt gtagctgctt tatttttctgg acaaggcgca   1800
caatataccc atatgtttaa tgatgttgca atgcaatggc cacaatttcg tttatgtgta   1860
aatgatatgg agaaagcaca ggaagaagtt atcaatgata aaagtgtgaa acgtatcagt   1920
caagttatgt ttcctcgtaa accatatgca agagaatcac ctttagacaa taaagaaatc   1980
tctaagactg aatattctca acaacaact gtcgctagtt cagtaggttt atttgaaatt   2040
ttccgtgatg ctggtttcgc tcctgctttt gttgctggtc attctttagg tgaatttagt   2100
gcattgtatg cagctggatt gattgatcgc gaagatttat tcaagttggt atgtaatcgt   2160
gcaatggcta tgagagatgc accaaaaaaa tctgctgatg gagcaatggc tgctgttatt   2220
ggtccaaatg cttcttcaat taagctttca gctcctgaag tatgggttgc taacaataac   2280
tctccatctc aaactgttat taccggtgca aattctggtg tacaagctga aacaagtaaa   2340
ttgaaaactc aaggtttccg tgtggttcat ttggcatgtg atgggcatt tcattcgcct   2400
catatggaaa atgctgaaaa gcaatttcaa aaagctcttt cagcagttaa gtttaataaa   2460
ccaactggtt cttctccaaa aattttcagc aatgtaactg gtggtgtatt tacggatcca   2520
aaaactgctt tgtcaagaca tatgactagt tctgtacaat ttcttactca aattaagaat   2580
atgtacgcgg ctggagctcg tgtctttatt gaatttggac caaaacaagt acttttccaaa   2640
ttggtcaatg aaattttttcc tggtgataca agcgttttaa ctgtttcggt gaatccagct   2700
agtgctaaag atagtgacat tcaattgcgt caagctgcag ttcaaatggc cgttgctggt   2760
gtagctctta ccgattttga taaatgggaa ctcaaagatc ctacccgtat gaaggaattc   2820
ccacgtaaga agactacttt gactttgtct gcagcaactt atgtctccaa gaaaactcta   2880
```

```
caggagcgtg aacgaatcat gaatgatggg cgaactgttt catgtgttca acgtattgaa    2940
aacactaata ctggtgagtt ggagaaattg aagaagcaat tgcaagataa agaaaatgag    3000
gttgtaagag ttcaagctct tgcaactcaa gcttcagctg atttgcaaaa taccaaagca    3060
gaattacaaa aagctcaagc aacaaaatct agtaatgcag catctgatgc ggtggtggca    3120
aaacataagg caattttatt ggcaatgtta gaagaacttg aaaccggcaa ggctgtagat    3180
tattcttcat tttcgaaagg tcaagttgca agtccagcta ccgttcgtgt cgtttcagct    3240
cctgttcaag cggctgctcc tgtgcaggta tctgcttctg ttgattctgg tttgttggca    3300
aaagcggaac aagttgtatt ggaagtattg catcgaagac tggttatgag actgagttg     3360 attgaattgg atatggaatt ggaaactgaa cttggtattg attctatcaa gagagtagaa    3420
attctttctg aagttcaagc tcaattgaat gttgaagcta agatgtaga tgctcttagt     3480 agaactcgta ctgttggtga agtgattgat gcaatgaaag ccgaaattgc tggtggtcaa    3540
ccagctgctc ctgttcaagt tgcagctcct actcaagtag ttgctcctgt tcaagcatct    3600
gctcctgttg attctggttt gttagcaaaa gcggaacaag ttgtattgga agtattggca    3660
tcgaagactg ttatgagac tgagttgatt gaattggata tggaattgga aaccgaactt     3720
ggtattgatt ctatcaagag agtagaaatt ctttctgaag ttcaagctca attgagtgtt    3780
gaagctaaag atgtagatgc tcttagtaga actcgtactg ttggtgaagt gattgatgca    3840
atgaaagccg aaattgctgg tggtcaacca gctgctcctg ttcaagttgc agctcctact    3900
caagtagttg ctcctgttca agcatctgct cctgttgatt ctggtttgtt agcaaaagcg    3960
gaacaagttg tattggaagt attggcatcg aagactggtt atgagactga gttgattgaa    4020
ttggatatgg aattggaaac cgaacttggt attgattcta tcaagagagt agaaattctt    4080
tctgaagttc aagctcaatt gagtgttgaa gctaaagatg tagatgctct tagtagaact    4140
cgtactgttg gtgaagtgat tgatgcaatg aaagctgaaa tttctggtgg tcagccagct    4200
gctcctgttc aagttgcagc tcctactcaa atagttgctc ctgttcaagt atccgctcct    4260
gttgattctg gtttgttagc aaaggcggaa caagtagtat tggaagtatt ggcatccaag    4320
actggttatg agactgagtt gattgaattg gatatggaat tggaaactga acttggtatt    4380
gattctatca agagagtaga aattctttct gaagttcaag ctcaattgag tgttgaagct    4440
aaagatgtag atgctcttag tagaactcgt actgttggtg aagtgattga tgcaatgaaa    4500
gctgaaattt ctggtggtca accaactgct cctgttcaag ttgcagctcc tactcaaata    4560
gttgctcctg ttcaagtatc tgctcctgtt gattctggtt tgttagcaaa ggcggaacaa    4620
gttgtattgg aagtattggc atcgaagact ggttatgaga ctgagttgat tgaattggat    4680
atggaattgg aaaccgaact tggtattgat tctatcaaga gagtagaaat tctttctgaa    4740
gttcaagctc aattgagtgt tgaagctaaa gatgtagatg ctcttagtag aactcgtact    4800
gttggtgaag tgattgatgc aatgaaagcc gaaatttctg gtggtcagcc agctgctcct    4860
gttcaagttg cagctcctac tcaaatagtt gctcctgttc aagcatctgc tcctgttgat    4920
tctggtttgt tggcaaaagc ggaacaagtt gtattggaag tgttagcatc caagactggt    4980
tatgaaactg agttgattga attagatatg gaattggaaa ccgaacttgg tattgattct    5040
atcaagagag tagaaattct ttctgaagtt caagctcaat tgagtgttga agctaaagat    5100
gtagatgctc ttagtagaac tcgtactgtt ggtgaagtga ttgatgcaat gaaagctgaa    5160
atttctggtg gtcaaccagc tgctcctgtt caagttgcag ctcctactca aatagttgct    5220
cctgttcaag tatctgctcc tgttgattct ggtttgttag caaaggcgga acaagttgta    5280
```

```
ttggaagtat tggcatctaa gactggttat gagactgagt tgattgaatt ggatatggaa    5340
ttggaaactg aacttggtat tgattctatc aagagagtag aaattctttc tgaagttcaa    5400
gctcaattga atgttgaagc taaagatgta gatgctctta gtagaactcg tactgttggt    5460
gaagtgattg atgcaatgaa agccgaaatt gctggtggtc aaccagctgc tcctgttcaa    5520
gttgcagctc ctgctccagt agttgctcct gttcaagtat ctactcctgt tgattctggt    5580
ttgttggcaa aagcggaaca agttgtattg gaagtgttag catgcaagac tggttatgaa    5640
actgagttga ttgaattgga tatggaattg gaaactgaac ttggtattga ttctatcaag    5700
agagtagaaa ttctttctga agttcaagct caattgagtg ttgaagctaa agatgtagat    5760
gctcttagta gaactcgtac tgttggtgaa gtgattgatg caatgaaagc cgaaatttct    5820
ggtggtcaac caactgctcc tgttcaagtt gcagctccta ctcaagtagt tgctcctgtt    5880
aaagtatcta ctcctgttga ttctggtttg ttagcaaagg cggaacaagt agtattggaa    5940
gtattggcat ctaagactgg ttatgaaact gagttgattg aattagatat ggaattggaa    6000
actgaacttg gtattgattc tatcaagaga gtagaaattc tttctgaagt tcaagctcaa    6060
ttgaatgtgg aagctaaaga tgtggatgct cttagtagaa ctcgtactgt tggtgaagtg    6120
attgatgcaa tgaaagccga aattgctggt gatcaacctg ctccagctgt agttccagtt    6180
caagctaaga gtggtgtagc caaccctgca cttttggcaa aggcggaaca agtagtattg    6240
gaagtattgg catccaagac cggttatgaa actgagctga ttgaattgga tatggaattg    6300
gaaactgaac ttggtattga ttcaatcaag agagtagaaa ttctgtccga agttcaagca    6360
gaattgagtg ttgaagcaaa agatgtagac gctctaagta gaacccgtac tgttggggaa    6420
gtgatcgatg caatgaaagc tgaaattgct ggcagtgctg tcacggttgc aactttggat    6480
gattcaacaa ttatggagga gacagatgat gaagatgaag actttatttt atacgatcat    6540
gtatacggaa gcgaatgtga agatcttagt ctgagttttt catccgtaaa gagcatcccg    6600
cgcgctgata aacttttgtt ggataacatt gctgaaaggc caattgttat tgtggattgt    6660
ggaacaaagc ttacaactga acttgcaaaa gctattggag aacgtgccgt ggttgctaca    6720
ttcagtgcac agagcttggt atcccgtgga ttcgttggta atcatttac tctaggaaat    6780 acagaagaaa gtgagatcga aaagatggtt tcaagcattg aatcttcgta tggaaaaatt    6840
ggtggctttg tttatcaaca ttttcatgat agcgactatg gtatgcaact ggatgggcg    6900 ttaatggcag cgaaacattt gaaagagtcc ctcaacgacc cgattaagaa tggaagaacc    6960 ttcttttttgg ctgttgcgcg tatgaatggt aaacttggta tggacaatgc ttcagttcat    7020
gatcaaggaa tagtggaatc atgcggtatc gccgaacgtg gtgctatctt tggtttgtgc    7080
aaaactttgg atttggaatg gcctaatgtt tttgctcgtg gtgttgatat tgctgaaggt    7140
atgagttata gtttggctgc ggaattgatt gttgatgaga tttcttgtgc aaatctttcc    7200
attcgggaat ctggttacac gattagcgga gaaagattca aactgaagc tcacaaattg    7260 gttactggaa agcctcatgc tccgattaag aagaaggatg ctttcctagt atctggtggt    7320
gctcgtggta ttactccact ttgtattcgt gaaattgcta agcagtgaa aggtggcact    7380 tacattttga tgggtcgatc agctttggct gatgaaccct tgtgggctaa tggtaaatcc    7440
ggaaaagatt tagataaagc tggtttggca tttttgaagg aagagtttgc agctgggcgt    7500
ggtagtaaac caactccaaa agttcacaaa tctttgattg ataaagtgct cggtattagg    7560
gaggttagag catctattgc aaatatagaa gcccatggag caaaagctat atatttgtct    7620
```

```
tgcgatgtat cttccgctga gaaagtaaag gctgcagtgc aaaaagttga aaaggagcat    7680
ctagttcgta ttactggtat tgtgcatgca tcaggcgttt tgagggataa attggttgag    7740
aacaaaactt tggatgattt caacgcagta tatggaacca agtaactgg actagtaaac     7800 ttgctgtcag cagtgaacat gaattttgtt cgtcatttgg ttatgtttag ttctttggct    7860
ggatatcatg gaaatgttgg tcaatctgat tatgcaatgg ctaacgaatc acttaacaag    7920
attggtttta gattgggtgc agcttattct caattgtgtg ttaaatctat ttgttttgga    7980
ccttgggatg gtggaatggt aactccagct ttgaaaaaac aatttcaatc aatgggtgtc    8040
cagattattc ctcgtgaagg tggcgcggag actgttgcaa gaatagtctt atcttcaaat    8100
ccttctcaag ttttagttgg caactggggt gttcctccag tttcaccttt gtcaaaatcg    8160
gcaactattg ttcaaacttt taccccctgag ttaaatccat ttctaaagtc tcatcaaatt    8220
catggtaaaa atgttttgcc tatgactgta gcaattggat atcttgctca cttggttaag    8280
aatttttatg ctggtcatca tttgtgggga gttgaagatg ctcaattgtt cagtggtgtt    8340
gtaattgacc atgcggtgca agctcaagtg aaattaacgg aacagagttt ggatgatgat    8400
ggcaaggtaa aagttcaagc tgttctgact gcttcaaacg ataatggaaa aatggtacct    8460
gcatacaaag cagtgattgt ttggggaaaa acaagtagac ctgcgtttat tttgaaagat    8520 tttttcattgc aagaatctaa ttctcgcagt gctgatgagt tgtatgatgg taaaactttg    8580
tttcatggtc cattatttcg tggaattacc aagttgttga atgtatctga tacttcacta    8640
acaactcaat gtaccaatat tgatttgact gctactgaac gtggtcaatt tgcggatatc    8700
gaacctgtga atcctttat ggcggatgct gcatttcaag ctatgcttgt atgggttaga     8760
aatttaagga atagtgcatc tttaccaaac aattgtgaaa gagtagatat ctataaacca    8820
atagcacctg gtgaaaagta ttacactact ttgcaagctt tgggtaatac ctccggttct    8880
gttctcaagt ctgtatttta tatgcacgat gaacaaggag aagtatttct atctggaaga    8940
gctagtgttg ttgtgaatga caagatggag ttttag                              8976
```

<210> SEQ ID NO 69
<211> LENGTH: 2991
<212> TYPE: PRT
<213> ORGANISM: Thraustochytrium sp.

<400> SEQUENCE: 69

```
Met Glu Asp Gln Arg Ile Ala Ile Val Gly Leu Ser Ala Ile Leu Pro
1               5                   10                  15

Ser Gly Glu Asn Val Arg Glu Ser Trp Glu Ala Ile Arg Asp Gly Leu
                20                  25                  30

Asn Cys Leu Ser Asp Leu Pro Ala Asp Arg Val Asp Val Thr Ala Tyr
            35                  40                  45

Tyr Asn Pro Thr Lys Gly Val Lys Asp Lys Ile Tyr Cys Lys Arg Gly
        50                  55                  60

Gly Phe Ile Pro Glu Tyr Glu Phe Asp Ser Arg Glu Phe Gly Leu Asn
65                  70                  75                  80

Met Leu Gln Met Glu Asp Ser Asp Ala Asn Gln Thr Leu Thr Leu Leu
                85                  90                  95

Lys Val Lys Glu Ala Leu Asp Asp Ala Asn Ile Pro Ala Phe Thr Asn
                100                 105                 110

Glu Lys Lys Asn Ile Gly Cys Val Leu Gly Ile Gly Gly Gly Gln Lys
            115                 120                 125

Ala Ser His Glu Phe Tyr Ser Arg Leu Asn Tyr Val Val Val Asp Lys
```

-continued

```
            130                 135                 140
Val Leu Arg Lys Met Gly Leu Pro Asp Glu Asp Val Glu Thr Ala Val
145                 150                 155                 160

Glu Lys Phe Lys Ala Asn Phe Pro Glu Trp Arg Leu Asp Ser Phe Pro
                165                 170                 175

Gly Phe Leu Gly Asn Val Thr Ala Gly Arg Cys Thr Asn Thr Phe Asn
            180                 185                 190

Met Glu Gly Met Asn Cys Val Val Asp Ala Ala Cys Ala Ser Ser Leu
                195                 200                 205

Ile Ala Ile Lys Val Ala Ile Asp Glu Leu Leu His Gly Asp Cys Asp
            210                 215                 220

Ala Met Ile Ala Gly Ala Thr Cys Thr Asp Asn Ala Leu Gly Met Tyr
225                 230                 235                 240

Met Ala Phe Ser Lys Thr Pro Val Phe Ser Thr Asp Gln Ser Cys Leu
                245                 250                 255

Ala Tyr Asp Glu Lys Thr Lys Gly Met Leu Ile Gly Glu Gly Ser Ala
            260                 265                 270

Met Phe Val Leu Lys Arg Tyr Ala Asp Ala Val Arg Asp Gly Asp Thr
                275                 280                 285

Val His Ala Val Ile Arg Ser Cys Ser Ser Ser Asp Gly Lys Ala
            290                 295                 300

Ser Gly Ile Tyr Thr Pro Thr Ile Ser Gly Gln Glu Glu Ala Ile Leu
305                 310                 315                 320

Arg Ala Tyr Arg Arg Ala Gly Val Ser Pro Asn Thr Ile Thr Leu Val
                325                 330                 335

Glu Gly His Gly Thr Gly Thr Pro Val Gly Asp Lys Ile Glu Leu Thr
            340                 345                 350

Ala Leu Arg Asn Val Phe Asp Lys Ala Tyr Gly Pro Gly His Lys Glu
                355                 360                 365

Glu Val Ala Val Gly Ser Ile Lys Ser Gln Ile Gly His Leu Lys Ala
            370                 375                 380

Val Ala Gly Cys Ala Gly Leu Val Lys Leu Val Met Ala Leu Lys His
385                 390                 395                 400

Lys Thr Leu Pro Gln Ser Ile Asn Val Glu Asn Pro Asn Leu Val
                405                 410                 415

Asp Gly Thr Val Ile Ser Asp Thr Thr Leu Tyr Ile Asn Thr Met Asn
            420                 425                 430

Arg Pro Trp Ile Thr Lys Pro Gly Val Pro Arg Arg Ala Gly Ile Ser
                435                 440                 445

Ser Phe Gly Phe Gly Gly Ala Asn Tyr His Ala Val Leu Glu Glu Phe
            450                 455                 460

Glu Pro Glu Gln Thr Lys Pro Tyr Arg Leu Asn Val Ser Ala Gln Pro
465                 470                 475                 480

Met Leu Leu His Ala Val Asn Ala Asn Ser Leu Gln Lys Leu Cys Glu
                485                 490                 495

Asp Gln Leu Lys Leu Leu Lys Glu Ser Arg Glu Lys Cys Val Asn Thr
            500                 505                 510

Lys Asn Thr Asp Tyr Val Ala Phe Ser Lys Phe Gln Asp Ser Phe Lys
                515                 520                 525

Leu Lys Gly Ser Val Pro Ser Gln His Ala Arg Val Gly Phe Ala Ser
            530                 535                 540

Lys Ser Ile Glu Asp Thr Ile Ser Ile Leu Ser Ala Ile Val Asn Arg
545                 550                 555                 560
```

```
Phe Gln Lys Asp Ile Thr Thr Thr Ser Trp Ala Leu Pro Lys Glu Gly
                565                 570                 575

Ala Ile Phe Arg Ser Thr Ala Leu Ile Asn Asp Asn Lys Ser Val Ala
            580                 585                 590

Ala Leu Phe Ser Gly Gln Gly Ala Gln Tyr Thr His Met Phe Asn Asp
        595                 600                 605

Val Ala Met Gln Trp Pro Gln Phe Arg Leu Cys Val Asn Asp Met Glu
    610                 615                 620

Lys Ala Gln Glu Glu Val Ile Asn Asp Lys Ser Val Lys Arg Ile Ser
625                 630                 635                 640

Gln Val Met Phe Pro Arg Lys Pro Tyr Ala Arg Glu Ser Pro Leu Asp
                645                 650                 655

Asn Lys Glu Ile Ser Lys Thr Glu Tyr Ser Gln Thr Thr Thr Val Ala
            660                 665                 670

Ser Ser Val Gly Leu Phe Glu Ile Phe Arg Asp Ala Gly Phe Ala Pro
        675                 680                 685

Ala Phe Val Ala Gly His Ser Leu Gly Glu Phe Ser Ala Leu Tyr Ala
    690                 695                 700

Ala Gly Leu Ile Asp Arg Glu Asp Leu Phe Lys Leu Val Cys Asn Arg
705                 710                 715                 720

Ala Met Ala Met Arg Asp Ala Pro Lys Lys Ser Ala Asp Gly Ala Met
                725                 730                 735

Ala Ala Val Ile Gly Pro Asn Ala Ser Ser Ile Lys Leu Ser Ala Pro
            740                 745                 750

Glu Val Trp Val Ala Asn Asn Ser Pro Ser Gln Thr Val Ile Thr
        755                 760                 765

Gly Ala Asn Ser Gly Val Gln Ala Glu Thr Ser Lys Leu Lys Thr Gln
770                 775                 780

Gly Phe Arg Val Val His Leu Ala Cys Asp Gly Ala Phe His Ser Pro
785                 790                 795                 800

His Met Glu Asn Ala Glu Lys Gln Phe Gln Lys Ala Leu Ser Ala Val
                805                 810                 815

Lys Phe Asn Lys Pro Thr Gly Ser Ser Pro Lys Ile Phe Ser Asn Val
            820                 825                 830

Thr Gly Gly Val Phe Thr Asp Pro Lys Thr Ala Leu Ser Arg His Met
        835                 840                 845

Thr Ser Ser Val Gln Phe Leu Thr Gln Ile Lys Asn Met Tyr Ala Ala
850                 855                 860

Gly Ala Arg Val Phe Ile Glu Phe Gly Pro Lys Gln Val Leu Ser Lys
865                 870                 875                 880

Leu Val Asn Glu Ile Phe Pro Gly Asp Thr Ser Val Leu Thr Val Ser
                885                 890                 895

Val Asn Pro Ala Ser Ala Lys Asp Ser Asp Ile Gln Leu Arg Gln Ala
            900                 905                 910

Ala Val Gln Met Ala Val Ala Gly Val Ala Leu Thr Asp Phe Asp Lys
        915                 920                 925

Trp Glu Leu Lys Asp Pro Thr Arg Met Lys Glu Phe Pro Arg Lys Lys
    930                 935                 940

Thr Thr Leu Thr Leu Ser Ala Ala Thr Tyr Val Ser Lys Lys Thr Leu
945                 950                 955                 960

Gln Glu Arg Glu Arg Ile Met Asn Asp Gly Arg Thr Val Ser Cys Val
                965                 970                 975
```

```
Gln Arg Ile Glu Asn Thr Asn Thr Gly Glu Leu Glu Lys Leu Lys Lys
                980             985                 990

Gln Leu Gln Asp Lys Glu Asn Glu  Val Val Arg Val Gln  Ala Leu Ala
        995             1000                1005

Thr Gln  Ala Ser Ala Asp Leu  Gln Asn Thr Lys Ala  Glu Leu Gln
    1010             1015              1020

Lys Ala  Gln Ala Thr Lys Ser  Ser Asn Ala Ala Ser  Asp Ala Val
    1025             1030              1035

Val Ala  Lys His Lys Ala Ile  Leu Leu Ala Met Leu  Glu Glu Leu
    1040             1045              1050

Glu Thr  Gly Lys Ala Val Asp  Tyr Ser Ser Phe Ser  Lys Gly Gln
    1055             1060              1065

Val Ala  Ser Pro Ala Thr Val  Arg Val Val Ser Ala  Pro Val Gln
    1070             1075              1080

Ala Ala  Ala Pro Val Gln Val  Ser Ala Ser Val Asp  Ser Gly Leu
    1085             1090              1095

Leu Ala  Lys Ala Glu Gln Val  Val Leu Glu Val Leu  Ala Ser Lys
    1100             1105              1110

Thr Gly  Tyr Glu Thr Glu Leu  Ile Glu Leu Asp Met  Glu Leu Glu
    1115             1120              1125

Thr Glu  Leu Gly Ile Asp Ser  Ile Lys Arg Val Glu  Ile Leu Ser
    1130             1135              1140

Glu Val  Gln Ala Gln Leu Asn  Val Glu Ala Lys Asp  Val Asp Ala
    1145             1150              1155

Leu Ser  Arg Thr Arg Thr Val  Gly Glu Val Ile Asp  Ala Met Lys
    1160             1165              1170

Ala Glu  Ile Ala Gly Gly Gln  Pro Ala Ala Pro Val  Gln Val Ala
    1175             1180              1185

Ala Pro  Thr Gln Val Val Ala  Pro Val Gln Ala Ser  Ala Pro Val
    1190             1195              1200

Asp Ser  Gly Leu Leu Ala Lys  Ala Glu Gln Val Val  Leu Glu Val
    1205             1210              1215

Leu Ala  Ser Lys Thr Gly Tyr  Glu Thr Glu Leu Ile  Glu Leu Asp
    1220             1225              1230

Met Glu  Leu Glu Thr Glu Leu  Gly Ile Asp Ser Ile  Lys Arg Val
    1235             1240              1245

Glu Ile  Leu Ser Glu Val Gln  Ala Gln Leu Ser Val  Glu Ala Lys
    1250             1255              1260

Asp Val  Asp Ala Leu Ser Arg  Thr Arg Thr Val Gly  Glu Val Ile
    1265             1270              1275

Asp Ala  Met Lys Ala Glu Ile  Ala Gly Gly Gln Pro  Ala Ala Pro
    1280             1285              1290

Val Gln  Val Ala Ala Pro Thr  Gln Val Val Ala Pro  Val Gln Ala
    1295             1300              1305

Ser Ala  Pro Val Asp Ser Gly  Leu Leu Ala Lys Ala  Glu Gln Val
    1310             1315              1320

Val Leu  Glu Val Leu Ala Ser  Lys Thr Gly Tyr Glu  Thr Glu Leu
    1325             1330              1335

Ile Glu  Leu Asp Met Glu Leu  Glu Thr Glu Leu Gly  Ile Asp Ser
    1340             1345              1350

Ile Lys  Arg Val Glu Ile Leu  Ser Glu Val Gln Ala  Gln Leu Ser
    1355             1360              1365

Val Glu  Ala Lys Asp Val Asp  Ala Leu Ser Arg Thr  Arg Thr Val
```

-continued

```
          1370               1375               1380
Gly Glu Val Ile Asp Ala Met Lys Ala Glu Ile Ser Gly Gly Gln
     1385               1390               1395

Pro Ala Ala Pro Val Gln Val Ala Ala Pro Thr Gln Ile Val Ala
     1400               1405               1410

Pro Val Gln Val Ser Ala Pro Val Asp Ser Gly Leu Leu Ala Lys
     1415               1420               1425

Ala Glu Gln Val Val Leu Glu Val Leu Ala Ser Lys Thr Gly Tyr
     1430               1435               1440

Glu Thr Glu Leu Ile Glu Leu Asp Met Glu Leu Glu Thr Glu Leu
     1445               1450               1455

Gly Ile Asp Ser Ile Lys Arg Val Glu Ile Leu Ser Glu Val Gln
     1460               1465               1470

Ala Gln Leu Ser Val Glu Ala Lys Asp Val Asp Ala Leu Ser Arg
     1475               1480               1485

Thr Arg Thr Val Gly Glu Val Ile Asp Ala Met Lys Ala Glu Ile
     1490               1495               1500

Ser Gly Gly Gln Pro Thr Ala Pro Val Gln Val Ala Ala Pro Thr
     1505               1510               1515

Gln Ile Val Ala Pro Val Gln Val Ser Ala Pro Val Asp Ser Gly
     1520               1525               1530

Leu Leu Ala Lys Ala Glu Gln Val Val Leu Glu Val Leu Ala Ser
     1535               1540               1545

Lys Thr Gly Tyr Glu Thr Glu Leu Ile Glu Leu Asp Met Glu Leu
     1550               1555               1560

Glu Thr Glu Leu Gly Ile Asp Ser Ile Lys Arg Val Glu Ile Leu
     1565               1570               1575

Ser Glu Val Gln Ala Gln Leu Ser Val Glu Ala Lys Asp Val Asp
     1580               1585               1590

Ala Leu Ser Arg Thr Arg Thr Val Gly Glu Val Ile Asp Ala Met
     1595               1600               1605

Lys Ala Glu Ile Ser Gly Gly Gln Pro Ala Ala Pro Val Gln Val
     1610               1615               1620

Ala Ala Pro Thr Gln Ile Val Ala Pro Val Gln Ala Ser Ala Pro
     1625               1630               1635

Val Asp Ser Gly Leu Leu Ala Lys Ala Glu Gln Val Val Leu Glu
     1640               1645               1650

Val Leu Ala Ser Lys Thr Gly Tyr Glu Thr Glu Leu Ile Glu Leu
     1655               1660               1665

Asp Met Glu Leu Glu Thr Glu Leu Gly Ile Asp Ser Ile Lys Arg
     1670               1675               1680

Val Glu Ile Leu Ser Glu Val Gln Ala Gln Leu Ser Val Glu Ala
     1685               1690               1695

Lys Asp Val Asp Ala Leu Ser Arg Thr Arg Thr Val Gly Glu Val
     1700               1705               1710

Ile Asp Ala Met Lys Ala Glu Ile Ser Gly Gly Gln Pro Ala Ala
     1715               1720               1725

Pro Val Gln Val Ala Ala Pro Thr Gln Ile Val Ala Pro Val Gln
     1730               1735               1740

Val Ser Ala Pro Val Asp Ser Gly Leu Leu Ala Lys Ala Glu Gln
     1745               1750               1755

Val Val Leu Glu Val Leu Ala Ser Lys Thr Gly Tyr Glu Thr Glu
     1760               1765               1770
```

```
Leu Ile Glu Leu Asp Met Glu Leu Glu Thr Glu Leu Gly Ile Asp
1775                1780                1785

Ser Ile Lys Arg Val Glu Ile Leu Ser Glu Val Gln Ala Gln Leu
1790                1795                1800

Asn Val Glu Ala Lys Asp Val Asp Ala Leu Ser Arg Thr Arg Thr
1805                1810                1815

Val Gly Glu Val Ile Asp Ala Met Lys Ala Glu Ile Ala Gly Gly
1820                1825                1830

Gln Pro Ala Ala Pro Val Gln Val Ala Ala Pro Ala Pro Val Val
1835                1840                1845

Ala Pro Val Gln Val Ser Thr Pro Val Asp Ser Gly Leu Leu Ala
1850                1855                1860

Lys Ala Glu Gln Val Val Leu Glu Val Leu Ala Cys Lys Thr Gly
1865                1870                1875

Tyr Glu Thr Glu Leu Ile Glu Leu Asp Met Glu Leu Glu Thr Glu
1880                1885                1890

Leu Gly Ile Asp Ser Ile Lys Arg Val Glu Ile Leu Ser Glu Val
1895                1900                1905

Gln Ala Gln Leu Ser Val Glu Ala Lys Asp Val Asp Ala Leu Ser
1910                1915                1920

Arg Thr Arg Thr Val Gly Glu Val Ile Asp Ala Met Lys Ala Glu
1925                1930                1935

Ile Ser Gly Gly Gln Pro Thr Ala Pro Val Gln Val Ala Ala Pro
1940                1945                1950

Thr Gln Val Val Ala Pro Val Lys Val Ser Thr Pro Val Asp Ser
1955                1960                1965

Gly Leu Leu Ala Lys Ala Glu Gln Val Val Leu Glu Val Leu Ala
1970                1975                1980

Ser Lys Thr Gly Tyr Glu Thr Glu Leu Ile Glu Leu Asp Met Glu
1985                1990                1995

Leu Glu Thr Glu Leu Gly Ile Asp Ser Ile Lys Arg Val Glu Ile
2000                2005                2010

Leu Ser Glu Val Gln Ala Gln Leu Asn Val Glu Ala Lys Asp Val
2015                2020                2025

Asp Ala Leu Ser Arg Thr Arg Thr Val Gly Glu Val Ile Asp Ala
2030                2035                2040

Met Lys Ala Glu Ile Ala Gly Asp Gln Pro Ala Pro Ala Val Val
2045                2050                2055

Pro Val Gln Ala Lys Ser Gly Val Ala Asn Pro Ala Leu Leu Ala
2060                2065                2070

Lys Ala Glu Gln Val Val Leu Glu Val Leu Ala Ser Lys Thr Gly
2075                2080                2085

Tyr Glu Thr Glu Leu Ile Glu Leu Asp Met Glu Leu Glu Thr Glu
2090                2095                2100

Leu Gly Ile Asp Ser Ile Lys Arg Val Glu Ile Leu Ser Glu Val
2105                2110                2115

Gln Ala Glu Leu Ser Val Glu Ala Lys Asp Val Asp Ala Leu Ser
2120                2125                2130

Arg Thr Arg Thr Val Gly Glu Val Ile Asp Ala Met Lys Ala Glu
2135                2140                2145

Ile Ala Gly Ser Ala Val Thr Val Ala Thr Leu Asp Asp Ser Thr
2150                2155                2160
```

```
Ile Met Glu Glu Thr Asp Asp Glu Asp Phe Ile Leu Tyr
    2165            2170            2175

Asp His Val Tyr Gly Ser Glu Cys Glu Asp Leu Ser Leu Ser Phe
    2180            2185            2190

Ser Ser Val Lys Ser Ile Pro Arg Ala Asp Lys Leu Leu Leu Asp
    2195            2200            2205

Asn Ile Ala Glu Arg Pro Ile Val Ile Val Asp Cys Gly Thr Lys
    2210            2215            2220

Leu Thr Thr Glu Leu Ala Lys Ala Ile Gly Glu Arg Ala Val Val
    2225            2230            2235

Ala Thr Phe Ser Ala Gln Ser Leu Val Ser Arg Gly Phe Val Gly
    2240            2245            2250

Lys Ser Phe Thr Leu Gly Asn Thr Glu Glu Ser Glu Ile Glu Lys
    2255            2260            2265

Met Val Ser Ser Ile Glu Ser Ser Tyr Gly Lys Ile Gly Gly Phe
    2270            2275            2280

Val Tyr Gln His Phe His Asp Ser Asp Tyr Gly Met Gln Leu Gly
    2285            2290            2295

Trp Ala Leu Met Ala Ala Lys His Leu Lys Glu Ser Leu Asn Asp
    2300            2305            2310

Pro Ile Lys Asn Gly Arg Thr Phe Phe Leu Ala Val Ala Arg Met
    2315            2320            2325

Asn Gly Lys Leu Gly Met Asp Asn Ala Ser Val His Asp Gln Gly
    2330            2335            2340

Ile Val Glu Ser Cys Gly Ile Ala Glu Arg Gly Ala Ile Phe Gly
    2345            2350            2355

Leu Cys Lys Thr Leu Asp Leu Glu Trp Pro Asn Val Phe Ala Arg
    2360            2365            2370

Gly Val Asp Ile Ala Glu Gly Met Ser Tyr Ser Leu Ala Ala Glu
    2375            2380            2385

Leu Ile Val Asp Glu Ile Ser Cys Ala Asn Leu Ser Ile Arg Glu
    2390            2395            2400

Ser Gly Tyr Thr Ile Ser Gly Glu Arg Phe Thr Thr Glu Ala His
    2405            2410            2415

Lys Leu Val Thr Gly Lys Pro His Ala Pro Ile Lys Lys Lys Asp
    2420            2425            2430

Ala Phe Leu Val Ser Gly Gly Ala Arg Gly Ile Thr Pro Leu Cys
    2435            2440            2445

Ile Arg Glu Ile Ala Lys Ala Val Lys Gly Gly Thr Tyr Ile Leu
    2450            2455            2460

Met Gly Arg Ser Ala Leu Ala Asp Glu Pro Leu Trp Ala Asn Gly
    2465            2470            2475

Lys Ser Gly Lys Asp Leu Asp Lys Ala Gly Leu Ala Phe Leu Lys
    2480            2485            2490

Glu Glu Phe Ala Ala Gly Arg Gly Ser Lys Pro Thr Pro Lys Val
    2495            2500            2505

His Lys Ser Leu Ile Asp Lys Val Leu Gly Ile Arg Glu Val Arg
    2510            2515            2520

Ala Ser Ile Ala Asn Ile Glu Ala His Gly Ala Lys Ala Ile Tyr
    2525            2530            2535

Leu Ser Cys Asp Val Ser Ser Ala Glu Lys Val Lys Ala Ala Val
    2540            2545            2550

Gln Lys Val Glu Lys Glu His Leu Val Arg Ile Thr Gly Ile Val
```

```
               2555                2560                2565
His Ala Ser Gly Val Leu Arg Asp Lys Leu Val Glu Asn Lys Thr
    2570                2575                2580

Leu Asp Asp Phe Asn Ala Val Tyr Gly Thr Lys Val Thr Gly Leu
    2585                2590                2595

Val Asn Leu Leu Ser Ala Val Asn Met Asn Phe Val Arg His Leu
    2600                2605                2610

Val Met Phe Ser Ser Leu Ala Gly Tyr His Gly Asn Val Gly Gln
    2615                2620                2625

Ser Asp Tyr Ala Met Ala Asn Glu Ser Leu Asn Lys Ile Gly Phe
    2630                2635                2640

Arg Leu Gly Ala Ala Tyr Ser Gln Leu Cys Val Lys Ser Ile Cys
    2645                2650                2655

Phe Gly Pro Trp Asp Gly Gly Met Val Thr Pro Ala Leu Lys Lys
    2660                2665                2670

Gln Phe Gln Ser Met Gly Val Gln Ile Ile Pro Arg Glu Gly Gly
    2675                2680                2685

Ala Glu Thr Val Ala Arg Ile Val Leu Ser Ser Asn Pro Ser Gln
    2690                2695                2700

Val Leu Val Gly Asn Trp Gly Val Pro Pro Val Ser Pro Leu Ser
    2705                2710                2715

Lys Ser Ala Thr Ile Val Gln Thr Phe Thr Pro Glu Leu Asn Pro
    2720                2725                2730

Phe Leu Lys Ser His Gln Ile His Gly Lys Asn Val Leu Pro Met
    2735                2740                2745

Thr Val Ala Ile Gly Tyr Leu Ala His Leu Val Lys Asn Phe Tyr
    2750                2755                2760

Ala Gly His His Leu Trp Gly Val Glu Asp Ala Gln Leu Phe Ser
    2765                2770                2775

Gly Val Val Ile Asp His Ala Val Gln Ala Gln Val Lys Leu Thr
    2780                2785                2790

Glu Gln Ser Leu Asp Asp Gly Lys Val Lys Val Gln Ala Val
    2795                2800                2805

Leu Thr Ala Ser Asn Asp Asn Gly Lys Met Val Pro Ala Tyr Lys
    2810                2815                2820

Ala Val Ile Val Leu Gly Lys Thr Ser Arg Pro Ala Phe Ile Leu
    2825                2830                2835

Lys Asp Phe Ser Leu Gln Glu Ser Asn Ser Arg Ser Ala Asp Glu
    2840                2845                2850

Leu Tyr Asp Gly Lys Thr Leu Phe His Gly Pro Leu Phe Arg Gly
    2855                2860                2865

Ile Thr Lys Leu Leu Asn Val Ser Asp Thr Ser Leu Thr Thr Gln
    2870                2875                2880

Cys Thr Asn Ile Asp Leu Thr Ala Thr Glu Arg Gly Gln Phe Ala
    2885                2890                2895

Asp Ile Glu Pro Val Asn Pro Phe Met Ala Asp Ala Ala Phe Gln
    2900                2905                2910

Ala Met Leu Val Trp Val Arg Asn Leu Arg Asn Ser Ala Ser Leu
    2915                2920                2925

Pro Asn Asn Cys Glu Arg Val Asp Ile Tyr Lys Pro Ile Ala Pro
    2930                2935                2940

Gly Glu Lys Tyr Tyr Thr Thr Leu Gln Ala Leu Gly Asn Thr Ser
    2945                2950                2955
```

```
Gly Ser  Val Leu Lys Ser  Val Phe Tyr  Met His Asp  Glu Gln Gly
    2960         2965          2970
Glu Val  Phe Leu Ser Gly  Arg Ala Ser  Val Val Val  Asn Asp Lys
    2975         2980          2985
Met Glu  Phe
    2990

<210> SEQ ID NO 70
<211> LENGTH: 5880
<212> TYPE: DNA
<213> ORGANISM: Thraustochytrium sp.

<400> SEQUENCE: 70
atggtgaaat taagtgttgg tgataatatt tgtcatgatc aacgtgttgc tgttgttggt     60
atggctgtta tgtatgctgg ttgtcaaaat caacatgaat tttggcaatc tttacaaggt    120
aaaaatatga attcaaaatc gatttcacaa aatcgtttag ttctgagta tagagaagaa     180 cattttaaac ctgaaagaag taatattcc gataccttt gtaatgaaag atatggttgt      240
attgatgaga atgttcaaag tgaacatgaa cttttattaa acttgcaaa agatgctatt     300 gcggatacaa aaggttctat tgatttgaat aaaaccggaa tcgttagtgg ttgcttatct    360
tttccaatgg ataatttaca aggtgattta ttaaatttgt atcaatgtca cattgaaaag    420
aaaattgggc caaatgcatt aaaagatgtg aatttatggt ctaaagaac caccaacgga     480 aaagatgata aaaagcttta ttttgatcct gcctctttcg tagctgaaca attagatatg    540
ggaccattac attatagttt agatgctgct tgtgcgtctg cactttatgt attaagactt    600
gctcaagatc atttattaag tggtgctgct gatacaatgt tatgtggtgc atcttgttta    660
cctgaacctt ttttattttt atctggtttt tctacttttc atgcaatgcc attatctggt    720
gatgtttctg ctcctttgca taaaacttca caaggtctta cacctggtga aggtggtgct    780
attatggtac ttaaacgatt aaatgatgca atccgtgatg gtgatagaat ttatggtact    840
ttacttggtg ctgaattaag taatgctggt tgtggttac cattgagtcc acatatgcca    900
agtgaatttg attgtatgga aaaagcttta caaagagtac acagattacc atcatctatt   960
caatatgttg agtgtcatgc aactggtaca ccacaaggtg ataaagttga aattgatgct   1020
atgacaaaat gttttggtga acatttacca aggtttggtt caacgaaagg gaattttggt   1080
catacacttg ttgctgctgg ttttgctggt atgtgtaaag tttattatc aatgcaatat    1140 ggtgaaatac caccaactcc aggtcttgaa aatccagaca atattatgca tgatttagtt   1200
gttactgaaa caattccatg gcctaataca atggtgatt tgaaacgtgc atgtttatct    1260
gcttttggat tcggtggtac taatgcacat gctgtatttg aagagtatcg ttcagattta   1320
caagcaaata aaactcttga aaatgaaagt aaaagtcatg aaatcttttc ttcatttaaa   1380
attgctattg ttggtatgga atctgaattt ggtactttga aggattaca agaatttgaa    1440 cgtgctattt acaatggtgg tcatggtca tgtgatttac ctgaaaatag atggagatttt    1500 cttggagaag ataaagaatt tttacaagct tgtggtttac aaaaattacc agagagttgt   1560
tatattaaag aagtggaaac tgattttaaa aggttacgtt taccaatgat acaggaggat   1620
attctaagac ctttacagtt gttagctgtt tcgattatcg acagagcact taacgcatct   1680
ggtgttaaac caaatggcaa agttgcagtt ttagttggat taggtactga tcttgaatta   1740
tatcgtcatc gtgctcgtgt tgcattaaag gaacgcctcc aaactgcggt caaagaagat   1800
attcctttac ttgaaaagtt aatgaactat gtcaatgata gaggtacaag tacatcatat   1860
```

```
acatcttata ttggaaattt ggttgcaact cgagtttcat cattatgggg ttttactggt   1920
ccatcattca cgattactga aggtgaaaat tccgtatatc gttgtcttga tttgggaaga   1980
tggttcttag ctaatggtga agtagatgct gttgttgttg ccggggttga tttatgtggt   2040
agtgctgaaa atcttttgt aaaatctcgt agaagtaaag tttccacaca aaatgaacca    2100
tttgcaaatt ttgaatcaaa tgctgatgga tattttgctg agatggttg tggagctttg    2160 gttttgaaac gattgagtga ttgtacggat tcaactgaaa aaatttatgc aacggtggat   2220
tcaattgctg ttggtgatga agttggccca actattaaac aagctttgaa gaatgcatcc   2280
atagcagcga aagatattga actggcagag ctatcagcaa gttcaggcaa acatcattct   2340
ggtagaatca cttgtgaaga tgaactaaat gaactgggtg aaattttcaa tgaaggtata   2400
caaagagttg caattggtag tgtgaaagct aatgttggag atgttggata tgcatctggt   2460
gcagcaagtt taatcaaaac ggctttgtgc ctgtacaacc gatatttacc aaagttacca   2520
aattggaata agccaacgaa agatgttgaa tggtccaaat catttttgt atgtgaacat    2580 tctagagcat ggttgaaaaa tgttgatgaa aatagacatg ctgtcgtttc tggagtttgc   2640
gaaaatggtt cgtgttatgg aatcgtaatg tctgatgtac aaggacatca tgaagaatcg   2700
aatcttgtta gtttagacaa aaatgaacca aaagtactgg gtatttacgg agattcagtt   2760
gatgatatcc tagttcagct caacaaatat cttgaaaaat tccttcaaga aactggaacg   2820
gctgcggctg cacaaaaagt taaatcacct acaatagata ttgactccaa tgtgtttgct   2880
gagatgctta atctaccgca ggataaaaac aaaaaatttg cggtcgcatt ggttaccaca   2940
ccaaataaac tccagcgtga aatagaactt gctgtgaagg gtattccacg ttgcgtaaaa   3000
gcaaaaagag attggtgttc tccatctgga agtattttg cttgtaatcc actcaaaagt    3060
gataatattg catttatgta tggtgaaggc cgaagcccat atgctggact gggatatgat   3120
ttgcatcgaa tttggcctat gctacacgag ttggttaaca atagaactac agaactttgg   3180
gatcaaggtg atagttggta tttacctcga tctagctctg ttgctgaaaa agaaaaagtc   3240
ttcggagatt ttgataagaa tcaaattgaa atgtttagat tgggtatttt tgtatcaatg   3300
tgtttcactg atatggccac tgaacttttg ggtttaaaac ccaaagccgc gtttggttta   3360
agtttgggtg aaatatctat gcttttgca ttttctaaaa agaataccaa gttgtccaaa    3420
gaattgaccc gtcgtctaaa agaagcaaaa gtttgggcat cacaattagc tgttgaattt   3480
gcagctattc gagatttgtg gaatattcca gctgataaat ctattgatga attttggcaa   3540
gggtattttg tttacgcaaa tcgaaccctg gtcgagaaca caattgggga gaataaattt   3600
gttcgtttgt tgattgtaaa tgattcgcaa agttgtctaa ttgccgggaa accagatgaa   3660
tgtcaaaaag ttattgagaa gcttcatttg aagctaccgg cggttccagt aactcagggt   3720
atgatcggtc attgcccaga agcaattcct tatctagatc aaatcagtca tattcatgaa   3780
atgcttgaaa ttccaaaacc cgaaaatgtg aaattgttta caactagtga aaacagagaa   3840
ttagtgtcga tgaaagattc cgtgtcaaaa ttggttgctg agatttatca gcatgttgct   3900
gattttccaa acatcgtgaa caaggttaaa gaaacttgca aaactgatat atttattgaa   3960
ttgggatcga acaattatcg atctggagct gtcaaaacaa tttaggtcc agaaatcgtt    4020 tctgttgcaa ttgataggca aaatgaaact gcatgggtc aactaatgaa gatggttgca    4080
tcgttgataa gtcatcgagt tccgggtgtt gaattgaaaa aactctatca tcctgaattg   4140
ctgaaatttg atccacaggc aaaaccgaat cgtttcatca gaaatataga actgaatgga   4200
```

```
tttttttgatc gtacgaatat tattgttgat aagcaactat cccctgcgga tccgaaactc    4260
gctgaaattg tgaacaatcg aaatatgcct aaagataatg tttatgtacc aattgaacgg    4320
gtgaaaacga tgataaaggc ggaaccagct aatttacaag tcagcgtggg aagtaaacca    4380
gttgttactg aaagaattag ttcggacgat aatctatttg aaaagttgtc agaaattaca    4440
aaatcttttg atggtgtaaa tgcgtgtact gaagcaatgt tgggagactc tggatttctc    4500
aaaacatatg aggttgacta tcctttgtac acaggtgcca tggctaaagg aattgcgtct    4560
gctgatttgg ttattgctgc tggtaaatca aagatcttgg catcatttgg agctggtggg    4620
ttggccttac aagtggtaga agatgccatt aaacaaatta agctgaatt ggggaacggt     4680 ccgtttgctg taaatttgat tcattcacca ttcgatccta gcttggagaa gggtaacgtt    4740 gatcttttc taaatataa cgttcgattt gttgaagtat ccgcatttat gtcattaacc      4800
cctcaggttg tacgatacag agccgctggt ttggccaaag caagagatgg atctgtgaaa    4860
attcaaaatc gtattattgc caaaatttca agaacagagt tagcggaact gttcttgaaa    4920
ccagcaccca aaaatatttt agatgcattg gttgcggatg gatctattag tcaagaacaa    4980
gcccaacttg cattacttgt gccaatggct gatgatatta ctgtggaagc tgattctggt    5040
gggcatactg acaatcgacc aattcatgtt ttgttacctt tgataattca gcaaagaaat    5100
agaatttgta aacaataccc aaaacattta aaagttcgaa tcggagcagc tggtggtatt    5160
ggatgcccga aggcagcatt tgctgcgttt gagatgggtg ctgcatacat tgcaactgga    5220
acggtaaatc aactttcaaa ggaagcaggt acttgtgact atgtacgtaa agtattgaat    5280
aaagctacat attcggatgt taccatggct ccagccgcag atatgttcga tcatggtgtt    5340
gaattacaag ttttgaagaa aggtactatg tttccttcac gtgctaaaaa actatacgat    5400
ttgttcaaaa aatacaaatc gattgaggaa ttaccagcag atgaggtgaa aaaacttgag    5460
caaaagtttt caaaaagtc gtttgatgaa gtatgggatg agaccaagaa ttactatatt    5520
aatcgtttac attctcccga aaaaattgaa cgtgctgaaa gagatgcaaa acttaaaatg    5580
tcgttatgtt ttcgttggta tttgtcgaag tcttccagat gggctaatac cggtgaatct    5640
ggaagagtgc aggattatca aatttggtgt ggtccagcaa ttgggtcata taatgatttt    5700
gcgaaaggat caccatgttt ggatcctgag attttgggta gttttccaag tgttgttcag    5760
attaataaac atattttacg tggtgcttgt ttctatcaaa gactctctca gttgaaatat    5820 ctgaattta actatgagga attagatacg ttaacatact ctgcatcgaa ttttatttaa    5880
```

<210> SEQ ID NO 71
<211> LENGTH: 1959
<212> TYPE: PRT
<213> ORGANISM: Thraustochytrium sp.

<400> SEQUENCE: 71

```
Met Val Lys Leu Ser Val Gly Asp Asn Ile Cys His Asp Gln Arg Val
1               5                   10                  15

Ala Val Val Gly Met Ala Val Met Tyr Ala Gly Cys Gln Asn Gln His
            20                  25                  30

Glu Phe Trp Gln Ser Leu Gln Gly Lys Asn Met Asn Ser Lys Ser Ile
        35                  40                  45

Ser Gln Asn Arg Leu Gly Ser Glu Tyr Arg Glu Glu His Phe Lys Pro
    50                  55                  60

Glu Arg Ser Lys Tyr Ser Asp Thr Phe Cys Asn Glu Tyr Gly Cys
65                  70                  75                  80
```

```
Ile Asp Glu Asn Val Gln Ser Glu His Glu Leu Leu Leu Lys Leu Ala
            85                  90                  95

Lys Asp Ala Ile Ala Asp Thr Lys Gly Ser Ile Asp Leu Asn Lys Thr
        100                 105                 110

Gly Ile Val Ser Gly Cys Leu Ser Phe Pro Met Asp Asn Leu Gln Gly
        115                 120                 125

Asp Leu Leu Asn Leu Tyr Gln Cys His Ile Glu Lys Lys Ile Gly Pro
        130                 135                 140

Asn Ala Leu Lys Asp Val Asn Leu Trp Ser Lys Arg Thr Thr Asn Gly
145                 150                 155                 160

Lys Asp Asp Lys Lys Ala Tyr Phe Asp Pro Ala Ser Phe Val Ala Glu
            165                 170                 175

Gln Leu Asp Met Gly Pro Leu His Tyr Ser Leu Asp Ala Ala Cys Ala
        180                 185                 190

Ser Ala Leu Tyr Val Leu Arg Leu Ala Gln Asp His Leu Leu Ser Gly
        195                 200                 205

Ala Ala Asp Thr Met Leu Cys Gly Ala Ser Cys Leu Pro Glu Pro Phe
        210                 215                 220

Phe Ile Leu Ser Gly Phe Ser Thr Phe His Ala Met Pro Leu Ser Gly
225                 230                 235                 240

Asp Val Ser Ala Pro Leu His Lys Thr Ser Gln Gly Leu Thr Pro Gly
            245                 250                 255

Glu Gly Gly Ala Ile Met Val Leu Lys Arg Leu Asn Asp Ala Ile Arg
        260                 265                 270

Asp Gly Asp Arg Ile Tyr Gly Thr Leu Leu Gly Ala Glu Leu Ser Asn
        275                 280                 285

Ala Gly Cys Gly Leu Pro Leu Ser Pro His Met Pro Ser Glu Phe Asp
        290                 295                 300

Cys Met Glu Lys Ala Leu Gln Arg Val His Arg Leu Pro Ser Ser Ile
305                 310                 315                 320

Gln Tyr Val Glu Cys His Ala Thr Gly Thr Pro Gln Gly Asp Lys Val
            325                 330                 335

Glu Ile Asp Ala Met Thr Lys Cys Phe Gly Glu His Leu Pro Arg Phe
        340                 345                 350

Gly Ser Thr Lys Gly Asn Phe Gly His Thr Leu Val Ala Ala Gly Phe
        355                 360                 365

Ala Gly Met Cys Lys Val Leu Leu Ser Met Gln Tyr Gly Glu Ile Pro
        370                 375                 380

Pro Thr Pro Gly Leu Glu Asn Pro Asp Asn Ile Met His Asp Leu Val
385                 390                 395                 400

Val Thr Glu Thr Ile Pro Trp Pro Asn Thr Asn Gly Asp Leu Lys Arg
            405                 410                 415

Ala Cys Leu Ser Ala Phe Gly Phe Gly Gly Thr Asn Ala His Ala Val
        420                 425                 430

Phe Glu Glu Tyr Arg Ser Asp Leu Gln Ala Asn Lys Thr Leu Glu Asn
        435                 440                 445

Glu Ser Lys Ser His Glu Ile Phe Ser Phe Lys Ile Ala Ile Val
        450                 455                 460

Gly Met Glu Ser Glu Phe Gly Thr Leu Lys Gly Leu Gln Glu Phe Glu
465                 470                 475                 480

Arg Ala Ile Tyr Asn Gly Gly His Gly Ala Cys Asp Leu Pro Glu Asn
            485                 490                 495

Arg Trp Arg Phe Leu Gly Glu Asp Lys Glu Phe Leu Gln Ala Cys Gly
```

```
            500                 505                 510
Leu Gln Lys Leu Pro Arg Gly Cys Tyr Ile Lys Glu Val Glu Thr Asp
            515                 520                 525
Phe Lys Arg Leu Arg Leu Pro Met Ile Gln Glu Asp Ile Leu Arg Pro
            530                 535                 540
Leu Gln Leu Leu Ala Val Ser Ile Ile Asp Arg Ala Leu Asn Ala Ser
545                 550                 555                 560
Gly Val Lys Pro Asn Gly Lys Val Ala Val Val Gly Leu Gly Thr
                565                 570                 575
Asp Leu Glu Leu Tyr Arg His Arg Ala Arg Val Ala Leu Lys Glu Arg
            580                 585                 590
Leu Gln Thr Ala Val Lys Glu Asp Ile Pro Leu Leu Glu Lys Leu Met
            595                 600                 605
Asn Tyr Val Asn Asp Arg Gly Thr Ser Thr Ser Tyr Thr Ser Tyr Ile
            610                 615                 620
Gly Asn Leu Val Ala Thr Arg Val Ser Ser Leu Trp Gly Phe Thr Gly
625                 630                 635                 640
Pro Ser Phe Thr Ile Thr Glu Gly Glu Asn Ser Val Tyr Arg Cys Leu
                645                 650                 655
Asp Leu Gly Arg Trp Phe Leu Ala Asn Gly Glu Val Asp Ala Val Val
            660                 665                 670
Val Ala Gly Val Asp Leu Cys Gly Ser Ala Glu Asn Leu Phe Val Lys
            675                 680                 685
Ser Arg Arg Ser Lys Val Ser Thr Gln Asn Glu Pro Phe Ala Asn Phe
            690                 695                 700
Glu Ser Asn Ala Asp Gly Tyr Phe Ala Gly Asp Gly Cys Gly Ala Leu
705                 710                 715                 720
Val Leu Lys Arg Leu Ser Asp Cys Thr Asp Ser Thr Glu Lys Ile Tyr
            725                 730                 735
Ala Thr Val Asp Ser Ile Ala Val Gly Asp Glu Val Gly Pro Thr Ile
            740                 745                 750
Lys Gln Ala Leu Lys Asn Ala Ser Ile Ala Ala Lys Asp Ile Glu Leu
            755                 760                 765
Ala Glu Leu Ser Ala Ser Ser Gly Lys His His Ser Gly Arg Ile Thr
            770                 775                 780
Cys Glu Asp Glu Leu Asn Glu Leu Gly Glu Ile Phe Asn Glu Gly Ile
785                 790                 795                 800
Gln Arg Val Ala Ile Gly Ser Val Lys Ala Asn Val Gly Asp Val Gly
                805                 810                 815
Tyr Ala Ser Gly Ala Ala Ser Leu Ile Lys Thr Ala Leu Cys Leu Tyr
                820                 825                 830
Asn Arg Tyr Leu Pro Lys Leu Pro Asn Trp Asn Lys Pro Thr Lys Asp
            835                 840                 845
Val Glu Trp Ser Lys Ser Phe Phe Val Cys Glu His Ser Arg Ala Trp
850                 855                 860
Leu Lys Asn Val Asp Glu Asn Arg His Ala Val Val Ser Gly Val Cys
865                 870                 875                 880
Glu Asn Gly Ser Cys Tyr Gly Ile Val Met Ser Asp Val Gln Gly His
                885                 890                 895
His Glu Glu Ser Asn Leu Val Ser Leu Asp Lys Asn Glu Pro Lys Val
            900                 905                 910
Leu Gly Ile Tyr Gly Asp Ser Val Asp Asp Ile Leu Val Gln Leu Asn
            915                 920                 925
```

```
Lys Tyr Leu Glu Lys Phe Leu Gln Glu Thr Gly Thr Ala Ala Ala Ala
            930                 935                 940

Gln Lys Val Lys Ser Pro Thr Ile Asp Ile Asp Ser Asn Val Phe Ala
945                 950                 955                 960

Glu Met Leu Asn Leu Pro Gln Asp Lys Asn Lys Lys Phe Ala Val Ala
                965                 970                 975

Leu Val Thr Thr Pro Asn Lys Leu Gln Arg Glu Ile Glu Leu Ala Val
                980                 985                 990

Lys Gly Ile Pro Arg Cys Val Lys Ala Lys Arg Asp Trp Cys Ser Pro
            995                 1000                1005

Ser Gly Ser Ile Phe Ala Cys Asn Pro Leu Lys Ser Asp Asn Ile
    1010                1015                1020

Ala Phe Met Tyr Gly Glu Gly Arg Ser Pro Tyr Ala Gly Leu Gly
    1025                1030                1035

Tyr Asp Leu His Arg Ile Trp Pro Met Leu His Glu Leu Val Asn
    1040                1045                1050

Asn Arg Thr Thr Glu Leu Trp Asp Gln Gly Asp Ser Trp Tyr Leu
    1055                1060                1065

Pro Arg Ser Ser Ser Val Ala Glu Lys Glu Lys Val Phe Gly Asp
    1070                1075                1080

Phe Asp Lys Asn Gln Ile Glu Met Phe Arg Leu Gly Ile Phe Val
    1085                1090                1095

Ser Met Cys Phe Thr Asp Met Ala Thr Glu Leu Leu Gly Leu Lys
    1100                1105                1110

Pro Lys Ala Ala Phe Gly Leu Ser Leu Gly Glu Ile Ser Met Leu
    1115                1120                1125

Phe Ala Phe Ser Lys Lys Asn Thr Lys Leu Ser Lys Glu Leu Thr
    1130                1135                1140

Arg Arg Leu Lys Glu Ala Lys Val Trp Ala Ser Gln Leu Ala Val
    1145                1150                1155

Glu Phe Ala Ala Ile Arg Asp Leu Trp Asn Ile Pro Ala Asp Lys
    1160                1165                1170

Ser Ile Asp Glu Phe Trp Gln Gly Tyr Phe Val Tyr Ala Asn Arg
    1175                1180                1185

Thr Leu Val Glu Asn Thr Ile Gly Glu Asn Lys Phe Val Arg Leu
    1190                1195                1200

Leu Ile Val Asn Asp Ser Gln Ser Cys Leu Ile Ala Gly Lys Pro
    1205                1210                1215

Asp Glu Cys Gln Lys Val Ile Glu Lys Leu His Leu Lys Leu Pro
    1220                1225                1230

Ala Val Pro Val Thr Gln Gly Met Ile Gly His Cys Pro Glu Ala
    1235                1240                1245

Ile Pro Tyr Leu Asp Gln Ile Ser His Ile His Glu Met Leu Glu
    1250                1255                1260

Ile Pro Lys Pro Glu Asn Val Lys Leu Phe Thr Thr Ser Glu Asn
    1265                1270                1275

Arg Glu Leu Val Ser Met Lys Asp Ser Val Ser Lys Leu Val Ala
    1280                1285                1290

Glu Ile Tyr Gln His Val Ala Asp Phe Pro Asn Ile Val Asn Lys
    1295                1300                1305

Val Lys Glu Thr Cys Lys Thr Asp Ile Phe Ile Glu Leu Gly Ser
    1310                1315                1320
```

-continued

Asn Asn Tyr Arg Ser Gly Ala Val Lys Thr Ile Leu Gly Pro Glu
1325                1330                1335

Ile Val Ser Val Ala Ile Asp Arg Gln Asn Glu Thr Ala Trp Gly
1340                1345                1350

Gln Leu Met Lys Met Val Ala Ser Leu Ile Ser His Arg Val Pro
1355                1360                1365

Gly Val Glu Leu Lys Lys Leu Tyr His Pro Glu Leu Leu Lys Phe
1370                1375                1380

Asp Pro Gln Ala Lys Pro Asn Arg Phe Ile Arg Asn Ile Glu Leu
1385                1390                1395

Asn Gly Phe Phe Asp Arg Thr Asn Ile Ile Val Asp Lys Gln Leu
1400                1405                1410

Ser Pro Ala Asp Pro Lys Leu Ala Glu Ile Val Asn Asn Arg Asn
1415                1420                1425

Met Pro Lys Asp Asn Val Tyr Val Pro Ile Glu Arg Val Lys Thr
1430                1435                1440

Met Ile Lys Ala Glu Pro Ala Asn Leu Gln Val Ser Val Gly Ser
1445                1450                1455

Lys Pro Val Val Thr Glu Arg Ile Ser Ser Asp Asp Asn Leu Phe
1460                1465                1470

Glu Lys Leu Ser Glu Ile Thr Lys Ser Phe Asp Gly Val Asn Ala
1475                1480                1485

Cys Thr Glu Ala Met Leu Gly Asp Ser Gly Phe Leu Lys Thr Tyr
1490                1495                1500

Glu Val Asp Tyr Pro Leu Tyr Thr Gly Ala Met Ala Lys Gly Ile
1505                1510                1515

Ala Ser Ala Asp Leu Val Ile Ala Ala Gly Lys Ser Lys Ile Leu
1520                1525                1530

Ala Ser Phe Gly Ala Gly Gly Leu Ala Leu Gln Val Val Glu Asp
1535                1540                1545

Ala Ile Lys Gln Ile Lys Ala Glu Leu Gly Asn Gly Pro Phe Ala
1550                1555                1560

Val Asn Leu Ile His Ser Pro Phe Asp Pro Ser Leu Glu Lys Gly
1565                1570                1575

Asn Val Asp Leu Phe Leu Lys Tyr Asn Val Arg Phe Val Glu Val
1580                1585                1590

Ser Ala Phe Met Ser Leu Thr Pro Gln Val Val Arg Tyr Arg Ala
1595                1600                1605

Ala Gly Leu Ala Lys Ala Arg Asp Gly Ser Val Lys Ile Gln Asn
1610                1615                1620

Arg Ile Ile Ala Lys Ile Ser Arg Thr Glu Leu Ala Glu Leu Phe
1625                1630                1635

Leu Lys Pro Ala Pro Lys Asn Ile Leu Asp Ala Leu Val Ala Asp
1640                1645                1650

Gly Ser Ile Ser Gln Glu Gln Ala Gln Leu Ala Leu Leu Val Pro
1655                1660                1665

Met Ala Asp Asp Ile Thr Val Glu Ala Asp Ser Gly Gly His Thr
1670                1675                1680

Asp Asn Arg Pro Ile His Val Leu Leu Pro Leu Ile Ile Gln Gln
1685                1690                1695

Arg Asn Arg Ile Cys Lys Gln Tyr Pro Lys His Leu Lys Val Arg
1700                1705                1710

Ile Gly Ala Ala Gly Gly Ile Gly Cys Pro Lys Ala Ala Phe Ala

Ala Phe Glu Met Gly Ala Ala Tyr Ile Ala Thr Gly Thr Val Asn
            1730                1735                1740

Gln Leu Ser Lys Glu Ala Gly Thr Cys Asp Tyr Val Arg Lys Val
    1745                1750                1755

Leu Asn Lys Ala Thr Tyr Ser Asp Val Thr Met Ala Pro Ala Ala
1760                1765                1770

Asp Met Phe Asp His Gly Val Glu Leu Gln Val Leu Lys Lys Gly
    1775                1780                1785

Thr Met Phe Pro Ser Arg Ala Lys Lys Leu Tyr Asp Leu Phe Lys
1790                1795                1800

Lys Tyr Lys Ser Ile Glu Glu Leu Pro Ala Asp Glu Val Lys Lys
    1805                1810                1815

Leu Glu Gln Lys Val Phe Lys Lys Ser Phe Asp Glu Val Trp Asp
1820                1825                1830

Glu Thr Lys Asn Tyr Tyr Ile Asn Arg Leu His Ser Pro Glu Lys
    1835                1840                1845

Ile Glu Arg Ala Glu Arg Asp Ala Lys Leu Lys Met Ser Leu Cys
1850                1855                1860

Phe Arg Trp Tyr Leu Ser Lys Ser Ser Arg Trp Ala Asn Thr Gly
    1865                1870                1875

Glu Ser Gly Arg Val Gln Asp Tyr Gln Ile Trp Cys Gly Pro Ala
1880                1885                1890

Ile Gly Ser Tyr Asn Asp Phe Ala Lys Gly Ser Pro Cys Leu Asp
    1895                1900                1905

Pro Glu Ile Leu Gly Ser Phe Pro Ser Val Val Gln Ile Asn Lys
1910                1915                1920

His Ile Leu Arg Gly Ala Cys Phe Tyr Gln Arg Leu Ser Gln Leu
    1925                1930                1935

Lys Tyr Leu Asn Phe Asn Tyr Glu Glu Leu Asp Thr Leu Thr Tyr
1940                1945                1950

Ser Ala Ser Asn Phe Ile
    1955

<210> SEQ ID NO 72
<211> LENGTH: 4368
<212> TYPE: DNA
<213> ORGANISM: Thraustochytrium sp.

<400> SEQUENCE: 72
atggttggtt tacaaatgaa aaagaaacca gtatgggaga tgagtaagga agaacaaagt      60
tctggaaaga atgttgtatt tgactatgat gaattgttgg aatttgctga aggtgatatt     120
ggtaaagtct ttggacctaa gtttgatatt atcgataagt atagtcgacg tgtacgttta     180
cctgcgagag aatatcttct agttaccaga gttactttga tggatgctga agttgggaat     240
ttcagagttg gatctagaat ggttactgaa tatgatgttc cagtaaatgg tgaactttca     300
caaggtggtg atgttccatg ggctgttctt gttgaatctg acaatgtga tcttatgtta     360 atatcttata tgggtattga ttttcaatgt aaaggtgatc gtgtctatcg attattaaat     420
actacgttga cgttttacgg tgttgctcat gagggtgaaa cactagtata cgatattcgt     480
gtaactggat tgcaaaaggg tatgcacggt gaaatctcca tgtttttttt tgaatatgat     540
tgttatgtga atgacgatt attaatcgaa atgagagatg ttgtgcggg atttttact     600 gatgaagaac ttgcagcagg taaggagtt attaaaactg ttgctgaact tcataaaaga     660

-continued

```
aaatctattg ttccaaaatc cattaaacct tttgctctaa atccagcagt acacaaaaca    720
atgttttctg aaaatgatat ggaaaaattg tgtgagcgtc aatgggaaaa tgtattgggt    780
agtggacttc aaggtattga ctacaagtta tgtgcacgga aaatgcttat gattgatcgt    840
attactaaaa tacaacataa tggtggtgca tatggtcttg gattattggt tggcgaaaaa    900
attcttgaac gtgatcattg gtattttcca tgccattttg taaaggatca agttatggct    960
ggctcacttg ttagtgatgg ttgcagtcag ctactaaaac tttatatgtt atggttgggt   1020
ttacatgatg tggttccaga ttttcaattt cgtccagttc ctggacaacc aaataaagtt   1080
cgttgccgtg acaaattag tccacatcgt ggtaaacttg tttatgttat ggaaataaga   1140
gaaatgggat tcaatgaatc aactggacaa ccatatgcta ttgctgatgt tgatattatt   1200
gatgtaaact atgaacttgg tcaatcattt gatatggctg atattgatag ttatggacgt   1260
ggtaatttgt caaagaaaat tgtggttgat tttaaaggaa ttgctttgca aatggaaggt   1320
accgtgaaat catcaaatat cattgattct tcaccaaaat caactattat acaaccacct   1380
ccaaattgtc ttcgtggtga tccactggca ccatcacaag ttacatggca tccaatggca   1440
ggagttaatg gggcaccagc tccttcattt agtccatctg attatccacc acgtgctgtt   1500
tgcttcaaac catttcctgg taatccttta gataacgatc atacacctgg taaaatgcct   1560
ttaacatggt ttaatatgtc cgagtttatg tgtggtaaag tatcaaattg tcttggacca   1620
gaatttaaga gatttgataa ctctaaaaca tccagaagtc ctgcctttga tcttgcactt   1680
gttacacgtg ttgtgagtgt atcagatatg gaatttaaac ctcatttaaa tattgatgtt   1740
aatccaagta agggtacaat gataggtgaa tttgattgcc ctgcagatgc gtggtttttt   1800
caaggatcat gtaacgatgg tcatatgccg tattctattg ttatggaaat tgctcttcaa   1860
acttctggtg tattaacttc agttttgaaa gcacctttga ctatggataa agatgatatt   1920
cttttccgca atttggatgc cactgctgaa atggttcgaa gtgatgttga ttgtagaggt   1980
aaaactatca aaaactttac tcaatgtacc ggttacagta tgctcggaaa aatgggaatt   2040
catagattca catttgaatt atctgttgat gatgtagttt tctacaaagg atcaacatct   2100
tttggttggt tcaccccctga agtattcgag tcacaagttg gtcttgataa tggtaaaaaa   2160
gtacaaccat ggtatttgga acaaaaatca tctaatgtag taacttatga cgttgcgtcc   2220
actgctggca aggataagtt attttcaaag attggatcta aggatgcaca agttcaaaga   2280
agaaatacac aatgtgagtt tctagatact atgcatatta ttccaaatac tggaaagtac   2340
aacaaaggtt atgctcatgg agaaaagaaa gttaatccaa acgactggtt cttttcctgt   2400
catttctggt ttgatcctgt gatgcctggt tcattaggta ttgaaagtat gtttcaactc   2460
attgaagcat tttcaattga tcaaggaatc gcttcaaaac atggtattgt gaatccaact   2520
tttgctcatt ccaatggaaa aacttcttgg aaatacagag gtcaattgaa taacaaaggt   2580
aaacgaatgg atagtgaaat tcatatcaaa gatattgtca aaaatgctga tggtactgtt   2640
gatttgattg ctgatggatt tttattggtt gattcactaa gagtatactc tgcagatgat   2700
cttcgcgtaa aaattgtacc gggaaccaaa gctgcaccta atcagtagc tgctgctcca   2760 agacatgttg caacaccaat tccaggagtg ccttcgaata caagcagtgt tgaaatcagt   2820
ttggaatctt tgaagaaaga attgttaaat cttgagaaac cattgtatct tgaaacttcc   2880
aatcatattg taaacaatt cggtgacgtt aacaatggcc aagcatccgt tattccacca   2940
tgcaccatca atgatttggg tgagcgtagt tttatggaaa catacaatgt tgttgcacca   3000
```

| | | |
|---|---|---|
| ctttacactg gagccatggc taaaggtatt gcatctgctg atttggtaat tgcagctggt | 3060 |
| aaaagaaaaa ttttgggttc ttttggcgct ggaggcttac caatgcactt ggttcgtgct | 3120 |
| tctgttgaaa aaatccaagc cgcacttcca gaaggtccat acgctgtcaa cttgattcat | 3180 |
| agtccattcg actcaaatct tgaaaaggga aatgtagatc tatttttgga aaaaggtgtt | 3240 |
| catgttgttg aagcatctgc attcactgct ctgaccactc aagtagttcg ttaccgtgca | 3300 |
| tgtggtttat ctcgggctaa agacggatct gtattgatca aaatagaat catcggtaaa | 3360 |
| gtttcaagaa ccgaattggc tgaaatgttt ttcagacctg caccacaaaa cttgcttgac | 3420 |
| aagcttattg ctagtggaga aatcactaaa gaacaagctt cattggcttt ggaagtacca | 3480 |
| atggctgatg atgtagctgt tgaagctgat agcggtggac atactgataa tagaccaatt | 3540 |
| catgtaatcc tacctttgat tatcaatcta cgaaatagaa ttcataaaga atgtggtttt | 3600 |
| cctgctgctt tgagagttcg cgttggtgct ggtggtggaa ttggttgtcc aagtgctgca | 3660 |
| gttgctgcat tcaatatggg agctgcattc ttgattactg gcagcgtcaa ccaagttagc | 3720 |
| aaacaatctg gtacgtgtga tatcgttaga aagcaattat ctgaagcttc gtattcagat | 3780 |
| attaccatgg caccagcggc tgatatgttt gatcaaggag tcgagcttca agtattaaaa | 3840 |
| aaaggaacta tgtttccatc tcgtgcaaag aaattgtatg aattattctg tatgtacaac | 3900 |
| tcatttgatg acatgccaaa aagcgaactt caaagactag agaagcgaat ttttcaaaaa | 3960 |
| tcgcttgcgg aagtttggga agaaactaaa gattttttata tcaatcgttt gaataatcct | 4020 |
| gagaagattg aacatgctga aagaaagat ccaaagttga agatgtcatt atgctttaga | 4080 |
| tggtatttgg gtttaagttc attttgggca acaatggaa ttaaagaaag atcaatggac | 4140 |
| tatcaaattt ggtgtggtcc agcgattggt tcatacaatg attttgtaaa aggaacttat | 4200 |
| ttggatcctg cagtagcagg ttcatatcca tgtgttgttc aaattaacat gcaaattcta | 4260 |
| cgcggtgctt gttttcttca acgagttcgt gcaatcaagc acgatccacg attggatatt | 4320 |
| gatgtcgatg aagatgtatt tacctatcgt ccagaatcaa ccctatag | 4368 |

<210> SEQ ID NO 73
<211> LENGTH: 1455
<212> TYPE: PRT
<213> ORGANISM: Thraustochytrium sp.

<400> SEQUENCE: 73

```
Met Val Gly Leu Gln Met Lys Lys Lys Pro Val Trp Glu Met Ser Lys
1               5                   10                  15

Glu Glu Gln Ser Ser Gly Lys Asn Val Val Phe Asp Tyr Asp Glu Leu
            20                  25                  30

Leu Glu Phe Ala Glu Gly Asp Ile Gly Lys Val Phe Gly Pro Lys Phe
        35                  40                  45

Asp Ile Ile Asp Lys Tyr Ser Arg Arg Val Arg Leu Pro Ala Arg Glu
    50                  55                  60

Tyr Leu Leu Val Thr Arg Val Thr Leu Met Asp Ala Glu Val Gly Asn
65                  70                  75                  80

Phe Arg Val Gly Ser Arg Met Val Thr Glu Tyr Asp Val Pro Val Asn
                85                  90                  95

Gly Glu Leu Ser Gln Gly Gly Asp Pro Trp Ala Val Leu Val Glu
            100                 105                 110

Ser Gly Gln Cys Asp Leu Met Leu Ile Ser Tyr Met Gly Ile Asp Phe
        115                 120                 125

Gln Cys Lys Gly Asp Arg Val Tyr Arg Leu Leu Asn Thr Thr Leu Thr
```

```
            130                 135                 140
Phe Tyr Gly Val Ala His Glu Gly Glu Thr Leu Val Tyr Asp Ile Arg
145                 150                 155                 160

Val Thr Gly Phe Ala Lys Gly Met His Gly Glu Ile Ser Met Phe Phe
                165                 170                 175

Phe Glu Tyr Asp Cys Tyr Val Asn Gly Arg Leu Leu Ile Glu Met Arg
            180                 185                 190

Asp Gly Cys Ala Gly Phe Phe Thr Asp Glu Glu Leu Ala Ala Gly Lys
        195                 200                 205

Gly Val Ile Lys Thr Val Ala Glu Leu His Lys Arg Lys Ser Ile Val
    210                 215                 220

Pro Lys Ser Ile Lys Pro Phe Ala Leu Asn Pro Ala Val His Lys Thr
225                 230                 235                 240

Met Phe Ser Glu Asn Asp Met Glu Lys Leu Cys Glu Arg Gln Trp Glu
                245                 250                 255

Asn Val Leu Gly Ser Gly Leu Gln Gly Ile Asp Tyr Lys Leu Cys Ala
            260                 265                 270

Arg Lys Met Leu Met Ile Asp Arg Ile Thr Lys Ile Gln His Asn Gly
        275                 280                 285

Gly Ala Tyr Gly Leu Gly Leu Leu Val Gly Glu Lys Ile Leu Glu Arg
    290                 295                 300

Asp His Trp Tyr Phe Pro Cys His Phe Val Lys Asp Gln Val Met Ala
305                 310                 315                 320

Gly Ser Leu Val Ser Asp Gly Cys Ser Gln Leu Leu Lys Leu Tyr Met
                325                 330                 335

Leu Trp Leu Gly Leu His Asp Val Val Pro Asp Phe Gln Phe Arg Pro
            340                 345                 350

Val Pro Gly Gln Pro Asn Lys Val Arg Cys Arg Gly Gln Ile Ser Pro
        355                 360                 365

His Arg Gly Lys Leu Val Tyr Val Met Glu Ile Arg Glu Met Gly Phe
    370                 375                 380

Asn Glu Ser Thr Gly Gln Pro Tyr Ala Ile Ala Asp Val Asp Ile Ile
385                 390                 395                 400

Asp Val Asn Tyr Glu Leu Gly Gln Ser Phe Asp Met Ala Asp Ile Asp
                405                 410                 415

Ser Tyr Gly Arg Gly Asn Leu Ser Lys Lys Ile Val Val Asp Phe Lys
            420                 425                 430

Gly Ile Ala Leu Gln Met Glu Gly Thr Val Lys Ser Ser Asn Ile Ile
        435                 440                 445

Asp Ser Ser Pro Lys Ser Thr Ile Ile Gln Pro Pro Asn Cys Leu
    450                 455                 460

Arg Gly Asp Pro Leu Ala Pro Ser Gln Val Thr Trp His Pro Met Ala
465                 470                 475                 480

Gly Val Asn Gly Ala Pro Ala Pro Ser Phe Ser Pro Ser Asp Tyr Pro
                485                 490                 495

Pro Arg Ala Val Cys Phe Lys Pro Phe Pro Gly Asn Pro Leu Asp Asn
            500                 505                 510

Asp His Thr Pro Gly Lys Met Pro Leu Thr Trp Phe Asn Met Ser Glu
        515                 520                 525

Phe Met Cys Gly Lys Val Ser Asn Cys Leu Gly Pro Glu Phe Lys Arg
    530                 535                 540

Phe Asp Asn Ser Lys Thr Ser Arg Ser Pro Ala Phe Asp Leu Ala Leu
545                 550                 555                 560
```

```
Val Thr Arg Val Val Ser Val Ser Asp Met Glu Phe Lys Pro His Leu
            565                 570                 575

Asn Ile Asp Val Asn Pro Ser Lys Gly Thr Met Ile Gly Glu Phe Asp
            580                 585                 590

Cys Pro Ala Asp Ala Trp Phe Phe Gln Gly Ser Cys Asn Asp Gly His
            595                 600                 605

Met Pro Tyr Ser Ile Val Met Glu Ile Ala Leu Gln Thr Ser Gly Val
            610                 615                 620

Leu Thr Ser Val Leu Lys Ala Pro Leu Thr Met Asp Lys Asp Asp Ile
625                 630                 635                 640

Leu Phe Arg Asn Leu Asp Ala Thr Ala Glu Met Val Arg Ser Asp Val
            645                 650                 655

Asp Cys Arg Gly Lys Thr Ile Lys Asn Phe Thr Gln Cys Thr Gly Tyr
            660                 665                 670

Ser Met Leu Gly Lys Met Gly Ile His Arg Phe Thr Phe Glu Leu Ser
            675                 680                 685

Val Asp Asp Val Val Phe Tyr Lys Gly Ser Thr Ser Phe Gly Trp Phe
            690                 695                 700

Thr Pro Glu Val Phe Glu Ser Gln Val Gly Leu Asp Asn Gly Lys Lys
705                 710                 715                 720

Val Gln Pro Trp Tyr Leu Glu Gln Lys Ser Ser Asn Val Val Thr Tyr
            725                 730                 735

Asp Val Ala Ser Thr Ala Gly Lys Asp Lys Leu Phe Ser Lys Ile Gly
            740                 745                 750

Ser Lys Asp Ala Gln Val Gln Arg Arg Asn Thr Gln Cys Glu Phe Leu
            755                 760                 765

Asp Thr Met His Ile Ile Pro Asn Thr Gly Lys Tyr Asn Lys Gly Tyr
            770                 775                 780

Ala His Gly Glu Lys Lys Val Asn Pro Asn Asp Trp Phe Phe Ser Cys
785                 790                 795                 800

His Phe Trp Phe Asp Pro Val Met Pro Gly Ser Leu Gly Ile Glu Ser
            805                 810                 815

Met Phe Gln Leu Ile Glu Ala Phe Ser Ile Asp Gln Gly Ile Ala Ser
            820                 825                 830

Lys His Gly Ile Val Asn Pro Thr Phe Ala His Ser Asn Gly Lys Thr
            835                 840                 845

Ser Trp Lys Tyr Arg Gly Gln Leu Asn Asn Lys Gly Lys Arg Met Asp
850                 855                 860

Ser Glu Ile His Ile Lys Asp Ile Val Lys Asn Ala Asp Gly Thr Val
865                 870                 875                 880

Asp Leu Ile Ala Asp Gly Phe Leu Leu Val Asp Ser Leu Arg Val Tyr
            885                 890                 895

Ser Ala Asp Asp Leu Arg Val Lys Ile Val Pro Gly Thr Lys Ala Ala
            900                 905                 910

Pro Lys Ser Val Ala Ala Ala Pro Arg His Val Ala Thr Pro Ile Pro
            915                 920                 925

Gly Val Pro Ser Asn Thr Ser Ser Val Glu Ile Ser Leu Glu Ser Leu
            930                 935                 940

Lys Lys Glu Leu Leu Asn Leu Glu Lys Pro Leu Tyr Leu Glu Thr Ser
945                 950                 955                 960

Asn His Ile Val Lys Gln Phe Gly Asp Val Asn Asn Gly Gln Ala Ser
            965                 970                 975
```

```
Val Ile Pro Pro Cys Thr Ile Asn Asp Leu Gly Glu Arg Ser Phe Met
        980                 985                 990

Glu Thr Tyr Asn Val Val Ala Pro Leu Tyr Thr Gly Ala Met Ala Lys
        995                 1000                1005

Gly Ile Ala Ser Ala Asp Leu Val Ile Ala Ala Gly Lys Arg Lys
        1010                1015                1020

Ile Leu Gly Ser Phe Gly Ala Gly Gly Leu Pro Met His Leu Val
        1025                1030                1035

Arg Ala Ser Val Glu Lys Ile Gln Ala Ala Leu Pro Glu Gly Pro
        1040                1045                1050

Tyr Ala Val Asn Leu Ile His Ser Pro Phe Asp Ser Asn Leu Glu
        1055                1060                1065

Lys Gly Asn Val Asp Leu Phe Leu Glu Lys Gly Val His Val Val
        1070                1075                1080

Glu Ala Ser Ala Phe Thr Ala Leu Thr Thr Gln Val Val Arg Tyr
        1085                1090                1095

Arg Ala Cys Gly Leu Ser Arg Ala Lys Asp Gly Ser Val Leu Ile
        1100                1105                1110

Lys Asn Arg Ile Ile Gly Lys Val Ser Arg Thr Glu Leu Ala Glu
        1115                1120                1125

Met Phe Phe Arg Pro Ala Pro Gln Asn Leu Leu Asp Lys Leu Ile
        1130                1135                1140

Ala Ser Gly Glu Ile Thr Lys Glu Gln Ala Ser Leu Ala Leu Glu
        1145                1150                1155

Val Pro Met Ala Asp Asp Val Ala Val Glu Ala Asp Ser Gly Gly
        1160                1165                1170

His Thr Asp Asn Arg Pro Ile His Val Ile Leu Pro Leu Ile Ile
        1175                1180                1185

Asn Leu Arg Asn Arg Ile His Lys Glu Cys Gly Phe Pro Ala Ala
        1190                1195                1200

Leu Arg Val Arg Val Gly Ala Gly Gly Gly Ile Gly Cys Pro Ser
        1205                1210                1215

Ala Ala Val Ala Ala Phe Asn Met Gly Ala Ala Phe Leu Ile Thr
        1220                1225                1230

Gly Ser Val Asn Gln Val Ser Lys Gln Ser Gly Thr Cys Asp Ile
        1235                1240                1245

Val Arg Lys Gln Leu Ser Glu Ala Ser Tyr Ser Asp Ile Thr Met
        1250                1255                1260

Ala Pro Ala Ala Asp Met Phe Asp Gln Gly Val Glu Leu Gln Val
        1265                1270                1275

Leu Lys Lys Gly Thr Met Phe Pro Ser Arg Ala Lys Lys Leu Tyr
        1280                1285                1290

Glu Leu Phe Cys Met Tyr Asn Ser Phe Asp Asp Met Pro Lys Ser
        1295                1300                1305

Glu Leu Gln Arg Leu Glu Lys Arg Ile Phe Gln Lys Ser Leu Ala
        1310                1315                1320

Glu Val Trp Glu Glu Thr Lys Asp Phe Tyr Ile Asn Arg Leu Asn
        1325                1330                1335

Asn Pro Glu Lys Ile Glu His Ala Glu Lys Lys Asp Pro Lys Leu
        1340                1345                1350

Lys Met Ser Leu Cys Phe Arg Trp Tyr Leu Gly Leu Ser Ser Phe
        1355                1360                1365

Trp Ala Asn Asn Gly Ile Lys Glu Arg Ser Met Asp Tyr Gln Ile
```

Trp Cys Gly Pro Ala Ile Gly Ser Tyr Asn Asp Phe Val Lys Gly
　　　1385　　　　　　　1390　　　　　　　1395

Thr Tyr Leu Asp Pro Ala Val Ala Gly Ser Tyr Pro Cys Val Val
1400　　　　　　　1405　　　　　　　1410

Gln Ile Asn Met Gln Ile Leu Arg Gly Ala Cys Phe Leu Gln Arg
　　　1415　　　　　　　1420　　　　　　　1425

Val Arg Ala Ile Lys His Asp Pro Arg Leu Asp Ile Asp Val Asp
1430　　　　　　　1435　　　　　　　1440

Glu Asp Val Phe Thr Tyr Arg Pro Glu Ser Thr Leu
　　　1445　　　　　　　1450　　　　　　　1455

<210> SEQ ID NO 74
<211> LENGTH: 1350
<212> TYPE: DNA
<213> ORGANISM: Thraustochytrium sp.

<400> SEQUENCE: 74

```
agaattgcta ttgttggatt atctgcgatt ttaccaagtg gtgaaaatgt tagagaatct      60
tgggaagcaa tacgtgatgg tttgaattgt ttaagtgatt tacctgcgga tcgtgttgat     120
gttactgcgt attataatcc aacaaaaggt gtaaaggata aaatttattg taaacgtggt     180
gggtttattc ctgaatatga atttgattct agagaatttg gacttaatat gttacaaatg     240
gaagattctg atgctaatca aacgttaact ttattaaagg ttaaagaagc attagatgat     300
gctaatatac ctgcatttac taatgagaaa aaaatatttg gttgtgttct tggtattggt     360
ggtggtcaaa aagcatctca tgaatttttat tcaagactta attatgttgt tgtggataaa     420
gttttaagaa aaatgggatt acctgatgag gatgttgaaa ctgctgttga aaagtttaaa     480
gctaattttc ctgaatggag attagattcc tttcctggtt ttcttggtaa tgttactgct     540
ggccgttgta ctaatacatt caatatggaa ggtatgaatt gtgttgtaga tgctgcttgt     600
gctagttctt taattgctat taagttgct attgatgaat tattacatgg tgattgtgat     660
gcaatgattg ctggtgcaac ttgtactgat aacgctcttg gtatgtatat ggcatttcca     720
aaaacacctg ttttttcaac tgatcaaagt tgtcttgcat atgatgaaaa acaaaaggt     780
atgcttattg gtgaaggttc agctatgttt gttttaaaac gttatgctga cgcagtgaga     840
gatggtgata ctgtacatgc tgttatacgt tcatgttcat catcatctga cggtaaagca     900
tctggtattt atacaccaac tatttctggt caagaagaag ctattcttag agcatatcgt     960
agagctggtg tatcaccaaa tactattact ttagttgaag acatggtac tggtacacca    1020
gtgggtgata aaattgaatt aacagcttta cgcaatgtat ttgataaagc atatggtcct    1080
ggtcataagg aagaagttgc tgttggaagt attaaaagtc aaattggtca tttgaaagct    1140
gttgctggtt gtgctggtct tgtgaaattg gttatggcat tgaaacataa aacactacct    1200
caaagtatta tgttgaaaaa tccacctaat ttagtggatg gtactgtcat tagtgatact    1260
actttatata ttaatacaat gaatcgtcca tggattacta agcctggtgt tccaagaaga    1320
gctggtatat ctagtttcgg atttggtggt                                     1350
```

<210> SEQ ID NO 75
<211> LENGTH: 450
<212> TYPE: PRT
<213> ORGANISM: Thraustochytrium sp.

<400> SEQUENCE: 75

```
Arg Ile Ala Ile Val Gly Leu Ser Ala Ile Leu Pro Ser Gly Glu Asn
1               5                   10                  15

Val Arg Glu Ser Trp Glu Ala Ile Arg Asp Gly Leu Asn Cys Leu Ser
            20                  25                  30

Asp Leu Pro Ala Asp Arg Val Asp Val Thr Ala Tyr Tyr Asn Pro Thr
        35                  40                  45

Lys Gly Val Lys Asp Lys Ile Tyr Cys Lys Arg Gly Gly Phe Ile Pro
    50                  55                  60

Glu Tyr Glu Phe Asp Ser Arg Glu Phe Gly Leu Asn Met Leu Gln Met
65                  70                  75                  80

Glu Asp Ser Asp Ala Asn Gln Thr Leu Thr Leu Leu Lys Val Lys Glu
                85                  90                  95

Ala Leu Asp Asp Ala Asn Ile Pro Ala Phe Thr Asn Glu Lys Lys Asn
                100                 105                 110

Ile Gly Cys Val Leu Gly Ile Gly Gly Gln Lys Ala Ser His Glu
            115                 120                 125

Phe Tyr Ser Arg Leu Asn Tyr Val Val Asp Lys Val Leu Arg Lys
    130                 135                 140

Met Gly Leu Pro Asp Glu Asp Val Glu Thr Ala Val Glu Lys Phe Lys
145                 150                 155                 160

Ala Asn Phe Pro Glu Trp Arg Leu Asp Ser Phe Pro Gly Phe Leu Gly
                165                 170                 175

Asn Val Thr Ala Gly Arg Cys Thr Asn Thr Phe Asn Met Glu Gly Met
            180                 185                 190

Asn Cys Val Val Asp Ala Ala Cys Ala Ser Ser Leu Ile Ala Ile Lys
            195                 200                 205

Val Ala Ile Asp Glu Leu Leu His Gly Asp Cys Asp Ala Met Ile Ala
    210                 215                 220

Gly Ala Thr Cys Thr Asp Asn Ala Leu Gly Met Tyr Met Ala Phe Ser
225                 230                 235                 240

Lys Thr Pro Val Phe Ser Thr Asp Gln Ser Cys Leu Ala Tyr Asp Glu
                245                 250                 255

Lys Thr Lys Gly Met Leu Ile Gly Glu Gly Ser Ala Met Phe Val Leu
            260                 265                 270

Lys Arg Tyr Ala Asp Ala Val Arg Asp Gly Asp Thr Val His Ala Val
    275                 280                 285

Ile Arg Ser Cys Ser Ser Ser Asp Gly Lys Ala Ser Gly Ile Tyr
    290                 295                 300

Thr Pro Thr Ile Ser Gly Gln Glu Glu Ala Ile Leu Arg Ala Tyr Arg
305                 310                 315                 320

Arg Ala Gly Val Ser Pro Asn Thr Ile Thr Leu Val Glu Gly His Gly
                325                 330                 335

Thr Gly Thr Pro Val Gly Asp Lys Ile Glu Leu Thr Ala Leu Arg Asn
            340                 345                 350

Val Phe Asp Lys Ala Tyr Gly Pro Gly His Lys Glu Glu Val Ala Val
            355                 360                 365

Gly Ser Ile Lys Ser Gln Ile Gly His Leu Lys Ala Val Ala Gly Cys
370                 375                 380

Ala Gly Leu Val Lys Leu Val Met Ala Leu Lys His Lys Thr Leu Pro
385                 390                 395                 400

Gln Ser Ile Asn Val Glu Asn Pro Pro Asn Leu Val Asp Gly Thr Val
                405                 410                 415

Ile Ser Asp Thr Thr Leu Tyr Ile Asn Thr Met Asn Arg Pro Trp Ile
```

-continued

```
                420              425              430
Thr Lys Pro Gly Val Pro Arg Arg Ala Gly Ile Ser Ser Phe Gly Phe
        435              440              445
Gly Gly
    450
```

<210> SEQ ID NO 76
<211> LENGTH: 921
<212> TYPE: DNA
<213> ORGANISM: Thraustochytrium sp.

<400> SEQUENCE: 76

```
ttttctggac aaggcgcaca atatacccat atgtttaatg atgttgcaat gcaatggcca      60
caatttcgtt tatgtgtaaa tgatatggag aaagcacagg aagaagttat caatgataaa     120
agtgtgaaac gtatcagtca agttatgttt cctcgtaaac catatgcaag agaatcacct     180
ttagacaata aagaaatctc taagactgaa tattctcaaa caacaactgt cgctagttca     240
gtaggtttat ttgaaatttt ccgtgatgct ggtttcgctc ctgcttttgt tgctggtcat     300
tctttaggtg aatttagtgc attgtatgca gctggattga ttgatcgcga agatttattc     360
aagttggtat gtaatcgtgc aatggctatg agagatgcac caaaaaaatc tgctgatgga     420
gcaatggctg ctgttattgg tccaaatgct tcttcaatta gctttcagc tcctgaagta     480
tgggttgcta caataactc tccatctcaa actgttatta ccggtgcaaa ttctggtgta     540
caagctgaaa caagtaaatt gaaaactcaa ggtttccgtg tggttcattt ggcatgtgat     600
ggggcatttc attcgcctca tatggaaaat gctgaaaagc aatttcaaaa agctctttca     660
gcagttaagt ttaataaacc aactggttct tctccaaaaa ttttcagcaa tgtaactggt     720
ggtgtattta cggatccaaa aactgctttg tcaagacata tgactagttc tgtacaattt     780
cttactcaaa ttaagaatat gtacgcggct ggagctcgtg tctttattga atttggacca     840
aaacaagtac tttccaaatt ggtcaatgaa attttccctg gtgatacaag cgttttaact     900
gtttcggtga atccagctag t                                              921
```

<210> SEQ ID NO 77
<211> LENGTH: 307
<212> TYPE: PRT
<213> ORGANISM: Thraustochytrium sp.

<400> SEQUENCE: 77

```
Phe Ser Gly Gln Gly Ala Gln Tyr Thr His Met Phe Asn Asp Val Ala
1               5                   10                  15

Met Gln Trp Pro Gln Phe Arg Leu Cys Val Asn Asp Met Glu Lys Ala
            20                  25                  30

Gln Glu Val Ile Asn Asp Lys Ser Val Lys Arg Ile Ser Gln Val
        35                  40                  45

Met Phe Pro Arg Lys Pro Tyr Ala Arg Glu Ser Pro Leu Asp Asn Lys
    50                  55                  60

Glu Ile Ser Lys Thr Glu Tyr Ser Gln Thr Thr Thr Val Ala Ser Ser
65                  70                  75                  80

Val Gly Leu Phe Glu Ile Phe Arg Asp Ala Gly Phe Ala Pro Ala Phe
                85                  90                  95

Val Ala Gly His Ser Leu Gly Glu Phe Ser Ala Leu Tyr Ala Ala Gly
            100                 105                 110

Leu Ile Asp Arg Glu Asp Leu Phe Lys Leu Val Cys Asn Arg Ala Met
        115                 120                 125
```

```
Ala Met Arg Asp Ala Pro Lys Lys Ser Ala Asp Gly Ala Met Ala Ala
    130                 135                 140

Val Ile Gly Pro Asn Ala Ser Ser Ile Lys Leu Ser Ala Pro Glu Val
145                 150                 155                 160

Trp Val Ala Asn Asn Ser Pro Ser Gln Thr Val Ile Thr Gly Ala
                165                 170                 175

Asn Ser Gly Val Gln Ala Glu Thr Ser Lys Leu Lys Thr Gln Gly Phe
            180                 185                 190

Arg Val Val His Leu Ala Cys Asp Gly Ala Phe His Ser Pro His Met
        195                 200                 205

Glu Asn Ala Glu Lys Gln Phe Gln Lys Ala Leu Ser Ala Val Lys Phe
    210                 215                 220

Asn Lys Pro Thr Gly Ser Ser Pro Lys Ile Phe Ser Asn Val Thr Gly
225                 230                 235                 240

Gly Val Phe Thr Asp Pro Lys Thr Ala Leu Ser Arg His Met Thr Ser
                245                 250                 255

Ser Val Gln Phe Leu Thr Gln Ile Lys Asn Met Tyr Ala Ala Gly Ala
            260                 265                 270

Arg Val Phe Ile Glu Phe Gly Pro Lys Gln Val Leu Ser Lys Leu Val
        275                 280                 285

Asn Glu Ile Phe Pro Gly Asp Thr Ser Val Leu Thr Val Ser Val Asn
    290                 295                 300

Pro Ala Ser
305

<210> SEQ ID NO 78
<211> LENGTH: 3303
<212> TYPE: DNA
<213> ORGANISM: Thraustochytrium sp.

<400> SEQUENCE: 78
gcaagtccag ctaccgttcg tgtcgtttca gctcctgttc aagcggctgc tcctgtgcag      60
gtatctgctt ctgttgattc tggtttgttg gcaaaagcgg aacaagttgt attggaagta     120
ttggcatcga agactggtta tgagactgag ttgattgaat ggatatggaa attggaaact     180
gaacttggta ttgattctat caagagagta gaaattcttt ctgaagttca agctcaattg     240
aatgttgaag ctaaagatgt agatgctctt agtagaactc gtactgttgg tgaagtgatt     300
gatgcaatga agccgaaaat tgctggtggt caaccagctg ctcctgttca agttgcagct     360
cctactcaag tagttgctcc tgttcaagca tctgctcctg ttgattctgg tttgttagca     420
aaagcggaac aagttgtatt ggaagtattg gcatcgaaga ctggttatga gactgagttg     480
attgaattgg atatggaatt ggaaaccgaa cttggtattg attctatcaa gagagtagaa     540
attctttctg aagttcaagc tcaattgagt gttgaagcta agatgtaga tgctcttagt     600 agaactcgta ctgttggtga agtgattgat gcaatgaaag ccgaaattgc tggtggtcaa     660
ccagctgctc ctgttcaagt tgcagctcct actcaagtag ttgctcctgt tcaagcatct     720
gctcctgttg attctggttt gttagcaaaa gcggaacaag ttgtattgga agtattggca     780
tcgaagactg gttatgagac tgagttgatt gaattggata tggaattgga aaccgaactt     840
ggtattgatt ctatcaagag agtagaaatt ctttctgaag ttcaagctca attgagtgtt     900
gaagctaaag atgtagatgc tcttagtaga actcgtactg ttggtgaagt gattgatgca     960
atgaaagctg aaatttctgg tggtcagcca gctgctcctg ttcaagttgc agctcctact    1020
```

-continued

```
caaatagttg ctcctgttca agtatccgct cctgttgatt ctggtttgtt agcaaaggcg    1080
gaacaagtag tattggaagt attggcatcc aagactggtt atgagactga gttgattgaa    1140
ttggatatgg aattggaaac tgaacttggt attgattcta tcaagagagt agaaattctt    1200
tctgaagttc aagctcaatt gagtgttgaa gctaaagatg tagatgctct tagtagaact    1260
cgtactgttg gtgaagtgat tgatgcaatg aaagctgaaa tttctggtgg tcaaccaact    1320
gctcctgttc aagttgcagc tcctactcaa atagttgctc ctgttcaagt atctgctcct    1380
gttgattctg gtttgttagc aaaggcggaa caagttgtat tggaagtatt ggcatcgaag    1440
actggttatg agactgagtt gattgaattg gatatggaat tggaaaccga acttggtatt    1500
gattctatca agagagtaga aattctttct gaagttcaag ctcaattgag tgttgaagct    1560
aaagatgtag atgctcttag tagaactcgt actgttggtg aagtgattga tgcaatgaaa    1620
gccgaaattt ctggtggtca gccagctgct cctgttcaag ttgcagctcc tactcaaata    1680
gttgctcctg ttcaagcatc tgctcctgtt gattctggtt tgttggcaaa agcggaacaa    1740
gttgtattgg aagtgttagc atccaagact ggttatgaaa ctgagttgat tgaattagat    1800
atggaattgg aaaccgaact tggtattgat tctatcaaga gagtagaaat tctttctgaa    1860
gttcaagctc aattgagtgt tgaagctaaa gatgtagatg ctcttagtag aactcgtact    1920
gttggtgaag tgattgatgc aatgaaagct gaaatttctg gtggtcaacc agctgctcct    1980
gttcaagttg cagctcctac tcaaatagtt gctcctgttc aagtatctgc tcctgttgat    2040
tctggtttgt tagcaaaggc ggaacaagtt gtattggaag tattggcatc taagactggt    2100
tatgagactg agttgattga attggatatg gaattggaaa ctgaacttgg tattgattct    2160
atcaagagag tagaaattct ttctgaagtt caagctcaat tgaatgttga agctaaagat    2220
gtagatgctc ttagtagaac tcgtactgtt ggtgaagtga ttgatgcaat gaaagccgaa    2280
attgctggtg gtcaaccagc tgctcctgtt caagttgcag ctcctgctcc agtagttgct    2340
cctgttcaag tatctactcc tgttgattct ggtttgttgg caaaagcgga acaagttgta    2400
ttggaagtgt tagcatgcaa gactggttat gaaactgagt tgattgaatt ggatatggaa    2460
ttggaaactg aacttggtat tgattctatc aagagagtag aaattctttc tgaagttcaa    2520
gctcaattga gtgttgaagc taaagatgta gatgctctta gtagaactcg tactgttggt    2580
gaagtgattg atgcaatgaa agccgaaatt tctggtggtc aaccaactgc tcctgttcaa    2640
gttgcagctc ctactcaagt agttgctcct gttaaagtat ctactcctgt tgattctggt    2700
ttgttagcaa aggcggaaca agtagtattg gaagtattgg catctaagac tggttatgaa    2760
actgagttga ttgaattaga tatggaattg gaaactgaac ttggtattga ttctatcaag    2820
agagtagaaa ttctttctga agttcaagct caattgaatg tggaagctaa agatgtggat    2880
gctcttagta gaactcgtac tgttggtgaa gtgattgatg caatgaaagc cgaaattgct    2940
ggtgatcaac ctgctccagc tgtagttcca gttcaagcta agagtggtgt agccaaccct    3000
gcacttttgg caaaggcgga acaagtagta ttggaagtat tggcatccaa gaccggttat    3060
gaaactgagc tgattgaatt ggatatggaa ttggaaactg aacttggtat tgattcaatc    3120
aagagagtag aaattctgtc cgaagttcaa gcagaattga gtgttgaagc aaaagatgta    3180
gacgctctaa gtagaacccg tactgttggg gaagtgatcg atgcaatgaa agctgaaatt    3240
gctggcagtg ctgtcacggt tgcaactttg gatgattcaa caattatgga ggagacagat    3300
gat                                                                 3303
```

```
<210> SEQ ID NO 79
<211> LENGTH: 1101
<212> TYPE: PRT
<213> ORGANISM: Thraustochytrium sp.

<400> SEQUENCE: 79

Ala Ser Pro Ala Thr Val Arg Val Val Ser Pro Val Gln Ala Ala
1               5                   10                  15

Ala Pro Val Gln Val Ser Ala Ser Val Asp Ser Gly Leu Leu Ala Lys
            20                  25                  30

Ala Glu Gln Val Val Leu Glu Val Leu Ala Ser Lys Thr Gly Tyr Glu
        35                  40                  45

Thr Glu Leu Ile Glu Leu Asp Met Glu Leu Glu Thr Glu Leu Gly Ile
    50                  55                  60

Asp Ser Ile Lys Arg Val Glu Ile Leu Ser Glu Val Gln Ala Gln Leu
65                  70                  75                  80

Asn Val Glu Ala Lys Asp Val Asp Ala Leu Ser Arg Thr Arg Thr Val
                85                  90                  95

Gly Glu Val Ile Asp Ala Met Lys Ala Glu Ile Ala Gly Gly Gln Pro
            100                 105                 110

Ala Ala Pro Val Gln Val Ala Ala Pro Thr Gln Val Val Ala Pro Val
        115                 120                 125

Gln Ala Ser Ala Pro Val Asp Ser Gly Leu Leu Ala Lys Ala Glu Gln
    130                 135                 140

Val Val Leu Glu Val Leu Ala Ser Lys Thr Gly Tyr Glu Thr Glu Leu
145                 150                 155                 160

Ile Glu Leu Asp Met Glu Leu Glu Thr Glu Leu Gly Ile Asp Ser Ile
                165                 170                 175

Lys Arg Val Glu Ile Leu Ser Glu Val Gln Ala Gln Leu Ser Val Glu
            180                 185                 190

Ala Lys Asp Val Asp Ala Leu Ser Arg Thr Arg Thr Val Gly Glu Val
        195                 200                 205

Ile Asp Ala Met Lys Ala Glu Ile Ala Gly Gly Gln Pro Ala Ala Pro
    210                 215                 220

Val Gln Val Ala Ala Pro Thr Gln Val Val Ala Pro Val Gln Ala Ser
225                 230                 235                 240

Ala Pro Val Asp Ser Gly Leu Leu Ala Lys Ala Glu Gln Val Val Leu
                245                 250                 255

Glu Val Leu Ala Ser Lys Thr Gly Tyr Glu Thr Glu Leu Ile Glu Leu
            260                 265                 270

Asp Met Glu Leu Glu Thr Glu Leu Gly Ile Asp Ser Ile Lys Arg Val
        275                 280                 285

Glu Ile Leu Ser Glu Val Gln Ala Gln Leu Ser Val Glu Ala Lys Asp
    290                 295                 300

Val Asp Ala Leu Ser Arg Thr Arg Thr Val Gly Glu Val Ile Asp Ala
305                 310                 315                 320

Met Lys Ala Glu Ile Ser Gly Gly Gln Pro Ala Ala Pro Val Gln Val
                325                 330                 335

Ala Ala Pro Thr Gln Ile Val Ala Pro Val Gln Val Ser Ala Pro Val
            340                 345                 350

Asp Ser Gly Leu Leu Ala Lys Ala Glu Gln Val Val Leu Glu Val Leu
        355                 360                 365

Ala Ser Lys Thr Gly Tyr Glu Thr Glu Leu Ile Glu Leu Asp Met Glu
    370                 375                 380
```

```
Leu Glu Thr Glu Leu Gly Ile Asp Ser Ile Lys Arg Val Glu Ile Leu
385                 390                 395                 400

Ser Glu Val Gln Ala Gln Leu Ser Val Glu Ala Lys Asp Val Asp Ala
            405                 410                 415

Leu Ser Arg Thr Arg Thr Val Gly Glu Val Ile Asp Ala Met Lys Ala
            420                 425                 430

Glu Ile Ser Gly Gly Gln Pro Thr Ala Pro Val Gln Val Ala Ala Pro
            435                 440                 445

Thr Gln Ile Val Ala Pro Val Gln Val Ser Ala Pro Val Asp Ser Gly
    450                 455                 460

Leu Leu Ala Lys Ala Glu Gln Val Val Leu Glu Val Leu Ala Ser Lys
465                 470                 475                 480

Thr Gly Tyr Glu Thr Glu Leu Ile Glu Leu Asp Met Glu Leu Glu Thr
            485                 490                 495

Glu Leu Gly Ile Asp Ser Ile Lys Arg Val Glu Ile Leu Ser Glu Val
            500                 505                 510

Gln Ala Gln Leu Ser Val Glu Ala Lys Asp Val Asp Ala Leu Ser Arg
            515                 520                 525

Thr Arg Thr Val Gly Glu Val Ile Asp Ala Met Lys Ala Glu Ile Ser
    530                 535                 540

Gly Gly Gln Pro Ala Ala Pro Val Gln Val Ala Ala Pro Thr Gln Ile
545                 550                 555                 560

Val Ala Pro Val Gln Ala Ser Ala Pro Val Asp Ser Gly Leu Leu Ala
            565                 570                 575

Lys Ala Glu Gln Val Val Leu Glu Val Leu Ala Ser Lys Thr Gly Tyr
            580                 585                 590

Glu Thr Glu Leu Ile Glu Leu Asp Met Glu Leu Glu Thr Glu Leu Gly
            595                 600                 605

Ile Asp Ser Ile Lys Arg Val Glu Ile Leu Ser Glu Val Gln Ala Gln
            610                 615                 620

Leu Ser Val Glu Ala Lys Asp Val Asp Ala Leu Ser Arg Thr Arg Thr
625                 630                 635                 640

Val Gly Glu Val Ile Asp Ala Met Lys Ala Glu Ile Ser Gly Gly Gln
            645                 650                 655

Pro Ala Ala Pro Val Gln Val Ala Ala Pro Thr Gln Ile Val Ala Pro
            660                 665                 670

Val Gln Val Ser Ala Pro Val Asp Ser Gly Leu Leu Ala Lys Ala Glu
            675                 680                 685

Gln Val Val Leu Glu Val Leu Ala Ser Lys Thr Gly Tyr Glu Thr Glu
    690                 695                 700

Leu Ile Glu Leu Asp Met Glu Leu Glu Thr Glu Leu Gly Ile Asp Ser
705                 710                 715                 720

Ile Lys Arg Val Glu Ile Leu Ser Glu Val Gln Ala Gln Leu Asn Val
            725                 730                 735

Glu Ala Lys Asp Val Asp Ala Leu Ser Arg Thr Arg Thr Val Gly Glu
            740                 745                 750

Val Ile Asp Ala Met Lys Ala Glu Ile Ala Gly Gly Gln Pro Ala Ala
            755                 760                 765

Pro Val Gln Val Ala Ala Pro Val Val Pro Val Gln Val
    770                 775                 780

Ser Thr Pro Val Asp Ser Gly Leu Leu Ala Lys Ala Glu Gln Val Val
785                 790                 795                 800

Leu Glu Val Leu Ala Cys Lys Thr Gly Tyr Glu Thr Glu Leu Ile Glu
```

```
            805                 810                 815
Leu Asp Met Glu Leu Glu Thr Glu Leu Gly Ile Asp Ser Ile Lys Arg
            820                 825                 830

Val Glu Ile Leu Ser Glu Val Gln Ala Gln Leu Ser Val Glu Ala Lys
            835                 840                 845

Asp Val Asp Ala Leu Ser Arg Thr Arg Thr Val Gly Glu Val Ile Asp
    850                 855                 860

Ala Met Lys Ala Glu Ile Ser Gly Gly Gln Pro Thr Ala Pro Val Gln
865                 870                 875                 880

Val Ala Ala Pro Thr Gln Val Ala Pro Val Lys Val Ser Thr Pro
            885                 890                 895

Val Asp Ser Gly Leu Leu Ala Lys Ala Glu Gln Val Val Leu Glu Val
            900                 905                 910

Leu Ala Ser Lys Thr Gly Tyr Glu Thr Glu Leu Ile Glu Leu Asp Met
            915                 920                 925

Glu Leu Glu Thr Glu Leu Gly Ile Asp Ser Ile Lys Arg Val Glu Ile
        930                 935                 940

Leu Ser Glu Val Gln Ala Gln Leu Asn Val Glu Ala Lys Asp Val Asp
945                 950                 955                 960

Ala Leu Ser Arg Thr Arg Thr Val Gly Glu Val Ile Asp Ala Met Lys
            965                 970                 975

Ala Glu Ile Ala Gly Asp Gln Pro Ala Pro Val Val Pro Val Gln
        980                 985                 990

Ala Lys Ser Gly Val Ala Asn Pro  Ala Leu Leu Ala Lys  Ala Glu Gln
            995                 1000                1005

Val Val  Leu Glu Val Leu Ala  Ser Lys Thr Gly Tyr  Glu Thr Glu
    1010                1015                1020

Leu Ile  Glu Leu Asp Met Glu  Leu Glu Thr Glu Leu  Gly Ile Asp
    1025                1030                1035

Ser Ile  Lys Arg Val Glu Ile  Leu Ser Glu Val Gln  Ala Glu Leu
    1040                1045                1050

Ser Val  Glu Ala Lys Asp Val  Asp Ala Leu Ser Arg  Thr Arg Thr
    1055                1060                1065

Val Gly  Glu Val Ile Asp Ala  Met Lys Ala Glu Ile  Ala Gly Ser
    1070                1075                1080

Ala Val  Thr Val Ala Thr Leu  Asp Asp Ser Thr Ile  Met Glu Glu
    1085                1090                1095

Thr Asp  Asp
    1100

<210> SEQ ID NO 80
<211> LENGTH: 255
<212> TYPE: DNA
<213> ORGANISM: Thraustochytrium sp.

<400> SEQUENCE: 80
gttgattctg gtttgttggc aaaagcggaa caagttgtat tggaagtatt ggcatcgaag      60
actggttatg agactgagtt gattgaattg gatatggaat tggaaactga acttggtatt     120
gattctatca agagagtaga aattctttct gaagttcaag ctcaattgaa tgttgaagct     180
aaagatgtag atgctcttag tagaactcgt actgttggtg aagtgattga tgcaatgaaa     240
gccgaaattg ctggt                                                      255

<210> SEQ ID NO 81
```

```
<211> LENGTH: 85
<212> TYPE: PRT
<213> ORGANISM: Thraustochytrium sp.

<400> SEQUENCE: 81

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Asn Val Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
            85

<210> SEQ ID NO 82
<211> LENGTH: 255
<212> TYPE: DNA
<213> ORGANISM: Thraustochytrium sp.

<400> SEQUENCE: 82
gttgattctg gtttgttagc aaaagcggaa caagttgtat tggaagtatt ggcatcgaag      60
actggttatg agactgagtt gattgaattg gatatggaat tggaaaccga acttggtatt     120
gattctatca agagagtaga aattctttct gaagttcaag ctcaattgag tgttgaagct     180
aaagatgtag atgctcttag tagaactcgt actgttggtg aagtgattga tgcaatgaaa     240
gccgaaattg ctggt                                                      255

<210> SEQ ID NO 83
<211> LENGTH: 85
<212> TYPE: PRT
<213> ORGANISM: Thraustochytrium sp.

<400> SEQUENCE: 83

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
            85

<210> SEQ ID NO 84
<211> LENGTH: 252
<212> TYPE: DNA
<213> ORGANISM: Thraustochytrium sp.

<400> SEQUENCE: 84
gttgattctg gtttgttagc aaaagcggaa caagttgtat tggaagtatt ggcatcgaag      60
actggttatg agactgagtt gattgaattg gatatggaat tggaaaccga acttggtatt     120
```

```
gattctatca agagagtaga aattctttct gaagttcaag ctcaattgag tgttgaagct      180
aaagatgtag atgctcttag tagaactcgt actgttggtg aagtgattga tgcaatgaaa      240
gctgaaattt ct                                                          252

<210> SEQ ID NO 85
<211> LENGTH: 85
<212> TYPE: PRT
<213> ORGANISM: Thraustochytrium sp.

<400> SEQUENCE: 85

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
                20                  25                  30

Glu Leu Glu Thr Glu Leu Gly Ile Asp Ser Ile Lys Arg Val Glu Ile
            35                  40                  45

Leu Ser Glu Val Gln Ala Gln Leu Ser Val Glu Ala Lys Asp Val Asp
        50                  55                  60

Ala Leu Ser Arg Thr Arg Thr Val Gly Glu Val Ile Asp Ala Met Lys
65                  70                  75                  80

Ala Glu Ile Ser Gly
                85

<210> SEQ ID NO 86
<211> LENGTH: 255
<212> TYPE: DNA
<213> ORGANISM: Thraustochytrium sp.

<400> SEQUENCE: 86
gttgattctg gtttgttagc aaaggcggaa caagtagtat tggaagtatt ggcatccaag       60
actggttatg agactgagtt gattgaattg gatatggaat tggaaactga acttggtatt      120
gattctatca agagagtaga aattctttct gaagttcaag ctcaattgag tgttgaagct      180
aaagatgtag atgctcttag tagaactcgt actgttggtg aagtgattga tgcaatgaaa      240
gctgaaattt ctggt                                                       255

<210> SEQ ID NO 87
<211> LENGTH: 85
<212> TYPE: PRT
<213> ORGANISM: Thraustochytrium sp.

<400> SEQUENCE: 87

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
                20                  25                  30

Glu Leu Glu Thr Glu Leu Gly Ile Asp Ser Ile Lys Arg Val Glu Ile
            35                  40                  45

Leu Ser Glu Val Gln Ala Gln Leu Ser Val Glu Ala Lys Asp Val Asp
        50                  55                  60

Ala Leu Ser Arg Thr Arg Thr Val Gly Glu Val Ile Asp Ala Met Lys
65                  70                  75                  80

Ala Glu Ile Ser Gly
                85

<210> SEQ ID NO 88
```

<211> LENGTH: 254
<212> TYPE: DNA
<213> ORGANISM: Thraustochytrium sp.

<400> SEQUENCE: 88

```
ttgattctgg tttgttagca aaggcggaac aagttgtatt ggaagtattg gcatcgaaga    60
ctggttatga gactgagttg attgaattgg atatggaatt ggaaaccgaa cttggtattg   120
attctatcaa gagagtagaa attctttctg aagttcaagc tcaattgagt gttgaagcta   180
aagatgtaga tgctcttagt agaactcgta ctgttggtga agtgattgat gcaatgaaag   240
ccgaaatttc tggt                                                    254
```

<210> SEQ ID NO 89
<211> LENGTH: 85
<212> TYPE: PRT
<213> ORGANISM: Thraustochytrium sp.

<400> SEQUENCE: 89

```
Val Asp Ser Gly Leu Leu Ala Lys Ala Glu Gln Val Val Leu Glu Val
1               5                   10                  15
Leu Ala Ser Lys Thr Gly Tyr Glu Thr Glu Leu Ile Glu Leu Asp Met
            20                  25                  30
Glu Leu Glu Thr Glu Leu Gly Ile Asp Ser Ile Lys Arg Val Glu Ile
        35                  40                  45
Leu Ser Glu Val Gln Ala Gln Leu Ser Val Glu Ala Lys Asp Val Asp
    50                  55                  60
Ala Leu Ser Arg Thr Arg Thr Val Gly Glu Val Ile Asp Ala Met Lys
65                  70                  75                  80
Ala Glu Ile Ser Gly
                85
```

<210> SEQ ID NO 90
<211> LENGTH: 255
<212> TYPE: DNA
<213> ORGANISM: Thraustochytrium sp.

<400> SEQUENCE: 90

```
gttgattctg gtttgttggc aaaagcggaa caagttgtat tggaagtgtt agcatccaag    60
actggttatg aaactgagtt gattgaatta gatatggaat tggaaaccga acttggtatt   120
gattctatca agagagtaga aattctttct gaagttcaag ctcaattgag tgttgaagct   180
aaagatgtag atgctcttag tagaactcgt actgttggtg aagtgattga tgcaatgaaa   240
gctgaaattt ctggt                                                    255
```

<210> SEQ ID NO 91
<211> LENGTH: 85
<212> TYPE: PRT
<213> ORGANISM: Thraustochytrium sp.

<400> SEQUENCE: 91

```
Val Asp Ser Gly Leu Leu Ala Lys Ala Glu Gln Val Val Leu Glu Val
1               5                   10                  15
Leu Ala Ser Lys Thr Gly Tyr Glu Thr Glu Leu Ile Glu Leu Asp Met
            20                  25                  30
Glu Leu Glu Thr Glu Leu Gly Ile Asp Ser Ile Lys Arg Val Glu Ile
        35                  40                  45
Leu Ser Glu Val Gln Ala Gln Leu Ser Val Glu Ala Lys Asp Val Asp
    50                  55                  60
```

Ala Leu Ser Arg Thr Arg Thr Val Gly Glu Val Ile Asp Ala Met Lys
 65                  70                  75                  80

Ala Glu Ile Ser Gly
            85

<210> SEQ ID NO 92
<211> LENGTH: 255
<212> TYPE: DNA
<213> ORGANISM: Thraustochytrium sp.

<400> SEQUENCE: 92
gttgattctg gtttgttagc aaaggcggaa caagttgtat tggaagtatt ggcatctaag      60
actggttatg agactgagtt gattgaattg gatatggaat tggaaactga acttggtatt     120
gattctatca agagagtaga aattctttct gaagttcaag ctcaattgaa tgttgaagct     180
aaagatgtag atgctcttag tagaactcgt actgttggtg aagtgattga tgcaatgaaa     240
gccgaaattg ctggt                                                      255

<210> SEQ ID NO 93
<211> LENGTH: 85
<212> TYPE: PRT
<213> ORGANISM: Thraustochytrium sp.

<400> SEQUENCE: 93

Val Asp Ser Gly Leu Leu Ala Lys Ala Glu Gln Val Val Leu Glu Val
  1               5                  10                  15

Leu Ala Ser Lys Thr Gly Tyr Glu Thr Glu Leu Ile Glu Leu Asp Met
             20                  25                  30

Glu Leu Glu Thr Glu Leu Gly Ile Asp Ser Ile Lys Arg Val Glu Ile
         35                  40                  45

Leu Ser Glu Val Gln Ala Gln Leu Asn Val Glu Ala Lys Asp Val Asp
     50                  55                  60

Ala Leu Ser Arg Thr Arg Thr Val Gly Glu Val Ile Asp Ala Met Lys
 65                  70                  75                  80

Ala Glu Ile Ala Gly
            85

<210> SEQ ID NO 94
<211> LENGTH: 255
<212> TYPE: DNA
<213> ORGANISM: Thraustochytrium sp.

<400> SEQUENCE: 94
gttgattctg gtttgttggc aaaagcggaa caagttgtat tggaagtgtt agcatgcaag      60
actggttatg aaactgagtt gattgaattg gatatggaat tggaaactga acttggtatt     120
gattctatca agagagtaga aattctttct gaagttcaag ctcaattgag tgttgaagct     180
aaagatgtag atgctcttag tagaactcgt actgttggtg aagtgattga tgcaatgaaa     240
gccgaaattt ctggt                                                      255

<210> SEQ ID NO 95
<211> LENGTH: 85
<212> TYPE: PRT
<213> ORGANISM: Thraustochytrium sp.

<400> SEQUENCE: 95

Val Asp Ser Gly Leu Leu Ala Lys Ala Glu Gln Val Val Leu Glu Val
  1               5                  10                  15

```
Leu Ala Cys Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ser Gly
            85

<210> SEQ ID NO 96
<211> LENGTH: 255
<212> TYPE: DNA
<213> ORGANISM: Thraustochytrium sp.

<400> SEQUENCE: 96
gttgattctg gtttgttagc aaaggcggaa caagtagtat tggaagtatt ggcatctaag      60
actggttatg aaactgagtt gattgaatta gatatggaat tggaaactga acttggtatt     120
gattctatca agagagtaga aattctttct gaagttcaag ctcaattgaa tgtggaagct     180
aaagatgtgg atgctcttag tagaactcgt actgttggtg aagtgattga tgcaatgaaa     240
gccgaaattc tggt                                                       255

<210> SEQ ID NO 97
<211> LENGTH: 85
<212> TYPE: PRT
<213> ORGANISM: Thraustochytrium sp.

<400> SEQUENCE: 97

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Asn Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
            85

<210> SEQ ID NO 98
<211> LENGTH: 255
<212> TYPE: DNA
<213> ORGANISM: Thraustochytrium sp.

<400> SEQUENCE: 98
gccaaccctg cacttttggc aaaggcggaa caagtagtat tggaagtatt ggcatccaag      60
accggttatg aaactgagct gattgaattg gatatggaat tggaaactga acttggtatt     120
gattcaatca agagagtaga aattctgtcc gaagttcaag cagaattgag tgttgaagca     180
aaagatgtag acgctctaag tagaacccgt actgttgggg aagtgatcga tgcaatgaaa     240
gctgaaattc tggc                                                       255
```

<210> SEQ ID NO 99
<211> LENGTH: 85
<212> TYPE: PRT
<213> ORGANISM: Thraustochytrium sp.

<400> SEQUENCE: 99

Ala Asn Pro Ala Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Glu Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
                85

<210> SEQ ID NO 100
<211> LENGTH: 2151
<212> TYPE: DNA
<213> ORGANISM: Thraustochytrium sp.

<400> SEQUENCE: 100
gtttcaagca ttgaatcttc gtatggaaaa attggtggct ttgtttatca acattttcat    60
gatagcgact atggtatgca acttggatgg gcgttaatgg cagcgaaaca tttgaaagag   120
tccctcaacg acccgattaa gaatggaaga accttctttt tggctgttgc gcgtatgaat   180
ggtaaacttg gtatggacaa tgcttcagtt catgatcaag gaatagtgga atcatgcggt   240
atcgccgaac gtggtgctat ctttggtttg tgcaaaactt ggatttggaa atggcctaat   300 gttttttgctc gtggtgttga tattgctgaa ggtatgagtt atagtttggc tgcggaattg   360
attgttgatg agatttcttg tgcaaatctt tccattcggg aatctggtta cacgattagc   420
ggagaaagat tcacaactga agctcacaaa ttggttactg gaaagcctca tgctccgatt   480
aagaagaagg atgctttcct agtatctggt ggtgctcgtg gtattactcc actttgtatt   540
cgtgaaattg ctaaagcagt gaaaggtggc acttacattt tgatgggtcg atcagctttg   600
gctgatgaac ccttgtgggc taatggtaaa tccggaaaag atttagataa agctggtttg   660
gcatttttga ggaagagtt tgcagctggg cgtggtagta aaccaactcc aaaagttcac   720
aaatctttga ttgataaagt gctcggtatt agggaggtta gagcatctat tgcaaatata   780
gaagcccatg gagcaaaagc tatatatttg tcttgcgatg tatcttccgc tgagaaagta   840
aaggctgcag tgcaaaaagt tgaaaaggag catctagttc gtattactgg tattgtgcat   900
gcatcaggcg ttttgaggga taaattggtt gagaacaaaa ctttggatga tttcaacgca   960
gtatatggaa ccaaagtaac tggactagta aacttgctgt cagcagtgaa catgaatttt  1020
gttcgtcatt tggttatgtt tagttctttg gctggatatc atggaaatgt tggtcaatct  1080
gattatgcaa tggctaacga atcacttaac aagattggtt ttagattggg tgcagcttat  1140
tctcaattgt gtgttaaatc tatttgtttt ggacttgggg atggtggaat ggtaactcca  1200
gctttgaaaa acaatttca atcaatgggt gtccagatta ttcctcgtga aggtggcgcg  1260
gagactgttg caagaatagt cttatcttca aatccttctc aagttttagt tggcaactgg  1320
ggtgttcctc cagtttcacc tttgtcaaaa tcggcaacta ttgttcaaac ttttaccccct  1380

-continued

```
gagttaaatc catttctaaa gtctcatcaa attcatggta aaaatgtttt gcctatgact    1440
gtagcaattg gatatcttgc tcacttggtt aagaattttt atgctggtca tcatttgtgg    1500
ggagttgaag atgctcaatt gttcagtggt gttgtaattg accatgcggt gcaagctcaa    1560
gtgaaattaa cggaacagag tttggatgat gatggcaagg taaaagttca agctgttctg    1620
actgcttcaa acgataatgg aaaaatggta cctgcataca aagcagtgat tgttttggga    1680
aaaacaagta gacctgcgtt tattttgaaa gattttcat tgcaagaatc taattctcgc     1740
agtgctgatg agttgtatga tggtaaaact ttgtttcatg gtccattatt tcgtggaatt    1800
accaagttgt tgaatgtatc tgatacttca ctaacaactc aatgtaccaa tattgatttg    1860
actgctactg aacgtggtca atttgcggat atcgaacctg tgaatccttt tatggcggat    1920
gctgcatttc aagctatgct tgtatgggtt agaaatttaa ggaatagtgc atctttacca    1980
aacaattgtg aaagagtaga tatctataaa ccaatagcac ctggtgaaaa gtattacact    2040
actttgcaag ctttgggtaa tacctccggt tctgttctca agtctgtatt ttatatgcac    2100
gatgaacaag gagaagtatt tctatctgga agagctagtg ttgttgtgaa t             2151
```

<210> SEQ ID NO 101
<211> LENGTH: 717
<212> TYPE: PRT
<213> ORGANISM: Thraustochytrium sp.

<400> SEQUENCE: 101

```
Val Ser Ser Ile Glu Ser Ser Tyr Gly Lys Ile Gly Gly Phe Val Tyr
1               5                   10                  15

Gln His Phe His Asp Ser Asp Tyr Gly Met Gln Leu Gly Trp Ala Leu
            20                  25                  30

Met Ala Ala Lys His Leu Lys Glu Ser Leu Asn Asp Pro Ile Lys Asn
        35                  40                  45

Gly Arg Thr Phe Phe Leu Ala Val Ala Arg Met Asn Gly Lys Leu Gly
    50                  55                  60

Met Asp Asn Ala Ser Val His Asp Gln Gly Ile Val Glu Ser Cys Gly
65                  70                  75                  80

Ile Ala Glu Arg Gly Ala Ile Phe Gly Leu Cys Lys Thr Leu Asp Leu
                85                  90                  95

Glu Trp Pro Asn Val Phe Ala Arg Gly Val Asp Ile Ala Glu Gly Met
            100                 105                 110

Ser Tyr Ser Leu Ala Ala Glu Leu Ile Val Asp Glu Ile Ser Cys Ala
        115                 120                 125

Asn Leu Ser Ile Arg Glu Ser Gly Tyr Thr Ile Ser Gly Glu Arg Phe
    130                 135                 140

Thr Thr Glu Ala His Lys Leu Val Thr Gly Lys Pro His Ala Pro Ile
145                 150                 155                 160

Lys Lys Lys Asp Ala Phe Leu Val Ser Gly Gly Ala Arg Gly Ile Thr
                165                 170                 175

Pro Leu Cys Ile Arg Glu Ile Ala Lys Ala Val Lys Gly Gly Thr Tyr
            180                 185                 190

Ile Leu Met Gly Arg Ser Ala Leu Ala Asp Glu Pro Leu Trp Ala Asn
        195                 200                 205

Gly Lys Ser Gly Lys Asp Leu Asp Lys Ala Gly Leu Ala Phe Leu Lys
    210                 215                 220

Glu Glu Phe Ala Ala Gly Arg Gly Ser Lys Pro Thr Pro Lys Val His
225                 230                 235                 240
```

```
Lys Ser Leu Ile Asp Lys Val Leu Gly Ile Arg Glu Val Arg Ala Ser
                245                 250                 255

Ile Ala Asn Ile Glu Ala His Gly Ala Lys Ala Ile Tyr Leu Ser Cys
            260                 265                 270

Asp Val Ser Ser Ala Glu Lys Val Lys Ala Ala Val Gln Lys Val Glu
        275                 280                 285

Lys Glu His Leu Val Arg Ile Thr Gly Ile Val His Ala Ser Gly Val
    290                 295                 300

Leu Arg Asp Lys Leu Val Glu Asn Lys Thr Leu Asp Asp Phe Asn Ala
305                 310                 315                 320

Val Tyr Gly Thr Lys Val Thr Gly Leu Val Asn Leu Leu Ser Ala Val
                325                 330                 335

Asn Met Asn Phe Val Arg His Leu Val Met Phe Ser Ser Leu Ala Gly
            340                 345                 350

Tyr His Gly Asn Val Gly Gln Ser Asp Tyr Ala Met Ala Asn Glu Ser
        355                 360                 365

Leu Asn Lys Ile Gly Phe Arg Leu Gly Ala Ala Tyr Ser Gln Leu Cys
    370                 375                 380

Val Lys Ser Ile Cys Phe Gly Pro Trp Asp Gly Gly Met Val Thr Pro
385                 390                 395                 400

Ala Leu Lys Lys Gln Phe Gln Ser Met Gly Val Gln Ile Ile Pro Arg
                405                 410                 415

Glu Gly Gly Ala Glu Thr Val Ala Arg Ile Val Leu Ser Ser Asn Pro
            420                 425                 430

Ser Gln Val Leu Val Gly Asn Trp Gly Val Pro Pro Val Ser Pro Leu
        435                 440                 445

Ser Lys Ser Ala Thr Ile Val Gln Thr Phe Thr Pro Glu Leu Asn Pro
    450                 455                 460

Phe Leu Lys Ser His Gln Ile His Gly Lys Asn Val Leu Pro Met Thr
465                 470                 475                 480

Val Ala Ile Gly Tyr Leu Ala His Leu Val Lys Asn Phe Tyr Ala Gly
                485                 490                 495

His His Leu Trp Gly Val Glu Asp Ala Gln Leu Phe Ser Gly Val Val
            500                 505                 510

Ile Asp His Ala Val Gln Ala Gln Val Lys Leu Thr Glu Gln Ser Leu
        515                 520                 525

Asp Asp Asp Gly Lys Val Lys Val Gln Ala Val Leu Thr Ala Ser Asn
    530                 535                 540

Asp Asn Gly Lys Met Val Pro Ala Tyr Lys Ala Val Ile Val Leu Gly
545                 550                 555                 560

Lys Thr Ser Arg Pro Ala Phe Ile Leu Lys Asp Phe Ser Leu Gln Glu
                565                 570                 575

Ser Asn Ser Arg Ser Ala Asp Glu Leu Tyr Asp Gly Lys Thr Leu Phe
            580                 585                 590

His Gly Pro Leu Phe Arg Gly Ile Thr Lys Leu Leu Asn Val Ser Asp
        595                 600                 605

Thr Ser Leu Thr Thr Gln Cys Thr Asn Ile Asp Leu Thr Ala Thr Glu
    610                 615                 620

Arg Gly Gln Phe Ala Asp Ile Glu Pro Val Asn Pro Phe Met Ala Asp
625                 630                 635                 640

Ala Ala Phe Gln Ala Met Leu Val Trp Val Arg Asn Leu Arg Asn Ser
                645                 650                 655

Ala Ser Leu Pro Asn Asn Cys Glu Arg Val Asp Ile Tyr Lys Pro Ile
```

```
                660             665              670
Ala Pro Gly Glu Lys Tyr Tyr Thr Thr Leu Gln Ala Leu Gly Asn Thr
            675              680             685

Ser Gly Ser Val Leu Lys Ser Val Phe Tyr Met His Asp Glu Gln Gly
        690             695              700

Glu Val Phe Leu Ser Gly Arg Ala Ser Val Val Asn
705             710             715
```

<210> SEQ ID NO 102
<211> LENGTH: 1311
<212> TYPE: DNA
<213> ORGANISM: Thraustochytrium sp.

<400> SEQUENCE: 102

```
ttaagtgttg gtgataatat ttgtcatgat caacgtgttg ctgttgttgg tatggctgtt      60
atgtatgctg gttgtcaaaa tcaacatgaa ttttggcaat ctttacaagg taaaaatatg     120
aattcaaaat cgatttcaca aaatcgttta ggttctgagt atagagaaga catttttaaa     180
cctgaaagaa gtaaatattc cgataccttt tgtaatgaaa gatatggttg tattgatgag     240
aatgttcaaa gtgaacatga acttttatta aaacttgcaa agatgctat tgcggataca      300
aaaggttcta ttgatttgaa taaaaccgga atcgttagtg gttgcttatc ttttccaatg     360
gataatttac aaggtgattt attaaatttg tatcaatgtc acattgaaaa gaaaattggg     420
ccaaatgcat taaaagatgt gaatttatgg tctaaaagaa ccaccaacgg aaaagatgat     480
aaaaaagctt attttgatcc tgcctctttc gtagctgaac aattagatat gggaccatta     540
cattatagtt tagatgctgc ttgtgcgtct gcactttatg tattaagact tgctcaagat     600
catttattaa gtggtgctgc tgatacaatg ttatgtggtg catcttgttt acctgaacct     660
tttttttattt tatctggttt ttctactttt catgcaatgc cattatctgg tgatgtttct     720
gctccttgc ataaaacttc acaaggtctt acacctggtg aaggtggtgc tattatggta     780
cttaaacgat taaatgatgc aatccgtgat ggtgatagaa tttatggtac tttacttggt     840
gctgaattaa gtaatgctgg ttgtggttta ccattgagtc cacatatgcc aagtgaattt     900
gattgtatgg aaaaagcttt acaaagagta cacagattac catcatctat tcaatatgtt     960
gagtgtcatg caactggtac accacaaggt gataaagttg aaattgatgc tatgacaaaa    1020
tgttttggtg aacattacc aaggtttggt tcaacgaaag ggaattttgg tcatacactt    1080
gttgctgctg gttttgctgg tatgtgtaaa gttttattat caatgcaata tggtgaaata    1140
ccaccaactc caggtcttga aaatccagac aatattatgc atgatttagt tgttactgaa    1200
acaattccat ggcctaatac aaatggtgat ttgaaacgtg catgtttatc tgcttttgga    1260
ttcggtggta ctaatgcaca tgctgtattt gaagagtatc gttcagattt a             1311
```

<210> SEQ ID NO 103
<211> LENGTH: 437
<212> TYPE: PRT
<213> ORGANISM: Thraustochytrium sp.

<400> SEQUENCE: 103

```
Leu Ser Val Gly Asp Asn Ile Cys His Asp Gln Arg Val Ala Val Val
1               5                  10                  15

Gly Met Ala Val Met Tyr Ala Gly Cys Gln Asn Gln His Glu Phe Trp
            20                  25                  30

Gln Ser Leu Gln Gly Lys Asn Met Asn Ser Lys Ser Ile Ser Gln Asn
        35                  40                  45
```

```
Arg Leu Gly Ser Glu Tyr Arg Glu His Phe Lys Pro Glu Arg Ser
     50                  55                  60

Lys Tyr Ser Asp Thr Phe Cys Asn Glu Arg Tyr Gly Cys Ile Asp Glu
 65                  70                  75                  80

Asn Val Gln Ser Glu His Glu Leu Leu Leu Lys Leu Ala Lys Asp Ala
                 85                  90                  95

Ile Ala Asp Thr Lys Gly Ser Ile Asp Leu Asn Lys Thr Gly Ile Val
            100                 105                 110

Ser Gly Cys Leu Ser Phe Pro Met Asp Asn Leu Gln Gly Asp Leu Leu
        115                 120                 125

Asn Leu Tyr Gln Cys His Ile Glu Lys Lys Ile Gly Pro Asn Ala Leu
    130                 135                 140

Lys Asp Val Asn Leu Trp Ser Lys Arg Thr Thr Asn Gly Lys Asp Asp
145                 150                 155                 160

Lys Lys Ala Tyr Phe Asp Pro Ala Ser Phe Val Ala Glu Gln Leu Asp
                165                 170                 175

Met Gly Pro Leu His Tyr Ser Leu Asp Ala Ala Cys Ala Ser Ala Leu
            180                 185                 190

Tyr Val Leu Arg Leu Ala Gln Asp His Leu Leu Ser Gly Ala Ala Asp
        195                 200                 205

Thr Met Leu Cys Gly Ala Ser Cys Leu Pro Glu Pro Phe Phe Ile Leu
    210                 215                 220

Ser Gly Phe Ser Thr Phe His Ala Met Pro Leu Ser Gly Asp Val Ser
225                 230                 235                 240

Ala Pro Leu His Lys Thr Ser Gln Gly Leu Thr Pro Gly Glu Gly Gly
                245                 250                 255

Ala Ile Met Val Leu Lys Arg Leu Asn Asp Ala Ile Arg Asp Gly Asp
            260                 265                 270

Arg Ile Tyr Gly Thr Leu Leu Gly Ala Glu Leu Ser Asn Ala Gly Cys
        275                 280                 285

Gly Leu Pro Leu Ser Pro His Met Pro Ser Glu Phe Asp Cys Met Glu
    290                 295                 300

Lys Ala Leu Gln Arg Val His Arg Leu Pro Ser Ser Ile Gln Tyr Val
305                 310                 315                 320

Glu Cys His Ala Thr Gly Thr Pro Gln Gly Asp Lys Val Glu Ile Asp
                325                 330                 335

Ala Met Thr Lys Cys Phe Gly Glu His Leu Pro Arg Phe Gly Ser Thr
            340                 345                 350

Lys Gly Asn Phe Gly His Thr Leu Val Ala Ala Gly Phe Ala Gly Met
        355                 360                 365

Cys Lys Val Leu Leu Ser Met Gln Tyr Gly Glu Ile Pro Pro Thr Pro
    370                 375                 380

Gly Leu Glu Asn Pro Asp Asn Ile Met His Asp Leu Val Val Thr Glu
385                 390                 395                 400

Thr Ile Pro Trp Pro Asn Thr Asn Gly Asp Leu Lys Arg Ala Cys Leu
                405                 410                 415

Ser Ala Phe Gly Phe Gly Gly Thr Asn Ala His Ala Val Phe Glu Glu
            420                 425                 430

Tyr Arg Ser Asp Leu
        435

<210> SEQ ID NO 104
<211> LENGTH: 1323
```

```
<212> TYPE: DNA
<213> ORGANISM: Thraustochytrium sp.

<400> SEQUENCE: 104
aaaattgcta ttgttggtat ggaatctgaa tttggtactt tgaaaggatt acaagaattt    60
gaacgtgcta tttacaatgg tggtcatggt gcatgtgatt tacctgaaaa tagatggaga   120
tttcttggag aagataaaga atttttacaa gcttgtggtt tacaaaaatt accaagaggt   180
tgttatatta agaagtggaa aactgatttt aaaaggttac gtttaccaat gatacaggag   240
gatattctaa gacctttaca gttgttagct gtttcgatta tcgacagagc acttaacgca   300
tctggtgtta aaccaaatgg caaagttgca gttttagttg gattaggtac tgatcttgaa   360
ttatatcgtc atcgtgctcg tgttgcatta aaggaacgcc tccaaactgc ggtcaaagaa   420
gatattcctt tacttgaaaa gttaatgaac tatgtcaatg atagaggtac aagtacatca   480
tatacatctt atattggaaa tttggttgca actcgagttt catcattatg gggtttttact   540
ggtccatcat tcacgattac tgaaggtgaa aattccgtat atcgttgtct tgatttggga   600
agatggttct tagctaatgg tgaagtagat gctgttgttg ttgccggggt tgatttatgt   660
ggtagtgctg aaaatctttt tgtaaaatct cgtagaagta agtttccac acaaaatgaa   720
ccatttgcaa attttgaatc aaatgctgat ggatattttg ctggagatgg ttgtggagct   780
ttggttttga aacgattgag tgattgtacg gattcaactg aaaaaattta tgcaacggtg   840
gattcaattg ctgttggtga tgaagttggc ccaactatta acaagctttt gaagaatgca   900
tccatagcag cgaaagatat tgaactggca gagctatcag caagttcagg caaacatcat   960
tctggtagaa tcacttgtga agatgaacta aatgaactgg gtgaaatttt caatgaaggt  1020
atacaaagag ttgcaattgg tagtgtgaaa gctaatgttg gagatgttgg atatgcatct  1080
ggtgcagcaa gtttaatcaa aacggctttg tgcctgtaca accgatattt accaaagtta  1140
ccaaattgga ataagccaac gaaagatgtt gaatggtcca atcatttttt tgtatgtgaa  1200
cattctagag catggttgaa aaatgttgat gaaaatagac atgctgtcgt ttctggagtt  1260
tgcgaaaatg gttcgtgtta tggaatcgta atgtctgatg tacaaggaca tcatgaagaa  1320
tcg                                                                1323

<210> SEQ ID NO 105
<211> LENGTH: 441
<212> TYPE: PRT
<213> ORGANISM: Thraustochytrium sp.

<400> SEQUENCE: 105

Lys Ile Ala Ile Val Gly Met Glu Ser Glu Phe Gly Thr Leu Lys Gly
1               5                   10                  15

Leu Gln Glu Phe Glu Arg Ala Ile Tyr Asn Gly Gly His Gly Ala Cys
            20                  25                  30

Asp Leu Pro Glu Asn Arg Trp Arg Phe Leu Gly Glu Asp Lys Glu Phe
        35                  40                  45

Leu Gln Ala Cys Gly Leu Gln Lys Leu Pro Arg Gly Cys Tyr Ile Lys
    50                  55                  60

Glu Val Glu Thr Asp Phe Lys Arg Leu Arg Leu Pro Met Ile Gln Glu
65                  70                  75                  80

Asp Ile Leu Arg Pro Leu Gln Leu Leu Ala Val Ser Ile Ile Asp Arg
                85                  90                  95

Ala Leu Asn Ala Ser Gly Val Lys Pro Asn Gly Lys Val Ala Val Leu
            100                 105                 110
```

Val Gly Leu Gly Thr Asp Leu Glu Leu Tyr Arg His Arg Ala Arg Val
            115                 120                 125

Ala Leu Lys Glu Arg Leu Gln Thr Ala Val Lys Glu Asp Ile Pro Leu
        130                 135                 140

Leu Glu Lys Leu Met Asn Tyr Val Asn Asp Arg Gly Thr Ser Thr Ser
145                 150                 155                 160

Tyr Thr Ser Tyr Ile Gly Asn Leu Val Ala Thr Arg Val Ser Ser Leu
                165                 170                 175

Trp Gly Phe Thr Gly Pro Ser Phe Thr Ile Thr Glu Gly Glu Asn Ser
            180                 185                 190

Val Tyr Arg Cys Leu Asp Leu Gly Arg Trp Phe Leu Ala Asn Gly Glu
        195                 200                 205

Val Asp Ala Val Val Ala Gly Val Asp Leu Cys Gly Ser Ala Glu
    210                 215                 220

Asn Leu Phe Val Lys Ser Arg Arg Ser Lys Val Ser Thr Gln Asn Glu
225                 230                 235                 240

Pro Phe Ala Asn Phe Glu Ser Asn Ala Asp Gly Tyr Phe Ala Gly Asp
                245                 250                 255

Gly Cys Gly Ala Leu Val Leu Lys Arg Leu Ser Asp Cys Thr Asp Ser
            260                 265                 270

Thr Glu Lys Ile Tyr Ala Thr Val Asp Ser Ile Ala Val Gly Asp Glu
        275                 280                 285

Val Gly Pro Thr Ile Lys Gln Ala Leu Lys Asn Ala Ser Ile Ala Ala
    290                 295                 300

Lys Asp Ile Glu Leu Ala Glu Leu Ser Ala Ser Ser Gly Lys His His
305                 310                 315                 320

Ser Gly Arg Ile Thr Cys Glu Asp Glu Leu Asn Glu Leu Gly Glu Ile
                325                 330                 335

Phe Asn Glu Gly Ile Gln Arg Val Ala Ile Gly Ser Val Lys Ala Asn
            340                 345                 350

Val Gly Asp Val Gly Tyr Ala Ser Gly Ala Ala Ser Leu Ile Lys Thr
        355                 360                 365

Ala Leu Cys Leu Tyr Asn Arg Tyr Leu Pro Lys Leu Pro Asn Trp Asn
    370                 375                 380

Lys Pro Thr Lys Asp Val Glu Trp Ser Lys Ser Phe Phe Val Cys Glu
385                 390                 395                 400

His Ser Arg Ala Trp Leu Lys Asn Val Asp Glu Asn Arg His Ala Val
                405                 410                 415

Val Ser Gly Val Cys Glu Asn Gly Ser Cys Tyr Gly Ile Val Met Ser
            420                 425                 430

Asp Val Gln Gly His His Glu Glu Ser
        435                 440

<210> SEQ ID NO 106
<211> LENGTH: 1353
<212> TYPE: DNA
<213> ORGANISM: Thraustochytrium sp.

<400> SEQUENCE: 106
cctacaatag atattgactc caatgtgttt gctgagatgc ttaatctacc gcaggataaa      60
aacaaaaaat ttgcggtcgc attggttacc acaccaaata aactccagcg tgaaatagaa     120
cttgctgtga agggtattcc acgttgcgta aaagcaaaaa gagattggtg ttctccatct     180
ggaagtattt ttgcttgtaa tccactcaaa agtgataata ttgcatttat gtatggtgaa     240

```
ggccgaagcc catatgctgg actgggatat gatttgcatc gaatttggcc tatgctacac    300
gagttggtta acaatagaac tacagaactt tgggatcaag gtgatagttg gtatttacct    360
cgatctagct ctgttgctga aaaagaaaaa gtcttcggag attttgataa gaatcaaatt    420
gaaatgttta gattgggtat ttttgtatca atgtgtttca ctgatatggc cactgaactt    480
ttgggtttaa acccaaagc cgcgtttggt ttaagtttgg gtgaaatatc tatgcttttt    540
gcattttcta aaagaatac caagttgtcc aaagaattga cccgtcgtct aaagaagca    600
aaagtttggg catcacaatt agctgttgaa tttgcagcta ttcgagattt gtggaatatt    660
ccagctgata atctattga tgaattttgg caagggtatt tgttttacgc aaatcgaacc    720
ctggtcgaga acacaattgg ggagaataaa tttgttcgtt tgttgattgt aaatgattcg    780
caaagttgtc taattgccgg gaaaccagat gaatgtcaaa aagttattga aagcttcat    840
ttgaagctac cggcggttcc agtaactcag ggtatgatcg gtcattgccc agaagcaatt    900
ccttatctag atcaaatcag tcatattcat gaaatgcttg aaattccaaa acccgaaat    960
gtgaaattgt ttacaactag tgaaaacaga gaattagtgt cgatgaaaga ttccgtgtca   1020
aaattggttg ctgagattta tcagcatgtt gctgattttc aaacatcgt gaacaaggtt   1080
aaagaaactt gcaaaactga tatatttatt gaattgggat cgaacaatta tcgatctgga   1140
gctgtcaaaa caattttagg tccagaaatc gtttctgttg caattgatag caaaatgaa   1200
actgcatggg gtcaactaat gaagatggtt gcatcgttga taagtcatcg agttccgggt   1260
gttgaattga aaaactcta tcatcctgaa ttgctgaaat ttgatccaca ggcaaaaccg   1320
aatcgtttca tcagaaatat agaactgaat gga                                1353
```

<210> SEQ ID NO 107  
<211> LENGTH: 451  
<212> TYPE: PRT  
<213> ORGANISM: Thraustochytrium sp.

<400> SEQUENCE: 107

```
Pro Thr Ile Asp Ile Asp Ser Asn Val Phe Ala Glu Met Leu Asn Leu
1               5                   10                  15

Pro Gln Asp Lys Asn Lys Lys Phe Ala Val Ala Leu Val Thr Thr Pro
            20                  25                  30

Asn Lys Leu Gln Arg Glu Ile Glu Leu Ala Val Lys Gly Ile Pro Arg
        35                  40                  45

Cys Val Lys Ala Lys Arg Asp Trp Cys Ser Pro Ser Gly Ser Ile Phe
    50                  55                  60

Ala Cys Asn Pro Leu Lys Ser Asp Asn Ile Ala Phe Met Tyr Gly Glu
65                  70                  75                  80

Gly Arg Ser Pro Tyr Ala Gly Leu Gly Tyr Asp Leu His Arg Ile Trp
                85                  90                  95

Pro Met Leu His Glu Leu Val Asn Asn Arg Thr Thr Glu Leu Trp Asp
            100                 105                 110

Gln Gly Asp Ser Trp Tyr Leu Pro Arg Ser Ser Val Ala Glu Lys
        115                 120                 125

Glu Lys Val Phe Gly Asp Phe Asp Lys Asn Gln Ile Glu Met Phe Arg
    130                 135                 140

Leu Gly Ile Phe Val Ser Met Cys Phe Thr Asp Met Ala Thr Glu Leu
145                 150                 155                 160

Leu Gly Leu Lys Pro Lys Ala Ala Phe Gly Leu Ser Leu Gly Glu Ile
                165                 170                 175
```

Ser Met Leu Phe Ala Phe Ser Lys Lys Asn Thr Lys Leu Ser Lys Glu
            180                 185                 190

Leu Thr Arg Arg Leu Lys Glu Ala Lys Val Trp Ala Ser Gln Leu Ala
        195                 200                 205

Val Glu Phe Ala Ala Ile Arg Asp Leu Trp Asn Ile Pro Ala Asp Lys
    210                 215                 220

Ser Ile Asp Glu Phe Trp Gln Gly Tyr Phe Val Tyr Ala Asn Arg Thr
225                 230                 235                 240

Leu Val Glu Asn Thr Ile Gly Glu Asn Lys Phe Val Arg Leu Leu Ile
                245                 250                 255

Val Asn Asp Ser Gln Ser Cys Leu Ile Ala Gly Lys Pro Asp Glu Cys
                260                 265                 270

Gln Lys Val Ile Glu Lys Leu His Leu Lys Leu Pro Ala Val Pro Val
            275                 280                 285

Thr Gln Gly Met Ile Gly His Cys Pro Glu Ala Ile Pro Tyr Leu Asp
    290                 295                 300

Gln Ile Ser His Ile His Glu Met Leu Glu Ile Pro Lys Pro Glu Asn
305                 310                 315                 320

Val Lys Leu Phe Thr Thr Ser Glu Asn Arg Glu Leu Val Ser Met Lys
                325                 330                 335

Asp Ser Val Ser Lys Leu Val Ala Glu Ile Tyr Gln His Val Ala Asp
                340                 345                 350

Phe Pro Asn Ile Val Asn Lys Val Lys Glu Thr Cys Lys Thr Asp Ile
            355                 360                 365

Phe Ile Glu Leu Gly Ser Asn Tyr Arg Ser Gly Ala Val Lys Thr
    370                 375                 380

Ile Leu Gly Pro Glu Ile Val Ser Val Ala Ile Asp Arg Gln Asn Glu
385                 390                 395                 400

Thr Ala Trp Gly Gln Leu Met Lys Met Val Ala Ser Leu Ile Ser His
                405                 410                 415

Arg Val Pro Gly Val Glu Leu Lys Lys Leu Tyr His Pro Glu Leu Leu
            420                 425                 430

Lys Phe Asp Pro Gln Ala Lys Pro Asn Arg Phe Ile Arg Asn Ile Glu
    435                 440                 445

Leu Asn Gly
    450

<210> SEQ ID NO 108
<211> LENGTH: 1203
<212> TYPE: DNA
<213> ORGANISM: Thraustochytrium sp.

<400> SEQUENCE: 108
ctcaaaacat atgaggttga ctatcctttg tacacaggtg ccatggctaa aggaattgcg      60
tctgctgatt tggttattgc tgctggtaaa tcaaagatct ggcatcatt tggagctggt     120 gggttggcct acaagtggt agaagatgcc attaaacaaa ttaaagctga attggggaac     180
ggtccgtttg ctgtaaattt gattcattca ccattcgatc ctagcttgga agggtaac      240 gttgatcttt ttctaaaata taacgttcga tttgttgaag tatccgcatt tatgtcatta     300 accctcagg ttgtacgata cagagccgct ggtttggcca aagcaagaga tggatctgtg     360
aaaattcaaa atcgtattat tgccaaaatt tcaagaacag agttagcgga actgttcttg     420
aaaccagcac ccaaaaatat tttagatgca ttggttgcgg atggatctat tagtcaagaa     480

```
caagcccaac ttgcattact tgtgccaatg gctgatgata ttactgtgga agctgattct    540
ggtgggcata ctgacaatcg accaattcat gttttgttac ctttgataat tcagcaaaga    600
aatagaattt gtaaacaata cccaaaacat ttaaaagttc gaatcggagc agctggtggt    660
attggatgcc cgaaggcagc atttgctgcg tttgagatgg gtgctgcata cattgcaact    720
ggaacggtaa atcaactttc aaaggaagca ggtacttgtg actatgtacg taaagtattg    780
aataaagcta catattcgga tgttaccatg gctccagccg cagatatgtt cgatcatggt    840
gttgaattac aagttttgaa gaaaggtact atgtttcctt cacgtgctaa aaactatac     900 gatttgttca aaaatacaa atcgattgag gaattaccag cagatgaggt gaaaaaactt     960
gagcaaaaag ttttcaaaaa gtcgtttgat gaagtatggg atgagaccaa gaattactat   1020
attaatcgtt tacattctcc cgaaaaaatt gaacgtgctg aaagagatgc aaaacttaaa   1080
atgtcgttat gttttcgttg gtatttgtcg aagtcttcca gatgggctaa taccggtgaa   1140
tctggaagag tgcaggatta tcaaatttgg tgtggtccag caattgggtc atataatgat   1200
ttt                                                                 1203
```

<210> SEQ ID NO 109
<211> LENGTH: 401
<212> TYPE: PRT
<213> ORGANISM: Thraustochytrium sp.

<400> SEQUENCE: 109

```
Leu Lys Thr Tyr Glu Val Asp Tyr Pro Leu Tyr Thr Gly Ala Met Ala
1               5                   10                  15

Lys Gly Ile Ala Ser Ala Asp Leu Val Ile Ala Ala Gly Lys Ser Lys
            20                  25                  30

Ile Leu Ala Ser Phe Gly Ala Gly Gly Leu Ala Leu Gln Val Val Glu
        35                  40                  45

Asp Ala Ile Lys Gln Ile Lys Ala Glu Leu Gly Asn Gly Pro Phe Ala
    50                  55                  60

Val Asn Leu Ile His Ser Pro Phe Asp Pro Ser Leu Glu Lys Gly Asn
65                  70                  75                  80

Val Asp Leu Phe Leu Lys Tyr Asn Val Arg Phe Val Glu Val Ser Ala
                85                  90                  95

Phe Met Ser Leu Thr Pro Gln Val Val Arg Tyr Arg Ala Ala Gly Leu
            100                 105                 110

Ala Lys Ala Arg Asp Gly Ser Val Lys Ile Gln Asn Arg Ile Ile Ala
        115                 120                 125

Lys Ile Ser Arg Thr Glu Leu Ala Glu Leu Phe Leu Lys Pro Ala Pro
    130                 135                 140

Lys Asn Ile Leu Asp Ala Leu Val Ala Asp Gly Ser Ile Ser Gln Glu
145                 150                 155                 160

Gln Ala Gln Leu Ala Leu Leu Val Pro Met Ala Asp Asp Ile Thr Val
                165                 170                 175

Glu Ala Asp Ser Gly Gly His Thr Asp Asn Arg Pro Ile His Val Leu
            180                 185                 190

Leu Pro Leu Ile Ile Gln Gln Arg Asn Arg Ile Cys Lys Gln Tyr Pro
        195                 200                 205

Lys His Leu Lys Val Arg Ile Gly Ala Ala Gly Gly Ile Gly Cys Pro
    210                 215                 220

Lys Ala Ala Phe Ala Ala Phe Glu Met Gly Ala Ala Tyr Ile Ala Thr
225                 230                 235                 240
```

```
Gly Thr Val Asn Gln Leu Ser Lys Glu Ala Gly Thr Cys Asp Tyr Val
                245                 250                 255

Arg Lys Val Leu Asn Lys Ala Thr Tyr Ser Asp Val Thr Met Ala Pro
            260                 265                 270

Ala Ala Asp Met Phe Asp His Gly Val Glu Leu Gln Val Leu Lys Lys
        275                 280                 285

Gly Thr Met Phe Pro Ser Arg Ala Lys Lys Leu Tyr Asp Leu Phe Lys
    290                 295                 300

Lys Tyr Lys Ser Ile Glu Glu Leu Pro Ala Asp Glu Val Lys Lys Leu
305                 310                 315                 320

Glu Gln Lys Val Phe Lys Ser Phe Asp Glu Val Trp Asp Glu Thr
                325                 330                 335

Lys Asn Tyr Tyr Ile Asn Arg Leu His Ser Pro Glu Lys Ile Glu Arg
            340                 345                 350

Ala Glu Arg Asp Ala Lys Leu Lys Met Ser Leu Cys Phe Arg Trp Tyr
        355                 360                 365

Leu Ser Lys Ser Ser Arg Trp Ala Asn Thr Gly Glu Ser Gly Arg Val
    370                 375                 380

Gln Asp Tyr Gln Ile Trp Cys Gly Pro Ala Ile Gly Ser Tyr Asn Asp
385                 390                 395                 400

Phe

<210> SEQ ID NO 110
<211> LENGTH: 1350
<212> TYPE: DNA
<213> ORGANISM: Thraustochytrium sp.

<400> SEQUENCE: 110
atggttggtt tacaaatgaa aagaaaacca gtatgggaga tgagtaagga agaacaaagt      60
tctggaaaga atgttgtatt tgactatgat gaattgttgg aatttgctga aggtgatatt     120
ggtaaagtct ttggacctaa gtttgatatt atcgataagt atagtcgacg tgtacgttta     180
cctgcgagag aatatcttct agttaccaga gttactttga tggatgctga agttgggaat     240
ttcagagttg gatctagaat ggttactgaa tatgatgttc cagtaaatgg tgaacttcta     300
caaggtggtg atgttccatg ggctgttctt gttgaatctg acaatgtga tcttatgtta     360 atatcttata tgggtattga ttttcaatgt aaaggtgatc gtgtctatcg attattaaat     420
actacgttga cgttttacgg tgttgctcat gagggtgaaa cactagtata cgatattcgt     480
gtaactggat ttgcaaaagg tatgcacggt gaaatctcca tgtttttttt tgaatatgat     540
tgttatgtga atggacgatt attaatcgaa atgagagatg gttgtgcggg attttttact     600
gatgaagaac ttgcagcagg taaggagtt attaaaactg ttgctgaact tcataaaaga     660
aaatctattg ttccaaaatc cattaaacct tttgctctaa atccagcagt acacaaaaca     720
atgttttctg aaaatgatat ggaaaaattg tgtgagcgtc aatgggaaaa tgtattgggt     780
agtggacttc aaggtattga ctacaagtta tgtgcacgga aatgcttat gattgatcgt     840 attactaaaa tacaacataa tggtggtgca tatggtcttg gattattggt tggcgaaaaa     900
attcttgaac gtgatcattg gtattttcca tgccattttg taaaggatca agttatggct     960
ggctcacttg ttagtgatgg ttgcagtcag ctactaaaac tttatatgtt atggttgggt    1020
ttacatgatg tggttccaga ttttcaattt cgtccagttc ctggacaacc aaataaagtt    1080
cgttgccgtg acaaattag tccacatcgt ggtaaacttg tttatgttat ggaaataaga    1140
gaaatgggat tcaatgaatc aactggacaa ccatatgcta ttgctgatgt tgatattatt    1200
```

```
gatgtaaact atgaacttgg tcaatcattt gatatggctg atattgatag ttatggacgt    1260
ggtaatttgt caaagaaaat tgtggttgat tttaaaggaa ttgctttgca aatggaaggt    1320
accgtgaaat catcaaatat cattgattct                                     1350
```

<210> SEQ ID NO 111
<211> LENGTH: 450
<212> TYPE: PRT
<213> ORGANISM: Thraustochytrium sp.

<400> SEQUENCE: 111

```
Met Val Gly Leu Gln Met Lys Lys Pro Val Trp Glu Met Ser Lys
1               5                   10                  15

Glu Glu Gln Ser Ser Gly Lys Asn Val Val Phe Asp Tyr Asp Glu Leu
            20                  25                  30

Leu Glu Phe Ala Glu Gly Asp Ile Gly Lys Val Phe Gly Pro Lys Phe
        35                  40                  45

Asp Ile Ile Asp Lys Tyr Ser Arg Arg Val Arg Leu Pro Ala Arg Glu
    50                  55                  60

Tyr Leu Leu Val Thr Arg Val Thr Leu Met Asp Ala Glu Val Gly Asn
65                  70                  75                  80

Phe Arg Val Gly Ser Arg Met Val Thr Glu Tyr Asp Val Pro Val Asn
                85                  90                  95

Gly Glu Leu Ser Gln Gly Asp Val Pro Trp Ala Val Leu Val Glu
            100                 105                 110

Ser Gly Gln Cys Asp Leu Met Leu Ile Ser Tyr Met Gly Ile Asp Phe
        115                 120                 125

Gln Cys Lys Gly Asp Arg Val Tyr Arg Leu Leu Asn Thr Thr Leu Thr
    130                 135                 140

Phe Tyr Gly Val Ala His Glu Gly Glu Thr Leu Val Tyr Asp Ile Arg
145                 150                 155                 160

Val Thr Gly Phe Ala Lys Gly Met His Gly Glu Ile Ser Met Phe Phe
                165                 170                 175

Phe Glu Tyr Asp Cys Tyr Val Asn Gly Arg Leu Leu Ile Glu Met Arg
            180                 185                 190

Asp Gly Cys Ala Gly Phe Phe Thr Asp Glu Glu Leu Ala Ala Gly Lys
        195                 200                 205

Gly Val Ile Lys Thr Val Ala Glu Leu His Lys Arg Lys Ser Ile Val
    210                 215                 220

Pro Lys Ser Ile Lys Pro Phe Ala Leu Asn Pro Ala Val His Lys Thr
225                 230                 235                 240

Met Phe Ser Glu Asn Asp Met Glu Lys Leu Cys Glu Arg Gln Trp Glu
                245                 250                 255

Asn Val Leu Gly Ser Gly Leu Gln Gly Ile Asp Tyr Lys Leu Cys Ala
            260                 265                 270

Arg Lys Met Leu Met Ile Asp Arg Ile Thr Lys Ile Gln His Asn Gly
        275                 280                 285

Gly Ala Tyr Gly Leu Gly Leu Leu Val Gly Glu Lys Ile Leu Glu Arg
    290                 295                 300

Asp His Trp Tyr Phe Pro Cys His Phe Val Lys Asp Gln Val Met Ala
305                 310                 315                 320

Gly Ser Leu Val Ser Asp Gly Cys Ser Gln Leu Leu Lys Leu Tyr Met
                325                 330                 335

Leu Trp Leu Gly Leu His Asp Val Val Pro Asp Phe Gln Phe Arg Pro
```

```
                340             345             350
Val Pro Gly Gln Pro Asn Lys Val Arg Cys Arg Gly Gln Ile Ser Pro
            355                 360                 365
His Arg Gly Lys Leu Val Tyr Val Met Glu Ile Arg Glu Met Gly Phe
        370                 375                 380
Asn Glu Ser Thr Gly Gln Pro Tyr Ala Ile Ala Asp Val Asp Ile
385                 390                 395                 400
Asp Val Asn Tyr Glu Leu Gly Gln Ser Phe Asp Met Ala Asp Ile Asp
                405                 410                 415
Ser Tyr Gly Arg Gly Asn Leu Ser Lys Lys Ile Val Asp Phe Lys
            420                 425                 430
Gly Ile Ala Leu Gln Met Glu Gly Thr Val Lys Ser Ser Asn Ile Ile
        435                 440                 445
Asp Ser
    450

<210> SEQ ID NO 112
<211> LENGTH: 1200
<212> TYPE: DNA
<213> ORGANISM: Thraustochytrium sp.

<400> SEQUENCE: 112
tgcttcaaac catttcctgg taatcccttta gataacgatc atacacctgg taaaatgcct      60
ttaacatggt ttaatatgtc cgagtttatg tgtggtaaag tatcaaattg tcttggacca     120
gaatttaaga gatttgataa ctctaaaaca tccagaagtc ctgcctttga tcttgcactt     180
gttacacgtg ttgtgagtgt atcagatatg gaatttaaac ctcatttaaa tattgatgtt     240
aatccaagta agggtacaat gataggtgaa tttgattgcc ctgcagatgc gtggtttttt     300
caaggatcat gtaacgatgg tcatatgccg tattctattg ttatggaaat tgctcttcaa     360
acttctggtg tattaacttc agttttgaaa gcacctttga ctatggataa agatgatatt     420
cttttccgca atttggatgc cactgctgaa atggttcgaa gtgatgttga ttgtagaggt     480
aaaactatca aaactttac tcaatgtacc ggttacagta tgctcggaaa atgggaatt      540 catagattca catttgaatt atctgttgat gatgtagttt tctacaaagg atcaacatct     600
tttggttggt tcaccccctga agtattcgag tcacaagttg gtcttgataa tggtaaaaaa     660
gtacaaccat ggtatttgga acaaaaatca tctaatgtag taacttatga cgttgcgtcc     720
actgctggca aggataagtt attttcaaag attggatcta aggatgcaca agttcaaaga     780
agaaatacac aatgtgagtt tctagatact atgcatatta ttccaaatac tggaaagtac     840
aacaaaggtt atgctcatgg agaaaagaaa gttaatccaa acgactggtt ctttttcctgt     900 catttctggt tgatcctgt gatgcctggt tcattaggta ttgaaagtat gtttcaactc     960
attgaagcat tttcaattga tcaaggaatc gcttcaaaac atggtattgt gaatccaact    1020
tttgctcatt ccaatggaaa aacttcttgg aaatacagag gtcaattgaa taacaaaggt    1080
aaacgaatgg atagtgaaat tcatatcaaa gatattgtca aaaatgctga tggtactgtt    1140
gatttgattg ctgatggatt tttattggtt gattcactaa gagtatactc tgcagatgat    1200

<210> SEQ ID NO 113
<211> LENGTH: 400
<212> TYPE: PRT
<213> ORGANISM: Thraustochytrium sp.

<400> SEQUENCE: 113
```

```
Cys Phe Lys Pro Phe Pro Gly Asn Pro Leu Asp Asn Asp His Thr Pro
  1               5                  10                  15

Gly Lys Met Pro Leu Thr Trp Phe Asn Met Ser Glu Phe Met Cys Gly
             20                  25                  30

Lys Val Ser Asn Cys Leu Gly Pro Glu Phe Lys Arg Phe Asp Asn Ser
         35                  40                  45

Lys Thr Ser Arg Ser Pro Ala Phe Asp Leu Ala Leu Val Thr Arg Val
     50                  55                  60

Val Ser Val Ser Asp Met Glu Phe Lys Pro His Leu Asn Ile Asp Val
 65              70                  75                  80

Asn Pro Ser Lys Gly Thr Met Ile Gly Glu Phe Asp Cys Pro Ala Asp
                 85                  90                  95

Ala Trp Phe Phe Gln Gly Ser Cys Asn Asp Gly His Met Pro Tyr Ser
            100                 105                 110

Ile Val Met Glu Ile Ala Leu Gln Thr Ser Gly Val Leu Thr Ser Val
        115                 120                 125

Leu Lys Ala Pro Leu Thr Met Asp Lys Asp Ile Leu Phe Arg Asn
130                 135                 140

Leu Asp Ala Thr Ala Glu Met Val Arg Ser Asp Val Asp Cys Arg Gly
145                 150                 155                 160

Lys Thr Ile Lys Asn Phe Thr Gln Cys Thr Gly Tyr Ser Met Leu Gly
                165                 170                 175

Lys Met Gly Ile His Arg Phe Thr Phe Glu Leu Ser Val Asp Asp Val
            180                 185                 190

Val Phe Tyr Lys Gly Ser Thr Ser Phe Gly Trp Phe Thr Pro Glu Val
        195                 200                 205

Phe Glu Ser Gln Val Gly Leu Asp Asn Gly Lys Lys Val Gln Pro Trp
210                 215                 220

Tyr Leu Glu Gln Lys Ser Ser Asn Val Val Thr Tyr Asp Val Ala Ser
225                 230                 235                 240

Thr Ala Gly Lys Asp Lys Leu Phe Ser Lys Ile Gly Ser Lys Asp Ala
                245                 250                 255

Gln Val Gln Arg Arg Asn Thr Gln Cys Glu Phe Leu Asp Thr Met His
            260                 265                 270

Ile Ile Pro Asn Thr Gly Lys Tyr Asn Lys Gly Tyr Ala His Gly Glu
        275                 280                 285

Lys Lys Val Asn Pro Asn Asp Trp Phe Ser Cys His Phe Trp Phe
290                 295                 300

Asp Pro Val Met Pro Gly Ser Leu Gly Ile Glu Ser Met Phe Gln Leu
305                 310                 315                 320

Ile Glu Ala Phe Ser Ile Asp Gln Gly Ile Ala Ser Lys His Gly Ile
                325                 330                 335

Val Asn Pro Thr Phe Ala His Ser Asn Gly Lys Thr Ser Trp Lys Tyr
            340                 345                 350

Arg Gly Gln Leu Asn Asn Lys Gly Lys Arg Met Asp Ser Glu Ile His
        355                 360                 365

Ile Lys Asp Ile Val Lys Asn Ala Asp Gly Thr Val Asp Leu Ile Ala
370                 375                 380

Asp Gly Phe Leu Leu Val Asp Ser Leu Arg Val Tyr Ser Ala Asp Asp
385                 390                 395                 400

<210> SEQ ID NO 114
<211> LENGTH: 1729
<212> TYPE: DNA
```

<213> ORGANISM: Thraustochytrium sp.

<400> SEQUENCE: 114

```
aggaatcgct tcaaaacatg gtattgtgaa tccaactttt gctcattcca atggaaaaac      60
ttcttggaaa tacagaggtc aattgaataa caaaggtaaa cgaatggata gtgaaattca     120
tatcaaagat attgtcaaaa atgctgatgg tactgttgat ttgattgctg atggattttt     180
attggttgat tcactaagag tatactctgc agatgatctt cgcgtaaaaa ttgtaccggg     240
aaccaaagct gcacctaaat cagtagctgc tgctccaaga catgttgcaa caccaattcc     300
aggagtgcct tcgaatacaa gcagtgttga aatcagtttg gaatctttga agaaagaatt     360
gttaaatctt gagaaaccat tgtatcttga aacttccaat catattgtaa aacaattcgg     420
tgacgttaac aatggccaag catccgttat tccaccatgc accatcaatg atttgggtga     480
gcgtagtttt atggaaacat acaatgttgt tgcaccactt tacactggag ccatggctaa     540
aggtattgca tctgctgatt tggtaattgc agctggtaaa agaaaaattt tgggttcttt     600
tggcgctgga ggcttaccaa tgcacttggt tcgtgcttct gttgaaaaaa tccaagccgc     660
acttccagaa ggtccatacg ctgtcaactt gattcatagt ccattcgact caaatcttga     720
aaagggaaat gtagatctat ttttggaaaa aggtgttcat gttgttgaag catctgcatt     780
cactgctctg accactcaag tagttcgtta ccgtgcatgt ggtttatctc gggctaaaga     840
cggatctgta ttgatcaaaa atagaatcat cggtaaagtt tcaagaaccg aattggctga     900
aatgtttttc agacctgcac cacaaaactt gcttgacaag cttattgcta gtggagaaat     960
cactaaagaa caagcttcat tggctttgga agtaccaatg gctgatgatg tagctgttga    1020
agctgatagc ggtggacata ctgataatag accaattcat gtaatcctac ctttgattat    1080
caatctacga aatagaattc ataaagaatg tggttttcct gctgctttga gagttcgcgt    1140
tggtgctggt ggtggaattg ttgtccaag tgctgcagtt gctgcattca atatgggagc    1200
tgcattcttg attactggca gcgtcaacca agttagcaaa caatctggta cgtgtgatat    1260
cgttagaaag caattatctg aagcttcgta ttcagatatt accatggcac cagcggctga    1320
tatgtttgat caaggagtcg agcttcaagt attaaaaaaa ggaactatgt ttccatctcg    1380
tgcaaagaaa ttgtatgaat tattctgtat gtacaactca tttgatgaca tgccaaaaag    1440
cgaacttcaa agactagaga gcgaattttt tcaaaaatcg cttgcggaag tttgggaaga    1500
aactaaagat ttttatatca atcgtttgaa taatcctgag aagattgaac atgctgagaa    1560
gaaagatcca aagttgaaga tgtcattatg ctttagatgg tatttgggtt taagttcatt    1620
ttgggcaaac aatggaatta agaaagatc aatggactat caaatttggt gtggtccagc    1680
gattggttca tacaatgatt ttgtaaaagg aacttatttg gatcctgca                1729
```

<210> SEQ ID NO 115
<211> LENGTH: 455
<212> TYPE: PRT
<213> ORGANISM: Thraustochytrium sp.

<400> SEQUENCE: 115

```
Asn Leu Glu Lys Pro Leu Tyr Leu Glu Thr Ser Asn His Ile Val Lys
 1               5                  10                  15

Gln Phe Gly Asp Val Asn Asn Gly Gln Ala Ser Val Ile Pro Pro Cys
            20                  25                  30

Thr Ile Asn Asp Leu Gly Glu Arg Ser Phe Met Glu Thr Tyr Asn Val
        35                  40                  45
```

```
Val Ala Pro Leu Tyr Thr Gly Ala Met Ala Lys Gly Ile Ala Ser Ala
     50                  55                  60

Asp Leu Val Ile Ala Ala Gly Lys Arg Lys Ile Leu Gly Ser Phe Gly
 65                  70                  75                  80

Ala Gly Gly Leu Pro Met His Leu Val Arg Ala Ser Val Glu Lys Ile
                 85                  90                  95

Gln Ala Ala Leu Pro Glu Gly Pro Tyr Ala Val Asn Leu Ile His Ser
            100                 105                 110

Pro Phe Asp Ser Asn Leu Glu Lys Gly Asn Val Asp Leu Phe Leu Glu
        115                 120                 125

Lys Gly Val His Val Val Glu Ala Ser Ala Phe Thr Ala Leu Thr Thr
130                 135                 140

Gln Val Val Arg Tyr Arg Ala Cys Gly Leu Ser Arg Ala Lys Asp Gly
145                 150                 155                 160

Ser Val Leu Ile Lys Asn Arg Ile Ile Gly Lys Val Ser Arg Thr Glu
                165                 170                 175

Leu Ala Glu Met Phe Phe Arg Pro Ala Pro Gln Asn Leu Leu Asp Lys
            180                 185                 190

Leu Ile Ala Ser Gly Glu Ile Thr Lys Glu Gln Ala Ser Leu Ala Leu
        195                 200                 205

Glu Val Pro Met Ala Asp Asp Val Ala Val Glu Ala Asp Ser Gly Gly
210                 215                 220

His Thr Asp Asn Arg Pro Ile His Val Ile Leu Pro Leu Ile Ile Asn
225                 230                 235                 240

Leu Arg Asn Arg Ile His Lys Glu Cys Gly Phe Pro Ala Ala Leu Arg
                245                 250                 255

Val Arg Val Gly Ala Gly Gly Ile Gly Cys Pro Ser Ala Ala Val
            260                 265                 270

Ala Ala Phe Asn Met Gly Ala Ala Phe Leu Ile Thr Gly Ser Val Asn
        275                 280                 285

Gln Val Ser Lys Gln Ser Gly Thr Cys Asp Ile Val Arg Lys Gln Leu
290                 295                 300

Ser Glu Ala Ser Tyr Ser Asp Ile Thr Met Ala Pro Ala Ala Asp Met
305                 310                 315                 320

Phe Asp Gln Gly Val Glu Leu Gln Val Leu Lys Lys Gly Thr Met Phe
                325                 330                 335

Pro Ser Arg Ala Lys Lys Leu Tyr Glu Leu Phe Cys Met Tyr Asn Ser
            340                 345                 350

Phe Asp Asp Met Pro Lys Ser Glu Leu Gln Arg Leu Glu Lys Arg Ile
        355                 360                 365

Phe Gln Lys Ser Leu Ala Glu Val Trp Glu Glu Thr Lys Asp Phe Tyr
370                 375                 380

Ile Asn Arg Leu Asn Asn Pro Glu Lys Ile Glu His Ala Glu Lys Lys
385                 390                 395                 400

Asp Pro Lys Leu Lys Met Ser Leu Cys Phe Arg Trp Tyr Leu Gly Leu
                405                 410                 415

Ser Ser Phe Trp Ala Asn Asn Gly Ile Lys Glu Arg Ser Met Asp Tyr
            420                 425                 430

Gln Ile Trp Cys Gly Pro Ala Ile Gly Ser Tyr Asn Asp Phe Val Lys
        435                 440                 445

Gly Thr Tyr Leu Asp Pro Ala
450                 455
```

<210> SEQ ID NO 116
<211> LENGTH: 903
<212> TYPE: DNA
<213> ORGANISM: Thraustochytrium sp.

<400> SEQUENCE: 116

```
tccattcggg aatctggtta cacgattagc ggagaaagat tcacaactga agctcacaaa      60
ttggttactg gaaagcctca tgctccgatt aagaagaagg atgctttcct agtatctggt     120
ggtgctcgtg gtattactcc actttgtatt cgtgaaattg ctaaagcagt gaaaggtggc     180
acttacattt tgatgggtcg atcagctttg gctgatgaac ccttgtgggc taatggtaaa     240
tccggaaaag atttagataa agctggtttg gcatttttga aggaagagtt tgcagctggg     300
cgtggtagta aaccaactcc aaaagttcac aaatctttga ttgataaagt gctcggtatt     360
agggaggtta gagcatctat tgcaaatata gaagcccatg gagcaaaagc tatatatttg     420
tcttgcgatg tatcttccgc tgagaaagta aaggctgcag tgcaaaaagt gaaaaggag      480
catctagttc gtattactgg tattgtgcat gcatcaggcg ttttgaggga taaattggtt     540
gagaacaaaa ctttggatga tttcaacgca gtatatggaa ccaaagtaac tggactagta     600
aacttgctgt cagcagtgaa catgaatttt gttcgtcatt tggttatgtt tagttctttg     660
gctggatatc atggaaatgt tggtcaatct gattatgcaa tggctaacga atcacttaac     720
aagattggtt ttagattggg tgcagcttat tctcaattgt gtgttaaatc tatttgtttt     780
ggaccttggg atggtggaat ggtaactcca gctttgaaaa aacaatttca atcaatgggt     840
gtccagatta ttcctcgtga aggtggcgcg gagactgttg caagaatagt cttatcttca     900
aat                                                                   903
```

<210> SEQ ID NO 117
<211> LENGTH: 201
<212> TYPE: PRT
<213> ORGANISM: Thraustochytrium sp.

<400> SEQUENCE: 117

Ser Ile Arg Glu Ser Gly Tyr Thr Ile Ser Gly Glu Arg Phe Thr Thr
1               5                   10                  15

Glu Ala His Lys Leu Val Thr Gly Lys Pro His Ala Pro Ile Lys Lys
            20                  25                  30

Lys Asp Ala Phe Leu Val Ser Gly Gly Ala Arg Gly Ile Thr Pro Leu
        35                  40                  45

Cys Ile Arg Glu Ile Ala Lys Ala Val Lys Gly Gly Thr Tyr Ile Leu
    50                  55                  60

Met Gly Arg Ser Ala Leu Ala Asp Glu Pro Leu Trp Ala Asn Gly Lys
65                  70                  75                  80

Ser Gly Lys Asp Leu Asp Lys Ala Gly Leu Ala Phe Leu Lys Glu Glu
                85                  90                  95

Phe Ala Ala Gly Arg Gly Ser Lys Pro Thr Pro Lys Val His Lys Ser
            100                 105                 110

Leu Ile Asp Lys Val Leu Gly Ile Arg Glu Val Arg Ala Ser Ile Ala
        115                 120                 125

Asn Ile Glu Ala His Gly Ala Lys Ala Ile Tyr Leu Ser Cys Asp Val
    130                 135                 140

Ser Ser Ala Glu Lys Val Lys Ala Ala Val Gln Lys Val Glu Lys Glu
145                 150                 155                 160

His Leu Val Arg Ile Thr Gly Ile Val His Ala Ser Gly Val Leu Arg
                165                 170                 175

Asp Lys Leu Val Glu Asn Lys Thr Leu Asp Asp Phe Asn Ala Val Tyr
            180                 185                 190
Gly Thr Lys Val Thr Gly Leu Val Asn
            195                 200

<210> SEQ ID NO 118
<211> LENGTH: 39
<212> TYPE: DNA
<213> ORGANISM: Thraustochytrium sp.

<400> SEQUENCE: 118
ctaaagtctc atcaaattca tggtaaaaat gttttgcct                    39

<210> SEQ ID NO 119
<211> LENGTH: 13
<212> TYPE: PRT
<213> ORGANISM: Thraustochytrium sp.

<400> SEQUENCE: 119

Leu Lys Ser His Gln Ile His Gly Lys Asn Val Leu Pro
1               5                   10

<210> SEQ ID NO 120
<211> LENGTH: 8976
<212> TYPE: DNA
<213> ORGANISM: Artificial Sequence
<220> FEATURE:
<223> OTHER INFORMATION: Codon-optimized PFA1

<400> SEQUENCE: 120
atggaggacc agcgtattgc gatcgttggc cttagcgcga tccttccctc gggcgagaac      60
gtccgcgagt cgtgggaggc gatccgtgac ggcctcaact gccttccgga cctgcccgcc     120
gaccgcgttg acgtcactgc ctactacaac cccacgaagg cgtcaagga caagatctac      180 tgcaagcgtg gtggcttcat ccccgagtac gagtttgact cgcgcgagtt cggcctcaac     240
atgcttcaga tggaggactc ggacgccaac cagaccctca ccctgctcaa ggttaaggag     300
gccctcgacg acgccaacat tcccgcgttt accaacgaga gaagaacat cggttgcgtc      360 ctcggtattg cggtggtca gaaggcctcg catgagttct acagccgcct caactacgtc      420
gtcgtggata aggtcctccg caagatgggc ctcccggacg aggacgtcga gactgctgtc     480
gagaagttca aggccaactt tcccgagtgg cgccttgact ccttccccgg ctttctcggt     540
aacgtcactg cgggccgctg caccaacacc ttcaacatgg agggcatgaa ctgcgtggtc     600
gatgccgcct gcgcctcgtc cctcatcgct atcaaggtcg ccatcgatga gctgctccac     660
ggcgattgcg acgcgatgat tgctggcgcg acgtgcaccg acaacgccct tggcatgtac     720
atggcctttt ccaagacccc cgtcttttcc acggaccaga gctgcctcgc ctacgacgag     780
aaaaccaagg gtatgctcat tggcgagggt tccgccatgt tcgtccttaa gcgctacgcc     840
gacgccgtcc gcgatggcga caccgtccac gccgtcatcc gctcgtgctc gtcctcctcc     900
gacggcaagg cgtcgggtat ctacacccc accatctcgg gccaggagga ggccatcctt      960
cgcgcctacc gtcgtgccgg cgtgagcccg aacacgatca cccttgtgga gggcatggc     1020 accggcaccc ccgtcggcga caagatcgag ctgaccgccc tccgcaacgt ctttgacaag    1080
gcctacggcc ctggccacaa ggaggaggtc gctgtgggct ccatcaagtc gcagatcggt    1140
cacctcaagg ccgtcgccgg ctgcgctggc ctcgtcaagc tcgtgatggc tctcaagcat    1200
aagacgctcc cgcagtccat caacgtcgag aacccgccca acctcgtcga tggcactgtc    1260

-continued

```
atctcggaca ccacgctcta catcaacacc atgaaccgcc cgtggatcac caagccgggc   1320 gtccccgtc gtgcgggcat ctccagcttc ggctttggcg gcgctaacta ccacgctgtc    1380
cttgaggagt tcgagcccga gcagaccaag ccctaccgcc tgaacgtttc ggcccagccg   1440
atgctcctcc acgccgtcaa cgcgaactcg ctccagaagc tctgcgagga ccagctcaag   1500
ctcctcaagg agtcccgcga gaagtgcgtc aacacgaaga acaccgacta cgtcgctttt   1560
tccaagtttc aggactcctt taagctcaag ggctccgtcc ccagccagca cgctcgcgtg   1620
ggctttgctt ccaagagcat cgaggacacg atttccattc ttagcgccat tgtcaaccgc   1680
ttccagaagg acatcacgac caccagctgg gcgctcccga aggagggcgc catctttcgc   1740
agcaccgccc tcatcaacga caacaagtcc gtggccgccc tgttctcggg tcagggcgct   1800
cagtacaccc acatgttcaa cgacgtcgcg atgcagtggc cgcagttccg cctctgcgtt   1860
aacgatatgg agaaggccca ggaggaggtg atcaacgaca agtcggttaa gcgcattagc   1920
caggtcatgt ttcccccgcaa gcccgacgcg cgcgagagcc cctcgacaa caaggagatc   1980 agcaagaccg agtactcgca gacgacgacc gtcgcctcgt ccgtcggcct ctttgagatt   2040
ttccgcgacg ccggctttgc cccggctttt gttgcgggcc actcgctcgg tgagttctcc   2100 gcccttacg ccgctggcct catcgaccgc gaggacctct ttaagctcgt gtgcaaccgc   2160
gccatggcta tgcgcgacgc ccccaagaag tccgctgacg gcgccatggc tgccgtcatc   2220
ggtccgaacg cctcgtccat caagctctcg gctcccgagg tttgggtcgc gaacaacaac   2280
tcgccctcgc agaccgtcat cactggtgcc aacagcggcg tccaggccga gacttcgaag   2340
ctcaagacgc agggtttccg cgtggtccac ctcgcctgcg acggcgcgtt tcacagcccg   2400
cacatggaga cgccgagaa gcagtttcag aaggccctct cggccgtcaa gttcaacaag   2460
cccaccggct cgtcccccaa gattttcagc aacgtcaccg gcggtgtctt taccgatcct   2520
aagacgcccc tctcccgcca catgactagc tcggtccagt ttctcaccca gatcaagaac   2580
atgtacgccg ctggcgcccg cgttttcatc gagttcggcc ccaagcaggt cctctcgaag   2640
ctcgtcaacg agattttccc gggcgacacc agcgtcctca ctgttagcgt gaaccctgcc   2700
tccgccaagg actcggacat ccagctccgc caggcggcc tgcagatggc ggtcgctggc   2760
gtcgctctca ccgactttga taagtgggag cttaaggacc cgaccccgcat gaaggagttc   2820 cctcgcaaga aaacgaccct cacccctctcc gccgctacct acgttagcaa gaaaacgctc   2880
caggagcgcg agcgtatcat gaacgacggt cgcactgtca gctgcgtgca gcgcatcgag   2940
aacacgaaca cgggcgagct tgagaagctc aagaagcagc tccaggacaa ggagaacgag   3000
gttgtccgcg tccaggccct tgccacccag gccagcgccg accttcagaa caccaaggct   3060
gagcttcaga aggctcaggc caccagtcg tcgaacgctg cctcggacgc cgtcgtcgcc   3120
aagcacaagg ccatcctcct cgctatgctg gaggagctgg agactggcaa ggccgtcgat   3180
tactccagct tttccaaggg tcaggttgcc tcccctgcga ccgttcgtgt cgtgtcggct   3240
cccgtgcagg ctgccgcacc ggttcaggtc agcgcctccg tggactcggg cctgctcgcg   3300
aaggcggagc aggtcgtgct tgaggtcctc gcctccaaga ccggctacga gactgagctt   3360
atcgagctgg acatggagct tgagactgag cttggtatcg attcgatcaa gcgcgtcgag   3420
attctttcgg aggtccaggc ccagctcaac gtggaggcca aggacgttga cgccctgtcg   3480
cgcacccgta cggtcggcga ggtcatcgat gccatgaagg cggagattgc cggcggtcag   3540
cctgctgccc ccgtccaggt cgctgcgccg acgcaggtcg tcgccccggt ccaggcctcc   3600
```

```
gcgcctgtcg atagcggcct cctcgccaag gcggagcagg tcgtccttga ggtgctcgct    3660
tccaagactg gttacgagac tgagcttatt gagcttgaca tggagctgga gactgagctt    3720
ggcattgact ccatcaagcg cgtggagatt ctgagcgagg tccaggccca gctcagcgtg    3780
gaggccaagg atgtcgatgc cctctcccgt acgcgcaccg tcggcgaggt cattgacgcg    3840
atgaaggccg agatcgcggg tggtcagccg gccgcccccg tccaggtcgc tgcccctacg    3900
caggtcgtcg ctcccgtcca ggccagcgct ccgtcgact cgggccttct tgctaaggcc     3960
gagcaggtcg tccttgaggt ccttgccagc aagactggct acgagactga gcttattgag    4020
cttgacatgg agcttgagac tgagcttggc atcgactcga ttaagcgcgt cgagatcctc    4080
agcgaggtcc aggcccagct ctccgtcgag gctaaggatg tggatgctct cagccgcacg    4140
cgcacggtgg gcgaggtcat tgatgccatg aaggcggaga tttccggcgg tcagcccgct    4200
gcccccgtcc aggtcgctgc tccgacccag atcgtcgccc cggtccaggt ttcggctccg    4260
gtggacagcg gcctccttgc caaggccgag caggtcgtcc ttgaggtcct cgccagcaag    4320
accggctacg agactgagct gatcgagctt gacatggagc ttgagactga gctgggcatc    4380
gattccatta gcgcgtcga gatcctctcg gaggtccagg cccagctcag cgtggaggcc     4440
aaggatgtcg atgccctctc gcgtacccgt accgtcggcg aggttatcga tgctatgaag    4500
gccgagatca gcgcggtca gcccacggcg cccgttcagg tcgctgcccc tacgcagatc     4560
gttgcccctg tccaggtcag cgctcccgtg acagcggcc cctcgctaa ggctgagcag       4620
gtggtgctgg aggtcctggc ctccaagacc ggctacgaga ctgagcttat cgagcttgac    4680
atggagcttg agactgagct tggcattgac agcatcaagc gtgtcgagat cctctccgag    4740
gtgcaggccc agctcagcgt ggaggccaag gacgttgacg cgctcagccg tacgcgcacc    4800
gttggcgagg tgatcgacgc catgaaggcc gagattagcg gtggtcagcc cgctgccccg    4860
gttcaggtgg ctgcccctac gcagatcgtc gcccccgtgc aagcttccgc ccctgtggac    4920
agcgccttc tcgccaaggc cgagcaggtc gtccttgagg tgctggcctc caagaccggc      4980
tacgagactg agctgatcga gcttgacatg gagctggaga ctgagcttgg catcgactcg    5040
atcaagcgcg tggagattct ctcggaggtc caggcccagc tctcggtcga ggccaaggac    5100
gtcgatgcgc tctcccgcac ccgcaccgtg ggcgaggtca tcgacgctat gaaggcggag    5160
atcagcggcg gtcagccggc ggccctgtg caggtggccg ctccgaccca gatcgtcgct      5220
cctgtccagg tttccgcccc ggtggactcg ggcctcctgg ctaaggccga gcaggtcgtc    5280
cttgaggtcc tcgcttccaa gaccggctac gagactgagc tgatcgagct ggacatggag    5340
cttgagactg agctgggcat cgattcgatc aagcgcgtcg agattctctc ggaggtccag    5400
gcccagctca cgttgaggc caaggacgtg acgccctct cgcgtactcg caccgttggc       5460
gaggttattg atgctatgaa ggccgagatc gccggtggtc agccggctgc ccctgttcag    5520
gttgctgccc ctgcgccggt ggtcgccccg gtccaggtgt ccaccccggt tgacagcggc    5580
ctccttgcca aggccgagca ggttgtgctg gaggtcctcg cctgcaagac gggctacgag    5640
actgagctta tcgagcttga catggagctg gagactgagc ttggcatcga ctccatcaaa    5700
cgcgtcgaga ttctttcgga ggtccaggcc cagctgtcgg tggaggctaa ggatgtcgat    5760
gccctcagcc gcacgcgcac ggtcggtgag gtcatcgatg ctatgaaggc cgagatttcg    5820
ggcggtcagc ccaccgcccc cgtgcaggtc gccgcgccca cccaggtcgt ggccccggtc    5880
aaggtttcca cgcccgtgga ctcgggcctt tcgccaaggg ccgagcaggt cgtgctggag    5940
gttctcgcct ccaagacggg ttacgagact gagctgattg agcttgacat ggagctggag    6000
```

```
actgagctgg gcattgactc catcaagcgc gtcgagatcc tctcggaggt ccaggcccag    6060
ctcaacgtcg aggccaagga cgtcgatgcc ctctcgcgca cccgcaccgt cggcgaggtc    6120
attgatgcca tgaaggccga gatcgctggc gatcagcctg ccccggctgt ggtcccggtg    6180
caggccaagt cgggtgtcgc gaaccccgcc ctcctcgcca aggcggagca ggtcgtgctg    6240
gaggtcctgg ccagcaagac gggctacgag actgagctta tcgagcttga catggagctt    6300
gagactgagc ttggtattga ctcgattaag cgcgttgaga tcctttccga ggtccaggcc    6360
gagctgtccg tggaggccaa ggatgtcgat gcgctctccc gcacccgcac ggtgggcgag    6420
gtcatcgacg ctatgaaggc cgagattgcc ggctccgcgg tcactgtcgc taccctttgac   6480 gactcgacca ttatggagga gactgacgac gaggacgagg actttatcct gtacgaccac    6540
gtctacggct ccgagtgcga ggatctctcg ctctcgttct cgtcggtcaa gtcgattcct    6600
cgcgcggaca agctcctgct ggacaacatt gccgagcgcc ccattgtcat tgtcgattgc    6660
ggcacgaagc tcacgaccga gctggcgaag gccatcggcg agcgcgctgt cgttgccacg    6720
ttctcggccc agtcgctcgt gtcccgtggc ttcgtgggca agagcttcac cctcggcaac    6780
accgaggagt cggagatcga aagatggtg tcctccatcg agtcgtccta cggcaagatc     6840
ggcggctttg tctaccagca ctttcatgac agcgactacg gtatgcagct cggctgggct    6900
ctcatggccg cgaagcacct caaggagtcc ctcaacgacc cgatcaagaa cggccgcacc    6960 ttttcctgg ctgtcgcccg catgaacggc aagctcggca tggacaacgc ctccgtccac     7020
gaccagggca tcgtcgagag ctgcggtatc gctgagcgtg gtgccatctt tggcctctgc    7080
aagaccctgg acctggagtg gcctaacgtg tttgcgcgcg gtgtggacat cgcggagggc    7140
atgtcctact ccctcgcggc cgagctgatc gtcgatgaga tcagctgcgc caaccttttcg   7200 atccgcgaga gcggctacac tattagcggc gagcgcttca ccacggaggc gcacaagctc    7260
gtcacgggca agcctcacgc gcccatcaag aagaaggacg cctttctcgt gtcgggtggt    7320
gctcgcggca tcacgcccct gtgcattcgc gagattgcca aggccgtcaa gggtggcacc    7380
tacattctca tgggccgctc ggcgctcgcg gacgagcccc tctgggctaa cggcaagagc    7440
ggcaaggacc tcgacaaggc cggcctcgcc ttccttaagg aggagttcgc tgccggccgt    7500
ggctcgaagc ccaccccccaa ggtccacaag tcgctcatcg acaaggtcct cggcatccgc   7560
gaggttcgcg cgtccatcgc caacatcgag gcgcacggcg ctaaggccat ctacctctcg    7620
tgcgatgtgt cgagcgccga gaaggtcaag gctgccgtcc agaaggtcga gaaggagcat    7680
ctcgtccgca tcacgggcat cgtgcacgcc tccggcgtcc tgcgcgacaa gctcgtcgag    7740
aacaagaccc tcgacgactt taacgctgtg tacggcacga aggtcacggg cctcgtcaac    7800
ctccttagcg ccgtcaacat gaacttcgtc cgccacctgg tgatgttctc gtcgctcgct    7860
ggttaccacg gcaacgtcgg ccagtcggac tacgctatgg ccaacgagag ccttaacaag    7920
atcggcttcc gtcttggtgc cgcgtactcc cagctctgcg tcaagtccat ctgcttcggc    7980
ccttgggatg gcggcatggt gacgccggcg ctcaagaagc agttccagtc catgggcgtt    8040
cagatcatcc ctcgcgaggg tggcgccgag actgtcgctc gcattgtgct ctcgtccaac    8100
cccagccagg tcctcgtcgg caactggggc gtcccgcccg tcagcccccct ctccaagtcg   8160 gccaccatcg tccagacctt taccccctgag cttaaccccct tcctcaagtc ccaccagatc   8220
cacggcaaga acgtcctgcc catgacggtc gccattggtt acctcgccca cctcgtgaag    8280 aactttacg ccggccacca cctctgggcc gtggaggacg cgcagctctt ctccggcgtc     8340
```

| | |
|---|---|
| gtcatcgacc acgccgtgca ggcccaggtc aagctcactg agcagagcct ggatgacgat | 8400 |
| ggcaaggtca aggtccaggc ggtgctcacc gcctcgaacg acaacggcaa gatggtgccg | 8460 |
| gcctacaagg ccgtcatcgt gctcggcaag acttcccgtc cggccttcat cctcaaggac | 8520 |
| tttttcgctcc aggagtccaa ctcgcgctcg gccgacgagc tgtacgacgg caagaccctg | 8580 |
| ttccacggcc cgctgttccg tggcatcacc aagctcctca acgtgtccga cactagcctc | 8640 |
| acgacccagt gcaccaacat cgatctcacc gccactgagc gcggccagtt tgccgacatc | 8700 |
| gagccggtca acccttttcat ggcggacgcc gccttccagg ccatgctcgt ctgggtccgc | 8760 |
| aacctccgta actccgccag ccttccgaac aactgcgagc gcgtcgatat ctacaagccc | 8820 |
| atcgcgcccg gcgagaagta ctacaccacg ctgcaggccc tcggcaacac ctccggctcg | 8880 |
| gttctcaagt ccgttttcta catgcatgac gagcagggcg aggtgttcct ctcgggccgc | 8940 |
| gccagcgtcg tggtcaacga taagatggaa ttctaa | 8976 |

<210> SEQ ID NO 121
<211> LENGTH: 5880
<212> TYPE: DNA
<213> ORGANISM: Artificial Sequence
<220> FEATURE:
<223> OTHER INFORMATION: Codon-optimized PFA2

<400> SEQUENCE: 121

| | |
|---|---|
| atggtgaagc tttccgttgg tgacaacatt tgccacgatc agcgcgtcgc cgtggtcggc | 60 |
| atggccgtca tgtacgccgg ctgccagaac cagcacgagt tttggcagag cctccagggt | 120 |
| aagaacatga acagcaagag catcagccag aaccgcctgg ctccgagtac cgcgaggag | 180 |
| cactttaagc cggagcgctc gaagtacagc gacaccttct gcaacgagcg ttacggctgc | 240 |
| atcgacgaga acgtccagag cgagcatgag ctcctcctga agctcgctaa ggacgcgatc | 300 |
| gccgatacca agggcagcat cgaccttaac aagaccggca ttgtctccgg ctgcctctcg | 360 |
| ttccctatgg ataaccttcca gggcgacctt ctcaacctct accagtgcca tattgagaag | 420 |
| aagatcggcc cgaacgccct caaggatgtc aacctctggt cgaagcgcac gaccaacggt | 480 |
| aaggacgata gaaggcctta cttcgatccc gccagcttcg tcgctgagca gcttgacatg | 540 |
| ggtcccctcc actactcgct cgacgctgcc tgcgcctccg ctctctacgt cctccgcctc | 600 |
| gcccaggacc acctcctcag cggtgccgcc gacaccatgc tctgcggcgc ctcgtgcctc | 660 |
| ccggagccct tttcatcct ttcgggctttt cgaccttcc acgccatgcc cctttcgggt | 720 |
| gacgtgtcgg cccctcttca agacgagc agggcctca ctcgggcga gggcggtgct | 780 |
| atcatggtcc tgaagcgcct caacgatgcc attgcgacg gcgaccgcat ctacggcacg | 840 |
| ctcctgggcg ccgagctttc caacgcgggt tgcggcctcc cgctctcccc gcacatgccg | 900 |
| tccgagttcg actgcatgga aaggccctc cagcgcgttc accgcctccc gtcctccatc | 960 |
| cagtacgtgg agtgccacgc cactggcacc ccgcagggcg acaaggtcga gatcgacgcc | 1020 |
| atgacgaagt gcttcggcga gcatctgcct cgcttcggct ccaccaaggg taacttcggc | 1080 |
| cacaccctcg tggctgctgg ctttgcgggc atgtgcaagg tcctcctctc gatgcagtac | 1140 |
| ggtgagattc ctcctacgcc tggcctggag aaccccgaca acattatgca cgatcttgtc | 1200 |
| gttaccgaga ctattccctg ccgaacacc aacggcgatc ttaagcgtgc gtgcctcagc | 1260 |
| gcctttggct ttggcggtac taacgcccac gccgtgttcg aggagtaccg cagcgacctt | 1320 |
| caggccaaca gacccttga gaacgagagc aagtcccacg atcttttc ctcctttaag | 1380 |
| attgccattg ttggcatgga gtccgagttt ggcactctca agggcctcca ggagttcgag | 1440 |

```
cgtgccatct acaacggcgg ccacggcgcg tgcgaccttc cggagaaccg ctggcgcttt    1500
ctcggtgagg acaaggagtt tctccaggcc tgcggcctcc agaagctccc gcgtggctgc    1560
tacatcaagg aggtcgagac tgactttaag cgccttcgcc tccccatgat ccaggaggac    1620
atcctccgcc cctccagct cctcgccgtg tcgatcatcg accgcgccct caacgccagc     1680
ggcgttaagc ccaacggcaa ggtcgccgtc ctcgtgggcc tcggcaccga tcttgagctc    1740
taccgccacc gcgctcgcgt cgccctgaag gagcgccttc agaccgccgt caaggaggac    1800 atcccctgc tggagaagct catgaactac gtgaacgacc gcggcacctc cacgtcctac     1860
acctcgtaca tcggcaacct cgttgcgacc cgcgtcagct cgctctgggg cttcaccggc    1920
cctagcttca cgatcacgga gggcgagaac tcggtttacc gttgcctcga cctcggccgc    1980
tggttcctcg ccaacggtga ggtcgatgcc gtggttgtcg ctggcgtgga tctctgcggc    2040
tcggccgaga acctgttcgt caagtcgcgc cgctccaagg tgtccaccca gaacgagccc    2100
tttgctaact ttgagtcgaa cgccgacggc tacttcgccg cgacggctg cggtgccctc     2160 gttctcaagc gcctttcgga ctgcactgac tccaccgaga agatctacgc gaccgtggac    2220
agcattgctg tcggcgacga ggtgggcccg actattaagc aggccctgaa gaacgcctcg    2280
atcgccgcga aggacatcga gctcgcggag ctctccgcct ccagcggcaa gcaccactcc    2340
ggccgcatca cctgcgagga cgagcttaac gagctcggcg agatcttcaa cgagggcatt    2400
cagcgcgtgg ccatcggcag cgtcaaggcc aacgtcggcg acgtcggcta cgcctccggt    2460
gctgccagcc tcatcaagac ggccctctgc ctctacaacc gctacctccc caagctcccc    2520
aactggaaca agccgaccaa ggacgtcgag tggtcgaaga gcttctttgt ctgcgagcac    2580
tcgcgcgcct ggctcaagaa cgtggacgag aaccgccacg cggtcgtgag cggcgtctgc    2640
gagaacggct cctgctacgg catcgtcatg agcgacgtcc agggccacca tgaggagtcg    2700
aacctcgtgt ccctcgataa gaacgagccc aaggtgctcg gtatctacgg cgattccgtg    2760
gacgatattc tggtccagct gaacaagtac ctggagaagt ccttcaggga gactggcact    2820
gctgcggctg cgcagaaggt gaagagcccc accattgaca tcgactcgaa cgtctttgcc    2880
gagatgctga accttcccca ggacaagaac aagaagtttg ccgtcgctct ggtcacgacc    2940
cccaacaagc tccagcgcga gattgagctc gccgttaagg gcatccctcg ctgcgtgaag    3000
gccaagcgcg actggtgctc ccctccggc agcatctttg cgtgcaaccc gctcaagtcg     3060
gacaacattg cctttatgta cggcgagggc cgctcgcctt acgccggcct cggctacgat    3120
ctccaccgca tctggcccat gcttcacgag ctcgtgaaca accgcacgac tgagctgtgg    3180
gaccagggtg actcgtggta cctgccgcgc agctcctccg tggccgagaa ggagaaggtc    3240
tttggcgact tcgacaagaa ccagatcgag atgttccgcc tcggtatttt cgtcagcatg    3300
tgctttaccg acatggcgac ggagctcctc ggccttaagc cgaaggccgc tttcggcctc    3360
tccctcggcg agatcagcat gctctttgct ttctcgaaga gaacaccaa gctctccaag     3420 gagcttactc gccgcctcaa ggaggccaag gtgtgggcgt cgcagctggc cgtcgagttc    3480
gccgccatcc gcgaccttg gaacatcccg gccgacaagt ccatcgatga gttctggcag    3540
ggttacttcg tttacgccaa ccgtacgctc gtggagaaca ccattggcga gaacaagttc    3600
gtccgcctcc ttatcgtcaa cgactcccag tcctgcctca ttgccggtaa gcccgatgag    3660
tgccagaagg tcatcgagaa gctccacctt aagctccccg ccgtccccgt cacccagggc    3720
atgattggcc actgccgga ggccattccc tacctcgacc agatcagcca catccacgag     3780
```

|  |  |  |  |  |  |
|---|---|---|---|---|---|
| atgcttgaga | tcccgaagcc | tgagaacgtc | aagctcttca | cgacgtccga | gaaccgcgag | 3840 |
| cttgtctcga | tgaaggactc | cgttagcaag | ctcgtcgcgg | agatctacca | gcacgtcgct | 3900 |
| gacttcccca | acattgtcaa | caaggtcaag | gagacttgca | agacggacat | tttcatcgag | 3960 |
| ctgggcagca | caactaccg | ttccggtgcc | gtcaagacta | tcctcggtcc | ggagatcgtg | 4020 |
| agcgttgcca | tcgaccgtca | gaacgagact | gcctggggcc | agctcatgaa | gatggtcgcc | 4080 |
| agcctgatct | cccaccgcgt | cccggcgtc | gagctcaaga | gctgtacca | tccggagctc | 4140 |
| ctgaagttcg | atccccaggc | caagcccaac | cgctttatcc | gcaacatcga | gctcaacggc | 4200 |
| ttttcgacc | gcacgaacat | catcgtcgat | aagcagcttt | ccctgcgga | cccgaagctc | 4260 |
| gccgagatcg | tcaacaaccg | caacatgccg | aaggataacg | tgtacgtccc | cattgagcgc | 4320 |
| gtcaagacga | tgatcaaggc | cgagcccgct | aacctccagg | tgtccgtcgg | ctcgaagccc | 4380 |
| gtggtcaccg | agcgtatctc | gtcggacgac | aacctctttg | agaagctctc | ggagatcact | 4440 |
| aagtccttcg | acggtgtcaa | cgcctgcacc | gaggccatgc | tcggcgattc | gggctttctc | 4500 |
| aagacgtacg | aggttgacta | cccgctctac | accggcgcta | tggccaaggg | tatcgcctcc | 4560 |
| gccgacctcg | tcattgcggc | gggtaagtcg | aagatccttg | cgtcctttgg | tgctggcggc | 4620 |
| ctcgctctcc | aggtggtcga | ggatgccatt | aagcagatca | aggctgagct | tggcaacggt | 4680 |
| cccttttgccg | tcaacctcat | ccactcgcct | ttcgacccct | cgcttgagaa | gggcaacgtt | 4740 |
| gaccttttcc | tcaagtacaa | cgtccgcttt | gtcgaggtga | cgcgttcat | gagcctcacc | 4800 |
| ccccaggtcg | ttcgctaccg | cgctgccggc | cttgccaagg | cccgtgacgg | ctcggtcaag | 4860 |
| attcagaacc | gcatcatcgc | caagatttcg | cgcacggagc | tggccgagct | cttcctcaag | 4920 |
| cccgctccga | gaacatcct | cgatgccctc | gttgccgacg | gctcgatttc | ccaggagcag | 4980 |
| gctcagctcg | cgctcctcgt | ccctatggcc | gatgacatca | ccgttgaggc | cgactccggt | 5040 |
| ggccacaccg | acaaccgccc | cattcatgtg | ctcctccccc | tcatcatcca | gcagcgcaac | 5100 |
| cgcatttgca | agcagtaccc | gaagcacctc | aaggtccgca | tcggcgctgc | cggtggcatc | 5160 |
| ggttgcccta | aggcggcttt | tgccgccttt | gagatgggtg | cggcctacat | cgccacgggc | 5220 |
| accgttaacc | agctctcgaa | ggaggccggc | acctgcgact | acgtgcgcaa | ggtgctcaac | 5280 |
| aaggccacct | actccgacgt | cacgatggct | cccgctgccg | acatgttcga | ccacggtgtc | 5340 |
| gagctccagt | tctcaagaa | gggcaccatg | tttccgtcgc | gcgccaagaa | gctctacgac | 5400 |
| ctctttaaga | agtacaagtc | gatcgaggag | ctccctgccg | acgaggtcaa | gaagctggag | 5460 |
| cagaaggttt | ttaagaagtc | gttcgacgag | gtctgggacg | agactaagaa | ctactacatt | 5520 |
| aaccgcctcc | actcccctga | gaagatcgag | cgcgcggagc | gtgacgccaa | gctgaagatg | 5580 |
| tcgctctgct | ttcgttggta | cctgagcaag | tcgtcccgct | gggccaacac | cggcgagtcg | 5640 |
| ggccgtgtcc | aggactacca | gatctggtgc | ggccccgcca | tcggctcgta | caacgacttc | 5700 |
| gcgaagggct | cgcccctgcct | tgaccctgag | atccttggct | cgttcccgtc | ggttgtccag | 5760 |
| atcaacaagc | atattctgcg | cggcgcttgc | ttctaccagc | gtctttcgca | gctcaagtac | 5820 |
| cttaacttca | actacgagga | gctcgatacg | ctcacctaca | gcgctagcaa | ctttatctaa | 5880 |

<210> SEQ ID NO 122
<211> LENGTH: 4368
<212> TYPE: DNA
<213> ORGANISM: Artificial Sequence
<220> FEATURE:
<223> OTHER INFORMATION: Codon-optimized PFA3

<400> SEQUENCE: 122

```
atggttggcc tgcagatgaa gaagaagcct gtgtgggaga gtgtcgaagga ggagcagtcg    60
tccggcaaga acgtcgtctt tgactacgac gagctcctcg aattcgcgga gggtgacatc   120
ggcaaggtgt tcggccccaa gtttgacatc atcgacaagt acagccgccg tgtgcgcctc   180
ccggcccgcg agtacctcct cgtcacccgt gtcacgctca tggatgccga ggtcggcaac   240
ttccgcgtcg gctcgcgcat ggtcaccgag tacgacgtcc cggtgaacgg cgagctttcc   300
cagggcggcg acgttccctg gccgtcctc gtcgagtcgg gccagtgcga cctcatgctt   360
atctcgtaca tgggcattga cttcagtgc aagggtgacc gcgtttaccg ccttctcaac   420
acgaccctca cgttctacgg tgtcgcccac gagggcgaga ctctcgttta cgacatccgc   480
gtcactggtt tcgccaaggg catgcacggc gagattagca tgttcttctt cgagtacgac   540
tgctacgtca acgccgcct gctcatcgag atgcgcgacg gttgcgctgg cttcttcacg   600
gacgaggagc tcgccgcggg caagggcgtc atcaagaccg tcgctgagct ccacaagcgc   660
aagtcgattg tgcccaagtc gatcaagcct tttgccctca ccccgccgt ccacaagacg   720
atgttcagcg agaacgacat ggagaagctt tgcgagcgcc agtgggagaa cgtcctcggc   780
tccggcctcc agggcatcga ctacaagctg tgcgcccgca agatgctcat gatcgaccgc   840
atcacgaaga tccagcacaa cggcggtgcg tacggcctcg gcctcctcgt tggcgagaag   900
attcttgagc gcgaccattg gtacttccct tgccacttcg tcaaggacca ggtgatggcg   960
ggctccctcg ttagcgacgg ctgctcgcag ctgctcaagc tttacatgct ttggctcggc  1020
ctccacgacg tggtccccga tttccagttc cgtcctgtcc ctggccagcc caacaaggtg  1080
cgctgccgtg gccagatcag cccccatcgt ggcaagctcg tgtacgtgat ggagattcgc  1140
gagatgggtt tcaacgagtc caccggccag ccctacgcga tcgctgacgt tgacattatc  1200
gatgtgaact acgagctcgg ccagtccttt gacatggccg acatcgactc gtacggccgt  1260
ggcaacctct ccaagaagat tgtcgtcgat ttcaagggca ttgcgctcca gatggagggc  1320
accgtcaaga gctccaacat catcgattcg tcccccaagt ccacgattat ccagccgccg  1380
cccaactgcc tccgcggcga tcctctcgcc ccctcgcagg tcacctggca cccgatggcc  1440
ggtgtcaacg gcgcccccgc cccctccttc agccgtcgg attaccctcc tcgtgccgtt  1500
tgctttaagc ccttccctgg caaccccctc gacaacgatc atacgccggg caagatgccg  1560
ctgacctggt ttaacatgtc ggagtttatg tgcggcaagg tcagcaactg ccttggccct  1620
gagtttaagc gcttcgacaa ctccaagacg agccgctccc cggccttcga cctggccctg  1680
gttacgcgcg tggtgtcggt cagcgatatg gagttcaagc cccacctcaa catcgacgtc  1740
aacccgtcga agggcacgat gattggcgag ttcgactgcc ccgctgacgc ctggttcttt  1800
cagggctcct gcaacgacgg ccacatgccg tacagcatcg tcatggagat cgcccttcag  1860
accagcggtg tcctcacctc cgtcctcaag gccccgctca ctatggacaa ggacgacatt  1920
ctctttcgca acctcgacgc caccgccgag atggtccgtt ccgacgtcga ttgccgcggt  1980
aagaccatca agaacttcac ccagtgcacc ggctacagca tgcttggcaa gatgggcatc  2040
caccgcttca cttttgagct ctcggtcgat gacgtcgtgt tttacaaggg ctcgaccagc  2100
tttggttggt tcacgccgga ggtgtttgag tcgcaggtcg gcctcgataa cggcaagaag  2160
gtccagccgt ggtatctgga gcagaagtcg tcgaacgtgg tgacgtacga tgtcgcctcg  2220
accgccggca aggacaagct cttctcgaag atcggctcga aggacgctca ggtccagcgt  2280
cgcaacaccc agtgcgagtt tctcgacacg atgcacatta ttccgaacac cggcaagtac  2340
```

```
aacaagggct acgcgcacgg tgagaagaag gtcaacccca acgactggtt cttctcctgc    2400 cactttggt tcgacccggt gatgcccggc tccctcggta ttgagtccat gttccagctc    2460
atcgaggcct tttcgattga ccagggtatc gcgtccaagc atggcatcgt gaaccctacc    2520
ttcgcgcact cgaacggcaa gacctcgtgg aagtaccgcg ccagctcaa caacaagggc    2580 aagcgcatgg acagcgagat tcacatcaag gatattgtca agaacgccga cggtactgtc    2640
gatctcatcg ccgatggttt tcttctcgtg gactcgcttc gcgtttacag cgccgatgac    2700
ctccgcgtca agatcgtccc cggcactaag gctgctccca agagcgtcgc ggccgctccg    2760
cgccatgtgg ccactccgat ccccggcgtc cctccaaca cctcctcggt ggagatctcg    2820
cttgagtccc ttaagaagga gctcctcaac ctggagaagc ccctctacct tgagacttcc    2880
aaccacatcg tcaagcagtt cggcgacgtt aacaacggcc aggcctccgt catccctccg    2940
tgcaccatta acgatctcgg tgagcgctcg tttatggaga cttacaacgt cgtcgctccc    3000
ctctacaccg gcgcgatggc gaagggcatc gcttcggcgg acctcgtcat cgctgccggt    3060
aagcgcaaga tcctcggcag cttcggcgcc ggtggcctcc cgatgcacct cgtgcgcgcc    3120
tcggtcgaga agatccaggc cgccctcccg gagggcccgt acgcggtcaa cctcatccac    3180 tcgccttcg actcgaacct tgagaagggt aacgtggacc tctttctgga aagggcgtc    3240 cacgtggtcg aggcctccgc ctttaccgcc ctcacgaccc aggtcgttcg ctaccgcgcc    3300
tgcggcctct cgcgtgctaa ggacggttcc gtgctgatta agaaccgcat catcggtaag    3360
gtcagccgca cggagcttgc cgagatgttc tttcgccctg ccccccagaa cctcctcgat    3420
aagctcatcg ccagcggcga gatcaccaag gagcaggcgt ccctcgctct tgaggttcct    3480
atggccgacg atgtcgctgt tgaggccgac tccggcggcc acaccgataa ccgtcccatc    3540
cacgtcatcc tcccgctgat tattaacctc cgcaaccgta tccacaagga gtgcggcttt    3600
cctgccgctc tccgcgtccg cgtcggcgct ggtggtggca tcggttgccc ctcggccgct    3660
gtcgccgcct tcaacatggg cgcggccttc ctgatcaccg gctccgttaa ccaggtgagc    3720
aagcagtccg gcacgtgcga cattgtgcgc aagcagctta gcgaggccag ctactccgac    3780
atcacgatgg ctcccgcccg tgacatgttc gaccagggcg tggagctcca ggtcctcaag    3840
aagggtacga tgtttccctc gcgcgccaag aagctctacg agctcttttg catgtacaac    3900
agctttgacg acatgccgaa gtccgagctc cagcgcctgg agaagcgcat tttccagaag    3960
agcctcgccg aggtctggga ggagactaag gacttttaca tcaaccgcct caacaacccg    4020
gagaagatcg agcacgccga gaagaaggac cccaagctca agatgtccct ttgctttcgc    4080
tggtatctcg gcctttcgag cttttgggcc aacaacggca tcaaggagcg cagcatggat    4140
taccagattt ggtgcggccc ggccattggc agctacaacg acttcgtgaa gggcaccatc    4200
ctcgaccccg ccgtcgccgg ttcgtacccc tgcgtggtcc agatcaacat gcagatcctc    4260
cgcggtgcgt gcttcctcca gcgcgtccgc gccattaagc acgacccgcg cctcgatatc    4320
gacgttgatg aggacgtctt tacctaccgc cccgagagca ccctctaa              4368
```

<210> SEQ ID NO 123
<211> LENGTH: 33
<212> TYPE: DNA
<213> ORGANISM: Artificial Sequence
<220> FEATURE:
<223> OTHER INFORMATION: Synthetic Primer pDS233
<220> FEATURE:
<221> NAME/KEY: misc_feature
<222> LOCATION: (25)..(25)
<223> OTHER INFORMATION: n is a, c, g, or t

```
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: y is c or t

<400> SEQUENCE: 123
tgatatggga ggaatgaatt gtgtngtnga ygc                                33

<210> SEQ ID NO 124
<211> LENGTH: 36
<212> TYPE: DNA
<213> ORGANISM: Artificial Sequence
<220> FEATURE:
<223> OTHER INFORMATION: Synthetic Primer pDS235
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: r is a or g
<220> FEATURE:
<221> NAME/KEY: misc_feature
<222> LOCATION: (34)..(34)
<223> OTHER INFORMATION: n is a, c, g, or t

<400> SEQUENCE: 124
ttccataaca aaatgataat tagctccncc raancc                             36

<210> SEQ ID NO 125
<211> LENGTH: 23
<212> TYPE: DNA
<213> ORGANISM: Artificial Sequence
<220> FEATURE:
<223> OTHER INFORMATION: Synthetic Primer prDS183
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (21)..(21)
<223> OTHER INFORMATION: n is a, c, g, or t

<400> SEQUENCE: 125
ggcggccaca ccgayaaymg ncc                                           23

<210> SEQ ID NO 126
<211> LENGTH: 22
<212> TYPE: DNA
<213> ORGANISM: Artificial Sequence
<220> FEATURE:
<223> OTHER INFORMATION: Synthetic Primer prDS184
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(20)
<223> OTHER INFORMATION: r is a or g

<400> SEQUENCE: 126
```

```
cggggccgca ccanayytgr ta                                                    22

<210> SEQ ID NO 127
<211> LENGTH: 17
<212> TYPE: DNA
<213> ORGANISM: Artificial Sequence
<220> FEATURE:
<223> OTHER INFORMATION: Synthetic Primer prDS181
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: s is c or g
<220> FEATURE:
<221> NAME/KEY: misc_feature
<222> LOCATION: (15)..(15)
<223> OTHER INFORMATION: n is a, c, g, or t

<400> SEQUENCE: 127
tccttcggng cngsngg                                                          17
```